(12) United States Patent
Igawa et al.

(10) Patent No.: US 11,248,053 B2
(45) Date of Patent: *Feb. 15, 2022

(54) METHOD OF MODIFYING ISOELECTRIC POINT OF ANTIBODY VIA AMINO ACID SUBSTITUTION IN CDR

(71) Applicant: Chugai Seiyaku Kabushiki Kaisha, Tokyo (JP)

(72) Inventors: Tomoyuki Igawa, Shizuoka (JP); Hiroyuki Tsunoda, Shizuoka (JP); Tatsuhiko Tachibana, Shizuoka (JP); Taichi Kuramochi, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 463 days.

This patent is subject to a terminal disclaimer.

(21) Appl. No.: 15/725,692

(22) Filed: Oct. 5, 2017

(65) Prior Publication Data

US 2018/0142027 A1    May 24, 2018

Related U.S. Application Data

(63) Continuation of application No. 14/741,786, filed on Jun. 17, 2015, now Pat. No. 9,828,429, which is a continuation of application No. 12/679,922, filed as application No. PCT/JP2008/067534 on Sep. 26, 2008, now Pat. No. 9,096,651.

(30) Foreign Application Priority Data

Sep. 26, 2007   (JP) ................ 2007-250165
Sep. 28, 2007   (JP) ................ 2007-256063

(51) Int. Cl.
*C07K 16/00*    (2006.01)
*G01N 33/68*    (2006.01)
*C07K 16/28*    (2006.01)
*A61K 39/395*   (2006.01)

(52) U.S. Cl.
CPC .... *C07K 16/2866* (2013.01); *A61K 39/39591* (2013.01); *C07K 16/00* (2013.01); *C07K 16/28* (2013.01); *G01N 33/6854* (2013.01); *C07K 2317/24* (2013.01); *C07K 2317/565* (2013.01); *C07K 2317/732* (2013.01)

(58) Field of Classification Search
CPC .. C07K 16/00–468; C07K 2317/90–94; C07K 2317/24; C07K 2317/565
See application file for complete search history.

(56) References Cited

U.S. PATENT DOCUMENTS

| | | |
|---|---|---|
| 4,208,479 A | 6/1980 | Maggio et al. |
| 4,444,878 A | 4/1984 | Paulus |
| 4,474,893 A | 10/1984 | Reading |
| 4,801,687 A | 1/1989 | Ngo |
| 5,126,250 A | 6/1992 | McDonough et al. |
| 5,322,678 A | 6/1994 | Morgan et al. |
| 5,455,030 A | 10/1995 | Ladner et al. |
| 5,468,634 A | 11/1995 | Liu |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,817,790 A | 10/1998 | Tsuchiya et al. |
| 5,827,733 A | 10/1998 | Lee et al. |
| 5,859,205 A | 1/1999 | Adair et al. |
| 5,945,311 A | 8/1999 | Lindhofer et al. |
| 5,990,286 A | 11/1999 | Khawli et al. |
| 5,994,524 A | 11/1999 | Matsushima et al. |
| 6,005,091 A | 12/1999 | Blackburn et al. |
| 6,010,902 A | 1/2000 | Ledbetter et al. |
| 6,018,032 A | 1/2000 | Koike et al. |
| 6,024,956 A | 2/2000 | Matsushima et al. |
| 6,025,158 A | 2/2000 | Gonzalez et al. |
| 6,074,642 A | 6/2000 | Wang et al. |
| 6,096,506 A | 8/2000 | Lee et al. |

(Continued)

FOREIGN PATENT DOCUMENTS

| | | |
|---|---|---|
| AR | 068564 | 11/2009 |
| AU | 2007/255753 | 12/2007 |

(Continued)

OTHER PUBLICATIONS

U.S. Appl. No. 15/228,965, Igawa et al., filed Oct. 7, 2016 (abandoned).
U.S. Appl. No. 15/288,965, Igawa et al., filed Oct. 17, 2016.
U.S. Appl. No. 15/263,617, Igawa et al., filed Sep. 13, 2016.
U.S. Appl. No. 12/680,087, Igawa et al., filed Jan. 3, 2011.
U.S. Appl. No. 11/910,128, Igawa et al., filed Oct. 7, 2008.
U.S. Appl. No. 14/680,250, Igawa et al., filed Apr. 7, 2015.
U.S. Appl. No. 14/962,293, Igawa et al., filed Dec. 8, 2015.
U.S. Appl. No. 13/497,269, Kuramochi et al., filed Jun. 1, 2012.
U.S. Appl. No. 13/637,415, Igawa et al., filed Sep. 26, 2012.
U.S. Appl. No. 15/495,026, Igawa et al., Apr. 24, 2017.

(Continued)

*Primary Examiner* — Jessica H Roark
(74) *Attorney, Agent, or Firm* — Fish & Richardson P.C.

(57) ABSTRACT

The present inventors provide methods for modifying the isoelectric point of an antibody while retaining its antigen-binding activity, comprising modifying the charge of at least one exposable amino acid residue on the surface of the complementarity determining region (CDR). The present invention also provides methods for purifying multispecific antibodies, comprising modifying isoelectric point, and methods for improving the plasma pharmacokinetics of antibodies, comprising modifying isoelectric point. The present invention further provides antibodies with a modified isoelectric point, pharmaceutical compositions comprising the antibodies as an active ingredient, and methods for producing the antibodies and compositions.

28 Claims, 62 Drawing Sheets

Specification includes a Sequence Listing.

(56) References Cited

U.S. PATENT DOCUMENTS

| | | |
|---|---|---|
| 6,126,980 A | 10/2000 | Smith et al. |
| 6,129,914 A | 10/2000 | Weiner |
| 6,165,745 A | 12/2000 | Ward et al. |
| 6,245,894 B1 | 6/2001 | Matsushima et al. |
| 6,309,636 B1 | 10/2001 | do Couto et al. |
| 6,329,511 B1 | 12/2001 | Vasquez et al. |
| 6,355,245 B1 | 3/2002 | Evans et al. |
| 6,458,355 B1 | 10/2002 | Hsei et al. |
| 6,485,943 B2 | 11/2002 | Slevens et al. |
| 6,677,436 B1 | 1/2004 | Sato et al. |
| 6,723,319 B1 | 4/2004 | Ito et al. |
| 6,737,056 B1 | 5/2004 | Presta |
| 6,821,505 B2 | 11/2004 | Ward |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |
| 7,052,873 B2 | 5/2006 | Tsuchiya |
| 7,122,637 B2 | 10/2006 | Presta |
| 7,217,797 B2 | 5/2007 | Hinton et al. |
| 7,247,302 B1 | 7/2007 | Rosok et al. |
| 7,261,893 B2 | 8/2007 | Geertruida et al. |
| 7,276,585 B2 | 10/2007 | Lazar et al. |
| 7,282,568 B2 | 10/2007 | Teeling et al. |
| 7,320,789 B2 | 1/2008 | Aghajanian et al. |
| 7,371,826 B2 | 5/2008 | Presta |
| 7,432,356 B2 | 10/2008 | Fung et al. |
| 7,479,543 B2 | 1/2009 | Tsuchiya et al. |
| 7,482,440 B2 | 1/2009 | Maeda et al. |
| 7,538,196 B2 | 5/2009 | Jung |
| 7,632,499 B2 | 12/2009 | Davies et al. |
| 7,632,924 B2 | 12/2009 | Cho et al. |
| 7,670,600 B2 | 3/2010 | Dall'Acqua et al. |
| 7,732,149 B2 | 6/2010 | Kojima et al. |
| 7,785,791 B2 | 8/2010 | Presta |
| 7,807,159 B2 | 10/2010 | Chin et al. |
| 7,820,800 B2 | 10/2010 | Rossi et al. |
| 7,888,486 B2 | 2/2011 | Walsh et al. |
| 8,030,461 B2 | 10/2011 | Kojima |
| 8,062,635 B2 | 11/2011 | Hattori et al. |
| 8,147,829 B2 | 4/2012 | Hariharan et al. |
| 8,188,231 B2 | 5/2012 | Lazar et al. |
| 8,217,147 B2 | 7/2012 | Stavenhagen et al. |
| 8,323,962 B2 | 12/2012 | Dall'Acqua et al. |
| 8,329,867 B2 | 12/2012 | Lazar et al. |
| 8,337,841 B2 | 12/2012 | Kojima |
| 8,367,805 B2 | 2/2013 | Chamberlain et al. |
| 8,415,459 B2 | 4/2013 | La Vallie et al. |
| 8,562,991 B2 | 10/2013 | Igawa et al. |
| 8,568,726 B2 | 10/2013 | Beaumont et al. |
| 8,575,317 B2 | 11/2013 | Kuramochi et al. |
| 8,592,562 B2 | 11/2013 | Kannan et al. |
| 8,604,174 B2 | 12/2013 | Babcook et al. |
| 8,637,641 B2 | 1/2014 | Dahiyat et al. |
| 8,753,629 B2 | 6/2014 | Lazar et al. |
| 8,765,124 B2 | 7/2014 | Saito et al. |
| 8,802,820 B2 | 8/2014 | Chamberlain et al. |
| 9,029,515 B2 | 5/2015 | Pons et al. |
| 9,051,373 B2 | 6/2015 | Lazar et al. |
| 9,079,949 B1 | 7/2015 | Andrien et al. |
| 9,096,651 B2 | 8/2015 | Igawa et al. |
| 9,228,017 B2 | 1/2016 | Igawa et al. |
| 9,315,577 B2 | 4/2016 | Foltz et al. |
| 9,334,331 B2 | 5/2016 | Igawa et al. |
| 9,340,615 B2 | 5/2016 | Maeda et al. |
| 9,399,680 B2 | 7/2016 | Kuramochi et al. |
| 9,527,926 B2 | 12/2016 | Ho et al. |
| 9,556,279 B2 | 1/2017 | Niwa et al. |
| 9,605,061 B2 | 3/2017 | Lazar et al. |
| 9,637,557 B2 | 5/2017 | Scheer et al. |
| 9,670,269 B2 | 6/2017 | Igawa et al. |
| 9,688,762 B2 | 6/2017 | Igawa et al. |
| 9,765,135 B2 | 9/2017 | Ruike et al. |
| 9,828,429 B2 * | 11/2017 | Igawa .................... A61P 43/00 |
| 9,969,800 B2 | 5/2018 | Igawa et al. |
| 9,975,966 B2 | 5/2018 | Nezu et al. |
| 10,000,560 B2 | 6/2018 | Ruike et al. |
| 10,011,858 B2 | 7/2018 | Igawa et al. |
| 10,022,319 B2 | 7/2018 | Igawa et al. |
| 10,023,630 B2 | 7/2018 | Ruike et al. |
| 10,024,867 B2 | 7/2018 | Igawa |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,253,100 B2 | 4/2019 | Igawa et al. |
| 10,385,122 B2 | 8/2019 | Ruike et al. |
| 10,435,458 B2 | 10/2019 | Kuramochi et al. |
| 10,450,381 B2 | 10/2019 | Igawa et al. |
| 10,519,229 B2 | 12/2019 | Igawa et al. |
| 10,618,965 B2 | 4/2020 | Igawa et al. |
| 10,662,245 B2 | 5/2020 | Igawa et al. |
| 10,738,111 B2 | 8/2020 | Ruike et al. |
| 10,774,148 B2 | 9/2020 | Kakehi et al. |
| 10,934,344 B2 | 3/2021 | Igawa et al. |
| 11,046,784 B2 | 6/2021 | Igawa et al. |
| 2001/0001663 A1 | 5/2001 | Kishimoto et al. |
| 2002/0062010 A1 | 5/2002 | Arathoon et al. |
| 2002/0082396 A1 | 6/2002 | Matsushima et al. |
| 2002/0142374 A1 | 10/2002 | Gallo et al. |
| 2002/0147326 A1 | 10/2002 | Chaiklin et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2003/0077283 A1 | 4/2003 | Ye |
| 2003/0125520 A1 | 7/2003 | Maeda |
| 2003/0187225 A1 | 10/2003 | Penichet et al. |
| 2003/0190311 A1 | 10/2003 | Dall'Acqua et al. |
| 2003/0207346 A1 | 11/2003 | Arathoon et al. |
| 2003/0215838 A1 | 11/2003 | Sprecher et al. |
| 2003/0216551 A1 | 11/2003 | Delovitch |
| 2003/0219441 A1 | 11/2003 | Thorpe et al. |
| 2003/0224397 A1 | 12/2003 | Lowman et al. |
| 2003/0224487 A1 | 12/2003 | Sprecher et al. |
| 2004/0071706 A1 | 4/2004 | Ito et al. |
| 2004/0081651 A1 | 4/2004 | Karpusas et al. |
| 2004/0110226 A1 | 6/2004 | Lazar et al. |
| 2004/0223970 A1 | 11/2004 | Afar et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0158825 A1 | 7/2005 | Power et al. |
| 2005/0164352 A1 | 7/2005 | Lauder et al. |
| 2005/0191293 A1 | 9/2005 | Deshpande et al. |
| 2005/0244403 A1 | 11/2005 | Lazar et al. |
| 2005/0261229 A1 | 11/2005 | Gillies et al. |
| 2005/0266425 A1 | 12/2005 | Zauderer et al. |
| 2006/0019342 A1 | 1/2006 | Dall Acqua et al. |
| 2006/0024298 A1 | 2/2006 | Lazar et al. |
| 2006/0057149 A1 | 3/2006 | Johnson et al. |
| 2006/0063228 A1 | 3/2006 | Kasaian et al. |
| 2006/0074225 A1 | 4/2006 | Chamberlain |
| 2006/0121022 A1 | 6/2006 | Koga et al. |
| 2006/0134105 A1 | 6/2006 | Lazar et al. |
| 2006/0134709 A1 | 6/2006 | Stavenhagen et al. |
| 2006/0134805 A1 | 6/2006 | Berg et al. |
| 2006/0141456 A1 | 6/2006 | Edwards et al. |
| 2006/0160184 A1 | 7/2006 | Hoogenboom et al. |
| 2006/0182743 A1 | 8/2006 | Bilsborough |
| 2006/0194280 A1 | 8/2006 | Dillon et al. |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0003546 A1 | 1/2007 | Lazar et al. |
| 2007/0009523 A1 | 1/2007 | Presta |
| 2007/0231329 A1 | 1/2007 | Lazar et al. |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0110757 A1 | 5/2007 | Wei et al. |
| 2007/0134234 A1 | 6/2007 | Smith et al. |
| 2007/0148163 A1 | 6/2007 | Takahashi et al. |

(56) References Cited

U.S. PATENT DOCUMENTS

| | | |
|---|---|---|
| 2007/0148164 A1 | 6/2007 | Farrington et al. |
| 2007/0148167 A1 | 6/2007 | Strohl |
| 2007/0160598 A1 | 7/2007 | Dennis et al. |
| 2007/0160611 A1 | 7/2007 | Yao et al. |
| 2007/0190056 A1 | 8/2007 | Kambadur et al. |
| 2007/0212357 A1 | 9/2007 | Pons et al. |
| 2007/0224174 A1 | 9/2007 | Kang et al. |
| 2007/0224188 A1 | 9/2007 | Allan et al. |
| 2007/0237767 A1 | 10/2007 | Lazar et al. |
| 2007/0253951 A1 | 11/2007 | Ng et al. |
| 2007/0269371 A1 | 11/2007 | Krummen et al. |
| 2007/0280945 A1 | 12/2007 | Stevens et al. |
| 2008/0050370 A1 | 2/2008 | Glaser et al. |
| 2008/0063635 A1 | 3/2008 | Takahashi et al. |
| 2008/0075712 A1 | 3/2008 | Hattori et al. |
| 2008/0089892 A1 | 4/2008 | Allan et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2009/0041770 A1 | 2/2009 | Chamberlain et al. |
| 2009/0053240 A1 | 2/2009 | Lazar et al. |
| 2009/0117097 A1 | 5/2009 | Igawa et al. |
| 2009/0136485 A1 | 5/2009 | Chu et al. |
| 2009/0202556 A1 | 8/2009 | Ohta et al. |
| 2009/0208416 A1 | 8/2009 | Moretta et al. |
| 2009/0221803 A1 | 9/2009 | Dall'Acqua et al. |
| 2009/0263392 A1 | 10/2009 | Igawa et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0166748 A1 | 7/2010 | Guild et al. |
| 2010/0216187 A1 | 8/2010 | Lasters et al. |
| 2010/0239577 A1 | 9/2010 | Igawa et al. |
| 2010/0247523 A1 | 9/2010 | Kano et al. |
| 2010/0249482 A1 | 9/2010 | Chung et al. |
| 2010/0285030 A1 | 11/2010 | Bowdish et al. |
| 2010/0286374 A1 | 11/2010 | Kannan et al. |
| 2010/0291072 A1 | 11/2010 | Lowman et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2010/0310556 A1 | 12/2010 | Higuchi et al. |
| 2010/0316636 A1 | 12/2010 | Radin et al. |
| 2010/0331527 A1 | 12/2010 | Davis et al. |
| 2011/0002931 A1 | 1/2011 | Tamburini |
| 2011/0044984 A1 | 2/2011 | Kittazawa et al. |
| 2011/0059093 A1 | 3/2011 | Bohrmann et al. |
| 2011/0076275 A1 | 3/2011 | Igawa et al. |
| 2011/0098450 A1 | 4/2011 | Igawa et al. |
| 2011/0105724 A1 | 5/2011 | Clegg et al. |
| 2011/0111406 A1 | 5/2011 | Igawa et al. |
| 2011/0129459 A1 | 6/2011 | Kuramochi et al. |
| 2011/0135662 A1 | 6/2011 | Finney et al. |
| 2011/0229459 A1 | 9/2011 | Kuramochi et al. |
| 2011/0229489 A1 | 9/2011 | Pons et al. |
| 2011/0236374 A1 | 9/2011 | Shitara et al. |
| 2011/0245473 A1 | 10/2011 | Igawa et al. |
| 2011/0287009 A1 | 11/2011 | Scheer et al. |
| 2012/0009188 A1 | 1/2012 | Behrens et al. |
| 2012/0010387 A1 | 1/2012 | Niwa et al. |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0149876 A1 | 6/2012 | Von Kreudenstein |
| 2012/0189639 A1 | 7/2012 | Schebye et al. |
| 2012/0237517 A1 | 9/2012 | Hattori et al. |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2012/0301488 A1 | 11/2012 | Zhang et al. |
| 2013/0011866 A1 | 1/2013 | Igawa et al. |
| 2013/0018174 A1 | 1/2013 | Igawa et al. |
| 2013/0022624 A1 | 1/2013 | Weaver et al. |
| 2013/0030156 A1 | 1/2013 | Apostolou et al. |
| 2013/0039913 A1 | 2/2013 | Labrijn et al. |
| 2013/0052196 A1 | 2/2013 | Apostolou et al. |
| 2013/0064836 A1 | 3/2013 | Diefenback-Streiber et al. |
| 2013/0085074 A1 | 4/2013 | Walker et al. |
| 2013/0085199 A1 | 4/2013 | Tamori et al. |
| 2013/0101581 A1 | 4/2013 | Kuramochi et al. |
| 2013/0115208 A1 | 5/2013 | Ho et al. |
| 2013/0131319 A1 | 5/2013 | Igawa et al. |
| 2013/0195849 A1 | 8/2013 | Spreter et al. |
| 2013/0209489 A1 | 8/2013 | Han et al. |
| 2013/0247236 A1 | 9/2013 | McWhirter et al. |
| 2013/0302399 A1 | 11/2013 | Feldhaus et al. |
| 2013/0303396 A1 | 11/2013 | Igawa et al. |
| 2013/0317203 A1 | 11/2013 | Igawa et al. |
| 2013/0330345 A1 | 12/2013 | Igawa et al. |
| 2013/0336963 A1 | 12/2013 | Igawa et al. |
| 2014/0037632 A1 | 2/2014 | Igawa et al. |
| 2014/0039165 A1 | 2/2014 | Kuramochi et al. |
| 2014/0051833 A1 | 2/2014 | Fischer et al. |
| 2014/0056878 A1 | 2/2014 | McConnell et al. |
| 2014/0105889 A1 | 4/2014 | Igawa et al. |
| 2014/0112883 A1 | 4/2014 | Ponath et al. |
| 2014/0112914 A1 | 4/2014 | Nezu et al. |
| 2014/0127209 A1 | 5/2014 | Grabstein et al. |
| 2014/0154270 A1 | 6/2014 | Wang et al. |
| 2014/0227292 A1 | 8/2014 | Flanagan et al. |
| 2014/0234340 A1 | 8/2014 | Igawa et al. |
| 2014/0255398 A1 | 9/2014 | Igawa et al. |
| 2014/0271459 A1 | 9/2014 | Dutzar et al. |
| 2014/0294833 A1 | 10/2014 | Desjarlais et al. |
| 2014/0303356 A1 | 10/2014 | Gramer et al. |
| 2014/0335089 A1 | 11/2014 | Igawa et al. |
| 2014/0363426 A1 | 12/2014 | Moore et al. |
| 2014/0363428 A1 | 12/2014 | Igawa et al. |
| 2014/0370018 A1 | 12/2014 | Igawa et al. |
| 2014/0377253 A1 | 12/2014 | Harding et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0118184 A1 | 4/2015 | Kawai |
| 2015/0166654 A1 | 6/2015 | Igawa et al. |
| 2015/0166666 A1 | 6/2015 | Igawa et al. |
| 2015/0175704 A1 | 6/2015 | Kuramochi et al. |
| 2015/0239966 A1 | 8/2015 | Baciu et al. |
| 2015/0247849 A1 | 9/2015 | Tamburini |
| 2015/0274809 A1 | 10/2015 | Igawa et al. |
| 2015/0284465 A1 | 10/2015 | Igawa et al. |
| 2015/0299305 A1 | 10/2015 | Andrien et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0024147 A1 | 1/2016 | Tustian et al. |
| 2016/0068592 A1 | 3/2016 | Chung et al. |
| 2016/0159915 A1 | 6/2016 | Igawa et al. |
| 2016/0176954 A1 | 6/2016 | Ruike et al. |
| 2016/0200807 A1 | 7/2016 | Ruike et al. |
| 2016/0222129 A1 | 8/2016 | Igawa et al. |
| 2016/0229908 A1 | 8/2016 | Igawa et al. |
| 2016/0229915 A1 | 8/2016 | Igawa et al. |
| 2016/0244526 A1 | 8/2016 | Igawa et al. |
| 2017/0022270 A1 | 1/2017 | Igawa et al. |
| 2017/0022287 A1 | 1/2017 | Igawa et al. |
| 2017/0022293 A1 | 1/2017 | Igawa et al. |
| 2017/0145111 A1 | 5/2017 | Hattori et al. |
| 2017/0181987 A1 | 6/2017 | Svensson et al. |
| 2017/0267783 A1 | 9/2017 | Nezu et al. |
| 2017/0275332 A1 | 9/2017 | Igawa et al. |
| 2018/0016327 A1 | 1/2018 | Murata et al. |
| 2018/0148509 A1 | 5/2018 | Kakehi et al. |
| 2018/0162902 A1 | 6/2018 | Igawa et al. |
| 2018/0244800 A1 | 8/2018 | Hattori et al. |
| 2018/0258163 A1 | 9/2018 | Igawa et al. |

(56) References Cited

U.S. PATENT DOCUMENTS

| | | |
|---|---|---|
| 2018/0282718 A1 | 10/2018 | Igawa et al. |
| 2019/0062368 A1 | 2/2019 | Igawa et al. |
| 2019/0085085 A1 | 3/2019 | Igawa et al. |
| 2019/0085095 A1 | 3/2019 | Natarajan et al. |
| 2019/0112390 A1 | 4/2019 | Hattori et al. |
| 2019/0185557 A1 | 6/2019 | Igawa et al. |
| 2019/0211081 A1 | 7/2019 | Igawa et al. |
| 2019/0233525 A1 | 8/2019 | Igawa et al. |
| 2019/0315884 A1 | 10/2019 | Igawa et al. |
| 2019/0330268 A1 | 10/2019 | Tanaka et al. |
| 2019/0352334 A1 | 11/2019 | Igawa et al. |
| 2019/0359728 A1 | 11/2019 | Hattori et al. |
| 2020/0002429 A1 | 1/2020 | Kuramochi et al. |
| 2020/0199241 A1 | 6/2020 | Igawa et al. |
| 2020/0207805 A1 | 7/2020 | Igawa et al. |
| 2020/0231688 A1 | 7/2020 | Igawa et al. |
| 2020/0277402 A1 | 9/2020 | Hattori et al. |
| 2021/0017286 A1 | 1/2021 | Kakehi et al. |
| 2021/0040147 A1 | 2/2021 | Igawa et al. |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0206862 A1 | 7/2021 | Igawa et al. |

FOREIGN PATENT DOCUMENTS

| | | |
|---|---|---|
| AU | 2008332271 | 6/2009 |
| AU | 2009290162 | 4/2010 |
| AU | 2010/206050 | 8/2010 |
| AU | 2011/244851 | 11/2011 |
| AU | 2014/250434 | 10/2015 |
| AU | 2015/227424 | 10/2015 |
| BR | PI0821145-0 | 6/2015 |
| BR | PI0821110-8 | 7/2015 |
| CA | 1 332 367 | 10/1994 |
| CA | 2 203 182 | 5/1996 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 700 394 | 4/2009 |
| CA | 2 700 498 | 4/2009 |
| CA | 2 700 986 | 4/2009 |
| CA | 2 708 065 | 6/2009 |
| CA | 2 708 532 | 6/2009 |
| CA | 2 721 052 | 10/2009 |
| CA | 2 819 530 | 6/2012 |
| CA | 2 831 770 | 10/2012 |
| CA | 2 899 589 | 8/2014 |
| CN | 1156460 | 8/1997 |
| CN | 1763097 | 4/2006 |
| CN | 101098890 | 1/2008 |
| CN | 101198698 | 6/2008 |
| CN | 101230102 | 7/2008 |
| CN | 101277976 | 10/2008 |
| CN | 101282992 | 10/2008 |
| CN | 100455598 | 1/2009 |
| CN | 101479381 | 7/2009 |
| CN | 101511871 | 8/2009 |
| CN | 101849006 | 9/2010 |
| CN | 102056946 | 5/2011 |
| CN | 1029469096 | 10/2011 |
| CN | 102271703 | 12/2011 |
| CN | 102325793 | 1/2012 |
| CN | 102471378 | 5/2012 |
| CN | 102597005 | 7/2012 |
| CN | 102844332 | 12/2012 |
| CN | 102782131 | 1/2013 |
| CN | 102918057 | 2/2013 |
| CN | 102993304 | 3/2013 |
| CN | 103097415 | 5/2013 |
| CN | 103221426 | 7/2013 |
| CN | 103328632 | 9/2013 |
| CN | 103429737 | 12/2013 |
| CN | 103476793 | 12/2013 |
| CN | 103492565 | 1/2014 |
| CN | 103833852 | 6/2014 |
| CN | 103975060 | 8/2014 |
| CN | 104302169 | 1/2015 |
| CN | 106459189 | 2/2017 |
| CN | 101874042 | 9/2018 |
| CO | 07124506 | 11/2007 |
| CO | 11080753 | 6/2011 |
| CO | 13047993 | 3/2013 |
| CO | 15075851 | 4/2015 |
| EA | 009026 | 10/2007 |
| EA | 2008/01027 | 10/2008 |
| EA | 2011/00300 | 12/2011 |
| EP | 0 361 902 | 4/1990 |
| EP | 0 369 566 | 5/1990 |
| EP | 0 329 185 | 4/1994 |
| EP | 0 628 639 A | 12/1994 |
| EP | 0 637 593 | 2/1995 |
| EP | 0 404 097 | 9/1996 |
| EP | 0 770 628 | 5/1997 |
| EP | 0 783 893 | 7/1997 |
| EP | 0 791 359 | 8/1997 |
| EP | 0 811 691 | 12/1997 |
| EP | 0 983 767 | 3/2000 |
| EP | 1 004 315 | 5/2000 |
| EP | 1 069 185 | 1/2001 |
| EP | 1 074 268 | 2/2001 |
| EP | 1 188 830 | 3/2002 |
| EP | 1 220 923 | 7/2002 |
| EP | 1 327 681 | 7/2003 |
| EP | 1 334 731 | 8/2003 |
| EP | 1 374 900 | 1/2004 |
| EP | 1 382 969 | 1/2004 |
| EP | 1 510 943 | 3/2005 |
| EP | 0 979 281 | 7/2005 |
| EP | 1 605 058 | 12/2005 |
| EP | 1 690 550 | 8/2006 |
| EP | 1 693 448 | 8/2006 |
| EP | 1 701 979 | 9/2006 |
| EP | 1 707 215 | 10/2006 |
| EP | 1 728 801 | 12/2006 |
| EP | 1 733 740 | 12/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 2 006 381 | 12/2008 |
| EP | 2 009 101 | 12/2008 |
| EP | 2 031 064 | 3/2009 |
| EP | 1 505 148 | 4/2009 |
| EP | 2 047 863 | 4/2009 |
| EP | 2 107 115 | 10/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 228 392 | 9/2010 |
| EP | 2 236 604 | 10/2010 |
| EP | 2 241 332 | 10/2010 |
| EP | 2 275 443 | 1/2011 |
| EP | 2 305 306 | 4/2011 |
| EP | 2 314 618 | 4/2011 |

(56) References Cited

FOREIGN PATENT DOCUMENTS

| | | |
|---|---|---|
| EP | 1 688 488 | 8/2011 |
| EP | 2 330 193 | 8/2011 |
| EP | 2 354 161 | 8/2011 |
| EP | 2 366 713 | 9/2011 |
| EP | 2 409 991 | 1/2012 |
| EP | 1 688 488 B9 | 3/2012 |
| EP | 2 431 393 | 3/2012 |
| EP | 2 471 813 A | 7/2012 |
| EP | 2 238 985 | 8/2012 |
| EP | 2 522 724 | 11/2012 |
| EP | 2 526 963 A | 11/2012 |
| EP | 2 543 727 | 1/2013 |
| EP | 2 578 233 | 4/2013 |
| EP | 2 644 698 | 10/2013 |
| EP | 2 647 706 | 10/2013 |
| EP | 2 647 707 | 10/2013 |
| EP | 2 679 681 | 1/2014 |
| EP | 2 698 431 | 2/2014 |
| EP | 1 509 770 B | 7/2014 |
| EP | 2 762 166 A | 8/2014 |
| EP | 2 762 493 A | 8/2014 |
| EP | 2 762 564 | 8/2014 |
| EP | 2 818 183 A | 12/2014 |
| EP | 2 853 898 | 4/2015 |
| EP | 2 889 377 | 7/2015 |
| EP | 2 905 290 | 8/2015 |
| EP | 2 914 634 | 9/2015 |
| EP | 2 940 043 | 11/2015 |
| EP | 2 975 055 | 1/2016 |
| EP | 3 059 246 A | 8/2016 |
| EP | 3 199 628 A | 8/2017 |
| EP | 3 240 804 | 11/2017 |
| EP | 3 263 132 A | 1/2018 |
| JP | 63-052890 | 3/1988 |
| JP | H01-144991 | 6/1989 |
| JP | 02-028200 | 1/1990 |
| JP | H02-501112 | 4/1990 |
| JP | 02-145187 | 6/1990 |
| JP | 2-163096 | 6/1990 |
| JP | H02-163085 | 6/1990 |
| JP | H03-500644 | 2/1991 |
| JP | 05-184383 | 7/1993 |
| JP | 05-199894 | 8/1993 |
| JP | 05-203652 | 8/1993 |
| JP | 05-213775 | 8/1993 |
| JP | 05-304992 | 11/1993 |
| JP | 07-67688 | 3/1995 |
| JP | 08-500979 | 2/1996 |
| JP | H08-217799 | 8/1996 |
| JP | 8-510555 | 11/1996 |
| JP | 09-506001 | 6/1997 |
| JP | 10-165184 | 6/1998 |
| JP | 10-511085 | 10/1998 |
| JP | 11-500915 | 1/1999 |
| JP | 11-500916 | 1/1999 |
| JP | 11-071288 | 3/1999 |
| JP | H11-504007 | 4/1999 |
| JP | 11-506310 | 6/1999 |
| JP | 3032287 | 4/2000 |
| JP | 2001-523971 | 11/2001 |
| JP | 2002-514406 | 5/2002 |
| JP | 2002-518041 | 6/2002 |
| JP | 2003-055398 | 2/2003 |
| JP | 2003-509049 | 3/2003 |
| JP | 2003-512019 | 4/2003 |
| JP | 2004-086862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-510212 | 4/2005 |
| JP | 2005-532805 | 11/2005 |
| JP | 2005-535341 | 11/2005 |
| JP | 2005-378266 | 12/2005 |
| JP | 2005-537009 | 12/2005 |
| JP | 2006-517525 | 7/2006 |
| JP | 2006-519583 | 8/2006 |
| JP | 3865418 | 1/2007 |
| JP | 2007-532139 | 11/2007 |
| JP | 2008-510466 | 4/2008 |
| JP | 2008-512995 | 5/2008 |
| JP | 2008-519860 | 6/2008 |
| JP | 2008-523140 | 7/2008 |
| JP | 2008-538920 | 11/2008 |
| JP | 2009-500458 | 1/2009 |
| JP | 2009-541352 | 11/2009 |
| JP | 2010-500020 | 1/2010 |
| JP | 2010-505436 | 2/2010 |
| JP | 2010-079667 | 3/2010 |
| JP | 2010-521194 | 6/2010 |
| JP | 2010-522701 | 7/2010 |
| JP | 2010-250830 | 11/2010 |
| JP | 2011-504096 | 2/2011 |
| JP | 2011-507963 | 3/2011 |
| JP | 2011-508604 | 3/2011 |
| JP | 2011-184418 | 9/2011 |
| JP | 2011-529700 | 12/2011 |
| JP | 2012-021004 | 2/2012 |
| JP | 2012-504970 | 3/2012 |
| JP | 2012-505833 | 3/2012 |
| JP | 2012-082201 | 4/2012 |
| JP | 2012-510281 | 5/2012 |
| JP | 2012-116837 | 6/2012 |
| JP | 2012-512641 | 6/2012 |
| JP | 4961501 | 6/2012 |
| JP | 2012-515160 | 7/2012 |
| JP | 2012-522527 | 9/2012 |
| JP | 2012-531418 | 12/2012 |
| JP | 2012-531439 | 12/2012 |
| JP | 5144499 | 2/2013 |
| JP | 2013-515509 | 5/2013 |
| JP | 2013-518131 | 5/2013 |
| JP | 2013-518606 | 5/2013 |
| JP | 2013-521772 | 6/2013 |
| JP | 2013-529084 | 7/2013 |
| JP | 2013-529190 | 7/2013 |
| JP | 2013-165716 | 8/2013 |
| JP | 2013-531486 | 8/2013 |
| JP | 2015-510764 | 9/2013 |
| JP | 2013-537425 | 10/2013 |
| JP | 2013-541594 | 11/2013 |
| JP | 5334319 | 11/2013 |
| JP | 2014-055145 | 3/2014 |
| JP | 5484060 | 5/2014 |
| JP | 2014-528906 | 10/2014 |
| JP | 2014-257647 | 12/2014 |
| JP | 2015-510769 | 4/2015 |
| JP | 5717624 | 5/2015 |
| JP | 5787446 | 5/2015 |
| JP | 2015-130883 | 7/2015 |
| JP | 2016-026190 | 2/2016 |
| JP | 2016-69329 | 5/2016 |
| JP | 6088703 | 3/2017 |
| JP | 2017-509312 | 4/2017 |
| JP | 2017-113013 | 6/2017 |
| JP | 6175590 | 8/2017 |
| JP | 2018-123125 | 8/2018 |
| JP | 2018-141025 | 9/2018 |
| JP | 6534615 | 6/2019 |
| JP | 2019-523295 | 8/2019 |
| JP | 5048866 | 10/2020 |
| KR | 2006/0010765 | 2/2006 |
| KR | 2007/0035482 | 3/2007 |
| KR | 2009/0107091 | 10/2009 |
| KR | 2010/0056467 | 5/2010 |
| KR | 2010/0074221 | 7/2010 |
| KR | 2010/0097721 | 9/2010 |
| KR | 2011/0103431 | 9/2011 |
| KR | 2012-0035192 | 4/2012 |
| KR | 2012/0123055 | 11/2012 |
| KR | 2013/0102113 | 9/2013 |
| KR | 2013/0102640 | 9/2013 |
| KR | 2013/0130765 | 12/2013 |
| KR | 2014/0005864 | 1/2014 |

(56) References Cited

FOREIGN PATENT DOCUMENTS

| | | |
|---|---|---|
| KR | 2017/0092449 | 8/2017 |
| NO | 20062087 | 7/2006 |
| RU | 94028282 | 7/1996 |
| RU | 2179862 | 2/2002 |
| RU | 2195960 | 1/2003 |
| RU | 2232773 | 7/2004 |
| RU | 2266298 | 12/2005 |
| RU | 2006/104842 | 8/2007 |
| RU | 2339696 | 11/2008 |
| RU | 2007/121679 | 12/2008 |
| RU | 2360925 | 7/2009 |
| RU | 2367667 | 9/2009 |
| RU | 2008/128133 | 1/2010 |
| RU | 2422460 | 6/2010 |
| RU | 2399381 | 9/2010 |
| RU | 2009/112723 | 10/2010 |
| RU | 2009/149451 | 7/2011 |
| RU | 2445975 | 3/2012 |
| RU | 2010/150931 | 6/2012 |
| RU | 2477137 | 3/2013 |
| RU | 2012/112067 | 10/2013 |
| SG | 183867 | 10/2012 |
| SG | 11201701119 R | 3/2017 |
| TW | 416960 | 1/2001 |
| TW | 200714313 | 4/2007 |
| TW | 2007/22517 | 6/2007 |
| TW | 200810778 | 3/2008 |
| TW | 200932266 | 8/2009 |
| TW | 2010/00127 | 1/2010 |
| TW | 2012/06466 | 2/2012 |
| TW | 2012/49872 | 12/2012 |
| TW | 2013/02219 | 1/2013 |
| TW | I452135 | 9/2014 |
| TW | I452136 | 9/2014 |
| TW | 2016/00112 | 1/2016 |
| TW | 2016/02132 | 1/2016 |
| TW | 2016/19193 | 6/2016 |
| TW | 2016/42902 | 12/2016 |
| TW | 2016/43190 | 12/2016 |
| TW | 2017/12032 | 4/2017 |
| TW | 1605057 | 11/2017 |
| TW | 2018/08331 | 3/2018 |
| TW | 2018/08992 | 3/2018 |
| TW | 2018/19409 | 6/2018 |
| TW | 1656133 | 4/2019 |
| TW | 2020/39553 | 11/2020 |
| WO | WO 88/04692 | 6/1988 |
| WO | WO 89/01343 | 2/1989 |
| WO | WO 91/01335 | 2/1991 |
| WO | WO 91/008770 | 6/1991 |
| WO | WO 91/13631 | 9/1991 |
| WO | 92/19759 | 11/1992 |
| WO | WO 93/011161 | 6/1993 |
| WO | WO 94/05690 | 3/1994 |
| WO | WO 94/10354 | 5/1994 |
| WO | WO 94/12215 | 6/1994 |
| WO | WO 94/13804 | 6/1994 |
| WO | WO 94/21681 | 9/1994 |
| WO | WO 95/01571 | 1/1995 |
| WO | WO 95/02187 | 1/1995 |
| WO | WO 95/14710 | 6/1995 |
| WO | WO 95/029697 | 11/1995 |
| WO | WO 95/33844 | 12/1995 |
| WO | WO 96/01653 | 1/1996 |
| WO | WO 96/02576 | 2/1996 |
| WO | WO 96/07754 | 3/1996 |
| WO | WO 96/11020 | 4/1996 |
| WO | WO 96/12503 | 5/1996 |
| WO | WO 1996/016673 | 6/1996 |
| WO | WO 96/23071 | 8/1996 |
| WO | WO 96/27011 | 9/1996 |
| WO | WO 1996/026964 | 9/1996 |
| WO | WO 96/33208 | 10/1996 |
| WO | WO 97/09351 | 3/1997 |
| WO | WO 97/10354 | 3/1997 |
| WO | WO 97/34631 | 9/1997 |
| WO | WO 98/03546 | 1/1998 |
| WO | WO 98/05787 | 2/1998 |
| WO | WO 98/42377 | 10/1998 |
| WO | WO 98/50431 | 11/1998 |
| WO | WO 99/03495 | 1/1999 |
| WO | WO 99/08707 | 2/1999 |
| WO | WO 99/010494 | 3/1999 |
| WO | WO 99/18212 | 4/1999 |
| WO | WO 99/47170 | 9/1999 |
| WO | WO 99/51642 | 10/1999 |
| WO | WO 99/51743 | 10/1999 |
| WO | WO 99/58572 | 11/1999 |
| WO | WO 99/067359 | 12/1999 |
| WO | WO 00/34317 | 6/2000 |
| WO | WO 00/42072 | 7/2000 |
| WO | WO 00/75314 | 12/2000 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 02/09641 | 2/2002 |
| WO | WO 02/30463 | 4/2002 |
| WO | WO 02 30985 | 4/2002 |
| WO | WO 02/33073 | 4/2002 |
| WO | WO 2002/030985 | 4/2002 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 03/012069 | 2/2003 |
| WO | WO 03/015819 | 2/2003 |
| WO | WO 03/020949 | 3/2003 |
| WO | WO 03/027248 | 4/2003 |
| WO | WO 03/035835 | 5/2003 |
| WO | WO 03/042231 | 5/2003 |
| WO | WO 03/057881 | 7/2003 |
| WO | WO 03/060090 | 7/2003 |
| WO | WO 03/074679 | 9/2003 |
| WO | WO 2003/087163 | 10/2003 |
| WO | WO 2003/091424 | 11/2003 |
| WO | WO 03/105757 | 12/2003 |
| WO | WO 2004/007553 | 1/2004 |
| WO | WO 2004/008147 | 1/2004 |
| WO | WO 2004/009618 | 1/2004 |
| WO | WO 2004/016740 | 2/2004 |
| WO | WO 2004/020579 | 3/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/058797 | 7/2004 |
| WO | WO 2004/060919 | 7/2004 |
| WO | WO 2004/065611 | 8/2004 |
| WO | WO 2004/068931 | 8/2004 |
| WO | WO 2004/085476 | 10/2004 |
| WO | WO 2004/091543 | 10/2004 |
| WO | WO 2004/092219 | 10/2004 |
| WO | WO 2004/096273 | 11/2004 |
| WO | WO 2004/097041 | 11/2004 |
| WO | WO 2004/099249 | 11/2004 |
| WO | WO 2004/108157 | 12/2004 |
| WO | WO 2004/111233 | 12/2004 |
| WO | WO 2004/113387 | 12/2004 |
| WO | WO 2005/000900 | 1/2005 |
| WO | WO 2005/005604 | 1/2005 |
| WO | WO 2005/020936 | 3/2005 |
| WO | WO 2005/023193 | 3/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/037315 | 4/2005 |
| WO | WO 2005/037867 | 4/2005 |
| WO | WO 2005/047307 | 5/2005 |
| WO | WO 2005/047327 | 5/2005 |
| WO | WO 2005/056606 | 6/2005 |

(56) References Cited

FOREIGN PATENT DOCUMENTS

| | | |
|---|---|---|
| WO | WO 2005/056759 | 6/2005 |
| WO | WO 2005/059106 | 6/2005 |
| WO | WO 2005/061000 | 7/2005 |
| WO | WO 2005/062916 | 7/2005 |
| WO | WO 2005/066204 | 7/2005 |
| WO | WO 2005/067620 | 7/2005 |
| WO | WO 2005/070963 | 8/2005 |
| WO | WO 2005/074607 | 8/2005 |
| WO | WO 2005/077981 | 8/2005 |
| WO | WO 2005/080429 | 9/2005 |
| WO | WO 2005/090405 | 9/2005 |
| WO | WO 2005/092925 | 10/2005 |
| WO | WO 2005/094446 | 10/2005 |
| WO | WO 2005/112564 | 12/2005 |
| WO | WO 2005/115452 | 12/2005 |
| WO | WO 2005/121180 | 12/2005 |
| WO | WO 2005/123126 | 12/2005 |
| WO | WO 2005/123780 | 12/2005 |
| WO | WO 2006/004663 | 1/2006 |
| WO | WO 2006/019447 | 2/2006 |
| WO | WO 2006/020114 | 2/2006 |
| WO | WO 2006/023144 | 3/2006 |
| WO | WO 2006/023403 | 3/2006 |
| WO | WO 2006/029879 | 3/2006 |
| WO | WO 2006/030200 | 3/2006 |
| WO | WO 2006/030220 | 3/2006 |
| WO | WO 2006/031370 | 3/2006 |
| WO | WO 2006/033386 | 3/2006 |
| WO | WO 2006/047340 | 5/2006 |
| WO | WO 2006/047350 | 5/2006 |
| WO | WO 2006/050166 | 5/2006 |
| WO | WO 2006/050491 | 5/2006 |
| WO | WO 2006/053301 | 5/2006 |
| WO | WO 2006/065208 | 6/2006 |
| WO | WO 2006/067913 | 6/2006 |
| WO | WO 2006/070286 | 7/2006 |
| WO | WO 2006/071877 | 7/2006 |
| WO | WO 2006/075668 | 7/2006 |
| WO | WO 2006/083182 | 8/2006 |
| WO | WO 2006/083183 | 8/2006 |
| WO | WO 2006/085967 | 8/2006 |
| WO | WO 2006/088855 | 8/2006 |
| WO | WO 2006/102095 | 9/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2006/113643 | 10/2006 |
| WO | WO 2006/113767 | 10/2006 |
| WO | WO 2006/116260 | 11/2006 |
| WO | WO 2006/116269 | 11/2006 |
| WO | WO 2006/118959 | 11/2006 |
| WO | WO 2006/119062 | 11/2006 |
| WO | WO 2006/119115 | 11/2006 |
| WO | WO 2006/121852 | 11/2006 |
| WO | WO 2006/130834 | 12/2006 |
| WO | WO 2007/001422 | 1/2007 |
| WO | WO 2007/008943 | 1/2007 |
| WO | WO 2007/009065 | 1/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/043641 | 4/2007 |
| WO | WO 2007/044411 | 4/2007 |
| WO | WO 2007/044616 | 4/2007 |
| WO | WO 2007/046489 | 4/2007 |
| WO | WO 2007/047112 | 4/2007 |
| WO | WO 2007/058194 | 5/2007 |
| WO | WO 2007/060411 | 5/2007 |
| WO | WO 2007/061029 | 5/2007 |
| WO | WO 2007/068411 | 6/2007 |
| WO | WO 2007/074880 | 7/2007 |
| WO | WO 2007/084253 | 7/2007 |
| WO | WO 2007/086490 | 8/2007 |
| WO | WO 2007/092772 | 8/2007 |
| WO | WO 2007/103134 | 9/2007 |
| WO | WO 2007/103549 | 9/2007 |
| WO | WO 2007/106585 | 9/2007 |
| WO | WO 2007/108559 | 9/2007 |
| WO | WO 2007/108756 | 9/2007 |
| WO | WO 2007/114319 | 10/2007 |
| WO | WO 2007/114325 | 10/2007 |
| WO | WO 2007/133816 | 11/2007 |
| WO | WO 2007/137984 | 12/2007 |
| WO | WO 2007/142325 | 12/2007 |
| WO | WO 2007/143168 | 12/2007 |
| WO | WO 2007/147901 | 12/2007 |
| WO | WO 2007/150015 | 12/2007 |
| WO | WO 2007/150016 | 12/2007 |
| WO | WO 2008/017963 | 2/2008 |
| WO | WO 2008/022152 | 2/2008 |
| WO | WO 2008/030706 | 3/2008 |
| WO | WO 2008/031056 | 3/2008 |
| WO | WO 2008/036688 | 3/2008 |
| WO | WO 2008/043822 | 4/2008 |
| WO | WO 2008/069889 | 6/2008 |
| WO | WO 2008/090901 | 7/2008 |
| WO | WO 2008/090960 | 7/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/103432 | 8/2008 |
| WO | WO 2008/113834 | 9/2008 |
| WO | WO 2008/118970 | 10/2008 |
| WO | WO 2008/119353 | 10/2008 |
| WO | WO 2008/121160 | 10/2008 |
| WO | WO 2008/130969 | 10/2008 |
| WO | WO 2008/132453 | 11/2008 |
| WO | WO 2008/143954 | 11/2008 |
| WO | WO 2008/145141 | 12/2008 |
| WO | WO 2008/145142 | 12/2008 |
| WO | WO 2008/150494 | 12/2008 |
| WO | WO 2009/000098 | 12/2008 |
| WO | WO 2009/000099 | 12/2008 |
| WO | WO 2009/012394 | 1/2009 |
| WO | WO 2009/014263 | 1/2009 |
| WO | WO 2009/026117 | 2/2009 |
| WO | WO 2009/032145 | 3/2009 |
| WO | WO 2009/032782 | 3/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/052439 | 4/2009 |
| WO | WO 2009/053358 | 4/2009 |
| WO | WO 2009/053368 | 4/2009 |
| WO | WO 2009/058346 | 5/2009 |
| WO | WO 2009/058492 | 5/2009 |
| WO | WO 2009/063965 | 5/2009 |
| WO | WO 2009/072598 | 6/2009 |
| WO | WO 2009/072604 | 6/2009 |
| WO | WO 2009/079649 | 6/2009 |
| WO | WO 2009/084659 | 7/2009 |
| WO | WO 2009/086320 | 7/2009 |
| WO | WO 2009/089004 | 7/2009 |
| WO | WO 2009/089846 | 7/2009 |
| WO | WO 2009/095235 | 8/2009 |
| WO | WO 2009/100309 | 8/2009 |
| WO | WO 2009/125825 | 10/2009 |
| WO | WO 2009/137880 | 11/2009 |
| WO | WO 2009/139822 | 11/2009 |
| WO | WO 2009/148148 | 12/2009 |
| WO | WO 2010/015608 | 2/2010 |
| WO | WO 2010/033736 | 3/2010 |
| WO | WO 2010/035769 | 4/2010 |
| WO | WO 2010/042904 | 4/2010 |
| WO | WO 2010/045193 | 4/2010 |
| WO | WO 2010/054403 | 5/2010 |
| WO | WO 2010/058860 | 5/2010 |

(56) References Cited

FOREIGN PATENT DOCUMENTS

| | | |
|---|---|---|
| WO | WO 2010/063746 | 6/2010 |
| WO | WO 2010/064090 | 6/2010 |
| WO | WO 2010/064456 | 6/2010 |
| WO | WO 2010/064697 | 6/2010 |
| WO | WO 2010/065078 | 6/2010 |
| WO | WO 2010/070094 | 6/2010 |
| WO | WO 2010/080065 | 7/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/131733 | 11/2010 |
| WO | WO 2010/151338 | 12/2010 |
| WO | WO 2010/151526 | 12/2010 |
| WO | WO 2010/151792 | 12/2010 |
| WO | WO 2011/021009 | 2/2011 |
| WO | WO 2011/090088 | 2/2011 |
| WO | WO 2011/025964 | 3/2011 |
| WO | WO 2011/037158 | 3/2011 |
| WO | WO 2011/043643 | 4/2011 |
| WO | WO 2011/063980 | 6/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/094593 | 8/2011 |
| WO | WO 2011/100271 | 8/2011 |
| WO | WO 2011/108502 | 9/2011 |
| WO | WO 2011/108714 | 9/2011 |
| WO | WO 2011/109338 | 9/2011 |
| WO | WO 2011/111007 | 9/2011 |
| WO | WO 2011/122011 | 10/2011 |
| WO | WO 2011/125674 | 10/2011 |
| WO | WO 2011/131746 | 10/2011 |
| WO | WO 2011/133886 | 10/2011 |
| WO | WO 2011/137362 | 11/2011 |
| WO | WO 2011/143545 | 11/2011 |
| WO | WO 2011/149046 | 12/2011 |
| WO | WO 2011/150008 | 12/2011 |
| WO | WO 2011/151432 | 12/2011 |
| WO | WO 2012/016227 | 2/2012 |
| WO | WO 2012/020096 | 2/2012 |
| WO | WO 2012/024242 | 2/2012 |
| WO | WO 2012/033953 | 3/2012 |
| WO | WO 2012/064627 | 5/2012 |
| WO | WO 2012/067176 | 5/2012 |
| WO | WO 2012/073985 | 6/2012 |
| WO | WO 2012/073992 | 6/2012 |
| WO | WO 2012/088247 | 6/2012 |
| WO | WO 2012/093704 | 7/2012 |
| WO | WO 2012/115241 | 8/2012 |
| WO | WO 2012/132067 | 10/2012 |
| WO | WO 2012/133782 | 10/2012 |
| WO | WO 2012/145238 | 10/2012 |
| WO | WO 2012/151481 | 11/2012 |
| WO | WO 2012/162067 | 11/2012 |
| WO | WO 2012/177653 | 12/2012 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047748 | 4/2013 |
| WO | WO 2013/047752 | 4/2013 |
| WO | WO 2013/060867 | 5/2013 |
| WO | WO 2013/065708 | 5/2013 |
| WO | WO 2014/081143 | 6/2013 |
| WO | WO 2013/124450 | 8/2013 |
| WO | WO 2013/125667 | 8/2013 |
| WO | WO 2013/131866 | 9/2013 |
| WO | WO 2013/136186 | 9/2013 |
| WO | WO 2013/138680 | 9/2013 |
| WO | WO 2013/149111 | 10/2013 |
| WO | WO 2013/152001 | 10/2013 |
| WO | WO 2013/157954 | 10/2013 |
| WO | WO 2013/158856 | 10/2013 |
| WO | WO 2013/166099 | 11/2013 |
| WO | WO 2013/181543 | 12/2013 |
| WO | WO 2013/186719 | 12/2013 |
| WO | WO 2014/006217 | 1/2014 |
| WO | WO 2014/028354 | 2/2014 |
| WO | WO 2014/030728 | 2/2014 |
| WO | WO 2014/043344 | 3/2014 |
| WO | WO 2014/047500 | 3/2014 |
| WO | WO 2011/044368 | 4/2014 |
| WO | WO 2014/051433 | 4/2014 |
| WO | WO 2014/054804 | 4/2014 |
| WO | WO 2014/067011 | 5/2014 |
| WO | WO 2014/074532 | 5/2014 |
| WO | WO 2014/100689 | 6/2014 |
| WO | WO 2014/114651 | 7/2014 |
| WO | WO 2014/119969 | 8/2014 |
| WO | WO 2014/144903 | 9/2014 |
| WO | WO 2014/145159 | 9/2014 |
| WO | WO 2014/145806 | 9/2014 |
| WO | WO 2014/160958 | 10/2014 |
| WO | WO 2014/163101 | 10/2014 |
| WO | WO 2014/182676 | 11/2014 |
| WO | WO 2014/184384 | 11/2014 |
| WO | WO 2014/190441 | 12/2014 |
| WO | WO 2015/022658 | 2/2015 |
| WO | WO 2015/023972 | 2/2015 |
| WO | WO 2015/046467 | 4/2015 |
| WO | WO 2015/046554 | 4/2015 |
| WO | WO 2015/063339 | 5/2015 |
| WO | WO 2015/111008 | 7/2015 |
| WO | WO 2015/127134 | 8/2015 |
| WO | WO 2015/134894 | 9/2015 |
| WO | WO 2015/156268 | 10/2015 |
| WO | WO 2015/162590 | 10/2015 |
| WO | WO 2015/174439 | 11/2015 |
| WO | WO 2015/194233 | 12/2015 |
| WO | WO 2016/000813 | 1/2016 |
| WO | WO 2016/136933 | 1/2016 |
| WO | WO 2016/047722 | 3/2016 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098356 | 6/2016 |
| WO | WO 2016/098357 | 6/2016 |
| WO | WO 2016/117346 | 7/2016 |
| WO | WO 2016/125495 | 8/2016 |
| WO | WO 2016/136933 | 9/2016 |
| WO | WO 2016/159213 | 10/2016 |
| WO | WO 2016/160756 | 10/2016 |
| WO | WO 2016/164708 | 10/2016 |
| WO | WO 2016/166014 | 10/2016 |
| WO | WO 2016/168613 | 10/2016 |
| WO | WO 2016/171202 | 10/2016 |
| WO | WO 2016/178980 | 11/2016 |
| WO | WO 2016/209956 | 12/2016 |
| WO | WO 2017/046994 | 3/2017 |
| WO | WO 2017/049011 | 3/2017 |
| WO | WO 2017/064615 | 4/2017 |
| WO | WO 2017/104779 | 6/2017 |
| WO | WO 2017/104783 | 6/2017 |
| WO | WO 2017/110981 | 6/2017 |
| WO | WO 2017/115773 | 7/2017 |
| WO | WO 2017/120523 | 7/2017 |
| WO | WO 2017/123636 | 7/2017 |
| WO | WO 2017/129585 | 8/2017 |
| WO | WO 2017/159287 | 9/2017 |
| WO | WO 2017/188356 | 11/2017 |
| WO | WO 2017/217524 | 12/2017 |
| WO | WO 2017/217525 | 12/2017 |
| WO | WO 2017/218515 | 12/2017 |
| WO | WO 2017/218592 | 12/2017 |
| WO | WO 2018/025982 | 2/2018 |
| WO | WO 2018/143266 | 8/2018 |

(56) References Cited

FOREIGN PATENT DOCUMENTS

| WO | WO 2018/169993 | 9/2018 |
|---|---|---|
| WO | WO 2018/181870 | 10/2018 |
| WO | WO 2018/184739 | 10/2018 |
| WO | WO 2019/084438 | 5/2019 |
| WO | WO 2019/088143 | 5/2019 |
| WO | WO 2019/112984 | 6/2019 |
| WO | WO 2020 027279 | 2/2020 |

OTHER PUBLICATIONS

U.S. Appl. No. 14/007,947, Igawa et al., filed Dec. 20, 2013.
U.S. Appl. No. 14/347,034, Igawa et al., filed Mar. 25, 2014.
U.S. Appl. No. 15/230,904, Igawa et al., filed Aug. 8, 2016.
U.S. Appl. No. 14/347,187, Igawa et al., filed Jul. 25, 2014.
U.S. Appl. No. 15/725,692, Igawa et al., filed Jun. 8, 2017.
U.S. Appl. No. 15/688,004, Ruike et al., filed Sep. 22, 2017.
U.S. Appl. No. 15/544,930, Kanagawa et al., filed Jul. 20, 2017.
U.S. Appl. No. 14/974,488, Ruike et al., filed Dec. 18, 2015.
U.S. Appl. No. 15/015,287, Igawa et al., filed Feb. 4, 2016 (Abandoned).
U.S. Appl. No. 15/467,654, Nezu et al., filed Mar. 23, 2017.
U.S. Appl. No. 15/875,847, Igawa et al., filed Jan. 19, 2018.
U.S. Appl. No. 15/617,008, Igawa et al., filed Jun. 8, 2017.
U.S. Appl. No. 14/019,117, Igawa et al., filed Sep. 5, 2013.
U.S. Appl. No. 14/019,712, Igawa et al., filed Sep. 6, 2013.
U.S. Appl. No. 13/593,139, Igawa et al., filed Aug. 27, 2012.
U.S. Appl. No. 13/889,484, Igawa et al., filed May 8, 2013.
U.S. Appl. No. 13/889,512, Igawa et al., filed May 8, 2013.
U.S. Appl. No. 12/936,587, Igawa et al., filed Jan. 3, 2011 (abandoned).
U.S. Appl. No. 13/434,643, Hattori et al., filed Mar. 29, 2012.
U.S. Appl. No. 14/921,590, Hattori et al., filed Oct. 23, 2015.
U.S. Appl. No. 15/402,580, Hattori et al., filed Jan. 10, 2017.
U.S. Appl. No. 14/741,786, Igawa et al., filed Jun. 17, 2015.
U.S. Appl. No. 13/990,158, Igawa et al., filed Mar. 28, 2014.
U.S. Appl. No. 14/347,187, Igawa et al., filed Mar. 25, 2014.
U.S. Appl. No. 14/897,498, Yamura et al., filed Dec. 10, 2015.
U.S. Appl. No. 15/688,004, Ruike et al.
U.S. Appl. No. 15/544,930, Ruike et al.
U.S. Appl. No. 15/015,287, Igawa et al., filed Feb. 4, 2016.
U.S. Appl. No. 15/701,630, Hattori et al., filed Sep. 12, 2017.
U.S. Appl. No. 15/725,692, Igawa et al., filed Oct. 5, 2017.
U.S. Appl. No. 15/688,004, Ruike et al., filed Aug. 28, 2017.
Akira et al., "Interleukin-6 in Biology & Medicine," Adv. Immunol., Dec. 31, 1993; 54:1-78.
Annual Report 2012 (Integrated Edition Including CSR Report) Mar. 27, 2013, 154 pages.
Araki et al., "Clinical improvement in a patient with neuromyelitis optica following therapy with the anti-IL-6 receptor monoclonal antibody tocilizumab," Mod Rheumatol. Jul. 2013 ;23(4) :827-31. doi: 10. 1007/s10165-012-0715-9. Epub Jul. 11, 2012.
Aricha et al., "Blocking of IL-6 suppresses experimental autoimmune myasthenia gravis," J Autoimmun , Mar. 2011;36(2):135-41. doi:10.1016/j.jaut.2010.12.001. Epub Dec. 30, 2010.
Buque et al., "Trial Watch: Immunomodulatory monoclonal antibodies for oncological indications," Oncoimmunology, Mar. 2, 2015:4(4):e1008814. eCollection 2015.
Cooper et al., "Variable domain-identical antibodies exhibit IgG subclass-related differences in affinity and kinetic constants as determined by surface plasmon resonance," Mol. Immunol., Jun. 1994; 31(8): 577-84.
Ejima et al., "Effective elution of antibodies by arginine and arginine derivatives in affinity column chromatography," Anal Biochem. Oct. 15, 2005;345(2):250-7.
Fukuzawa et al., "Long lasting neutralization of C5 by SKY59, a novel recycling antibody, is a potential therapy for complement-mediated diseases," Sci. Rep. Apr. 24, 2017; 7(1):1080. doi: 10.1038/ s41598-017-01087-7.
Gershoni et al., "Epitope Mapping," BioDrugs, May 2007;21(3):145-56.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/ jbc.M115.672790. Epub Dec. 7, 2015.
Hattori, Introduction of ART-Ig and application to hemophilia A treatment, Chugai Seiyaku ni Okeru Dokuji no Kakushinteki Kotai Gijutsu. Dec. 2012; 18: 42-57.
Hirano et al., "Complementary DNA for a novel human interleukin (BSF-2) that induces B lymphocytes to produce immunoglobulin," Nature, 324: 73-76 (Nov. 1986).
Hirata et al., "Characterization of IL-6 Receptor Expression by Monoclonal and Polyclonal Antibodies," J Immunol. Nov. 1, 1989;143(9) :2900-6.
Huang et al., "A Monoclonal Anti-Human IL-6 Receptor Antibody Inhibits the Proliferation of Human Myeloma Cells," Hybridoma. Oct. 1993:12(5) :621-30.
Iwai et al., "Therapeutic Agents for Gastric Cancer," Igan Chiryoyaku, Yakkyoku, Jan. 5, 2016:67(1)138-41 (with English translation).
Kabat et al., National Institute of Health, Publ'n No. 91-3242, Sequences of Proteins of Immunological Interest, vol. 1 p. 647-60 (5th ed. 1991).
Kitazawa et al., "A bispecific antibody to factors IXa and X restores factor VIII hemostatic activity in a hemophilia A model," Nat Med. Oct. 2012;18(10):1570-4. doi: 10.1038/nm.2942. Epub Sep. 30, 2012.
Klinger et al., "Harnessing T cells to fight cancer with BiTE((R)) antibody constructs—past developments and future directions," Immunol. Rev., Mar. 2016:270(1):193-208. doi:10.1111/imr.12393.
Krieckaert et al., "Immunogenicity of biologic therapies—we need tolerance," Nat Rev Rheumatol. Oct. 2010;6(10) :558-9. doi: 10. 1038/nrrheum. 2010. 153.
Labrijn et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.
Larkin et al., "Combined Nivolumab and Ipilimumab or Monotherapy in Untreated Melanoma,". N. Engl. J. Med., Jul. 2, 2015:373(1):23-34. doi:10.1056/NEJMoa1504030. Epub May 31, 2015.
Lotz et al., "B Cell Stimulating Factor 2/Interleukin 6 is a Costimulant for Human Thymocytes and T Lymphocytes," J. Exp. Med., Mar. 1, 1988; 167(3): 1253-1258.
Montero-Julian et al., "Pharmacokinetic Study of Anti-Interleukin-6 (IL-6) Therapy With Monoclonal Antibodies: Enhancement of IL-6 Clearance by Cocktails of Anti-IL-6 Antibodies," Blood. Feb. 15, 1995;85(4):917-24.
Nishimoto et al., "Humanized anti-interleukin-6 receptor antibody treatment of multicentric Castleman disease," Blood, 106:2627-32 (Oct. 15, 2005).
Novick et al., "Monoclonal Antibodies to the Soluble Human IL-6 Receptor: Affinity Purification, ELISA, and Inhibition of Ligand Binding," Hybridoma. Feb. 1991;10(1) :137-46.
Okabe, Proprietary Innovative Antibody Engineering Technologies in Chugai Pharmaceutical: Dec. 18, 2012, 78 pages.
Peters et al., "Engineering an improved IgG4 molecule with reduced disulfide bond heterogeneity and increased Fab domain thermal stability," J Biol Chem. Jul. 13, 2012;287(29): 24525-33. doi:. 10.1074/jbc.M112.369744. Epub May 18, 2012.
Reichert, "Antibodies to watch in 2014," mAbs, 6(4): 799-802 (Jul./Aug. 2014).
Rojas et al., "Formation, Distribution, and Elimination of Infliximab and AntiInfliximab Immune Complexes in Cynomolgus Monkeys," J Pharmacol Exp Ther. May 2005;313(2):578-85. Epub Jan. 12, 2005.
Ruggeri et al., "von Willebrand Factor and von Willebrand Disease," Blood, Oct. 1987;70(4):895-904.
Taga et al., "Interleukin-6 Triggers the Association of Its Receptor with a Possible Signal Transducer, gp130," Cell. Aug. 11, 1989; 58(3): 873-581.
Taga et al., "Receptors for B Cell Stimulatory Factor 2," J. Exp. Med. Oct. 1, 1987; 166(4): 967-981.
Vidarsson et al., "IgG subclasses and allotypes: from structure to effector functions," Front Immunol. Oct. 20, 2014;5:520. doi: 10.3389/fimmu.2014.00520. eCollection 2014.

(56) References Cited

OTHER PUBLICATIONS

Yamasaki et al., "Cloning and Expression of the Human Interleukin-6 (BSF-2/IFNb 2) Receptor," Science. Aug. 12, 1988:241 (4867):825-8.
U.S. Appl. No. 10/575,905, Hattori et al., filed Apr. 30, 2017 (abandoned).
U.S. Appl. No. 15/963,345, Hattori et al., filed Apr. 26, 2018.
U.S. Appl. No. 13/497,269, Kuramochi et al., Jun. 1, 2012.
U.S. Appl. No. 15/203,904, Igawa et al., filed Aug. 8, 2016.
U.S. Appl. No. 14/974,350, Ruike et al. filed Dec. 18, 2015.
U.S. Appl. No. 61/313,102, Pons, filed Mar. 11, 2010.
Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1(1):1-6. doi: 10. 4103/ 2277-9175. 98122. Epub Jul. 6, 2012.
Alignment of constant region sequences from WO 2009/125825 (document submitted in EP opposition and posted by EPO on Feb. 2, 2018), 1 page.
Alignment of the amino acid sequences of the Fc regions of antibodies exemplified in EP 2275443 (document submitted in EP opposition and posted by EPO on Feb. 2, 2018), 1 page.
Alignment of variable heavy and light chain amino acid sequences from WO 2009/125825 (document submitted in EP opposition and posted by EPO on Feb. 2, 2018), 2 pages.
Atherton et al., "Acid-base balance: maintenance of plasma pH," Anaesthesia & Intensive Care Medicine, Nov. 2009, 10(11):557-61 (Abstract only).
Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.
Besada, "Potential patient benefit of a subcutaneous formulation of a tocilizumab for the treatment of rheumatoid arthritis: a critical review," Patient Prefer and Adherence, Aug. 1, 2014, 8:1051-9. doi: 10.2147/PPA. S34958. eCollection 2014.
Breitbart et al., "Highly Specific Detection of Myostatin Prodomain by an Immunoradiometric Sandwich Assay in Serum of Healthy Individuals and Patients," PloS One, Nov. 15, 2013, 8(11):e80454 doi 10.1371/journal.pone.0080454 eCollection 2013.
Bulun, "Endometriosis," New Eng J Med, Jan. 2009, 360(3):268-279.
Canfield et al., "The Binding Affinity of Human IgG for its High Affinity Fc Receptor Is Determined by Multiple Amino Acids in the CH2 Domain and Is Modulated by the Hinge Region," J Exp Med, Jun. 1, 1991, 173(6):1483-91.
Claims as granted for Publication No. EP 2275443 (document submitted in EP opposition), 6 pages.
Datta-Mannan et al., "Humanized IgG1 Variants with Differential Binding Properties to the Neonatal Fc Receptor: Relationship to Pharmacokinetics in Mice and Primates," Drug Metab Dispos. Jan. 2007, 35(1):86-94. Epub Oct. 18, 2006.
Davydov, "Omalizuman (Xolair) for Treatment of Asthma," Am Fam Physician, Jan. 15, 2005.
Declaration of Nimish Gera, Ph.D., CV and Exhibits, Sep. 1, 2016 (submitted in the matter of EP 2275443, Opposition thereto by Alexion Pharmaceuticals, Inc), 24 pages.
Donnez et al., "Current thinking on the pathogenesis of endometriosis," Gynecol Obstet Invest, Dec. 2002, 54(Suppl 1):52-62.
EMA product information: Annexes to file of the tocilizumab preparation RoActemra (WC500054890), published Jan. 8, 2010, 109 pages.
EPO Register Extract EP 1915397 (document submitted in EP opposition and posted by EPO on Feb. 2, 2018), 4 pages.
Experimental data characterizing the binding of rituximab to its antigen CD20 and to human FcRn (document submitted in EP opposition and posted by EPO on Feb. 5, 2018), 6 pages.
Experimental information regarding off-rate of Xolair Fab for binding to human IgE at pH7.4 and pH5.5 (document submitted in EP opposition and posted by EPO on Feb. 2, 2018), 3 pages.
Expert Declaration by Dr. Madhusudan Natarajan, submitted in EP opposition regarding EP 2552955 and posted by EPO on Feb. 5, 2018, 4 pages.
Geneseq Accession No. AEM45140, Feb. 22, 2007, "Light chain constant region of therapeutic human IgG antibody," 1 page.
Giclas et al., "Preparation and characterization of monoclonal antibodies against the fifth component of rabbit complement (C5)," J. Immunol. Methods, Dec. 24, 1987, 105(2):201-9.
Giudice et al., "Endometriosis," Lancet, Nov. 2004, 364(9447):1789-1799.
Goebl et al., "Neonatal Fe Receptor Mediates Internalization of Fe Transfected Human Endothelial Cells," Molecular Biology of the Cell, Dec. 2008, 19(12):5490-5505.
Golay et al., "Mechanism of action of therapeutic monoclonal antibodies: Promises and pitfalls if in vitro and in vivo assays," Archived of Biochemistry and Biophysics, Oct. 2012, 526:146-153.
Guo, "Recurrence of endometriosis and its control," Hum Reprod Update, Jul.-Aug. 2009 (Epub Mar. 2009), 15(4):441-461.
Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.
Horiuchi et al., "Complement-targeted therapy: development of C5- and C5a-targeted inhibition," Inflammation and Regeneration, Jun. 3, 2016, 36:11.
Hotzel et al., "A strategy for risk mitigation of antibodies with fast clearance," mAbs, Nov.-Dec. 2012, 4(6):753-60. doi: 10.4161/mabs. 22189.
Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis., Sep. 2014, 73(9):1626-34. doi: 10. 1136/annrheumdis-2013-204405. Epub Dec. 2, 2013.
Irani et al., "Molecular properties of human IgG subclasses and their implications for designing therapeutic monoclonal antibodies against infectious diseases," Molecular Immunology, Oct. 2015, 67(2 Pt A):171-82. Doi:10.1016/ j. molimm 2015.03.255. Epub Apr. 18, 2015.
Iwabe et al., "Pathogenetic significance of increased levels of interleukin-8 in the peritoneal fluid of patients with endometriosis," Fertil Steril, May 1998, 69(5):924-930.
Kabat et al., "Identical V Region Amino Acid Sequences and Segments of Sequences in Antibodies of Different Specificities," The Journal of Immunology, Sep. 1, 1991, 147(5):1709-19.
Kim et al., "Antibody light chain variable domains and their biophysically improved versions for human immunotherapy," mAbs, Jan.-Feb. 2014, 6(1):219-35 doi: 10.4161/mabs 26844.
Kim et al., "Production of a Polyclonal Anti-Myostatin Antibody and the Effects of in Ovo Administration of the Antibody on Posthatch Broiler Growth and Muscle Mass," Poult Sci., Jun. 2007, 86(6):1196-205.
King et al., Applications and Engineering of Monoclonal Antibodies, 1998:68-71.
Li et al., "Framework selection can influence pharmacokinetics of a humanized therapeutic antibody through differences in molecule charge," mAbs, Sep.-Oct. 2014, 6(5):1255-64 doi:104161/mabs 29809 Epub Oct. 30, 2014.
Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res., Jun. 15, 2001, 61(12):4744-9.
O'Donovan et al., "EGFR and HER-2 Antagonists in Breast Cancer," Anticancer Res., May-Jun. 2007, 27(3A):1285-94.
Official Action dated Oct. 13, 2016, issued for EP Application No. 11714860.1 and submitted as evidence during EP opposition, 3 pages.
Presta et al., "Humanization of an Anti-Vascular Endothelial Growth Factor Monoclonal Antibody for the Therapy of Solid Tumors and Other Disorders," Cancer Res., Oct. 15, 1997, 57(20):4593-9.
Product labelling information for Rituxan (Rituximab), dated Nov. 1997, 2 pages.

(56) References Cited

OTHER PUBLICATIONS

Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-57.
Rother et al., "Discovery and development of the complement inhibitor eculizumab for the treatment of paroxysmal nocturnal hemoglobinuria," Nature Biotechnol., Nov. 2007, 25(11):1256-64.
Russo et al., "The CXCL8/IL-8 chemokine family and its receptors in inflammatory diseases," Expert Rev Clin Immunol, May 2014, 10(5):593-619.
Ryman et al., "Pharmacokinetics of Monoclonal Antibodies," CPT Pharmacometrics Syst Pharmacol. Sep. 2017, 6(9):576-588. doi: 10.1002/psp4.12224. Epub Jul. 29, 2017.
Stancovski et al., "Mechanistic Aspects of the Opposing Effects of Monoclonal Antibodies to the ERBB2 Receptor on Tumor Growth," Proceedings of the National Academy of Sciences USA, Oct. 1, 1991, 88:8691-8695.
Summary of information about antibodies in Examples of patent (document submitted in EP opposition and posted by EPO on Apr. 13, 2018); 3 pages.
Supplementary information provided by opponent, 3 pages, published Feb. 20, 2018.
Vaccaro et al., "Divergent activities of an engineered antibody in murine and human systems have implications for therapeutic antibodies," Proc Natl Acad Sci USA, Dec. 5, 2006, 103(49):18709-14 Epub Nov. 20, 2006.
Vercellini et al., "Postoperative oral contraceptive exposure and risk of endometrioma recurrence," Am J Obstet Gynecol, May 2008 (Epub Feb. 2008), 198(5):504.
Waelbroeck et al., "The pH Dependence of Insulin Binding," J Biol Chem., Jul. 25, 1982, 257(14):8284-91.
Ward et al., "Evidence to support the cellular mechanism involved in serum IgG homeostasis in humans," Int Immunol., Feb. 2003, 15(2):187-95.
Welch et al., "Adalimumab (Humira) for the Treatment of Rheumatoid Arthritis" Am Fam. Physician, Dec. 15, 2008, 78(12):1406-1408.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.
Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-83. doi: 10. 1016/ J. dib. 2016.07.044. eCollection Sep. 2016.
Yang et al., "Maximizing in vivo target clearance by design of pH-dependent target binding antibodies with altered affinity to FcRn," mAbs, Oct. 2017, 9(7):1105-1117. doi: 10. 1080/19420862. 2017. 1359455. Epub Aug. 8, 2017.
Yarilin et al., Fundamentals of Immunology M: Medicina, 1999, pp. 169-172, 354-8 (with English translation), 21 pages.
Yarilin, Fundamentals of Immunology, M.: Medicina, 1999, pp. 172-174 (with English translation), 8 pages.
Yeung et al., "A Therapeutic Anti-VEGF Antibody with Increased Potency Independent of Pharmacokinetic Half-life," Cancer Res., Apr. 15, 2010, 70(8):3269-77. doi: 10. 1158/ 0008-5472. CAN-09-4580. Epub Mar. 30, 2010.
Ying et al., "Large Yellow Croaker MSTN-1 Prodomain Prokaryotic Expression, Polyclonal Antibody Preparation and Antibody Function Identification," Chinese Journal of Cell Biology, Oct. 2014, 36(10):1344-1349 (with English abstract).
Abe et al., "Novel Protein A Resin: Synthetic Polymer Matrix Design Impact on Antibody Binding Capacity," JSR Technical Review No. 119, 2012, p. 1-5 [online], [retrieved on Feb. 17, 2017], retrieved from the internet: <URL:http://www.jsr.co.jp/pdf/rd/tec119-1.pdf > (with English translation).
Cruse et al., Atlas of Immunology, CRC Press LLC, 2004, Chapter 3 "Antigens and Immunogens", p. 109.
Decision of the EPO Opposition Division for EP 2 006 381 on Jul. 25, 2018, 17 pages.
GE Healthcare Life Sciences, Dynamic binding capacity study on MabSelect SuReTM LX for capturing high-titer monoclonal antibodies, Application note 28-9875-25-AA, 2011, [online], [retrieved on Feb. 17, 2017], retrieved from the internet: ,http://www.processdevelopmentforum.com/images/articles/28/9875-25_AA_AN_DBC_study_on_MabSelect_SuRe_LX_final.pdf>.
Geneseq Accession No. ARZ17615, Aug. 21, 2008, "Human antibody IgG2 heavy chain constant region SEQ ID No. 36".
Sequence alignments and modification scheme (document filed during Oral Proceedings in EPO opposition for EP 2 006 381 mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," J Nucl Med, Jan. 1991, 32(1):116-22.
U.S. Appl. No. 12/680,112, Igawa et al., Jun. 23, 2010 (abandoned).
U.S. Appl. No. 16/041,976, Igawa et al., filed Jul. 23, 2018 (abandoned).
U.S. Appl. No. 14/347,034, filed Igawa et al., filed Mar. 25, 2014 (abandoned).
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Medesan et al., "Comparative studies of rat IgG to further delineate the Fc:FcRn interaction site," Eur J Immunol, Jul. 1998, 28(7):2092-100.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma. 2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
U.S. Appl. No. 16/298,032, Igawa et al., field Mar. 11, 2019.
U.S. Appl. No. 14/019,712, Igawa et al., filed Sep. 6, 2014 (abandoned).
Choi et al., "Crystal structures of Immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Devanaboyina et al., "The effect of pH dependence of antibody-antigen interactions on subcellular tracking dynamics," mAbs, Nov. 1, 2013, 5(6):851-9.
Feige et al., "How antibodies fold," Trends Biochem Sci, Apr. 2010, 35(4):189-98. doi: 10.1016/j.tibs.2009.11.005. Epub Dec. 21, 2009.
Goulet et al., "Kinetic mechanism of controlled Fab-arm exchange for the formation of bispecific immunoglobulin G1 antibodies," J Biol Chem, Jan. 12, 2018, 293(2):651-661. doi: 10.1074/jbc.RA117. 000303. Epub Nov. 17, 2017.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
Schroter et al., "A genetic approach to engineer antibody pH-switches using combinatorial histidine scanning libraries and yeast display," mAbs, Jan./Feb. 2015, 7(1):138-51. doi:10.4161/19420862. 2014.985993.
U.S. Appl. No. 13/582,073, Kuramochi et al., filed Aug. 31, 2012.
U.S. Appl. No. 13/959,489, Igawa et al., filed Aug. 5, 2013.
U.S. Appl. No. 13/885,421, Igawa et al., filed Aug. 30, 2013.
U.S. Appl. No. 14/047,316, Kuramochi et al., filed Oct. 7, 2013.
U.S. Appl. No. 15/467,654, Nezu et al.
U.S. Appl. No. 15/495,026, Igaga et al., filed Apr. 24, 2017.
[NoAuthor Listed] "Hemophilia and von Willebrand's disease: 2. Management. Association of Hemophilia Clinic Directors of Canada," CMAJ., 153(2):147-157, Jul. 15, 1995.

(56) References Cited

OTHER PUBLICATIONS

Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, 27:215-227 (1993).
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] Retrieved from the Internet on Feb. 29, 2012: http://web.archive.org/web20090221052902/ http://www.algonomics.com/proteinengineering/tripole_applications. php, 2 pages (Feb. 21, 2009).
Allard et al., "Antigen binding properties of highly purified bispecific antibodies," Mol Immunol., Oct. 1992;29(10):1219-27.
Allen et al., "Interchain disulfide bonding in human IgG2 antibodies probed by site-directed mutagenesis," Biochemistry, 48(17):3755-66 (2009).
Allen et al., "Novel mechanism for gonadotropin-releasing hormone neuronal migration involving Gas6/Ark signaling to p38 mitogen-activated protein kinase," Mol. Cell. Biol., 22(2):599-613 (2002).
Alley et al., "Antibody-drug conjugates: targeted drug delivery for cancer," Curr Opin Chem Biol., Aug. 2010;14(4):529-37. doi: 10.1016/j.cbpa.2010.06.170. Epub Jul. 17, 2010.
Almagro et al., "Humanization of antibodies," Front Biosci., Jan. 1, 2008;13:1619-33.
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009;58(1):95.109. Epub Jul. 2, 2008.
Amersham Biosciences, "Affinity Chromatography: Principles and Methods," Edition AD, pp. 16-18, 137 (2002).
Amersham Biosciences, "Protein Purification Handbook, " Edition AC, 98 pages (2001).
Amigorena et al., "Cytoplasmic domain heterogeneity and functions of IgG Fc receptors in B lymphocytes," Science, Jun. 26, 1992;256(5065):1808-12.
Amigorena et al., "Fc gamma RII expression in resting and activated B lymphocytes," Eur J. Immunol., Aug. 1989;19(8):1379-85.
Araujo et al., "Increased rheumatoid factor interference observed during immunogenicity assessment of an Fe-engineered therapeutic antibody," J Pharm Biomed Anal., Jul. 15, 2011;55(5):1041-9. doi: 10.1016/j.jpba.2011.03.008. Epub Mar. 11, 2011.
Armour et al., "Differential binding to human FcgammaRIIa and FcgammaRIIb receptors by human IgG wildtype and mutant antibodies," Mol Immunol., 40(9):585-93 (2003).
Armour et al., "Recombinant human IgG molecules lacking Fcgamma receptor I binding and monocyte triggering activities," Eur. J. Immunol., 29(8):2613-24 (1999).
Arndt et al., "Factors influencing the dimer to monomer transition of an antibody single-chain Fv fragment," Biochemistry, 37(37):12918-12926, Sep. 15, 1998.
Aslan et al., "Engineering a novel, stable dimeric streptavidin with lower isoelectric point," J. Biotechnol., 128(2):213-25 (2007).
Asselta et al., "Factor V deficiency," Semin Thromb Hemost., 35(4):382-389, Jun. 2009.
Atwell et al., "Stable heterodimers from remodeling the domain interface of a homodimer using a phage display library," J. Mol. Biol., 270:26-35 (1997).
Baerga-Ortiz et al., "Two different proteins that compete for binding to thrombin have opposite kinetic and thermodynamic profiles," Protein Sci., 13(1):166-76 (2004).
Baeuerle et al., "BiTE: Teaching antibodies to engage T-cells for cancer therapy," Curr Opin Mol Ther., 11(1):22-30 (2009).
Bajaj et al., "A monoclonal antibody to factor IX that inhibits the factor VIII:Ca potentiation of factor X activation," J Biol Chem., 260(21):11574-11580, Sep. 25, 1985.
Baker et al., "Conversion of a T cell antagonist into an agonist by repairing a defect in the TCR/peptide/MHC interface: implications for TCR signaling," Immunity, 13:475-484 (2000).
Bartelds et al., "Clinical response to adalimumab. relationship to anti-adalimumab antibodies and serum adalimumab concentrations in rheumatoid arthritis," Ann Rheum. Dis., 66:921-926.
Batra et al., "Pharmacokinetics and biodistribution of genetically engineered antibodies," Curr Opin Biotechnol., Dec. 2002;13(6):603-8.
Bayry et al., "Immuno affinity purification of foot and mouth disease virus type specific antibodies using recombinant protein adsorbed to polystyrene wells," J. Virol. Methods, 81:21-30 (1999).
Bebbington et al., "High-level expression of a recombinant antibody from myeloma cells using a glutamine synthetase gene as an amplifiable selectable marker," Biotechnology (N Y)., 10(2):169-175, Feb. 1992.
Bellosta et al., "Signaling through the ARK tyrosine kinase receptor protects from apoptosis in the absence of growth stimulation," Oncogene., 15(20):2387-97 (1997).
Bender et al., "Immunogenicity, efficacy and adverse events of adalimumab in RA patients,". Rheumatol. Int., 27:269-274 (2007).
Bendig, "Humanization of rodent monoclonal antibodies by CDR grafting," METHODS: A Comparison to Methods in Enzymology, 8:83-93 (1995).
Berglund et al., "The epitope space of the human proteome," Protein Sci., Apr. 2008;17(4):606-13.
Beringhelli et al., "pH and ionic strength dependence of protein (un)folding and ligand binding to bovine beta-lactoglobulins A and B," Biochemistry, Dec. 24, 2002;41(51):15415-22.
Bessos et al., "The characterization of a panel of monoclonal antibodies to human coagulation factor IX," Thromb Res., 40(6):863-867, Dec. 15, 1985.
Bian et al., "Discovery of promiscuous HLA-II-restricted T cell epitopes with TEPITOPE," Methods, 34(4):468-475, Dec. 2004.
Bilsborough, "IL-31 is associated with cutaneous lymphocyte antigen-positive skin homing T cells in patients with atopic dermatitis," J. Allergy Clin. Immunol., 117(2):418-25 (2006).
Binz et al., "Engineering novel binding proteins from nonimmunoglobulin domains," Nat. Biotechnol., 23:1257-68 (2005).
Blank et al., Decreased transcription of the human FCGR2B gene mediated by the -343 G/C promoter polymorphism and association with systemic lupus erythematosus. Hum Genet., Jul. 2005;117(2-3):220-7.
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Bogdanovich et al., "Functional improvement of dystrophic muscle by myostatin blockade," Nature, Nov. 28, 2002;420(6914):418-21.
Bolton-Maggs et al., "Haemophilias A and B," Lancet, 361(9371):1801-1809, May 24, 2003.
Borrebaeck et al., "Antibody evolution beyond Nature," Nat Biotechnol., Dec. 2002;20(12):1189-90.
Borrok et al., "pH-dependent Binding Engineering Reveals an FcRn Affinity Threshold That Governs lgG Recycling," J Biol Chem. Feb. 13, 2015;290(7) :4282-90. doi: 10. 1074/ jbc. M114. 603712. Epub Dec. 23, 2014.
Boruchov et al., "Activating and inhibitory IgG Fc receptors on human DCs mediate opposing. functions," J Clin Invest., 115(10):2914-23 (2005).
Bos et al., "Enhanced transfection of a bacterial plasmid into hybridoma cells by electroporation: application for the selection of hybrid hybridoma (quadroma) cell lines," Hybridoma, 11(1):41-51, Feb. 1992.
Boumpas et al., "A short course of BG9588 (anti-CD40 ligand antibody) improves serologic activity and decreases hematuria in patients with proliferative lupus glomerulonephritis," Arthritis Rheum., 48(3):719-27 (2003).
Bowen, Haemophilia A and haemophilia B: molecular insights, Mol Pathol., Feb. 2002;55(1):1-18.
Bowie et al., "Deciphering the message in protein sequences: tolerance to amino acid substitutions," Science, 247:1306-1310 (1990).
Branden and Tooze, "Recognition of Foreign Molecules by the Immune System," Introduction to Protein Structure, 2d Ed., Garland Publishing, pp. 299-323 (1999).

(56) References Cited

OTHER PUBLICATIONS

Brandstetter et al., "X-ray structure of clotting factor IXa: active site and module structure related to Xase activity and hemophilia B," Proc Natl Acad Sci U S A, Oct. 10, 1995;92(21):9796800.

Brennan et al., "Preparation of bispecific antibodies by chemical recombination of monoclonal immunoglobulin G1 fragments," Science, 229(4708):81-83, Jul. 5, 1985.

Brenner et al., "Errors in genome annotation," Trends in Genetics, Apr. 1999;15:132-133.

Brinkman et al., "Phospholipid-binding domain of factor VIII is involved in endothelial cell-mediated activation of factor X by factor IXa," Arterioscler Thromb Vasc Biol., 22(3):511-516, Mar. 1, 2002.

Brown et al., "Tolerance of single, but not multiple, amino acid replacements in antibody $V_H$ CDR2: a means of minimizing B cell wastage from somatic hypermutation?," J. Immunol., 156(9):3285-91 (1996).

Bruhns et al., Specificity and affinity of human Fcgamma receptors and their polymorphic variants for human IgG subclasses, Blood, 113(16):3716-25 (2009).

Budagian et al., "A promiscuous liaison between IL-15 receptor and Axl receptor tyrosine kinase in cell death control," EMBO J., 24(24):4260-70.

Burges et al., "Effective relief of malignant ascites in patients with advanced ovarian cancer by a trifunctional anti-EpCAM×anti-CD3 antibody: a phase I/II study," Clin. Cancer Res., 13(13):3899-905 (2007).

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).

Burmeister et al., "Crystal structure of the complex of rat neonatal Fc receptor with Fc," Nature, Nov. 24, 1994;372(6504):379-83.

CALBIOCHEM® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.

Campoli et al., "Immunotherapy of Malignant Disease with Tumor Antigen-Specific Monoclonal Antibodies," Clin Cancer Res. Jan. 1, 2010;16(1):11-20. Epub Dec. 22, 2009.

Carter, "Bispecific human IgG by design," J. Immunol. Methods, 248:7-15 (2001).

Casset et al., "A peptide mimetic of an anti-CD4 monoclonal antibody by rational design," Biochem Biophys Res Commun., Jul. 18, 2003;307:198-205.

Cemerski et al., "Suppression of mast Fc domain biologic engineered to bind cell degranulation through a dual-targeting tandem IgE-IgG with high affinity to FcγRIIb," Immunol Lett., 143(1):34-43.

Chamow et al., "A humanized, bispecific immunoadhesin-antibody that retargets CD3+ effectors to kill HIV-1-infected cells," J. Immunol., 153(9):4268-80 (1994).

Chan et al., "Therapeutic antibodies for autoimmunity and inflammation," Nat Rev Immunol. May 2010;10(5):301-16. doi: 10.1038/nri2761.

Chappel et al., "Identification of a secondary engineered human IgG antibody," J Biol Fc gamma RI binding site within a genetically. Chem., Nov. 25, 1993;268(33):25124-31.

Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.

Chatellier et al., "Functional mapping of conserved residues located at the VL and VH domain interface of a Fab," J Mol Biol., 264(1):1-6, Nov. 22, 1996.

Chau et al., "HuM291(Nuvion), a humanized Fc receptor-nonbinding antibody against CD3, anergizes peripheral blood T cells as partial agonist of the T cell receptor," Transplantation., 71(7):941-50 (2001).

Chen et al., "Enhancement and destruction of antibody function by somatic mutation: unequal occurrence is controlled by V gene combinatorial associations," EMBO J., Jun. 15, 1995;14(12):2784-94.

Chen et al., "Association of a transmembrane polymorphism of Fcgamma receptor IIb (FCGR2B) with systemic lupus erythematosus in Taiwanese patients," Arthritis Rheum., Dec. 2006;54(12):3908-17.

Chen et al., "Defective secretion of an immunoglobulin caused by mutations in the heavy chain complementarity determining region 2," J Exp Med., Aug. 1, 1994;180(2):577-86.

Chen et al., "Generation and analysis of random point mutations in an antibody CDR2 sequence: many mutated antibodies lose their ability to bind antigen," J Exp Med., Sep. 1, 1992;176(3):855-66.

Chen et al., "Selection and analysis of an optimized anti-VEGF antibody: crystal structure of an affinity-matured Fab in complex with antigen," J Mol Biol., Nov. 5, 1999;293(4):865-81.

Chien et al., "Significant structural and functional change of an antigen-binding site by a distant amino acid substitution: proposal of a structural mechanism," Proc. Natl. Acad. Sci. U.S.A., 86(14):5532-6 (1989).

Chirino et al., "Minimizing the immunogenicity of protein therapeutics," Drug Discov. Today., 9:82-90 (2004).

Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.

Chu et al., "Accumulation of succinimide in a recombinant monoclonal antibody in mildly acidic buffers under elevated temperatures," Pharm Res., Jun. 2007;24(6):1145-56. Epub Mar. 24, 2007.

Chu et al., "Inhibition of B cell receptor-mediated activation of primary human B cells by coengagement of CD19 and FcgammaRIIb with Fc-engineered antibodies," Mol Immunol., 45(15):3926-33 (2008).

Chu et al., "Reduction of total IgE by targeted coengagement of IgE B-cell receptor and FcγRIIb with Fc-engineered antibody," J Allergy Clin Immunol., 129(4):1102-15 (2012).

Chugai Seiyaku Kabushiki Kaisha's letter dated Jun. 12, 2013, regarding oral proceedings scheduled on Jun. 26, 2013, in App. Ser. No. EP 06 73 0769.4—1412.

Chung et al., "Expression of the proto-oncogene Axl in renal cell carcinoma," DNA Cell Biol., 22(8):533-40 (2003).

Chuntharapai et al., "Isotype-dependent inhibition of tumor growth in vivo by monoclonal antibodies to death receptor 4," J Immunol., 166(8):4891-8 (2001).

Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.

Clark, "IgG effector mechanisms," Chem Immunol., 1997;65:88-110.

Clynes et al., "Fc receptors are required in passive and active immunity to melanoma," Proc Natl Acad Sci U.S.A., Jan. 20, 1998;95(2):652-6.

Clynes et al., "Inhibitory Fc receptors modulate in vivo cytotoxicity against tumor targets," Nat Med., Apr. 2000;6(4):443-6.

Cole et al., "Human IgG2 variants of chimeric anti-CD3 are nonmitogenic to T cells," J. Immunol., 159(7):3613-21 (1997).

Colman et al., "Effects of amino acid sequence changes on antibody-antigen interactions," Res Immunol., Jan. 1994;145(1):33-6.

Coloma et al., "Position effects of variable region carbohydrate on the affinity and in vivo behavior of an anti-(1-->6) dextran antibody," J Immunol., Feb. 15, 1999;162(4):2162-70.

Comper and Glasgow, "Charge selectivity in kidney ultrafiltration," Kidney Int., 47:1242-51 (1995).

Cordoba et al., "Non-enzymatic hinge region fragmentation of antibodies in solution," J. Chromatogr. B. Analyt. Technol. Biomed. Life Sci., 818(2):115-21 (2005).

Couto et al., "Anti-BA46 Monoclonal Antibody Mc3. Humanization Using a Novel Positional Consensus and in Vivo and in Vitro Characterization," Cancer Res., 55:1717-22 (1995).

Craven et al., "Receptor tyrosine kinases expressed in metastatic colon cancer," Int. J. Cancer, 60(6):791-7 (1995).

(56) References Cited

OTHER PUBLICATIONS

Dahlback, "Blood coagulation," Lancet, 355(9215):1627-32 (2000).
Dall'Acqua et al., "Antibody humanization by framework shuffling," Methods, May 2005;36(1):43-60.
Dall'Acqua et al., "Increasing the affinity of a human IgG1 for the neonatal Fc receptor: biological consequences," J. Immunol., Nov. 1, 2002;169(9):5171-80.
Dall'Acqua et al., "Modulation of the effector functions of a human IgG1 through engineering of its hinge region," J. Immunol., 177(2):1129-38 (2006).
Dall'Acqua et al., "Properties of human IgGls engineered for enhanced binding to the neonatal Fc receptor (FcRn)," J Biol Chem., Aug. 18, 2006;281(33):23514-24. Epub Jun. 21, 2006.
Damschroder et al., "Framework shuffling of antibodies to reduce immunogenicity and manipulate functional and biophysical properties," Mol. Immunol., Apr. 2007;44(11):3049-60. Epub Jan. 22, 2007.
Datta-Mannan et al., "Monoclonal antibody clearance. Impact of modulating the interaction of IgG with the neonatal Fc receptor," J Biol Chem., Jan. 19, 2007;282(3):1709-17. Epub Nov. 29, 2006.
Davda et al., "Properties of a general PK/PD model of antibody-ligand interactions for therapeutic antibodies that bind to soluble endogenous targets," MAbs, Sep.-Oct. 2010;2(5):576-88. doi: 10.4161/mabs.2.5.12833. Epub Sep. 1, 2010.
Davie et al., "The coagulation cascade: initiation, maintenance, and regulation," Biochemistry, 30(43):10363-10370, Oct. 29, 1991.
Davies et al., "Antibody VH domains as small recognition units," Biotechnology (N Y)., 13(5):475-479, May 1995.
Davies et al., "Affinity improvement of single antibody VH domains: residues in all three hypervariable regions affect antigen binding," Immunotechnology, 2(3):169-79 (1996).
De Bono et al., "ING-1, a monoclonal antibody targeting Ep-CAM in patients with advanced adenocarcinomas," Clin Cancer Res., 10(22):7555-65 (2004).
De Groot et al., "Reducing risk, improving outcomes: bioengineering less immunogenic protein therapeutics," Clin Immunol., May 2009;131(2):189-201. doi: 10.1016/j.clim.2009.01.009. Epub Mar. 6, 2009.
De Groot et al., "De-immunization of therapeutic proteins by T-cell epitope modification," Dev Biol. (Basel), 2005;122:171-94.
De Pascalis et al., "Grafting of "abbreviated" complementarity-determining regions containing specificity-determining residues essential for ligand contact to engineer a less immunogenic humanized monoclonal antibody," J. Immunol., 169(6):3076-84 (2002).
Deen et al., "Structural determinants of glomerular permeability," Am. J. Physiol. Renal. Physiol., 281:F579-F596 (2001).
Del Rio et al., "An Engineered Penicillin Acylase with Altered Surface Charge Is More Stable in Alkaline pH," Ann. NY Acad. Sci., 799:61-64 (1996).
Deng et al., "An Agonist Murine Monoclonal Antibody to the Human c-Mpl Receptor Stimulates Megakaryocytopoiesis," Blood, 92:1981-88 (1998).
Deng et al., "Pharmacokinetics of humanized monoclonal anti-tumor necrosis factor-{alpha} antibody and its neonatal Fc receptor variants in mice and cynomolgus monkeys," Drug Metab. Dispos., Apr. 2010;38(4):600-5. doi: 10.1124/dmd.109.031310. Epub Jan. 13, 2010.
Desai et al., "Fc gamma receptor IIB on dendritic cells enforces peripheral tolerance by inhibiting effector T cell responses," J Immunol., May 15, 2007;178(10):6217-26.
Desjarlais et al., "Optimizing engagement of the immune system by anti-tumor antibodies: an engineer's perspective," Drug Discov Today, Nov. 2007;12(21-22):898-910. Epub Oct. 22, 2007.
Dhiman et al., "Gene expression microarrays: a 21st century tool for directed vaccine design," Vaccine, 20(1-2):22-30, Oct. 12, 2001.
Dhodapkar et al., "Selective blockade of inhibitory Fcgamma receptor enables human dendritic cell maturation with IL-12p70 production and immunity to antibody-coated tumor cells," Proc Natl Acad Sci USA, 102(8):2910-5 (2005).

Diaz et al., "Effects of engineering charged amino acids in the CH3 domains on antibody heavy chain dimerization," Philippine Science Letters. 2011;4(1):48-55.
Dillon et al., "Interleukin 31, a cytokine produced by activated T cells, induces dermatitis in mice," Nat. Immunol., 5(7):752-760 (2004).
Dillon et al., "Structural and functional characterization of disulfide isoforms of the human IgG2 subclass," J. Biol. Chem., 283:16206-15 (2008).
Diveu et al., "GPL, a novel cytokine receptor related to GP130 and leukemia inhibitory factor receptor," J. Biol. Chem., 278(50):49850-49859 (2003).
Dmytrijuk et al., "FDA report: eculizumab (Soliris) for the treatment of patients with paroxysmal nocturnal hemoglobinuria," Oncologist, 13(9):993-1000, Sep. 10, 2008.
Duffau et al., "Platelet CD154 potentiates interferon-alpha secretion by plasmacytoid dendritic cells in systemic lupus erythematosus," Sci Transl Med., 2(47):47ra63 (2010).
Dufner et al., "Harnessing phage and ribosome display for antibody optimization," Trends Biotechnol., Nov. 2006;24(11):523-9. Epub Sep. 26, 2006.
Dumont et al., "Monomeric Fc fusions: impact on pharmacokinetic and biological activity of protein therapeutics," BioDrugs., 20(3):151-60 (2006).
Ejima et al, "Effects of Acid Exposure on the Conformation, Stability, and Aggregation of Monoclonal Antibodies," Proteins. Mar. 1, 2007;66(4):954-62.
Elliott et al., "Activation of the erythropoietin (EPO) receptor by bivalent anti-EPO receptor antibodies," J. Biol. Chem., 271(40):24691-7 (1996).
Epstein, "Non-randomness of amino-acid changes in the evolution of homologous proteins," Nature, Jul. 22, 1967;215(5099):355-9.
Ewert et al., "Stability improvement of antibodies for extracellular and intracellular applications: CDR grafting to stable frameworks and structure-based framework engineering," Methods, 34:184-199 (2004).
Fay et al., "Chapter 2B Nonenzymatic cofactors: factor VIII," Comprehensive Biochemistry, 13:35-37 (1986).
Fay et al., "The size of human factor VIII heterodimers and the effects produced by thrombin," Biochim Biophys Acta., 871(3):268-78 (1986).
Fay, "Activation of factor VIII and mechanisms of cofactor action," Blood Rev., Mar. 2004;18(1):1-15.
Figini et al., "In vitro assembly of repertoires of antibody chains on the surface of phage by renaturation," J Mol Biol., May 27, 1994;239(1):68-78.
Fillipovich, Biochemical basis of human life, VLADOS, 2005:49-50 (with English translation).
Floto et al., "Loss of function of a lupus-associated FcgammaRIIb polymorphism through exclusion from lipid rafts," Nat Med., Oct. 2005;11(10):1056-8.
Fournier et al., "Activation of human peripheral IgM+ B cells is transiently inhibited by BCR-independent aggregation of Fc gammaRIIB," J Immunol., Oct. 15, 2008;181(8):5350-9.
Francois et al., "Construction of a bispecific antibody reacting with the alpha- and beta-chains of the human IL-2 receptor. High affinity cross-linking and high anti-proliferative efficiency," J. Immunol., 150(10):4610-4619, May 15, 1993.
Fridell et al., "GAS6 induces Axl-mediated chemotaxis of vascular smooth muscle cells," J. Biol. Chem., 273(12):7123-6 (1998).
Fujii, "Antibody affinity maturation by random mutagenesis," Methods Mo. Biol., 2004;248:345-59.
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Gen Bank Accession No. AAG00910.2, "recombinant IgG2 heavy chain, partial [*Homo sapiens*]," May 14, 2001, 1 page.
Genbank Accession No. AAC26541, "anti BoNT/A Hc scFv antibody, partial [synthetic construct]," Aug. 1, 2001, 3 pages.
Gerstner et al., "Sequence plasticity in the antigen-binding site of a therapeutic anti-HER2 antibody," J Mol Biol., Aug. 30, 2002;321(5):851-62.

(56) References Cited

OTHER PUBLICATIONS

Gessner et al., "The IgG Fc receptor family," Ann. Hematol., 76:231-248 (1998).
Ghetie et al., "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15(7):637-40 (1997).
Ghetie et al., "Multiple roles for the major histocompatibility complex class I-related receptor FcRn," Annu Rev Immunol., 2000;18:739-66.
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Gonzales et al., "Minimizing the immunogenicity of antibodies for clinical application," Tumour. Biol., Jan.-Feb. 2005;26(1):31-43.
Goode et al., "The glomerular basement membrane charge-selectivity barrier: an oversimplified concept?" Nephrol Dial Transplant., Sep. 1996;11(9):1714-6.
Goruppi et al., "Requirement of phosphatidylinositol 3-kinase-dependent pathway and Src for Gas6-Axl mitogenic and survival activities in NIH 3T3 fibroblasts," Mol. Cell Biol., 17(8):4442-53 (1997).
Gramer et al., "Production of stable bispecific IgG1 by controlled Fab-arm exchange: scalability from bench to large-scale manufacturing by application of standard approaches," MAbs., Nov-.Dec. 2013;5(6):962-73. doi: 10.4161/mabs.26233. Epub Aug. 22, 2013.
Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J. Immunol., May 1993;23(5):1098-104.
Griffin et al., "Analysis of heavy and light chain sequences of conventional camelid antibodies from *Camelus dromedarius* and *Camelus bactrianus species*," J Immunol Methods, Mar. 2014;405:35-46. doi: 10.1016/j.jim.2014.01.003. Epub Jan. 18, 2014.
Grosse-Hovest et al., "A recombinant bispecific single-chain antibody induces targeted, supra-agonistic CD28-stimulation and tumor cell killing," Eur J Immunol., 33(5):1334-1340, May 2003.
Gunasekaran et al., "Enhancing antibody Fc heterodimer formation through electrostatic steering effects: applications to bispecific molecules and monovalent IgG," J. Biol. Chem., 285(25):19637-46(2010).
Gupta et al., "Affinity chromatography and co-chromatography of bispecific monoclonal antibody immunoconjugates," J. Biochem. Biophys. Methods, 51:203-216 (2002).
Gussow et al., "Humanization of monoclonal antibodies," Methods Enzymol., 203:99-121 (1991).
Guyre et al., "Increased potency of Fc-receptor-targeted antigens," Cancer Immunol. Immunother., 45(3-4):146-8 (1997).
Haagen et al., "Unprimed CD4+ and CD8+ T cells can be rapidly activated by a CD3xCD19 bispecific antibody to proliferate and become cytotoxic," Cancer Immunol Immunother., Dec. 1994;39(6):391-6.
Hafizi et al., "Interaction of Axl receptor tyrosine kinase with C1-TEN, a novel C1 domain-containing protein with homology to tensin," Biochem. Biophys. Res. Commun., 299(5):793-800 (2002).
Hafizi et al., "Signalling and functional diversity within the Axl subfamily of receptor tyrosine kinases," Cytokine Growth Factor Rev., 17(4):295-304 (2006).
Hamers-Casierman et al., "Naturally occurring antibodies devoid of light chains," Nature, Jun. 3, 1993;363(6428):446-8.
Hamilton, "Molecular engineering: applications to the clinical laboratory," Clin. Chem., 39(9):1988-97 (1993).
Hammerling et al., "Use of hybrid antibody with anti-gamma-G and anti-ferritin specificities in locating cell surface antigens by electron microscopy," J Exp Med., 128(6):1461-1473, Dec. 1, 1968.

Hanes et al., "Picomolar affinity antibodies from a fully synthetic naive library selected and evolved by ribosome display," Nat. Biotechnol., 18(12):1287-1292 (2000).
Hanson et al., "Catalytic antibodies and their applications," Curr. Opin. Biotechnol., 16:631-636 (2005).
Haringman et al., "A randomized controlled trial with an anti-CCL2 (anti-monocyte chemotactic protein 1) monoclonal antibody in patients with rheumatoid arthritis," Arthritis Rheum., 54(8):2387-92 (2006).
Haviland et al., "Complete cDNA sequence of human complement pro-05. Evidence of truncated transcripts derived from a single copy gene," J Immunol., 146(1):362-368, Jan. 1, 1991.
He et al., "Humanization and pharmacokinetics of a monoclonal antibody with specificity for both E- and P-selectin," J. Immunol., 160:1029-35 (1998).
Helfrich et al., "A rapid and versatile method for harnessing scFv antibody fragments with various biological effector functions," J. Immunol. Methods, 237(1-2):131-45 (2000).
Hess et al., "Cancer therapy with trifunctional antibodies. linking innate and adaptive immunity," Future Oncol. Jan. 2012;8(1):73•85. doi: 10.2217/ fon.11.138.
Heyman, "Feedback regulation by IgG antibodies," Immunol Lett., Aug. 5, 2003;88(2):157-61.
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J Biol. Chem., Feb. 20, 2004;279(8):6213-6. Epub Dec. 29, 2003.
Hird et al., "Tumour localisation with a radioactively labelled reshaped human monoclonal antibody," Br J Cancer, Nov. 1991;64(5):911-4.
Hironiwa et al., "Calcium-dependent antigen binding as a novel modality for antibody recycling by endosomal antigen dissociation," MAbs., 2016;8(1):65-73. doi: 10.1080/19420862.2015. 1110660. Epub Oct. 23, 2015.
Hoar et al., "Characterisation of monoclonal antibodies to human factor X/Xa. Initial observations with a quantitative ELISA procedure," J Immunol Methods., 136(2):269-278, Feb. 15, 1991.
Holash et al., "VEGF-Trap: a VEGF blocker with potent antitumor effects," Proc Natl Acad Sci U.S.A., Aug. 20, 2002;99(17):11393-8.
Holers, "The spectrum of complement alternative pathway-mediated diseases," Immunol Rev., 223:300-316, Jun. 2008.
Holland et al., "Multiple roles for the receptor tyrosine kinase axl in tumor formation," Cancer. Res., Oct. 15, 2005;65(20):9294-303.
Holliger et al., "Diabodies": small bivalent and bispecific antibody fragments, Proc Natl Acad Sci U S A., 90(14):6444-6448, Jul. 15, 1993.
Holm et al., "Functional mapping and single chain construction of the anti-cytokeratin 8 monoclonal antibody TS1," Mol Immunol., Feb. 2007;44(6):1075-84.
Holt et al., "Domain antibodies: proteins for therapy," Trends Biotechnol., 21(11):484-90 (2003).
Hombach et al., "A CD16/CD30 bispecific monoclonal antibody induces lysis of Hodgkin's cells by unstimulated natural killer cells in vitro and in vivo," Int J Cancer, 55:830-6 (1993).
Hong et al., "Enhanced cellular uptake and transport of polyclonal immunoglobulin G and fab after their cationization," J Drug Target., 2000;8(2):67-77.
Hoodless et al., "Mechanism and function of signaling by the TGF beta superfamily," Curr Top. Microbiol Immunol., 1998;228:235-72.
Hoyer, L.W., "The factor VIII complex: structure and function," Blood, 58(1):1-13 (1981).
Hsia et al., "Treatment of acquired factor X inhibitor by plasma exchange with concomitant intravenous immunoglobulin and corticosteroids," Am J Hematol., 83(4):318-320, Apr. 2008.
Hu et al., "Development and characterization of a novel fusion protein composed of a human IgG1 heavy chain constant region and a single-chain fragment variable antibody against Venezuelan equine encephalitis virus," J Biochem., 133(1):59-66 (2003).
Huse et al., "Generation of a large combinatorial library of the immunoglobulin repertoire in phage lambda," Science, 246(4935):1275-1281, Dec. 8, 1989.

(56) References Cited

OTHER PUBLICATIONS

Hwang et al., "Use of human germline genes in a CDR homology-based approach to antibody humanization," Methods, 36:35-42 (2005).
Igawa et al., "pH-dependent antigen-binding antibodies as a novel therapeutic modality," Biochim Biophys Acta., Nov. 30, 2014;1844(11):1943-1950.
Igawa et al., "Antibody optimization technologies for developing next generation antibody therapeutics," Bio Industry, 28(7):15-21 (2011) (with English translation).
Igawa et al., "Antibody recycling by engineered pH-dependent antigen binding improves the duration of antigen neutralization," Nat. Biotechnol., 28(11):1203-7 (2010).
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).
Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.
IMGT Scientific charts depicting the correspondence between Eu and Kabat numberings for the human IgG constant region, created May 17, 2001 and last updated Aug. 13, 2014.
Ishii et al., "FcRn, a critical regulator of antibody pharmacokinetics," Folia Pharmacol. Jpn., 136(5):280-284 (2010) (with English translation).
Ito et al., "Expression of receptor-type tyrosine kinase, Axl, and its ligand, Gas6, in pediatric thyroid carcinomas around Chernobyl," Thyroid., 12(11):971-5 (2002).
Ito et al., "The His-probe method: effects of histidine residues introduced into the complementarity-determining regions of antibodies on antigen-antibody interactions at different pH values," FEBS Lett., Aug. 31, 1992;309:85-8.
Iwabe et al., "Pathogenetic significance of increased levels• of interleukin-a in the peritoneal fluid of patients with endometriosis," Fertil Steril. May 1998:69(5):924-30.
Iwahashi et al., "CDR substitutions of a humanized monoclonal antibody (CC49): contributions of individual CDRs to antigen binding and immunogenicity," Mol Immunol., Oct.-Nov. 1999;36(15-16):1079-91.
Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.
Jain et al., "Engineering antibodies for clinical applications," Trends Biotechnol., 25(7):307-16 (2007).
Janeway et al., "Structure of the Antibody Molecule and Immunoglobulin Genes," Immunobiology, 3rd Edition, Garland Press, 3:1-3:11 (1997).
Janeway et al., Immunobiology, 5th edition. 2001 :Extract from Chapter 3, pp. 93-122.
Janeway et al., Immunobiology, 5th edition. 2001 :Extract from Chapter 4, pp. 123-154.
Jefferis et al., "Interaction sites on human IgG-Fc for FcgammaR: current Models," Immunol. Lett., Jun. 3, 2002;82(1-2):57-65.
Jefferis et al., "Recognition sites on human IgG for Fc gamma receptors: the role of glycosylation," Immunol. Lett., 44(2-3):111-7 (1995).
Jendeberg et al., "Engineering of Fc(1) and Fc(3) from human immunoglobulin G to analyse subclass specificity for staphylococcal protein A," J. Immunol. Methods., 201(1):25-34 (1997).
Jirholt et al., "Exploiting sequence space: shuffling in vivo formed complementarity determining regions into a master framework," Gene., Jul. 30, 1998;215(2):471-6.
Johnson et al., "Kabat database and its applications: 30 years after the first variability plot," Nucleic Acids Res., 28(1):214-218, Jan. 1, 2000.

Johnson et al., "Cation exchange—HPLC and mass spectrometry reveal C-terminal amidation of an IgG1 heavy chain," Anal. Biochem., 360:75-83 (2007).
Jones et al., "Growth factor receptor interplay and resistance in cancer," Endocr Relat Cancer. Dec. 2006;13 Suppl 1:S45.51.
Jones et al., "Identification and removal of a promiscuous CD4+ T cell epitope from the C1 domain of factor VIII," Thromb. Haemost., 3:991-1000 (2005).
Ju et al., "Conversion of the interleukin 1 receptor antagonist into an agonist by site-specific mutagenesis," Proc. Natl. Acad. Sci. U.S.A., 88:2658-2662 (1991).
Jung et al., "The importance of framework residues H6, H7 and H10 in antibody heavy chains experimental evidence for a new structural subclassification of antibody V(H) domains," J Mol. Biol., 309(3):701-716, Jun. 8, 2001.
Juszczak et al., "Ipilimumab: a novel immunomodulating therapy causing autoimmune. hypophysitis: a case report and review," Eur J Endocrinol., Jul. 2012;167(1):1-5. doi: 10.1530/EJE-12-0167. Epub Apr. 10, 2012.
Kabat et al., Sequence of Proteins of Immunological Interest, $5^{th}$ Edition 1991, p. 690 and p. 693.
Kai et al., "Switching constant domains enhances agonist activities of antibodies to a thrombopoietin receptor," Nat. Biotechnol., 26(2):209-11 (2008).
Kamei et al., "Quantitative methods for developing Fc mutants with extended half-lives," Biotechnol Bioeng., 92(6):748-760, Dec. 20, 2005.
Kang et al., "Linkage of recognition and replication functions by assembling combinatorial antibody Fab libraries along phage surfaces," Proc Natl Acad Sci U S A., 88(10):4363-4366, May 15, 1991.
Karpovsky et al., "Production of target-specific effector cells using hetero-cross-linked aggregates containing anti-target cell and anti-Fc gamma receptor antibodies," J Exp Med., 160(6):1686-1701, Dec. 1, 1984.
Kashmiri et al., "Generation, characterization, and in vivo studies of humanized anticarcinoma antibody CC49," Hybridoma, 14:461-473 (1995).
Katayose et al., "MUC1-specific targeting immunotherapy with bispecific antibodies: inhibition of xenografted human bile duct carcinoma growth," Cancer Res., Sep. 15, 1996;56(18):4205-12.
Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Kerschbaumer et al., "An antibody specific for coagulation factor IX enhances the activity of the intrinsic factor X-activating complex," J. Biol. Chem., 279(39):40445-50 (2004).
Khalifa et al., "Effects on interaction kinetics of mutations at the VH-VL interface of Fabs depend on the structural context," J Mol Recognit., 13(3):127-139, May-Jun. 2000.
Khawli et al., "Improved tumor localization and radioimaging with chemically modified monoclonal antibodies," Cancer Biother Radiopharm., Jun. 1996;11(3):203-15.
Kim et al., "Mammalian type I interferon receptors consists of two subunits: IFNaR1 and IFNaR2," Gene, 196(1-2):279-286, Sep. 1, 1997.
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with $99_mTc$," Bioconjug Chem., May-Jun. 1999;10(3):447-53.
Kim et al., "Lowering of pI by acylation improves the renal uptake of 99mTc-labeled anti-Tac dsFv: effect of different acylating reagents," Nucl Med Biol., Nov. 2002;29(8):795-801.
Kim et al., "Mapping the site on human IgG for binding of the MHC class I-related receptor, FcRn,". Eur. J. Immunol., Sep. 1999;29(9):2819-25.
Kingsley et al., "The TGF-beta superfamily: new members, new receptors, and new genetic tests of function in different organisms," Genes Dev., Jan. 1994;8(2):133-46.

(56) References Cited

OTHER PUBLICATIONS

Kipriyanov et al., "Bispecific tandem diabody for tumor therapy with improved antigen binding and pharmacokinetics," J Mol Biol., 293(1):41-56, Oct. 15, 1999.
Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.
Kobayashi et al., "A monoclonal antibody specific for a distinct region of hen egg-white lysozyme," Mol. Immunol., 19:619-30 (1982).
Kobayashi et al., "The pharmacokinetic characteristics of glycolated humanized anti-Tac Fabs are determined by their isoelectric points," Cancer Res., Jan. 15, 1999;59(2):422-30.
Kohrt et al., "Stimulation of natural killer cells with a CD137-specific antibody enhances trastuzumab efficacy in xenotransplant models of breast cancer," J Clin Invest., 122(3):1066-75 (2012).
Komissarov et al., "Site-specific mutagenesis of a recombinant anti-single-stranded DNA Fab. Role of heavy chain complementarity-determining region 3 residues in antigen interaction," J Biol Chem., Oct. 24, 1997;272(43):26864-70.
Kontermann, "Dual targeting strategies with bispecific antibodies," MAbs. Mar.-Apr. 2012,4(2):182-97. doi: 10.4161/mabs.4.2.19000. Epub Mar. 1, 2012.
Kontermann, "Recombinant bispecific antibodies for cancer therapy," Acta Pharmacol Sin., 26(1):1-9, Jan. 2005.
Korn et al., "Recombinant bispecific antibodies for the targeting of adenoviruses to CEA-expressing tumour cells: a comparative analysis of bacterially expressed single-chain diabody and tandem scFv," J Gene Med., 6(6):642-651, Jun. 2004.
Kranenborg et al., "Development and characterization of anti-renal cell carcinoma x antichelate bispecific monoclonal antibodies for two-phase targeting of renal cell carcinoma," Cancer Res., 55:5864s-5867s (1995).
Krauss et al., "Impact of antibody framework residue VH-71 on the stability of a humanised anti-MUC1 scFv and derived immunoenzyme," Br. J. Cancer, 90:1863-70 (2004).
Kreutz et al., "Efficient bispecific monoclonal antibody purification using gradient thiophilic affinity chromatography," J. Chromatogr. B, 714:161-170 (1998).
Kripriyanov et al., "Effect of domain order on the activity of bacterially produced bispecific single-chain Fv antibodies," J Mol Biol., 330(1):99-111, Jun. 27, 2003.
Kroesen et al., "Phase I study of intravenously applied bispecific antibody in renal cell cancer patients receiving subcutaneous interleukin 2," Br J Cancer., 70(4):652-661, Oct. 1994.
Kufer et al., "A revival of bispecific antibodies," Trends Biotechnol., 22(5):238-44 (2004).
Kumar et al., "The second PDZ domain of INAD is a type I domain involved in binding to eye protein kinase C. Mutational analysis and naturally occurring variants," J Biol Chem., 276(27):24971-24977, Epub May 7, 2001.
Kurfis et al., "Role of Arg182 in the second extracellular loop of angiotensin II receptor AT2 in ligand binding," Biochem. Biophys. Res. Commun., 263:816-819 (1999).
Kurokawa et al., "Enhanced fibronolysis by a bispecific monoclonal antibody reactive to fibrin and tissue plasminogen activator," Bio/Technology, 7:1163-1167, Nov. 1989.
Kussie et al., "A single engineered amino acid substitution changes antibody fine specificity," J Immunol., Jan. 1, 1994;152(1):146-52.
Labrijn et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.
Labrijn et al., "Species-specific determinants in the IgG CH3 domain enable Fab-arm exchange. By affecting the noncovalent CH3-CH3 interaction strength," J Immunol., Sep. 15, 2011;187(6):3238-46. doi: 10.4049/jimmunol.1003336. Epub Aug. 12, 2011.
Lacroix-Desmazes et al, "Dynamics of factor VIII interactions determine its immunologic fate in hemophilia A," Blood. Jul. 15, 2008;112(2):240-9. doi: 10.1182/blood-2008-02-124941. Epub May 9, 2008.
Lansdorp et al., "Purification and analysis of bispecific tetrameric antibody complexes," Mol. Immunol., 27:659-666 (1990).
Lapan et al., "Interaction of the A1 subunit of factor VIIIa and the serine protease domain of factor X identified by zero-length cross-linking," Thromb Haemost., 80(3):418-422, Sep. 1998.
Lay et al., "Sulfasalazine suppresses drug resistance and invasiveness of lung adenocarcinoma cells expressing AXL," Cancer Res., 67(8):3878-87 (2007).
Lazar et al., "Engineered antibody Fc variants with enhanced effector function," Proc Natl Acad Sci U S A., 103(11):4005-4010, Epub Mar. 6, 2006.
Lazar et al., "Transforming growth factor alpha: mutation of aspartic acid 47 and leucine 48 results in different biological activities," Mol. Cell. Biol., 8:1247-1252 (1988).
Le Doussal et al., "Bispecific monoclonal antibody-mediated targeting of an indium-111-labeled DTPA dimer to primary colorectal tumors: pharmacokinetics, biodistribution, scintigraphy and immune response," J Nucl Med., 34(10):1662-1671, Oct. 1993.
Le Gall et al., "Effect of linker sequences between the antibody variable domains on the formation, stability and biological activity of a bispecific tandem diabody," Protein Eng Des Sel., 17(4):357-366, Epub May 4, 2004.
Lebegue et al., "Production and characterization of hybrid monoclonal antibodies with IgG1/IgG3 double isotype," C R Acad Sci III., 1990;310(9):377-82.
Lederman et al., "A single amino acid substitution in a common African allele of the CD4 molecule ablates binding of the monoclonal antibody, OKT4," Mol Immunol., Nov. 1991;28(11):1171-81.
Lee et al., "Genetic analysis of the role of proteolysis in the activation of latent myostatin," PLoS One, Feb. 20, 2008;3(2):e1628.
Lee et al., "Regulation of myostatin activity and muscle growth," Proc Natl Acad Sci U S A., Jul. 31, 2001;98(16):9306-11.
Lenting et al., "The life cycle of coagulation factor VIII in view of its structure and function," Blood, 92(11):3983-3996, Dec. 1, 1998.
Leong et al., "Adapting pharmacokinetic properties of a humanized anti-interleukin-8 antibody for therapeutic applications using site-specific pegylation," Cytokine, Nov. 7, 2001;16(3):106-19.
Levin et al., "Optimizing the affinity and specificity of proteins with molecular display," Mol. Biosyst., 2(1):49-57 (2006) (Epub Nov. 8, 2005).
Lewis et al., "Differential responses of human tumor cell lines to anti-p185HER2 monoclonal antibodies," Cancer Immunol Immunother., 37(4):255-63 (1993).
Li et al., "beta-Endorphin omission analogs: dissociation of immunoreactivity from other biological activities," Proc Natl Acad Sci U.S.A. Jun. 1980;77(6):3211-4.
Li et al., "Apoptotic and antitumor activity of death receptor antibodies require inhibitory Fcγ receptor engagement," Proc Natl Acad Sci U S A., Jul. 3, 2012;109(27):10966-71.
Li et al., "CD72 down-modulates BCR-induced signal transduction and diminishes survival in primary mature B lymphocytes," J Immunol., May 1, 2006;176(9):5321-8.
Li et al., "Construction and characterization of a humanized anti-human CD3 monoclonal antibody 12F6 with effective immunoregulation functions," Immunology, Dec. 2005;116(4):487-98.
Li et al., "Inhibitory Fcγ receptor engagement drives adjuvant and anti-tumor activities of agonistic CD40 antibodies," Science, 333(6045):1030-4 (2011).
Liang et al., "Immunity against a therapeutic xenoprotein/Fc construct delivered by gene transfer is reduced through binding to the inhibitory receptor FcγRIIb," J Gene Med., 13(9):470-7 (2011).
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Lindhofer et al., "Preferential Species-Restricted Heavy/Light Chain Pairing in Rat/Mouse Quadromas," J. Immunol., 155:219-225 (1995).

(56) References Cited

OTHER PUBLICATIONS

Lindsay, "Chapter 4: Determination of the Kinetics and Mechanism of tg-FIX Activation by Factor XIa," 49-75 (2004).
Link et al., "Production and characterization of a bispecific IgG capable of inducing T-cell-mediated lysis of malignant B cells," Blood, 81(12):3343-3349, Jun. 15, 1993.
Liu et al., "Functional interactions between arginine-133 and aspartate-88 in the human reduced folate carrier: evidence for a charge-pair association," Biochem J., 358(Pt 2):511-516, Sep. 1, 2001.
Liu et al., "Heterogeneity of monoclonal antibodies," J Pharm Sci., Jul. 2008;97(7):2426-47.
Lloyd et al., "The production of a bispecific anti-CEA, anti-hapten (4-amino-phthalate) hybrid-hybridoma," J Natl Med Assoc., Oct. 1991;83(10):901-4.
Lobo et al., "Antibody pharmacokinetics and pharmacodynamics," J. Pharm. Sci., 93:2645-68 (2004).
Lofqvist et al., "Haemophilia prophylaxis in young patients—a long-term follow-up," J Intern Med., 241(5):395-400, May 1997.
Lu et al., "Di-diabody: a novel tetravalent bispecific antibody molecule by design," J Immunol Methods., 279(1-2):219-232, Aug. 2003.
Lu et al., "Fab-scFv fusion protein: an efficient approach to production of bispecific antibody fragments," J Immunol Methods., 267(2):213-226, Sep. 15, 2002.
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267:7246-57 (2000).
Lutterbuese et al., "T cell-engaging BiTE antibodies specific for EGFR potently eliminate KRAS- and BRAF-mutated colorectal cancer cells," Proc Natl Acad Sci U S A., Jul. 13, 2010;107(28):12605-10. doi: 10.1073/pnas.1000976107. Epub Jun. 28, 2010.
Luttrell et al., "Reaction coupling of chelation and antigen binding in the calcium ion-dependent antibody binding of cyclic AMP," J Biol Chem., Nov. 15, 1991;266(32):21626-30.
MacCallum et al., "Antibody-antigen interactions: contact analysis and binding site topography," J. Mol. Biol., 262:732-45 (1996).
Mackay et al., "Selective dysregulation of the FcgammaIIB receptor on memory B cells in SLE," J Exp Med., Sep. 4, 2006;203(9):2157-64.
Maeda et al., "pH-dependent receptor/ligand sorting of ligands for epidermal growth dissociation as a determining factor for intracellular factor receptors in rat hepatocytes," J. Control Release, 82(1):71-82 (2002).
Maier et al., "Assessment of fully automated antibody homology modeling protocols in molecular operating environment," Proteins., Aug. 2014;82(8):1599-610. doi: 10.1002/prot.24576. Epub Apr. 23, 2014.
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Maity et al., "Equilibrium unfolding of dimeric and engineered monomeric forms of lambda Cro (F58W) repressor and the effect of added salts: evidence for the formation of folded monomer induced by sodium perchlorate," Arch Biochem Biophys, 434(1):93-107, Feb, 1, 2005.
Malbec et al., "Antibodies against growth factor receptors can inhibit the proliferation of transformed cells via a cis-interaction 33 with inhibitory FcR," Immunol Lett., Mar. 30, 2012;143(1):28-33.
Male et al., "Antibodies" Immunology, 7th Edition (2006), published by Elsevier Ltd., pp. 59-86.
Manger et al., "Fcgamma receptor IIa polymorphism in Caucasian patients with systemic lupus erythematosus: association with clinical symptoms," Arthritis Rheum., 41(7):1181-9 (1998).
Manz et al., Bioanalytical Chemistry, World Scientific Publishing Co., p. 7 (2003).
Manzke et al., "Single-step purification of bispecific monoclonal antibodies for immunotherapeutic use by hydrophobic interaction chromatography," J. Immunol. Methods, 1997;208:65-73.
Mariuzza et al., "The structural basis of antigen-antibody recognition," Annu. Rev. Biophys. Chem., 16:139-59 (1987).
Marks et al., "By-passing immunization. building high affinity human antibodies by chain shuffling," Biotechnology (N.Y.), 10(7):779-83 (1992).
Marshall et al., "Rational design and engineering of therapeutic proteins," Drug Discov Today, Mar. 1, 2003;8(5):212-21.
Marti et al., "Inverse electrostatic effect: electrostatic repulsion in the unfolded state stabilizes a leucine zipper," Biochemistry, 43(39):12436-47 (2004).
Martin et al., "Crystal structure at 2.8 A of an FcRn/heterodimeric Fc complex: mechanism of pH-dependent binding," Mol Cell., Apr. 2001;7(4):867-77.
Martin et al., "Preclinical safety and immune-modulatng effects of therapeutic monoclonal antibodies to interleukin-6 and tumor necrosis factor-$\alpha$ in cynomolgus macaques," J Immunotoxicol., Jul. 1, 2004;1(3):131-9. doi:10.1080/15476910490894904.
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta. Pharmacol. Sin., Jun. 2005;26:649-58.
Marvin et al., "Redesigning an antibody fragment for faster association with its antigen," Biochemistry, 42:7077-83 (2003).
Massino et al., "Quantitative analysis of the products of IgG chain recombination in hybrid hybridomas based on affinity chromatography and radioimmunoassay," J Immunol Methods., 201(1):57-66, Feb. 14, 1997.
Maxfield et al., "Endocytic recycling," Nat. Rev. Mol. Cell Biol., 5(2):121-32 (2004).
Maynard et al., "Antibody engineering," Annu. Rev. Biomed. Eng., 2:339-76 (2000).
Mazda et al., "Regulation of Muscle Homeostasis and Metabolism by the TGF-$\beta$ Superfamily Cytokine, Myostatin/growth Differentiation Factor 8 (GDF8)," Journal of Kyoto prefectural university of medicine. 2013;122(3):133-41.
McCafferty et al., "Phage antibodies: filamentous phage displaying antibody variable domains," Nature, 348(6301):552-554, Dec. 6, 1990.
McCloskey et al., "GAS6 mediates adhesion of cells expressing the receptor tyrosine kinase Axl," J. Biol. Chem., 272(37):23285-91 (1997).
McCroskery et al., "Improved muscle healing through enhanced regeneration and reduced fibrosis in myostatin-null mice," J Cell Sci., Aug. 1, 2005;118(Pt 15):3531-41.
McPhee et al., "Engineering human immunodeficiency virus 1 protease heterodimers as macromolecular inhibitors of viral maturation," Proc Natl Acad Sci U S A., Oct. 15, 1996;93(21):11477-81.
McPherron et al., "Double muscling in cattle due to mutations in the myostatin gene," Proc Natl Acad Sci U S A., Nov. 11, 1997;94(23):12457-61.
McPherron et al., "Regulation of skeletal muscle mass in mice by a new TGF-beta superfamily member," Nature, May 1, 1997;387(6628):83-90.
Medesan et al., "Delineation of the amino acid residues involved in transcytosis and catabolism of mouse IgG1," J Immunol., Mar. 1, 1997;158(5):2211-7.
Menegatti et al., "Factor X deficiency," Semin Thromb Hemost., 35(4):407-415, Jun. 2009.
Merchant et al., "An efficient route to human bispecific IgG," Nat. Biotechnol., 16:677-681 (1998).
Meric et al., "Expression profile of tyrosine kinases in breast cancer," Clin. Cancer Res., 8(2):361-7 (2002).
Mertens et al., "Factor VIII-factor IX interactions: molecular sites involved in enzyme-cofactor complex assembly," Thromb Haemost., 82(2):209-217, Aug. 1999.
Meyer et al., "Bevacizumab immune complexes activate platelets and induce thrombosis in FCGR2A transgenic mice," J Thromb Haemost., Jan. 2009;7(1):171-81. Epub Oct. 30, 2008.

(56) References Cited

OTHER PUBLICATIONS

Mezzanzanica et al., "Human Ovarian Carcinoma Lysis by Cytotoxic T Cells Targeted by Bispecific Monoclonal Antibodies: Analysis of the Antibody Components," Intl Cancer. Apr. 15, 1988;41(4):609-15.
Mi et al., "Targeting the neonatal fc receptor for antigen delivery using engineered fc fragments," J Immunol., 181(11):7550-61 (2008).
Michaelsen et al., "A mutant human IgG molecule with only one C1q binding site can activate complement and induce lysis of target cells," Eur J Immunol., Jan. 2006;36(1):129-38.
Mihara et al., "Tocilizumab inhibits signal transduction mediated by both mIL-6R and sIL-6R, but not by the receptors of other members of IL-6 cytokine family," Int. Immunopharmacol., 5(12):1731-40 (2005).
Milstein et al., "Hybrid hybridomas and their use in immunohistochemistry," Nature, 305(5934):537-540, Oct. 6-12, 1983.
Miyazaki et al., "Generation of bispecific IgG, which mimics the cofactor function of blood coagulation factor VIII," Seikagaku, Poster sessions (2P-B-161) (2006).
Mollnes et al., "Identification of a human C5 beta-chain epitope exposed in the native complement component but concealed in the SC5b-9 complex," Scand J Immunol., 28(3):307-312, Sep. 1988.
Morell et al., "Metabolic properties of IgG subclasses in man," J Clin. Invest., 49(4):673-80.
Morgan et al., "The N-terminal end of the CH2 domain of chimeric human IgG1 anti-HLA-DR is necessary for C1q, Fc gamma RI and Fc gamma RIII binding," Immunology., Oct. 1995;86(2):319-24.
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Morrison, "Two heads are better than one," Nat Biotechnol. Nov. 2007;25(11):1233-4.
Murata et al., "Anti-Digoxin Fab Variants Generated by Phage Display," Mol Biotechnol. Jun. 2013:54(2):269-77. doi : 10. 1007/s12033-012-9564-1.
Murtaugh et al., "A combinatorial histidine scanning library approach to engineer highly pH-dependent protein switches," Protein Sci., 20(9):1619-31 doi:10.1002/pro 696 (2011).
Muta et al., "A 13-amino-acid motif in the cytoplasmic domain of Fc gamma RIIb modulates B-cell receptor signaling," Nature, Mar. 3, 1994;368(6466):70-3.
Nakamura et al., "Fcgamma receptor IIB-deficient mice develop Goodpasture's syndrome upon immunization with type IV collagen: a novel murine model for autoimmune glomerular basement membrane disease," J Exp Med., Mar. 6, 2000;191(5):899-906.
Nakano et al., "Prevention of growth arrest-induced cell death of vascular smooth muscle cells by a product of growth arrest-specific gene, gas6," FEBS Lett., 387(1):78-80 (1996).
Nakano et al., "Vascular smooth muscle cell-derived, Gla-containing growth-potentiating factor for Ca(2+)-mobilizing growth factors," J. Biol. Chem., 270(11):5702-5 (1995).
Nakano et al., Anti-glypican 3 antibodies cause ADCC against human hepatocellular carcinoma cells, Biochem Biophys Res Commun. Jan. 9, 2009;378(2):279-84. doi: 10.1016/ j.bbrc.2008.11.033. Epub Nov. 18, 2008.
Nam et al., "Current evidence for the management of rheumatoid arthritis with biological disease-modifying antirheumatic drugs: a systematic literature review informing the EULAR recommendations for the management of RA," Ann Rheum Dis., Jun. 2010;69(6):976-86. doi: 10.1136/ard.2009.126573. Epub May 6, 2010.
Narhi et al., "Asn to Lys mutations at three sites which are N-glycosylated in the mammalian protein decrease the aggregation of *Escherichia coli*-derived erythropoietin," Protein Eng., 14(2):135-140, Feb. 2001.
National Haemophilia Foundation (NHF) Medical and Scientific Advisory Council (MASAC) Recommendations Concerning Prophylaxis, Medical Bulletin. #193, 1994.

Natsume et al., "Improving effector functions of antibodies for cancer treatment: Enhancing ADCC and CDC," Drug Des Devel Ther. Sep. 21, 2009;3:7-16.
Neis et al., "Enhanced expression levels of IL-31 correlate with IL-4 and IL-13 in atopic and allergic contact dermatitis," J. Allergy Clin. Immunol., 118(4):930-937 (2006).
Nemoto et al., "Overexpression of protein tyrosine kinases in human esophageal cancer," Pathobiology., 65(4):195-203, 1997.
Nesterova et al., "Glypican-3 as a novel target for an antibody-drug conjugate," AACR Abstract No. 656, Los Angeles, CA (Apr. 4-18, 2007).
Neubauer et al., "Expression of ax1, a transforming receptor tyrosine kinase, in normal and malignant hematopoiesis," Blood, 84(6):1931-41.
Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.
Nicholas et al., "Regulation of the immune response. I. Reduction in ability of specific antibody to inhibit long-lasting IgG immunological priming after removal of the Fc fragment," J Exp Med., Jun. 1, 1969;129(6):1183-201.
Nieba et al., "Disrupting the hydrophobic patches at the antibody variable/constant domain interface: improved in vivo folding and physical characterization of an engineered scFv fragment," Protein Eng., 10(4):435-444, Apr. 1997.
Niebecker et al., "Safety of therapeutic monoclonal antibodies," Curr Drug Safi, 5(4):275-86 (2010).
Nilsson et al., "Induction of split tolerance and clinical cure in high-responding hemophiliacs with factor IX antibodies," Proc Natl Acad Sci U S A., 83(23):9169-9173, Dec. 1986.
Nilsson et al., "Twenty-five years' experience of prophylactic treatment in severe haemophilia A and B," J Intern Med., 232(1):25-32, Jul. 1992.
Nimmerjahn et al., "Fcgamma receptors as regulators of immune responses," Nat Rev Immunol., Jan. 2008;8(1):34-47.
Nishimoto et al., "Humanized anti-interleukin-6 receptor antibody treatment of multicentric Castleman disease," Blood, 106:2627-32 (2005).
Nishimoto et al., "Interleukin 6: from bench to bedside," Nat. Clin. Pract. Rheumatol., 2:619-626 (2006).
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008;112(10):3959-64. doi: 10.1182/blood-2008-05-155846. Epub Sep. 10, 2008.
Nishimura et al., "Genetic variants in C5 and poor response to eculizumab," N Engl J Med., 370(7):632-639, Feb. 13, 2014.
Nitta et al., "Preliminary trial of specific targeting therapy against malignant glioma," Lancet., 335(8686):368-371, Feb. 17, 1990.
Nohaile et al., "Altering dimerization specificity by changes in surface electrostatics," Proc Natl Acad Sci U S A. Mar. 13, 2001;98(6):3109-3114. Epub Feb. 27, 2001.
O'Bryan et al., "ax1, a transforming gene isolated from primary human myeloid leukemia cells, encodes a novel receptor tyrosine kinase," Mol. Cell Biol., 11(10):5016-31 (1991).
O'Shea et al., "Peptide 'Velcro': design of a heterodimeric coiled coil," Curr Biol., Oct. 1, 1993;3(10):658-67.
Ohno et al., "Antigen-binding specificities of antibodies are primarily determined by seven residues of VH," Proc. Natl. Acad. Sci. U.S.A., 82(9):2945-9 (1985).
Ohsugi et al., Pharm. Stage, 7:13-18 (2007) (English translation included).
Okubo, "The production and characterization of four monoclonal antibodies to human factor X," J Nara Med Ass., 38(1):20-28, Jan. 8, 1987.
Olferiev et al., "The role of activating protein 1 in the transcriptional regulation of the human FCGR2B promoter mediated by the -343 G -> C polymorphism associated with systemic lupus erythematosus," J Biol Chem., Jan. 19, 2007;282(3):1738-46.

(56) References Cited

OTHER PUBLICATIONS

Onda et al., "Lowering the Isoelectric Point of the Fv Portion of Recombinant Immunotoxins Leads to Decreased Nonspecific Animal Toxicity without Affecting Antitumor Activity," Cancer. Res., 61:5070-77 (2001).
Ono et al., "The humanized anti-HM1.24 antibody effectively kills multiple myeloma cells by human effector cell-mediated cytotoxicity," Mol Immunol., Apr. 1999;36(6):387-95.
Ozhegov et al., Tolkovyi Slovar Russkogo iazyka: 2004, p. 292 (with an English translation of the relevant passage defining "control").
Padlan et al., "Identification of specificity-determining residues in antibodies," FASEB J., 9:133-139 (1995).
Padlan et al., "Structure of an antibody-antigen complex: crystal structure of the HyHEL-10 Fab-lysozyme complex," Proc. Natl. Acad. Sci. USA, 86:5938-5942 (1989).
Padlan, "X-ray crystallography of antibodies," Adv Protein Chem., 1996;49:57-133.
Pakula et al., "Genetic Analysis of Protein Stability and Function," Annu. Rev. Genet., 1989;23:289-310.
Pan et al., "Blocking neuropilin-1 function has an additive effect with anti-VEGF to inhibit tumor growth," Cancer Cell, Jan. 2007;11(1):53-67.
Panka et al., "Variable region framework differences result in decreased or increased affinity of variant anti-digoxin antibodies," Proc. Natl. Acad. Sci. U.S.A., 85(9):3080-4 (1988).
Pardridge et al., "Enhanced cellular uptake and in vivo biodistribution of a monoclonal antibody following cationization," J Pharm Sci., Aug. 1995;84(8):943-8.
Pardridge et al., "Enhanced endocytosis in cultured human breast carcinoma cells and in vivo biodistribution in rats of a humanized monoclonal antibody after cationization of the protein," J Pharmacol Exp Ther., Jul. 1998; 286(1):548-54.
Patton et al., "An acid dissociation bridging ELISA for detection of antibodies directed against therapeutic proteins in the presence of antigen," J Immunol Methods, Sep. 2005;304(1-2):189-95.
Paul, "Structure and function of immunoglobulins," Fundamental Immunology, Third Edition, 292-295 (1993).
Paul, William ed., Fundamental Immunology, 3$^{rd}$ edition, p. 242 (1993).
Pavlaki et al., "Matrix metalloproteinase inhibitors (MMPIs): the beginning of phase I or the termination of phase III clinical trials," Cancer Metastasis Rev., 22(2-3):177-203 (2003).
Pavlinkova et al., "Charge-modified single chain antibody constructs of monoclonal antibody CC49: Generation, characterization, pharmacokinetics, and biodistribution analysis," Nucl Med Biol., Jan. 1999;26(1):27-34.
Pavlou et al., "The therapeutic antibodies market to 2008," Eur. J. Pharm. Biopharm., Apr. 2005;59(3):389-96.
Pejchal et al., "A Conformational Switch in Human Immunodeficiency Virus gp41 Revealed by the Structures of Overlapping Epitopes Recognized by Neutralizing Antibodies," J Virol. Sep. 2009 ; 83 (17) : 8451-62. do i : 10. 1128/ JVI. 00685-09. Epub Jun. 10, 2009.
Petkova et al., "Enhanced half-life of genetically engineered human IgG1 antibodies in a humanized FcRn mouse model: potential application in humorally mediated autoimmune disease," Int Immunol., Dec. 2006;18(12):1759-69. Epub Oct. 31, 2006.
Pini et al., "Design and use of a phage display library Human antibodies with subnanomolar affinity against a marker of angiogenesis eluted from a two-dimensional gel," J. Biol. Chem., 273(34):21769-76 (1998).
Piper et al., "Interferon therapy in primary care," Prim Care Update Ob Gyns, 8(4):163-169, Jul. 2001.
Poduslo et al., "Polyamine modification increases the permeability of proteins at the blood-nerve and blood-brain barriers," J. Neurochem., 66:1599-1609 (1996).
Pokkuluri et al., "A domain flip as a result of a single amino-acid substitution," Structure, 6(8):1067-1073, Aug. 15, 1998.
Pons et al., "Energetic analysis of an antigen/antibody interface: alanine scanning mutagenesis and double mutant cycles on the HyHEL-10/lysozyme interaction," Protein Sci., May 1999; 8(5):958-68.
Portolano et al., "Lack of Promiscuity in Autoantigen-Specific H and L Chain Combinations as Revealed by Human H and L Chain "Roulette"," J. Immunol., 150(3):880-887 (1993).
Presta et al., "Molecular engineering and design of therapeutic antibodies," Curr. Opin. Immunol., 20(4):460-70. doi: 10.1016/j.coi.2008.06.012 (2008).
Presta, "Engineering of therapeutic antibodies to minimize immunogenicity and optimize function," Adv. Drug Deliv. Rev., 58(5-6):640-56 (2006).
Price et al., "Tissue factor and tissue factor pathway inhibitor," Anaesthesia, 59(5):483-492, May 2004.
Qiao et al., "Dependence of antibody-mediated presentation of antigen on FcRn," Proc Natl Acad Sci USA, 105(27):9337-42 (2008).
Queen et al., "A humanized antibody that binds to the interleukin 2 receptor," Proc. Natl. Acad. Sci. U.S.A., 86(24):10029-10033 (1989).
R&D Systems (R&D Systems, Anti-human IL-31 RA Antibody, Catalog #AF2769, Oct. 2008), 1 page.
R&D Systems (R&D Systems, Biotinylated Anti-human IL-31 RA Antibody, Catalog #BAF2769, Nov. 2005), 1 page.
Raap et al., "Correlation of IL-31 serum levels with severity of atopic dermatitis," J. Allergy Clin. Immunol., 122(2):421-423 (2008).
Radaev et al., "The Structure of a Human Type III Fcγ Receptor in Complex with Fc*," J Biol Chem. May 11, 2001;276(19):16469•77. Epub Jan. 31, 2001.
Radaev et al., "The role of Fc glycosylation and the binding of peptide inhibitors," J Biol Chem., May 11, 2001;276(19):16478-83.
Rader et al., "A phage display approach for rapid antibody humanization. designed combinatorial V gene libraries," Proc Natl Acad Sci U S A. 95(15):8910-8915, Jul. 21, 1998.
Raffen et al., "Reengineering immunoglobulin domain interactions by introduction of charged residues," Protein Eng. Apr, 1998;11:303-9.
Rajpal et al., A general method for greatly improving the affinity of antibodies by using combinatorial libraries, Proc. Natl. Acad. Sci. USA, 102:8466-71 (2005).
Raposo et al., "Epitope-specific anitbody response is controlled by immunoglobulin Vh polymorphisms," J Exp Med. Mar. 10, 2014:211 (3) :405-11. do i : 10. 1084/ jem. 20130968. Epub Feb. 17, 2014.
Rathanaswami et al., "Demonstration of an in vivo generated sub-picomolar affinity fully human monoclonal antibody to interleukin-8," Biochem. Biophys. Res. Commun., 334:1004-13 (2005).
Ravetch et al., "Immune inhibitory receptors," Science, Oct. 6, 2000;290(5489):84-9.
Reddy et al., "Elimination of Fc receptor-dependent effector functions of a modified IgG4 monoclonal antibody to human CD4," J. Immunol., 164(4):1925-33 (2000).
Reichert et al., "Development trends for monoclonal antibody cancer therapeutics," Nat Rev Drug Discov., May 2007; 6(5):349-56.
Reichert et al., "Monoclonal antibody successes in the clinic," Nat. Biotechnol., Sep. 2005;23(9):1073-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Reist et al., "Human IgG2 constant region enhances in vivo stability of anti-tenascin antibody 81C6 compared with its murine parent," Clin Cancer Res., Oct. 1998;4(10):2495-502.
Reverberi et al., "Factors affecting the antigen-antibody reaction," Blood Transfus., Nov. 2007;5(4):227-40. doi: 10.2450/2007.0047-07.
Richards et al., "Optimization of antibody binding to FcgammaRIIa enhances macrophage phagocytosis of tumor cells," Mol Cancer Ther., 7(8):2517-27 (2008).
Ridgway et al., "'Knobs-into-holes' engineering of antibody $C_H3$ domains for heavy chain heterodimerization," Protein Eng., 9:617-621 (1996).

(56) References Cited

OTHER PUBLICATIONS

Riechelmann et al., "Adoptive therapy of head and neck squamous cell carcinoma with antibody coated immune cells: a pilot clinical trial," Cancer Immunol Immunother. Sep. 2007;56(9):1397-406. Epub Feb. 2, 2007.
Riechelmann et al., "Phase I trial with the CD44v6-targeting immunoconjugate bivatuzumab mertansine in head and neck squamous cell carcinoma," Oral Oncol., Sep. 2008;44(9):823-9. doi: 10.1016/j.oraloncology.2007.10.009. Epub Jan. 18, 2008.
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Robles-Carrillo et al., "Anti-CD4OL immune complexes potently activate platelets in vitro and cause thrombosis in FCGR2A transgenic mice," J Immunol., 185(3):1577-83 (2010).
Roguska et al., "Humanization of murine monoclonal antibodies through variable domain resurfacing," Proc Natl Acad Sci U.S.A., 91:969-73 (1994).
Roitt et al., Immunology, M., Mir, (2000), pp. 110, 150, and 537-539 (in Russian, with what is believed to be a published English equivalent of those pages).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Roitt et al., Immunology, M., Mir, 5th Edition (2000), pp. 97-113 [In Russian: Roitt et al. (Document ID _) is pages from a 2000 Russian edition of Immunology. In lieu of an English translation, applicant cites Male et al. (Document ID _ which is believed to be the corresponding pages from an English language edition of Immunology].
Roopenian et al., "FcRn: the neonatal Fc receptor comes of age," Nat Rev Immunol., Sep. 2007;7(9):715-25. Epub Aug. 17, 2007.
Rothe et al., "Recombinant proteins in rheumatology—recent advances," N Biotechnol. Sep. 2011;28(5):502.10. doi: 10.1016/j.nbt.2011.03.019. Epub Apr. 5, 2011.
Rothe et al., "Ribosome display for improved biotherapeutic molecules," Expert Opin. Biol. Ther., 6:177-187 (2006).
Rudikoff et al., "Single amino acid substitution altering antigen-binding specificity," Proc Natl Acad Sci. U.S.A., Mar. 1982;79(6):1979-83.
Ruef et al., "A bispecific antifibrin-antiplatelet urokinase conjugate (BAAUC) induces enhanced clot lysis and inhibits platelet aggregation," Thromb Haemost., 82(1):109-114, Jul. 1999.
Ruf et al., "Pharmacokinetics and in vivo stability of intraperitoneally administered therapeutic antibody catumaxomab," J. Clin. Oncol., 26 (May 20 suppl) (2008), abstr 14006.
Russo et al., "The CXCL8/IL-8 chemokine family and its receptors in inflammatory diseases," Expert Rev Clin Immunol., May 2014;10(5):593-619. doi: 10.1586/1744666X.2014.894886. Epub Mar. 29, 2014.
Sainaghi et al., "Gas6 induces proliferation in prostate carcinoma cell lines expressing the Axl receptor," J. Cell. Physiol., 204(1):36-44 (2005).
Saito et al., "Establishment of Factor VIII Mimetic Antibodies and Their In Vitro Activities in Hemophilia A," 2006 National Hemophilia Foundation Symposia.
Saito et al., "Factor VIII Mimetic Antibody: (1) Establishment and Characterization of Anti-factor IX/anti-factor X Bispecific Antibodies," 2005 International Society of Thrombosis and Haemostasis, vol. 3, Issue Supplement s1, p. #OR160.
Salfeld et al., "Isotype selection in antibody engineering," Nat. Biotechnol., 25:1369-72 (2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).

Salmon et al., "Fc gamma RIIA alleles are heritable risk factors for lupus nephritis in African Americans," J Clin Invest., 97(5):1348-54 (1996).
Sampei et al., "Identification and multidimensional optimization of an asymmetric bispecific IgG antibody mimicking the function of factor VIII cofactor activity," PLoS One, 2013;8(2):e57479. doi: 10.1371/journal.pone.0057479. Epub Feb. 28, 2013.
Sarkar et al., "Rational cytokine design for increased lifetime and enhanced potency using pH-activated "histidine switching"," Nat Biotechnol., Sep. 2002;20(9):908-13. Epub Aug. 5, 2002.
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Sato et al., "Properties of two VEGF receptors, Flt-1 and KDR, in signal transduction," Ann N Y Acad Sci., 902:201-205; discussion 205-207, May 2000.
Sato et al., "Reshaping a human antibody to inhibit the interleukin 6-dependent tumor cell growth," Cancer Res., 53:851-856 (1993).
Satoh et al., "Non-fucosylated therapeutic antibodies as next-generation therapeutic antibodies," Expert Opin Biol Ther., 6(11):1161-73 (2006).
Sawabu et al., "Growth arrest-specific gene 6 and Axl signaling enhances gastric cancer cell survival via Akt pathway," Mol. Carcinog., 46(2):155-64 (2007).
Scappaticci et al., "Arterial thromboembolic events in patients with metastatic carcinoma treated chemotherapy and bevacizumab," J Natl Cancer Inst., 99(16):1232-9 (2007).
Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.
Schaeffer et al., "The Rat Glomerular Filtration Barrier Does Not Show Negative Charge Selectivity," Microcirculation, Oct. 2002;9(5):329-42.
Schlereth et al., "T-cell activation and B-cell depletion in chimpanzees treated with a bispecific anti-CD19/anti-CD3 single-chain antibody construct," Cancer Immunol Immunother. May 2006;55(5):503-14. Epub Jul. 20, 2005.
Schmidt et al., "Structure-function relationships in factor IX and factor IXa," Trends Cardiovasc Med., Jan. 2003;13(1):39-45.
Schmidt et al., Human Physiology, Moscow, 2:431-436 (1996), and English translation: Schmidt et al., "Hemostatis and Coagulation," Human Physiology, R.F. Schmidt, G. Thews (Eds.), Second, Completely Revised Edition, 418-423 [translated by Marguerite A. Biederman-Thorson], Springer-Verlag, 1989 [Translation].
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989 [Translation].
Schmitz et al., "Phage display: a molecular tool for the generation of antibodies—a review," Placenta., Mar.-Apr. 2000;21 Suppl A:S106-12.
Schuster et al., "Signaling of human ciliary neurotrophic factor (CNTF) revisited. The interleukin-6 receptor can serve as an alpha-receptor for CTNF," J Biol Chem., Mar. 14, 2003;278(11):9528-35.
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intra-chain disulfide bonds," Mol Immunol., Jan. 2001;38(1):1-8.
Sebastian et al., "Treatment of non-small cell lung cancer patients with the trifunctional monoclonal antibody catumaxomab (anti-EpCAMxanti-CD3): a phase I study," Cancer Immunol Immunother. Oct. 2007; 56{10}:1637•44. Epub Apr. 5, 2007.
Sebba et al., "Tocilizumab: the first interleukin-6-receptor inhibitor," Am J Health Syst Pharm., Aug. 1, 2008;65(15):1413-8. doi: 10.2146/ajhp070449.
Seda et al., "B-cell receptor signalling and its crosstalk with other pathways in normal and malignant cells," Eur J Haematol., Aug. 1, 2014. doi: 10.1111/ejh.12427.

(56) References Cited

OTHER PUBLICATIONS

Segal et al., "Introduction: bispecific antibodies," J Immunol Methods., 248(1-2):1-6, Feb. 1, 2001.
Segal et al., "Bispecific antibodies in cancer therapy," Curr. Opin. Immunol., 11:558-562 (1999).
Seimetz et al., "Development and approval of the trifunctional antibody catumaxomab (anti-EpCAM×anti-CD3) as a targeted cancer immunotherapy," Cancer Treat Rev. Oct. 2010;36(6):458.67. Epub Mar. 27, 2010.
Shalaby et al., "Development of humanized bispecific antibodies reactive with cytotoxic lymphocytes and tumor cells overexpressing the HER2 protooncogene," J Exp Med., 175(1):217-225, Jan. 1, 1992.
Sharifi et al., "Improving monoclonal antibody pharmacokinetics via chemical modification," Q J Nucl Med., Dec. 1998;42(4):242-9.
Shaul, "Exploring the charge space of protein-protein association: a proteomic study," Proteins, 60:341-352 (2005).
Shieh et al., "Expression of axl in lung adenocarcinoma and correlation with tumor progression," Neoplasia., 7(12):1058-64 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001;276(9):6591-604. Epub Nov. 28, 2000.
Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. #P0038.
Shima, "Factor VIII Mimetic Antibody: (2) In Vitro Assessment of Cofactor Activity in Hemophilia A," Rinsho Ketsueki, 46(8):777(#WS-36-5), Aug. 30, 2005 (English translation).
Shima, M., "Bispecific antibodies to coagulation factors IXa and X mimic the function of factor VIII," 2006 World Federation of Haemophilia (Haemophilia, 12(Suppl. 2):98 (2006)).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003;278(5):3466-73. Epub Nov. 8, 2002.
Shirahata, Minna ni yakudatsu ketsuyubyo no kiso to rinsho. Iyaku (Medicine and Drug). Journal Co., Ltd., 280-9 (2009) (including English translation).
Shire et al., "Challenges in the development of high protein concentration formulations," J. Pharm. Sci., 93:1390-1402 (2004).
Sims et al., "HMGB1 and RAGE in inflammation and cancer," Annu Rev Immunol., 28:367-88 (2010).
Singer et al., Genes & Genomes 1:63 (1998) (in Russian, with English translation).
Singer et al., Genes & Genomes, 1991;67-69.
Singer et al., Genes & Genomes, 1998;1:63-64.
Sinha et al., "Electrostatics in protein binding and function," Curr. Protein Pept. Sci., 3(6):601-14 (2002).
Smans et al., "Bispecific antibody-mediated lysis of primary cultures of ovarian carcinoma cells using multiple target antigens," Int. J. Cancer, 83:270-277 (1999).
Smith et al., "The challenges of genome sequence annotation or 'the devil is in the details'," Nature Biotechnology, Nov. 1997;15:1222-1223.
Smith et al., "FcgammaRIIB in autoimmunity and infection: evolutionary and therapeutic implications," Nat Rev Immunol., May;10(5):328-43 (2010).
Smolen et al., "Interleukin-6: a new therapeutic target," Arthritis Res Ther., 2006;8 Suppl 2:S5. Epub Jul. 28, 2006.
Soeda et al., "Factor VIII Taitei Kotai (1) Ko FIXa/FX bispecific Kotai no Sakusei oyobi characterization," Rinsho Ketsueki, 46(8):728 (2005) (including English translation).

Soeda et al., "Phage library-ho ni yori Sakusei shita Ko-FIXa/Ko-FX bispecific Kotai no FVIII Taitei Sayo," Japanese Journal of Thrombosis and Hemstasis, 16(5):526 (2005) (including English translation).
Sonkoly et al., "IL-31: a new link between T cells and pruritus in atopic skin inflammation," J. Allergy Clin. Immunol., 117:411-417 (2006).
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.
Staerz et al., "Hybrid antibodies can target sites for attack by T cells," Nature. Apr. 18-24, 1985; 314(6012):628-31.
Staerz et al., "Hybrid hybridoma producing a bispecific monoclonal antibody that can focus effector T-cell activity," Proc Natl Acad Sci U.S.A., 83:1453-7 (1986).
Stenhoff et al., "Vitamin K-dependent Gas6 activates ERK kinase and stimulates growth of cardiac fibroblasts," Biochem. Biophys. Res. Commun., 319(3):871-8 (2004).
Stickney et al., "Bifunctional antibody: a binary radiopharmaceutical delivery system for imaging colorectal carcinoma," Cancer Res., 51(24):6650-6655, Dec. 15, 1991.
Strand et al., "Biologic therapies in rheumatology: lessons learned, future directions," Nat. Rev. Drug Discov., 6:75-92 (2007).
Strohl, "Optimization of Fc-mediated effector functions of monoclonal antibodies," Curr Opin Biotechnol., Dec. 2009;20(6):685-91. doi: 10.1016/j.copbio.2009.10.011. Epub Nov. 4, 2009.
Su et al., Expression profile of FcgammaRIIb on leukocytes and its dysregulation in systemic lupus erythematosus, J Immunol., 178(5):3272-80 (2007).
Sun et al., "Coexpression of Gas6/Axl in human ovarian cancers," Oncology, 66(6):450-7 (2004).
Suresh et al., "Advantages of bispecific hybridomas in one-step immunocytochemistry and mmunoassays," Proc Natl Acad Sci U S A., 83(20):7989-7993, Oct. 1986.
Suresh et al., "Bispecific monoclonal antibodies from hybrid hybridomas," Methods Enzymol., 1986;121:210-228.
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J. Immunol., 184(4):1968-76 (2010).
Szlama et al., "Latent myostatin has significant activity and this activity is controlled more efficiently by WFIKKN1 than by WFIKKN2," FEBS J., Aug. 2013;280(16):3822-39. doi: 10.1111/febs.12377. Epub Jul. 5, 2013.
Tabrizi et al "Elimination mechanisms of therapeutic monoclonal antibodies," Drug Discov Today, Jan. 2006;11(1-2):81-8.
Takeuchi et al., "The Japanese experience with biologic therapies for rheumatoid arthritis," Nat Rev Rheumatol., Nov. 2010;6(11):644-52. doi: 10.1038/nrrheum.2010.154. Epub Sep. 28, 2010.
Taki, The Journal of Japanese Society on Thrombosis and Hemostasis. 13(1):109-113, Feb. 2, 2002.
Takkinen et al., "Affinity and Specificity Maturation by CDR Walking," Antibody Engineering, Springer Lab Manuals, pp. 540-545 (2001).
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Tan et al., "Contributions of a highly conserved VH/VL hydrogen bonding interaction to scFv folding stability and refolding efficiency," Biophys J., 75(3):1473-1482, Sep. 1998.
Tan et al., "Engineering the isoelectric point of a renal cell carcinoma targeting antibody greatly enhances scFv solubility," Immunotechnology, Oct. 1998;4(2):107-114.
Tarditi et al., "Selective high-performance liquid chromatographic purification of bispecific monoclonal antibodies," J. Chromatogr., 599(1-2):13-20 (1992).
Teeling et al., "The biological activity of human CD20 monoclonal antibodies is linked to unique epitopes on CD20," J Immunol., Jul. 1, 2006;177(1):362-71.

(56) References Cited

OTHER PUBLICATIONS

Ten Kate et al., "Effect of isoelectric point on biodistribution and inflammation. imaging with indium-111-labelled IgG," Eur. J. Nucl. Med., 1990;17(6-8):305-9 (abstract).
Thies et al., "The alternatively folded state of the antibody C(H)3 domain," J Mol Biol., 309(5):1077-1085, Jun. 22, 2001.
Trinh et al., "Ipilimumab in the treatment of melanoma," Expert Opin Biol Ther., Jun. 2012;12(6):773-82. doi: 10.1517/14712598. 2012.675325. Epub Apr. 14, 2012.
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsuchiya, Credit Suisse Seminar, "Therapeutic Antibody," at Fuji-Gotemba Laboratories, p. 21 (2006) [Translation].
Tsurushita et al., "Design of humanized antibodies: From anti-Tac to Zenapax," Methods, 36:69-83 (2005).
Unkeless et al., "Structure and Function of Human and Murine Receptors for IgG," Annu Rev Immunol. 1988;6:251.81.
Vaccaro et al., "Engineering the Fc region of immunoglobulin G to modulate in vivo antibody levels," Nat Biotechnol., Oct. 2005;23(10):1283-8. Epub Sep. 25, 2005.
Vaisitti et al., "Cationization of monoclonal antibodies: another step towards the "magic bullet"?," J Biol Regul Homeost Agents., Jul.-Dec. 2005;19(3-4):105-12.
Vajdos et al., "Comprehensive functional maps of the antigen-binding site of an anti-EibB2 antibody obtained with shotgun scanning mutagenesis," J Mol Biol., Jul. 5, 2002;320(2):415-28.
Vajkoczy et al., "Dominant-negative inhibition of the Axl receptor tyrosine kinase suppresses brain tumor cell growth and invasion and prolongs survival," Proc. Natl. Acad. Sci. U.S.A., 103(15):5799-804 (2006).
Van Der Neut Kolfschoien et al., "Anti-inflammatory activity of human IgG4 antibodies by dynamic Fab arm exchange," Science, Sep. 14, 2007;317(5844):1554-7.
Van Loghem et al., "Staphylococcal protein A and human IgG subclasses and allotypes," Scand. J. Immunol., 15(3):275-8 (1982).
Van Walle et al.,"Immunogenicity screening in protein drug development," Expert Opin Biol Ther., Mar. 2007;7(3):405-418.
Vargas-Madrazo et al., "An improved model of association for VH-VL immunoglobulin domains asymmetries between VH and VL in the packing of some interface residues," J Mol Recognit., 16(3):113-120, May-Jun. 2003.
Varnum et al., "Axl receptor tyrosine kinase stimulated by the vitamin K-dependent protein encoded by growth-arrest-specific gene 6," Nature, 373(6515):623-6 (1995).
Vaughan et al., "Human antibodies with sub-nanomolar affinities isolated from a large non-immunized phage display library," Nat Biotechnol., Mar. 1996;14(3):309-14.
Vehar et al., "Structure of human factor VIII," Nature, 312(5992):337-42 (1984).
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, 121(3):392-404 (2007).
Veri et al., "Therapeutic control of B cell activation via recruitment of Fcgamma receptor IIb (CD32B) inhibitory function with a novel bispecific antibody scaffold," Arthritis Rheum., 62(7):1933-43 (2010).
Wagner et al., "Loss of myostatin attenuates severity of muscular dystrophy in mdx mice," Ann Neurol., Dec. 2002;52(6):832-6.
Wally et al., "Identification of a novel substitution in the constant region of a gene coding for an amyloidogenic kappa1 light chain," Biochim Biophys Acta., May 31, 1999;1454(1):49-56.

Wang et al., "Conserved amino acid networks involved in antibody variable domain interactions," Proteins, Jul. 2009;76(1):99-114. doi: 10.1002/prot.22319.
Wang et al., "HMG-1 as a late mediator of endotoxin lethality in mice," Science, 285(5425):248-51 (1999).
Wang et al., "Polyethylene Glycol-modified Chimeric Toxin Composed of Transforming Growth Factor alpha and Pseudomonas Exotoxin," Cancer. Res., 53:4588-4594 (1993).
Ward et al., "Binding activities of a repertoire of single immunoglobulin variable domains secreted from *Escherichia coli*," Nature, 1989;341:544-546.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987;26(13):4131-8.
Warmerdam et al., Molecular basis for a polymorphism of human Fc gamma receptor II. (CD32), J Exp Med., 172(1):19-25 (1990).
Warnaar et al., "Purification of bispecific F(ab')2 from murine trinoma OC/TR with specificity for CD3 and ovarian cancer," Hybridoma, 13:519-526 (1994).
Weiner et al., "A human tumor xenograft model of therapy with a bispecific monoclonal antibody targeting c-erbB-2 and CD16," Cancer Res., 53(1):94-100, Jan. 1, 1993.
Weiner et al., "The role of T cell activation in anti-CD3 x antitumor bispecific antibody therapy," J Immunol., 152(5):2385-2392, Mar. 1, 1994.
Weiner et al., "Monoclonal antibodies: versatile platforms for cancer immunotherapy," Nat Rev Immunol., May 2010;10(5):317-27. doi: 10.1038/nri2744.
Wenink et al., "The inhibitory Fc gamma IIb receptor dampens TLR4-mediated immune responses and is selectively up-regulated on dendritic cells from rheumatoid arthritis patients with quiescent disease," J Immunol., Oct. 1, 2009;183(7):4509-20.
Wernersson et al., "IgG-mediated enhancement of antibody responses is low in Fc receptor gamma chain-deficient mice and increased in Fc gamma RII-deficient mice," J Immunol., Jul. 15, 1999;163(2):618-22.
Whittemore et al "Inhibition of myostatin in adult mice increases skeletal muscle mass and strength," Biochem Biophys Res Commun., Jan. 24, 2003;300(4):965-71.
Wiens et al., "Mutation of a single conserved residue in VH complementarity-determining region 2 results in a severe Ig secretion defect," J Immunol., Aug. 15, 2001;167(4):2179-86.
Wiens et al., "Somatic mutation in VH complementarity-determining region 2 and framework region 2: differential effects on antigen binding and Ig secretion," J Immunol., Aug. 1, 1997;159(3):1293-302.
Wilson et al., "An Fcγ receptor-dependent mechanism drives antibody-mediated target-receptor signaling in cancer cells," Cancer Cell, 19(1):101-13 (2011).
Winkler et al., "Changing the antigen binding specificity by single point mutations of an anti-p24 (HIV-1) antibody," J. Immunol., 165:4505-14 (2000).
Wood et al., "Expression of active human factor VIII from recombinant DNA clones," Nature, 312(5992):330-7 (1984).
Worn et al., "Stability engineering of antibody single-chain Fv fragments," J Mol Biol., 305(5):989-1010, Feb. 2, 2001.
Wozniak-Knopp et al., "Introducing antigen-binding sites in structural loops of immunoglobulin constant domains Fc fragments with engineered HER2/neu-binding sites and antibody properties," Protein Eng Des Sel. Apr. 2010;23(4):289-97. doi: 10.1093/ protein/gzq005. Epub Feb. 11, 2010.
Wu et al., "Multimerization of a chimeric anti-CD20 single-chain Fv-Fc fusion protein is mediated through variable domain exchange," Protein Eng., 14(12):1025-1033, Dec. 2001.
Wu et al., "Structure-based engineering of a monoclonal antibody for improved solubility," Protein Eng Des Sel., Aug. 2010;23(8):643-51. doi: 10.1093/protein/gzq037. Epub Jun. 11, 2010.
Wu et al., "Development of motavizumab, an ultra-potent antibody for the prevention of respiratory syncytial virus infection in the upper and lower respiratory tract," J. Mol. Biol., 368:652-665 (2007).

(56) References Cited

OTHER PUBLICATIONS

Wu et al., "Humanization of a murine monoclonal antibody by simultaneous optimization of framework and CDR residues," J. Mol. Biol., 294(1):151-62 (1999).
Wypych et al., "Human IgG2 antibodies display disulfide-mediated structural isoforms," J. Biol. Chem., 283(23):16194-16205 (2008).
Xiang et al., "Production of murine V-human Cr1 chimeric anti-TAG72 antibody using V region cDNA amplified by PCR," Mol Immunol., 27(8):809-817, Aug. 1990.
Xiang et al., "Study of B72.3 combining sites by molecular modeling and site-directed mutagenesis," Protein Eng., 13(5):339-44 (2000).
Xiao et al., "Pharmacokinetics of anti-hepcidin monoclonal antibody Ab 12B9m and hepcidin in cynomolgus monkeys," AAPS J., Dec. 2010;12(4):646-57. doi: 10.1208/s12248-010-9222-0. Epub Aug. 25, 2010.
Xu et al., "Fc gamma Rs modulate cytotoxicity of anti-Fas antibodies: implications for agonistic antibody-based therapeutics," J Immunol., 171(2):562-8 (2003).
Yagi et al., "Interleukin-31 stimulates production of inflammatory mediators from human colonic subepithelial myofibroblasts," Int. J. Mol. Med., 19(6):941-946 (2007).
Yamagata et al., "Synaptic adhesion molecules," Curr. Opin. Cell Biol., 15(5):621-32 (2003).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "CDR walking mutagenesis for the affinity maturation of a potent human anti-HIV-1 antibody into the picomolar range," J. Mol. Biol., Dec. 1, 1995;254(3):392-403.
Yang et al., "Tailoring structure-function and pharmacokinetic properties of single-chain Fv proteins by site-specific PEGylation," Protein Eng., Oct. 2003;16(10):761-70.
Yeung et al., "Engineering human IgG1 affinity to human neonatal Fc receptor: impact of affinity improvement on pharmacokinetics in primates," J. Immunol., 182(12):7663-71 (2009).
Yuasa et al., "Deletion of fcgamma receptor IIB renders H-2(b) mice susceptible to collagen-induced arthritis," J Exp Med., Jan. 4, 1999;189(1):187-94.
Zalevsky et al., "Enhanced antibody half-life improves in vivo activity," Nat. Biotechnol., 28(2):157-9 (2010).
Zeidler et al., "Simultaneous Activation of T Cells and Accessory Cells by a New Class of Intact Bispecific Antibody Results in Efficient Tumor Cell Killing1," J Immunol. Aug. 1, 1999;163(3):1246-52.
Zhang et al., "Effective therapy for a murine model of human anaplastic large-cell lymphoma with the anti-CD30 monoclonal antibody, HeFi-1,does not require activating Fc receptors," Blood, 108(2):705-10 (2006).
Zhang et al., "Immune complex/Ig negatively regulate TLR4-triggered inflammatory response in macrophages through Fc gamma RIIb-dependent PGE2 production," J Immunol., Jan. 1, 2009;182(1):554-62.
Zheng et al., "Translational pharmacokinetics and pharmacodynamics of an FcRn-variant anti-CD4 monoclonal antibody from preclinical model to phase I study," Clin Pharmacol Ther., Feb. 2011;89(2):283-90. doi: 10.1038/clpt.2010.311. Epub Dec. 29, 2010.
Zhu et al., "Remodeling domain interfaces to enhance heterodimer formation," Protein Sci., 6(4):781-788, Apr. 1997.
Zhu et al., "MHC class I-related neonatal Fc receptor for IgG is functionally expressed in monocytes, intestinal macrophages, and dendritic cells," J. Immunol., 166(5):3266-76 (2001).
Zimmers et al., "Induction of cachexia in mice by systemically administered myostatin," Science, May 24, 2002;296(5572):1486-8.
Zuckier et al., "Chimeric human-mouse IgG antibodies with shuffled constant region exons demonstrate that multiple domains contribute to in vivo half-life," Cancer Res., 58:3905-08 (1998).
Zuo et al., "An efficient route to the production of an IgG-like bispecific antibody," Protein Eng., 13(5):361-7 (2000).
Zwick et al., "The long third complementarity-determining region of the heavy chain is important in the activity of the broadly neutralizing anti-human immunodeficiency virus type 1 antibody 2F5," J Virol., Mar. 2004;78(6):3155-61.
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/066590, dated Oct. 20, 2009, 2 pages.
International Preliminary Report on Patentability for App. Ser. No. PCT/JP2009/066590, dated May 10, 2011, 6 pages.
International Preliminary Report on Patentability for App. Ser. No. PCT/JP2008/067499, dated Apr. 7, 2010, 6 pages.
USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed on Dec. 6, 2011, 15 pages.
USPTO Non Final Office Action in U.S. Appl. No. 12/680,112, dated Feb. 29, 2012, 8 pages.
Fish & Richardson P.C., Amendment in Reply to Action dated Feb. 29, 2012 in U.S. Appl. No. 12/680,112, filed on Aug. 27, 2012, 12 pages.
USPTO Restriction Requirement in U.S. Appl. No. 12/680,112, dated Sep. 19, 2012, 6 pages.
Fish & Richardson P.C., Amendment and Reply to Restriction Requirement dated Sep. 19, 2012 in U.S. Appl. No. 12/680,112, filed on Oct. 17, 2012, 13 pages.
Examiner Dong Jiang, USPTO Non Final Office Action in U.S. Appl. No. 12/680,112, dated Feb. 4, 2013, 9 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed on Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed on Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed on Sep. 11, 2012, 12 pages.
International Preliminary Report on Patentability for U.S. Appl. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed on Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed on Jul. 2, 2013, 18 pages.
USPTO Final Office Action in U.S. Appl. No. 12/679,922, dated Aug. 2, 2013, 12 pages.
Fish & Richardson P.C., Amendment in Reply to Action dated Aug. 2, 2013 in U.S. Appl. No. 12/679,922, filed on Jan. 29, 2014, 24 pages.
USPTO Non-Final Office Action in U.S. Appl. No. 12/679,922, dated Mar. 18, 2014, 11 pages.

(56) References Cited

OTHER PUBLICATIONS

Fish & Richardson P.C., Amendment in Reply to Action dated Mar. 18, 2014 in U.S. Appl. No. 12/679,922, filed on Jun. 18, 2014, 13 pages.
USPTO Final Office Action in U.S. Appl. No. 12/679,922, dated Jul. 28, 2014, 12 pages.
Fish & Richardson P.C., Amendment in Reply to Action dated Jul. 28, 2014 in U.S. Appl. No. 12/679,922, filed on Dec. 29, 2014, 23 pages.
USPTO Notice of Allowance in U.S. Appl. No. 12/679,922, dated Mar. 30, 2015, 12 pages.
USPTO Non-Final Office Action in U.S. Appl. No. 14/741,786, dated Jun. 10, 2016, 19 pages.
Fish & Richardson P.C., Reply to Office Action dated Jun. 10, 2016, in U.S. Appl. No. 14/741,786, filed Sep. 9, 2016 37 pages.
USPTO Final Office Action in U.S. Appl. No. 14/741,786, dated Oct. 18, 2016, 11 pages.
USPTO Non-Final Office Action in U.S. Appl. No. 14/741,786, dated Feb. 7, 2017, 9 pages.
USPTO Notice of Allowance in U.S. Appl. No. 14/741,786, dated Jul. 26, 2017, 9 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed on Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed on Jul. 25, 2012, 1 page.
USPTO Non-Final Office Action in U.S. Appl. No. 12/936,587, dated Nov. 7, 2012, 13 pages.
International Search Report for U.S. Appl. No. PCT/JP2009/057309, dated Jul. 7, 2009, 8 pages.
International Preliminary Report on Patentability for U.S. Appl. No. PCT/JP2009/057309, dated Nov. 30, 2010, 7 pages.
European Search Report for App. Ser. No. EP 09 72 9337, dated Nov. 3, 2011, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
European Search Report for App. Ser. No. 07 74 0474, dated Mar. 16, 2009, 5 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
USPTO Final Office Action in U.S. Appl. No. 10/575,905, dated Feb. 24, 2011, 7 pages.
Fish & Richardson P.C., Amendment in Reply to Action dated Jun. 23, 2010 in U.S. Appl. No. 10/575,193, filed Dec. 22, 2010, 13 pages.
USPTO Notice of Allowance in U.S. Appl. No. 10/575,193, dated Mar. 18, 2011, 11 pages.
Fish & Richardson P.C., Amendment in U.S. Appl. No. 10/575,193, filed Jun. 17, 2011, 15 pages.
USPTO Notice of Allowance in U.S. Appl. No. 10/575,193, dated Jul. 13, 2011, 8 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.

Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
USPTO Non-Final Office Action in U.S. Appl. No. 12/295,075, dated Jun. 7, 2013, 17 pages.
Fish & Richardson P.C., Amendment in Reply to Action dated Jun. 7, 2013, in U.S. Appl. No. 12/295,075, filed Nov. 6, 2013, 16 pages.
USPTO Final Office Action in U.S. Appl. No. 12/295,075, dated Jan. 27, 2014, 15 pages.
Fish & Richardson P.C., Amendment in Reply to Action dated Jan. 27, 2014, in U.S. Appl. No. 12/295,075, filed Jul. 24, 2014, 15 pages.
USPTO Advisory Action in U.S. Appl. No. 12/295,075, dated Aug. 22, 2014, 3 pages.
USPTO Final Office Action in U.S. Appl. No. 12/295,075, dated Jul. 27, 2015, 32 pages.
Fish & Richardson P.C., Amendment in Reply to Action dated Jul. 27, 2015, in U.S. Appl. No. 12/295,075, filed Jan. 27, 2016, 26 pages.
USPTO Notice of Allowance in U.S. Appl. No. 12/295,075, dated Apr. 14, 2016, 9 pages.
USPTO Restriction Requirement in U.S. Appl. No. 11/910,836, dated Mar. 18, 2011, 7 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
International Preliminary Report on Patentability for App. Ser. No. PCT/JP2009/070376, dated Jul. 5, 2011, 11 pages.
USPTO Non-Final Office Action U.S. Appl. No. 12/680,087, dated Oct. 27, 2011, 6 pages.
Fish & Richardson P.C., Amendment and Reply to Action dated Oct. 27, 2011 in U.S. Appl. No. 12/680,087, filed on Jan. 26, 2012, 6 pages.
USPTO Notice of Allowance in U.S. Appl. No. 12/680,087, dated Feb. 24, 2012, 5 pages.
USPTO Notice of Allowance in U.S. Appl. No. 12/680,087, dated Jun. 25, 2012, 11 pages.
USPTO Notice of Allowance in U.S. Appl. No. 12/680,087, dated Nov. 26, 2012, 7 pages.
USPTO Notice of Allowance in U.S. Appl. No. 12/680,087, dated Apr. 15, 2013, 9 pages.
International Preliminary Report on Patentability for App. Ser. No. PCT/JP2010/058166, dated Dec. 16, 2011, 15 pages.
USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed on Jun. 29, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed on Nov. 8, 2012, 14 pages.
USPTO Non-Final Office Action U.S. Appl. No. 12/680,082, dated Feb. 14, 2013, 12 pages.

(56) References Cited

OTHER PUBLICATIONS

International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
USPTO Restriction Requirement in U.S. Appl. No. 13/434,643, dated Jul. 27, 2012, 6 pages.
Fish & Richardson P.C., Response to Restriction Requirement dated Jul. 27, 2012 and Preliminary Amendment in U.S. Appl. No. 13/434,643, filed on Jan. 24, 2013, 10 pages.
USPTO Non-Final Office Action in U.S. Appl. No. 13/434,643, dated Feb. 12, 2013, 17 pages.
Fish & Richardson P.C., Amendment in Reply to Office Action dated Feb. 12, 2013 in U.S. Appl. No. 13/434,643, filed on May 13, 2013, 18 pages.
USPTO Final Office Action in U.S. Appl. No. 13/434,643, dated Jul. 11, 2013, 19 pages.
USPTO Restriction Requirement in U.S. Appl. No. 12/745,781, dated Sep. 4, 2012, 10 pages.
Fish & Richardson P.C., Response to Restriction Requirement dated Sep. 4, 2012 in U.S. Appl. No. 12/745,781, filed on Sep. 21, 2012, 176 pages.
USPTO Non-Final Office Action in U.S. Appl. No. 12/745,781, dated Oct. 18, 2012, 21 pages.
Fish & Richardson P.C., Amendment in Reply to Office Action dated Oct. 18, 2012 in U.S. Appl. No. 12/745,781, filed on Apr. 17, 2013, 23 pages.
USPTO Final Office Action in U.S. Appl. No. 12/745,781, dated May 21, 2013, 16 pages.
International Preliminary Report on Patentability for App. Ser. No. PCT/JP2010/073361, dated Aug. 14, 2012, 7 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
Fish & Richardson P.C., Response to Restriction Requirement dated Dec. 6, 2012 in U.S. Appl. No. 13/497,269, filed May 1, 2013, 2 pages.
USPTO Restriction Requirement in U.S. Appl. No. 12/809,138, dated Dec. 13, 2012, 8 pages.
Fish & Richardson P.C., Response to Restriction Requirement dated Dec. 13, 2012 in U.S. Appl. No. 12/809,138, filed on Apr. 5, 2013, 2 pages.
USPTO Restriction Requirement in U.S. Appl. No. 13/320,317, dated Dec. 18, 2012, 13 pages.
Fish & Richardson P.C., Response to Restriction Requirement dated Dec. 18, 2012 in U.S. Appl. No. 13/320,317, filed Jan. 18, 2013, 3 pages.
USPTO Non-Final Ofice Action in U.S. Appl. No. 13/320,317, dated Dec. Apr. 25, 2013, 25 pages.
International Search Report for App. Ser. No. PCT/JP2011/001888, dated Nov. 2, 2011, 7 pages.
USPTO Restriction Requirement in U.S. Appl. No. 13/257,145, dated Mar. 20, 2013, 11 pages.
Fish & Richardson P.C., Preliminary Amendment and Response to Restriction Requirement dated Mar. 20, 2013 in U.S. Appl. No. 13/257,145, filed on Apr. 22, 2013, 7 pages.
USPTO Non-Final Office Action in U.S. Appl. No. 13/257,145, dated Jul. 2, 2013, 20 pages.
USPTO Restriction Requirement in U.S. Appl. No. 13/524,528, dated Mar. 21, 2013, 7 pages.
International Preliminary Report on Patentability for App. Ser. No. PCT/JP2011/076486, dated Jun. 12, 2013, 9 pages.
International Search Report for App. Ser No. PCT/JP2011/076486, dated Dec. 27, 2011, 4 pages.
International Preliminary Report on Patentability for App. Ser. No. PCT/JP2012/058603, dated Oct. 8, 2013, 11 pages.

International Search Report for App. Ser. No. PCT/JP2012/058603, dated May 29, 2012, 2 pages.
International Search Report for App. Ser. No. PCT/JP2012/075083, dated Oct. 23, 2012, 2 pages.
International Preliminary Report on Patentability for App. Ser. No. PCT/JP2012/075083, dated Apr. 1, 2014, 8 pages.
International Search Report for App. Ser. No. PCT/JP2012/006218, dated Mar. 26, 2013, 11 pages.
Notice of Opposition against EP 1 876 236, dated May 20, 2015, in the name of Chugai Seiyaku Kabushiki Kaisha brought by Novo Nordisk A/S, 23 pages.
Notice of Opposition against EP 1 876 236, dated May 22, 2015, in the name of Chugai Seiyaku Kabushiki Kaisha brought by Baxalta Innovations GmbH, 37 pages.
Chugai Seiyaku Kabushiki Kaisha's letter dated Jun. 12, 2013, regarding oral proceedings scheduled on Jun. 26, 2013, in App. Ser. No. EP 06 73 0769.4-13 1412.
USPTO Non-Final Office Action in U.S. Appl. No. 13/595,139, dated Nov. 14, 2012, 10 pages.
Fish & Richardson P.C., Amendment in Reply to Office Action dated Nov. 14, 2012 in U.S. Appl. No. 13/595,139, filed on May 14, 2013, 19 pages.
USPTO Final Office Action in U.S. Appl. No. 13/595,139, dated Aug. 1, 2013, 8 pages.
USPTO Notice of Allowance in U.S. Appl. No. 13/595,139, dated Oct. 11, 2013, 15 pages.
USPTO Non-Final Office Action in U.S. Appl. No. 13/595,139, dated Mar. 13, 2015, 12 pages.
Fish & Richardson P.C., Amendment and Reply to Office Action dated Mar. 13, 2015 in U.S. Appl. No. 13/595,139, filed on Jun. 11, 2015, 19 pages.
USPTO Non-Final Office Action in U.S. Appl. No. 13/595,139, dated Aug. 3, 2015, 13 pages.
Fish & Richardson P.C., Reply to Office Action dated Aug. 3, 2015 in U.S. Appl. No. 13/595,139, filed on Dec. 2, 2015, 28 pages.
USPTO Final Office Action in U.S. Appl. No. 13/595,139, dated Feb. 12, 2016, 12 pages.
Fish & Richardson P.C., Reply to Office Action dated Feb. 12, 2016 in U.S. Appl. No. 13/595,139, filed on Jul. 11, 2016, 4 pages.
USPTO Non-Final Office Action in U.S. Appl. No. 13/595,139, dated Nov. 23, 2016, 11 pages.
Fish & Richardson P.C., Reply to Office Action dated Nov. 23, 2016 in U.S. Appl. No. 13/595,139, filed on Mar. 22, 2016, 29 pages.
USPTO Final Office Action in U.S. Appl. No. 13/595,139, dated May 30, 2017, 23 pages.
International Search Report for App. Ser. No. PCT/JP2016/003616, dated Nov. 25, 2016, 4 pages.
Sondermann et al., "The 3.2-Å crystal structure of the human IgG1 Fc fragment-FcγRIII complex,". Nature, Jul. 20, 2000, 406(6793): 267-273.
Yarilin, Fundamentals of Immunology, M.: Medicina, 1999, pp. 181-184 (with English translation).
[Anonymous] "Rabbit Antibody to Human pro-Myostatin (amino acids 79-92)," Meridian Life Science Inc., Nov. 13, 2015 (Nov. 13, 2015), XP055478289, Retrieved from the Internet: URL:https://meridianlifescience.com/biospecs/K24340R.pdf [retrieved on May 24, 2018]; 1 page.
[Anonymous] "Blog entry," Jun. 1, 2014 (Jun. 1, 2014), Retrieved from the Internet: URL:https://www.thunderspace.org/male-supplements/the-chemical-pe thread-7.html92 [retrieved on May 23, 2018]; 4 pages.
[Anonymous] "polyclonal human pro-Myostatin (aa 79-92) antibody," Immun Diagnostik Antibodies Catalogue, Jun. 30, 2016 (Jun. 30, 2016), Retrieved from the Internet: URL:https://www.immundiagnostik.com/fileadmin/pdf/AK3004.pdf [retrieved on May 24, 2018]; 1 page.
[Anonymous] "Mouse GDF-8/Myostatin Propeptide Antibody," R&D Catalogue AF 1539, Feb. 6, 2018 (Feb. 6, 2018), XP055478493, Retrieved from the Internet: URL:https://resources.rndsystems.com/pdfs/datasheets/af1539.pdf [retrieved on May 25, 2018]; 2 pages.
Alexion Initiates Simultaneous Registration Trials of ALXN1210 for Patients with Paroxysmal Nocturnal Hemoglobinuria (PNH) and Atypical Hemolytic Uremic Syndrome (aHUS), Press Release,

(56) References Cited

OTHER PUBLICATIONS

Alexion Pharmaceuticals, Inc. [online] (retrieved on Jun. 6, 2018), retrieved from the Internet:<URL: http://ir.alexion.com/releasedetail.cfm?releaseid=995788>; 5 pages.
Chaparro-Riggers et al., "Increasing Serum Half-life and Extending Cholesterol Lowering in Vivo by Engineering Antibody with pH-sensitive Binding to PCSK9," J Biol Chem, Mar. 30, 2012, 287(14):11090-7. doi: 10.1074/jbc.M111.319764. Epub Jan. 31, 2012.
Chihara et al., "Interleukin 6 signaling promotes anti-aquaporin 4 autoantibody production from plasmablasts in neuromyelitis optica," Proc Natl Acad Sci USA, Mar. 2011, 108(9):3701-3706.
European Medicines Agency, No. WC500054212, Jun. 22, 2016, pp. 1-41, XP002780707 Retrieved from the Internet: URL: http://www.ema.europa.eu/docs/en_GB/document_library/EPAR_-_Scientific_Discussion/human/000791/WC500054212.pdf; 41 pages.
Feagan et al., "Ustekinumab as Induction and Maintenance Therapy for Crohn's Disease," N Engl. J Med, Nov. 17, 2016, 375(20):1946-1960.
Han et al., "Targeting the Myostatin Signaling Pathway to Treat Muscle Wasting Diseases," Curr Opin Support Palliat Care, Dec. 2011, 5(4):334-41. doi: 10.1097/SPC.0b013e32834b&lf9.
Hill et al., "The Myostatin Propeptide and the Follistatin-related Gene Are Inhibitory Binding Proteins of Myostatin in Normal Serum," J Biol Chem, Oct. 25, 2002, 277(43):40735-41. Epub Aug. 22, 2002.
Jaeger, Clinical Immunology and Allergology, 2nd edition, M.: Medicina, 1990, 2:484-5 (with English translation).
Kawahata, Alnylam Pharmaceuticals, Mar. 22, 2016, XP055471916 Retrieved from the Internet: URL: http://www.alnylam.com/web/assets/ERA-EDTA_CC5_Ph-1_052216.pdf; 21 pages.
Kim et al., "Production of a Monoclonal Anti-Myostatin Antibody and the Effects of In Ovo Administration of the Antibody on Posthatch Broiler Growth and Muscle Mass," Poult Sci, Jun. 2006, 85(6):1062-71.
OriGene Technologies, Inc., AP02123SU-N, Polyclonal Antibody to Myostatin (79-92)—Serum, Mar. 19, 2013, https://ml.acris-antibodies.com/pdf/AP02123SU-N.pdf.
Popov et al., "The Stoichiometry and Affinity of the Interaction of Murine Fc Fragments with the MHC Class I-Related Receptor, FcRn," Mol Immunol, Apr. 1996, 33(6):521-30.
Richter et al., "Special Section on DMPK of Therapeutic Proteins—Minireview Subcutaneous Absorption of Biotherapeutics: Knowns and Unknowns," Drug Metab Dispos, Nov. 2014, 42(11):1881-9. doi: 10.1124/dmd.114.059238. Epub Aug. 6, 2014.
Roitt et al., Immunology, M., Mir, 2000, 373-4 (with English translation); 9 pages.
Sampei et al., Non-antigen-contacting region of an asymmetric bispecific antibody to factors IXa/X significantly affects factor VIII-mimetic activity, mAbs, 2015, 7(1):120-8. doi: 10.4161/19420862.2015.989028.
Soliris (R) (eculizumab) injection, for intravenous use, BLA:125166, Jan. 13, 2017, Suppl-417, Label, Drugs@FDA [online] (retrieved on Jun. 6, 2018), retrieved from the Internet <URL: https://www.accessdatafda.gov/scripts/cder/daf/index.cfm?event=overview.process&applno=125166>.
Yarilin, Fundamentals of Immunology, M: Medicina, 1999, pp. 175, 182 (with English translation); 4 pages.
Zheng et al., Minipig as a potential translatable model for monoclonal antibody pharmacokinetics after intravenous and subcutaneous administration, mAbs, Mar.-Apr. 2012, 4(2):243-55. doi:10.4161/mabs.4.2.19387. Epub Mar. 1, 2012.
International Search Report for App. Ser. No. PCT/JP2015/006323, dated Jul. 12, 2018, 23 pages.
International Search Report for App. Ser. No. PCT/JP2017/028346, dated Oct. 31, 2017, 5 pages.
U.S. Appl. No. 15/712,727, Hattori et al., filed Jun. 3, 2016 (abandoned).
De Felice et al., "Formation of amyloid aggregates from human lysozyme and its disease-associated variants using hydrostatic pressure," FASEB J., Jul. 2004, 18(10):1099-101. (doi:10.1096/fj.03-1072fje; PMID 15155566).
Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).
Actemra (tocilizumab), Highlights of Prescribing Information, as revised in Aug. 2017 (1 page).
Ando et al., "Tocilizumab, a Proposed Therapy for the Cachexia of Interleukin6-Expressing Lung Cancer," Plos One, Jul. 10, 2014, 9(7):e102436. doi: 10.1371/journal.pone.0102436. eCollection 2014.
Barrabes et al., "Effect of sialic acid content on glycoprotein pI analyzed by two-dimensional electrophoresis," Electrophoresis, Sep. 2010, 31(17):2903-12. doi: 10.1002/elps.200900764.
Costa et al., "Efficacy of tocilizumab in a patient with refractory psoriatic arthritis," Clin Rheumatol, Sep. 2014, 33(9):1355-7.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23. doi: 10.1007/s00296-009-1075-4. Epub Jul. 29, 2009.
Honda et al., "Marginal zone B cells exacerbate endotoxic shock via interleukin-6 secretion induced by Fca/mR-coupled TLR4 signalling," Nat Commun, May 5, 2016, 7:11498. doi: 10.1038/ncomms11498.
Iijima et al., "Tocilizumab improves systemic rheumatoid vasculitis with necrotizing crescentic glomerulonephritis," Mod Rheumatol, Jan. 2015, 25(1):138-42. doi: 0.3109/14397595.2013.874748. Epub Feb. 18, 2014.
Kishimoto, "Interleukin-6 and its Receptor in Autoimmunity," J Autoimmun, Apr. 1992, 5 Suppl A:123-32.
Kondo et al., "A case of overlap syndrome successfully treated with tocilizumab: a hopeful treatment for refractory dermatomyositis?," Rheumatology (Oxford), Oct. 2014, 53(10):1907-8. doi: 10.1093/rheymatology/keu234. Epub May 23, 2014.
Mihara et al., "Anti-interleukin 6 receptor antibody inhibits murine AA-amyloidosis," J Rheymatol, Jun. 2004, 31(6):1132-8.
Mori et al., "Novel models of cancer-related anemia in mice inoculated with IL-6-producing tumor cells," Biomed Res, Feb. 2009, 30(1):47-51.
Motozawa et al., "Unique circumferential peripheral keratitis in relapsing polychondritis," Medicine (Baltimore), Oct. 2017, 96(41):e7951. doi: 10.1097/MD.0000000000007951.
Narazaki et al., "Therapeutic effect of tocilizumab on two patients with polymyositis," Rheumatology (Oxford), Jul. 2011, 50(7):1344-6. doi: 10.1093/rheumatology/ker152. Epub Apr. 2011.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6. doi: 10.1073/pnas.0802218105. Epub Jun. 24, 2008.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10.1007/s10165-011-0416-9. Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Silpa-Archa et al., "Outcome of tocilizumab treatment in refractory ocular inflammatory diseases," Acta Ophthalmol, Sep. 2016, 94(6):e400-6. doi: 10.1111/aos.13015. Epub Mar. 24, 2016.
Suzuki et al., "Anti-murine IL-6 receptor antibody inhibits IL-6 effects in vivo," Immunol Lett, Sep. 1991, 30(1):17-21.
U.S. Appl. No. 10/575,905, Hattori et al., filed Apr. 30, 2007.
U.S. Appl. No. 15/203,904, Igawa et al., filed Aug. 8, 2016 (abandoned).
U.S. Appl. No. 16/155,673, filed Oct. 9, 2018, Igawa et al.
U.S. Appl. No. 15/553,609, Kakehi et al., filed Aug. 25, 2017.
U.S. Appl. No. 16/226,798, Hattori et al., filed Dec. 20, 2018.

(56) References Cited

OTHER PUBLICATIONS

U.S. Appl. No. 15/490,936, Igawa et al., filed Apr. 19, 2017.
U.S. Appl. No. 14/520,423, Igawa et al., filed Oct. 22, 2014.
U.S. Appl. No. 14/340,883, Kuramochi et al., filed Jul. 25, 2014.
U.S. Appl. No. 13/357,145, Igawa et al., filed Nov. 22, 2011 (abandoned).
U.S. Appl. No. 13/518,861, Igawa et al., filed Oct. 4, 2012 (abandoned).
U.S. Appl. No. 16/155,673, Igawa et al., filed Oct. 9, 2018.
U.S. Appl. No. 13/582,073, Kuramochi et al., filed Dec. 20, 2012.
U.S. Appl. No. 15/132,996, Igawa et al., filed Apr. 19, 2016.
U.S. Appl. No. 15/288,965, Igawa et al., filed Oct. 7, 2016.
U.S. Appl. No. 14/007,947, Igawa et al., filed Sep. 26, 2013.
U.S. Appl. No. 15/963,449, Ruike et al., filed Apr. 26, 2018.
U.S. Appl. No. 15/976,288, Igawa et al., filed May 10, 2018.
U.S. Appl. No. 15/963,221, Nezu et al., filed Apr. 26, 2018.
U.S. Appl. No. 16/019,752, Ruike et al., filed Jun. 22, 2018.
Davie, "A Brief Historical Review of the Waterfall/Cascade of Blood Coagulation," J Biol Chem, Dec. 19, 2003, 278(51):50819-32. Epub Oct. 21, 2003.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (submitted by the Opponent during EPO opposition procedure for EP 2 006 381), 4 pages.
Granted claims of EP 2 275 443 (submitted on May 24, 2019 by the Patentee during EPO Opposition Procedure for EP 2 202 245), 1 page.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
U.S. Appl. No. 16/536,385, Hattori et al., filed Aug. 9, 2019.
U.S. Appl. No. 16/448,088, Igawa et al., filed Jun. 21, 2019.
U.S. Appl. No. 14/007,947, Igawa et al., filed Dec. 30, 2013.
U.S. Appl. No. 16/480,047, Shinomiya et al., filed Jul. 23, 2019.
Interleukin 6, Wikipedia, Feb. 22, 2019, XP055598802, (URL:https://protect-us.mimecast.com/s/6UxpCmZ28nsAp18JuGhTki?domain=en.wikipedia.org), retrieved on Jun. 24, 2019, 20 pages.
Antibodies from www.bioinforg.uk: Dr. Andrew C.R. Martin's Group, downloaded Jul. 11, 2018, 9 pages.
Beiboer et al., "Guided Selection of a Pan Carcinoma Specific Antibody Reveals Similar Binding Characteristics yet Structural Divergence Between the Original Murine Antibody and its Human Equivalent," J Mol Biol, Feb. 25, 2000, 296(3):833-49.
Biacore Sensor Surface Handbook, GE Healthcare, 2005, pp. 1-100.
Chugai NMO Clinical Trial Webinar, Sakura Star Study, dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI—No. 121786; submitted to Clinicaltrials.jp on Jan. 31, 2014; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI—No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, A phase I, multiple-dose study of SA237, Study JapicCTI—No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V12=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on

(56) References Cited

OTHER PUBLICATIONS

Jul. 22, 2014; downloaded from ClinicalTrials.gov archive on Sep. 5, 2019 as https://clinicaltrials.gov/ct2/history/NCT02073279?V_2=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V7=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.
Edwards et al., "The Remarkable Flexibility of the Human Antibody Repertoire: Isolation of Over One Thousand Different Antibodies to a Single Protein, BLyS," J Mol Biol, Nov. 14, 2003, 334(1):103-18.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 ashttps://www.clinicaltrialsregister.eu/ctr-search/trial/2013-003752-21/DE, 7 pages.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 ashttps://www.clinicaltrialsregister.eu/ctr-search/trial/2013-003752-21/IT, 5 pages.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/PL, 7 pages.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 ashttps://www.clinicaltrialsregister.eu/ctr-search/trial/2013-003752-21/ES, 7 pages.
F. Hoffmann—La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.
F. Hoffmann—La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Croatia; submitted to clinicaltrialsregister.eu on Dec. 15, 2016; downloaded from clinicaltrialsregister.eu archive on Sep. 5, 2019 ashttps://www.clinicaltrialsregister.eu/ctr-search/trial/2015-005431-41/CR, 6 pages.
F. Hoffmann—La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Poland; submitted to clinicaltrialsregister.eu on Apr. 7, 2016; downloaded from clinicaltrialsregister.eu archive on Sep. 5, 2019 ashttps://www.clinicaltrialsregister.eu/ctr-search/trial/2015-005431-41/PL, 6 pages.
Goel et al., "Plasticity within the Antigen-Combining Site May Manifest as Molecular Mimicry in the Humoral Immune Response," J Immunol, Dec. 15, 2004, 173(12):7358-67.
Harvey et al., Lippincott's Illustrated Reviews: Immunology, Second Edition, Chapter 2, "Antigens and Receptors," pp. 11-23 and Chapter 11, "Lymphocyte Effector Functions," pp. 141-157 (2013).
Igawa et al., "Engineered Monoclonal Antibody with Novel Antigen-Sweeping Activity In Vivo," PLoS One, May 7, 2013, 8(5):e63236. doi: 10.1371/journal.pone.0063236. Print 2013.
Kanyavuz et al., "Breaking the law: unconventional strategies for antibody diversification," Nat Rev Immunol, Jun. 2019, 19(6):355-368. doi: 10.1038/s41577-019-0126-7.
King, Applications and Engineering of Monoclonal Antibodies, 2005, pp. 1-236.
Kipriyanov et al., "Generation of Recombinant Antibodies," Mol Biotechnol, Sep. 1999, 12(2):173-201.
Klimka et al., "Human anti-CD30 recombinant antibodies by guided phage antibody selection using cell panning," Br J Cancer, Jul. 2000, 83(2):252-60.

(56) References Cited

OTHER PUBLICATIONS

Labrijn et al., "Therapeutic IgG4 antibodies engage in Fab-arm exchange with endogenous human IgG4 in vivo," Nat Biotechnol, Aug. 2009, 27(8):767-771 (with Supporting Online Material).
Lloyd et al., "Modelling the human immune response: performance of a $10^{11}$ human antibody repertoire against a broad panel of therapeutically relevant antigens," Protein Eng Des Sel, Mar. 2009, 22(3):159-68. doi: 10.1093/protein/gzn058. Epub Oct. 29, 2008.
Lund et al., "Multiple interactions of IgG with its core oligosaccharide can modulate recognition by complement and human Fc gamma receptor I and influence the synthesis of its oligosaccharide chains," The Journal of Immunology, Dec. 1996, 157(11):4963-4969.
Mellman, "The Importance of Being Acid: The Role of Acidification in Intracellular Membrane Traffic," J Exp Biol, Nov. 1992, 172:39-45.
Okiyama et al., "Therapeutic Effects of Interleukin-6 Blockade in a Murine Model of Polymyositis That Does Not Require Interleukin-17A," Arthritis Rheum, Aug. 2009, 60(8):2505-12.
Pirruccello-Straub, "Blocking extracellular activation of myostatin as a strategy for treating muscle wasting," Scientific Reports, Feb. 2, 2018, 8:2292.
Technical data sheet, "Polyclonal Antisera: Anti-Human C5," Quidel online catalogue, Jan. 1, 2010, pp. 1-1.
Yada et al., Lippincott's Illustrated Reviews: Immunology Second Edition, Nov. 30, 2013, Chapter 2, pp. 11-23 and Chapter 11, pp. 149-165 (Japanese version with English translation).
U.S. Appl. No. 10/575,193, filed Oct. 24, 2006, and issued as U.S. Pat. No. 8,062,635 on Nov. 22, 20111, Hattori et al.
U.S. Appl. No. 12/680,082, filed Jun. 25, 2010, and issued as U.S. Pat. No. 9,688,762 on Jun. 27, 22017, Igawa et al.
U.S. Appl. No. 13/497,269, filed Jun. 1, 20121, and issued as U.S. Pat. No. 10,150,808 on Dec. 11, 2018, Kuramochi et al.
U.S. Appl. No. 13/582,073, filed Dec. 20, 2012, and issued as U.S. Pat. No. 435,458 on Oct. 8, 2019, Kuramochi et al.
U.S. Appl. No. 14/019,117, Igawa et al., filed Sep. 5, 2013 (abandoned0.
U.S. Appl. No. 14/047,316, filed Oct. 7, 2013, and issued as U.S. Pat. No. 9,339,680 on Jul. 26, 2016, Kuramochi et al.
U.S. Appl. No. 14/974,488, filed Dec. 18, 2015, and issued as US Patent No. 10,000,560 on Jun. 19, 2018, Ruike et al.
U.S. Appl. No. 15/172,727, Hattori et al., filed Jun. 3, 2016.
U.S. Appl. No. 15/560,143, Kuramochi et al., filed Sep. 4, 2019.
U.S. Appl. No. 16/815,089, Igawa et al., filed Mar. 11, 2020.
U.S. Appl. No. 16/825,513, Hattori et al., filed Mar. 20, 2020.
Adlersberg et al., The Immunoglobulin Hinge (Interdomain) Region, Ric Clin Lab, Jul.-Sep. 1976, 6(3):191-205.
Aleshin et al., "Crystal Structure of C5b-6 Suggests Structural Basis for Priming Assembly of the Membrane Attack Complex," J Biol Chem, Jun. 1, 2012, 287(23):19642-19652. doi: 10.1074/jbc.M112.361121. Epub Apr. 12, 2012.
ALPROLIX® Intravenous, May 2019 revised ($9^{th}$ edition) (with English translation).
Altshuler et al., "Production of Recombinant Antibodies and Methods for Increasing Their Affinity," Progress of Biological Chemistry, 2010, 50:207 (with English translation).
Annotated amino acid sequence of the variable heavy (VH) and variable light (VL) domains of the monoclonal antibodies bevacizumab/Avastin, adalimumab/Humira, omalizumab/Xolair, and rituximab/Mabthera, dated Jul. 2019, 10 pages (submitted to the EPO with the written submission to attend oral proceedings on Sep. 6, 2019 by Opponent 1 in EP 11714860.1).
Arici, "Local Cytokines in Endometrial Tissue: The Role of Interleukin-8 in the Pathogenesis of Endometriosis," Ann NY Acad Sci, Mar. 2002, 955:101-109; discussion 118, pp. 396-406.
Astermark et al., "A randomized comparison of bypassing agents in hemophilia complicated by an inhibitor: the FEIBA NovoSeven Comparative (FENOC) Study," Blood, Jan. 15, 2007, 109(2):546-551. Epub Sep. 21, 2006.

Buckler, vol. 4 "Molecular Medicine and Medicinal Chemistry," Section 2.4 "Library Selection," Antibody Drug Discovery, edited by Clive Wood, 2012, pp. 49-57.
Chattopadhyay et al., "Interleukin-31 and Oncostatin-M Mediate Distinct Signaling Reactions and Response Patterns in Lung Epithelial Cells," J Biol Chem, Feb. 2, 2007, 282(5):3014-3026. doi:10.1074/jbc.M609655200.
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Coppola et al., "Acquired Inhibitors of Coagulation Factors: Part I—Acquired Hemophilia A,". Semin Thromb Hemost, Jul. 2012, 38(5):433-446. doi: 10.1055/s-0032-1315757. Epub Jun. 27, 2012.
Decision of the Opposition Division, dated Dec. 19, 2019, in EP 2 552 955, 18 pages (document submitted by Patentee (Chugai Seiyaku Kabushiki Kaisha) in the grounds of appeal on Apr. 28, 2020 in EP 2 552 955).
Declaration of Mr. Shigehisa Yatsuta of Genetyx Corporation, signed Dec. 20, 2019, 5 pages (document submitted in Opposition against EP 2 202 245).
Evidence for the publication date of Zalevsky et al., Nat Biotechnol, Feb. 2010, 28(2):157-9, 1 page (submitted to the EPO with the written submission to attend oral proceedings on Sep. 6, 2019 by Opponent 1 in EP 11714860.1).
Expert Declaration of J. Boucneau, dated Sep. 6, 2019, 13 pages (submitted to the EPO with the written submission to attend oral proceedings on Sep. 6, 2019 by Opponent 1 in EP 11714860.1).
Filmus et al., "Protein family review," Genome Biol, May 22, 2008, 9(5):224, 6 pages. doi:10.1186/gb-2008-9-5-224.
Franchini et al., "Acquired haemophilia A: A 2013 update," Thromb Haemost, Dec. 2013, 110(6):1114-1120. doi:10.1160/TH13-05-0363. Epub Sep. 5, 2013.
GenBank Accession No. AAA51925.1 (complement component C5 [*Homo sapiens*], Oct. 31, 1994, 3 pages.
Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7087. Epub Dec. 9, 2004.
Guidelines for the Management of Hemophilia, World Federation of Hemophilia, 2005, 52 pages.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
Hagiwara et al., "Effect of Emicizumab in improving coagulation ability in the presence of minor amount of Factor IX," Japanese Journal of Thrombosis and Hemostasis, 2017, 28(2):190 0-012 (with English translation).
Igawa et al., "Sweeping antibody as a novel therapeutic antibody modality capable of eliminating soluble antigens from circulation," Immunol Rev, Mar. 2016, 270(1):132-151.
Ishii et al., "Molecular design of antibody drugs," Journal of Pharmaceutical Science and Technology, Japan, 2014, 74(1):4-11 (with English translation).
Koyko et al., Chapter 4 "Antibody Structure and Function," Immunology: Teaching Aid, Moscow, 2008, pp. 61-62 (with English translation).
Kruse-Jarres, "Inhibitors: our greatest challenge. Can we minimize the incidence?," Haemophilia, Jan. 2013, 19 Suppl 1:2-7. doi: 10.1111/hae.12049.
Lillicrap, "von Willebrand disease: advances in pathogenetic understanding, diagnosis, and therapy," Blood, Nov. 28, 2013, 122(23):3735-3740. doi: 10.1182/blood-2013-06-498303. Epub Sep. 24, 013.
Marri et al., Chapter 4, Human Biochemistry, Moscow, Mir, 1993, 1:34 (with English translation).
Minami et al., "Bispecific Antibody ACE910 Improves Coagulation Function in Plasma of Patients with Factor XI Deficiency," Japanese Journal of Thrombosis and Hemostasis, 2015, 26(2):188 0-024 (with English translation).

(56) References Cited

OTHER PUBLICATIONS

Miyata, "Factor IX Abnormality—Molecular Defects of Factor IX," Japanese Journal of Thrombosis and Hemostasis, 1991, 2(1):1-11 (with English translation).

Muramatsu, "Latent myostatin specific elimination by sweeping antibody® is a novel therapeutic approach to improve muscle strength," Neuromuscular Disorders, Oct. 1, 2019, 29(Supplement 1):S86.

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213. doi: 10. 1111/jth.12474.

Muto et al., "Anti-factor IXa/X bispecific antibody ACE910 prevents joint bleeds in a long-term primate model of acquired hemophilia A," Blood, Nov. 13, 2014, 124(20):3165-3171. doi: 10. 1182/blood-2014-07-585737. Epub Oct. 1, 2014.

Nishimura et al., "Factor IX Fukuoka—Substitution of ASN$^{92}$ by His in the second epidermal growth factor-like domain results in defective interaction with factors VIIIa/X," Journal of Biological Chemistry, 1993, 268(32):24041-24046.

Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

Proprietor's (Chugai Seiyaku Kabushiki Kaisha) Submission dated Sep. 5, 2016 in EP11714860.1, 6 pages (submitted to the EPO with the written submission to attend oral proceedings on Sep. 6, 2019 by Opponent 1 in EP 11714860.1).

Proprietor's (Chugai Seiyaku Kabushiki Kaisha) Submission dated Sep. 19, 2016 in EP11714860.1, 3 pages (submitted to the EPO with the written submission to attend oral proceedings on Sep. 6, 2019 by Opponent 1 EP 11714860.1).

Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 5 in EP 11714860.1).

Rich et al., A global benchmark study using affinity-based biosensors, Anal Biochem, Mar. 15, 2009, 386(2):194-216. doi: 10.1016/j.ab.2008.11.021. Epub Nov. 27, 2008.

Shima et al., "Factor VIII—Mimetic Function of Humanized Bispecific Antibody in Hemophilia A," The New England Journal of Medicine, May 2016, 374(21):2044-2053. doi: 10.1056/NEJMoa1511769.

Shima, "The Forefront and Prospects of Hemophilia Treatment," The Journal of the Japan Pediatric Society, Mar. 1, 2017, 121(3):543-552 (with English translation).

Sigma product information for ACES buffer, 1 page (submitted to the EPO with the written submission to attend oral proceedings on Sep. 6, 2019 by Opponent 1 in EP 11714860.1).

Singer et al., "The Genetic Molecules," Genes & Genomes, 1998, 1:63-64 (with what are believed to be the corresponding pages from an English version of Genes & Genomes).

Skoog et al., "Calculation of the isoelectric points of polypeptides from the amino acid composition," trends in analytical chemistry, 1986, 5(4):82-83.

Table summarizing alleged lack of novelty over WO 2009/086320A, dated Jul. 9, 2009, 4 pages (submitted to the EPO with the written submission to attend oral proceedings on Sep. 6, 2019 by Opponent 1 in EP 11714860.1).

Tarantino et al., "Safety of human plasma-derived clotting factor products and their role in haemostasis in patients with haemophilia: meeting report," Haemophilia, Sep. 2007, 13(5):663-669.

Tarantul, "Antibodies," Explanatory Biotechnological Dictionary, Moscow, 2009, p. 72 (with English translation).

Uchida et al., "A first-in-human phase 1 study of ACE910, a novel factor VIII—mimetic bispecific antibody, in healthy subjects," Blood, Mar. 2016, 127(13):1633-1641. doi: 10.1182/blood-2015-06-650226. Epub Dec. 1, 2015.

Wang et al., "Complement C5a, C5a receptor and their antagonists: research advances," J Int Pharm Res, 2010, 37(3):181-186 (with English translation).

Wenig et al., "Structure of the streptococcal endopeptidase IdeS, a cysteine proteinase with strict specificity for IgG," Proc Nat Acad Sci USA, Dec. 14, 2004, 101(50):17371-17376.

Wolfman et al., "Activation of latent myostatin by the BMP-1/tolloid family of metalloproteinases," Proc Natl Acad Sci USA, Dec. 23, 2003, 100(26):15842-15846. Epub Dec. 11, 2003.

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

U.S. Appl. No. 12/295,039, Igawa et al., filed Jan. 20, 2009.

U.S. Appl. No. 12/295,075, filed Jan. 20, 2009, and issued as U.S. Pat. No. 9,670,269 on Jun. 6, 2017, Igawa et al.

U.S. Appl. No. 12/679,922, filed Oct. 1, 2010, and issued as U.S. Pat. No. 9,096,651 on Aug. 4, 2015, Igawa et al.

U.S. Appl. No. 12/680,082, filed Jun. 25, 2010, and issued as U.S. Pat. No. 9,688,762 on Jun. 27, 2017, Igawa et al.

U.S. Appl. No. 12/680,087, filed Jan. 3, 2011, and issued as U.S. Pat. No. 8,562,991 on Oct. 22, 2013, Igawa et al.

U.S. Appl. No. 12/680,112, Igawa et al., filed Jun. 23, 2010 (abandoned).

U.S. Appl. No. 12/745,781, Kuramochi et al., filed Sep. 13, 2010 (abandoned).

U.S. Appl. No. 12/809,138, filed Mar. 1, 2011, and issued as U.S. Pat. No. 8,575,317 on Nov. 5, 2013, Kuramochi et al.

U.S. Appl. No. 13/257,112, filed Nov. 22, 2011, and issued as U.S. Pat. No. 9,228,017 on Jan. 5, 2016, Igawa et al.

U.S. Appl. No. 13/257,145, Igawa et al., filed Nov. 22, 2011 (abandoned).

U.S. Appl. No. 13/320,317, filed Feb. 1, 2012, and issued as U.S. Pat. No. 9,340,615 on May 17, 2016, Maeda et al.

U.S. Appl. No. 13/434,643, Hattori et al., filed Mar. 29, 2012 (abandoned).

U.S. Appl. No. 13/497,269, filed Jun. 1, 2012, and issued as U.S. Pat. No. 10,150,808 on Dec. 11, 2018, Kuramochi et al.

U.S. Appl. No. 13/518,861, Igawa et al., field Oct. 4, 2012 (abandoned).

U.S. Appl. No. 13/524,528, Igawa et al., filed Jun. 15, 2012 (abandoned).

U.S. Appl. No. 13/582,073, filed Dec. 20, 2012, and issued as U.S. Pat. No. 10,435,458 on Oct. 8, 2019, Kuramochi et al.

U.S. Appl. No. 13/637,415, Igawa et al., filed Feb. 4, 2013.

U.S. Appl. No. 13/885,421, filed Aug. 30, 2013, and issued as U.S. Pat. No. 9,334,331 on May 10, 2016, Igawa et al.

U.S. Appl. No. 13/959,489, Igawa et al., filed Aug. 5, 2013 (abandoned).

U.S. Appl. No. 14/007,947, filed Dec. 30, 2013, and issued as U.S. Pat. No. 10,618,965, on Apr. 14, 2020, Igawa et al.

U.S. Appl. No. 14/019,117, Igawa et al., filed Sep. 5, 2013 (abandoned).

U.S. Appl. No. 14/019,712, Igawa et al., filed Sep. 6, 2013 (abandoned).

U.S. Appl. No. 14/047,316, filed Oct. 7, 2013, and issued as U.S. Pat. No. 9,399,680 on Jul. 26, 2016, Kuramochi et al.

U.S. Appl. No. 14/340,883, Kuramochi et al., filed Jul. 25, 2014 (abandoned).

U.S. Appl. No. 14/347,034, Igawa et al., filed Mar. 25, 2014 (abandoned).

U.S. Appl. No. 14/347,187, filed Jul. 25, 2014, and issued as U.S. Pat. No. 10,253,100 on Apr 9, 2019, Igawa et al.

U.S. Appl. No. 14/520,423, filed Oct. 22, 2014, and issued as U.S. Pat. No. 10,662,245 on May 26, 2020, Igawa et al.

U.S. Appl. No. 14/680,250, filed Apr. 7, 2015, and issued as U.S. Pat. No. 10,253,091 on Apr. 9, 2019, Igawa et al.

U.S. Appl. No. 14/741,786, filed Jun. 17, 2015, and issued as U.S. Pat. No. 9,828,429 on Nov. 28, 2017, Igawa et al.

U.S. Appl. No. 14/921,590, Hattori et al., filed Oct. 23, 2015 (abandoned).

U.S. Appl. No. 14/962,293, filed Dec. 8, 2015, and issued as U.S. Pat. No. 10,066,018 on Sep. 4, 2018, Igawa et al.

U.S. Appl. No. 14/974,350, filed Dec. 18, 2015, and issued as U.S. Pat. No. 9,765,135 on Sep. 19, 2017, Ruike et al.

(56) References Cited

OTHER PUBLICATIONS

U.S. Appl. No. 14/974,488, filed Dec. 18, 2015, and issued as U.S. Pat. No. 10,000,560 on Jun. 19, 2018, Ruike et al.
U.S. Appl. No. 15/015,287, filed Feb. 4, 2016, and issued as U.S. Pat. No. 9,969,800 on May 15, 2018, Igawa et al.
U.S. Appl. No. 15/024,063, Igawa et al., filed Mar. 23, 2016.
U.S. Appl. No. 15/050,145, Igawa et al., filed Feb. 22, 2016.
U.S. Appl. No. 15/132,996, filed Apr. 19, 2016, and issued as U.S. Pat. No. 10,450,381 on Oct. 22, 2019, Igawa et al.
U.S. Appl. No. 15/172,727, Hattori et al., filed Jun. 3, 2016 (abandoned).
U.S. Appl. No. 15/210,353, Igawa et al., filed Jul. 14, 2016.
U.S. Appl. No. 15/210,360, Igawa et al., filed Jul. 14, 2016.
U.S. Appl. No. 15/230,904, Igawa et al., filed Aug. 8, 2016 (abandoned).
U.S. Appl. No. 15/263,617, Igawa et al., filed Sep. 13, 2016 (abandoned).
U.S. Appl. No. 15/288,965, Igawa et al., filed Oct. 7, 2016 (abandoned).
U.S. Appl. No. 15/402,580, Hattori et al., filed Jan. 10, 2017 (abandoned).
U.S. Appl. No. 15/467,654, filed Mar. 23, 2017, and issued as U.S. Pat. No. 9,975,966 on May 22, 2018, Nezu et al.
U.S. Appl. No. 15/490,936, filed Apr. 19, 2017, and issued as U.S. Pat. No. 10/934,344 on Mar. 2, 2021.
U.S. Appl. No. 15/495,026, Igawa et al., filed Apr. 24, 2017.
U.S. Appl. No. 15/544,930, Murata et al., filed Jul. 20, 2017.
U.S. Appl. No. 15/553,609, filed Aug. 25, 2017, and issued as U.S. Pat. No. 10,774,148 on Sep. 15, 2020, Kakehi et al.
U.S. Appl. No. 15/562,186, Igawa et al., filed Sep. 27, 2017.
U.S. Appl. No. 15/614,842, Igawa et al., filed Jun. 6, 2017.
U.S. Appl. No. 15/617,008, Igawa et al., filed Jun. 8, 2017 (abandoned).
U.S. Appl. No. 15/688,004, filed Aug. 28, 2017, and issued as U.S. Pat. No. 10,023,630 on Jul. 17, 2018, Ruike et al.
U.S. Appl. No. 15/701,630, Hattori et al., filed Sep. 12, 2017 (abandoned).
U.S. Appl. No. 15/782,256, Igawa et al., filed Oct. 12, 2017.
U.S. Appl. No. 15/875,847, Igawa et al., filed Jan. 19, 2018 (abandoned).
U.S. Appl. No. 15/963,221, filed Apr. 26, 2018, and issued as U.S. Pat. No. 11,001,643 on May 11, 2021.
U.S. Appl. No. 15/963,345, Hattori et al., filed Apr. 26, 2018 (abandoned).
U.S. Appl. No. 15/963,449, filed Apr. 26, 2018 and issued as U.S. Pat. No. 10,738,111 on Aug. 11, 2020, Ruike et al.
U.S. Appl. No. 15/963,455, Ruike et al., filed Apr. 26, 2018.
U.S. Appl. No. 15/976,288, filed May 10, 2018, and issued as U.S. Pat. No. 10,519,229 on Dec. 31, 2019, Igawa et al.
U.S. Appl. No. 16/019,752, filed Jun. 27, 2018, and issued as U.S. Pat. No. 10,385,122 on Aug. 20, 2019, Ruike et al.
U.S. Appl. No. 16/028,140, Igawa et al., filed Jul. 5, 2018.
U.S. Appl. No. 16/041,976, Igawa et al., filed Jul. 23, 2018.
U.S. Appl. No. 16/061,454, Tanaka et al., filed Jun. 12, 2018.
U.S. Appl. No. 16/065,192, Ruike et al., filed Jun. 22, 2018.
U.S. Appl. No. 16/083,975, Kinoshita et al., filed Sep. 11, 2018.
U.S. Appl. No. 16/093,495, Saeki et al., filed Oct. 12, 2018.
U.S. Appl. No. 16/155,673, Igawa et al., filed Oct. 9, 2018 (abandoned).
U.S. Appl. No. 16/226,798, Hattori et al., filed Dec. 20, 2018 (abandoned).
U.S. Appl. No. 16/264,735, Igawa et al., filed Feb. 1, 2019.
U.S. Appl. No. 16/298,032, Igawa et al., filed Mar. 11, 2019.
U.S. Appl. No. 16/323,142, Kakiuchi et al., filed Feb. 4, 2019.
U.S. Appl. No. 16/448,088, Igawa et al., filed Jun. 21, 2019 (abandoned).
U.S. Appl. No. 16/459,791, Igawa et al., filed Jul. 2, 2019.
U.S. Appl. No. 16/480,047, Shinomiya et al., filed Jul. 23, 2019 (abandoned).
U.S. Appl. No. 17/076,938, Igawa et al., filed Oct. 22, 2020.
U.S. Appl. No. 17/130,736, Hattori et al., filed Dec. 22, 2020.
U.S. Appl. No. 16/008,486, Igawa et al., filed Jun. 14, 2018.
U.S. Appl. No. 17/263,961, Shinoyima et al., filed Jan. 27, 2021.
Abe et al., "Effect of $\beta_2$-microglobulin adsorption column on dialysis-related amyloidosis," Kidney Int, Oct. 2003, 64(4):1522-1528. doi: 10.1046/j.1523-1755.2003.00235.x.
Alignment sequences 1047 and 30, Jan. 26, 2021, 1 page (document cited in the office action dated Feb. 2, 2021 for EP 15869566.8).
Alignment sequences 472 and 24, Jan. 26, 2021, 1 page (document cited in the office action dated Feb. 2, 2021 for EP 15869566.8).
Altshuler et al., "Production of Recombinant Antibodies and Methods to Increase Their Affinity," Advances in Biological Chemistry, 2010, vol. 50, pp. 203-204, 215, 219-228 (with English translation).
Bork, "Powers and Pitfalls in Sequence Analysis: The 70% Hurdle," Genome Res, Apr. 2000, 10(4):398-400.
Burmester et al., "Efficacy and safety of subcutaneous tocilizumab versus intravenous tocilizumab in combination with traditional DMARDs in patients with RA at week 97 (SUMMACTA)," Ann Rheum Dis, Jan. 2016, 75(1):68-74.
D'Angelo et al., "Many Routes to an Antibody Heavy-Chain CDR3: Necessary, Yet Insufficient, for Specific Binding," Front Immunol, Mar. 8, 2018, 9:395. doi: 10.3389/fimmu.2018.00395.
Dagbay et al., "Structural basis of specific inhibition of extracellular activation of pro- or latent myostatin by the monoclonal antibody SRK-015," J Biol Chem, Apr. 17, 2020, 295(16):5404-5418.
Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i. PMID: 9649307.
Declaration of Christian Beil, signed Jun. 18, 2020, 6 pages (submitted by the opponent in Opposition against EP 3 050 963).
Declaration of Muramatsu Hiroyasu, signed Oct. 21, 2020, 5 pages (document cited in the office action dated Feb. 2, 2021 for EP 15869566.8).
Di Stefano et al., "Role of Interleukin-8 in the Pathogenesis and Treatment of COPD," Chest, Sep. 2004, 126(3):676-678. doi: 10.1378/chest.126.3.676.
Diamond et al., "Somatic mutation of the T15 heavy chain gives rise to an antibody with autoantibody specificity," Proc Natl Acad Sci USA, Sep. 1984, 81(18):5841-5844.
Fakhouri et al., "C3 glomerulopathy: a new classification," Nat Rev Nephrol, Aug. 2010, 6(8):494-499. doi: 10.1038/nrneph.2010.85. Epub Jul. 6, 2010. PMID: 20606628.
Feng et al., "Glypican-3 antibodies: A new therapeutic target for liver cancer," FEBS Lett, Jan. 21, 2014, 588(2):377-382. doi: 10.1016/j.febslet.2013.10.002. Epub Oct. 15, 2013.
Helguera et al., Chapter 23 "Antibody-Cytokine Fusion Proteins for the Therapy of Cancer," Methods Mol Med, 2005, 109:347-373. doi: 10.1385/1-59259-862-5:347. PMID: 15585931.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Kabat et al., "Sequences of Proteins of Immunological Interest," 1991, National Institute of Health Publication No. 91-3242, pp. 103, 310.
Kontermann et al., Chapter 4 "Mouse Immune Libraries for the Generation of ScFv Fragments Directed Against Human Cell Surface Antigens," 1:47-62 and Chapter 27 "Engineering of the Fc Region for Improved PK (FcRn Interaction)," Antibody Engineering, 2010, 1:415-427.
Krieg et al., "Functional Analysis of B and T Lymphocyte Attenuator Engagement on CD4+ and CD8+ T Cells," J Immunol, Nov. 15, 2005, 175(10):6420-64277. doi: 10.4049/jimmunol.175.10.6420. PMID: 16272294.
Makarova et al., "Experience of using eculizumab in children with atypical hemolytic-uremic syndrome," Nephrology, 2014, 18(3):84-88 (with English translation).
Marchalonis et al., "Antigenic mapping of a human lambda light chain: correlation with three dimensional structure," J Protein Chem, Apr. 1992, 11(2):129-137.

(56) References Cited

OTHER PUBLICATIONS

Mayilyan, "Complement genetics, deficiencies, and disease associations," Protein Cell, Jul. 2012, 3(7):487-496. doi: 10.1007/s13238-012-2924-6. Epub Jul. 10, 2012. PMID: 22773339; PMCID: PMC4875391.
Mease et al., "Secukinumab Inhibition of Interleukin-17A in Patients with Psoriatic Arthritis," N Engl J Med, Oct. 2015, 373(14):1329-1339.
Morris, "Epitope Mapping of Protein Antigens by Competition ELISA," The Protein Protocols Handbook, Jan. 1, 1996, pp. 595-600.
Otomo et al., "Structure of the heterodimeric complex between CAD domains of CAD and ICAD," Nat Struct Biol, Aug. 2000, 7(8):658-662. doi: 10.1038/77957. PMID: 10932250.
Raghavan et al., "Fc Receptors and Their Interactions with Immunoglobulins," Annu Rev Cell Dev Biol, 1996, 12:181-220.
Reference table: IMGT exon, EU and Kabat numbering of residues within the human IgG1 sequence; retrievied from the Internet: http://www.imgt.org/IMGTScientificChart/Numbering/HuIGHGnber.html on Jun. 1, 2020, 4 pages.
Roitt et al., Chapter 3 "Antibodies," Immunology, Moscow, Mir, 2000, pp. 110-111, 151 (with corresponding pages from an English version of Immunology).
Shirakawa et al., "Glypican-3 is a useful diagnostic marker for a component of hepatocellular carcinoma in human liver cancer," Int J Oncol, Mar. 2009, 34(3):649-656.
Siberil et al., "Molecular aspects of human FcγR interactions with IgG: Functional and therapeutic consequences," Immunol Lett, Aug. 15, 2006, 106(2):111-118. Epub Jun. 12, 2006.
Sikkink et al., "Biochemical and aggregation analysis of Bence Jones proteins from different light chain diseases," Amyloid, Mar. 2008, 15(1):29-39.
Stavenhagen et al., "Enhancing the potency of therapeutic monoclonal antibodies via Fc optimization," Adv Enzyme Regul, 2008, 48:152-164.
Tarantul, "Denaturation," Explanatory Biotechnological Dictionary, Russian-English, Moscow, Languages of Slavic cultures, 2009, p. 228 (with English translation).
Taylor et al., "A new era for hemophilia B treatment," Blood, Apr. 7, 2016, 127(14):1734-1736.
Watts et al., "Gene silencing by siRNAs and antisense oligonucleotides in the laboratory and the clinic," J Pathol, Jan. 2012, 226(2):365-379. doi:10.1002/path.2993.
WHO Drug Information, International Nonproprietary Names (INN), 2018, vol. 32 No. 2, pp. 283, 303-304.
USPTO Non-Final Office Action in U.S. Appl. No. 11/910,128, dated Nov. 28, 2016, 17 pages.
U.S. Appl. No. 10/575,193, filed Oct. 24, 2006, and issued as U.S. Pat. No. 8,062,635 on Nov. 22, 2011, *Hattori et al.*.
U.S. Appl. No. 10/575,905, *Hattori et al.*, filed Apr. 30, 2007 (abandoned).
U.S. Appl. No. 11/910,128, filed Oct. 7, 2008, and issued as U.S. Pat. No. 10,011,858 on Jul. 3, 2018, *Igawa et al.*,.
U.S. Appl. No. 11/910,836, *Hattori et al.*, filed Jan. 12, 2009 (abandoned).
U.S. Appl. No. 12/295,039, filed Jan. 20, 2009 and issued as U.S. Pat. No. 11,046,784 on Jun. 29, 2021, *Igawa et al.*
U.S. Appl. No. 17/359,867, *Igawa et al.*, filed Jun. 28, 2021.
U.S. Appl. No. 12/295,075, filed Jan. 20, 2009, and issued as U.S. Pat. No. 9,670,269 on Jun. 6, 2016, *Igawa et al.*
U.S. Appl. No. 16/496,089, *Shima et al.*, filed Sep. 20, 2019.
U.S. Appl. No. 16/514,467, *Ruike et al.*, filed Jul. 19, 2019.
U.S. Appl. No. 16/536,385, *Hattori et al.*, filed Aug. 9, 2019 (abandoned).
U.S. Appl. No. 16/560,143, *Kuramochi et al.*, filed Sep. 4, 2019.
U.S. Appl. No. 16/697,310, *Igawa et al.*, filed Nov. 27, 2019.
U.S. Appl. No. 16/806,027, *Igawa et al.*, filed Mar. 2, 2020.
U.S. Appl. No. 16/815,089, *Igawa et al.*, filed Mar. 11, 2020 (abandoned).
U.S. Appl. No. 16/825,513, *Hattori et al.*, filed Mar. 20, 2020 (abandoned).
U.S. Appl. No. 16/838,415, *Igawa et al.*, filed Apr. 2, 2020.
U.S. Appl. No. 16/889,066, *Ruike et al.*, filed Jun. 1, 2020.
U.S. Appl. No. 16/928,129, *Shinomiya et al.*, filed Jul. 14, 2020.
U.S. Appl. No. 16/983,115, *Kakehi et al.*, filed Aug. 3, 2020.
U.S. Appl. No. 17/076,938, *Igawa et al.*, filed Oct. 22, 2020 (abandoned).
U.S. Appl. No. 17/336,538, *Igawa et al.*, filed Jun. 2, 2021.
U.S. Appl. No. 17/097,298, *Igawa et al.*, filed Nov. 13, 2020.
U.S. Appl. No. 17/130,736, *Hattori et al.*, filed Dec. 22, 2020 (abandoned).
U.S. Appl. No. 17/389,534, *Hattori et al.*, filed Jul. 30, 2021.
U.S. Appl. No. 17/263,961, *Shinomiya et al.*, filed Jan. 27, 2021.
U.S. Appl. No. 16/758,128, *Hosoguchi et al.*, filed Apr. 22, 2020.
U.S. Appl. No. 17/225,273, *Nezu et al.*, filed Apr. 8, 2021.
U.S. Appl. No. 17/333,256, *Kakiuchi et al.*, filed May 28, 2021.
U.S. Appl. No. 17/352,652, *Kinoshita et al.*, filed Jun. 21, 2021.
U.S. Appl. No. 16/539,765, Igawa et al. filed Aug. 13, 2019.
U.S. Appl. No. 17/144,342, Igawa et al. filed Jan. 8, 2021.
Aalberse et al., "IgG4 breaking the rules," Immunology, Jan. 2002, 105( 1) :9-19.
Annex 1 Accompanying Response to Statement of Grounds of Appeal of Opponent 2 (Alexion Pharmaceuticals, Inc.), dated Sep. 16, 2020, in opposition against EP 2 552 955, 29 pages.
Annex from opponent 2's submission of Jun. 7, 2018, 13 pages (cited by opponent during the opposition proceedings of EP 2 202 245 on May 19, 2021).
Antibodies in Example 29 of EP 2 202 245, 2 pages (cited by opponent during the opposition proceedings of EP 2 202 245 on May 19, 2020).
Application as filed for EP 2 698 431, 375 pages (document cited during opposition proceedings of EP 2 698 431 on Jun. 23, 2021).
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Datta-Mannan et al., "FcRn Affinity-Pharmacokinetic Relationship of Five Human IgG4 Antibodies Engineered for Improved In Vitro FcRn Binding Properties in Cynomolgus Monkeys," DrugMetab Dispos. Aug. 2012;40(8): 545-1555.
English translation of PCT/JP2011/072550, 283 pages, corresponding to WO 2012/132067, cited in IDS filed on Oct. 5, 2017. The translation was submitted in the opposition proceeding for EP 2 698 431 on Jun. 23, 2021.
English translation of PCT/JP2012/054624, 110 pages, corresponding to WO 2012/115241, cited in IDS filed on Oct. 5, 2017. The document was submitted in the opposition proceeding for EP 2 698 431 on Jun. 23, 2021.
EUTM register extract—Biacore, 4 pages (document downloaded on Aug. 26, 2020, submitted in opposition proceedings of EP 2 552 955, and posted by EPO on Sep. 15, 2020).
Glatter, "Evaluation of Small-Angle Scattering Data from Lamellar and Cylindrical Particles by the Indirect Transformation Method," J Appl Ciyst, 1980, 13, pp. 577-584.
Golay et al., "Design and Validation of a Novel Generic Platform for the Production of Tetravalent IgG1-like Bispecific Antibodies," J Immunol, Apr. 1, 2016, 196 (7):3199-3211.
Guidance on the use of International Nonproprietary Names (INNs) for Pharmaceutical Substances, World Health Organisation, 2017, 54 pages (document submitted in opposition proceedings of EP 2 552 955 and posted by EPO on Sep. 16, 2020).
Han et al., "Monoclonal antibodies: interspecies scaling with minimal preclinical information," Ther Deliv, Mar. 2011, 2(3):359-368.
Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.
Jung et al., "Aglycosylated IgG variants expressed in bacteria that selectively bind FcKRI potentiate tumor cell killing by monocyte-dendritic cells," Proc Natl Acad Sci USA, Jan. 12, 2010, 107(2):604-609.

(56) References Cited

OTHER PUBLICATIONS

Lescar et al., "Crystal Structure of a Cross-reaction Complex between Fab F9.13.7 and Guinea Fowl Lysozyme," J Biol Chem, Jul. 28, 1995, 270(30), 18067-18076.

Mazor et al., "Improving target cell specificity using a novel monovalent bispecific IgG design," mAbs, Mar./Apr. 7, 2015(2):377-389.

Mimoto et al., "Engineered antibody Fc variant with selectively enhanced FcγRIIb binding over both FcγRIIa(R131) and FcγRIIa(H131)," Protein Eng Des Sei, Oct. 2013, 26(10):589-598. doi: 10.1093/protein/gzt022. Epub Jun. 5, 2013.

Moore et al., "Engineered Fc variant antibodies with enhanced ability to recruit complement and mediate effector functions," mAbs, Mar.-Apr. 2, 2010(2): 181-189.

Muller et al., "The first constant domain ($C_H1$ and $C_L$) of an antibody used as heterodimerization domain for bispecific miniantibodies," FEBS Lett, Jan. 30, 1998, 422(2):259-264.

Nishimura et al., "An Optimized Crovalimab Dose and Regimen Reduced the Formation of Drug-Target-Drug Complexes in Patients with Paroxysmal Nocturnal Hemoglobinuria from the Phase I/II Composer Trial," Blood, 2020, 136 (Supplement 1):2-3.

Notice of Opposition of Opponent 1 (Ablynx N.V.), dated Feb. 2, 2018, against EP 2 552 955, 50 pages.

Statement of Facts and Arguments in Support of Opposition by Opponent 2 (Alexion Pharmaceuticals, Inc.), dated Feb. 2, 2018, submitted in opposition against EP 2 552 955, 39 pages.

Opposition of Opponent 5 (Shire Human Genetic Therapies, Inc.), dated Feb. 5, 2018, against EP 2 552 955, 70 pages.

Padlan, "Anatomy of the Antibody Molecule," Mol Immunol, Feb. 1994, 31(3):169-217.

PCT/JP2011/001888, filed Mar. 30, 2011, corresponding to WO 2011/122011, cited in IDS filed on Oct. 5, 2017, 203 pages (document cited in opposition proceedings against EP 2 698 431 on Jun. 23, 2021).

Presta et al., "Engineering therapeutic antibodies for improved function," Biochem Soc Trans, Aug. 30, 2002(4):487-490.

Roitt et al., Chapter 3 "Antibodies," Immunology, 2006, pp. 62-68.

Roth et al., "The complement C5 inhibitor crovalimab in paroxysmal nocturnal hemoglobinuria," Blood, Mar. 19, 2020, 135(12):912-920. doi: 10.1182/blood.2019003399.

Screenshots of Genetyx software, 3 pages (document cited by opponent during the opposition proceedings of EP 2 202 245 on May 22, 2020).

Screenshots of the web-based calculator, 9 pages (document cited by opponent during the opposition proceedings of EP 2 202 245 on May 22, 2020).

Sections of the Genetyx manual pertaining to isoelectric point, 5 pages (document cited by opponent during the opposition proceedings of EP 2 202 245 on May 22, 2020) (with English translation).

Response by Opponent 1 (Ablynx N.V.), dated Sep. 6, 2019, submitted in opposition against EP 2 552 955, 57 pages.

Final Written Submissions of Opponent 2 (Alexion Pharmaceuticals, Inc.), dated Sep. 6, 2019, submitted in opposition against EP 2 552 955, 26 pages.

Reply from Opponent 5 (Shire Human Genetic Therapies, Inc.), dated Sep. 6, 2019, submitted in opposition against EP 2 552 955, 15 pages.

Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.

Wang et al., "Monoclonal Antibodies with Identical Fc Sequences Can Bind to FcRn Differentially with Pharmacokinetic Consequences," DrugMetab Dispos, Sep. 2011, 3 9(9): 1469-1477. doi: 10.1124/dmd.111.039453. Epub May 24, 2011.

Wang et al., "Applications of Eculizumab, a humanized anti-complement factor C5 monoclonal antibody," Chinese Journal of Clinical Pharmacology and Therapeutics, 2015, 20(4)455-459 (with English abstract).

Wong et al., "Anticomplement C5 therapy with eculizumab for the treatment of paroxysmal nocturnal hemoglobinuria and atypical hemolytic uremic syndrome," Transl Res, Feb. 2015, 165(2):306-320.

\* cited by examiner

| | HCDR1 | HCDR2 | HCDR3 | LCDR1 | LCDR2 | LCDR3 |
|---|---|---|---|---|---|---|
| WT | SDHAWS (SEQ ID NO: 1) | YISYSGITYNPSLKS (SEQ ID NO: 2) | SLARTTAMDY (SEQ ID NO: 3) | RASQDISSYLN (SEQ ID NO: 4) | YTSRLHS (SEQ ID NO: 5) | QQGNTLPYT (SEQ ID NO: 6) |
| RD_68 | WDHAWS (SEQ ID NO: 26) | | | | | |
| RD_12 | | YISYSGITSYNPSLKS (SEQ ID NO: 44) | | | | |
| RD_61 | | YISYSGITNYNPSLKS (SEQ ID NO: 45) | | | | |
| RD_79 | | YISYSGIRTYNPSLKS (SEQ ID NO: 43) | | | | |
| RD_82 | | EISYSGITTYNPSLKS (SEQ ID NO: 42) | | | | |
| RD_2 | | | ILARTTAMDY (SEQ ID NO: 46) | | | |
| RD_3 | | | SLARATAMDY (SEQ ID NO: 51) | | | |
| RD_4 | | | VLARTTAMDY (SEQ ID NO: 47) | | | |
| RD_6 | | | LLARATAMDY (SEQ ID NO: 57) | | | |
| RD_80 | | | ILARTTAMDY (SEQ ID NO: 48) | | | |
| RD_78 | | | SIARTTVLDY (SEQ ID NO: 65) | | | |
| RD_81 | | | SLARITSMDY (SEQ ID NO: 54) | | | |
| RD_83 | | | SLARITAMDY (SEQ ID NO: 52) | | | |
| RD_84 | | | SIARTTAMDY (SEQ ID NO: 50) | | | |
| RD_26 | | | | RASRDISSYLN (SEQ ID NO: 67) | | |
| RD_72 | | | | RASQDISSELN (SEQ ID NO: 69) | | QQSNTLPYT (SEQ ID NO: 75) |
| RD_22 | | | | | | QQGNSLPYT (SEQ ID NO: 78) |
| RD_23 | | | | | | QQGNRLPYT (SEQ ID NO: 76) |
| RD_28 | | | | | | QQGNTLPYT (SEQ ID NO: 72) |
| RDC_15L | | | | | | SQGNTLPYT (SEQ ID NO: 74) |

FIG. 4-1

| | HCDR1 | HCDR2 | HCDR3 | LCDR1 | LCDR2 | LCDR3 |
|---|---|---|---|---|---|---|
| WT | SDHAWS (SEQ ID NO: 1) | YISYSGITTYNPSLKS (SEQ ID NO: 2) | SLARTTAMDY (SEQ ID NO: 3) | RASQDISSYLN (SEQ ID NO: 4) | YTSRLHS (SEQ ID NO: 5) | QQGNTLPYT (SEQ ID NO: 6) |
| RD_37 | <u>T</u>DHAWS (SEQ ID NO: 27) | | | | | |
| RD_8 | <u>D</u>DHAWS (SEQ ID NO: 28) | | | | | |
| RD_9 | SDHA<u>L</u>S (SEQ ID NO: 40) | | | | | |
| RD_11 | <u>N</u>DHAWS (SEQ ID NO: 29) | | | | | |
| RD_30 | SDHA<u>V</u>S (SEQ ID NO: 41) | | | | | |
| RD_31 | <u>R</u>DHAWS (SEQ ID NO: 30) | | | | | |
| RD_32 | <u>V</u>DHAWS (SEQ ID NO: 31) | | | | | |
| RD_33 | <u>E</u>DHAWS (SEQ ID NO: 32) | | | | | |
| RD_34 | <u>A</u>DHAWS (SEQ ID NO: 33) | | | | | |
| RD_35 | <u>Q</u>DHAWS (SEQ ID NO: 34) | | | | | |
| RD_36 | <u>Y</u>DHAWS (SEQ ID NO: 35) | | | | | |
| RD_38 | <u>L</u>DHAWS (SEQ ID NO: 36) | | | | | |
| RD_42 | <u>H</u>DHAWS (SEQ ID NO: 37) | | | | | |
| RD_45 | <u>E</u>DHAWS (SEQ ID NO: 38) | | | | | |
| RD_46 | <u>C</u>DHAWS (SEQ ID NO: 39) | | | | | |
| RD_5 | | | <u>L</u>LARTTAMDY (SEQ ID NO: 49) | | | |
| RD_18 | | | | <u>E</u>ASQDISSYLN (SEQ ID NO: 66) | | |
| RD_20 | | | | RAS<u>I</u>DISSYLN (SEQ ID NO: 68) | | |
| RD_27 | | | | RASQDISSYL<u>S</u> (SEQ ID NO: 70) | | |
| RD_73 | | | | RASQDISS<u>E</u>LN (SEQ ID NO: 69) | | |
| RD_29 | | | | | | <u>N</u>QGNTLPYT (SEQ ID NO: 73) |
| RDC_14H | | | SLAR<u>S</u>TAMDY (SEQ ID NO: 53) | | | |
| PF_3H | | | SLARTT<u>V</u>MDY (SEQ ID NO: 55) | | | |
| PF_4H | | | SLARTTAL<u>D</u>Y (SEQ ID NO: 56) | | | |

FIG. 4-2

| | HCDR1 | HCDR2 | HCDR3 | LCDR1 | LCDR2 | LCDR3 |
|---|---|---|---|---|---|---|
| WT | SDHAWS (SEQ ID NO: 1) | YISYSGITYNPSLKS (SEQ ID NO: 2) | SLARTTAMDY (SEQ ID NO: 3) | RASQDISSYLN (SEQ ID NO: 4) | YTSRLHS (SEQ ID NO: 5) | QQGNTLPYT (SEQ ID NO: 6) |
| RDC_2H | | | VLARATAMDY (SEQ ID NO: 58) | | | |
| RDC_3H | | | ILARATAMDY (SEQ ID NO: 59) | | | |
| RDC_4H | | | ILARATAMDY (SEQ ID NO: 60) | | | |
| RDC_5H | | | VLARITAMDY (SEQ ID NO: 61) | | | |
| RDC_6H | | | ILARITAMDY (SEQ ID NO: 62) | | | |
| RDC_7H | | | ILARITAMDY (SEQ ID NO: 63) | | | |
| RDC_8H | | | LLARITAMDY (SEQ ID NO: 64) | | | |
| RDC_27H | | YISYSGITNYNPSLKS (SEQ ID NO: 45) | LLARATAMDY (SEQ ID NO: 57) | | | |
| RDC_28H | | YISYSGITNYNPSLKS (SEQ ID NO: 45) | VLARATAMDY (SEQ ID NO: 58) | | | |
| RDC_30H | | YISYSGITNYNPSLKS (SEQ ID NO: 45) | ILARATAMDY (SEQ ID NO: 59) | | | |
| RDC_29H | | YISYSGITNYNPSLKS (SEQ ID NO: 45) | VLARITAMDY (SEQ ID NO: 61) | | | |
| RDC_32H | | YISYSGITNYNPSLKS (SEQ ID NO: 45) | ILARITAMDY (SEQ ID NO: 62) | | | |
| RDC_11L | | | | | | QQGNRLPYT (SEQ ID NO: 79) |

FIG. 5

A: M14ΔGK  B: IgG4  C: IgG1  D: M11ΔGK  E: IgG2  F: M17ΔGK

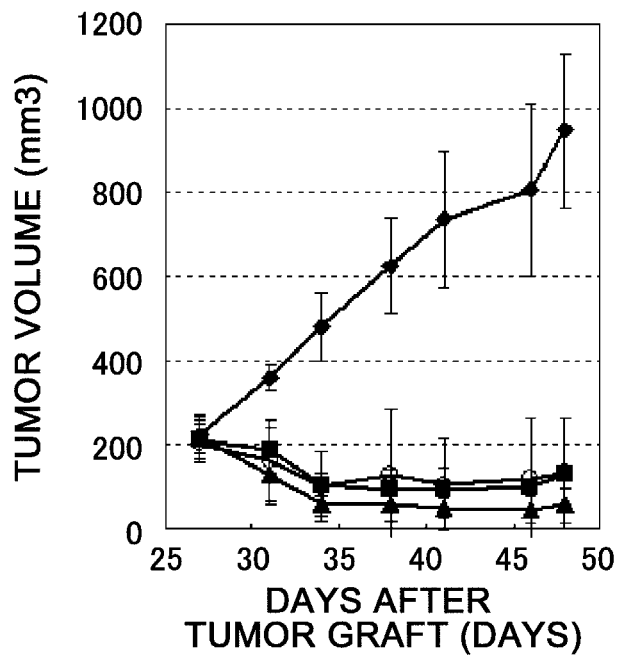
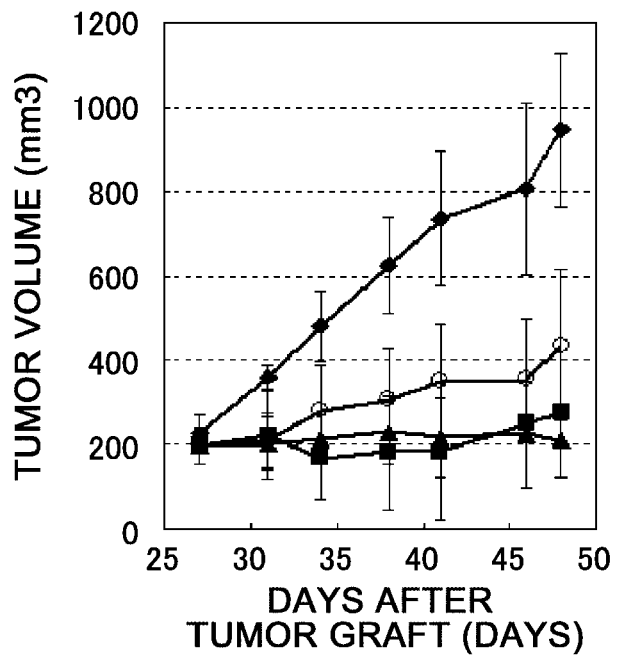
FIG. 55

SEQUENCE LISTING

<160> NUMBER OF SEQ ID NOS: 246

<210> SEQ ID NO 1
<211> LENGTH: 6
<212> TYPE: PRT
<213> ORGANISM: Mus musculus

<400> SEQUENCE: 1

Ser Asp His Ala Trp Ser
1               5

<210> SEQ ID NO 2
<211> LENGTH: 16
<212> TYPE: PRT
<213> ORGANISM: Mus musculus

<400> SEQUENCE: 2

Tyr Ile Ser Tyr Ser Gly Ile Thr Thr Tyr Asn Pro Ser Leu Lys Ser
1               5                   10                  15

<210> SEQ ID NO 3
<211> LENGTH: 10
<212> TYPE: PRT
<213> ORGANISM: Mus musculus

<400> SEQUENCE: 3

Ser Leu Ala Arg Thr Thr Ala Met Asp Tyr
1               5                   10

<210> SEQ ID NO 4
<211> LENGTH: 11
<212> TYPE: PRT
<213> ORGANISM: Mus musculus

<400> SEQUENCE: 4

Arg Ala Ser Gln Asp Ile Ser Ser Tyr Leu Asn
1               5                   10

<210> SEQ ID NO 5
<211> LENGTH: 7
<212> TYPE: PRT
<213> ORGANISM: Mus musculus

<400> SEQUENCE: 5

Tyr Thr Ser Arg Leu His Ser
1               5

<210> SEQ ID NO 6
<211> LENGTH: 9
<212> TYPE: PRT
<213> ORGANISM: Mus musculus

<400> SEQUENCE: 6

Gln Gln Gly Asn Thr Leu Pro Tyr Thr
1               5

<210> SEQ ID NO 7
<211> LENGTH: 30
<212> TYPE: PRT
<213> ORGANISM: Homo sapiens

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr
            20                  25                  30

<210> SEQ ID NO 8
<211> LENGTH: 14
<212> TYPE: PRT
<213> ORGANISM: Homo sapiens

<400> SEQUENCE: 8

Trp Val Arg Gln Pro Pro Gly Arg Gly Leu Glu Trp Ile Gly
1               5                   10

<210> SEQ ID NO 9
<211> LENGTH: 32
<212> TYPE: PRT
<213> ORGANISM: Homo sapiens

<400> SEQUENCE: 9

Arg Val Thr Met Leu Arg Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30

<210> SEQ ID NO 10
<211> LENGTH: 11
<212> TYPE: PRT
<213> ORGANISM: Homo sapiens

<400> SEQUENCE: 10

Trp Gly Gln Gly Ser Leu Val Thr Val Ser Ser
1               5                   10

<210> SEQ ID NO 11
<211> LENGTH: 23
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 12
<211> LENGTH: 15
<212> TYPE: PRT
<213> ORGANISM: Homo sapiens

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Homo sapiens

<400> SEQUENCE: 13

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

```
<210> SEQ ID NO 14
<211> LENGTH: 10
<212> TYPE: PRT
<213> ORGANISM: Homo sapiens

<400> SEQUENCE: 14

Phe Gly Gln Gly Thr Lys Val Glu Ile Lys
1               5                   10

<210> SEQ ID NO 15
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 15

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 16
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
```

```
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 17

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 18
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
    50                      55                      60

Leu Ser Ser Val Val Thr Val Pro Ser Ser Leu Gly Thr Gln Thr
65                      70                      75                      80

Tyr Ile Cys Asn Val Asn His Lys Pro Ser Asn Thr Lys Val Asp Lys
                85                      90                      95

Lys Val Glu Pro Lys Ser Cys Asp Lys Thr His Thr Cys Pro Pro Cys
                100                     105                     110

Pro Ala Pro Glu Leu Leu Gly Gly Pro Ser Val Phe Leu Phe Pro Pro
                115                     120                     125

Lys Pro Lys Asp Thr Leu Met Ile Ser Arg Thr Pro Glu Val Thr Cys
130                     135                     140

Val Val Val Asp Val Ser His Glu Asp Pro Glu Val Lys Phe Asn Trp
145                     150                     155                     160

Tyr Val Asp Gly Val Glu Val His Asn Ala Lys Thr Lys Pro Arg Glu
                165                     170                     175

Glu Gln Tyr Asn Ser Thr Tyr Arg Val Val Ser Val Leu Thr Val Leu
                180                     185                     190

His Gln Asp Trp Leu Asn Gly Lys Glu Tyr Lys Cys Lys Val Ser Asn
                195                     200                     205

Lys Ala Leu Pro Ala Pro Ile Glu Lys Thr Ile Ser Lys Ala Lys Gly
                210                     215                     220

Gln Pro Arg Glu Pro Gln Val Tyr Thr Leu Pro Pro Ser Arg Asp Glu
225                     230                     235                     240

Leu Thr Lys Asn Gln Val Ser Leu Thr Cys Leu Val Lys Gly Phe Tyr
                245                     250                     255

Pro Ser Asp Ile Ala Val Glu Trp Glu Ser Asn Gly Gln Pro Glu Asn
                260                     265                     270

Asn Tyr Lys Thr Thr Pro Pro Val Leu Asp Ser Asp Gly Ser Phe Phe
                275                     280                     285

Leu Tyr Ser Lys Leu Thr Val Asp Lys Ser Arg Trp Gln Gln Gly Asn
                290                     295                     300

Val Phe Ser Cys Ser Val Met His Glu Ala Leu His Asn His Tyr Thr
305                     310                     315                     320

Gln Lys Ser Leu Ser Leu Ser Pro Gly Lys
                325                     330

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                       10                      15

Ser Thr Ser Glu Ser Thr Ala Ala Leu Gly Cys Leu Val Lys Asp Tyr
                20                      25                      30

Phe Pro Glu Pro Val Thr Val Ser Trp Asn Ser Gly Ala Leu Thr Ser
                35                      40                      45

Gly Val His Thr Phe Pro Ala Val Leu Gln Ser Ser Gly Leu Tyr Ser
    50                      55                      60

Leu Ser Ser Val Val Thr Val Pro Ser Ser Asn Phe Gly Thr Gln Thr
65                      70                      75                      80

Tyr Thr Cys Asn Val Asp His Lys Pro Ser Asn Thr Lys Val Asp Lys

```
             85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val His Gln Asp Trp
                180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
        210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
290                 295                 300
Ser Val Met His Glu Ala Leu His Asn His Tyr Thr Gln Lys Ser Leu
305                 310                 315                 320
Ser Leu Ser Pro Gly Lys
            325

<210> SEQ ID NO 21
<211> LENGTH: 327
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 22
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser
        115

<210> SEQ ID NO 23
<211> LENGTH: 107
<212> TYPE: PRT
<213> ORGANISM: Artificial
<220> FEATURE:
```

<223> OTHER INFORMATION: An artificially synthesized peptide sequence

<400> SEQUENCE: 23

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105
```

<210> SEQ ID NO 24
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240
```

-continued

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 25
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

-continued

```
Thr Pro Pro Val Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu

<210> SEQ ID NO 26
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 26

Trp Asp His Ala Trp Ser
1               5

<210> SEQ ID NO 27
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 27

Thr Asp His Ala Trp Ser
1               5

<210> SEQ ID NO 28
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 28

Asp Asp His Ala Trp Ser
1               5

<210> SEQ ID NO 29
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 29

Asn Asp His Ala Trp Ser
1               5

<210> SEQ ID NO 30
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 30

Arg Asp His Ala Trp Ser
1               5

<210> SEQ ID NO 31
<211> LENGTH: 6
```

```
<212> TYPE: PRT
<213> ORGANISM: Artificial
<220> FEATURE:
<223> OTHER INFORMATION: An artificially synthesized peptide sequence

<400> SEQUENCE: 31

Val Asp His Ala Trp Ser
1               5

<210> SEQ ID NO 32
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 32

Phe Asp His Ala Trp Ser
1               5

<210> SEQ ID NO 33
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 33

Ala Asp His Ala Trp Ser
1               5

<210> SEQ ID NO 34
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 34

Gln Asp His Ala Trp Ser
1               5

<210> SEQ ID NO 35
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 35

Tyr Asp His Ala Trp Ser
1               5

<210> SEQ ID NO 36
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 36

Leu Asp His Ala Trp Ser
1               5

<210> SEQ ID NO 37
<211> LENGTH: 6
<212> TYPE: PRT
```

```
<213> ORGANISM: Artificial
<220> FEATURE:
<223> OTHER INFORMATION: An artificially synthesized peptide sequence

<400> SEQUENCE: 37

His Asp His Ala Trp Ser
1               5

<210> SEQ ID NO 38
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 38

Glu Asp His Ala Trp Ser
1               5

<210> SEQ ID NO 39
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 39

Cys Asp His Ala Trp Ser
1               5

<210> SEQ ID NO 40
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 40

Ser Asp His Ala Ile Ser
1               5

<210> SEQ ID NO 41
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 41

Ser Asp His Ala Val Ser
1               5

<210> SEQ ID NO 42
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 42

Phe Ile Ser Tyr Ser Gly Ile Thr Thr Tyr Asn Pro Ser Leu Lys Ser
1               5                   10                  15

<210> SEQ ID NO 43
<211> LENGTH: 16
<212> TYPE: PRT
<213> ORGANISM: Artificial
```

```
<220> FEATURE:
<223> OTHER INFORMATION: An artificially synthesized peptide sequence

<400> SEQUENCE: 43

Tyr Ile Ser Tyr Ser Gly Ile Arg Thr Tyr Asn Pro Ser Leu Lys Ser
1               5                   10                  15

<210> SEQ ID NO 44
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 44

Tyr Ile Ser Tyr Ser Gly Ile Thr Ser Tyr Asn Pro Ser Leu Lys Ser
1               5                   10                  15

<210> SEQ ID NO 45
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 45

Tyr Ile Ser Tyr Ser Gly Ile Thr Asn Tyr Asn Pro Ser Leu Lys Ser
1               5                   10                  15

<210> SEQ ID NO 46
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 46

Ile Leu Ala Arg Thr Thr Ala Met Asp Tyr
1               5                   10

<210> SEQ ID NO 47
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 47

Val Leu Ala Arg Thr Thr Ala Met Asp Tyr
1               5                   10

<210> SEQ ID NO 48
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 48

Thr Leu Ala Arg Thr Thr Ala Met Asp Tyr
1               5                   10

<210> SEQ ID NO 49
<211> LENGTH: 10
<212> TYPE: PRT
<213> ORGANISM: Artificial
<220> FEATURE:
```

<223> OTHER INFORMATION: An artificially synthesized peptide sequence

<400> SEQUENCE: 49

Leu Leu Ala Arg Thr Thr Ala Met Asp Tyr
1               5                   10

<210> SEQ ID NO 50
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 50

Ser Thr Ala Arg Thr Thr Ala Met Asp Tyr
1               5                   10

<210> SEQ ID NO 51
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 51

Ser Leu Ala Arg Ala Thr Ala Met Asp Tyr
1               5                   10

<210> SEQ ID NO 52
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 52

Ser Leu Ala Arg Ile Thr Ala Met Asp Tyr
1               5                   10

<210> SEQ ID NO 53
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 53

Ser Leu Ala Arg Ser Thr Ala Met Asp Tyr
1               5                   10

<210> SEQ ID NO 54
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 54

Ser Leu Ala Arg Thr Thr Ser Met Asp Tyr
1               5                   10

<210> SEQ ID NO 55
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 55

Ser Leu Ala Arg Thr Thr Val Met Asp Tyr
1               5                   10

<210> SEQ ID NO 56
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 56

Ser Leu Ala Arg Thr Thr Ala Leu Asp Tyr
1               5                   10

<210> SEQ ID NO 57
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 57

Leu Leu Ala Arg Ala Thr Ala Met Asp Tyr
1               5                   10

<210> SEQ ID NO 58
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 58

Val Leu Ala Arg Ala Thr Ala Met Asp Tyr
1               5                   10

<210> SEQ ID NO 59
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 59

Ile Leu Ala Arg Ala Thr Ala Met Asp Tyr
1               5                   10

<210> SEQ ID NO 60
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 60

Thr Leu Ala Arg Ala Thr Ala Met Asp Tyr
1               5                   10

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

```
<400> SEQUENCE: 61

Val Leu Ala Arg Ile Thr Ala Met Asp Tyr
1               5                   10

<210> SEQ ID NO 62
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 62

Ile Leu Ala Arg Ile Thr Ala Met Asp Tyr
1               5                   10

<210> SEQ ID NO 63
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 63

Thr Leu Ala Arg Ile Thr Ala Met Asp Tyr
1               5                   10

<210> SEQ ID NO 64
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 64

Leu Leu Ala Arg Ile Thr Ala Met Asp Tyr
1               5                   10

<210> SEQ ID NO 65
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 65

Ser Thr Ala Arg Thr Thr Val Leu Asp Tyr
1               5                   10

<210> SEQ ID NO 66
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 66

Phe Ala Ser Gln Asp Ile Ser Ser Tyr Leu Asn
1               5                   10

<210> SEQ ID NO 67
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 67
```

```
Arg Ala Ser Arg Asp Ile Ser Ser Tyr Leu Asn
1               5                   10
```

<210> SEQ ID NO 68
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 68

```
Arg Ala Ser Thr Asp Ile Ser Ser Tyr Leu Asn
1               5                   10
```

<210> SEQ ID NO 69
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 69

```
Arg Ala Ser Gln Asp Ile Ser Ser Phe Leu Asn
1               5                   10
```

<210> SEQ ID NO 70
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 70

```
Arg Ala Ser Gln Asp Ile Ser Ser Tyr Leu Ser
1               5                   10
```

<210> SEQ ID NO 71
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 71

```
Tyr Gly Ser Arg Leu His Ser
1               5
```

<210> SEQ ID NO 72
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 72

```
Gly Gln Gly Asn Thr Leu Pro Tyr Thr
1               5
```

<210> SEQ ID NO 73
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 73

Asn Gln Gly Asn Thr Leu Pro Tyr Thr
1               5

<210> SEQ ID NO 74
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 74

Ser Gln Gly Asn Thr Leu Pro Tyr Thr
1               5

<210> SEQ ID NO 75
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 75

Gln Gln Ser Asn Thr Leu Pro Tyr Thr
1               5

<210> SEQ ID NO 76
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 76

Gln Gln Gly Asn Arg Leu Pro Tyr Thr
1               5

<210> SEQ ID NO 77
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 77

Gln Gln Gly Asn Ser Leu Pro Tyr Thr
1               5

<210> SEQ ID NO 78
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 78

Gly Gln Gly Asn Ser Leu Pro Tyr Thr
1               5

<210> SEQ ID NO 79
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 79

Gly Gln Gly Asn Arg Leu Pro Tyr Thr

```
<210> SEQ ID NO 80
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 80

Gln Val Gln Leu Gln Glu Ser Gly Pro Gly Leu Val Lys Pro Ser Gln
1               5                  10                  15

Thr Leu Ser Leu Thr Cys Thr Val Ser Gly Tyr Ser Ile Thr
            20                  25                  30

<210> SEQ ID NO 81
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 81

Gln Val Gln Leu Gln Glu Ser Gly Pro Gly Leu Val Arg Pro Ser Glu
1               5                  10                  15

Thr Leu Ser Leu Thr Cys Thr Val Ser Gly Tyr Ser Ile Thr
            20                  25                  30

<210> SEQ ID NO 82
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 82

Gln Val Gln Leu Gln Glu Ser Gly Pro Gly Leu Val Arg Pro Ser Gln
1               5                  10                  15

Thr Leu Ser Leu Thr Cys Ala Val Ser Gly Tyr Ser Ile Thr
            20                  25                  30

<210> SEQ ID NO 83
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 83

Gln Val Gln Leu Gln Glu Ser Gly Pro Gly Leu Val Arg Pro Ser Gln
1               5                  10                  15

Thr Leu Ser Leu Thr Cys Thr Val Ser Gly Tyr Ser Ile Ser
            20                  25                  30

<210> SEQ ID NO 84
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 84

Gln Val Gln Leu Gln Glu Ser Gly Pro Gly Leu Val Lys Pro Ser Glu
1               5                  10                  15
```

```
Thr Leu Ser Leu Thr Cys Ala Val Ser Gly Tyr Ser Ile Ser
            20                  25                  30
```

<210> SEQ ID NO 85
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 85

```
Trp Val Arg Gln Pro Pro Gly Glu Gly Leu Glu Trp Ile Gly
1               5                   10
```

<210> SEQ ID NO 86
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 86

```
Arg Val Thr Ile Leu Arg Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30
```

<210> SEQ ID NO 87
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 87

```
Arg Val Thr Met Ser Arg Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30
```

<210> SEQ ID NO 88
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 88

```
Arg Val Thr Met Leu Arg Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 89
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 89

```
Arg Val Thr Met Leu Arg Asp Thr Ser Lys Asn Gln Phe Ser Leu Arg
1               5                   10                  15

Leu Ser Ser Val Thr Ala Ala Asp Thr Ala Ala Tyr Tyr Cys Ala Arg
            20                  25                  30
```

<210> SEQ ID NO 90
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 90

```
Arg Val Thr Ile Ser Arg Asp Thr Ser Lys Asn Gln Phe Ser Leu Lys
1               5                   10                  15

Leu Ser Ser Val Thr Ala Ala Asp Thr Ala Ala Tyr Tyr Cys Ala Arg
            20                  25                  30
```

<210> SEQ ID NO 91
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 91

```
Trp Gly Glu Gly Ser Leu Val Thr Val Ser Ser
1               5                   10
```

<210> SEQ ID NO 92
<211> LENGTH: 23
<212> TYPE: PRT
<213> ORGANISM: Artificial
<220> FEATURE:
<223> OTHER INFORMATION: An artificially synthesized peptide sequence

<400> SEQUENCE: 92

```
Asp Ile Gln Met Thr Gln Ser Pro Ser Ser Leu Ser Ala Ser Val Gly
1               5                   10                  15

Asp Ser Val Thr Ile Thr Cys
            20
```

<210> SEQ ID NO 93
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 93

```
Trp Tyr Gln Gln Lys Pro Gly Lys Ala Pro Glu Leu Leu Ile Tyr
1               5                   10                  15
```

<210> SEQ ID NO 94
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 94

```
Gly Val Pro Ser Arg Phe Ser Gly Ser Gly Ser Gly Thr Asp Phe Thr
1               5                   10                  15

Phe Thr Ile Ser Ser Leu Glu Pro Glu Asp Ile Ala Thr Tyr Tyr Cys
            20                  25                  30
```

<210> SEQ ID NO 95
<211> LENGTH: 32
<212> TYPE: PRT

```
<213> ORGANISM: Artificial
<220> FEATURE:
<223> OTHER INFORMATION: An artificially synthesized peptide sequence

<400> SEQUENCE: 95

Gly Val Pro Ser Arg Phe Ser Gly Ser Gly Ser Gly Thr Asp Phe Thr
1               5                   10                  15

Phe Thr Ile Ser Ser Leu Gln Ala Glu Asp Ile Ala Thr Tyr Tyr Cys
            20                  25                  30

<210> SEQ ID NO 96
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 96

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ala Ala Thr Tyr Tyr Cys
            20                  25                  30

<210> SEQ ID NO 97
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 97

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 98
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 98

Phe Gly Gln Gly Thr Lys Val Glu Ile Glu
1               5                   10

<210> SEQ ID NO 99
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 99

Tyr Ile Ser Tyr Ser Gly Ile Thr Thr Tyr Asn Pro Ser Leu Lys Gly
1               5                   10                  15

<210> SEQ ID NO 100
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 100
```

```
Tyr Ile Ser Tyr Ser Gly Ile Thr Asn Tyr Asn Pro Ser Leu Lys Gly
1               5                   10                  15

<210> SEQ ID NO 101
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 101

Gln Ala Ser Gln Asp Ile Ser Ser Tyr Leu Asn
1               5                   10

<210> SEQ ID NO 102
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 102

Tyr Thr Ser Glu Leu His Ser
1               5

<210> SEQ ID NO 103
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 103

Tyr Gly Ser Glu Leu His Ser
1               5

<210> SEQ ID NO 104
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 105
```

```
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 105

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu
            100                 105

<210> SEQ ID NO 106
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 106

Gly Gly Gly Gly Ser Gly Gly Gly Ser Gly Gly Gly Gly Ser
1               5                   10                  15

<210> SEQ ID NO 107
<211> LENGTH: 414
<212> TYPE: DNA
<213> ORGANISM: Artificial
<220> FEATURE:
<223> OTHER INFORMATION: An artificially synthesized nucleotide sequence

<400> SEQUENCE: 107
atgggatgga gctgtatcat cctcttcttg gtagcaacag ctacaggtgt ccactcccag    60
gtccaactgc aggagagcgg tccaggtctt gtgagaccta gccagaccct gagcctgacc   120
tgcaccgtgt ctggctactc aattaccagc gatcatgcct ggagctgggt tcgccagcca   180
cctggacgag gtcttgagtg gattggatac attagttata gtggaatcac aacctataat   240
ccatctctca aatccagagt gacaatgctg agagacacca gcaagaacca gttcagcctg   300
agactcagca gcgtgacagc cgccgacacc gcggtttatt attgtgcaag atccctagct   360
cggactacgg ctatggacta ctggggtcaa ggcagcctcg tcacagtctc ctca         414

<210> SEQ ID NO 108
<211> LENGTH: 378
<212> TYPE: DNA
<213> ORGANISM: Artificial
<220> FEATURE:
<223> OTHER INFORMATION: An artificially synthesized nucleotide sequence

<400> SEQUENCE: 108
atgggatgga gctgtatcat cctcttcttg gtagcaacag ctacaggtgt ccactccgac    60
atccagatga cccagagccc aagcagcctg agcgccagcg tgggtgacag agtgaccatc   120
```

```
acctgtagag ccagccagga catcagcagt tacctgaatt ggtaccagca gaagccagga    180
aaggctccaa agctgctgat ctactacacc tccagactgc actctggtgt gccaagcaga    240
ttcagcggta gcggtagcgg taccgacttc accttcacca tcagcagcct ccagccagag    300
gacatcgcta cctactactg ccaacagggt aacacgcttc catacacgtt cggccaaggg    360
accaaggtgg aaatcaaa                                                  378
```

<210> SEQ ID NO 109
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 109

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
```

```
              305                 310                 315                 320
Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 110
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 110

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
                35                  40                  45

Ile Gly Tyr Ile Ser Tyr Ser Gly Ile Thr Thr Tyr Asn Pro Ser Leu
            50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
                210                 215                 220

Cys Pro Pro Cys Pro Ala Pro Glu Phe Leu Gly Gly Pro Ser Val Phe
```

```
                    225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 111
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 111

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
                35                  40                  45

Ile Gly Tyr Ile Ser Tyr Ser Gly Ile Thr Thr Tyr Asn Pro Ser Leu
                50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 112
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 112

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
```

65                  70                  75                  80
Leu Arg Leu Ser Ser Val Thr Ala Ala Asp Thr Ala Val Tyr Tyr Cys
                    85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 113
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 113

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Arg | Pro | Ser | Gln |
| 1 | | | | 5 | | | | | 10 | | | | | 15 |
| Thr | Leu | Ser | Leu | Thr | Cys | Thr | Val | Ser | Gly | Tyr | Ser | Ile | Thr | Ser | Asp |
| | | | 20 | | | | | 25 | | | | | 30 | | |
| His | Ala | Trp | Ser | Trp | Val | Arg | Gln | Pro | Pro | Gly | Arg | Gly | Leu | Glu | Trp |
| | | | 35 | | | | | 40 | | | | | 45 | | |
| Ile | Gly | Tyr | Ile | Ser | Tyr | Ser | Gly | Ile | Thr | Thr | Tyr | Asn | Pro | Ser | Leu |
| | 50 | | | | | 55 | | | | | 60 | | | | |
| Lys | Ser | Arg | Val | Thr | Met | Leu | Arg | Asp | Thr | Ser | Lys | Asn | Gln | Phe | Ser |
| 65 | | | | | 70 | | | | | 75 | | | | | 80 |
| Leu | Arg | Leu | Ser | Ser | Val | Thr | Ala | Ala | Asp | Thr | Ala | Val | Tyr | Tyr | Cys |
| | | | | 85 | | | | | 90 | | | | | 95 | |
| Ala | Arg | Ser | Leu | Ala | Arg | Thr | Thr | Ala | Met | Asp | Tyr | Trp | Gly | Gln | Gly |
| | | | 100 | | | | | 105 | | | | | 110 | | |
| Ser | Leu | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Asn | Phe | Gly | Thr | Gln | Thr | Tyr | Thr | Cys | Asn | Val | Asp | His | Lys | Pro |
| | | 195 | | | | | 200 | | | | | 205 | | | |
| Ser | Asn | Thr | Lys | Val | Asp | Lys | Thr | Val | Glu | Arg | Lys | Ser | Cys | Val | Glu |
| | 210 | | | | | 215 | | | | | 220 | | | | |
| Cys | Pro | Pro | Cys | Pro | Ala | Pro | Pro | Val | Ala | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Asp | Val | Ser | His | Glu | Asp | Pro | Glu | Val | Gln |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Phe | Asn | Ser | Thr | Phe | Arg | Val | Val | Ser | Val | Leu |
| | 290 | | | | | 295 | | | | | 300 | | | | |
| Thr | Val | Val | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Gly | Leu | Pro | Ser | Ser | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Arg | Glu | Glu | Met | Thr | Lys | Asn | Gln | Val | Ser | Leu | Thr | Cys | Leu | Val | Lys |
| | | 355 | | | | | 360 | | | | | 365 | | | |
| Gly | Phe | Tyr | Pro | Ser | Asp | Ile | Ala | Val | Glu | Trp | Glu | Ser | Asn | Gly | Gln |
| | 370 | | | | | 375 | | | | | 380 | | | | |
| Pro | Glu | Asn | Asn | Tyr | Lys | Thr | Thr | Pro | Pro | Val | Leu | Asp | Ser | Asp | Gly |
| 385 | | | | | 390 | | | | | 395 | | | | | 400 |
| Ser | Phe | Phe | Leu | Tyr | Ser | Lys | Leu | Thr | Val | Asp | Lys | Ser | Arg | Trp | Gln |
| | | | | 405 | | | | | 410 | | | | | 415 | |

```
Gln Gly Asn Val Phe Ser Cys Ser Val Met His Glu Ala Leu His Asn
                420                 425                 430

His Tyr Thr Gln Lys Ser Leu Ser Leu Ser Pro
            435                 440
```

<210> SEQ ID NO 114
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 114

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335
```

```
Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu
        435                 440
```

<210> SEQ ID NO 115
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 115

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro
        435                 440                 445

<210> SEQ ID NO 116
<211> LENGTH: 327
<212> TYPE: PRT
<213> ORGANISM: Artificial
<220> FEATURE:
<223> OTHER INFORMATION: An artificially synthesized peptide sequence

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

```
Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
            195                 200                 205

Gly Leu Pro Ser Ser Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro
                325

<210> SEQ ID NO 117
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205
```

Ser Asn Thr Lys Val Asp Lys Thr Val Glu Arg Lys Ser Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
        245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
            435                 440

<210> SEQ ID NO 118
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 118

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 119
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 119

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Ser Cys Val Glu
    210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Phe Arg Val Val Ser Val Leu
    290                 295                 300
Thr Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro
        435                 440

<210> SEQ ID NO 120
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 120

Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
                20                  25                  30
His Ala Trp Ser Trp Val Arg Gln Pro Pro Gly Arg Gly Leu Glu Trp
            35                  40                  45
Ile Gly Tyr Ile Ser Tyr Ser Gly Ile Thr Thr Tyr Asn Pro Ser Leu
        50                  55                  60
Lys Ser Arg Val Thr Met Leu Arg Asp Thr Ser Lys Asn Gln Phe Ser
65                  70                  75                  80
```

```
Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Glu Ser Thr Ala Ala Leu
130             135                 140

Gly Cys Leu Val Lys Asp Tyr Phe Pro Glu Pro Val Thr Val Ser Trp
145             150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
            210                 215                 220

Cys Pro Pro Cys Pro Ala Pro Pro Val Ala Gly Pro Ser Val Phe Leu
225             230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290             295                 300

Thr Val Val His Gln Asp Trp Leu Asn Gly Lys Glu Tyr Lys Cys Lys
305             310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385             390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 121
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 121
```

```
Tyr Ile Ser Tyr Ser Gly Ile Thr Thr Tyr Asn Pro Ser Leu Gln Asp
1               5                   10                  15
```

<210> SEQ ID NO 122
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 122

```
Tyr Ile Ser Tyr Ser Gly Ile Thr Asn Tyr Asn Pro Ser Leu Gln Asp
1               5                   10                  15
```

<210> SEQ ID NO 123
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 123

```
Arg Ala Ser Glu Asp Ile Ser Ser Tyr Leu Asn
1               5                   10
```

<210> SEQ ID NO 124
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 124

```
Gln Ala Ser Glu Asp Ile Ser Ser Tyr Leu Asn
1               5                   10
```

<210> SEQ ID NO 125
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 125

```
Tyr Thr Ser Arg Leu Glu Ser
1               5
```

<210> SEQ ID NO 126
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 126

```
Tyr Gly Ser Glu Leu Glu Ser
1               5
```

<210> SEQ ID NO 127
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 127

```
Arg Val Thr Ile Ser Arg Asp Thr Ser Lys Asn Gln Phe Ser Leu Lys
```

```
                1               5                  10                  15
Leu Ser Ser Val Thr Ala Ala Asp Thr Ala Val Tyr Tyr Cys Ala Arg
                20                  25                  30

<210> SEQ ID NO 128
<211> LENGTH: 32
<212> TYPE: PRT
<213> ORGANISM: Homo sapiens

<400> SEQUENCE: 128

Arg Val Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 129
<211> LENGTH: 32
<212> TYPE: PRT
<213> ORGANISM: Homo sapiens

<400> SEQUENCE: 129

Arg Val Thr Ile Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 130
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 130

Trp Gly Gln Gly Ile Leu Val Thr Val Ser Ser
1               5                   10

<210> SEQ ID NO 131
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 131

Trp Gly Glu Gly Ile Leu Val Thr Val Ser Ser
1               5                   10

<210> SEQ ID NO 132
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 132

Trp Gly Gln Gly Thr Leu Val Thr Val Ser Ser
1               5                   10

<210> SEQ ID NO 133
<211> LENGTH: 11
<212> TYPE: PRT
<213> ORGANISM: Artificial
<220> FEATURE:
<223> OTHER INFORMATION: An artificially synthesized peptide sequence
```

<400> SEQUENCE: 133

Trp Gly Glu Gly Thr Leu Val Thr Val Ser Ser
1               5                   10

<210> SEQ ID NO 134
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 135
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 135

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Tyr Trp Gly Gln Gly
            100                 105                 110

Ile Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                    245                 250                 255
Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 136
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 136

Asp Ile Gln Met Thr Gln Ser Pro Ser Ser Leu Ser Ala Ser Val Gly
1               5                   10                  15

Asp Ser Val Thr Ile Thr Cys Gln Ala Ser Glu Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 137
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 137

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 138
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 138

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 139
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 139

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Ala His Tyr Thr Gln Lys Ser Leu Ser Leu Ser Pro
        435                 440                 445
```

<210> SEQ ID NO 140
<211> LENGTH: 267
<212> TYPE: PRT
<213> ORGANISM: Homo sapiens

<400> SEQUENCE: 140

```
Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
                20                  25                  30

Gln Gln Tyr Leu Ser Tyr Asn Ser Leu Arg Gly Glu Ala Glu Pro Cys
            35                  40                  45

Gly Ala Trp Val Trp Glu Asn Gln Val Ser Trp Tyr Trp Glu Lys Glu
        50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
                100                 105                 110

Asn Gly Glu Glu Phe Met Asn Phe Asp Leu Lys Gln Gly Thr Trp Gly
            115                 120                 125

Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
                180                 185                 190

Phe Ser Val Leu Thr Cys Ser Ala Phe Ser Phe Tyr Pro Pro Glu Leu
            195                 200                 205

Gln Leu Arg Phe Leu Arg Asn Gly Leu Ala Ala Gly Thr Gly Gln Gly
        210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
                260                 265
```

<210> SEQ ID NO 141

```
<211> LENGTH: 99
<212> TYPE: PRT
<213> ORGANISM: Homo sapiens

<400> SEQUENCE: 141

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 142
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 142

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
```

```
                225                 230                 235                 240
        Phe Pro Pro Lys Pro Lys Asp Thr Leu Met Ile Ser Arg Thr Pro Glu
                        245                 250                 255

Val Thr Cys Val Val Val Asp Val Ser Gln Glu Asp Pro Glu Val Gln
                        260                 265                 270

Phe Asn Trp Tyr Val Asp Gly Val Glu Val His Asn Ala Lys Thr Lys
                        275                 280                 285

Pro Arg Glu Glu Gln Phe Asn Ser Thr Phe Arg Val Val Ser Val Leu
                        290                 295                 300

Thr Val Val His Gln Asp Trp Leu Asn Gly Lys Glu Tyr Lys Cys Lys
        305                 310                 315                 320

Val Ser Asn Lys Gly Leu Pro Ala Pro Ile Glu Lys Thr Ile Ser Lys
                        325                 330                 335

Thr Lys Gly Gln Pro Arg Glu Pro Gln Val Tyr Thr Leu Pro Pro Ser
                        340                 345                 350

Gln Glu Glu Met Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
        385                 390                 395                 400

Ser Phe Phe Leu Tyr Ser Lys Leu Thr Val Asp Lys Ser Arg Trp Gln
                        405                 410                 415

Glu Gly Asn Val Phe Ser Cys Ser Val Met His Glu Ala Leu His Asn
                        420                 425                 430

His Tyr Thr Gln Lys Ser Leu Ser Leu Ser Pro
                        435                 440

<210> SEQ ID NO 143
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 143

Gln Val Gln Leu Gln Glu Ser Gly Pro Gly Leu Val Arg Pro Ser Gln
        1               5                   10                  15

Thr Leu Ser Leu Thr Cys Thr Val Ser Gly Tyr Ser Ile Thr Ser Asp
                        20                  25                  30

His Ala Trp Ser Trp Val Arg Gln Pro Pro Gly Arg Gly Leu Glu Trp
                        35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
        65                  70                  75                  80

Leu Arg Leu Ser Ser Val Thr Ala Ala Asp Thr Ala Val Tyr Tyr Cys
                        85                  90                  95

Ala Arg Ser Leu Ala Arg Thr Thr Ala Met Asp Tyr Trp Gly Gln Gly
                        100                 105                 110

Ser Leu Val Thr Val Ser Ser Ala Ser Thr Lys Gly Pro Ser Val Phe
                        115                 120                 125

Pro Leu Ala Pro Ser Ser Lys Ser Thr Ser Gly Gly Thr Ala Ala Leu
                        130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 144
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 144

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60
```

```
Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 145
<211> LENGTH: 119
<212> TYPE: PRT
<213> ORGANISM: Mus musculus
```

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Tyr Trp Gly Gln Gly
            100                 105                 110

Ile Leu Val Thr Val Ser Ser
        115

<210> SEQ ID NO 146
<211> LENGTH: 107
<212> TYPE: PRT
<213> ORGANISM: Mus musculus

<400> SEQUENCE: 146

Asp Ile Gln Met Thr Gln Ser Pro Ser Ser Leu Ser Ala Ser Val Gly
1               5                   10                  15

Asp Ser Val Thr Ile Thr Cys Gln Ala Ser Glu Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 147
<211> LENGTH: 120
<212> TYPE: PRT
<213> ORGANISM: Mus musculus

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys

```
                     85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser
            115                 120

<210> SEQ ID NO 148
<211> LENGTH: 107
<212> TYPE: PRT
<213> ORGANISM: Mus musculus

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys
            100                 105

<210> SEQ ID NO 149
<211> LENGTH: 122
<212> TYPE: PRT
<213> ORGANISM: Mus musculus

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
            115                 120

<210> SEQ ID NO 150
<211> LENGTH: 108
<212> TYPE: PRT
<213> ORGANISM: Mus musculus

<400> SEQUENCE: 150

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Arg Gly Arg
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Phe Tyr Cys Gln Gln Tyr Gly Ser Ser Pro
                 85                  90                  95

Arg Thr Phe Gly Gln Gly Thr Lys Val Glu Ile Lys
            100                 105
```

<210> SEQ ID NO 151
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 151

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 152
<211> LENGTH: 330
<212> TYPE: PRT
<213> ORGANISM: Artificial
<220> FEATURE:
<223> OTHER INFORMATION: An artificially synthesized peptide sequence

<400> SEQUENCE: 152

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Ala His Tyr Thr
305                 310                 315                 320

Gln Lys Ser Leu Ser Leu Ser Pro Gly Lys
            325                 330

<210> SEQ ID NO 153
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Ala His Tyr Thr Gln Lys Ser Leu
305                 310                 315                 320

Ser Leu Ser Pro

-continued

```
<210> SEQ ID NO 154
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 154
```

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | | 35 | | | | | 40 | | | | | 45 | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Asn | Phe | Gly | Thr | Gln | Thr |
|---|---|---|---|---|---|---|---|---|---|---|---|---|---|---|---|
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Thr | Val | Glu | Arg | Lys | Ser | Cys | Val | Glu | Cys | Pro | Pro | Cys | Pro | Ala | Pro |
|---|---|---|---|---|---|---|---|---|---|---|---|---|---|---|---|
| | | | 100 | | | | | 105 | | | | | 110 | | |

| Pro | Val | Ala | Gly | Pro | Ser | Val | Phe | Leu | Phe | Pro | Pro | Lys | Pro | Lys | Asp |
|---|---|---|---|---|---|---|---|---|---|---|---|---|---|---|---|
| | | | 115 | | | | | 120 | | | | | 125 | | |

| Thr | Leu | Met | Ile | Ser | Arg | Thr | Pro | Glu | Val | Thr | Cys | Val | Val | Val | Asp |
|---|---|---|---|---|---|---|---|---|---|---|---|---|---|---|---|
| | 130 | | | | | 135 | | | | | 140 | | | | |

| Val | Ser | His | Glu | Asp | Pro | Glu | Val | Gln | Phe | Asn | Trp | Tyr | Val | Asp | Gly |
|---|---|---|---|---|---|---|---|---|---|---|---|---|---|---|---|
| 145 | | | | | 150 | | | | | 155 | | | | | 160 |

| Val | Glu | Val | His | Asn | Ala | Lys | Thr | Lys | Pro | Arg | Glu | Glu | Gln | Phe | Asn |
|---|---|---|---|---|---|---|---|---|---|---|---|---|---|---|---|
| | | | | 165 | | | | | 170 | | | | | 175 | |

| Ser | Thr | Phe | Arg | Val | Val | Ser | Val | Leu | Thr | Val | Val | His | Gln | Asp | Trp |
|---|---|---|---|---|---|---|---|---|---|---|---|---|---|---|---|
| | | | 180 | | | | | 185 | | | | | 190 | | |

| Leu | Asn | Gly | Lys | Glu | Tyr | Lys | Cys | Lys | Val | Ser | Asn | Lys | Gly | Leu | Pro |
|---|---|---|---|---|---|---|---|---|---|---|---|---|---|---|---|
| | | | 195 | | | | | 200 | | | | | 205 | | |

| Ala | Pro | Ile | Glu | Lys | Thr | Ile | Ser | Lys | Thr | Lys | Gly | Gln | Pro | Arg | Glu |
|---|---|---|---|---|---|---|---|---|---|---|---|---|---|---|---|
| | 210 | | | | | 215 | | | | | 220 | | | | |

| Pro | Gln | Val | Tyr | Thr | Leu | Pro | Pro | Ser | Arg | Glu | Glu | Met | Thr | Lys | Asn |
|---|---|---|---|---|---|---|---|---|---|---|---|---|---|---|---|
| 225 | | | | | 230 | | | | | 235 | | | | | 240 |

| Gln | Val | Ser | Leu | Thr | Cys | Leu | Val | Lys | Gly | Phe | Tyr | Pro | Ser | Asp | Ile |
|---|---|---|---|---|---|---|---|---|---|---|---|---|---|---|---|
| | | | | 245 | | | | | 250 | | | | | 255 | |

| Ala | Val | Glu | Trp | Glu | Ser | Asn | Gly | Gln | Pro | Glu | Asn | Asn | Tyr | Lys | Thr |
|---|---|---|---|---|---|---|---|---|---|---|---|---|---|---|---|
| | | | 260 | | | | | 265 | | | | | 270 | | |

| Thr | Pro | Pro | Met | Leu | Asp | Ser | Asp | Gly | Ser | Phe | Phe | Leu | Tyr | Ser | Lys |
|---|---|---|---|---|---|---|---|---|---|---|---|---|---|---|---|
| | | 275 | | | | | 280 | | | | | 285 | | | |

| Leu | Thr | Val | Asp | Lys | Ser | Arg | Trp | Gln | Gln | Gly | Asn | Val | Phe | Ser | Cys |
|---|---|---|---|---|---|---|---|---|---|---|---|---|---|---|---|
| | 290 | | | | | 295 | | | | | 300 | | | | |

| Ser | Val | Met | His | Glu | Ala | Leu | His | Asn | His | Tyr | Thr | Gln | Lys | Ser | Leu |
|---|---|---|---|---|---|---|---|---|---|---|---|---|---|---|---|
| 305 | | | | | 310 | | | | | 315 | | | | | 320 |

| Ser | Leu | Ser | Pro | Gly | Lys |
|---|---|---|---|---|---|
| | | | | 325 | |

```
<210> SEQ ID NO 155
<211> LENGTH: 326
<212> TYPE: PRT
<213> ORGANISM: Artificial
<220> FEATURE:
<223> OTHER INFORMATION: An artificially synthesized peptide sequence
```

```
<400> SEQUENCE: 155

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 156
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 156

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
65          50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 157
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 157

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 158
<211> LENGTH: 445
<212> TYPE: PRT

<213> ORGANISM: Artificial
<220> FEATURE:
<223> OTHER INFORMATION: An artificially synthesized peptide sequence

<400> SEQUENCE: 158

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
```

```
                            385                 390                 395                 400

Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly Lys
                    435                 440                 445

<210> SEQ ID NO 159
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 159

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

His Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Ala Arg Ile Thr Ala Met Asp Tyr Trp Gly Glu Gly
                100                 105                 110

Thr Leu Val Thr Val Ser Ser
            115

<210> SEQ ID NO 160
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

His Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Tyr Trp Gly Gln Gly
                100                 105                 110

Ile Leu Val Thr Val Ser Ser
            115
```

```
<210> SEQ ID NO 161
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 161

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser
        115

<210> SEQ ID NO 162
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 162

Asp Ile Gln Met Thr Gln Ser Pro Ser Ser Leu Ser Ala Ser Val Gly
1               5                   10                  15

Asp Ser Val Thr Ile Thr Cys Gln Ala Ser Glu Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 163
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 163

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
```

```
            20                  25                  30
Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
                100                 105
```

<210> SEQ ID NO 164
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 164

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Ala His Tyr Thr
305                 310                 315                 320

Gln Lys Ser Leu Ser Leu Ser Pro
                325

<210> SEQ ID NO 165
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 165

Asp Asp His Ala Val Ser
1               5

<210> SEQ ID NO 166
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 166

Phe Ile Ser Tyr Ser Gly Ile Thr Asn Tyr Asn Pro Thr Leu Gln Asp
1               5                   10                  15

<210> SEQ ID NO 167
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 167

Leu Leu Ala Arg Ala Thr Ala Met Asp Val
1               5                   10

<210> SEQ ID NO 168
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 168

Tyr Gly Ser Glu Leu Glu Ser
1               5

<210> SEQ ID NO 169
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 169

His Asp His Ala Trp Ser
1               5

<210> SEQ ID NO 170
<211> LENGTH: 16
```

<212> TYPE: PRT
<213> ORGANISM: Artificial
<220> FEATURE:
<223> OTHER INFORMATION: An artificially synthesized peptide sequence

<400> SEQUENCE: 170

Phe Ile Ser Tyr Ser Gly Ile Thr Asn Tyr Asn Pro Ser Leu Gln Gly
1               5                   10                  15

<210> SEQ ID NO 171
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 171

Ser Leu Ala Arg Thr Thr Ala Met Asp Tyr
1               5                   10

<210> SEQ ID NO 172
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 172

Gln Ala Ser Thr Asp Ile Ser Ser His Leu Asn
1               5                   10

<210> SEQ ID NO 173
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 173

Tyr Gly Ser His Leu Leu Ser
1               5

<210> SEQ ID NO 174
<211> LENGTH: 16
<212> TYPE: PRT
<213> ORGANISM: Artificial
<220> FEATURE:
<223> OTHER INFORMATION: An artificially synthesized peptide sequence

<400> SEQUENCE: 174

Phe Ile Ser Tyr Ser Gly Ile Thr Asn Tyr Asn Pro Thr Leu Gln Gly
1               5                   10                  15

<210> SEQ ID NO 175
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 175

Gln Ala Ser Arg Asp Ile Ser Ser His Leu Asn
1               5                   10

<210> SEQ ID NO 176
<211> LENGTH: 119
<212> TYPE: PRT

```
<213> ORGANISM: Artificial
<220> FEATURE:
<223> OTHER INFORMATION: An artificially synthesized peptide sequence

<400> SEQUENCE: 176

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 177
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 177

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 178
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 178

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Thr Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser
            115

<210> SEQ ID NO 179
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 179

Asp Ile Gln Met Thr Gln Ser Pro Ser Ser Leu Ser Ala Ser Val Gly
 1               5                  10                  15

Asp Ser Val Thr Ile Thr Cys Gln Ala Ser Arg Asp Ile Ser Ser His
                 20                  25                  30

Leu Asn Trp Tyr Gln Gln Lys Pro Gly Lys Ala Pro Glu Leu Leu Ile
             35                  40                  45

Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu
                100                 105

<210> SEQ ID NO 180
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 180

Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
                 20                  25                  30

His Ala Trp Ser Trp Val Arg Gln Pro Pro Gly Glu Gly Leu Glu Trp
             35                  40                  45

Ile Gly Phe Ile Ser Tyr Ser Gly Ile Thr Asn Tyr Asn Pro Ser Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
```

```
                    115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 181
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 181

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
```

Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
             195                 200                 205

Phe Asn Arg Gly Glu Cys
             210

<210> SEQ ID NO 182
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 182

Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
             20                  25                  30

His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Thr Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Gln Gly
             100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser

```
                180                 185                 190
Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440

<210> SEQ ID NO 183
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 183

Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
            50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
            85                  90                  95

Thr Phe Gly Gln Gly Thr Lys Val Glu Ile Glu Arg Thr Val Ala Ala
```

```
                100                 105                 110
Pro Ser Val Phe Ile Phe Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 184
<211> LENGTH: 32
<212> TYPE: PRT
<213> ORGANISM: Artificial
<220> FEATURE:
<223> OTHER INFORMATION: An artificially synthesized peptide sequence

<400> SEQUENCE: 184

Arg Val Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 185
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 185

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Ala His Tyr Thr Gln Lys Ser Leu Ser Leu Ser Pro
            435                 440                 445

<210> SEQ ID NO 186
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 186

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser
            20                  25                  30

<210> SEQ ID NO 187
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 187
```

-continued

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
    195                 200                 205

Ser Asn Thr Lys Val Asp Lys Thr Val Glu Arg Lys Ser Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415
```

Gln Gly Asn Val Phe Ser Cys Ser Val Met His Glu Ala Leu His Asn
              420                 425                 430

His Tyr Thr Gln Lys Ser Leu Ser Leu Ser Pro Gly Lys
        435                 440                 445

<210> SEQ ID NO 188
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 188

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 189
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 189

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

```
Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 190
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 190

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
        210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 191
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 191

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 192
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 193
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 193

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                    165                 170                 175
Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 194
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 194

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
```

```
                195                 200                 205
Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro

<210> SEQ ID NO 195
<211> LENGTH: 115
<212> TYPE: PRT
<213> ORGANISM: Artificial
<220> FEATURE:
<223> OTHER INFORMATION: Humanized antibody H chain

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 196
<211> LENGTH: 115
<212> TYPE: PRT
<213> ORGANISM: Artificial
<220> FEATURE:
<223> OTHER INFORMATION: Humanized antibody H chain

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Ile Arg Gln Pro Pro Gly Gln Gly Leu Glu Trp Ile
            35                  40                  45

Gly Ala Ile Asp Pro Lys Thr Gly Asp Thr Ala Tyr Ser Gln Lys Phe
```

```
                    50                  55                  60
Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 197
<211> LENGTH: 115
<212> TYPE: PRT
<213> ORGANISM: Artificial
<220> FEATURE:
<223> OTHER INFORMATION: Humanized antibody H chain

<400> SEQUENCE: 197

Gln Val Gln Leu Val Gln Ser Gly Ala Glu Val Lys Lys Pro Gly Ala
 1               5                  10                  15

Ser Val Thr Val Ser Cys Lys Ala Ser Gly Tyr Thr Phe Thr Asp Tyr
                 20                  25                  30

Glu Met His Trp Val Arg Gln Ala Pro Gly Glu Gly Leu Glu Trp Met
             35                  40                  45

Gly Ala Leu Asp Pro Lys Thr Gly Asp Thr Ala Tyr Ser Gln Ser Phe
         50                  55                  60

Gln Asp Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 198
<211> LENGTH: 115
<212> TYPE: PRT
<213> ORGANISM: Artificial
<220> FEATURE:
<223> OTHER INFORMATION: Humanized antibody H chain

<400> SEQUENCE: 198

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Glu Met His Trp Val Arg Gln Ala Pro Gly Lys Gly Leu Glu Trp Met
             35                  40                  45

Gly Ala Leu Asn Pro Lys Thr Gly Asp Thr Ala Tyr Ser Gln Lys Phe
         50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Arg Gly Thr Leu Val Thr
            100                 105                 110
```

Val Ser Ser
    115

<210> SEQ ID NO 199
<211> LENGTH: 115
<212> TYPE: PRT
<213> ORGANISM: Artificial
<220> FEATURE:
<223> OTHER INFORMATION: Humanized antibody H chain

<400> SEQUENCE: 199

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Gln Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
    115

<210> SEQ ID NO 200
<211> LENGTH: 115
<212> TYPE: PRT
<213> ORGANISM: Artificial
<220> FEATURE:
<223> OTHER INFORMATION: Humanized antibody H chain

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Lys Gly Leu Glu Trp Ile
        35                  40                  45

Gly Ala Ile Asn Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Arg Gly Thr Leu Val Thr
            100                 105                 110

Val Ser Ser
    115

<210> SEQ ID NO 201
<211> LENGTH: 112
<212> TYPE: PRT
<213> ORGANISM: Artificial
<220> FEATURE:
<223> OTHER INFORMATION: Humanized antibody L chain -continued

```
<400> SEQUENCE: 201

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 202
<211> LENGTH: 112
<212> TYPE: PRT
<213> ORGANISM: Artificial
<220> FEATURE:
<223> OTHER INFORMATION: Humanized antibody L chain

<400> SEQUENCE: 202

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 203
<211> LENGTH: 112
<212> TYPE: PRT
<213> ORGANISM: Artificial
<220> FEATURE:
<223> OTHER INFORMATION: Humanized antibody L chain

<400> SEQUENCE: 203

Asp Val Val Met Thr Gln Ser Pro Leu Ser Leu Pro Val Thr Pro Gly
1               5                   10                  15

Glu Pro Ala Ser Ile Ser Cys Arg Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80
```

Ser Ser Leu Gln Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 204
<211> LENGTH: 112
<212> TYPE: PRT
<213> ORGANISM: Artificial
<220> FEATURE:
<223> OTHER INFORMATION: Humanized antibody L chain

<400> SEQUENCE: 204

Asp Val Val Met Thr Gln Ser Pro Leu Ser Leu Pro Val Thr Pro Gly
1               5                   10                  15

Gln Pro Ala Ser Ile Ser Cys Arg Ala Ser Arg Ser Leu Val His Ser
            20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Pro Thr Phe Gly Arg Gly Thr Lys Leu Glu Ile Lys
            100                 105                 110

<210> SEQ ID NO 205
<211> LENGTH: 112
<212> TYPE: PRT
<213> ORGANISM: Artificial
<220> FEATURE:
<223> OTHER INFORMATION: Humanized antibody L chain

<400> SEQUENCE: 205

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ser Leu Val His Ser
            20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 206
<211> LENGTH: 112
<212> TYPE: PRT
<213> ORGANISM: Artificial
<220> FEATURE:
<223> OTHER INFORMATION: Humanized antibody L chain

<400> SEQUENCE: 206

Asp Ile Val Met Thr Gln Ser Pro Leu Ser Leu Pro Val Thr Pro Gly

```
1               5                   10                  15
Gln Pro Ala Ser Ile Ser Cys Arg Ala Ser Arg Ser Leu Val His Ser
                20                  25                  30

Asn Arg Asn Thr Tyr Leu His Trp Tyr Gln Gln Lys Pro Gly Gln Ala
                35                  40                  45

Pro Arg Leu Leu Ile Tyr Lys Val Ser Asn Arg Phe Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Arg Gly Thr Lys Leu Glu Ile Lys
                100                 105                 110
```

<210> SEQ ID NO 207
<211> LENGTH: 545
<212> TYPE: PRT
<213> ORGANISM: Homo sapiens

<400> SEQUENCE: 207

```
Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
                20                  25                  30

Val Pro Gly Ser Asp Leu Gln Val Cys Leu Pro Lys Gly Pro Thr Cys
                35                  40                  45

Cys Ser Arg Lys Met Glu Glu Lys Tyr Gln Leu Thr Ala Arg Leu Asn
                50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
                100                 105                 110

Leu Thr Pro Gln Ala Phe Glu Phe Val Gly Glu Phe Phe Thr Asp Val
                115                 120                 125

Ser Leu Tyr Ile Leu Gly Ser Asp Ile Asn Val Asp Asp Met Val Asn
                130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
                165                 170                 175

Ala Arg Arg Asp Leu Lys Val Phe Gly Asn Phe Pro Lys Leu Ile Met
                180                 185                 190

Thr Gln Val Ser Lys Ser Leu Gln Val Thr Arg Ile Phe Leu Gln Ala
                195                 200                 205

Leu Asn Leu Gly Ile Glu Val Ile Asn Thr Thr Asp His Leu Lys Phe
                210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
                245                 250                 255

Val Met Gln Gly Cys Met Ala Gly Val Val Glu Ile Asp Lys Tyr Trp
                260                 265                 270
```

```
Arg Glu Tyr Ile Leu Ser Leu Glu Glu Leu Val Asn Gly Met Tyr Arg
            275                 280                 285
Ile Tyr Asp Met Glu Asn Val Leu Leu Gly Leu Phe Ser Thr Ile His
    290                 295                 300
Asp Ser Ile Gln Tyr Val Gln Lys Asn Ala Gly Lys Leu Thr Thr Thr
305                 310                 315                 320
Ile Gly Lys Leu Cys Ala His Ser Gln Gln Arg Gln Tyr Arg Ser Ala
                325                 330                 335
Tyr Tyr Pro Glu Asp Leu Phe Ile Asp Lys Lys Val Leu Lys Val Ala
            340                 345                 350
His Val Glu His Glu Glu Thr Leu Ser Ser Arg Arg Glu Leu Ile
        355                 360                 365
Gln Lys Leu Lys Ser Phe Ile Ser Phe Tyr Ser Ala Leu Pro Gly Tyr
    370                 375                 380
Ile Cys Ser His Ser Pro Val Ala Glu Asn Asp Thr Leu Cys Trp Asn
385                 390                 395                 400
Gly Gln Glu Leu Val Glu Arg Tyr Ser Gln Lys Ala Ala Arg Asn Gly
                405                 410                 415
Met Lys Asn Gln Phe Asn Leu His Glu Leu Lys Met Lys Gly Pro Glu
            420                 425                 430
Pro Val Val Ser Gln Ile Ile Asp Lys Leu Lys His Ile Asn Gln Leu
    435                 440                 445
Leu Arg Thr Met Ser Met Pro Lys Gly Arg Val Leu Asp Lys Asn Leu
450                 455                 460
Asp Glu Glu Gly Phe Glu Ala Gly Asp Cys Gly Asp Asp Glu Asp Glu
465                 470                 475                 480
Cys Ile Gly Gly Ala Gly Asp Gly Met Ile Lys Val Lys Asn Gln Leu
                485                 490                 495
Arg Phe Leu Ala Glu Leu Ala Tyr Asp Leu Asp Val Asp Asp Ala Pro
            500                 505                 510
Gly Asn Ser Gln Gln Ala Thr Pro Lys Asp Asn Glu Ile Ser Thr Phe
    515                 520                 525
His Asn Leu Gly Asn Val His Ser Pro Leu Lys His His His His His
530                 535                 540
His
545

<210> SEQ ID NO 208
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 208
ggatcctgcg catgaaaaag cctgaactca cc                                32

<210> SEQ ID NO 209
<211> LENGTH: 29
<212> TYPE: DNA
<213> ORGANISM: Artificial
<220> FEATURE:
<223> OTHER INFORMATION: An artificially synthesized primer sequence

<400> SEQUENCE: 209
gcggccgcct attcctttgc cctcggacg                                    29
```

<210> SEQ ID NO 210
<211> LENGTH: 10939
<212> TYPE: DNA
<213> ORGANISM: Cricetulus griseus

<400> SEQUENCE: 210

```
gagctcaatt aaccctcact aaagggagtc gactcgatcc tttacagaaa acttgcaaac    60
cctcttggag tagaaaagta gtagtatctg acacaagtat cagcaaaatg caaacttctc   120
cccatcccca gaaaaccatt ataaaaaccc ccatatctta tgcccaactg tagtgatata   180
ttatttatga tttattaaaa cttgcttaag gattcagaaa gcaaagtcag ccttaagcta   240
tagagaccag gcagtcagtg gtggtacaca cctttaatcc caggactcag gattaagaag   300
tagacggacc tctgttagtt caagtctacc attacctaca caagagtgaa gagtaaccga   360
tctcatgcct ttgatcccag cagctgggat catgtgcatt caatcccagc attcgggagt   420
tatataagac aggagcaagg tctcagagct ggcattcatt ctccagccac attgaggata   480
ggaaaacatt gaagtgtcag gatgctgagg agaggcagca gtttgaggtt tggtagaacc   540
aggatcacct tttggtctga ggtagagtaa gaactgtggc tggctgcttt gcttttctga   600
tcttcagctt gaagcttgaa ctccaatatt tgtctctggg tctattatta tcatgttaca   660
cctaacttta aagctgattt acgcaagaca gttgtaggtg gacctttctt tcctgcccac   720
cagttcccaa ataactgaca cggagactca atattaatta taaatgattg gttaatagct   780
cagtcttgtt actggctaac tcttacattt taaattaact catttccatc cctttacttg   840
ctgccatgtg gttcatggct tgttcaagtc ctgcttcttc tgtctctggc tggtgatgcc   900
tctggttctg ccctttatcc cagaattctc ctagtctggc tctcctgccc agctataggc   960
cagtcagctg tttattaacc aatgagaata atacatattt atagtgtaca aagattgctc  1020
ctcaacaccc aatttttttat gtgcaacctg agaatctgga ctcattgccc tcatgcttgc  1080
agaggcggca cccttaccca ctaagccacc tttctagccc tgttgctttt gttttttgag  1140
acaggttcca ctatgtagcc caggctggcc tcaaactgac cattctcctg cctaaacctc  1200
ccgaacactg gaattatagt caaggcctac ctgccctggc attttcacac tttatttcc   1260
tggctgagtc cattgacttt acactcatca aggttgaacc agttggagtt taattacagt  1320
gccaatcgca ctgaatccca cataatcaaa caacttcaag gaagcaaaaa accagttttt  1380
cctgaagatc aatgtcagct tgcctgattc agaatagacc cccgaaaaaa ggcaaatgct  1440
tgataaccaa tttcttctta ttgttcaatc ccctgctgct gtgtgtaagc tcctgagaaa  1500
ggacagtaag gggacattca tgatcagaga aagagcccca actcccccc cagccccacc   1560
cccaccctgt ccacagtctg ttggtttggt ttcccctgg ctgacaccca gaaatcacaa   1620
cataatcacc taggtcactg taacaagttc ctttctggaa aatgctacaa atgatattgg  1680
taacatgagt aatgaataat gcctggagtc caactccctt gtgacccagc aatgttttcc  1740
gtgggtgctc ccttccccag ctgcaggcct gacatgtacc ttaaaaagcc tccctggag   1800
gacagaattt tgtgggtact atagtgttct cacaaatact tccctaata cccttactta   1860
gttaccataa ataacatgca gcccctggtg aggcacacag ggctccaatg tacagcttct  1920
cagacactgc aggaaccttc ctctcctaat gcagcactgg tctcttcagg ctggacagca  1980
ggaacccata ccactccaat cctagtgtgg agtagagctg tctacgaaaa ccagcagatc  2040
tatagctaaa tgtgtttcaa ttttatgctt tgacaaattg tactgacccc accccacccc  2100
cttccccctt gctgtgctgg gaattgaacc caggaccttg tgcatgccag gcaagtactc  2160
```

```
taacactgag ctatagcccc aatctttcat ccaagtctct atgtgtgccc acactcgctt    2220
tttattttga gacaaaaggt tcttattttg agataaggtc tcactatgtt gccttgactt    2280
tttttttttt ttttttttga acttttgacc ttcctacctc agctgagact acaagtcttt    2340
taccatcagg cccggctgat ggtaaaataa cagtatttga aatagtttaa acacatcatc    2400
ttaatggtca accacacaat ttccgaaatg ttgctggctc agtctggggc aaacctgtcc    2460
gccccaacat tggtgctagg aagaaagcac agacaagtag ccctcccagc tcaggagtaa    2520
aagacctgga gggggtggcc cacttcggtc aagttcacgg gatggggagg ggtaccctcc    2580
tccagtagtg gtggtatttg gcagttcctc caccgacgcc ctctggaagc acctgcttgg    2640
acccgcaaag ccaggaatgc agcttcctca agggactcgc cagcgagggt aacaggacag    2700
aggcgtccca gagggctggg gcggaaggg gaagacagg gtcggcctta gatagggcaa    2760
agggccttct ggctgtgttc ccggggtaac cgccccacca cgcctggagc ccgacgtggc    2820
gagcgatggg gacagcgagc aggaagtcgt actgggagg gccgcgtagc agatgcagcc    2880
gagggcggcg ctgccaggta cacccgaggg caccgcgggg gtgagcgcca ggtccctgaa    2940
ccagccaggc ctccagagcc gagtccggcg gaccgacggt acgttctgga atgggaaggg    3000
atccgggaca ccgaattgct gcattgaggg gctcagaggt tctgatgtgg gagtccagaa    3060
agggttttat ctaccggagg tgatgtgact tccggcctct ggaagtgctg ttggagtctc    3120
tgggaccttg ggtcctctcg actaggtttg aaggggtga aatagggta gggagaaagg    3180 agaggactgc agcaatgtct tcccgaacga cctgggttcg ggaggggtcg aaggacaagg    3240
ggctgttgtg gggggtcttc agacgcggag gggtggtatt ctattttctg ggaagatggt    3300
gtcgatgcac ttgaccaagt ctagtcgatc tgaagaggct aggggaacag acagtgagag    3360
aggatggtgg agggagtggc agaacccttc cagaaactgg gagaggctct agcacctgca    3420
accccttccc tggcctccgg ggagtcccag aagagggcag gaccatggac acaggtgcat    3480
tcgtgccggc gcgctccggc ctggcgaagg tgcgcgctct tggaggccgc gggagggcca    3540
gacgcgcgcc cggagagctg gccctttaag gctacccgga ggcgtgtcag gaaatgcgcc    3600
ctgagcccgc ccctcccgga acgcggcccg agacctggca agctgagacg gaactcggaa    3660
ctagcactcg gctcgcggcc tcggtgaggc cttgcgcccg ccatgcctct gtcattgccc    3720
ctcgggccgc ctccctgaac ctccgtgacc gccctgcagt cctccctccc ccccttcgac    3780
tcggcgggcg cttccgggcg ctcccgcagc ccgccctcca cgtagcccac acctccctct    3840
cggcgctccg cttcccacgc ggtccccgac ctgttctttc ctcctccacc ctgcccttct    3900
gtccctctcc cttcctttct cccctcgact cgtcccctatt aggcaacagc cctgtggtc    3960 cagccggcca tggctgtcaa ggctcacacc cttagctagg ccccttctcc cttccctggg    4020
tcttgtctca tgacccctg cccgcccgg gagcgagcgc gatgtggagc agtgcctctg    4080
gcaagcagaa cttcacccaa gccatgtgac aattgaaggc tgtaccccca gaccctaaca    4140
tcttggagcc ctgtagacca gggagtgctt ctggccgtgg ggtgacctag ctcttctacc    4200
accatgaaca gggcccctct gaagcggtcc aggatcctgc gcatggcgct gactggaggc    4260
tccactgcct ctgaggaggc agatgaagac agcaggaaca agccgtttct gctgcgggcg    4320
ctgcagatcg cgctggtcgt ctctctctac tgggtcacct ccatctccat ggtattcctc    4380
aacaagtacc tgctggacag ccccctcctg cagctggata ccctatctt cgtcactttc    4440 taccaatgcc tggtgacctc tctgctgtgc aagggcctca gcactctggc cacctgctgc    4500
cctggcaccg ttgacttccc caccctgaac ctggaccta aggtggcccg cagcgtgctg    4560
```

```
ccactgtcgg tagtcttcat tggcatgata agtttcaata acctctgcct caagtacgta    4620 gggtggcct  tctacaacgt ggggcgctcg ctcaccaccg tgttcaatgt gcttctgtcc    4680
tacctgctgc tcaaacagac cacttccttc tatgccctgc tcacatgtgg catcatcatt    4740
ggtgagtggg gcccgggggc tgtgggagca ggatgggcat cgaactgaag ccctaaaggt    4800
caacactgta ggtaccttta cttactgtcc caggtccctt gcatcagcag ttacaggaag    4860
agccctgtag aaaacaaata acttccttat ggtcattcaa caagttaggg acccagccag    4920
ggtgaaaata atgttagcag caactacagc aaagatggct ctcgccactt gcatgattaa    4980
aatgtgccag gtactcagat ctaagcattg gatccacatt aactcaacta atccctatta    5040
caaggtaaaa tatatccgaa ttttacagag ggaaaaccaa ggcacagaga ggctaagtag    5100
cttgaccagg atcacacagc taataatcac tgacatagct gggatttaaa cataagcagt    5160
tacctccata gatcacacta tgaccaccat gccactgttc cttctcaaga gttccaggat    5220
cctgtctgtc cagttctctt taagaggac  aacacatctg acattgctac cttgaggtaa    5280
catttgaaat agtgggtaga catatgtttt aagttttatt cttactttttt atgtgtgtgt    5340 gtttgggggg ccaccacagt gtatgggtgg agataagggg acaacttaag aattggtcct    5400
ttctcccacc acatgggtgc tgaggtctga actcaggtca tcaggattgg cacaaatccc    5460
tttacccact gagccatttc actggtccaa tatatgtgtg cttttaagag ctttaacta    5520 ttttcccaga tgtgaatgtc ctgctgatca ttatccccctt ttacccggaa gccctctggg    5580
aggtgccatc cctgtggtcg tctgcataca aatggggaaa ctgcaactca gagaaacaag    5640
gctacttgcc agggccccac aagtaagata ggctgggatg ccatcccaga ctggccacac    5700
tccctggcct gtgcttcaag ccagtttact ttgttcctgc ccattggaag ttagcatgtt    5760
gcagtcaaac acaataacta caggccaaaa gtgcttttaa attaaagtca gatgaacttt    5820
taaacatcca gagctcctca actgcaggag ttacaacctg attctgcaac catctttgca    5880
gtgcccggta gtcatatgta gctagaggct cttggctagg acagcatgtg ttaggaaaca    5940
tctggccctg agatcattga attgagtgac tgctgggtga caaagaccaa ggcatccgtt    6000
ccctgagagt cctgggcaag cagcaatgtg accttcattt gtacctactc aggttcttta    6060
tctgtcctgt ttgacctact tagtctcctc tggtgtctca gaggcccagg ctgggtactc    6120
tggatgtcag gatcaggcca atgcgcacat ctgccctaga aatgtccccc tggttgagca    6180
gctcctgaat ccatcggtaa agggtctgga ccagggagga gtcagataaa agctgacag    6240 cactggggga ctccatgggg aactcccacc tgccccaca  catccatcct aagagaactg    6300
gtattccttg tttcctcttt gtcctacaag gcaccctggg atcccacttc agtctcccag    6360
ccttgccagg gttagagggc atgagcctcc ttgtggggaa tttagatgca agaaggtaca    6420
gtcactagag aacctgagct cagatcccca aagtaaccag tacctgatag tgaggcagct    6480
gagaaccgca gcagcctgcc tgagtggctg aactctgcgg cctccggaac tggccccaac    6540
tgttgggtct cctcttcctt cctcctgtga gggagggccc atctctgata agtgctgtgg    6600
ggactctaga gtagggagga ggaggagcaa tctaagcagg ccttactgag aagtccttgc    6660
tggcatgtgg ctgcctgagg agtacagact gggaacaccc atttgaatga gtaaggtttt    6720
tcctgaaggc catggggagc cacggaggaa atcattttta gttacaagac aaagagtaga    6780
ttggttaaca tgggagcaag gacatggccc caatttcat  agatgaagga aattggaact    6840
cagagaggtt aagtaacttc tcccaaatag ctcagcttca aaatcacaga acagtcagag    6900
```

```
tctagatctc tctgatgcct gtgatggtcc tgccattcca tgttgctgat ccctgtggca    6960
tcagtaagcc tctaccttgt gggaatgcag gatctaaatg aagagaggaa gtgctggccc    7020
catgctgtgg tctggaaagc tatgcaggct ctttgagcag agagtgaccc acaagtgaat    7080
agagtcctat gagactcaaa gcaacatcca cccttaagca gctctaacca aatgctcaca    7140
ctgagggagc caaagccaag ttagagtcct gtgcttgccc aaggtcactt tgcctggccc    7200
tcctcctata gcacccgtgt tatcttatag ccctcattac agtgattaca attataatta    7260
gagaggtaac agggccacac tgtccttaca cattccctg ctagattgta gctgggagag     7320
ggggagatgt aggtggctgg gggagtggga gggaagatgc agattttcat tctgggctct    7380
actccctcag ccattttttg gtgtgggagt tagactttgg atatgttgat gatgaggtaa    7440
gggccacaga acagtctgaa ctgtggtatc agaatcctgt ccctctccct ctctcctcat    7500
ccctcttcac cttgtcactc ctctgtctgc tacaggtggt ttctggctgg gtatagacca    7560
agagggagct gagggcaccc tgtccctcat aggcaccatc ttcggggtgc tggccagcct    7620
ctgcgtctcc ctcaatgcca tctataccaa gaaggtgctc ccagcagtgg acaacagcat    7680
ctggcgccta accttctata caatgtcaa tgcctgtgtg ctcttcttgc ccctgatggt     7740
tctgctgggt gagctccgtg ccctccttga ctttgctcat ctgtacagtg cccacttctg    7800
gctcatgatg acgctgggtg gcctcttcgg ctttgccatt ggctatgtga caggactgca    7860
gatcaaattc accagtcccc tgacccacaa tgtatcaggc acagccaagg cctgtgcgca    7920
gacagtgctg gccgtgctct actatgaaga gactaagagc ttcctgtggt ggacaagcaa    7980
cctgatggtc ctgggtggct cctcagccta tacctgggtc aggggctggg agatgcagaa    8040
gacccaagag gaccccagct ccaaagaggg tgagaagagt gctattgggg tgtgagcttc    8100
ttcagggacc tgggactgaa cccaagtggg gcctacacag cactgaaggc ttcccatgga    8160
gctagccagt gtggccctga gcaatactgt ttacatcctc cttggaatat gatctaagag    8220
gagccagggt ctttcctggt aatgtcagaa agctgccaaa tctcctgtct gccccatctt    8280
gttttgggaa aaccctacca ggaatggcac ccctacctgc ctcctcctag agcctgtcta    8340
cctccatatc atctctgggg ttgggaccag ctgcagcctt aagggctgg attgatgaag     8400 tgatgtcttc tacacaaggg agatgggttg tgatcccact aattgaaggg atttgggtga    8460
ccccacacct ctgggatcca gggcaggtag agtagtagct taggtgctat taacatcagg    8520
aacacctcag cctgcctttg aagggaagtg ggagcttggc caagggagga aatggccatt    8580
ctgccctctt cagtgtggat gagtatggca gacctgttca tggcagctgc accctggggt    8640
ggctgataag aaaacattca cctctgcatt tcatatttgc agctctagaa cggggggagag   8700 ccacacatct tttacgggtt aagtagggtg atgagctcct ccgcagtccc taaccccagc    8760
tttacctgcc tggcttccct tggcccagct acctagctgt actcccttc tgtactcttc     8820 tcttctccgt catggcctcc cccaacacct ccatctgcag gcaggaagtg gagtccactt    8880
gtaacctctg ttcccatgac agagccctt gaatacctga cccctcatg acagtaagag      8940 acatttatgt tctctggggc tggggctgaa ggagcccact ggttctcact tagcctatct    9000
ggctcctgtc acaaaaaaaa aaaagaaaa aaaaaaagca taaaccaagt tactaagaac     9060
agaagttggt ttataacgtt ctgggcagc aaagcccaga tgaagggacc catcgaccct     9120
ctctgtccat atcctcatgc tgcagaagta caggcaagct cctttaagcc tcatatagga    9180
acactagcct cactcatgag ggtttttactc catgacctgt caacctcaaa gccttcaaca   9240
tgaggactcc aacgtaaatt tggggacaga agcactcaga ccatacccca gcaccacacc    9300
```

-continued

```
ctcctaacct cagggtagct gtcattctcc tagtctcctc tcttgggcct ttagaacccc    9360
catttccttg gggtaatgtc tgatgttttt gtccctgtca taaaaagatg gagagactgt    9420
gtccagcctt tgattcctac ttcctacaat cccaggttct aatgaagttt gtggggcctg    9480
atgccctgag ttgtatgtga tttaataata aaaaagcaag atacagcatg tgtgtggact    9540
gagtgagggc cacagggatc taaaagccaa gtgtgagggg acccagctac agcaggcagc    9600
atcctgagcc tggaatctct tcaggacaag aattctccat atacctacct actctgggga    9660
gtaggtggcc agagttcaag cttcccttag taccaactac cactggctgt gctcttactg    9720
aaggcagaca tggcactgag tgctgtccat ctgtcactca tctccacagc cattcctaat    9780
gtgtggggtg ggagccatca ccaaacccca ttttcagata aggacacagg ctcagagagg    9840
cttgtgtgga gaaagtagc agcagaattc agagagctgg gtctcctgca gcaccttgga     9900
ctgccagcag ccacagtgct tgtcacacag cacatactca aaagaatgcc agcccctca     9960
gcctagagtg cctggccttt ctttcagatg aggaagaggg tcaaagctgt tagcttgccc   10020
accatatgac cacatacatg accaacagct tgagggaggg aggattactg tggctcccag   10080
cctgagaggt gggacaccca aatgtattag gtccttgaat cagggctgac cttgtgattc   10140
agtcactcct accagaatgc tggggaatgg ggatgccaaa ggcaaggag gctttctaag   10200
gtgtggtgta agataggcat ttctgcttcc atgtacacct gtgagcagag taggaaggcc   10260
ctgtggagaa tatatcccac aaaccagtag cccttcctgg cagtgggtga atactgccac   10320
cctatacccc tatgcaaggc cagtagaacc acccaaccca caacatctag agaaattaca   10380
ggtcatctta agcctctaaa ttgtggagaa actcgacatg cgcacgattc ctaacctgct   10440
agcctagggt gcggggtgga taatttaagg aaactggggt ttcttataga atcggaggct   10500
ccatgaagtc accctgacaa gaggtcagca atagccagca gcagtggcta ctcctaagcc   10560
tccagacaga gcaccctgtg aatgtaccct attctcacat ctgggtgtct ataggtgtga   10620
ctgggtcaga tgtcacccag gccattgcaa tgggcccta gccccatggg gtgttgggat   10680
agcagccaag cagctcccat gctgagatac tgcctgcagt agactgatgg ataagaaaac   10740
aaggcccaaa atgttttctt tccagacttg atctttcttt gttcaaaaat gctgttttcc   10800
cttaaacttg cccaaaccca ttgttttgca gttgaggaaa ataaggcata gaaagattaa   10860
aggaagtttc tgaggttaca gagcaaagta ctggcttcac ctgaaataga caggtgtgcc   10920
ctgatcctga tttgagctc                                                 10939
```

<210> SEQ ID NO 211
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 211
atgcatgcca ccatgaaaaa gcctgaactc acc          33

<210> SEQ ID NO 212
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 212

```
ggatcccagg ctttacactt tatgcttc                                              28
```

<210> SEQ ID NO 213
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 213

```
gctgtctgga gtactgtgca tctgc                                                 25
```

<210> SEQ ID NO 214
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 214

```
ggaatgcagc ttcctcaagg gactcgc                                               27
```

<210> SEQ ID NO 215
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 215

```
tgcatcaggt cggagacgct gtcgaac                                               27
```

<210> SEQ ID NO 216
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 216

```
gcactcgtcc gagggcaaag gaatagc                                               27
```

<210> SEQ ID NO 217
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 217

```
tgtgctggga attgaaccca ggac                                                  24
```

<210> SEQ ID NO 218
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 218

```
ctacttgtct gtgctttctt cc                                                    22
```

<210> SEQ ID NO 219
<211> LENGTH: 27
<212> TYPE: DNA
<213> ORGANISM: Artificial

```
<220> FEATURE:
<223> OTHER INFORMATION: An artificially synthesized primer sequence

<400> SEQUENCE: 219
ctcgactcgt ccctattagg caacagc                                           27

<210> SEQ ID NO 220
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 220
tcagaggcag tggagcctcc agtcagc                                           27

<210> SEQ ID NO 221
<211> LENGTH: 449
<212> TYPE: PRT
<213> ORGANISM: Homo sapiens

<400> SEQUENCE: 221
```

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Val Leu Ala Arg Ile Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn

```
                    275                 280                 285
Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 222
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 222

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 223
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 223

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Leu Leu Ala Arg Ala Thr Ala Met Asp Tyr Trp Gly Gln Gly
                100                 105                 110

Ile Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 224
<211> LENGTH: 214
<212> TYPE: PRT
<213> ORGANISM: Homo sapiens

<400> SEQUENCE: 224

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gly Gln Gly Asn Arg Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 225
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 225

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 226
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 226

Asp Ile Gln Met Thr Gln Ser Pro Ser Ser Leu Ser Ala Ser Val Gly
1               5                   10                  15

Asp Ser Val Thr Ile Thr Cys Gln Ala Ser Glu Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 227
<211> LENGTH: 449
<212> TYPE: PRT
<213> ORGANISM: Homo sapiens

<400> SEQUENCE: 227

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp

-continued

```
                35                  40                  45
Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 228
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 228

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 229
<211> LENGTH: 214
<212> TYPE: PRT
<213> ORGANISM: Homo sapiens

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 230
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 230

Asp Ile Gln Met Thr Gln Ser Pro Ser Ser Leu Ser Ala Ser Val Gly
1               5                   10                  15

```
Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 231
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 231

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Glu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 232
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 232

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 233
<211> LENGTH: 445
<212> TYPE: PRT
<213> ORGANISM: Homo sapiens

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

-continued

Glu Met His Trp Ile Arg Gln Pro Gly Lys Gly Leu Glu Trp Ile
         35                  40                  45

Gly Ala Ile Asn Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Arg Gly Thr Leu Val Thr
                100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
 130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
        435                 440                 445

<210> SEQ ID NO 234
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 234

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
50                  55                  60

Lys Gly Arg Val Thr Leu Thr Ala Asp Lys Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln

```
                370                 375                 380
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 235
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 235

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
                20                  25                  30

Glu Met His Trp Ile Arg Gln Pro Pro Gly Glu Gly Leu Glu Trp Ile
            35                  40                  45

Gly Ala Ile Asp Pro Lys Thr Gly Asp Thr Ala Tyr Ser Glu Ser Phe
        50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 236
<211> LENGTH: 219
<212> TYPE: PRT
<213> ORGANISM: Homo sapiens

<400> SEQUENCE: 236

Asp Ile Val Met Thr Gln Ser Pro Leu Ser Leu Pro Val Thr Pro Gly
1               5                   10                  15

Gln Pro Ala Ser Ile Ser Cys Arg Ala Ser Arg Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Arg Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 237
<211> LENGTH: 219
<212> TYPE: PRT
<213> ORGANISM: Artificial
<220> FEATURE:
<223> OTHER INFORMATION: An artificially synthesized peptide sequence

<400> SEQUENCE: 237

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 238
<211> LENGTH: 219
<212> TYPE: PRT
<213> ORGANISM: Artificial
<220> FEATURE:
<223> OTHER INFORMATION: An artificially synthesized peptide sequence

<400> SEQUENCE: 238

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95
```

```
Thr His Val Pro Pro Thr Phe Gly Gln Gly Thr Lys Val Glu Ile Glu
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 239
<211> LENGTH: 447
<212> TYPE: PRT
<213> ORGANISM: Homo sapiens

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
```

245                 250                 255

Pro Glu Val Thr Cys Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 240
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala

-continued

```
                165                 170                 175
Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Ser Cys
            210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Phe Arg Val Val Ser
            290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 241
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 241

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Met Asn Trp Val Arg Gln Ala Pro Gly Gln Gly Leu Glu Trp Met
            35                  40                  45

Gly Leu Ile Asn Pro Tyr Asn Gly Gly Thr Ser Tyr Asn Asp Gln Phe
        50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                         85                  90                  95
Ala Arg Asp Gly Tyr Asp Asp Gly Pro Tyr Thr Met Asp Tyr Trp Gly
                    100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Ser Cys
            210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 242
<211> LENGTH: 214
<212> TYPE: PRT
<213> ORGANISM: Homo sapiens

<400> SEQUENCE: 242

Asp Ile Gln Met Thr Gln Ser Pro Ser Ser Leu Ser Ala Ser Val Gly
1               5                   10                  15
```

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 243
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys Gln Thr Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

-continued

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 244
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro
    435                 440                 445

<210> SEQ ID NO 245
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 245

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Gln Phe
50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Gly Tyr Asp Asp Gly Pro Tyr Thr Met Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Asn Phe Gly Thr Gln Thr Tyr Thr Cys Asn Val Asp His
    195                 200                 205

Lys Pro Ser Asn Thr Lys Val Asp Lys Thr Val Glu Arg Lys Ser Cys
210                 215                 220

```
Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445

<210> SEQ ID NO 246
<211> LENGTH: 514
<212> TYPE: PRT
<213> ORGANISM: Homo sapiens

<400> SEQUENCE: 246

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160
```

```
Arg Phe Arg Thr Val Asn Ser Thr Ser Trp Met Glu Val Asn Phe Ala
                165             170             175

Lys Asn Arg Lys Asp Lys Asn Gln Thr Tyr Asn Leu Thr Gly Leu Gln
            180             185             190

Pro Phe Thr Glu Tyr Val Ile Ala Leu Arg Cys Ala Val Lys Glu Ser
            195             200             205

Lys Phe Trp Ser Asp Trp Ser Gln Glu Lys Met Gly Met Thr Glu Glu
        210             215             220

Glu Ala Pro Cys Gly Leu Glu Leu Trp Arg Val Leu Lys Pro Ala Glu
225             230             235             240

Ala Asp Gly Arg Arg Pro Val Arg Leu Leu Trp Lys Lys Ala Arg Gly
                245             250             255

Ala Pro Val Leu Glu Lys Thr Leu Gly Tyr Asn Ile Trp Tyr Tyr Pro
                260             265             270

Glu Ser Asn Thr Asn Leu Thr Glu Thr Met Asn Thr Thr Asn Gln Gln
            275             280             285

Leu Glu Leu His Leu Gly Gly Glu Ser Phe Trp Val Ser Met Ile Ser
            290             295             300

Tyr Asn Ser Leu Gly Lys Ser Pro Val Ala Thr Leu Arg Ile Pro Ala
305             310             315             320

Ile Gln Glu Lys Ser Phe Gln Cys Ile Glu Val Met Gln Ala Cys Val
                325             330             335

Ala Glu Asp Gln Leu Val Val Lys Trp Gln Ser Ser Ala Leu Asp Val
                340             345             350

Asn Thr Trp Met Ile Glu Trp Phe Pro Asp Val Asp Ser Glu Pro Thr
            355             360             365

Thr Leu Ser Trp Glu Ser Val Ser Gln Ala Thr Asn Trp Thr Ile Gln
            370             375             380

Gln Asp Lys Leu Lys Pro Phe Trp Cys Tyr Asn Ile Ser Val Tyr Pro
385             390             395             400

Met Leu His Asp Lys Val Gly Glu Pro Tyr Ser Ile Gln Ala Tyr Ala
                405             410             415

Lys Glu Gly Val Pro Ser Glu Gly Pro Glu Thr Lys Val Glu Asn Ile
                420             425             430

Gly Val Lys Thr Val Thr Ile Thr Trp Lys Glu Ile Pro Lys Ser Glu
            435             440             445

Arg Lys Gly Ile Ile Cys Asn Tyr Thr Ile Phe Tyr Gln Ala Glu Gly
        450             455             460

Gly Lys Gly Phe Ser Lys Thr Val Asn Ser Ser Ile Leu Gln Tyr Gly
465             470             475             480

Leu Glu Ser Leu Lys Arg Lys Thr Ser Tyr Ile Val Gln Val Met Ala
            485             490             495

Ser Thr Ser Ala Gly Gly Thr Asn Gly Thr Ser Ile Asn Phe Lys Thr
            500             505             510

Leu Ser
```

METHOD OF MODIFYING ISOELECTRIC POINT OF ANTIBODY VIA AMINO ACID SUBSTITUTION IN CDR

CROSS-REFERENCE TO RELATED APPLICATIONS

This application is a continuation of U.S. application Ser. No. 14/741,786, filed on Jun. 17, 2015, which is a continuation of U.S. application Ser. No. 12/679,922 (now U.S. Pat. No. 9,096,651), having a 371(c) date of Oct. 1, 2010, which is the National Stage of International Application No. PCT/JP2008/067534, filed on Sep. 26, 2008, which claims the benefit of Japanese Application Nos. 2007-250165, filed on Sep. 26, 2007, and 2007-256063, filed on Sep. 28, 2007. The contents of the US and PCT applications referenced above are incorporated herein by reference in their entireties.

TECHNICAL FIELD

The present invention relates to methods for modifying the isoelectric point (pI) of an antibody while retaining its antigen-binding activity through amino acid substitutions in the CDR; methods for controlling antibody pharmacokinetics in plasma (pharmacokinetics in blood); pharmaceutical compositions comprising as an active ingredient an antibody with a modified isoelectric point; methods for producing the compositions; and such.

The present invention also relates to methods for controlling the plasma half-lives of anti-IL-6 receptor antibodies, anti-glypican 3 antibodies, and anti-IL-31 receptor antibodies by modifying amino acid residues that are exposed on the surface of the CDR regions of the antibodies; antibodies (anti-IL-6 receptor antibodies, anti-glypican 3 antibodies, and anti-IL-31 receptor antibodies) whose plasma half-life is controlled through modification of amino acid residues; pharmaceutical compositions comprising such an antibody as an active ingredient; and methods for producing the compositions.

Furthermore, the present invention relates to pharmaceutical compositions comprising an anti-IL-6 receptor antibody as an active ingredient, methods for producing the compositions, and such.

BACKGROUND ART

Antibodies are drawing attention as pharmaceuticals as they have long half-life in plasma and few adverse effects. Of them, a number of IgG-type antibody pharmaceuticals are available on the market and many antibody pharmaceuticals are currently under development (Non-patent Documents 1 and 2). Most of the antibody pharmaceuticals available on the market are chimeric antibodies, humanized antibodies, or human antibodies. Currently, many antibody pharmaceuticals are being developed which have more superior characteristics with improved drug efficacy, convenience, and cost from modification of humanized antibodies or human antibodies. Various technologies applicable to these antibody pharmaceuticals have been developed, including those that enhance effector function, antigen-binding activity, phramacokinetics, or stability, and those that reduce the risk of immunogenicity. For methods of enhancing drug efficacy or reducing dosage, techniques that enhance antibody-dependent cell-mediated cytotoxicity (ADCC) or complement-dependent cytotoxicity (CDC) through amino acid substitution in the Fc domain of an IgG antibody have been reported (Non-patent Documents 3 and 4). Furthermore, affinity maturation has been reported as a technique for enhancing antigen-binding activity or antigen-neutralizing activity (Non-patent Document 5). This technique enables enhancement of antigen-binding activity through introduction of amino acid mutations into the CDR region of a variable region or such.

A problem encountered with current antibody pharmaceuticals is high production cost associated with the administration of extremely large quantities of protein. The preferred form of administration is thought to be subcutaneous formulation for chronic autoimmune diseases. In general, it is necessary that subcutaneous formulations are high concentration formulations. From the perspective of stability or such, the concentration limit for IgG-type antibody formulations is in general thought to be about 100 mg/ml (Non-patent Document 6). Low-cost, convenient antibody pharmaceuticals with more superior characteristics that can be administered subcutaneously in longer intervals can be provided by increasing the half-life of an antibody in the plasma to prolong its therapeutic effect and thereby reduce the amount of protein administered.

FcRn is closely involved in the long plasma half-life of antibodies. The plasma half-life of antibody is known to be different between antibody isotypes. IgG1 and IgG2 have the longest half-life in plasma, while IgG3 and IgG4 have a shorter half-life (Non-patent Document 7). A reported method for prolonging the plasma half-lives of IgG1 and IgG2 antibodies, which have a superior half-life in plasma, comprises substituting amino acids in the constant region to enhance the binding to FcRn (Non-patent Documents 8 to 10). However, introduction of artificial amino acid mutations into a constant region is encountered with the problem of immunogenicity. On the other hand, a method that comprises introducing amino acid mutations into antibody variable regions for improving antibody pharmacokinetics has recently been reported (Patent Document 1).

Patent Document 1 describes that the pharmacokinetics of IgG can be controlled by modifying its isoelectric point, and the plasma half-life of an antibody can be prolonged by reducing the isoelectric point of the antibody without loss of antigen-binding activity through introduction of amino acid substitutions into the antibody variable region framework. Specifically, the isoelectric point of an antibody can be reduced without loss of antigen-binding activity, for example, by introducing amino acid substitutions at H10, H12, H23, H39, H43, and H105, Kabat's numbering. It is also possible to introduce amino acid mutations into other framework sequences without loss of binding activity. In some cases, however, introduction of amino acid substitutions into framework sequences alone is thought to be insufficient for significant reduction of isoelectric point. This is because a human antibody sequence is generally used as a framework sequence after amino acid substitution to reduce immunogenicity, but human antibody framework sequences are highly conserved and have low diversity, and thus there is little flexibility for amino acid substitution. Therefore, when amino acid substitution into the framework alone is insufficient to reduce the isoelectric point of an antibody, it would be difficult to further reduce the isoelectric point.

In contrast, CDR sequences have an enormous diversity due to somatic mutations, and because they have the diversity needed for acquiring antigen-binding activity, there is significantly greater flexibility for amino acid substitution compared to framework sequences. However, amino acid substitution in CDR sequence is generally known to affect the antigen-binding activity of an antibody, as CDR sequence is the most important factor for strong antigen-binding activity. Thus, it is difficult to reduce the isoelectric point of an antibody by substituting amino acids in its CDR sequence without considerable loss of antigen-binding activity. Furthermore, CDR sequence varies greatly depending on the type of antigen; thus, regardless of antibody specificity, it has been believed to be very difficult to substitute amino acids in an antibody CDR sequence without considerable loss of the antibody's antigen-binding activity. In fact, this can be inferred from many findings described below.

In general, antibodies derived from a nonhuman animal species are humanized by CDR grafting, in which a human framework sequence is grafted to the CDR sequence of the nonhuman animal species. If a humanized antibody obtained by CDR grafting does not have a comparable binding activity as the chimeric antibody, the binding activity can be recovered from substituting a portion of the framework sequence which determines the CDR structure with amino acids of the antibody framework sequence of the nonhuman animal species from which the antibody is derived (Non-patent Document 11). The CDR sequence and structure are very important for the antigen-binding activity and specificity of an antibody. Furthermore, the antigen-binding activity of an antibody is generally known to be reduced when antibody CDR residues are modified by isomerization of aspartic acid residues, deamidation of aspartic acid residues, or oxidation of methionine residues in antibody CDR (Non-patent Document 12), and this also suggests that CDR sequence is very important for the antigen-binding activity of antibodies. In addition, it has been further reported that not only the antigen-binding activity but also the expression level of an antibody is often considerably reduced when amino acid substitutions are introduced into the heavy chain CDR2 sequence of an antibody (Non-patent Documents 13 to 15). In particular, the expression level of an antibody is known to be markedly reduced when amino acid substitution is introduced at H51 (Non-patent Document 16). Furthermore, the antigen-binding activity has been reported to be considerably reduced in almost all cases when mutations are introduced into the heavy chain CDR3 sequence of an antibody (Non-patent Documents 17 and 18). Alternatively, the antigen-binding activity of an antibody is often markedly reduced when amino acids in the antibody CDR are substituted with alanine by alanine scanning mutagenesis (Non-patent Documents 19 to 23). The effect of alanine substitution on antigen-binding activity is thought to depend on antibody specificity. In sum, the antigen-binding activity of an antibody is generally considered to be reduced by amino acid substitution in the CDR sequence, and there is no previous report on positions of amino acids whose substitution does not significantly reduce the antigen-binding activity of an antibody regardless of its antibody specificity.

In antibody engineering to produce antibody molecules with more superior characteristics, almost all amino acid substitutions introduced into antibody CDR sequences are aimed at affinity maturation. Affinity maturation is a method for obtaining antibodies with improved antigen-binding activity, and is generally conducted by displaying on phages or ribosomes an antibody library comprising randomized CDR sequences derived from the CDR sequences of a parent antibody molecule and panning on the antigen. This method enables discovery of amino acid substitutions in antibody CDR sequence that improve antigen-binding activity (Non-patent Documents 5 and 24 to 26). However, amino acid substitutions found by the above-described method which improve antigen-binding activity are different depending on the antibody specificity. Thus, there is no previous report on positions of amino acids in CDR sequence whose substitution improves the antigen-binding activity regardless of the antibody specificity. Other than affinity maturation for modifying CDR sequence, methods for improving expression levels of antibodies in mammalian cells by substituting amino acids at specific positions in the CDR sequence (Patent Document 2) are reported. According to Patent Document 2, the expression levels of antibodies in mammalian cells can be improved independently of the antibody specificity by substituting amino acids at specific positions in the CDR sequence with a particular sequence. Alternatively, some reports describe deimmunization where the immunogenicity of an antibody is reduced by avoiding T cell epitopes in the antibody CDR sequence. However, there is no previous report on methods for substituting amino acids in an antibody, regardless of its antibody specificity, to remove T cell epitopes from the CDR sequence without loss of binding activity (Non-patent Documents 27 and 28).

As described above, the antibody CDR sequence is closely involved in antigen binding. Therefore, amino acid substitutions in CDR sequence generally impair binding activity. The effect of amino acid substitution in CDR sequence on antigen binding differs depending on the antibody specificity. Patent Document 1 describes some examples on the control of isoelectric point by amino acid substitution in CDR; however, the antigen-binding activity can be impaired in some kinds of antibodies. Alternatively, methods have been reported for improving the expression of antibodies independently of the antibody specificity by common amino acid substitutions; however, there is no previous report on methods for improving an antibody's antigen-binding activity or removing T cell epitopes without considerable loss of an antibody's antigen-binding activity. There is absolutely no report on antibody CDR sequences whose amino acids can be substituted without considerable loss of the antibody's antigen-binding activity regardless of the antibody specificity.

Documents of related prior arts for the present invention are described below.

[Non-patent Document 1] Janice M Reichert, Clark J Rosensweig, Laura B Faden & Matthew C Dewitz. Monoclonal antibody successes in the clinic. Nature Biotechnology (2005) 23:1073-1078

[Non-patent Document 2] Pavlou A K, Belsey M J. The therapeutic antibodies market to 2008. Eur J Pharm Biopharm. 2005 April; 59(3):389-96

[Non-patent Document 3] Presta L G. Engineering of therapeutic antibodies to minimize immunogenicity and optimize function. Adv Drug Deliv Rev. 2006 Aug. 7; 58(5-6):640-56

[Non-patent Document 4] Kim S J, Park Y, Hong H J. Antibody engineering for the development of therapeutic antibodies. Mol Cells. 2005 Aug. 31; 20(1):17-29 Review

[Non-patent Document 5] Fujii I. Antibody affinity maturation by random mutagenesis. Methods Mol Biol. (2004) 248:345-59

[Non-patent Document 6] Shire S J, Shahrokh Z, Liu J. Challenges in the development of high protein concentration formulations. J Pharm Sci. 2004 June; 93(6):1390-402

[Non-patent Document 7] Salfeld J G. Isotype selection in antibody engineering. Nat Biotechnol. 2007 December; 25(12):1369-72

[Non-patent Document 8] Hinton P R, Johlfs M G, Xiong J M, Hanestad K, Ong K C, Bullock C, Keller S, Tang M T, Tso J Y, Vasquez M, Tsurushita N. Engineered human IgG antibodies with longer serum half-lives in primates. J Biol Chem. 2004 Feb. 20; 279(8):6213-6

[Non-patent Document 9] Hinton P R, Xiong J M, Johlfs M G, Tang M T, Keller S, Tsurushita N. An engineered human IgG1 antibody with longer serum half-life. J Immunol. 2006 Jan. 1; 176(1):346-56

[Non-patent Document 10] Ghetie V, Popov S, Borvak J, Radu C, Matesoi D, Medesan C, Ober R J, Ward E S. Increasing the serum persistence of an IgG fragment by random mutagenesis. Nat Biotechnol. 1997 July; 15(7): 637-40

[Non-patent Document 11] Almagro J C, Fransson J. Humanization of antibodies. Front Biosci. 2008 Jan. 1; 13:1619-33

[Non-patent Document 12] Liu H, Gaza-Bulseco G, Faldu D, Chumsae C, Sun J. Heterogeneity of monoclonal antibodies. J Pharm Sci. 2008 July; 97(7):2426-47

[Non-patent Document 13] Chen C, Roberts V A, Rittenberg M B. Generation and analysis of random point mutations in an antibody CDR2 sequence: many mutated antibodies lose their ability to bind antigen. J Exp Med. 1992 Sep. 1; 176(3):855-66

[Non-patent Document 14] Chen C, Martin™, Stevens S, Rittenberg M B. Defective secretion of an immunoglobulin caused by mutations in the heavy chain complementarity determining region 2. J Exp Med. 1994 Aug. 1; 180(2):577-86

[Non-patent Document 15] Wiens G D, Heldwein K A, Stenzel-Poore M P, Rittenberg M B. Somatic mutation in VH complementarity-determining region 2 and framework region 2: differential effects on antigen binding and Ig secretion. J Immunol. 1997 Aug. 1; 159(3):1293-302

[Non-patent Document 16] Wiens G D, Lekkerkerker A, Veltman I, Rittenberg M B. Mutation of a single conserved residue in VH complementarity-determining region 2 results in a severe Ig secretion defect. J Immunol. 2001 Aug. 15; 167(4):2179-86

[Non-patent Document 17] Zwick M B, Komori H K, Stanfield R L, Church S, Wang M, Parren P W, Kunert R, Katinger H, Wilson I A, Burton D R. The long third complementarity-determining region of the heavy chain is important in the activity of the broadly neutralizing anti-human immunodeficiency virus type 1 antibody 2F5. J Virol. 2004 March; 78(6):3155-61

[Non-patent Document 18] Komissarov A A, Marchbank M T, Calcutt M J, Quinn T P, Deutscher S L. Site-specific mutagenesis of a recombinant anti-single-stranded DNA Fab. Role of heavy chain complementarity-determining region 3 residues in antigen interaction. J Biol Chem. 1997 Oct. 24; 272(43):26864-70

[Non-patent Document 19] Gerstner R B, Carter P, Lowman H B. Sequence plasticity in the antigen-binding site of a therapeutic anti-HER2 antibody. J Mol Biol. 2002 Aug. 30; 321(5):851-62

[Non-patent Document 20] Vajdos F F, Adams C W, Breece T N, Presta L G, de Vos A M, Sidhu S S. Comprehensive functional maps of the antigen-binding site of an anti-ErbB2 antibody obtained with shotgun scanning mutagenesis. J Mol Biol. 2002 Jul. 5; 320(2):415-28

[Non-patent Document 21] Pons J, Rajpal A, Kirsch J F. Energetic analysis of an antigen/antibody interface: alanine scanning mutagenesis and double mutant cycles on the HyHEL-10/lysozyme interaction. Potein Sci. 1999 May; 8(5):958-68

[Non-patent Document 22] Leong S R, DeForge L, Presta L, Gonzalez T, Fan A, Reichert M, Chuntharapai A, Kim K J, Tumas D B, Lee W P, Gribling P, Snedecor B, Chen H, Hsei V, Schoenhoff M, Hale V, Deveney J, Koumenis I, Shahrokh Z, McKay P, Galan W, Wagner B, Narindray D, Hebert C, Zapata G. Adapting pharmacokinetic properties of a humanized anti-interleukin-8 antibody for therapeutic applications using site-specific pegylation. Cytokine. 2001 Nov. 7; 16(3):106-19

[Non-patent Document 23] Xiang J, Srivamadan M, Raj ala R, Jia Z. Study of B72.3 combining sites by molecular modeling and site-directed mutagenesis. Protein Eng. 2000 May; 13(5):339-44

[Non-patent Document 24] Rothe A, Hosse R J, Power B E. Ribosome display for improved biotherapeutic molecules. Expert Opin Biol Ther. 2006 February; 6(2):177-87

[Non-patent Document 25] Schmitz U, Versmold A, Kaufmann P, Frank H G. Phage display: a molecular tool for the generation of antibodies—a review. Placenta. 2000 March-April; 21 Suppl A:S106-12

[Non-patent Document 26] Rajpal A, Beyaz N, Haber L, Cappuccilli G, Yee H, Bhatt R R, Takeuchi T, Lerner R A, Crea R. A general method for greatly improving the affinity of antibodies by using combinatorial libraries. Proc Natl Acad Sci USA. 2005 Jun. 14; 102(24):8466-71

[Non-patent Document 27] De Groot A S, Knopp P M, Martin W. De-immunization of therapeutic proteins by T-cell epitope modification. Dev Biol (Basel). (2005) 122:171-94

[Non-patent Document 28] www.algonomics.com/proteinengineering/tripole_applications.php

[Patent Document 1] WO/2007/114319

[Patent Document 2] US/2006/0019342

DISCLOSURE OF THE INVENTION

Problems to be Solved by the Invention

The present invention was achieved in view of the above circumstances. An objective of the present invention is to provide methods for modifying the isoelectric point of a polypeptide comprising an antibody variable region while retaining its antigen-binding activity; methods for controlling antibody half-life in plasma; pharmaceutical compositions comprising as an active ingredient an antibody with controlled plasma half-life; and methods for producing the antibodies and pharmaceutical compositions comprising the antibody as an active ingredient.

Another objective of the present invention is to provide methods for controlling plasma half-lives of anti-IL-6 receptor antibodies, anti-glypican 3 antibodies, and anti-IL-31 receptor antibodies by modifying amino acid residues exposed on the surface of the CDR regions of the antibodies; anti-IL-6 receptor antibodies, anti-glypican 3 antibodies, and anti-IL-31 receptor antibodies whose plasma half-life is controlled by modifying amino acid residues; methods for producing such antibodies; and pharmaceutical compositions comprising such an antibody as an active ingredient.

Furthermore, another objective of the present invention is to provide pharmaceutical compositions that comprise second-generation molecules, which are more superior than the humanized anti-IL-6 receptor IgG1 antibody TOCILIZUMAB, and methods for producing such pharmaceutical compositions. The second-generation molecules have been improved to exhibit enhanced antigen-neutralizing activity and retention in plasma, and thus produce a prolonged therapeutic effect even when the frequency of administration is reduced; and they have also been improved to have reduced immunogenicity and improved safety and physical properties, by modifying amino acid sequences of the variable and constant regions of TOCILIZUMAB.

Means for Solving the Problems

The present inventors conducted dedicated studies on methods for modifying the isoelectric point of polypeptides comprising an antibody variable region while retaining the antigen-binding activity of the variable region. As a result, the present inventors identified specific amino acid positions within the amino acid sequence of a complementarity determining region (CDR) of an antibody variable region, that allow for modification of the isoelectric point while retaining the antigen-binding activity of the variable region. Furthermore, the present inventors discovered that the plasma half-life of a polypeptide comprising an antibody variable region could be regulated by controlling the isoelectric point of the polypeptide, and that heteromultimers of a polypeptide comprising an antibody variable region could be efficiently produced by utilizing differences in the isoelectric point. Specifically, the present inventors identified specific amino acid positions in a CDR sequence constituting an antibody variable region, that allow one to control the charge on the surface of an antibody molecule without affecting the antibody structure and function such as the antigen-binding activity of the antibody variable region. In addition, the present inventors demonstrated that the plasma half-life of a polypeptide comprising an antibody variable region could be regulated by controlling the charge on antibody surface to modify the isoelectric point, and that antibodies with controlled plasma half-lives indeed retained their antigen-binding activities. Furthermore, the present inventors demonstrated that the tumor growth-suppressing effect of antibodies that exhibit cytotoxicity in cancer cells could be enhanced by controlling the plasma half-life of the antibodies, and thereby completed the present invention. In addition, the present inventors demonstrated that heterodimers comprising antibodies that bind to two or more different types of antigens could be isolated and purified by modifying their isoelectric points by controlling the CDR charge.

Furthermore, the present inventors conducted dedicated studies to produce second-generation molecules that are more superior than the first-generation humanized anti-IL-6 receptor IgG1 antibody TOCILIZUMAB, and have been improved to exhibit enhanced drug efficacy and retention in plasma, and thus produce a prolonged therapeutic effect even when the frequency of administration is reduced. They have also been improved to have reduced immunogenicity and improved safety and physical properties (stability and homogeneity), by modifying amino acid sequences of the variable and constant regions of TOCILIZUMAB. As a result, the present inventors discovered multiple CDR mutations in the variable regions of TOCILIZUMAB that enable to improve the antigen-binding activity (affinity). The present inventors thus successfully improved the affinity significantly using a combination of such mutations. The present inventors also successfully improved plasma retention by modifying the variable region sequence to lower the isoelectric point of an antibody. Furthermore, the present inventors successfully reduced immunogenicity risk by removing some of the in silico-predicted T-cell epitope peptides in the variable regions and the mouse sequences that remain in the framework of TOCILIZUMAB. In addition, the present inventors successfully increased the stability at higher concentrations. Furthermore, the present inventors also successfully discovered novel constant region sequences that do not bind to Fcγ receptor and that improve the stability under acidic conditions, heterogeneity originated from disulfide bonds in the hinge region, heterogeneity originated from the heavy chain C terminus, and stability in high concentration formulations, while minimizing the generation of new T-cell epitope peptides in the constant region of TOCILIZUMAB. The present inventors successfully discovered second-generation molecules that are more superior to TOCILIZUMAB by combining amino acid sequence modifications in the CDR, variable, and constant regions.

More specifically, the present invention provides:

[1] a method for modifying the isoelectric point of a polypeptide comprising an antibody variable region while retaining the antigen-binding activity of the variable region, which comprises modifying the charge of at least one exposable amino acid residue on the surface of complementarity determining region (CDR) of the polypeptide;

[2] the method of [1], wherein the polypeptide comprising an antibody variable region further comprises an FcRn-binding domain;

[3] the method of [1], wherein the polypeptide comprising an antibody variable region is an IgG antibody;

[4] the method of [1], wherein the polypeptide comprising an antibody variable region is a chimeric antibody, humanized antibody, or human antibody;

[5] the method of [1], wherein the polypeptide comprising an antibody variable region is a multispecific polypeptide that binds to at least two types of antigens;

[6] the method of [1], wherein the charge of amino acid residue is modified by amino acid substitution;

[7] the method of [1], wherein the modification in the charge of amino acid residue results in a change of 1.0 or more in the theoretical isoelectric point;

[8] the method of [1], wherein the exposable amino acid residue on the surface of the CDR region is at least one amino acid residue selected from amino acid residues at positions 31, 61, 62, 64, and 65 in the heavy chain variable region and positions 24, 27, 53, 54, and 55 in the light chain variable region according to Kabat's numbering system;

[9] a polypeptide comprising an antibody variable region with a modified isoelectric point, which is obtained by the method of any one of [1] to [8];

[10] a method for controlling the plasma pharmacokinetics of a polypeptide comprising an antibody variable region, which comprises modifying the isoelectric point of the polypeptide by the method of any one of [1] to [8];

[11] the method of [10], wherein the control of pharmacokinetics refers to increase or decrease of any one of the parameters of clearance (CL) in plasma, area under the concentration curve (AUC), mean retention time in plasma, and half-life in plasma (t1/2);

[12] a polypeptide comprising an antibody variable region whose pharmacokinetics in plasma is controlled, which is obtained by the method of [10];

[13] a method for producing a polypeptide comprising an antibody variable region with a modified isoelectric point, which comprises:
(a) modifying a nucleic acid encoding a polypeptide so as to modify the charge of at least one exposable amino acid residue on the surface of the CDR region of the polypeptide;
(b) culturing a host cell to express the nucleic acid; and
(c) collecting the polypeptide comprising an antibody variable region from the host cell culture;

[14] the method of [13], wherein the polypeptide comprising an antibody variable region further comprises an FcRn-binding domain;

[15] the method of [13], wherein the polypeptide comprising an antibody variable region is an IgG antibody;
[16] the method of [13], wherein the polypeptide comprising an antibody variable region is a chimeric antibody, humanized antibody, or human antibody;
[17] the method of [13], wherein the polypeptide comprising an antibody variable region is a multispecific polypeptide that binds to at least two types of antigens;
[18] the method of [13], wherein the charge of amino acid residue is modified by amino acid substitution;
[19] the method of [13], wherein the modification in the charge of amino acid residue results in a change of 1.0 or more in the theoretical isoelectric point;
[20] the method of [13], wherein the exposable amino acid residue on the surface of the CDR region is at least one amino acid residue selected from amino acid residues at positions 31, 61, 62, 64, and 65 in the heavy chain variable region and positions 24, 27, 53, 54, and 55 in the light chain variable region according to Kabat's numbering system;
[21] a polypeptide comprising an antibody variable region with a modified isoelectric point, which is obtained by the method of any one of [13] to [20];
[22] a method for producing a polypeptide comprising an antibody variable region whose pharmacokinetics in plasma is controlled, which comprises modifying the isoelectric point of the polypeptide comprising an antibody variable region by the method of any one of [13] to [20];
[23] the method [22], wherein the control of pharmacokinetics refers to increase or decrease of any one of the parameters of clearance (CL) in plasma, area under the concentration curve (AUC), mean retention time in plasma, and half-life in plasma (t1/2);
[24] a polypeptide comprising an antibody variable region whose pharmacokinetics in plasma is controlled, which is produced by the method of 22;
[25] a method for producing a multispecific polypeptide comprising a first polypeptide and a second polypeptide each of which comprises an antibody variable region, which comprises:
(a) modifying a nucleic acid encoding a polypeptide so as to modify the charge of at least one exposable amino acid residue on the surface of the CDR region of the first polypeptide and second polypeptide, specifically modifying both or either one of a nucleic acid encoding the amino acid residues of the first polypeptide and a nucleic acid encoding the amino acid residues of the second polypeptide, so as to increase the difference between the isoelectric points of the first polypeptide and second polypeptide when compared to before modification;
(b) culturing a host cell to express the nucleic acids; and
(c) collecting a multispecific antibody from the host cell culture;
[26] the method of [25], wherein the step of collecting the multispecific polypeptide comprising the first polypeptide and second polypeptide from the host cell culture is achieved by a standard chromatography;
[27] the method of [25], wherein the nucleic acid is modified so that the peaks for homomultimer of the first polypeptide, homomultimer of the second polypeptide, and heteromultimer of the first polypeptide and second polypeptide are more clearly separated in a standard chromatographic analysis when compared to those before modification;
[28] the method of [25], wherein the multispecific polypeptide is a multispecific antibody;
[29] a multispecific antibody that is produced by the method of [27];
[30] the multispecific antibody of [29], which is a bispecific antibody;
[31] an antibody whose isoelectric point is modified as compared to the antibody before modification while retaining the antigen-binding activity, which comprises a human-derived framework region (FR), a human constant region, and a CDR selected from the group consisting of human-derived CDRs, nonhuman animal-derived CDRs, and synthetic CDRs, wherein at least one exposable amino acid residue on the surface of the CDR region is different in the charge from the amino acid residue at the corresponding position in the wild type CDR;
[32] the antibody of [31], wherein the human constant region comprises a human Fc domain;
[33] the antibody of [31], whose pharmacokinetics in plasma is controlled by modifying the isoelectric point;
[34] an IgG antibody whose isoelectric point is modified when compared to that before amino acid modification, wherein the charge of at least one amino acid residue selected from amino acid residues at positions 31, 61, 62, 64, and 65 in the heavy chain variable region and positions 24, 27, 53, 54, and 55 in the light chain variable region according to Kabat's numbering system;
[35] the antibody of [34], wherein the modified amino acid is selected from the amino acid residues in either of groups (a) and (b) below:
(a) glutamic acid (E) and aspartic acid (D); and
(b) lysine (K), arginine (R), and histidine (H);
[36] a multispecific antibody comprising a first polypeptide and a second polypeptide, whose isoelectric points are different from each other, and at least one amino acid residue of the first polypeptide selected from amino acid residues at positions 31, 61, 62, 64, and 65 in the heavy chain variable region and positions 24, 27, 53, 54, and 55 in the light chain variable region according to Kabat's numbering system is charged;
[37] the antibody of [36], wherein at least one amino acid residue of the second polypeptide selected from amino acid residues at positions 31, 61, 62, 64, and 65 in the heavy chain variable region and positions 24, 27, 53, 54, and 55 in the light chain variable region according to Kabat's numbering system has no charge or has a charge opposite to the charge of the selected amino acid residue of the first polypeptide;
[38] the antibody of [36], wherein the amino acid residue having a charge and the amino acid residue having an opposite charge as a combination are each selected from the different group of:
(a) glutamic acid (E) and aspartic acid (D); and
(b) lysine (K), arginine (R), and histidine (H);
[39] the multispecific antibody comprising a first polypeptide and a second polypeptide of [36], which gives separated peaks for the homomultimer of the first polypeptide and the homomultimer of the second polypeptide in a standard chromatographic analysis;
[40] a composition comprising a pharmaceutically acceptable carrier and the antibody of any one of [31] to [39];
[41] a nucleic acid encoding a polypeptide that constitutes the antibody of any one of [31] to [39];
[42] a host cell comprising the nucleic acid of [41];
[43] a method for producing the antibody of any one of [31] to [39], which comprises the steps of culturing the host cell of [42] and collecting the polypeptide from the cell culture; and
[44] a method for substituting an exposable amino acid residue on the surface of the complementarity determining region (CDR) of a polypeptide comprising an antibody variable region while retaining the antigen-binding activity of the polypeptide, which comprises substituting at least one amino acid residue selected from amino acid residues at positions 31, 61, 62, 64, and 65 in the heavy chain variable region and positions 24, 27, 53, 54, and 55 in the light chain variable region according to Kabat's numbering system.

The present invention also provides:

[1] a method for producing a glypican 3 antibody with controlled blood pharmacokinetics, which comprises the steps of:
(a) modifying a nucleic acid encoding at least one amino acid residue so as to modify the charge of at least one exposable amino acid residue on the surface of the glypican 3 antibody;
(b) culturing a host cell comprising the nucleic acid so as to express the nucleic acid; and
(c) collecting the glypican 3 antibody from the host cell culture;

[2] the method of [1], wherein the control of blood pharmacokinetics refers to increase or decrease of any one of the parameters of half-life in blood, mean retention time in blood, and clearance in blood;

[3] the method of [1], wherein the charge of the amino acid residue is modified by amino acid substitution in step (a);

[4] the method of [1], wherein the exposable amino acid residue on the surface of the glypican 3 antibody is located in a region other than the FcRn-binding domain of the glypican 3 antibody;

[5] the method of [4], wherein the FcRn-binding domain comprises an Fc domain;

[6] the method of [1], wherein the glypican 3 antibody is an IgG antibody;

[7] the method of [6], wherein the amino acid residue whose charge is to be modified is an amino acid residue in the heavy chain variable region or light chain variable region of the IgG antibody;

[8] the method of [7], wherein the glypican 3 antibody is a glypican 3 antibody comprising a complementarity determining region (CDR), human-derived framework region (FR), and human constant region, and wherein the modification of charge of the amino acid residue in step (a) is modification of at least one exposable amino acid residue on the surface of CDR or FR of the antibody to be modified to an amino acid residue having a different charge;

[9] the method of [8], wherein the glypican 3 antibody is an antibody with reduced content of fucose linked to its Fc domain;

[10] a glypican 3 antibody, which is produced by the method of any one of [1] to [9];

[11] a method for stabilizing an glypican 3 antibody that comprises a complementarity determining region (CDR), human-derived framework region (FR), and human constant region, which comprises modifying at least one amino acid residue constituting the glypican 3 antibody to increase the Tm value, and which comprises the steps of:
(a) modifying a nucleic acid encoding at least one amino acid residue to increase the Tm value of the glypican 3 antibody to be modified;
(b) culturing a host cell comprising the nucleic acid so as to express the nucleic acid; and
(c) collecting the antibody from the host cell culture;

[12] the method of [11], wherein the amino acid residue in step (a) is located within the heavy or light chain FR1 and/or FR2 region;

[13] the method of [12], wherein the amino acid residue of the heavy chain FR2 region of [12] is substituted with an amino acid residue of an FR2 region of the VH4 subclass;

[14] the method of [12], wherein the amino acid residue of the light chain FR2 region of [12] is substituted with an amino acid residue of an FR2 region of the VK3 subclass;

[15] a method for controlling the cytotoxicity of an antibody, which comprises the steps of;
(a) modifying a nucleic acid encoding at least one amino acid so as to modify the charge of at least one exposable amino acid on the surface of an antibody that has cytotoxicity;
(b) culturing a host cell comprising the nucleic acid so as to express the nucleic acid; and
(c) collecting the antibody from the host cell culture;

[16] the method of [15], wherein the control of blood pharmacokinetics refers to control of any one of the parameters of half-life in blood, mean retention time in blood, and clearance in blood;

[17] the method of [15], wherein the charge of the amino acid residue is modified by amino acid substitution in step (a);

[18] the method of [15], wherein the exposable amino acid residue on the antibody surface is located in a region other than the FcRn-binding domain of the antibody;

[19] the method of [18], wherein the FcRn-binding domain comprises an Fc domain;

[20] the method of [15], wherein the glypican 3 antibody is an IgG antibody;

[21] the method of [20], wherein the amino acid residue whose charge is to be modified is an amino acid residue in the heavy chain variable region or light chain variable region of the IgG antibody;

[22] the method of [21], wherein the antibody comprises a complementarity determining region (CDR) derived from a nonhuman animal, human-derived framework region (FR), and human constant region, and wherein the modification of charge of the amino acid residue in step (a) is modification of at least one exposable amino acid residue on the surface of CDR or FR of the antibody to be modified to an amino acid residue having a different charge;

[23] the method of [22], wherein the antibody is an antibody with reduced content of fucose linked to its Fc domain;

[24] an antibody which is produced by the method of any one of [15] to [23];

[25] the method of [24], wherein the antibody is a glypican 3 antibody;

[26] an antibody which comprises a heavy chain variable region comprising one or more of:
(a) substitution of T for K at amino acid position 19;
(b) substitution of E for Q at amino acid position 43;
(c) substitution of S for K at amino acid position 63;
(d) substitution of Q for K at amino acid position 65; and
(e) substitution of D for G at amino acid position 66;
in the heavy chain variable region of SEQ ID NO: 195; and a light chain variable region comprising one or more of:
(f) substitution of E for Q at amino acid position 27;
(g) substitution of T for K at amino acid position 79; and
(h) substitution of S for R at amino acid position 82;
in the light chain variable region of SEQ ID NO: 201;

[27] the antibody of [26], which comprises the heavy chain of SEQ ID NO: 197 and the light chain of SEQ ID NO: 203;

[28] the antibody of [26], which comprises the heavy chain of SEQ ID NO: 198 and the light chain of SEQ ID NO: 204;

[29] an antibody which comprises a heavy chain variable region comprising one or more of:
(a) substitution of K for Q at amino acid position 43;
(b) substitution of N for D at amino acid position 52; and
(c) substitution of R for Q at amino acid position 107;
in the heavy chain variable region of SEQ ID NO: 195; and a light chain variable region comprising one or more of:
(d) substitution of Q for E at amino acid position 17;
(e) substitution of R for Q at amino acid position 27; and
(f) substitution of R for Q at amino acid position 105;
in the light chain variable region of SEQ ID NO: 201;
[30] the antibody of [29], which comprises the heavy chain variable region of SEQ ID NO: 198 and the light chain variable region of SEQ ID NO: 204;
[31] the antibody of [29], which comprises the heavy chain variable region of SEQ ID NO: 199 and the light chain variable region of SEQ ID NO: 205;
[32] the antibody of any one of [26] to [31], which comprises a human antibody constant region;
[33] a composition comprising the antibody of [32] and a pharmaceutically acceptable carrier;
[34] a therapeutic agent for cancer, which comprises the antibody of [32] as an active ingredient;
[35] the therapeutic agent for cancer of [34], wherein the cancer is liver cancer;
[36] a nucleic acid encoding a polypeptide constituting the antibody of any one of [26] to [31];
[37] a host cell comprising the nucleic acid of [36]; and
[38] a method for producing the antibody of any one of [26] to [31], which comprises the steps of culturing the host cell of [37] and collecting the polypeptide from the cell culture.

Furthermore, the present invention provides:
[1] an anti-IL-6 receptor antibody of any one of:
(a) an antibody that comprises a heavy chain variable region comprising CDR1 in which Ser at position 1 in the amino acid sequence of SEQ ID NO: 1 has been substituted with another amino acid;
(b) an antibody that comprises a heavy chain variable region comprising CDR1 in which Trp at position 5 in the amino acid sequence of SEQ ID NO: 1 has been substituted with another amino acid;
(c) an antibody that comprises a heavy chain variable region comprising CDR2 in which Tyr at position 1 in the amino acid sequence of SEQ ID NO: 2 has been substituted with another amino acid;
(d) an antibody that comprises a heavy chain variable region comprising CDR2 in which Thr at position 8 in the amino acid sequence of SEQ ID NO: 2 has been substituted with another amino acid;
(e) an antibody that comprises a heavy chain variable region comprising CDR2 in which Thr at position 9 in the amino acid sequence of SEQ ID NO: 2 has been substituted with another amino acid;
(f) an antibody that comprises a heavy chain variable region comprising CDR3 in which Ser at position 1 in the amino acid sequence of SEQ ID NO: 3 has been substituted with another amino acid;
(g) an antibody that comprises a heavy chain variable region comprising CDR3 in which Leu at position 2 in the amino acid sequence of SEQ ID NO: 3 has been substituted with another amino acid;
(h) an antibody that comprises a heavy chain variable region comprising CDR3 in which Thr at position 5 in the amino acid sequence of SEQ ID NO: 3 has been substituted with another amino acid;
(i) an antibody that comprises a heavy chain variable region comprising CDR3 in which Ala at position 7 in the amino acid sequence of SEQ ID NO: 3 has been substituted with another amino acid;
(j) an antibody that comprises a heavy chain variable region comprising CDR3 in which Met at position 8 in the amino acid sequence of SEQ ID NO: 3 has been substituted with another amino acid;
(k) an antibody that comprises a heavy chain variable region comprising CDR3 in which Ser at position 1 and Thr at position 5 in the amino acid sequence of SEQ ID NO: 3 have been substituted with other amino acids;
(l) an antibody that comprises a heavy chain variable region comprising CDR3 in which Leu at position 2, Ala at position 7, and Met at position 8 in the amino acid sequence of SEQ ID NO: 3 have been substituted with other amino acids;
(m) an antibody that comprises a light chain variable region comprising CDR1 in which Arg at position 1 in the amino acid sequence of SEQ ID NO: 4 has been substituted with another amino acid;
(n) an antibody that comprises a light chain variable region comprising CDR1 in which Gln at position 4 in the amino acid sequence of SEQ ID NO: 4 has been substituted with another amino acid;
(o) an antibody that comprises a light chain variable region comprising CDR1 in which Tyr at position 9 in the amino acid sequence of SEQ ID NO: 4 has been substituted with another amino acid;
(p) an antibody that comprises a light chain variable region comprising CDR1 in which Asn at position 11 in the amino acid sequence of SEQ ID NO: 4 has been substituted with another amino acid;
(q) an antibody that comprises a light chain variable region comprising CDR2 in which Thr at position 2 in the amino acid sequence of SEQ ID NO: 5 has been substituted with another amino acid;
(r) an antibody that comprises a light chain variable region comprising CDR3 in which Gln at position 1 in the amino acid sequence of SEQ ID NO: 6 has been substituted with another amino acid;
(s) an antibody that comprises a light chain variable region comprising CDR3 in which Gly at position 3 in the amino acid sequence of SEQ ID NO: 6 has been substituted with another amino acid;
(t) an antibody that comprises a light chain variable region comprising CDR1 in which Tyr at position 9 in the amino acid sequence of SEQ ID NO: 4 has been substituted with another amino acid, and CDR3 in which Gly at position 3 in the amino acid sequence of SEQ ID NO: 6 has been substituted with another amino acid;
(u) an antibody that comprises a light chain variable region comprising CDR3 in which Thr at position 5 in the amino acid sequence of SEQ ID NO: 6 has been substituted with another amino acid;
(v) an antibody that comprises a light chain variable region comprising CDR3 in which Gln at position 1 and Thr at position 5 in the amino acid sequence of SEQ ID NO: 6 have been substituted with other amino acids;
(w) an antibody that comprises a heavy chain variable region comprising CDR2 in which Thr at position 9 in the amino acid sequence of SEQ ID NO: 2 has been substituted with another amino acid, and CDR3 in which Ser at position 1 and Thr at position 5 in the amino acid sequence of SEQ ID NO: 3 have been substituted with other amino acids;
(x) an antibody that comprises the heavy chain variable region of (k) and the light chain variable region of (v); and
(y) the antibody of (x) that further comprises the CDR2 of (e);
[2] an anti-IL-6 receptor antibody that comprises a light chain variable region comprising CDR2 in which Thr at position 2 in the amino acid sequence of SEQ ID NO: 5 has been substituted with another amino acid;

[3] an anti-IL-6 receptor antibody of any one of:
(a) an antibody that comprises a heavy chain variable region comprising FR1 in which Arg at position 13 in the amino acid sequence of SEQ ID NO: 7 has been substituted with another amino acid;
(b) an antibody that comprises a heavy chain variable region comprising FR1 in which Gln at position 16 in the amino acid sequence of SEQ ID NO: 7 has been substituted with another amino acid;
(c) an antibody that comprises a heavy chain variable region comprising FR1 in which Thr at position 23 in the amino acid sequence of SEQ ID NO: 7 has been substituted with another amino acid;
(d) an antibody that comprises a heavy chain variable region comprising FR1 in which Thr at position 30 in the amino acid sequence of SEQ ID NO: 7 has been substituted with another amino acid;
(e) an antibody that comprises a heavy chain variable region comprising FR1 in which Arg at position 13, Gln at position 16, Thr at position 23, and Thr at position 30 in the amino acid sequence of SEQ ID NO: 7 have been substituted with other amino acids;
(f) an antibody that comprises a heavy chain variable region comprising FR2 in which Arg at position 8 in the amino acid sequence of SEQ ID NO: 8 has been substituted with another amino acid;
(g) an antibody that comprises a heavy chain variable region comprising FR3 in which Met at position 4 in the amino acid sequence of SEQ ID NO: 9 has been substituted with another amino acid;
(h) an antibody that comprises a heavy chain variable region comprising FR3 in which Leu at position 5 in the amino acid sequence of SEQ ID NO: 9 has been substituted with another amino acid;
(i) an antibody that comprises a heavy chain variable region comprising FR3 in which Arg at position 16 in the amino acid sequence of SEQ ID NO: 9 has been substituted with another amino acid;
(j) an antibody that comprises a heavy chain variable region comprising FR3 in which Val at position 27 in the amino acid sequence of SEQ ID NO: 9 has been substituted with another amino acid;
(k) an antibody that comprises a heavy chain variable region comprising FR3 in which Met at position 4, Leu at position 5, Arg at position 16, and Val at position 27 in the amino acid sequence of SEQ ID NO: 9 have been substituted with other amino acids;
(l) an antibody that comprises a heavy chain variable region comprising FR4 in which Gln at position 3 in the amino acid sequence of SEQ ID NO: 10 has been substituted with another amino acid;
(m) an antibody that comprises a light chain variable region comprising FR1 in which Arg at position 18 in the amino acid sequence of SEQ ID NO: 11 has been substituted with another amino acid;
(n) an antibody that comprises a light chain variable region comprising FR2 in which Lys at position 11 in the amino acid sequence of SEQ ID NO: 12 has been substituted with another amino acid;
(o) an antibody that comprises a light chain variable region comprising FR3 in which Gln at position 23 in the amino acid sequence of SEQ ID NO: 13 has been substituted with another amino acid;
(p) an antibody that comprises a light chain variable region comprising FR3 in which Pro at position 24 in the amino acid sequence of SEQ ID NO: 13 has been substituted with another amino acid;
(q) an antibody that comprises a light chain variable region comprising FR3 in which Ile at position 27 in the amino acid sequence of SEQ ID NO: 13 has been substituted with another amino acid;
(r) an antibody that comprises a light chain variable region comprising FR3 in which Gln at position 23, Pro at position 24, and Ile at position 27 in the amino acid sequence of SEQ ID NO: 13 have been substituted with other amino acids;
(s) an antibody that comprises a light chain variable region comprising FR4 in which Lys at position 10 in the amino acid sequence of SEQ ID NO: 14 has been substituted with another amino acid;
(t) an antibody that comprises a heavy chain variable region comprising FR4 in which Ser at position 5 in the amino acid sequence of SEQ ID NO: 10 has been substituted with another amino acid;
(u) an antibody that comprises a heavy chain variable region comprising FR4 in which Gln at position 3 and Ser at position 5 in the amino acid sequence of SEQ ID NO: 10 have been substituted with other amino acids;
(v) an antibody that comprises a heavy chain variable region comprising FR3 comprising the amino acid sequence of SEQ ID NO: 184;
(w) an antibody that comprises a heavy chain variable region comprising the FR1 of (e), FR2 of (f), FR3 of (k), and FR4 of (l) or (u);
(x) an antibody that comprises a light chain variable region comprising the FR1 of (m), FR2 of (n), FR3 of (r), and FR4 of (s); and
(y) an antibody that comprises the heavy chain variable region of (w) and the light chain variable region of (x);
[4] an anti-IL-6 receptor antibody of any one of:
(a) an antibody that comprises a heavy chain variable region comprising CDR1 in which Ser at position 1 in the amino acid sequence of SEQ ID NO: 1 has been substituted with another amino acid;
(b) an antibody that comprises a heavy chain variable region comprising CDR2 in which Thr at position 9 in the amino acid sequence of SEQ ID NO: 2 has been substituted with another amino acid;
(c) an antibody that comprises a heavy chain variable region comprising CDR2 in which Ser at position 16 in the amino acid sequence of SEQ ID NO: 2 has been substituted with another amino acid;
(d) an antibody that comprises a heavy chain variable region comprising CDR2 in which Thr at position 9 and Ser at position 16 in the amino acid sequence of SEQ ID NO: 2 have been substituted with other amino acids;
(e) an antibody that comprises a light chain variable region comprising CDR1 in which Arg at position 1 in the amino acid sequence of SEQ ID NO: 4 has been substituted with another amino acid;
(f) an antibody that comprises a light chain variable region comprising CDR2 in which Thr at position 2 in the amino acid sequence of SEQ ID NO: 5 has been substituted with another amino acid;
(g) an antibody that comprises a light chain variable region comprising CDR2 in which Arg at position 4 in the amino acid sequence of SEQ ID NO: 5 has been substituted with another amino acid;
(h) an antibody that comprises a light chain variable region comprising CDR2 in which Thr at position 2 and Arg at position 4 in the amino acid sequence of SEQ ID NO: 5 have been substituted with other amino acids;

(i) an antibody that comprises a light chain variable region comprising CDR3 in which Thr at position 5 in the amino acid sequence of SEQ ID NO: 6 has been substituted with another amino acid;
(j) an antibody that comprises a heavy chain variable region comprising the CDR1 of (a), CDR2 of (d), and CDR3 comprising the amino acid sequence of SEQ ID NO: 3;
(k) an antibody that comprises a light chain variable region comprising the CDR1 of (e), CDR2 of (h), and CDR3 of (i); and
(l) an antibody that comprises the heavy chain variable region of (j) and the light chain variable region of (k);
[5] an anti-IL-6 receptor antibody of any one of:
(a) an antibody that comprises a heavy chain variable region comprising CDR1 in which Ser at position 1 in the amino acid sequence of SEQ ID NO:1 has been substituted with another amino acid, CDR2 in which Thr at position 9 and Ser at position 16 in the amino acid sequence of SEQ ID NO: 2 have been substituted with other amino acids, and CDR3 in which Ser at position 1 and Thr at position 5 in the amino acid sequence of SEQ ID NO: 3 have been substituted with other amino acids;
(b) an antibody that comprises a light chain variable region comprising CDR1 in which Arg at position 1 in the amino acid sequence of SEQ ID NO: 4 has been substituted with another amino acid, CDR2 in which Thr at position 2 and Arg at position 4 in the amino acid sequence of SEQ ID NO:5 have been substituted with other amino acids, and CDR3 in which Gln at position 1 and Thr at position 5 in the amino acid sequence of SEQ ID NO:6 have been substituted with other amino acids;
(c) an antibody that comprises a heavy chain variable region comprising the amino acid sequence of SEQ ID NO: 22;
(d) an antibody that comprises a light chain variable region comprising the amino acid sequence of SEQ ID NO: 23;
(e) an antibody that comprises the heavy chain variable region of (a) and the light chain variable region of (b); and
(f) an antibody that comprises the heavy chain variable region of (c) and the light chain variable region of (d);
[6] a human antibody constant region of any one of:
(a) a human antibody constant region that comprises deletions of both Gly at position 329 (446 in the EU numbering system) and Lys at position 330 (447 in the EU numbering system) in the amino acid sequence of SEQ ID NO: 19;
(b) a human antibody constant region that comprises deletions of both Gly at position 325 (446 in the EU numbering system) and Lys at position 326 (447 in the EU numbering system) in the amino acid sequence of SEQ ID NO: 20; and
(c) a human antibody constant region that comprises deletions of both Gly at position 326 (446 in the EU numbering system) and Lys at position 327 (447 in the EU numbering system) in the amino acid sequence of SEQ ID NO: 21;
[7] an IgG2 constant region in which the amino acids at positions 209 (330 in the EU numbering system), 210 (331 in the EU numbering system), and 218 (339 in the EU numbering system) in the amino acid sequence of SEQ ID NO: 20 have been substituted with other amino acids;
[8] an IgG2 constant region in which the amino acid at position 276 (397 in the EU numbering system) in the amino acid sequence of SEQ ID NO: 20 has been substituted with another amino acid;
[9] an IgG2 constant region in which the amino acid at position 14 (131 in the EU numbering system), 102 (219 in the EU numbering system), and/or 16 (133 in the EU numbering system) in the amino acid sequence of SEQ ID NO: 20 has been substituted with another amino acid;
[10] the IgG2 constant region of [9], wherein the amino acids at positions 20 (137 in the EU numbering system) and 21 (138 in the EU numbering system) in the amino acid sequence of SEQ ID NO: 20 have been substituted with other amino acids;
[11] an IgG2 constant region in which His at position 147 (268 in the EU numbering system), Arg at position 234 (355 in the EU numbering system), and/or Gln at position 298 (419 in the EU numbering system) in the amino acid sequence of SEQ ID NO: 20 has been substituted with another amino acid;
[12] an IgG2 constant region in which the amino acids at positions 209 (330 in the EU numbering system), 210 (331 in the EU numbering system), 218 (339 in the EU numbering system), 276 (397 in the EU numbering system), 14 (131 in the EU numbering system), 16 (133 in the EU numbering system), 102 (219 in the EU numbering system), 20 (137 in the EU numbering system), and 21 (138 in the EU numbering system) in the amino acid sequence of SEQ ID NO: 20 have been substituted with other amino acids;
[13] the IgG2 constant region of [12], which further comprises deletions of both Gly at position 325 (446 in the EU numbering system) and Lys at position 326 (447 in the EU numbering system);
[14] an IgG2 constant region in which the amino acids at positions 276 (397 in the EU numbering system), 14 (131 in the EU numbering system), 16 (133 in the EU numbering system), 102 (219 in the EU numbering system), 20 (137 in the EU numbering system), and 21 (138 in the EU numbering system) in the amino acid sequence of SEQ ID NO: 20 have been substituted with other amino acids;
[15] the IgG2 constant region of [14], which further comprises deletions of both Gly at position 325 (446 in the EU numbering system) and Lys at position 326 (447 in the EU numbering system);
[16] an IgG2 constant region in which the Cys at position 14 (131 in the EU numbering system), Arg at position 16 (133 in the EU numbering system), Cys at position 102 (219 in the EU numbering system), Glu at position 20 (137 in the EU numbering system), Ser at position 21 (138 in the EU numbering system), His at position 147 (268 in the EU numbering system), Arg at position 234 (355 in the EU numbering system), and Gln at position 298 (419 in the EU numbering system) in the amino acid sequence of SEQ ID NO: 20 have been substituted with other amino acids;
[17] the IgG2 constant region of [16], which further comprises deletions of both Gly at position 325 (446 in the EU numbering system) and Lys at position 326 (447 in the EU numbering system);
[18] an IgG2 constant region in which the Cys at position 14 (131 in the EU numbering system), Arg at position 16 (133 in the EU numbering system), Cys at position 102 (219 in the EU numbering system), Glu at position 20 (137 in the EU numbering system), Ser at position 21 (138 in the EU numbering system), His at position 147 (268 in the EU numbering system), Arg at position 234 (355 in the EU numbering system), Gln at position 298 (419 in the EU numbering system), and Asn at position 313 (434 in the EU numbering system) in the amino acid sequence of SEQ ID NO: 20 have been substituted with other amino acids;
[19] the IgG2 constant region of [18], which further comprises deletions of both Gly at position 325 (446 in the EU numbering system) and Lys at position 326 (447 in the EU numbering system);

[20] an IgG4 constant region in which the amino acid at position 289 (409 in the EU numbering system) in the amino acid sequence of SEQ ID NO: 21 has been substituted with another amino acid;
[21] an IgG4 constant region in which the amino acids at position 289 (409 in the EU numbering system), positions 14, 16, 20, 21, 97, 100, 102, 103, 104, and 105 (131, 133, 137, 138, 214, 217, 219, 220, 221, and 222 in the EU numbering system, respectively), and positions 113, 114, and 115 (233, 234, and 235 in the EU numbering system, respectively), have been substituted with other amino acids, and the amino acid at position 116 (236 in the EU numbering system) has been deleted from the amino acid sequence of SEQ ID NO: 21;
[22] the IgG4 constant region of [21], which further comprises deletions of both Gly at position 326 (446 in the EU numbering system) and Lys at position 327 (447 in the EU numbering system);
[23] an IgG2 constant region in which Ala at position 209 (330 in the EU numbering system), Pro at position 210 (331 in the EU numbering system), Thr at position 218 (339 in the EU numbering system), Cys at position 14 (131 in the EU numbering system), Arg at position 16 (133 in the EU numbering system), Cys at position 102 (219 in the EU numbering system), Glu at position 20 (137 in the EU numbering system), and Ser at position 21 (138 in the EU numbering system) in the amino acid sequence of SEQ ID NO: 20 have been substituted with other amino acids;
[24] the IgG2 constant region of [23], which further comprises deletions of both Gly at position 325 (446 in the EU numbering system) and Lys at position 326 (447 in the EU numbering system);
[25] an IgG2 constant region in which Cys at position 14 (131 in the EU numbering system), Arg at position 16 (133 in the EU numbering system), Cys at position 102 (219 in the EU numbering system), Glu at position 20 (137 in the EU numbering system), and Ser at position 21 (138 in the EU numbering system) in the amino acid sequence of SEQ ID NO: 20 have been substituted with other amino acids;
[26] the IgG2 constant region of [25], which further comprises deletions of both Gly at position 325 (446 in the EU numbering system) and Lys at position 326 (447 in the EU numbering system);
[27] a constant region comprising the amino acid sequence of SEQ ID NO: 24;
[28] a constant region comprising the amino acid sequence of SEQ ID NO: 118;
[29] a constant region comprising the amino acid sequence of SEQ ID NO: 25;
[30] a constant region comprising the amino acid sequence of SEQ ID NO: 151;
[31] a constant region comprising the amino acid sequence of SEQ ID NO: 152;
[32] a constant region comprising the amino acid sequence of SEQ ID NO: 153;
[33] a constant region comprising the amino acid sequence of SEQ ID NO: 164;
[34] a human antibody constant region comprising the amino acid sequence of SEQ ID NO: 194 (M40ΔGK);
[35] a human antibody constant region comprising the amino acid sequence of SEQ ID NO: 192 (M86ΔGK);
[36] an antibody comprising the constant region of any one of [6] to [35];
[37] the antibody of [36], which binds to an IL-6 receptor;
[38] an anti-IL-6 receptor antibody whose binding activity to an IL-6 receptor is 1 nM or less;
[39] an anti-IL-6 receptor antibody, wherein the measured isoelectric point of the full-length antibody is 7.0 or lower or the theoretical isoelectric point of the variable region is 5.0 or lower;
[40] an anti-IL-6 receptor antibody, wherein the increase in the ratio of antibody aggregate after one month at 25° C. in a buffer containing 20 mM Histidine-HCl and 150 mM NaCl at pH 6.5 to 7.0 is 0.3% or less when the concentration of the antibody is 100 mg/ml; and
[41] a pharmaceutical composition comprising the antibody of any one of [36] to [40].

BRIEF DESCRIPTION OF THE DRAWINGS

FIG. 4-1 is a diagram showing a list of CDR mutations that improve the affinity or neutralizing activity in comparison with WT.
FIG. 4-2 is the continuation of FIG. 4-1.
FIG. 5 is a diagram showing a list of CDR mutations that in combination improve the affinity or neutralizing activity.

FIG. 55A shows the antitumor activity of the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model when each test antibody was administered to the mouse model at a dose of 5 mg/kg, wherein the black diamond shows the activity for the administration of vehicle, the black triangle shows the effect of the administration of the Hspd1.8Lspd1.6 (Hd1.8Ld1.6) antibody, the white circle shows the effect of the administration of the Hspu2.2Lspu2.2 (Hu2.2Lu2.2) antibody, and the black square shows the effect of the administration of the H0L0 antibody.

FIG. 55B shows the antitumor activity of the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model when each test antibody was administered to the mouse model at a dose of 1 mg/kg, wherein the black diamond shows the activity for the administration of vehicle, the black triangle shows the effect of the administration of the Hspd1.8Lspd1.6 (Hd1.8Ld1.6) antibody, the white circle shows the effect of the administration of the Hspu2.2Lspu2.2 (Hu2.2Lu2.2) antibody, and the black square shows the effect of the administration of the H0L0 antibody.

MODE FOR CARRYING OUT THE INVENTION

Figure 1:
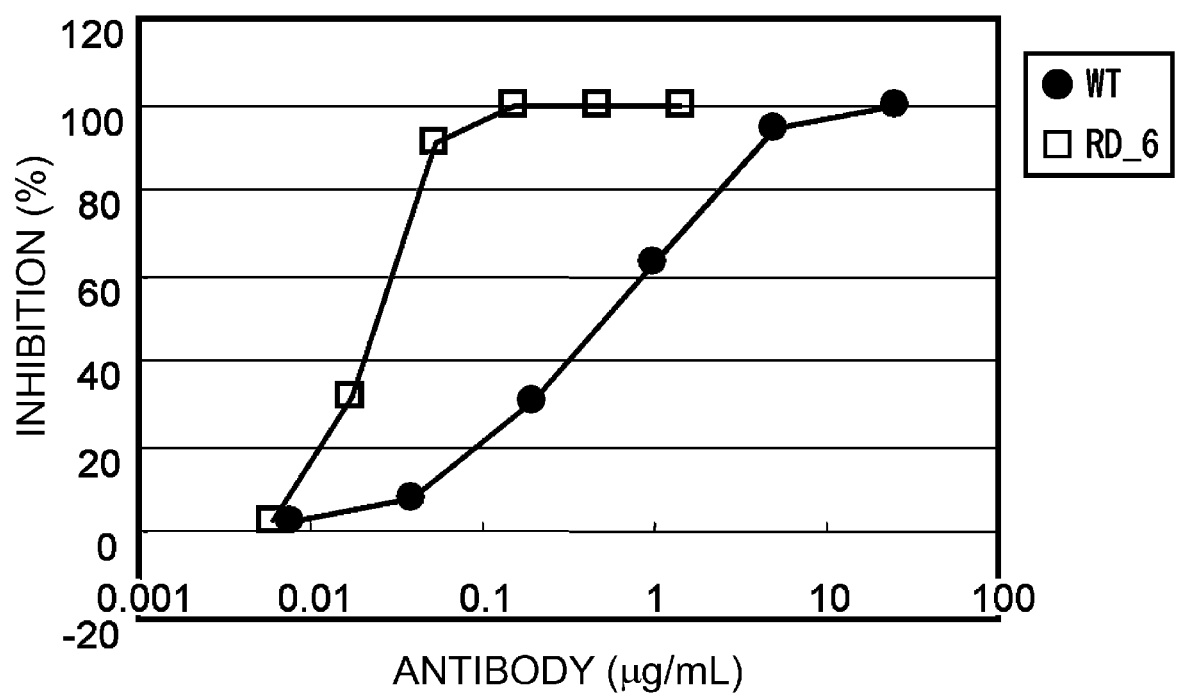
FIG. 1 is a graph showing the BaF/gp130-neutralizing activities of WT and RD_6.

The present invention provides methods for modifying the isoelectric point of a polypeptide comprising an antibody variable region while retaining the antigen-binding activity of the variable region, which comprise modifying the charge of at least one exposable amino acid residue on the polypeptide's CDR surface. The present invention also provides polypeptides comprising an antibody variable region with a modified isoelectric point obtained by the above methods; for example, antibodies that comprise a human-derived framework region (FR), human constant region, and CDR selected from the group consisting of human-derived CDRs, nonhuman animal-derived CDRs, and synthetic CDRs, in which at least one exposable amino acid residue on the CDR surface is an amino acid residue having a different charge from that of the amino acid residue at the corresponding position in the wild-type CDR, and have a modified isoelectric point compared to before modification while retaining their antigen-binding activity.

In a preferred embodiment, the methods of the present invention comprise modifying the charge of at least one exposable amino acid residue on the antibody surface. Specifically, the pharmacokinetics of an antibody in plasma (pharmacokinetics in blood) can be controlled by modifying the charges of amino acid residues in the antibody to change the antibody's isoelectric point. As a result of modification, for example, the antibody with controlled pharmacokinetics in plasma can exert superior antitumor activity against cancer cells than the original antibody.

In the methods of the present invention, "retaining the antigen-binding activity" means having at least 80% or more, preferably 85% or more, and more preferably 90% or more of the binding activity of the peptide before modification. As long as sufficient binding activity for binding to the antigen can be retained for the antibody to exert its function, the affinity determined at 37° C. under physiological conditions may be, for example, 100 nM or less, preferably 50 nM or less, more preferably 10 nM or less, and still more preferably 1 nM or less. Whether a polypeptide comprising an antibody variable region with a modified isoelectric point obtained by the methods of the present invention retains the antigen-binding activity can be tested by known methods such as Biacore (intermolecular interaction analysis), cell proliferation assay, ELISA (enzyme-linked immunosorbent assay), EIA (enzyme immunoassay), RIA (radioimmunoassay), and fluorescence immunoassay.

"Polypeptides of the present invention comprising an antibody variable region" include, but are not limited to, for example, antibodies, minibodies (low molecular weight antibodies), and scaffold proteins.

In the present invention, any scaffold protein is acceptable as long as it is a peptide that has a stable three-dimensional structure and is capable of binding to at least an antigen. Such peptides include, for example, fragments of antibody variable regions, fibronectin, protein A domain, LDL receptor A domain, lipocalin, and other molecules described in Nygren et al. (Current Opinion in Structural Biology, (1997) 7:463-469; Journal of Immunol Methods, (2004) 290:3-28), Binz et al. (Nature Biotech. (2005) 23:1257-1266), and Hosse et al. (Protein Science, (2006) 15:14-27).

Herein, the term "antibody" is used in the broadest sense, and includes monoclonal antibodies, polyclonal antibodies, and mutant antibodies (such as chimeric antibodies, humanized antibodies, minibodies (including antibody fragments), and multispecific antibodies) as long as they display a desired biological activity. In the present invention, the methods of antibody modification of the present invention can be used favorably on these antibodies when they are obtained (produced).

The "antibodies" of the present invention include antibodies in which the charge of amino acid residues has been modified as described above, and whose amino acid sequences have been further modified by amino acid substitutions, deletions, additions, and/or insertions. The "antibodies" also include antibodies whose amino acid sequences have been modified by amino acid substitutions, deletions, additions, and/or insertions, or chimerization, humanization, or such, and in which the charge of amino acid residues has been further modified. Modifications may be performed at the same time when mouse antibodies are humanized, or further modifications may be performed on humanized antibodies.

Amino acid sequence modifications, such as amino acid substitutions, deletions, additions, and/or insertions, and humanization and chimerization, can be achieved by methods known to those skilled in the art. When the antibodies of the present invention are prepared as recombinant antibodies, likewise, the amino acid sequences of the antibody variable and constant regions may also be modified by amino acid substitutions, deletions, additions, and/or insertions, or chimerization, humanization and the like.

The antibodies of the present invention may be derived from any animal, such as a mouse, human, rat, rabbit, goat, or camel. Furthermore, the antibodies may be modified, for example, chimeric antibodies, and in particular, modified antibodies that include amino acid substitutions in their sequence, such as humanized antibodies. The antibodies may be any kind of antibody, such as antibody modification products linked with various molecules, antibody fragments, and minibodies.

"Chimeric antibodies" are antibodies prepared by combining sequences derived from different animals. An example is an antibody having heavy and light chain variable (V) regions from a mouse antibody and heavy and light chain constant (C) regions from a human antibody. Chimeric antibodies can be prepared by known methods. To obtain such chimeric antibodies, for example, a DNA encoding an antibody variable region may be ligated with a DNA encoding a human antibody constant region; the resulting ligation product is inserted into an expression vector; and the construct is introduced into a host to produce the chimeric antibody.

The minibodies of the present invention are not particularly limited by their structure nor their method of production, so long as they have antigen-binding activity. Some minibodies have an activity greater than that of a whole antibody (Orita et al., Blood, (2005) 105:562-566). Herein, the "minibodies" are not particularly limited, so long as they are a portion of a whole antibody (for example, whole IgG). However, the minibodies preferably include a heavy chain variable region (VH) or a light chain variable region (VL). Examples of preferred antibody fragments are Fab, F(ab')$_2$, Fab', and Fv. The amino acid sequence of a heavy chain variable region or light chain variable region in an antibody fragment may be modified by substitutions, deletions, additions, and/or insertions. Furthermore, some portions of a heavy chain variable region and light chain variable region may be deleted, so long as the resulting fragments retain their antigen-binding ability. For example, of the antibody fragments described above, "Fv" is a minimal antibody fragment composed of the complete antigen-recognition and binding sites. "Fv" is a dimer (VH-VL dimer) composed of one unit of heavy chain variable region and one unit of light chain variable region bound very strongly by non-covalent bonding. An antigen-binding site is formed on the surface of the VH-VL dimer by the three CDRs of each variable region. Six CDRs confer an antigen-binding site to the antibody. However, even one variable region (or half of an Fv composed of only three antigen-specific CDRs) has the ability to recognize and bind to an antigen, although its affinity is lower than that of the complete binding site. Thus, molecules smaller than Fv are also included in the context of minibodies of the present invention. The variable regions of a minibody may also be chimerized or humanized.

The minibodies preferably include both a heavy chain variable region and a light chain variable region. Examples of suitable minibodies include antibody fragments such as Fab, Fab', F(ab')2, and Fv, and scFv (single-chain Fv), which can be prepared using antibody fragments (Huston et al., Proc. Natl. Acad. Sci. USA (1988) 85:5879-83; Pluckthun "The Pharmacology of Monoclonal Antibodies" Vol. 113, Resenburg and Moore (eds.), Springer Verlag, New York, pp. 269-315, (1994)), diabodies (Holliger et al., Proc. Natl. Acad. Sci. USA (1993) 90:6444-8; EP 404097; WO93/11161; Johnson et al., Method in Enzymology (1991) 203: 88-98; Holliger et al., Protein Engineering (1996) 9:299-305; Perisic et al., Structure (1994) 2:1217-26; John et al., Protein Engineering (1999) 12(7):597-604; Atwell et al., Mol. Immunol. (1996) 33:1301-12), sc(Fv)2 (Hudson et al., J Immunol. Methods (1999) 231:177-89; Orita et al., Blood (2005) 105:562-566), triabodies (Journal of Immunological Methods (1999) 231:177-89), and tandem diabodies (Cancer Research (2000) 60:4336-41).

An antibody fragment can be prepared by treating an antibody with an enzyme, for example, a protease such as papain or pepsin (see Morimoto et al., J. Biochem. Biophys. Methods (1992) 24:107-17; Brennan et al., Science (1985) 229:81). Alternatively, antibody fragments can also be produced by genetic recombination based on its amino acid sequence.

A minibody having a structure that results from modification of an antibody fragment can be prepared using antibody fragments obtained by enzyme treatment or genetic recombination. Alternatively, after constructing a gene which encodes a whole minibody, and introducing the construct into an expression vector, the minibody may be expressed in appropriate host cells (see, for example, Co et al., J. Immunol. (1994) 152:2968-76; Better and Horwitz, Methods Enzymol. (1989) 178:476-96; Pluckthun and Skerra, Methods Enzymol. (1989) 178:497-515; Lamoyi, Methods Enzymol. (1986) 121:652-63; Rousseaux et al., Methods Enzymol. (1986) 121:663-9; Bird and Walker, Trends Biotechnol. (1991) 9:132-7).

The above described "scFVs" are single-chain polypeptides that include two variable regions linked together via a linker or such, as required. The two variable regions in an scFv are typically one heavy chain variable region and one light chain variable region, but an scFv may include two heavy chain variable regions or two light chain variable regions. In general, scFv polypeptides include a linker between the heavy chain variable region and light chain variable region, thereby forming a paired portion of heavy chain variable region and light chain variable region required for antigen binding. A peptide linker composed of ten or more amino acids is typically used as the linker between heavy chain variable region and light chain variable region when forming an intramolecular paired portion between heavy chain variable region and light chain variable region. However, the linkers of the scFv of the present invention are not limited to such peptide linkers, so long as they do not inhibit the formation of an scFv. To review scFv, see Pluckthun "The Pharmacology of Monoclonal Antibody", Vol. 113 (Rosenburg and Moore ed., Springer Verlag, NY, pp. 269-315 (1994)).

The term "diabodies (Db)" refers to bivalent antibody fragments constructed by gene fusion (P. Holliger et al., Proc. Natl. Acad. Sci. USA 90: 6444-6448 (1993); EP 404,097; WO93/11161 and such). Diabodies are dimers composed of two polypeptide chains, wherein each polypeptide chain includes within the same chain a light chain variable region and a heavy chain variable region connected with a linker short enough to disable interaction of these two regions, for example a linker of about five amino acid residues. Light chain variable region and heavy chain variable region encoded on the same polypeptide chain will form a dimer because the linker between light chain variable region and heavy chain variable region is too short to form a single chain variable region fragment. Therefore, the resulting diabody has two antigen-binding sites. Herein, when light chain variable region and heavy chain variable region directed against two different epitopes (a and b) are expressed simultaneously as combinations of VLa-VHb and VLb-VHa connected with a linker of about five residues, they are secreted as bispecific Db.

Since diabodies include two molecules of scFvs, they thus composed of four variable regions, and as a result have two antigen-binding sites. When the objective is to form a diabody, unlike as in the case with scFvs that do not form dimers, ordinarily, linkers forming a connection between heavy chain variable region and light chain variable region in each scFv molecules are linkers of about five amino acids when used as peptide linkers. However, scFv linkers for diabody formation are not limited to such peptide linkers so long as they do not interfere with scFv expression and diabody formation.

Of the several antibody isotypes, IgG antibody has a significantly larger molecular weight, and its major metabolic pathway is not renal excretion. IgG antibody, which comprises an Fc domain as part of the molecule, is known to be recycled through a salvage pathway via fetal Fc receptor (FcRn) expressed in endothelial cells of blood vessels or such, and thus has a longer in vivo half-life. IgG antibody is thought to be mainly metabolized via a metabolic pathway in endothelial cells (He X Y, Xu Z, Melrose J, Mullowney A, Vasquez M, Queen C, Vexler V, Klingbeil C, Co M S, Berg E L. Humanization and pharmacokinetics of a monoclonal antibody with specificity for both E- and P-selectin. J Immunol. (1998) 160 (2):1029-35). Specifically, it is thought that when nonspecifically incorporated into endothelial cells, IgG antibody is recycled via binding to FcRn while free IgG antibody is metabolized. The plasma half-life of IgG antibody is shortened when its Fc domain has been modified to reduce its FcRn-binding activity. In contrast, the plasma half-life of IgG antibody can be prolonged by modifying amino acid residues that constitute the Fc domain to increase the FcRn-binding activity (J Immunol. (1998) 160 (2):1029-35). As described above, conventional methods for controlling the plasma pharmacokinetics of IgG antibody are based on modifying the FcRn-binding activity through modification of amino acid residues that constitute the Fc domain. However, as described in the Examples below, the present invention revealed that the plasma half-life of an antibody depends on its isoelectric point with a high correlation. Specifically, the present invention demonstrated that the plasma half-life of antibody could be controlled without modifying the amino acid sequence that constitutes the Fc, whose modification potentially results in acquisition of immunogenicity.

Without intending to adhere to a particular theory, the present inventors currently believe the following theory. The rate of non-specific IgG antibody uptake by endothelial cells is thought to depend on the physicochemical Coulomb interaction between IgG antibody and the negatively charged cell surface. Thus, a decrease (increase) of the isoelectric point of IgG antibody reduces (enhances) the Coulomb interaction, which decreases (increases) the non-specific uptake by endothelial cells, and as a result, the metabolism in endothelial cells is reduced (enhanced). This enables to control the pharmacokinetics in plasma. Since the Coulomb interaction between endothelial cells and the negative charge on cell surface is a physicochemical interaction, it is thought that the interaction does not exclusively depend on the amino acid sequence that constitutes the antibody. Thus, the methods of the present invention for controlling the pharmacokinetics in plasma are applicable not only to specific antibodies but also to any polypeptides comprising an antibody variable region. Preferred peptides include peptides with a molecular weight of 50,000 or more, more preferably 100,000 or more, and still more preferably 140,000 or more. Since the major metabolic pathway of such peptides is not renal excretion, it is amply possible to attain the effect of controlling plasma pharmacokinetics in the present invention. Herein, the impairment (enhancement) of the Coulomb interaction means a increase (decrease) in the Coulomb force, which is a repulsive force.

The polypeptides of the present invention comprising the FcRn-binding domain are not limited to IgG antibodies. The polypeptides may be any proteins as long as they can bind to (have the binding activity or affinity to) Fc receptor (FcRn). Preferably, the polypeptides of the present invention comprising the FcRn-binding domain are proteins comprising an antibody Fc domain or an Fc-like domain, but are not limited thereto. The Fc domain may be a modified Fc domain, for example, an Fc domain described in J Immunol. (1998) 160 (2):1029-35 cited above. The polypeptides of the present invention comprising the FcRn-binding domain include, for example, IgG antibodies. Furthermore, modified forms of the antibodies (proteins) are also included in the polypeptides of the present invention comprising an FcRn-binding domain, as long as they can bind to FcRn. The most preferred polypeptides of the present invention comprising an FcRn-binding domain include, for example, IgG antibodies.

When an IgG antibody is used as the antibody of the present invention, it may be of any subtype as long as it is an antibody molecule of the IgG type. The antibody may be a multispecific (for example, bispecific) IgG antibody. Such a bispecific antibody is an antibody that has specificities to two types of different epitopes, and includes antibodies that recognize different antigens and those recognize different epitopes in a single antigen. When antibody molecules are minibodies such as scFv and Fab whose major metabolic pathway is renal excretion, their pharmacokinetics in plasma cannot be regulated by controlling the isoelectric points as described above. However, the present invention is applicable to any kinds of antibody molecules as long as they are polypeptides comprising an antibody variable region whose major metabolic pathway is not renal excretion. Such polypeptides include, for example, scFv-Fc, dAb-Fc, and Fc fusion proteins. Since the major metabolic pathway of these molecules is not renal excretion, their pharmacokinetics in plasma can be controlled by modifying isoelectric point using the methods of the present invention. Antibody molecules to which the present invention is applicable also include antibody-like molecules. "Antibody-like molecules" refers to molecules that function via binding to their target molecules (Binz H K, Amstutz P, Pluckthun A. Engineering novel binding proteins from nonimmunoglobulin domains. Nat Biotechnol. 2005 October; 23(10):1257-68), and include, for example, DARPins, affibodies, and avimers.

When an antibody of the present invention is, for example, a bispecific anti-glypican 3 antibody, it can bind specifically not only to glypican 3 but also to an epitope of an antigen other than glypican 3. Such non-glypican 3 antigens preferably include, for example, surface antigens that allow for specific binding to NK cells, cytotoxic T cells, LAK cells, and other cells to recruit these cells. It was reported that in the presence of a bispecific antibody prepared from antibody MUSE11 which recognizes an adenocarcinoma-related antigen MUC1 and antibody OKT3 which recognizes a LAK cell surface antigen, LAK cells exerted cytotoxic activity against bile duct carcinoma (Katayose Y, Kudo T, Suzuki M, Shinoda M, Saijyo S, Sakurai N, Saeki H, Fukuhara K, Imai K, Matsuno S. MUC1-specific targeting immunotherapy with bispecific antibodies: inhibition of xenografted human bile duct carcinoma growth. Cancer Res. (1996) 56(18):4205-12). Glypican 3 antibodies with improved plasma pharmacokinetics, which are provided by the present invention, can be preferably used instead of the MUSE11 antibody which recognizes MUC1. Furthermore, bispecific glypican 3 antibodies that recognize different epitopes on a glypican 3 molecule can also be used as preferred antibodies of the present invention.

The above-mentioned "bispecific antibody" may be, for example, an antibody having a structure in which a heavy chain variable region and a light chain variable region are linked in a single chain (for example, sc(Fv)2). The bispecific antibody may also be an antibody-like molecule (for example, scFv-Fc) produced by fusing an scFv (or sc(Fv)2), in which a heavy chain variable region and a light chain variable region are linked, to an Fc domain (a constant region lacking the CH1 domain). A multispecific antibody consisting of scFv-Fc has an (scFv)2-Fc type structure with VH1-linker-VL1-Fc as the first polypeptide and VH2-linker-VL2-Fc as the second polypeptide. Alternatively, the bispecific antibody may be an antibody-like molecule in which a single domain antibody is linked with an Fc domain (Curr. Opin. Drug Discov. Devel. (2006) 9(2):184-93).

In the present invention, the charge of amino acid residues can be modified through amino acid substitution. Amino acid substitution can be achieved by the methods described below.

In order to retain antigen-binding activity, as the target of substitution in the present invention, the exposable amino acid residue on the surface of the CDR region is preferably at least one amino acid residue selected from amino acid residues at positions 31, 61, 62, 64, and 65 in the heavy chain variable region and at positions 24, 27, 53, 54, and 55, Kabat's numbering, in the light chain variable region. Such amino acid substitutions are advantageous in that the original function (antigen-binding activity or such) of the polypeptides comprising an antibody variable region before amino acid substitution is retained and that the substitutions can be achieved regardless of antibody specificity.

Furthermore, the present invention provides methods for controlling pharmacokinetics of polypeptides comprising an antibody variable region by modifying their isoelectric points. Polypeptides comprising an antibody variable region with controlled pharmacokinetics obtained by such methods are also included in the present invention.

Herein, "controlled plasma pharmacokinetics" means that when the antibody pharmacokinetics in plasma is compared before and after modification of amino acids constituting an antibody, the pharmacokinetics in plasma has been changed in a desired direction. Specifically, when one desires to prolong the half-life (in plasma) of an antibody as a drug, "controlled plasma pharmacokinetics" means prolongation of the antibody half-life in plasma. Alternatively, when one desires to shorten the antibody half-life in plasma, "controlled plasma pharmacokinetics" means shortening of the antibody half-life in plasma.

In the present invention, whether the antibody pharmacokinetics in plasma has been changed in a desired direction, that is, whether the pharmacokinetics in plasma has been controlled as intended can be appropriately assessed by kinetic tests using, for example, mice, rats, rabbits, dogs, monkeys, or others. In the present invention, "prolongation of the half-life in plasma" or "shortening of the half-life in plasma" can also be assessed using instead of half-life in plasma (t1/2), any one of the parameters: mean retention time in plasma, clearance (CL) in plasma, and area under the concentration curve (AUC) (Pharmacokinetics: Enshuniyoru Rikai (Understanding through practice). Nanzando). The "controlled plasma kinetics" achieved according the present invention can be appropriately assessed using the parameters, for example, by carrying out noncompartmental analysis according to the protocol appended to the in vivo kinetics analysis software WinNonlin (Pharsight).

The antibody function can be sustained by controlling the pharmacokinetics in plasma. For example, the methods of the present invention can be applied to sustain the function of antibodies having cytotoxicity, and regulate the duration of the functions that the polypeptides have before modification, such as cytotoxic effect, antagonistic activity, and agonistic activity.

Herein, "exposable amino acid residue on the surface" typically refers to an amino acid residue located on the surface of a polypeptide constituting an antibody. "Amino acid residue located on the surface of a polypeptide" refers to an amino acid residue whose side chain can be in contact with solvent molecules (which are in general water molecules). However, the whole side chain is not necessarily in contact with solvent molecules. When at least a portion of the side chain is in contact with solvent molecules, the amino acid residue is defined as an "amino acid located on the surface". Those skilled in the art can prepare a homology model for a polypeptide or antibody by homology modeling or such using commercially available softwares. Based on the homology model, amino acid residues on the surface of a polypeptide that constitutes an appropriate antibody can be selected as "amino acid residues on the polypeptide surface".

Herein, the "exposable amino acid residues on the surface" are not particularly limited; however, the amino acid residues are preferably located in an antibody domain other than the FcRn-binding domain. Such preferred FcRn-binding domain includes, for example, Fc domain.

In the present invention, amino acid residues whose charge is to be modified are preferably amino acid residues that constitute an antibody heavy or light chain variable region. Specifically, the variable region preferably includes CDR and FR.

Those skilled in the art can suitably select surface amino acid residues in the antibody variable region using homology models produced by homology modeling and such. For example, surface amino acid residues in the antibody variable region are preferably selected from amino acid residues of heavy chain variable regions H1, H3, H5, H8, H10, H12, H13, H15, H16, H19, H23, H25, H26, H31, H39, H42, H43, H44, H46, H61, H62, H64, H65, H68, H71, H72, H73, H75, H76, H81, H82b, H83, H85, H86, H105, H108, H110, and H112, Kabat's numbering. For example, in the heavy chain FR region of the humanized glypican 3 antibody of SEQ ID NO: 195, examples of surface amino acids are amino acid residues at positions 1, 3, 5, 8, 10, 12, 13, 15, 16, 19, 23, 25, 26, 39, 42, 43, 44, 46, 69, 72, 73, 74, 76, 77, 82, 85, 87, 89, 90, 107, 110, 112, and 114, without being limited thereto. For the heavy chain CDR region, surface amino acids can be selected using similar homology models. Specifically, the amino acid residue H97, Kabat's numbering, is exposed on the surface of most antibodies, and for example, Ser at position 101 in the heavy chain CDR of the humanized glypican 3 antibody of SEQ ID NO: 195 corresponds to that amino acid residue. Other amino acid residues in the heavy chain CDR of the humanized glypican 3 antibody of SEQ ID NO: 195 preferably include amino acid residues at positions 52, 54, 62, 63, 65, and 66.

In the light chain variable region, surface amino acid residues in the antibody variable region are preferably selected from amino acid residues L1, L3, L7, L8, L9, L11, L12, L16, L17, L18, L20, L22, L24, L27, L38, L39, L41, L42, L43, L45, L46, L49, L53, L54, L55, L57, L60, L63, L65, L66, L68, L69, L70, L74, L76, L77, L79, L80, L81, L85, L100, L103, L105, L106, and L107, Kabat's numbering. Amino acid residues at positions 1, 3, 7, 8, 9, 11, 12, 16, 17, 18, 20, 22, 43, 44, 45, 46, 48, 49, 50, 54, 62, 65, 68, 70, 71, 73, 74, 75, 79, 81, 82, 84, 85, 86, 90, 105, 108, 110, 111, and 112 in the humanized glypican 3 antibody of SEQ ID NO: 195 are examples of surface amino acids. However, the surface amino acids of the present invention are not limited thereto. Furthermore, for the light chain CDR region, surface amino acid residues can be selected using homology models similar to those used for determining surface amino acid residues in the heavy chain CDR. Amino acid residues in light chain CDR of the humanized glypican 3 antibody of SEQ ID NO: 201 preferably include amino acid residues at positions 24, 27, 33, 55, and 59.

Specifically, in the methods of the present invention, "modification" of an amino acid residue refers to substitution of a different amino acid residue for an original amino acid residue, deletion of an original amino acid residue, addition of an extra amino acid residue, and so on. The "modification" preferably refers to substitution of a different amino acid residue for an original amino acid residue. Specifically, in the present invention, "modification of the charge of an amino acid residue" preferably refers to amino acid substitutions.

Such "modification of the charge of an amino acid residue" in a glypican 3 antibody of the present invention is preferably achieved, for example, by modifying the charge of at least one amino acid residue selected from the amino acid residues at positions 19, 43, 52, 54, 62, 63, 65, 66, and 107 in the heavy chain variable region constituting the humanized glypican 3 antibody of SEQ ID NO: 195. Alternatively, the modification is preferably achieved, for example, by modifying the charge of at least one amino acid residue selected from the amino acid residues at positions 17, 24, 27, 33, 55, 59, 79, 82, and 105 in the light chain variable region constituting the humanized glypican 3 antibody of SEQ ID NO: 201. Of the amino acid residues mentioned above, it is not necessary to modify amino acid residues other than the ones whose charge has already been modified, as long as the modification has achieved the intended effect of controlling the pharmacokinetics in plasma. However, these amino acid residues can be appropriately modified to be electrically neutral or to have the same type of charge as the modified amino acid residues.

The above-described "modification of the charge of an amino acid residue" in the CDR of an anti-human IL-6 receptor antibody (6R_a_H1L1) of the present invention is preferably achieved while retaining its antigen-binding activity, for example, by modifying at least one amino acid residue selected from the amino acid residues at positions 31, 64, and 65, Kabat's numbering, in the heavy chain variable region constituting anti-human IL-6 receptor antibody of SEQ ID NO: 221. Alternatively, the modification is preferably achieved, for example, by modifying the charge of at least one amino acid residue selected from the amino acid residues at positions 24, 27, 53, and 55, Kabat's numbering, in the light chain variable region constituting the anti-human IL-6 receptor antibody of SEQ ID NO: 224. Among the amino acid residues mentioned above, it is not necessary to modify amino acid residues other than the ones whose charge has already been modified, as long as the modification has achieved the intended effect of controlling the pharmacokinetics in plasma. However, these amino acid residues can be appropriately modified to be electrically neutral or to have the same type of charge as the modified amino acid residues.

The above-described "modification of the charge of an amino acid residue" in the CDR of an anti-human IL-6 receptor antibody (6R_b_H1L1) of the present invention is preferably achieved while retaining the antigen-binding activity, for example, by modifying the charge of at least one amino acid residue selected from the amino acid residues in the heavy chain variable region constituting the anti-human IL-6 receptor antibody of SEQ ID NO: 227, for example, the amino acid residue at position 31, Kabat's numbering. Alternatively, the modification is preferably achieved, for example, by modifying the charge of at least one amino acid residue selected from the amino acid residues at positions 24, 53, 54, and 55, Kabat's numbering, in the light chain variable region constituting the anti-human IL-6 receptor antibody of SEQ ID NO: 229. Among the amino acid residues mentioned above, it is not necessary to modify amino acid residues other than the ones whose charge has already been modified, as long as the modification has achieved the intended effect of controlling the pharmacokinetics in plasma. However, these amino acid residues can be appropriately modified to be electrically neutral, or to have the same type of charge as the modified amino acid residues.

The above-described "modification of the charge of an amino acid residue" in the CDR of an anti-human GPC3 antibody of the present invention is preferably achieved while retaining the antigen-binding activity, for example, by modifying the charge of at least one amino acid residue selected from the amino acid residues at positions 61, 62, 64, and 65, Kabat's numbering, in the heavy chain variable region constituting the anti-human GPC3 antibody of SEQ ID NO: 233. Alternatively, the modification is preferably achieved, for example, by modifying the charge of at least one amino acid residue selected from the amino acid residues at positions 24 and 27, Kabat's numbering, in the light chain variable region constituting the anti-human GPC3 antibody of SEQ ID NO: 236. Among the amino acid residues mentioned above, it is not necessary to modify amino acid residues other than the ones whose charge has already been modified, as long as the modification has achieved the intended effect of controlling the pharmacokinetics in plasma. However, these amino acid residues can be appropriately modified to be electrically neutral, or to have the same type of charge as the modified amino acid residues.

The above-described "modification of the charge of an amino acid residue" in the CDR of an anti-human IL-31 receptor antibody of the present invention is preferably achieved while retaining the antigen-binding activity, for example, by modifying the charge of at least one amino acid residue selected from the amino acid residues at positions 61, 62, 64, and 65, Kabat's numbering, in the heavy chain variable region constituting the anti-human IL-31 receptor antibody of SEQ ID NO: 239. Alternatively, the modification is preferably achieved, for example, by modifying the charge of at least one amino acid residue selected from the amino acid residues at positions 24 and 54, Kabat's numbering, in the light chain variable region constituting the anti-human IL-31 receptor antibody of SEQ ID NO: 242. Among the amino acid residues mentioned above, it is not necessary to modify amino acid residues other than the ones whose charge has already been modified, as long as the modification has achieved the intended effect of controlling the pharmacokinetics in plasma. However, these amino acid residues can be appropriately modified to be electrically neutral, or to have the same type of charge as the modified amino acid residues.

Amino acids are known to include charged amino acids. Generally known amino acids having positive charge (positively charged amino acids) are lysine (K), arginine (R), and histidine (H). Known amino acids having negative charge (negatively charged amino acids) include aspartic acid (D) and glutamic acid (E). Others are known to be non-charged amino acids.

Preferably, the above-described "modified amino acid residues" are appropriately selected from the amino acid residues in either of groups (a) and (b) below:
(a) glutamic acid (E) and aspartic acid (D); and
(b) lysine (K), arginine (R), and histidine (H).
However, the amino acid residues are not limited to these examples.

In a preferred embodiment, amino acid residues are substituted by non-charged amino acid residues when the original amino acid residues (before modification) already have charge. Specifically, the modification of the present invention includes: (1) substitution of a non-charged amino acid for a charged amino acid; (2) substitution of an amino acid having opposite charge for a charged amino acid; and (3) substitution of a charged amino acid for a non-charged amino acid.

In the present invention, amino acid residues constituting an antibody are preferably modified so as to change the isoelectric point of the antibody. When there are multiple amino acid residues to be modified, they may include a few non-charged amino acid residues.

Examples of preferred "modification of the charge of an amino acid residue" in a glypican 3 antibody of the present invention are described below. Modifications to increase the isoelectric point value include, for example, introduction of at least one substitution selected from Q43K, D52N, and Q107R in the heavy chain variable region constituting the humanized glypican 3 antibody of SEQ ID NO: 195. More preferably, the sequence is substituted with the amino acid sequence of SEQ ID NO: 198. Modifications to increase the isoelectric point value also include, for example, introduction of at least one substitution selected from E17Q, Q27R, and Q105R in the light chain variable region constituting the humanized glypican 3 antibody of SEQ ID NO: 201. More preferably, the sequence is substituted with the amino acid sequence of SEQ ID NO: 204. Meanwhile, modifications to decrease the isoelectric point value include, for example, introduction of at least one substitution selected from K19T, Q43E, K63S, K65Q, and G66D in the heavy chain variable region constituting the humanized glypican 3 antibody of SEQ ID NO: 195. More preferably, the sequence is substituted with the amino acid sequence of SEQ ID NO: 197. Modifications to decrease the isoelectric point value also include, for example, introduction of at least one substitution selected from Q27E, K79T, and R82S in the light chain variable region constituting the humanized glypican 3 antibody of SEQ ID NO: 201. More preferably, the sequence is substituted with the amino acid sequence of SEQ ID NO: 203.

Examples of preferred "modification of the charge of an amino acid residue" in an anti-human IL-6 receptor antibody (6R_a_H1L1) provided by the present invention include substitutions of at least one amino acid selected from the amino acid substitutions listed in Table 20.

Examples of preferred "modification of the charge of an amino acid residue" in an anti-human IL-6 receptor antibody (6R_b_H1L1) provided by the present invention include substitutions of at least one amino acid selected from the amino acid substitutions listed in Table 22.

Examples of preferred "modification of the charge of an amino acid residue" in an anti-human GPC3 antibody provided by the present invention include substitutions of at least one amino acid selected from the amino acid substitutions listed in Table 24.

Examples of preferred "modification of the charge of an amino acid residue" in an anti-human IL-31 receptor antibody provided by the present invention include substitutions of at least one amino acid selected from the amino acid substitutions listed in Table 27.

In the present invention, the number of amino acid residues to be modified is not particularly limited. For example, when modifying an antibody variable region, it is preferable to modify a sufficient but minimal number of amino acid residues for achieving controlled plasma pharmacokinetics as intended to avoid loss of the antigen-binding activity and to prevent an increase in immunogenicity. Alternatively, amino acid modifications for increasing the antigen-binding activity may be appropriately combined with amino acid modifications to decrease immunogenicity.

The antigen-binding activity of an antibody can be determined using known methods, for example, enzyme-linked immunosorbent assay (ELISA), enzyme immunoassay (EIA), radioimmunoassay (MA), and fluorescence immunoassay. The methods are described in a standard text, Antibodies A Laboratory Manual (Ed Harlow, David Lane, Cold Spring Harbor Laboratory, 1988).

Methods for determining the cell-binding activity of an antibody include, for example, the methods described on pages 359 to 420 in Antibodies A Laboratory Manual (Ed Harlow, David Lane, Cold Spring Harbor Laboratory, 1988). Specifically, the activity can be assessed using cells as an antigen based on the principle of Biacore, cell proliferation assay, ELISA, or FACS (fluorescence activated cell sorting). When ELISA is used, the cell-binding activity of an antibody is quantitatively assessed by comparing the levels of signals generated in the enzyme reaction. Specifically, a test antibody is added to each ELISA plate immobilized with forced expression cells, and cell-bound test antibody is detected using an enzyme-labeled antibody that recognizes the test antibody. Alternatively, when FACS is used, the cell-binding activity of antibodies can be compared by preparing a dilution series of a test antibody and determining the titer of binding to forced expression cells for each of the antibodies.

When an antigen is not immobilized on a carrier such as an ELISA plate but is expressed on the surface of cells suspended in buffer or such, the binding of an antibody to the antigen can be assayed by using FACS. Flow cytometers that are used in this assay include, for example, FACSCanto™ II, FACSAria™, FACSArray™, FACSVantage™ SE, and FACSCalibur™ (all of which are from BD Biosciences); and EPICS ALTRA HyPerSort, Cytomics FC 500, EPICS XL-MCL ADC, EPICS XL ADC, and Cell Lab Quanta/Cell Lab Quanta SC (all of which are from Beckman Coulter).

Preferred methods for determining the antigen-binding activity of an antibody include, for example, analytical methods which comprise: reacting a test antibody with cells expressing the antigen, staining the cells with an FITC-labeled secondary antibody that recognizes the test antibody, assaying the cells using FACSCalibur (BD), and then determining the fluorescence intensity using CellQuest Software (BD). When FACSCalibur is used for the measurement, after staining the cells with an FITC-labeled secondary antibody that specifically recognizes the test antibody bound to the antigen on the surface of the antigen-expressing cells in the methods described above, the binding can be assessed by comparing the geometric mean value (test Geo-Mean value) with a control Geo-Mean value obtained using a control antibody. The geometric mean values are obtained by a method that analyzes fluorescence intensity using CellQuest Software. A formula to determine the Geo-Mean values (geometric means) is described in CellQuest Software User's Guide (BD Biosciences).

In order to not increase the in vivo immunogenicity in humans administered with an antibody, the amino acid sequences after modification in the present invention are preferably human sequences (sequences of a human-derived natural antibody), but are not limited thereto. Furthermore, in order to turn each of the modified FRs (FR1, FR2, FR3, and FR4) into a human sequence, mutations are preferably introduced into positions other than those that have been modified for modification of isoelectric point. The method of replacing each FR with a human sequence in this manner has been reported in a non-patent document (Ono K, Ohtomo T, Yoshida K, Yoshimura Y, Kawai S, Koishihara Y, Ozaki S, Kosaka M, Tsuchiya M. The humanized anti-HM1.24 antibody effectively kills multiple myeloma cells by human effector cell-mediated cytotoxicity. Mol. Immunol. (1999) 36(6):387-395). Furthermore, to modify the isoelectric point of an antibody, each FR can be modified into another human FR with a modified isoelectric point (for example, FR3 can be replaced with another human FR for a lower isoelectric point). Such a humanization method has been reported in a non-patent document (Dall'Acqua W F, Damschroder M M, Zhang J, Woods R M, Widjaja L, Yu J, Wu H. Antibody humanization by framework shuffling. Methods. (2005) 36(1):43-60).

Furthermore, when a polypeptide of interest with controlled pharmacokinetics in plasma cannot be produced by slight modifications to the surface charge, the desired antibody with controlled pharmacokinetics in plasma can be preferably obtained by repeating modification of surface charge and evaluation of pharmacokinetics in plasma.

In a non-patent document (J Immunol. (1998) 160(2):1029-35), chimeric EP5C7.g4, a chimeric anti-E, P-selectin antibody (IgG4), and HuEP5C7.g4, a humanized anti-E, P-selectin antibody (IgG4) were compared, and their pharmacokinetics in Rhesus monkey plasma were shown to be comparable to each other. In another non-patent document (Gobburu J V, Tenhoor C, Rogge M C, Frazier D E Jr, Thomas D, Benjamin C, Hess D M, Jusko W J. Pharmacokinetics/dynamics of 5c8, a monoclonal antibody to CD154 (CD40 ligand) suppression of an immune response in monkeys. J Pharmacol Exp Ther. (1998) 286(2):925-30), a chimeric anti-CD154 antibody, ch5d8, and a humanized anti-CD154 antibody, Hu5c8 were compared, and their pharmacokinetics in cynomolgus monkey plasma were revealed to be comparable. Furthermore, another non-patent document (Kashmiri S V, Shu L, Padlan E A, Milenic D E, Schlom J, Hand P H., Generation, characterization, and in vivo studies of humanized anticarcinoma antibody CC49. Hybridoma. (1995) 14 (5):461-73) showed that a chimeric antibody cCC49 and a humanized antibody HuCC49 had comparable pharmacokinetics in mouse plasma. In addition, non-patent documents (Graves S S, Goshorn S C, Stone D M, Axworthy D B, Reno J M, Bottino B, Searle S, Henry A, Pedersen J, Rees A R, Libby R T. Molecular modeling and preclinical evaluation of the humanized NR-LU-13 antibody. Clin Cancer Res. (1999) 5(4):899-908; Couto J R, Blank E W, Peterson J A, Ceriani R L. Anti-BA46 monoclonal antibody Mc3: humanization using a novel positional consensus and in vivo and in vitro characterization. Cancer Res. (1995) 55(8):1717-22) showed that mouse and humanized antibodies exhibited the same pharmacokinetic characteristics and distribution in mouse plasma. This suggests that the pharmacokinetics and distribution in plasma of the chimeric antibody and humanized antibody are comparable because both mouse and human Fcs are cross-reactive to mouse FcRn. As seen from these examples, a chimeric antibody and a humanized antibody sharing the same CDR exhibit the same pharmacokinetic characteristics in plasma. Specifically, when an antibody is humanized by known methods such as that described in a non-patent document (Nat Biotechnol. (1997) 15(7):637-40), the pharmacokinetics of the humanized antibody in plasma is comparable to that of the chimeric antibody; thus, humanized antibodies with controlled pharmacokinetics in plasma cannot be produced by known methods.

However, with the methods of the present invention, a humanized antibody whose pharmacokinetics in plasma is controlled (specifically, whose half-life in plasma is prolonged or shortened) as compared to the chimeric antibody can be produced by modifying exposable amino acid residues on the surface of the chimeric antibody in the process of humanization to modify the isoelectric point of the antibody. Exposable amino acids on the surface of a humanized antibody may be modified to control its pharmacokinetics in plasma at the time of antibody humanization. Alternatively, the isoelectric point of a humanized antibody may further be modified by using a humanized antibody as a starting material and modifying the exposable amino acid residues on its surface.

In the present invention, the isoelectric point can be determined by isoelectric focusing, which is known to those skilled in the art. The theoretical isoelectric point can be determined using gene and amino acid sequence analysis software (GENETYX and the like). This is useful for the present invention when considerable modification of the isoelectric point is necessary, for example, for sufficient control of plasma pharmacokinetics or other purposes. It is particularly preferred when it is necessary to modify the theoretical isoelectric point by 1.0 or more, and is more preferred when the isoelectric point needs to be modified by 3.0 or more.

In a non-patent document (Adams C W, Allison D E, Flagella K, Presta L, Clarke J, Dybdal N, McKeever K, Sliwkowski M X. Humanization of a recombinant monoclonal antibody to produce a therapeutic HER dimerization inhibitor, pertuzumab. Cancer Immunol Immunother. (2006) 55(6):717-27), three kinds of humanized antibodies, trastuzumab, bevacizumab, and pertuzumab, which were produced via humanization using a same human antibody FR sequence, showed nearly comparable pharmacokinetics in plasma. Specifically, when produced via humanization using a same FR sequence, antibodies exhibit nearly comparable pharmacokinetics in plasma. In addition to the process of humanization described above, the methods of the present invention enable to control the concentration of an antibody (in plasma) as a drug by modifying the isoelectric point of the antibody through modification of exposable amino acid residues on the surface of the antibody.

The methods of the present invention are also applicable to human antibodies. Human antibodies whose plasma pharmacokinetics is controlled (specifically, half-life in plasma is prolonged or shortened) as compared to the original human antibodies prepared in the first step can be produced by modifying their isoelectric points through modification of exposable amino acid residues on the surface of human antibodies prepared from human antibody libraries, human antibody-producing mice, or such.

The antibody half-life in plasma is prolonged when its isoelectric point value is decreased. Conversely, the antibody half-life in plasma is shortened when its isoelectric point value is increased. Higher isoelectric points are known to improve the transfer of antibodies into tissues (Vaisitti T, Deaglio S, Malavasi F. Cationization of monoclonal antibodies: another step towards the "magic bullet"?, J Biol Regul HomeostAgents. (2005) 19(3-4):105-12; Pardridge W M, Buciak J, Yang J, Wu D. Enhanced endocytosis in cultured human breast carcinoma cells and in vivo biodistribution in rats of a humanized monoclonal antibody after cationization of the protein. (1998) 286(1):548-54). However, such antibodies exhibit increased immunogenicity and cell internalization activity, and hence further improvement is needed to yield effective antibodies for cancer therapies that are based on mechanisms such as cytotoxic activities, ADCC and CDC, which are inhibited by cell internalization activity. Specifically, it is not understood whether an increase or decrease of the isoelectric point value enhances the antitumor effect of antibodies effective for cancer therapies that are based on mechanisms such as cytotoxic activities, ADCC and CDC, which are inhibited by cell internalization activity. In the present invention, modified antibodies with decreased or increased isoelectric point were produced from humanized antibodies and their antitumor effects were compared to see which modification gives a stronger antitumor effect. Surprisingly, the result showed that humanized antibodies with reduced isoelectric point exerted a more superior effect on liver cancer.

Antibodies produced by further modification of the above-described antibodies with modified charge of amino acid residues as a starting material by substitution, deletion, addition, and/or insertion of amino acid residues are included in the "antibodies" of the present invention. Antibodies produced by further modification of the charge of the amino acid residues of antibodies whose amino acid sequence has been modified by amino acid substitution, deletion, addition and/or insertion of amino acid residues, or chimerization, humanization, or such are also included in the "antibodies" of the present invention.

Preferred modifications for improving the characteristics of antibodies provided by the present invention include, for example, modifications to improve antibody stability (hereinafter referred to as "modification of stability"). In an aqueous solution, an antibody exists in equilibrium between two states, namely, native state and inactive denaturation state. As seen from the second law of thermodynamics ($\Delta G = \Delta H - T\Delta S$), the stability of the native state depends on the Gibbs free energy change $\Delta G$ in the system, as well as the balance between enthalpy change $\Delta H$ (reflecting changes in hydrophobic interaction, hydrogen bonding, and the like in the polypeptide chain) and entropy change $\Delta S$ (reflecting changes in solvation and degree of conformational freedom), both of which contribute to Gibbs free energy change. Positive $\Delta G$ values imply that a protein is more stable in the native state than in the denaturation state. The greater the positive value of $\Delta G$ is, the more stable the protein is in the native state. In order to denature a protein, it is necessary to remove forces that contribute to this stability. For example, when a protein solution is exposed to high temperature, conformational freedom is increased, resulting in impairment of factors that contribute to protein stability. This leads to protein thermal denaturation. The term $-T\Delta S$ is dominant in such denaturation. The $\Delta H$ for protein unfolding caused by thermal denaturation can be directly determined by differential scanning calorimetry (DSC), as specifically described in the Examples herein. A DSC curve for the protein thermal denaturation process gives an endothermic peak at a temperature called denaturation midpoint (Tm), which is intrinsic to individual test proteins. The denaturation enthalpy is determined by integrating the peak. The Tm value generally serves as an indicator for thermal stability. The thermal capacity change ($\Delta Cp$) in protein denaturation can also be determined by DSC. The thermal capacity change associated with thermal denaturation is primarily caused by hydration of amino acid residues not exposed on the molecular surface in the native state but exposed to solvent molecules as a result of protein denaturation.

As described above, the "modification" of amino acid residues in the methods provided by the present invention specifically means substitution of a different amino acid residue for an original amino acid residue, deletion of an original amino acid residue, addition of an extra amino acid residue, and the like. The preferred modification is substitution of a different amino acid residue for an original amino acid residue. Specifically, in the present invention, modification by amino acid substitution is preferred for modification of antibody stability. Stability modification achieved by modifying amino acid residues of an antibody increases the Tm value of the antibody. Specifically, the Tm value is preferably used as an indicator for modification of antibody stability.

For a glypican 3 antibody provided by the present invention, "stability modification" is preferably achieved, for example, by modifying at least one amino acid residue selected from the amino acid residues at positions 37, 40, 48, and 51 in the heavy chain variable region constituting the humanized glypican 3 antibody of SEQ ID NO: 195. Alternatively, "stability modification" is preferably achieved, for example, by modifying at least one amino acid residue selected from the amino acid residues at positions 2, 25, 42, 48, 50, 83, and 84 in the light chain variable region constituting the humanized glypican 3 antibody of SEQ ID NO: 201. Of the above-mentioned amino acid residues, it is not necessary to modify amino acid residues other than those already underwent stability modification, as long as the desired Tm is achieved. However, these amino acid residues can be appropriately modified to have a comparable or higher Tm than the humanized glypican 3 antibody before modification.

Stability modification can be carried out by randomly modifying each amino acid residue constituting the humanized antibody to be modified. Alternatively, stability modification can be carried out by substituting a portion of the amino acid sequence constituting a humanized antibody to be modified with the amino acid sequence of a known antibody with high Tm that structurally corresponds to the portion of the amino acid sequence of the humanized antibody to be modified. Positions of amino acid residues to be modified are not particularly limited; however, amino acid residues in the FR region can be preferably modified. Alternatively, amino acid residues in the CDR region can also be appropriately modified as long as the modification does not impair the antigen-binding activity. Furthermore, the number of amino acid residues to be modified is not particularly limited, and a particular segment within the FR region may be substituted with a desired segment. All of the segments in the FR region, FR1, FR2, FR3, and FR4, or a combination of one or more of the segments may be modified.

Preferred FR region segments for modification include, for example, FR2 regions of the heavy chain and light chain. Specifically, the preferred modification includes, for example, modification of amino acid residues to modify the FR2 of the heavy chain of a humanized glypican 3 antibody of the VH1b subclass, which is shown in SEQ ID NO: 195, to an FR2 of the VH4 subclass, namely, V37I which is substitution of isoleucine for valine at position 37, and similarly modifications of A40P, M48I, and L51I. Alternatively, the preferred modification includes, for example, modification of the light chain FR2 region of a humanized glypican 3 antibody of the VK2 subclass, which is shown in SEQ ID NO: 201, to an FR2 of the VK3 subclass, namely, modifications of L42Q, S48A, and Q50R, as well as modification of V2I which corresponds to modification of FR1 to a germ-line sequence.

Amino acid sequence modifications such as amino acid substitutions, deletions, additions, and/or insertions, and humanization and chimerization can be preferably achieved by methods known to those skilled in the art. When the antibodies of the present invention are prepared as recombinant antibodies, likewise, the amino acid sequences of the antibody variable and constant regions may also be preferably modified by amino acid substitutions, deletions, additions, and/or insertions.

Antibodies derived from any animal, such as mouse, human, rat, rabbit, goat, or camel antibodies, are preferably used in the present invention. Furthermore, modified antibodies that include amino acid substitutions in their sequence, such as chimeric antibodies and in particular humanized antibodies can be preferably used. Antibody modification products linked with various molecules can also be preferably used.

"Chimeric antibodies" are antibodies prepared by combining sequences derived from different animals. A preferred example is an antibody having heavy and light chain variable regions from a mouse antibody and heavy and light chain constant regions from a human antibody. Chimeric antibodies can be prepared by known methods. For example, a DNA encoding an antibody variable region and a DNA encoding a human antibody constant region are fused in frame, the resulting recombinant DNA is inserted into a commonly used expression vector, a host introduced with the vector is cultured, and a chimeric antibody is appropriately obtained or isolated from the cell culture.

"Humanized antibodies" are also referred to as reshaped human antibodies, and can be obtained by linking the CDR of a nonhuman mammalian antibody, for example mouse antibody, and the FR of a human antibody. A DNA sequence encoding a humanized antibody can be synthesized by overlap PCR, using several oligonucleotides as templates. Materials and methods for overlap PCR is described in WO98/13388 or the like. A DNA encoding the variable region of a humanized antibody of the present invention can be obtained by overlap PCR using several oligonucleotides designed to include oligonucleotide sequences that overlap with each other, and they are ligated in frame with a DNA encoding the human antibody constant region to form a codon sequence. The DNA thus ligated is then inserted into an expression vector in an expressible manner, and introduced into a host.

Methods for identifying CDRs are known (Kabat et al., Sequence of Proteins of Immunological Interest (1987), National Institute of Health, Bethesda, Md.; Chothia et al.; Nature (1989) 342:877). General genetic recombination techniques suitable for this purpose are also known (see European Patent Application Publication EP 125023; and WO96/02576). For example, the CDR of a nonhuman animal antibody such as a mouse antibody can be determined, and a DNA is prepared such that it encodes an antibody in which the CDR is ligated with the FR of a human antibody. Human antibody FRs linked via CDRs are selected such that the CDRs form a suitable antigen binding site. If required, amino acid residues in the FRs of an antibody variable region may be modified so that the CDRs of the reshaped human antibody can form a suitable antigen binding site (Sato, K. et al., Cancer Res. (1993) 53:851-856). Modifiable amino acid residues in the FRs include residues that directly bind to an antigen via non-covalent bonds (Amit et al., Science (1986) 233:747-53), residues that have some impact or effect on the CDR structure (Chothia et al., J. Mol. Biol. (1987) 196:901-17), and residues involved in the interaction between heavy chain variable region and light chain variable region (Patent Publication EP 239400).

A commonly used expression vector inserted with the DNA is transformed or transduced into a host cell, and the humanized antibody encoded by the DNA is produced and isolated from the cell culture by culturing the host cell.

When the antibodies of the present invention are humanized or human antibodies, the constant regions of these antibodies are preferably derived from human antibodies. For example, Cγ1, Cγ2, Cγ3, and Cγ4 can be used for the heavy chain constant region, while $C_\kappa$ and $C\lambda$, can be preferably used for the light chain constant region. The human antibody constant region may be modified as required to improve antibody or its production stability. A chimeric antibody of the present invention preferably includes a variable region of an antibody derived from a nonhuman mammal and a constant region of a human antibody. A humanized antibody preferably includes CDRs of an antibody derived from a nonhuman mammal and FRs and constant regions of a human antibody. A human antibody preferably includes CDRs of an antibody derived from human and FRs and constant regions of a human antibody. The constant regions of the human antibodies include specific amino acid sequences that correspond to the isotype of IgG (IgG1, IgG2, IgG3, and IgG4), IgM, IgA, IgD, and IgE. The constant regions of the humanized antibodies provided by the present invention may be the constant regions of antibodies of any isotype. Without being limited thereto, a constant region of human IgG is preferably used. The FRs of a human antibody to be used as FRs of the humanized and human antibodies are not particularly limited, and may be derived from an antibody of any isotype.

In order to reduce immunogenicity, a germ-line sequence can be substituted for all or some of the amino acid residues constituting the FR region using a method similar to the one described in a non-patent document (Mol Immunol. (1999) 36(6):387-395). This is based on the rational prediction that germ-line sequences have lower immunogenicity. The amino acid sequence constituting the FR region of a humanized antibody is aligned and compared with germ-line amino acid sequences (Abhinandan K. R. and Martin C. R., J. Mol. Biol. (2007) 369:852-862). Amino acid residues constituting an FR region of a humanized antibody that are found to be different in the above comparison can be substituted with germ-line amino acid residues, as long as the substitution does not result in the loss of antigen-binding activity. Specifically, such substitutions include, for example, substitutions of I for L at position 70, R for T at position 87, and A for T at position 97, which are the amino acid residues that constitute the heavy chain variable region of SEQ ID NO: 195. Furthermore, the substitutions also include substitution of A for S at position 25, in which is the amino acid residue that constitutes the light chain variable region of SEQ ID NO: 201.

One or more of the amino acids constituting the variable and constant regions of modified chimeric, human, or humanized antibodies of the present invention may be modified by deletion, substitution, insertion, and/or addition, as long as the antibodies exhibit binding specificity to an antigen.

Since the immunogenicity of chimeric, humanized, and human antibodies comprising human-derived sequences in the human body has been attenuated, they are expected to be useful when administered to humans for therapeutic purposes or such.

Known sequences can be used for the genes encoding the heavy chain or light chain of antibodies before introduction of mutations by methods of the present invention. Alternatively, new sequences for antibody genes can be obtained by methods known to those skilled in the art. For example, they may be preferably obtained from an antibody library. The genes can also be cloned from monoclonal antibody-producing hybridomas by a known method such as RT-PCR using their mRNA as template.

Regarding antibody libraries, many antibody libraries are already known. Since methods for producing antibody libraries are also known, those skilled in the art can appropriately obtain or produce antibody libraries. Examples include antibody phage libraries disclosed by Clackson et al., Nature (1991) 352:624-8; Marks et al., J. Mol. Biol. (1991) 222:581-97; Waterhouses et al., Nucleic Acids Res. (1993) 21:2265-6; Griffiths et al., EMBO J. (1994) 13:3245-60; Vaughan et al., Nature Biotechnology (1996) 14:309-14; and Japanese Patent Kohyo Publication No. (JP-A) H20-504970 (unexamined Japanese national phase publication corresponding to a non-Japanese international publication). In addition, known methods such as methods that use eukaryotic cells in preparing libraries (WO95/15393 pamphlet) and ribosome display methods may be preferably used. Furthermore, techniques for obtaining human antibodies by panning using human antibody libraries are also known. For example, single chain antibodies (scFvs) obtained by fusing human antibody heavy and light chain variable regions in frame are expressed on the surface of phages using phage display methods. Then, phages that bind to antigens are selected to isolate genes encoding antibody-binding scFv from the phages. The DNA sequences encoding the variable regions of heavy and light chains of antibodies that bind to the antigens can be determined by sequencing the genes. A human antibody can be appropriately obtained by inserting an antibody gene comprising the sequences into suitable expression vectors, and expressing the gene in suitable host cells as described later. These methods are already well known, and one can refer to WO92/01047, WO92/20791, WO93/06213, WO93/11236, WO93/19172, WO95/01438, and WO95/15388.

Basically, known techniques are used for methods for obtaining genes encoding antibodies from monoclonal antibody-producing hybridomas. The details will be described later; briefly, antibody genes are preferably obtained by immunizing an animal with a desired sensitizing antigen according to conventional immunization methods, fusing the immune cells obtained from the animal with known parent cells by common cell fusion methods, screening monoclonal antibody-producing cells (hybridomas) by common screening methods, synthesizing cDNAs of antibody variable regions from mRNAs of the obtained hybridomas as template using reverse transcriptase, and linking them with DNAs encoding the desired antibody constant regions in inflame.

More specifically, preferable examples are shown below, but are not particularly limited thereto. Sensitizing antigens for obtaining the antibodies provided by the present invention include both complete antigens with immunogenicity and incomplete antigens composed of haptens and such that do not show immunogenicity. For example, full length proteins, and their partial polypeptides and peptides may be preferably used. The soluble GPC3 core protein of SEQ ID NO: 207 is a suitable example. In addition, it is known that substances composed of polysaccharides, nucleic acids, lipids, and such may act as antigens. Thus, there are no particular limitations on antigens of the antibodies of the present invention. Antigens can be prepared by methods known to those skilled in the art, and they can be prepared, for example, by the following methods using baculoviruses (for example, WO98/46777). When the immunogenicity of an antigen is low, it can be preferably linked to a macromolecule that has immunogenicity, such as albumin, and then used to immunize animals. When transmembrane molecules are used as antigens, extracellular polypeptide fragments of the molecules can be used as a preferable sensitizing antigen. Alternatively, cells expressing the molecules on their surface may also be used as a sensitizing antigen. When sensitizing antigens are insoluble molecules, the molecules may be solubilized by linking with water-soluble molecules, and the solubilized binding molecules are preferably used as a sensitizing antigen.

Antibody-producing cells can be preferably obtained by immunizing animals using suitable sensitizing antigens described above. Alternatively, antibody-producing cells can be prepared by in vitro immunization of lymphocytes that can produce antibodies. Various vertebrate animals and mammals can be used as the animals for immunization. In particular, rodents, lagomorphas, and primates are generally used. Examples of such animals include mice, rats, and hamsters for rodents, rabbits for lagomorphas, and monkeys including the cynomolgus monkey, rhesus monkey, hamadryas, and chimpanzees for primates. In addition, transgenic animals carrying human antibody gene repertoires are also known, and human antibodies can be preferably obtained by using these animals (see WO96/34096; Mendez et al., Nat. Genet. (1997) 15:146-56). Instead of using such transgenic animals, desired human antibodies having binding activity against antigens can be obtained by, for example, in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H1-59878 (examined, approved Japanese patent application published for opposition)). Furthermore, desired human antibodies can be preferably obtained by immunizing transgenic animals carrying on their genomes a complete repertoire of human antibody genes with desired antigens (see WO93/12227, WO92/03918, WO94/02602, WO96/34096, and WO96/33735).

Animal immunization can be carried out by appropriately diluting and suspending a sensitizing antigen in Phosphate-Buffered Saline (PBS), physiological saline, or such, and forming an emulsion by mixing an adjuvant if necessary, and then intraperitoneally or subcutaneously injecting the sensitizing antigen into animals. After that, the sensitizing antigen mixed with Freund's incomplete adjuvant is preferably administered several times every 4 to 21 days. Production of antibodies against the sensitizing antigen in the immunized animals can be confirmed by measuring the antibody titer in animal sera using conventional methods, for example, known methods such as enzyme-linked immunosorbent assay (ELISA) and flow cytometry (FACS).

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). Hybridomas can be preferably produced, for example, by the methods of Milstein et al. (G. Kohler and C. Milstein, Methods Enzymol. (1981) 73:3-46). Monoclonal antibodies that specifically bind to an antigen protein produced by the hybridomas can be obtained by culturing and growing the hybridomas thus obtained. The binding specificity of the monoclonal antibodies to the antigen proteins can be appropriately measured using known analysis methods, such as immunoprecipitation, radioimmunoassay (MA), and enzyme-linked immunosorbent assay (ELISA), and flow cytometry (FACS). Thereafter, hybridomas that produce antibodies of interest whose specificity, affinity, or activity has been determined can be subcloned by methods such as limiting dilution if necessary. Finally, the monoclonal antibodies produced by the hybridomas can be isolated.

Next, genes encoding the selected antibodies can be cloned from hybridomas or antibody-producing cells (sensitized lymphocytes and such) using probes that may specifically bind to the genes (for example, oligonucleotides complementary to sequences encoding the antibody constant regions). Cloning by RT-PCR is also possible by using the mRNA obtained from hybridomas or antibody-producing cells (sensitized lymphocytes and such) as template. Immunoglobulins are classified into five different classes, IgA, IgD, IgE, IgG, and IgM according to their structures and functions. These classes are further divided into several isotypes (for example, IgG1, IgG2, IgG3, and IgG4; IgA1 and IgA2; and such). The class and subclass of antibodies provided by the present invention are not particularly limited and may be any of these classes or subclasses; however, IgG is a particularly preferred class.

It is possible to modify genes encoding amino acid sequences constituting heavy chain and light chain using genetic engineering techniques. Genetically modified antibodies such as chimeric antibodies and humanized antibodies that have been artificially modified for the purpose of decreasing heterologous antigenicity against humans and such can be appropriately produced for antibodies such as mouse antibodies, rat antibodies, rabbit antibodies, hamster antibodies, sheep antibodies, and camel antibodies by modifying nucleic acid residues that encode the amino acid sequences constituting the antibodies. Chimeric antibodies are antibodies composed of the heavy chain and light chain variable regions derived from a nonhuman mammalian antibody, for example, mouse antibody, and the heavy chain and light chain constant regions of a human antibody. They can be obtained by ligating the DNA encoding a variable region of a mouse antibody to the DNA encoding a constant region of a human antibody, incorporating them into an expression vector, and introducing the vector into a host for production of the antibody. A humanized antibody, which is also called a reshaped human antibody, is an antibody in which a human antibody FR is ligated in frame with the CDR of a nonhuman mammalian antibody, for example, mouse antibody, to form a codon sequence. A DNA sequence encoding this humanized antibody can be obtained by overlap PCR using several oligonucleotides as templates. The materials and methods for overlap PCR are described in WO98/13388 or the like.

A DNA encoding the variable region of a recombinant antibody of the present invention can be obtained by overlap PCR using several oligonucleotides designed to include oligonucleotide sequences that overlap with each other, and they are ligated in frame with a DNA encoding the human antibody constant region to form a codon sequence. The DNA thus ligated can be incorporated into an expression vector in an expressible manner, and the vector can be introduced into a host. An antibody encoded by the DNA is expressed by culturing the host. Expressed antibodies are obtained by suitably purifying the culture solution of the host or such (see EP239400 and WO96/02576). Human antibody FRs to be ligated via the CDR are selected when the CDR forms a favorable antigen-binding site against the antigen. If necessary, amino acid residues in the FR of an antibody variable region may be substituted such that the CDR of the reshaped human antibody forms an appropriate antigen-binding site against the antigen (K. Sato et al., Cancer Res. (1993) 53:851-856).

In addition to the humanization described above, antibodies may be modified to improve their biological properties such as binding activity to an antigen recognized by the antibody. In the present invention, such modifications can be carried out using methods such as site-directed mutagenesis (see for example, Kunkel Proc. Natl. Acad. Sci. USA (1985) 82:488), PCR mutagenesis, and cassette mutagenesis. In general, mutant antibodies whose biological properties have been improved show amino acid sequence identity and/or similarity of 70% or higher, more preferably 80% or higher, and even more preferably 90% or higher (for example, 95% or higher, 97%, 98%, 99%, etc.), when compared to the amino acid sequence of the antibody to be modified (namely, an antibody from which the modified antibody is prepared). Herein, sequence identity and/or similarity is defined as the ratio of amino acid residues that are homologous (same residues) or similar (amino acid residues classified into the same group based on the general properties of amino acid side chains) to the amino acid residues of an antibody from which the modified antibody is prepared, after the sequence identity value has been maximized by sequence alignment and gap introduction, if necessary. Generally, naturally-occurring amino acid residues are classified into groups based on the characteristics of their side chains: (1) hydrophobic: alanine, isoleucine, valine, methionine, and leucine; (2) neutral hydrophilic: asparagine, glutamine, cysteine, threonine, and serine; (3) acidic: aspartic acid and glutamic acid; (4) basic: arginine, histidine, and lysine; (5) residues that affect the orientation of the chain: glycine and proline; and (6) aromatic: tyrosine, tryptophan, and phenylalanine.

In a preferred embodiment, modifications that are aimed at enhancing antibody functions preferably include, for example, enhancement of the cytotoxic activity of antibodies including humanized antibodies. Such preferred cytotoxic activities include, for example, ADCC and CDC. Herein, CDC refers to cytotoxic activity of the complement system. When a specific antibody binds to an antigen on the target cell surface, cells carrying Fcγ receptor (immune cells and others) bind to the Fc via Fcγ receptor, and the cytotoxic activity exerted against target cells is referred to as ADCC. Whether a test antibody has ADCC or CDC can be assessed by known methods (for example, Current protocols in Immunology, Chapter 7. Immunologic studies in humans, Editor, John E, Coligan et al., John Wiley & Sons, Inc., (1993)).

Specifically, first, effector cells, complement solutions, and target cells are prepared.

(1) Preparation of Effector Cells

Spleens are excised from CBA/N mice or the like, and then spleen cells are separated in RPMI1640 medium (Invitrogen). Effector cells can be prepared by washing the cells with the same medium containing 10% fetal bovine serum (FBS, HyClone) and then adjusting the cell concentration to $5 \times 10^6$ cells/ml.

(2) Preparation of Complement Solution

Complement solutions can be prepared by 10× dilution of Baby Rabbit Complement (CEDARLANE) in a medium (Invitrogen) containing 10% FBS.

(3) Preparation of Target Cells

Target cells expressing the antigen protein to which a test antibody binds can be radio-labeled by incubating them with 0.2 mCi of [$^{51}$Cr] sodium chromate (GE Healthcare Bioscience) in DMEM supplemented with 10% FBS at 37° C. for one hour. Cells expressing the antigen protein to which a test antibody binds include cells transformed with the gene encoding the antigen protein to which a test antibody binds, ovary cancer cells, prostate cancer cells, breast cancer cells, uterine cancer cells, liver cancer cells, lung cancer cells, pancreatic cancer cells, stomach cancer cells, urinary bladder cancer cells, and colon cancer cells. The target cells can be prepared by washing the radio-labeled cells three times with RPMI1640 medium supplemented with 10% FBS and adjusting the cell concentration to $2 \times 10^5$ cells/ml.

ADCC and CDC can be determined by the method described below. ADCC assay is carried out by adding 50 µl/well each of target cells and test antibody into a 96-well round-bottomed plate (Becton Dickinson) and incubating it on ice for 15 minutes. Then, 100 µl of the effector cells is added, and the resulting reaction mixture is incubated in a carbon dioxide gas incubator for four hours. The test antibody can be appropriately used at a final concentration in a range of 0 to 10 µg/ml. After incubation, 100 µl of supernatant is sampled and its radioactivity is determined using a gamma counter (COBRAII AUTO-GAMMA, MODEL D5005, Packard Instrument Company). The cytotoxic activity (%) can be calculated from the obtained radioactivity value according to the following formula:

$$(A-C)/(B-C) \times 100$$

where A represents the radioactivity (cpm) of each test antibody sample, B represents the radioactivity (cpm) of a sample containing 1% NP-40 (Nacalai Tesque), and C represents the radioactivity (cpm) of a sample containing target cells alone.

CDC assay is carried out by adding 50 µl/well each of target cells and test antibody into a 96-well flat-bottomed plate (Becton Dickinson) and incubating it on ice for 15 minutes. Then, 100 µl of the complement solution is added, and the resulting reaction mixture is incubated in a carbon dioxide gas incubator for four hours. The test antibody can be appropriately used at a final concentration in a range of 0 to 3 µg/ml. After incubation, 100 µl of supernatant is sampled and its radioactivity is determined using a gamma counter. The cytotoxic activity can be calculated by the same method used for ADCC determination.

The cytotoxic activity of the antibody conjugate is determined by adding 50 µl/well each of target cells and test antibody conjugate in a 96-well flat-bottomed plate (Becton Dickinson) and incubating it on ice for 15 minutes. The plate is incubated in a carbon dioxide gas incubator for one to four hours. The antibody can be appropriately used at a final concentration in a range of 0 to 3 µg/ml. After incubation, 100 µl of supernatant is sampled and its radioactivity is determined using a gamma counter. The cytotoxic activity can be calculated by the same method used for ADCC determination.

As described above, the heavy chain and light chain variable regions of an antibody generally consist of three CDRs and four FRs. In a preferred embodiment of the present invention, amino acid residues to be subjected to "modification" can be appropriately selected, for example, from amino acid residues constituting a CDR or FR.

By using public databases such as Kabat, those skilled in the art can readily obtain an amino acid sequence constituting an antibody variable region FR that actually exists in an organism such as human or mouse.

In a preferred embodiment, the present invention provides humanized antibodies whose pharmacokinetics in plasma is controlled by the methods of the present invention. Such humanized antibodies include, for example, humanized antibodies comprising nonhuman animal-derived CDR, human-derived FR, and human constant region, and whose pharmacokinetics in plasma is controlled relative to a chimeric antibody sharing the same constant region, in which at least one exposable amino acid residue on the surface of the antibody CDR or FR has opposite charge to the amino acid residue at the corresponding position in the CDR or FR of the original antibody.

In another preferred embodiment, the present invention provides human antibodies whose pharmacokinetics in plasma is controlled by the methods of the present invention. Such human antibodies include, for example, human antibodies comprising the human-derived CDR, human-derived FR, and human constant region, and whose pharmacokinetics in plasma is controlled relative to a chimeric antibody sharing the same constant region, in which at least one exposable amino acid residue on the surface of the antibody CDR or FR has opposite charge to the amino acid residue at the corresponding position in the CDR or FR of the original antibody.

The human constant region preferably refers to a region comprising the wild-type human Fc domain; however, modified Fc can also be preferably used. The "modified Fc" includes Fc in which amino acid residues constituting the Fc are modified, and Fc in which modification of the Fc domain is altered. Specifically, such alteration of modification preferably includes, for example, modification of the type of glycosylation in the Fc domain. A specific preferred example is the "antibody with reduced content of fucose linked to the antibody Fc domain" specifically disclosed in the Reference Experimental Examples herein.

The "antibody with reduced content of fucose linked to the antibody Fc domain" refers to an antibody whose fucose content is significantly reduced relative to a control antibody, preferably one with undetectable fucose. In general, fucose is added to the N-glycoside linkage sugar chains linked at two sites in the Fc domains of two molecules of heavy chain constituting a single antibody molecule. Herein, the "antibody with reduced content of fucose linked to the antibody Fc domain" refers to an antibody, which when compared to such a common antibody as control, has a fucose content of 50% or less, preferably 25% or less, more preferably 10% or less, still more preferably 0% of the total sugar chain content in the control antibody. Fucose content can be determined by the specific analytical methods described below in the Reference Experimental Examples. Methods for preparing such antibodies with reduced fucose content are described in the Reference Experimental Examples herein. Such methods also preferably include, for example, the preparation methods using animal cells that are deficient in fucosyl transferase (Biotechnol Bioeng. (2004) 87(5):614-22) and preparation methods using animal cells with altered complex-type branched sugar chain modification (Biotechnol Bioeng. (2006) 93(5):851-61). Furthermore, the preparation methods also preferably include those that use non-animal cells such as plant cells (Nature Biotechnology (2006) 24:1591-7) or yeast cells (Nature Biotechnology (2006) 24:210-5) as host cells.

In a preferred embodiment, the present invention relates to a method for producing a polypeptide comprising an antibody variable region with a modified isoelectric point, which comprises:
(a) modifying a nucleic acid encoding a polypeptide so as to modify the charge of at least one exposable amino acid residue on the surface of the CDR region of the polypeptide;
(b) culturing a host cell to express the nucleic acid; and
(c) collecting the polypeptide comprising an antibody variable region from the host cell culture.

In another preferred embodiment, the present invention relates to a method for producing a polypeptide comprising an antibody variable region with controlled pharmacokinetics in plasma, which comprises:
(a) modifying a nucleic acid encoding a polypeptide so as to modify the charge of at least one exposable amino acid residue on the surface of the CDR region of the polypeptide;
(b) culturing a host cell to express the nucleic acid; and
(c) collecting the polypeptide comprising an antibody variable region from the host cell culture.

Furthermore, the polypeptides comprising an antibody variable region with controlled plasma pharmacokinetics produced by the methods are also included in the present invention.

The present invention provides methods for producing multispecific polypeptides comprising a first polypeptide and a second polypeptide each comprising an antibody variable region. In addition, the present invention provides multispecific polypeptides produced by the methods. A preferred embodiment of the production methods of the present invention is a method comprising modifying both or either one of a nucleic acid encoding the amino acid residues of a first polypeptide and a nucleic acid encoding the amino acid residues of a second polypeptide, so as to increase the difference between the isoelectric points of the first polypeptide and second polypeptide. That is, multispecific antibodies can be produced based on difference in isoelectric points, and the difference can be increased by modifying the charges of the amino acid residues in the first polypeptide and second polypeptide. More specifically, a preferred production method comprises the following steps of:

(a) modifying a nucleic acid encoding a polypeptide so as to modify the charge of at least one exposable amino acid residue on the surface of the CDR region of the first polypeptide and second polypeptide, specifically modifying both or either one of a nucleic acid encoding the amino acid residues of a first polypeptide and a nucleic acid encoding the amino acid residues of a second polypeptide, so as to increase the difference between the isoelectric points of the first polypeptide and second polypeptide when compared to before modification;

(b) culturing host cells to express the nucleic acids; and (c) collecting a multispecific antibody from the host cell culture.

In the present invention, "polypeptides" generally refers to peptides and proteins whose length is approximately ten amino acids or longer. Polypeptides are generally derived from organisms, but are not particularly limited thereto, and for example, they may be composed of an artificially designed sequence. They may also be naturally derived polypeptides, synthetic polypeptides, recombinant polypeptides, or such. Additionally, fragments of the above-mentioned polypeptides are also included in the polypeptides of the present invention.

In the present invention, "multispecific polypeptides comprising a first polypeptide and a second polypeptide each comprising an antibody variable region" refers to a polypeptide comprising a variable region of an antibody that binds to two or more types of different epitopes, or different epitopes in a single antigen. Polypeptides comprising an antibody variable region include, for example, the antibodies, minibodies, and scaffold proteins mentioned above.

In the present invention, the phrase "the difference between the isoelectric points of the polypeptides is increased" means that the isoelectric points of two or more polypeptides are made unequal by modifying the charges of the amino acids on the surface of each polypeptide, or increasing the difference between the isoelectric points of two or more polypeptides. The difference in the isoelectric points can be observed, for example, by using a technique such as isoelectric focusing. In the present invention, the isoelectric points are preferably changed without altering the structure and function (activity) of the polypeptides.

That is, the present invention provides a method for producing a multispecific polypeptide comprising a first polypeptide and a second polypeptide, wherein the method comprises the steps of:

(a) modifying both or either one of a nucleic acid encoding the amino acid residues of the first polypeptide and a nucleic acid encoding the amino acid residues of the second polypeptide, so that the difference between the isoelectric point of the first polypeptide and that of the second polypeptide will be 1.0 or more, preferably 1.2 or more, and more preferably 1.5 or more;

(b) culturing host cells to express the nucleic acids; and (c) collecting the multispecific antibody from the host cell culture.

Furthermore, the present invention provides a method of modifying multispecific polypeptides for purification of multispecific antibodies comprising the first polypeptide and second polypeptide. A preferred embodiment of the purification method of the present invention is a method comprising the step of modifying both or either one of a nucleic acid encoding the amino acid residues of a first polypeptide and a nucleic acid encoding the amino acid residues of a second polypeptide, so as to increase the difference between the isoelectric points of the first polypeptide and second polypeptide. That is, the difference in isoelectric points is introduced into the polypeptides by modifying the charges of the amino acid residues of the first polypeptide and second polypeptide. Multispecific antibodies can be purified using this difference in isoelectric points. More specifically, a purification method comprises the following steps of:

(a) modifying a nucleic acid encoding a polypeptide so as to modify the charge of at least one exposable amino acid residue on the surface of the CDR region of the first polypeptide and second polypeptide, specifically modifying both or either one of a nucleic acid encoding the amino acid residues of the first polypeptide and a nucleic acid encoding the amino acid residues of the second polypeptide, so as to increase the difference between the isoelectric points of the first polypeptide and second polypeptide when compared to before modification;

(b) culturing host cells to express the nucleic acids; and (c) purifying said multispecific antibody from the host cell culture by standard chromatography.

Methods for producing multispecific antibodies which comprise the purification steps of the above-mentioned purification methods are also included in the present invention.

In the methods of the present invention, the phrase "modification of nucleic acids" refers to modifying nucleic acid sequences to form codons corresponding to the amino acid residues that are introduced by "modification" of the present invention. More specifically, the phrase refers to modifying nucleic acids constituting codons to be modified to codons encoding amino acid residues introduced by the modification. Usually, the phrase means gene manipulation or mutagenesis that modifies at least one nucleotide of a codon to produce a codon that encodes an amino acid residue of interest. More specifically, a codon encoding the original amino acid residue is replaced by a codon encoding the amino acid residue to be introduced by the modification. Such nucleic acid modifications can be carried out appropriately by those skilled in the art using known techniques, for example, site-directed mutagenesis or PCR mutagenesis.

The nucleic acids of the present invention are generally cloned (inserted) into suitable vectors and then introduced into host cells. These vectors are not particularly limited as long as the inserted nucleic acids are stably maintained. For example, when *Escherichia coli* (*E. coli*) is used as a host, the cloning vectors are preferably pBluescript vectors (Stratagene) and such, while various commercially available vectors may be used. When vectors are used for the purpose of producing the polypeptides of the present invention, expression vectors are particularly useful. There is no particular limitation on expression vectors, so long as they can express polypeptides in test tubes, *E. coli*, cultured cells, or individual organisms. For example, preferred vectors include pBEST vector (Promega) for expression in test tubes, pET vector (Invitrogen) in *E. coli*, the pME18S-FL3 vector (GenBank Accession No. AB009864) in cultured cells, and the pME18S vector (Mol. Cell Biol. (1998) 8:466-472) in individual organisms. Insertion of the DNAs of the present invention into vectors can be performed, for example, by standard methods such as ligase reactions using restriction enzyme sites (Current protocols in Molecular Biology edit. Ausubel et al., (1987) Publish. John Wiley & Sons. Section 11.4-11.11).

There is no particular limitation on the above-mentioned host cells, and various host cells are used depending on the purpose. Cells used for expressing polypeptides include bacterial cells (for example, *Streptococcus, Staphylococcus, E. coli, Streptomyces*, and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods, such as the calcium phosphate precipitation method, electroporation method (Current protocols in Molecular Biology edit. Ausubel et al., (1987) Publish. John Wiley & Sons. Section 9.1-9.9), lipofection method, and microinjection method.

For secreting host cell-expressed polypeptides (antibodies) into the lumen of the endoplasmic reticulum, periplasmic space, or extracellular environment, suitable secretion signals can be incorporated into the antibodies of interest. These signals may be intrinsic or foreign to the polypeptides (antibodies) of interest.

When the polypeptides (antibodies) of the present invention are secreted into culture media, the polypeptides (antibodies) produced by the above-mentioned methods can be harvested by collecting the media. When the antibodies of the present invention are produced inside cells, the cells first are lysed, and then these antibodies are collected.

The antibodies of the present invention can be preferably collected and purified from recombinant cell cultures using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

In the present invention, polypeptides with nucleic acid modification are preferably a homomultimer of a first polypeptide, a homomultimer of a second polypeptide, and a heteromultimer of the first polypeptide and second polypeptide. Examples of the homomultimer of a first polypeptide, the homomultimer of a second polypeptide, and the heteromultimer of the first polypeptide and second polypeptide include those described in Examples, but are not limited thereto.

Examples of standard chromatography in the present invention include cation exchange chromatography, anion exchange chromatography, hydrophobic chromatography, hydroxyapatite chromatography, hydrophobic charge interaction chromatography, and chromatofocusing, but are not limited thereto.

In the above-mentioned methods of the present invention, a first polypeptide and a second polypeptide preferably comprise a heavy chain variable region. The variable region may comprise, for example, a CDR and an FR.

Furthermore, in the above-mentioned methods of the present invention, a variable region of a multispecific antibody preferably comprises a light chain variable region.

Additionally, in the above-mentioned methods of the present invention, a first polypeptide and a second polypeptide preferably comprise heavy chain constant regions. Such heavy chain constant regions preferably generate difference between the isoelectric points of the first polypeptide and second polypeptide. Examples of such heavy chain constant regions include heavy chain constant regions of antibodies having different isoelectric points. The isoelectric point difference can be introduced into the first polypeptide and the second polypeptide using the heavy chain constant regions of IgG1, IgG2, IgG3, or IgG4 which have isoelectric points that are originally different from each other. Alternatively, the amino acids in the heavy chain constant regions of the first polypeptide and the second polypeptide that cause differences in isoelectric point among these subclasses can be modified alone, or in combination with adjacent amino acids that do not have any effect on the isoelectric points to generate non-wild-type human constant regions, and isoelectric point difference can be introduced into the two constant regions. Examples of positions to be modified for introducing isoelectric point difference into the constant regions include, for example, positions 137, 196, 203, 214, 217, 233, 268, 274, 276, 297, 355, 392, 419, and 435, EU numbering, in the heavy chain constant region.

Furthermore, since removal of sugar chains from a heavy chain constant region generates isoelectric point difference, position 297, which is a glycosylated site, is another example of a position to be modified for introducing isoelectric point difference.

For methods that comprise the above-mentioned first polypeptide and second polypeptide comprising a heavy chain constant region, methods that combine with the method in which the above-mentioned first polypeptide and second polypeptide comprise a heavy chain variable region, and/or the method in which the multispecific antibody comprises a third polypeptide comprising a light chain variable region, and a first polypeptide and a second polypeptide that each forms a multimer with the third polypeptide, are included in the present invention.

Multispecific polypeptides produced by the above-mentioned methods are also included in the present invention.

Furthermore, in an embodiment, when the first polypeptide in the multispecific antibody provided by the present invention comprises a heavy chain variable region, at least one amino acid residue at positions 31, 61, 62, 64, and 65, Kabat's numbering, in the heavy chain variable region is made to carry a charge so that "the difference of isoelectric points will be increased". In another embodiment, when the polypeptide comprises a light chain variable region, at least one amino acid residue at positions 24, 27, 53, 54, and 55, Kabat's numbering, in the light chain variable region is made to carry a charge so that "the difference of isoelectric points will be increased". Of the amino acid residues of the first polypeptide indicated by the above-mentioned numbering, amino acid residues other than the charged amino acid residue may have the same type of charge as that of the charged amino acid residue, or may be uncharged, or may have the opposite charge of that of the charged amino acid residue, as long as the isoelectric point of the first polypeptide and that of the second polypeptide are different.

The above-mentioned multispecific antibodies of the present invention comprise a second polypeptide that preferably has the opposite charge of that of the charged amino acid residue in the first polypeptide, or is uncharged. More specifically, the second polypeptide in the multispecific antibodies comprises a heavy chain variable region, and at least one amino acid residue at positions 31, 61, 62, 64, and 65, Kabat's numbering, in the region is uncharged or has the opposite charge of that of the amino acid residue selected to carry a charge in the variable region in the first polypeptide. In addition, when the second polypeptide comprises a light chain variable region, at least one amino acid residue at positions 24, 27, 53, 54, and 55, Kabat's numbering, in the light chain variable region is uncharged or has the opposite charge of that of the amino acid residue selected to carry a charge in the variable region in the first polypeptide. Of the amino acid residues of the second polypeptide indicated by the above-mentioned numbering, amino acid residues other than the charged amino acid residue may have the same type of charge as that of the charged amino acid residue, or may be uncharged, or may have the opposite charge of that of the charged amino acid residue, as long as the isoelectric point of the first polypeptide and that of the second polypeptide are different.

To lower isoelectric points in multispecific antibodies comprising an antibody constant region, it is desirable to apply, for example, an IgG2 or IgG4 sequence to position 137, an IgG1, IgG2, or IgG4 sequence to position 196, an IgG2 or IgG4 sequence to position 203, an IgG2 sequence to position 214, an IgG1, IgG3, or IgG4 sequence to position 217, an IgG1, IgG3, or IgG4 sequence to position 233, an IgG4 sequence to position 268, an IgG2, IgG3, or IgG4 sequence to position 274, an IgG1, IgG2, or IgG4 sequence to position 276, an IgG4 sequence to position 355, an IgG3 sequence to position 392, an IgG4 sequence to position 419, and an IgG1, IgG2, or IgG4 sequence to position 435. To increase isoelectric points, it is desirable to apply, for example, an IgG1 or IgG3 sequence to position 137, an IgG3 sequence to position 196, the IgG1 or IgG3 sequence to position 203, an IgG1, IgG3, or IgG4 sequence to position 214, an IgG2 sequence to position 217, an IgG2 sequence to position 233, an IgG1, IgG2, or IgG3 sequence to position 268, an IgG1 sequence to position 274, an IgG3 sequence to position 276, an IgG1, IgG2, or IgG3 sequence to position 355, an IgG1, IgG2, or IgG4 sequence to position 392, an IgG1, IgG2, or IgG3 sequence to position 419, and an IgG3 sequence to position 435.

It is not necessary to apply all of these sequences, as long as there is sufficient difference between the isoelectric points of the two heavy chains.

Regarding the above-mentioned antibodies, the phrase "having the same type of charge" means, for example, that the above-mentioned amino acid residue in the heavy chain variable region according to Kabat's numbering and the above-mentioned amino acid residue in the heavy chain constant region according to EU numbering both carry an amino acid residue included in either of the groups (a) and (b) below.
(a) glutamic acid (E) and aspartic acid (D); and
(b) lysine (K), arginine (R), and histidine (H).

The phrase, "having the opposite charge" means that, for example, at least one of the above-mentioned amino acid residues, by Kabat's numbering or EU numbering, in the second polypeptide comprising a heavy chain variable region and/or a heavy chain constant region is included in either one of the above-mentioned groups (a) or (b), and its corresponding amino acid residue at a position in the heavy chain variable region and/or heavy chain constant region comprised in the first polypeptide is included in the other group.

More specifically, the present invention provides multispecific antibodies, in which the above-mentioned amino acid residues having the same type of charge are selected from the amino acid residues included in either one of the above-mentioned group (a) or (b).

In a preferred embodiment of the present invention, if the original amino acid residue (before modification) is already charged, it may be modified to be an uncharged amino acid residue.

In the present invention, an amino acid residue is preferably modified such that the difference between the isoelectric points of the first polypeptide and that of the second polypeptide will be increased. Furthermore, when multiple amino acid residues are introduced by modification, a few uncharged amino acid residues may be included in these amino acid residues.

Furthermore, the present invention relates to compositions (agents) comprising a polypeptide with controlled plasma pharmacokinetics in the present invention (for example, an IgG antibody) and a pharmaceutically acceptable carrier.

In the present invention, "pharmaceutical compositions" generally refers to agents for treating or preventing, or testing and diagnosing diseases.

The pharmaceutical compositions of the present invention can be preferably formulated by methods known to those skilled in the art. For example, such pharmaceutical compositions can be used parenterally in the form of injections, which are sterile solutions or suspensions prepared with water or another pharmaceutically acceptable liquid. For example, such compositions may be formulated by appropriately combining with a pharmaceutically acceptable carrier or medium, specifically, sterile water, physiological saline, vegetable oil, emulsifier, suspension, surfactant, stabilizer, flavoring agent, excipient, vehicle, preservative, binder, or such, and mixed in a unit dose form that meets the generally accepted requirements for preparation of pharmaceuticals. In such preparations, the amount of active ingredient is adjusted such that a suitable amount within a specified range is obtained.

Sterile compositions for injection can be formulated using vehicles such as distilled water for injection, according to standard protocols for formulation.

Aqueous solutions for injection include, for example, physiological saline and isotonic solutions containing glucose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), and non-ionic surfactants (polysorbate 80™, HCO-50, and such) may be used in combination.

Oils include sesame and soybean oils. Benzyl benzoate and/or benzyl alcohol can be used as solubilizers in combination. Buffers (for example, phosphate buffer and sodium acetate buffer), soothing agents (for example, procaine hydrochloride), stabilizers (for example, benzyl alcohol and phenol), and/or antioxidants can also be combined. Prepared injections are generally filled into appropriate ampules.

The pharmaceutical compositions of the present invention are preferably administered parenterally. For example, the compositions may be in the form of injections, transnasal agents, transpulmonary agents, or transdermal agents. For example, such compositions can be administered systemically or locally by intravenous injection, intramuscular injection, intraperitoneal injection, subcutaneous injection, or such.

The administration methods can be appropriately selected in consideration of a patient's age and symptoms. The dosage of a pharmaceutical composition comprising an antibody or a polynucleotide encoding an antibody may be set, for example, within the range of 0.0001 to 1,000 mg/kg weight for each administration. Alternatively, the dosage may be, for example, from 0.001 to 100,000 mg per patient. However, in the present invention, the dosage is not necessarily limited to the ranges described above. Although the dosage and administration method vary depending on a patient's weight, age, symptoms, and such, those skilled in the art can select appropriate dosage and administration methods in consideration of the factors described above.

The present invention also provides nucleic acids encoding antibodies with controlled pharmacokinetics in plasma (for example, humanized glypican 3 antibodies). Furthermore, vectors that carry these nucleic acids are also included in the present invention.

The present invention also provides host cells carrying the above-described nucleic acids. The host cells are not particularly limited and include, for example, bacterial cells such as *E. coli* and various animal cells. The host cells may be preferably used, for example, as a production system to produce and express the antibodies of the present invention. More specifically, the present invention provides a production system for the production of antibodies using the host cells. In vitro and in vivo systems for production of polypeptides are preferably used. Eukaryotic cells or prokaryotic cells are preferable examples used in an in vitro production system.

Eukaryotic cells that are used as host cells include, for example, animal cells, plant cells, and fungal cells. Animal cells include: mammalian cells, for example, CHO (J. Exp. Med. (1995) 108:945), COS, HEK293, 3T3, myeloma, BHK (baby hamster kidney), HeLa, and Vero; amphibian cells such as *Xenopus laevis* oocytes (Valle, et al., Nature (1981) 291:338-340); and insect cells such as Sf9, Sf21, and Tn5. For expressing the antibodies of the present invention, CHO-DG44, CHO-DX11B, COST cells, HEK293 cells, and BHK cells can be suitably used. Of the animal cells, CHO cells are particularly preferable for large-scale expression. Vectors can be introduced into a host cell by, for example, calcium phosphate methods, DEAE-dextran methods, methods using cationic liposome DOTAP (Boehringer-Mannheim), electroporation methods, or lipofection methods.

It is known that plant cells such as *Nicotiana tabacum*-derived cells and *Lemna minor* cells are protein production systems, and these cells can be used to produce antibodies of the present invention by methods that culture calluses from these cells. Protein expression systems that use fungal cells including yeast cells, for example, cells of the genus *Saccharomyces* (*Saccharomyces cerevisiae, Saccharomyces pombe*, etc.), and cells of filamentous fungi, for example, the genus *Aspergillus* (*Aspergillus niger*, etc.) are known, and these cells can be used as a host to produce antibodies of the present invention.

When prokaryotic cells are used, production systems that use bacterial cells are preferably used. Production systems that use bacterial cells including *Bacillus subtilis* as well as *E. coli* described above are known, and they can preferably be used to produce antibodies of the present invention.

When an antibody is produced using a host cell of the present invention, a polynucleotide encoding an antibody of the present invention may be expressed by culturing the host cell transformed with an expression vector comprising the polynucleotide. Culturing can be preferably performed according to known methods. For example, when animal cells are used as a host, DMEM, MEM, RPMI 1640, or IMDM may be preferably used as the culture medium. The culture medium may be preferably used with serum supplement solutions such as FBS or fetal calf serum (FCS). Alternatively, cells can be cultured in serum-free cultures. The preferred pH is about 6 to 8 during the course of culturing, although it depends on the host cell. Incubation is carried out typically at about 30° C. to 40° C. for about 15 to 200 hours. Medium is exchanged, aerated, or agitated, as necessary.

Meanwhile, as systems for producing antibodies in vivo, for example, those using animals and those using plants may be preferably used. A polynucleotide encoding an antibody of the present invention is introduced into an animal or plant to produce a glypican 3 antibody in the body of the animal or the plant, and then the antibody is collected. The "host" of the present invention includes such animals and plants.

When animals are used as a host, production systems that use mammals or insects are available. Mammals such as goat, pig, sheep, mouse, and cattle may be preferably used (Vicki Glaser, SPECTRUM Biotechnology Applications (1993)). When mammals are used, transgenic animals may be used.

For example, a polynucleotide encoding an antibody of the present invention may be prepared as a fusion gene with a gene encoding a polypeptide specifically produced in milk, such as goat β-casein. Next, polynucleotide fragments containing this fusion gene are injected into goat embryos, which are then introduced back into female goats. The antibody of interest can be obtained from milk produced by the transgenic goats, which are born from the goats that received the embryos, or by their offspring. Appropriate hormones may be administered to the transgenic goats to increase the volume of milk containing the antibody produced by the transgenic goats (Ebert et al., Bio/Technology (1994) 12:699-702).

Insects such as silkworms may be used for producing antibodies of the present invention. When silkworms are used, baculoviruses carrying a polynucleotide encoding an antibody of interest can be used to infect silkworms, so that a glypican 3 antibody of interest can be obtained from the body fluids of these silkworms (Susumu et al., Nature (1985) 315:592-594).

Plants used for producing antibodies of the present invention include, for example, tobacco. When tobacco is used, a polynucleotide encoding an antibody of interest is inserted into a plant expression vector, for example, pMON 530, and then the vector is introduced into a bacterium such as *Agrobacterium tumefaciens*. The bacteria are then used to infect tobacco such as *Nicotiana tabacum*, and the desired glypican 3 antibody can be obtained from the infected leaves of the tobacco (Ma et al., Eur. J. Immunol. (1994) 24:131-138). Alternatively, the same bacteria can be used to infect *Lemna minor*, and after cloning, the desired glypican 3 antibody can be obtained from the infected cells of *Lemna minor* (Cox K. M. et al., Nat. Biotechnol. 2006 December; 24(12):1591-1597).

The antibody thus obtained may be isolated from the inside or outside (such as the medium and milk) of host cells, and purified as a substantially pure and homogenous antibody. Methods used for separating and purifying an antibody are not limited, and methods used in standard polypeptide purification may be applied. Antibodies may be isolated and purified by appropriately selecting or combining, for example, chromatographic columns, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

Chromatographies include, for example, affinity chromatography, ion exchange chromatography, hydrophobic chromatography, gel filtration chromatography, reverse-phase chromatography, and adsorption chromatography (Strategies for Protein Purification and Characterization: A Laboratory Course Manual. Ed Daniel R. Marshak et al., (1996) Cold Spring Harbor Laboratory Press). These chromatographies can be carried out using liquid phase chromatography such as HPLC and FPLC. Examples of columns for affinity chromatography include protein A columns and protein G columns. Examples of the columns that use protein A include Hyper D, POROS, and Sepharose F. F. (Pharmacia).

Another preferred embodiment of the present invention includes a method for producing an antibody with controlled plasma pharmacokinetics in the present invention, wherein the method comprises the steps of culturing the host cells of the present invention as described above and collecting the glypican 3 antibody from the cell culture.

The present invention provides pharmaceutical compositions comprising second-generation molecules that are more superior to the humanized anti-IL-6 receptor IgG1 antibody TOCILIZUMAB, and have been improved to exhibit enhanced drug efficacy and retention in plasma, and thus produce a prolonged therapeutic effect even when the frequency of administration is reduced. They have also been improved to have reduced immunogenicity and improved safety and physical properties, by modifying amino acid sequences of the variable and constant regions of TOCILIZUMAB; and methods for producing such pharmaceutical compositions. The present invention also provides antibody constant regions that are suitable for pharmaceuticals.

The present invention relates to anti-IL-6 receptor antibodies exhibiting superior antigen-binding activity, neutralizing activity, retention in plasma, stability, and/or homogeneity, and reduced immunogenicity risk.

Preferably, the anti-IL-6 receptor antibody is a humanized PM-1 antibody (TOCILIZUMAB). More specifically, the present invention provides humanized PM-1 antibodies with enhanced antigen-binding activity, humanized PM-1 antibodies with enhanced neutralizing activity, humanized PM-1 antibodies showing improved retention in plasma, humanized PM-1 antibodies with reduced immunogenicity risk, humanized PM-1 antibodies with improved stability, and humanized PM-1 antibodies with improved homogeneity, all of which have been achieved through amino acid substitution.

Humanized PM-1 antibodies bind to the human IL-6 receptor, and thus inhibit the binding between human IL-6 and the human IL-6 receptor. Herein, SEQ IDs in the Sequence Listing correspond to the amino acid sequences of humanized PM-1 antibodies shown below.

Heavy chain amino acid sequence: SEQ ID NO: 15
Light chain amino acid sequence: SEQ ID NO: 16
Heavy chain variable region amino acid sequence: SEQ ID NO: 17
Light chain variable region amino acid sequence: SEQ ID NO: 18
Heavy chain CDR1 (HCDR1) amino acid sequence: SEQ ID NO: 1
Heavy chain CDR2 (HCDR2) amino acid sequence: SEQ ID NO: 2
Heavy chain CDR3 (HCDR3) amino acid sequence: SEQ ID NO: 3
Heavy chain FR1 (HFR1) amino acid sequence: SEQ ID NO: 7
Heavy chain FR2 (HFR2) amino acid sequence: SEQ ID NO: 8
Heavy chain FR3 (HFR3) amino acid sequence: SEQ ID NO: 9
Heavy chain FR4 (HFR4) amino acid sequence: SEQ ID NO: 10
Light chain CDR1 (LCDR1) amino acid sequence: SEQ ID NO: 4
Light chain CDR2 (LCDR2) amino acid sequence: SEQ ID NO: 5
Light chain CDR3 (LCDR3) amino acid sequence: SEQ ID NO: 6
Light chain FR1 (LFR1) amino acid sequence: SEQ ID NO: 11
Light chain FR2 (LFR2) amino acid sequence: SEQ ID NO: 12
Light chain FR3 (LFR3) amino acid sequence: SEQ ID NO: 13
Light chain FR4 (LFR4) amino acid sequence: SEQ ID NO: 14

<Antibodies with Enhanced Affinity and Neutralizing Activity>

The present invention provides anti-human IL-6 receptor antibodies exhibiting strong human IL-6 receptor-binding and/or neutralizing activity. More specifically, the present invention provides the following antibodies of (a) to (y), and methods for producing the antibodies:

(a) An anti-human IL-6 receptor antibody comprising a heavy chain CDR1 in which Ser at position 1 in the amino acid sequence of SEQ ID NO: 1 (HCDR1) has been substituted with another amino acid.

The type of amino acid after substitution is not particularly limited; however, substitution to Trp (RD_68), Thr (RD_37), Asp (RD_8), Asn (RD_11), Arg (RD_31), Val (RD_32), Phe (RD_33), Ala (RD_34), Gln (RD_35), Tyr (RD_36), Leu (RD_38), His (RD_42), Glu (RD_45), or Cys (RD_46) is preferred.

A sequence resulting from the substitution of Trp for Ser at position 1 in the amino acid sequence of SEQ ID NO: 1 is shown in SEQ ID NO: 26.

A sequence resulting from the substitution of Thr for Ser at position 1 in the amino acid sequence of SEQ ID NO: 1 is shown in SEQ ID NO: 27.

A sequence resulting from the substitution of Asp for Ser at position 1 in the amino acid sequence of SEQ ID NO: 1 is shown in SEQ ID NO: 28.

A sequence resulting from the substitution of Asn for Ser at position 1 in the amino acid sequence of SEQ ID NO: 1 is shown in SEQ ID NO: 29.

A sequence resulting from the substitution of Arg for Ser at position 1 in the amino acid sequence of SEQ ID NO: 1 is shown in SEQ ID NO: 30.

A sequence resulting from the substitution of Val for Ser at position 1 in the amino acid sequence of SEQ ID NO: 1 is shown in SEQ ID NO: 31.

A sequence resulting from the substitution of Phe for Ser at position 1 in the amino acid sequence of SEQ ID NO: 1 is shown in SEQ ID NO: 32.

A sequence resulting from the substitution of Ala for Ser at position 1 in the amino acid sequence of SEQ ID NO: 1 is shown in SEQ ID NO: 33.

A sequence resulting from the substitution of Gln for Ser at position 1 in the amino acid sequence of SEQ ID NO: 1 is shown in SEQ ID NO: 34.

A sequence resulting from the substitution of Tyr for Ser at position 1 in the amino acid sequence of SEQ ID NO: 1 is shown in SEQ ID NO: 35.

A sequence resulting from the substitution of Leu for Ser at position 1 in the amino acid sequence of SEQ ID NO: 1 is shown in SEQ ID NO: 36.

A sequence resulting from the substitution of His for Ser at position 1 in the amino acid sequence of SEQ ID NO: 1 is shown in SEQ ID NO: 37.

A sequence resulting from the substitution of Glu for Ser at position 1 in the amino acid sequence of SEQ ID NO: 1 is shown in SEQ ID NO: 38.

A sequence resulting from the substitution of Cys for Ser at position 1 in the amino acid sequence of SEQ ID NO: 1 is shown in SEQ ID NO: 39.

(b) An anti-human IL-6 receptor antibody comprising a heavy chain CDR1 in which Trp at position 5 in the amino acid sequence of SEQ ID NO: 1 (HCDR1) has been substituted with another amino acid.

The type of amino acid after substitution is not particularly limited; however, substitution to Ile (RD_9) or Val (RD_30) is preferred.

A sequence resulting from the substitution of Ile for Trp at position 5 in the amino acid sequence of SEQ ID NO: 1 is shown in SEQ ID NO: 40.

A sequence resulting from the substitution of Val for Trp at position 5 in the amino acid sequence of SEQ ID NO: 1 is shown in SEQ ID NO: 41.

(c) An anti-human IL-6 receptor antibody comprising a heavy chain CDR2 in which Tyr at position 1 in the amino acid sequence of SEQ ID NO: 2 (HCDR2) has been substituted with another amino acid.

The type of amino acid after substitution is not particularly limited; however, substitution to Phe (RD_82) is preferred.

A sequence resulting from the substitution of Phe for Tyr at position 1 in the amino acid sequence of SEQ ID NO: 2 is shown in SEQ ID NO: 42.

(d) An anti-human IL-6 receptor antibody comprising a heavy chain CDR2 in which Thr at position 8 in the amino acid sequence of SEQ ID NO: 2 (HCDR2) has been substituted with another amino acid.

The type of amino acid after substitution is not particularly limited; however, substitution to Arg (RD_79) is preferred.

A sequence resulting from the substitution of Arg for Thr at position 8 in the amino acid sequence of SEQ ID NO: 2 is shown in SEQ ID NO: 43.

(e) An anti-human IL-6 receptor antibody comprising a heavy chain CDR2 in which Thr at position 9 in the amino acid sequence of SEQ ID NO: 2 (HCDR2) has been substituted with another amino acid.

The type of amino acid after substitution is not particularly limited; however, substitution to Ser (RD_12) or Asn (RD_61) is preferred.

A sequence resulting from the substitution of Ser for Thr at position 9 in the amino acid sequence of SEQ ID NO: 2 is shown in SEQ ID NO: 44.

A sequence resulting from the substitution of Asn for Thr at position 9 in the amino acid sequence of SEQ ID NO: 2 is shown in SEQ ID NO: 45.

(f) An anti-human IL-6 receptor antibody comprising a heavy chain CDR3 in which Ser at position 1 in the amino acid sequence of SEQ ID NO: 3 (HCDR3) has been substituted with another amino acid.

The type of amino acid after substitution is not particularly limited; however, substitution to Ile (RD_2), Val (RD_4), Thr (RD_80), or Leu (RD_5) is preferred.

A sequence resulting from the substitution of Ile for Ser at position 1 in the amino acid sequence of SEQ ID NO: 3 is shown in SEQ ID NO: 46.

A sequence resulting from the substitution of Val for Ser at position 1 in the amino acid sequence of SEQ ID NO: 3 is shown in SEQ ID NO: 47.

A sequence resulting from the substitution of Thr for Ser at position 1 in the amino acid sequence of SEQ ID NO: 3 is shown in SEQ ID NO: 48.

A sequence resulting from the substitution of Leu for Ser at position 1 in the amino acid sequence of SEQ ID NO: 3 is shown in SEQ ID NO: 49.

(g) An anti-human IL-6 receptor antibody comprising a heavy chain CDR3 in which Leu at position 2 in the amino acid sequence of SEQ ID NO: 3 (HCDR3) has been substituted with another amino acid.

The type of amino acid after substitution is not particularly limited; however, substitution to Thr (RD_84) is preferred.

A sequence resulting from the substitution of Thr for Leu at position 2 in the amino acid sequence of SEQ ID NO: 3 is shown in SEQ ID NO: 50.

(h) An anti-human IL-6 receptor antibody comprising a heavy chain CDR3 in which Thr at position 5 in the amino acid sequence of SEQ ID NO: 3 (HCDR3) has been substituted with another amino acid.

The type of amino acid after substitution is not particularly limited; however, substitution to Ala (RD_3) or Ile (RD_83) is preferred. In addition, the substitution of Ser (RDC_14H) for Thr at position 5 is also preferred.

A sequence resulting from the substitution of Ala for Thr at position 5 in the amino acid sequence of SEQ ID NO: 3 is shown in SEQ ID NO: 51.

A sequence resulting from the substitution of Ile for Thr at position 5 in the amino acid sequence of SEQ ID NO: 3 is shown in SEQ ID NO: 52.

A sequence resulting from the substitution of Ser for Thr at position 5 in the amino acid sequence of SEQ ID NO: 3 is shown in SEQ ID NO: 53.

(i) An anti-human IL-6 receptor antibody comprising a heavy chain CDR3 in which Ala at position 7 in the amino acid sequence of SEQ ID NO: 3 (HCDR3) has been substituted with another amino acid.

The type of amino acid after substitution is not particularly limited; however, substitution to Ser (RD_81) or Val (PF_3H) is preferred.

A sequence resulting from the substitution of Ser for Ala at position 7 in the amino acid sequence of SEQ ID NO: 3 is shown in SEQ ID NO: 54.

A sequence resulting from the substitution of Val for Ala at position 7 in the amino acid sequence of SEQ ID NO: 3 is shown in SEQ ID NO: 55.

(j) An anti-human IL-6 receptor antibody comprising a heavy chain CDR3 in which Met at position 8 in the amino acid sequence of SEQ ID NO: 3 (HCDR3) has been substituted with another amino acid.

The type of amino acid after substitution is not particularly limited; however, substitution to Leu (PF_4H) is preferred.

A sequence resulting from the substitution of Leu for Met at position 8 in the amino acid sequence of SEQ ID NO: 3 is shown in SEQ ID NO: 56.

(k) An anti-human IL-6 receptor antibody comprising a heavy chain CDR3 in which Ser at position 1 and Thr at position 5 in the amino acid sequence of SEQ ID NO: 3 (HCDR3) have been substituted with other amino acids.

The type of amino acid after substitution is not particularly limited; however, substitutions of Leu for Ser at position 1 and Ala for Thr at position 5 (RD_6) are preferred. Other preferred substitutions include: substitutions of Val for Ser at position 1 and Ala for Thr at position 5 (RDC_2H); substitutions of Ile for Ser at position 1 and Ala for Thr at position 5 (RDC_3H); substitutions of Thr for Ser at position 1 and Ala for Thr at position 5 (RDC_4H); substitutions of Val for Ser at position 1 and Ile for Thr at position 5 (RDC_5H); substitutions of Ile for Ser at position 1 and Ile for Thr at position 5 (RDC_6H); substitutions of Thr for Ser at position 1 and Ile for Thr at position 5 (RDC_7H); and substitutions of Leu for Ser at position 1 and Ile for Thr at position 5 (RDC_8H).

A sequence resulting from the substitutions of Leu for Ser at position 1 and Ala for Thr at position 5 in the amino acid sequence of SEQ ID NO: 3 is shown in SEQ ID NO: 57.

A sequence resulting from the substitutions of Val for Ser at position 1 and Ala for Thr at position 5 in the amino acid sequence of SEQ ID NO: 3 is shown in SEQ ID NO: 58.

A sequence resulting from the substitutions of Ile for Ser at position 1 and Ala for Thr at position 5 in the amino acid sequence of SEQ ID NO: 3 is shown in SEQ ID NO: 59.

A sequence resulting from the substitutions of Thr for Ser at position 1 and Ala for Thr at position 5 in the amino acid sequence of SEQ ID NO: 3 is shown in SEQ ID NO: 60.

A sequence resulting from the substitutions of Val for Ser at position 1 and Ile for Thr at position 5 in the amino acid sequence of SEQ ID NO: 3 is shown in SEQ ID NO: 61.

A sequence resulting from the substitutions of Ile for Ser at position 1 and Ile for Thr at position 5 in the amino acid sequence of SEQ ID NO: 3 is shown in SEQ ID NO: 62.

A sequence resulting from the substitutions of Thr for Ser at position 1 and Ile for Thr at position 5 in the amino acid sequence of SEQ ID NO: 3 is shown in SEQ ID NO: 63.

A sequence resulting from the substitutions of Leu for Ser at position 1 and Ile for Thr at position 5 in the amino acid sequence of SEQ ID NO: 3 is shown in SEQ ID NO: 64.

(1) An anti-human IL-6 receptor antibody comprising a heavy chain CDR3 in which Leu at position 2, Ala at position 7, and Met at position 8 in the amino acid sequence of SEQ ID NO: 3 (HCDR3) have been substituted with other amino acids.

The type of amino acid after substitution is not particularly limited; however, substitutions of Thr for Leu at position 2, Val for Ala at position 7, and Leu for Met at position 8 (RD_78) are preferred.

A sequence resulting from the substitutions of Thr for Leu at position 2, Val for Ala at position 7, and Leu for Met at position 8 in the amino acid sequence of SEQ ID NO: 3 is shown in SEQ ID NO: 65.

(m) An anti-human IL-6 receptor antibody comprising a light chain CDR1 in which Arg at position 1 in the amino acid sequence of SEQ ID NO: 4 (LCDR1) has been substituted with another amino acid.

The type of amino acid after substitution is not particularly limited; however, substitution to Phe (RD_18) is preferred.

A sequence resulting from the substitution of Phe for Arg at position 1 in the amino acid sequence of SEQ ID NO: 4 is shown in SEQ ID NO: 66.

(n) An anti-human IL-6 receptor antibody comprising a light chain CDR1 in which Gln at position 4 in the amino acid sequence of SEQ ID NO: 4 (LCDR1) has been substituted with another amino acid.

The type of amino acid after substitution is not particularly limited; however, substitution to Arg (RD_26) or Thr (RD_20) is preferred.

A sequence resulting from the substitution of Arg for Gln at position 4 in the amino acid sequence of SEQ ID NO: 4 is shown in SEQ ID NO: 67.

A sequence resulting from the substitution of Thr for Gln at position 4 in the amino acid sequence of SEQ ID NO: 4 is shown in SEQ ID NO: 68.

(o) An anti-human IL-6 receptor antibody comprising a light chain CDR1 in which Tyr at position 9 in the amino acid sequence of SEQ ID NO: 4 (LCDR1) has been substituted with another amino acid.

The type of amino acid after substitution is not particularly limited; however, substitution to Phe (RD_73) is preferred.

A sequence resulting from the substitution of Phe for Tyr at position 9 in the amino acid sequence of SEQ ID NO: 4 is shown in SEQ ID NO: 69.

(p) An anti-human IL-6 receptor antibody comprising a light chain CDR1 in which Asn at position 11 in the amino acid sequence of SEQ ID NO: 4 (LCDR1) has been substituted with another amino acid.

The type of amino acid after substitution is not particularly limited; however, substitution to Ser (RD_27) is preferred.

A sequence resulting from the substitution of Ser for Asn at position 11 in the amino acid sequence of SEQ ID NO: 4 is shown in SEQ ID NO: 70.

(q) An anti-human IL-6 receptor antibody comprising a light chain CDR2 in which Thr at position 2 in the amino acid sequence of SEQ ID NO: 5 (LCDR2) has been substituted with another amino acid.

The type of amino acid after substitution is not particularly limited; however, substitution to Gly is preferred.

A sequence resulting from the substitution of Gly for Thr at position 2 in the amino acid sequence of SEQ ID NO: 5 is shown in SEQ ID NO: 71.

(r) An anti-human IL-6 receptor antibody comprising a light chain CDR3 in which Gln at position 1 in the amino acid sequence of SEQ ID NO: 6 (LCDR3) has been substituted with another amino acid.

The type of amino acid after substitution is not particularly limited; however substitution to Gly (RD_28), Asn (RD_29), or Ser (RDC_15L) is preferred.

A sequence resulting from the substitution of Gly for Gln at position 1 in the amino acid sequence of SEQ ID NO: 6 is shown in SEQ ID NO: 72.

A sequence resulting from the substitution of Asn for Gln at position 1 in the amino acid sequence of SEQ ID NO: 6 is shown in SEQ ID NO: 73.

A sequence resulting from the substitution of Ser for Gln at position 1 in the amino acid sequence of SEQ ID NO: 6 is shown in SEQ ID NO: 74.

(s) An anti-human IL-6 receptor antibody comprising a light chain CDR3 in which Gly at position 3 in the amino acid sequence of SEQ ID NO: 6 has been substituted with another amino acid.

The type of amino acid after substitution is not particularly limited; however, substitution to Ser is preferred.

A sequence resulting from the substitution of Ser for Gly at position 3 in the amino acid sequence of SEQ ID NO: 6 is shown in SEQ ID NO: 75.

(t) An anti-human IL-6 receptor antibody comprising a light chain CDR1 in which Tyr at position 9 in the amino acid sequence of SEQ ID NO: 4 (LCDR1) has been substituted with another amino acid, and a light chain CDR3 in which Gly at position 3 in the amino acid sequence of SEQ ID NO: 6 (LCDR3) has been substituted with another amino acid.

The type of amino acid after substitution is not particularly limited; however, Tyr at position 9 in the amino acid sequence of SEQ ID NO: 4 (LCDR1) is preferably substituted with Phe, while Gly at position 3 in the amino acid sequence of SEQ ID NO: 6 (LCDR3) is preferably substituted with Ser (RD_72).

(u) An anti-human IL-6 receptor antibody comprising a light chain CDR3 in which Thr at position 5 in the amino acid sequence of SEQ ID NO: 6 (LCDR3) has been substituted with another amino acid.

The type of amino acid after substitution is not particularly limited; however, substitution to Arg (RD_23) or Ser is preferred.

A sequence resulting from the substitution of Arg for Thr at position 5 in the amino acid sequence of SEQ ID NO: 6 is shown in SEQ ID NO: 76.

A sequence resulting from the substitution of Ser for Thr at position 5 in the amino acid sequence of SEQ ID NO: 6 is shown in SEQ ID NO: 77.

(v) An anti-human IL-6 receptor antibody comprising a light chain CDR3 in which Gln at position 1 and Thr at position 5 in the amino acid sequence of SEQ ID NO: 6 (LCDR3) have been substituted with other amino acids.

The type of amino acid after substitution is not particularly limited; however, substitutions of Gly for Gln at position 1 and Ser for Thr at position 5 (RD_22) are preferred. Other preferred substitutions include substitutions of Gly for Gln at position 1 and Arg for Thr at position 5 (RDC_11L).

A sequence resulting from the substitutions of Gly for Gln at position 1 and Ser for Thr at position 5 in the amino acid sequence of SEQ ID NO: 6 is shown in SEQ ID NO: 78.

A sequence resulting from the substitutions of Gly for Gln at position 1 and Arg for Thr at position 5 in the amino acid sequence of SEQ ID NO: 6 is shown in SEQ ID NO: 79.

(w) An anti-human IL-6 receptor antibody comprising a heavy chain CDR2 in which Thr at position 9 in the amino acid sequence of SEQ ID NO: 2 (HCDR2) has been substituted with another amino acid, and a heavy chain CDR3 in which Ser at position 1 and Thr at position 5 in the amino acid sequence of SEQ ID NO: 3 (HCDR3) have been substituted with other amino acids.

Thr at position 9 in the amino acid sequence of SEQ ID NO: 2 (HCDR2) is preferably replaced with Asn. Furthermore, preferred combinations of amino acids for substitutions of Ser at position 1 and Thr at position 5 in the amino acid sequence of SEQ ID NO: 3 (HCDR3) include: Leu and Ala (RDC_27H); Val and Ala (RDC_28H); Ile and Ala (RDC_30H); Thr and Ala (RDC_4H); Val and Ile (RDC_29H); Ile and Ile (RDC_32H); Thr and Ile (RDC_7H); and Leu and Ile (RDC_8H).

(x) An antibody that comprises a variable region comprising the heavy chain CDR3 of (k) and a variable region comprising the light chain CDR3 of (v).

(y) The antibody of (x), which further comprises the heavy chain CDR2 of (e).

The present invention provides antibodies comprising at least the amino acid substitution of any one of (a) to (y) described above and methods for producing the antibodies. Thus, the antibodies of the present invention can also comprise other amino acid substitutions in addition to the amino acid substitution of any one of (a) to (y) described above. Furthermore, the antibodies of the present invention also include antibodies comprising a combination of any amino acid substitutions of (a) to (y) described above. The amino acid substitutions of (a) to (y) described above include substitutions of the CDR amino acid sequences described above to other amino acids. Amino acid substitutions other than those of (a) to (y) described above include, for example, amino acid sequence substitutions, deletions, additions, and/or insertions in other CDR regions. Such substitutions also include amino acid sequence substitutions, deletions, additions, and/or insertions in the FR regions. Such substitutions further include substitutions, deletions, additions, and/or insertions in the constant regions.

Furthermore, the antibodies of the present invention also include antibodies in which a high affinity CDR discovered in the present invention is grafted into any framework other than a humanized PM-1 antibody. The antibodies of the present invention also include antibodies in which the loss of affinity as a result of grafting a high affinity CDR discovered in the present invention into any framework other than a humanized PM-1 antibody has been compensated by mutations introduced into the FR to restore the original affinity (see, for example, Curr. Opin. Biotechnol. 1994 August; 5(4):428-33), and antibodies in which the loss has been compensated by mutations introduced into the CDR region to restore the original affinity (see, for example, US 2006/0122377).

In the present invention, the amino acid substitution of any one of (a) to (y) described above is preferably introduced into a humanized PM-1 antibody. Humanized PM-1 antibodies introduced with the amino acid substitution of any one of (a) to (y) described above have strong IL-6 receptor-neutralizing activity. Humanized PM-1 antibodies introduced with the amino acid substitution of any one of (a) to (y) described above are effective as therapeutic agents for IL-6-associated inflammatory diseases such as rheumatoid arthritis.

Antibodies comprising the amino acid substitution of any one of (a) to (y) described above can also be referred to as, for example, (1) or (2) described below. An example of antibody comprising the substitution of (a) is described here; other antibodies comprising the substitution of any one of (b) to (y) can also be referred to in the same way.

(1) An antibody that comprises a heavy chain variable region comprising CDR1 comprising an amino acid sequence in which Ser at position 1 in the amino acid sequence of SEQ ID NO: 1 has been substituted with another amino acid (2) An antibody that comprises a heavy chain comprising CDR1 comprising an amino acid sequence in which Ser at position 1 in the amino acid sequence of SEQ ID NO: 1 has been substituted with another amino acid <Antibodies with Enhanced Binding Activity>

The present invention further provides anti-IL-6 receptor antibodies with strong IL-6 receptor-binding activity. Herein, "anti-IL-6 receptor antibodies with strong IL-6 receptor-binding activity" typically refers to antibodies whose affinity is measured to be 1 nM or less at 37° C. under physiological conditions, preferably 0.1 nM or less, and more preferably 0.04 nM or less. Such anti-IL-6 receptor antibodies with strong IL-6 receptor binding activity are assumed to have an enhanced activity of neutralizing the biological activity of the antigen.

There is no limitation on the type of amino acid substitutions introduced to the present invention's anti-IL-6 receptor antibodies with strong IL-6 receptor binding activity. Such amino acid substitutions include, for example, the above-described amino acid substitutions.

The type of IL-6 receptor is not particularly limited; however, human IL-6 receptor is preferred.

The binding activity can be determined by methods known to those skilled in the art, for example, using Biacore or such, based on surface plasmon resonance (SPR).

<Antibodies Having a CDR Sequence with Reduced Immunogenicity Risk>

The present invention also provides anti-IL-6 receptor antibodies with reduced immunogenicity, in particular, humanized PM-1 antibodies. The immunogenicity is assumed to be enhanced when the sequence of an antibody contains a T-cell epitope that binds to HLA. Thus, the immunogenicity risk for an antibody can be reduced by removing the T-cell epitope from the antibody sequence through sequence substitution.

The present invention provides light chain variable regions of humanized anti-human IL-6 receptor antibodies with reduced immunogenicity, in particular, those of humanized PM-1 antibodies, from which T-cell epitopes have been removed through substituting other amino acids in the antibody amino acid sequences, in particular, CDR sequences. The present invention also provides antibodies comprising such light chain variable regions.

More specifically, the present invention provides light chain CDR2 in which Thr at position 2 in the amino acid sequence of SEQ ID NO: 5 (LCDR2) has been substituted with another amino acid. The present invention also provides light chain variable regions comprising such light chain CDR2. The present invention also provides anti-IL-6 receptor antibodies comprising such light chain variable region. The amino acid sequence after substitution is not particularly limited; however, substitution to Gly is preferred. A sequence comprising the substitution of Gly for Thr at position 2 in the amino acid sequence of SEQ ID NO: 5 is shown in SEQ ID NO: 71. The amino acid substitution is preferably introduced into a light chain variable region of a humanized PM-1 antibody.

<FR and CDR of H53/L28>

The present invention also provides anti-human IL-6 receptor antibodies with improved plasma pharmacokinetic, increased stability, and/or reduced immunogenicity. The half-lives of IgGs sharing the same Fc domain in plasma have been found to be correlated to isoelectric points with a high correlation coefficient. Then, the present inventors tried modifying the isoelectric points of the variable regions of two antibodies against different antigens, and successfully controlled their half-lives in plasma without modifying their Fc domains irrespective of the antigen specificity. The rate of non-specific antibody uptake by endothelial cells is assumed to depend on the physicochemical Coulomb interaction between IgG and negatively charged cell surface. Lowering the isoelectric point of IgG impairs the Coulomb interaction, which reduces the non-specific uptake by endothelial cells, and as a result, the metabolism in endothelial cells is reduced. This can prolong the retention in plasma.

Specifically, the present invention provides anti-human IL-6 receptor antibodies with reduced isoelectric point and improved retention in plasma, by substituting amino acids in the amino acid sequence of an anti-IL-6 receptor antibody, in particular, a humanized PM-1 antibody. Specifically, the humanized PM-1 antibody is modified to reduce its isoelectric point by substituting other amino acids at H13 (amino acid at position 13 in SEQ ID NO: 7), H16 (amino acid at position 16 in SEQ ID NO: 7), H43 (amino acid at position 8 in SEQ ID NO: 8), H81 (amino acid at position 16 in SEQ ID NO: 9), H105 (amino acid at position 3 in SEQ ID NO: 10), L18 (amino acid at position 18 in SEQ ID NO: 11), L45 (amino acid at position 11 in SEQ ID NO: 12), L79 (amino acid at position 23 in SEQ ID NO: 13), L107 (amino acid at position 10 in SEQ ID NO: 14), H31 (amino acid at position 1 in SEQ ID NO: 1), L24 (amino acid at position 1 in SEQ ID NO: 4), and/or L53 (amino acid at position 4 in SEQ ID NO: 5), Kabat's numbering (Kabat E A et al., 1991 Sequences of Proteins of Immunological Interest. NIH). These substitutions can lower the isoelectric point of a humanized PM-1 antibody without affecting its binding activity and stability. Some amino acid residues originated from the mouse sequence remain unsubstituted in the humanized PM-1 antibody to maintain its binding activity even after humanization of the mouse sequence. More specifically, amino acids at H27 (amino acid at position 27 in SEQ ID NO: 7), H28 (amino acid at position 28 in SEQ ID NO: 7), H29 (amino acid at position 29 in SEQ ID NO: 7), H30 (amino acid at position 30 in SEQ ID NO: 7), and H71 in the humanized PM-1 antibody (positions are numbered according to Kabat's numbering system described above) are of the mouse sequence. HFR1 can be converted into a human sequence by substituting H13, H16, H23, and H30, which enables to produce an antibody whose immunogenicity risk is lower than that of the humanized PM-1 antibody. Furthermore, since the humanized PM-1 antibody is an antibody humanized by CDR grafting, its stability may be further improved. Antibodies can be stabilized, for example, by substituting hydrophilic amino acids for amino acid residues exposed on the surface of the antibody variable region. Alternatively, antibodies can also be stabilized by modifying the CDR sequence to a consensus sequence. The humanized PM-1 antibody can be stabilized by a substitution of Ile for Met at H69 (amino acid position 4 in SEQ ID NO: 9) (stabilization of the hydrophobic core), Ser for Leu at H70 (amino acid at position 5 in SEQ ID NO: 9) (conversion of the surface-exposed residue to a hydrophilic residue), Asn for Thr at H58 (amino acid at position 9 in SEQ ID NO: 2) (modification of the heavy chain CDR2 to a consensus sequence), Gly for Ser at H65 (amino acid at position 16 in SEQ ID NO: 2) (substitution of Gly in the β turn region and modification of the heavy chain CDR2 to a consensus sequence), or Ser for Thr at L93 (amino acid at position 5 in SEQ ID NO: 6) (conversion of the surface-exposed residue to a hydrophilic residue) (positions are numbered according to Kabat's numbering system described above). Alternatively, in silico-predicted T-cell epitopes can be removed by substituting Gly for Thr at L51 at position 2 in LCDR2 (SEQ ID NO: 5) described above, and this can reduce the immunogenicity risk without affecting the binding activity and stability. Anti-IL-6 receptor antibodies with improved stability and antibody pharmacokinetics in plasma, as well as reduced immunogenicity can be obtained by using these amino acid substitutions in combination.

Such antibodies include, for example, the antibodies of (1) to (37) below.

(1) An antibody that comprises a heavy chain variable region comprising FR1 in which Arg at position 13 in the amino acid sequence of SEQ ID NO: 7 has been substituted with another amino acid.

The type of amino acid after substitution is not particularly limited; however, substitution to Lys is preferred.

A sequence resulting from the substitution of Lys for Arg at position 13 in the amino acid sequence of SEQ ID NO: 7 is shown in SEQ ID NO: 80.

(2) An antibody that comprises a heavy chain variable region comprising FR1 in which Gln at position 16 in the amino acid sequence of SEQ ID NO: 7 has been substituted with another amino acid.

The type of amino acid after substitution is not particularly limited; however, substitution of Glu is preferred.

A sequence resulting from the substitution of Glu for Gln at position 16 in the amino acid sequence of SEQ ID NO: 7 is shown in SEQ ID NO: 81.

(3) An antibody that comprises a heavy chain variable region comprising FR1 in which Thr at position 23 in the amino acid sequence of SEQ ID NO: 7 has been substituted with another amino acid.

The type of amino acid after substitution is not particularly limited; however, substitution to Ala is preferred.

A sequence resulting from the substitution of Ala for Thr at position 23 in the amino acid sequence of SEQ ID NO: 7 is shown in SEQ ID NO: 82.

(4) An antibody that comprises a heavy chain variable region comprising FR1 in which Thr at position 30 in the amino acid sequence of SEQ ID NO: 7 has been substituted with another amino acid.

The type of amino acid after substitution is not particularly limited; however, substitution to Ser is preferred.

A sequence resulting from the substitution of Ser for Thr at position 30 in the amino acid sequence of SEQ ID NO: 7 is shown in SEQ ID NO: 83.

(5) An antibody that comprises a heavy chain variable region comprising FR1 in which Arg at position 13, Gln at position 16, Thr at position 23, and Thr at position 30 in the amino acid sequence of SEQ ID NO: 7 have been substituted with other amino acids.

The type of amino acid after substitution is not particularly limited; however, substitutions of Lys for Arg at position 13, Glu for Gln at position 16, Ala for Thr at position 23, and Ser for Thr at position 30 are preferred.

A sequence resulting from the substitutions of Lys for Arg at position 13, Glu for Gln at position 16, Ala for Thr at position 23, and Ser for Thr at position 30 in the amino acid sequence of SEQ ID NO: 7 is shown in SEQ ID NO: 84.

(6) An antibody that comprises a heavy chain variable region comprising FR2 in which Arg at position 8 in the amino acid sequence of SEQ ID NO: 8 has been substituted with another amino acid.

The type of amino acid after substitution is not particularly limited; however, substitution to Glu is preferred.

A sequence resulting from the substitution of Glu for Arg at position 8 in the amino acid sequence of SEQ ID NO: 8 is shown in SEQ ID NO: 85.

(7) An antibody that comprises a heavy chain variable region comprising FR3 in which Met at position 4 in the amino acid sequence of SEQ ID NO: 9 has been substituted with another amino acid.

The type of amino acid after substitution is not particularly limited; however, substitution to Ile is preferred.

A sequence resulting from the substitution of Ile for Met at position 4 in the amino acid sequence of SEQ ID NO: 9 is shown in SEQ ID NO: 86.

(8) An antibody that comprises a heavy chain variable region comprising FR3 in which Leu at position 5 in the amino acid sequence of SEQ ID NO: 9 has been substituted with another amino acid.

The type of amino acid after substitution is not particularly limited; however, substitution to Ser is preferred.

A sequence resulting from the substitution of Ser for Leu at position 5 in the amino acid sequence of SEQ ID NO: 9 is shown in SEQ ID NO: 87.

(9) An antibody that comprises a heavy chain variable region comprising FR3 in which Arg at position 16 in the amino acid sequence of SEQ ID NO: 9 has been substituted with another amino acid.

The type of amino acid after substitution is not particularly limited; however, substitution to Lys is preferred.

A sequence resulting from the substitution of Lys for Arg at position 16 in the amino acid sequence of SEQ ID NO: 9 is shown in SEQ ID NO: 88.

(10) An antibody that comprises a heavy chain variable region comprising FR3 in which Val at position 27 in the amino acid sequence of SEQ ID NO: 9 has been substituted with another amino acid.

The type of amino acid after substitution is not particularly limited; however, substitution to Ala is preferred.

A sequence resulting from the substitution of Ala for Val at position 27 in the amino acid sequence of SEQ ID NO: 9 is shown in SEQ ID NO: 89.

(11) An antibody that comprises a heavy chain variable region comprising FR3 in which Met at position 4, Leu at position 5, Arg at position 16, and Val at position 27 in the amino acid sequence of SEQ ID NO: 9 (HFR3) have been substituted with other amino acids.

The type of amino acid after substitution is not particularly limited; however, substitutions of Ile for Met at position 4, Ser for Leu at position 5, Lys for Arg at position 16, and Ala for Val at position 27 are preferred.

A sequence resulting from the substitutions of Ile for Met at position 4, Ser for Leu at position 5, Lys for Arg at position 16, and Ala for Val at position 27 in the amino acid sequence of SEQ ID NO: 9 is shown in SEQ ID NO: 90.

(12) An antibody that comprises a heavy chain variable region comprising FR4 in which Gln at position 3 in the amino acid sequence of SEQ ID NO: 10 (HFR4) has been substituted with another amino acid.

The type of amino acid after substitution is not particularly limited; however, substitution to Glu is preferred.

A sequence resulting from the substitution of Glu for Gln at position 3 in the amino acid sequence of SEQ ID NO: 10 is shown in SEQ ID NO: 91.

(13) An antibody that comprises a light chain variable region comprising FR1 in which Arg at position 18 in the amino acid sequence of SEQ ID NO: 11 (LFR1) has been substituted with another amino acid.

The type of amino acid after substitution is not particularly limited; however, substitution to Ser is preferred.

A sequence resulting from the substitution of Ser for Arg at position 18 in the amino acid sequence of SEQ ID NO: 11 is shown in SEQ ID NO: 92.

(14) An antibody that comprises a light chain variable region comprising FR2 in which Lys at position 11 in the amino acid sequence of SEQ ID NO: 12 (LFR2) has been substituted with another amino acid.

The type of amino acid after substitution is not particularly limited; however, substitution to Glu is preferred.

A sequence resulting from the substitution of Glu for Lys at position 11 in the amino acid sequence of SEQ ID NO: 12 is shown in SEQ ID NO: 93.

(15) An antibody that comprises a light chain variable region comprising FR3 in which Gln at position 23 in the amino acid sequence of SEQ ID NO: 13 has been substituted with another amino acid.

The type of amino acid after substitution is not particularly limited; however, substitution to Glu is preferred.

A sequence resulting from the substitution of Glu for Gln at position 23 in the amino acid sequence of SEQ ID NO: 13 is shown in SEQ ID NO: 94.

(16) An antibody that comprises a light chain variable region comprising FR3 in which Pro at position 24 in the amino acid sequence of SEQ ID NO: 13 has been substituted with another amino acid.

The type of amino acid after substitution is not particularly limited; however, substitution to Ala is preferred.

A sequence resulting from the substitution of Ala for Pro at position 24 in the amino acid sequence of SEQ ID NO: 13 is shown in SEQ ID NO: 95.

(17) An antibody that comprises a light chain variable region comprising FR3 in which Ile at position 27 in the amino acid sequence of SEQ ID NO: 13 has been substituted with another amino acid.

The type of amino acid after substitution is not particularly limited; however, substitution to Ala is preferred.

A sequence resulting from the substitution of Ala for Ile at position 27 in the amino acid sequence of SEQ ID NO: 13 is shown in SEQ ID NO: 96.

(18) An antibody that comprises a light chain variable region comprising FR3 in which Gln at position 23, Pro at position 24, and Ile at position 27 in the amino acid sequence of SEQ ID NO: 13 (LFR3) have been substituted with other amino acids.

The type of amino acid after substitution is not particularly limited; however, substitutions of Glu for Gln at position 23, Ala for Pro at position 24, and Ala for Ile at position 27 are preferred.

A sequence resulting from the substitutions of Glu for Gln at position 23, Ala for Pro at position 24, and Ala for Ile at position 27 in the amino acid sequence of SEQ ID NO: 13 is shown in SEQ ID NO: 97.

(19) An antibody that comprises a light chain variable region comprising FR4 in which Lys at position 10 in the amino acid sequence of SEQ ID NO: 14 (LFR4) has been substituted with another amino acid.

The type of amino acid after substitution is not particularly limited; however, substitution to Glu is preferred.

A sequence resulting from the substitution of Glu for Lys at position 10 in the amino acid sequence of SEQ ID NO: 14 is shown in SEQ ID NO: 98.

(20) An antibody that comprises a heavy chain variable region comprising FR4 in which Ser at position 5 in the amino acid sequence of SEQ ID NO: 10 (HFR4) has been substituted with another amino acid.

The type of amino acid after substitution is not particularly limited; however, substitution to Thr is preferred.

A sequence resulting from the substitution of Thr for Ser at position 5 in the amino acid sequence of SEQ ID NO: 10 is shown in SEQ ID NO: 132.

(21) An antibody that comprises a heavy chain variable region comprising FR4 in which Gln at position 3 and Ser at position 5 in the amino acid sequence of SEQ ID NO: 10 (HFR4) have been substituted with other amino acids.

The type of amino acid after substitution is not particularly limited; however, substitutions of Glu for Gln at position 3 and Thr for Ser at position 5 are preferred.

A sequence resulting from the substitutions of Glu for Gln at position 3 and Thr for Ser at position 5 in the amino acid sequence of SEQ ID NO: 10 is shown in SEQ ID NO: 133.

(22) An antibody that comprises a heavy chain variable region of a humanized PM-1 antibody comprising the amino acid substitutions of (5), (6), (11), and (21).

(23) An antibody that comprises a light chain variable region of a humanized PM-1 antibody comprising the amino acid substitutions of (13), (14), (18), and (19).

(24) An antibody that comprises the heavy chain variable region of (22) and the light chain variable region of (23).

(25) An antibody that comprises a heavy chain variable region comprising CDR1 in which Ser at position 1 in the amino acid sequence of SEQ ID NO: 1 (HCDR1) has been substituted with another amino acid.

The type of amino acid after substitution is not particularly limited; however, substitution of Asp is preferred.

A sequence resulting from the substitution of Asp for Ser at position 1 in the amino acid sequence of SEQ ID NO: 1 is shown in SEQ ID NO: 28.

(26) An antibody that comprises a heavy chain variable region comprising CDR2 in which Ser at position 16 in the amino acid sequence of SEQ ID NO: 2 has been substituted with another amino acid.

The type of amino acid after substitution is not particularly limited; however, substitution of Gly is preferred.

A sequence resulting from the substitution of Gly for Ser at position 16 in the amino acid sequence of SEQ ID NO: 2 is shown in SEQ ID NO: 99.

(27) An antibody that comprises a heavy chain variable region comprising CDR2 in which Thr at position 9 and Ser at position 16 in the amino acid sequence of SEQ ID NO: 2 (HCDR2) have been substituted with other amino acids.

The type of amino acid after substitution is not particularly limited; however, substitutions of Asn for Thr at position 9 and Gly for Ser at position 16 are preferred.

A sequence resulting from the substitutions of Asn for Thr at position 9 and Gly for Ser at position 16 in the amino acid sequence of SEQ ID NO: 2 is shown in SEQ ID NO: 100.

(28) An antibody that comprises a light chain variable region comprising CDR1 in which Arg at position 1 in the amino acid sequence of SEQ ID NO: 4 (LCDR1) has been substituted with another amino acid.

The type of amino acid after substitution is not particularly limited; however, substitution of Gln is preferred.

A sequence resulting from the substitution of Gln for Arg at position 1 in the amino acid sequence of SEQ ID NO: 4 is shown in SEQ ID NO: 101.

(29) An antibody that comprises a light chain variable region comprising CDR2 in which Arg at position 4 in the amino acid sequence of SEQ ID NO: 5 has been substituted with another amino acid.

The type of amino acid after substitution is not particularly limited; however, substitution to Glu is preferred.

A sequence resulting from the substitution of Glu for Arg at position 4 in the amino acid sequence of SEQ ID NO: 5 is shown in SEQ ID NO: 102.

(30) An antibody that comprises a light chain variable region comprising CDR2 in which Thr at position 2 and Arg at position 4 in the amino acid sequence of SEQ ID NO: 5 (LCDR2) have been substituted with other amino acids.

The type of amino acid after substitution is not particularly limited; however, substitutions of Gly for Thr at position 2 and Glu for Arg at position 4 are preferred.

A sequence resulting from the substitutions of Gly for Thr at position 2 and Glu for Arg at position 4 in the amino acid sequence of SEQ ID NO: 5 is shown in SEQ ID NO: 103.

(31) An antibody that comprises a light chain variable region comprising CDR3 in which Thr at position 5 in the amino acid sequence of SEQ ID NO: 6 (LCDR3) has been substituted with another amino acid.

The type of amino acid after substitution is not particularly limited; however, substitution to Ser is preferred.

A sequence resulting from the substitution of Ser for Thr at position 5 in the amino acid sequence of SEQ ID NO: 6 is shown in SEQ ID NO: 77.

(32) An antibody that comprises a heavy chain variable region comprising the amino acid substitutions of (25) and (27).
(33) An antibody that comprises a light chain variable region comprising the amino acid substitutions of (28), (30), and (31).
(34) An antibody that comprises the heavy chain variable region of (32) and the light chain variable region of (33).
(35) An antibody that comprises a heavy chain variable region comprising the amino acid sequence of SEQ ID NO: 104 (heavy chain variable region of H53/L28).
(36) An antibody that comprises a light chain variable region comprising the amino acid sequence of SEQ ID NO: 105 (light chain variable region of H53/L28).
(37) An antibody that comprises the heavy chain variable region of (35) and the light chain variable region of (36).

Any amino acid substitutions of (1) to (37) described above are preferably introduced into a humanized PM-1 antibody. The present invention provides antibodies comprising at least the amino acid substitution of any one of (1) to (37) described above and methods for producing those antibodies. Thus, the antibodies of the present invention also include antibodies comprising other amino acid substitutions in addition to the amino acid substitution of any one of (1) to (37) described above. The antibodies of the present invention also include antibodies comprising combinations of multiple amino acid substitutions of (1) to (37) described above. The amino acid substitutions of (1) to (37) described above include, for example, substitutions in the amino acid sequences of FR and CDR described above. Amino acid substitutions other than those of (1) to (37) described above include other substitutions, deletions, additions, and/or insertions in FR and CDR sequences than those described above. The amino acid substitutions also include substitutions, deletions, additions, and/or insertions in the amino acid sequences of constant regions.

Furthermore, in addition to those described above, amino acid modifications that result in a lower isoelectric point without loss of the activity of anti-IL-6 receptor antibody, include, for example, substitutions of Lys at position 15 and/or Ser at position 16 in the amino acid sequence of SEQ ID NO: 2 with other amino acids. The type of amino acid after substitution is not particularly limited; however, substitutions of Gln for Lys at position 15 and Asp for Ser at position 16 are preferred. A sequence comprising the substitutions of Gln for Lys at position 15 and Asp for Ser at position 16 in the amino acid sequence of SEQ ID NO: 2 is shown in SEQ ID NO: 121. Alternatively, such amino acid substitutions may also be introduced into the amino acid sequence of SEQ ID NO: 100. A sequence comprising the substitutions of Gln for Lys at position 15 and Asp for Gly at position 16 in the amino acid sequence of SEQ ID NO: 100 is shown in SEQ ID NO: 122. Thus, the present invention provides antibodies that comprise a heavy chain variable region comprising CDR2 in which Lys at position 15 and/or Ser at position 16 in the amino acid sequence of SEQ ID NO: 2 or 100 have been substituted with other amino acids.

Other modifications that result in a lower isoelectric point include substitution of Gln at position 4 in the amino acid sequence of SEQ ID NO: 4 has been substituted with another amino acid. The type of amino acid after substitution is not particularly limited; however, substitution to Glu is preferred. An amino acid sequence comprising the substitution of Glu for Gln at position 4 in the amino acid sequence of SEQ ID NO: 4 is shown in SEQ ID NO: 123. Alternatively, this amino acid substitution may also be introduced into the amino acid sequence of SEQ ID NO: 101. An amino acid sequence comprising the substitution of Glu for Gln at position 4 in the amino acid sequence of SEQ ID NO: 101 is shown in SEQ ID NO: 124. Thus, the present invention provides antibodies that comprise a light chain variable region comprising CDR1 in which Gln at position 4 in the amino acid sequence of SEQ ID NO: 4 or 101 has been substituted with another amino acid.

Other modifications that result in a lower isoelectric point include substitution of His at position 6 in the amino acid sequence of SEQ ID NO: 5 with another amino acid. The type of amino acid after substitution is not particularly limited; however, substitution to Glu is preferred. An amino acid sequence comprising the substitution of Glu for His at position 6 in the amino acid sequence of SEQ ID NO: 5 is shown in SEQ ID NO: 125. Alternatively, this amino acid substitution may also be introduced into the amino acid sequence of SEQ ID NO: 103. An amino acid sequence comprising the substitution of Glu for His at position 6 in the amino acid sequence of SEQ ID NO: 103 is shown in SEQ ID NO: 126. Thus, the present invention provides antibodies that comprise a light chain variable region comprising CDR2 in which His at position 6 in the amino acid sequence of SEQ ID NO: 5 or 103 has been substituted with another amino acid.

Furthermore, modifications that result in reduced immunogenicity risk include substitution of Val for Ala at position 27 (H89, Kabat's numbering) in the amino acid sequence of heavy chain FR3 of SEQ ID NO: 90. An amino acid sequence comprising the substitution of Val for Ala at position 27 in the amino acid sequence of SEQ ID NO: 90 is shown in SEQ ID NO: 127. Thus, the present invention provides antibodies that comprise a heavy chain variable region comprising FR3 in which Val has been substituted for Ala at position 27 in the amino acid sequence of SEQ ID NO: 90.

The only mouse sequence that remains in the amino acid sequences of heavy chain FR3 of SEQ ID NO: 9 and 90 is Arg at position 6 (H71, Kabat's numbering). Anti-human IL-6 receptor antibodies having a framework consisting entirely of human sequences can be produced by using as a FR3 sequence, the human sequence of human VH1 subclass (SEQ ID NO: 128) or human VH3 subclass (SEQ ID NO: 129) where Arg is conserved at H71. Thus, the present invention provides antibodies that comprise a heavy chain variable region comprising the FR3 of SEQ ID NO: 128 or 129.

Furthermore, modifications that improve stability include substitution of Ile for Ser at position 5 (H107, Kabat's numbering) in the amino acid sequence of heavy chain FR4 of SEQ ID NO: 10. An amino acid sequence comprising the substitution of Ile for Ser at position 5 in the amino acid sequence of SEQ ID NO: 10 is shown in SEQ ID NO: 130. Alternatively, this amino acid sequence may also be introduced into the amino acid sequence of SEQ ID NO: 91. An amino acid sequence comprising the substitution of Ile for Ser at position 5 in the amino acid sequence of SEQ ID NO: 91 is shown in SEQ ID NO: 131. Thus, the present invention provides antibodies that comprise a heavy chain variable region comprising FR4 in which Ile has been substituted for Ser at position 5 in the amino acid sequence of SEQ ID NO: 10 or 91.

Such amino acid substitutions are preferably introduced into the humanized PM-1 antibody, H53/L28 (an antibody comprising the heavy chain variable region of SEQ ID NO: 104 and the light chain variable region of SEQ ID NO: 105), or PF1 antibody (an antibody comprising the heavy chain variable region of SEQ ID NO: 22 and the light chain variable region of SEQ ID NO: 23). The present invention provides antibodies comprising at least such amino acid substitutions and methods for producing the antibodies. Thus, the antibodies of the present invention include antibodies comprising, in addition to such amino acid substitutions, the amino acid substitution of any one of (1) to (37) described above and/or other amino acid substitutions than those of (1) to (37) described above. Amino acid substitutions other than those of (1) to (37) described above include other substitutions, deletions, additions, and/or insertions in FR and CDR sequences than those described above. The amino acid substitutions also include substitutions, deletions, additions, and/or insertions in the amino acid sequences of constant regions.

<Anti-Human IL-6 Receptor Antibodies with Low Isoelectric Point>

The present invention also provides anti-IL-6 receptor antibodies with a low isoelectric point. The antibodies of the present invention with low isoelectric point include antibodies in which the measured isoelectric point of the whole antibody is low and antibodies in which the theoretical isoelectric point of the variable region (VH/VL) is low.

Herein, "anti-IL-6 receptor antibodies in which the measured isoelectric point of the whole antibody is low" typically refers to antibodies in which the measured isoelectric point is 7.5 or less, preferably 7.0 or less, and more preferably 6.0 or less. The measured isoelectric point can be determined by methods known to those skilled in the art, for example, non-denaturation gel isoelectric focusing or capillary isoelectric focusing.

Herein, "anti-IL-6 receptor antibodies in which the theoretical isoelectric point of the variable region is low" typically refers to antibodies in which the theoretical isoelectric point is 5.5 or less, preferably 5.0 or less, and more preferably 4.0 or less. The theoretical isoelectric point can be determined by methods known to those skilled in the art. For example, the theoretical isoelectric points of heavy chain variable region and light chain variable region of a variable region can be computed by using software such as GENETYX (GENETYX CORPORATION).

There is no limitation on the type of amino acid substitution to be introduced to obtain anti-IL-6 receptor antibodies of the present invention with low isoelectric point. Such amino acid substitutions include, for example, the amino acid substitutions described above. Such anti-IL-6 receptor antibodies with low isoelectric point are assumed to show prolonged retention in plasma.

The type of IL-6 receptor is not particularly limited; however, human IL-6 receptor is preferred.

<Anti-Human IL-6 Receptor Antibodies that are Stable at High Concentrations>

Furthermore, the present invention provides anti-IL-6 receptor antibodies that are stable at high concentrations.

Herein, "stable at high concentrations" means that the increase in the proportion of aggregates of anti-IL-6 receptor antibody ([peak area for aggregate in gel filtration chromatogram]/[total peak area in gel filtration chromatogram]×100) generated in a high-concentration antibody solution (100 mg/ml) at 25° C. in one month is 0.3% or less, preferably 0.2% or less, and more preferably 0.1% or less when the antibody is in a buffer of pH 6.5 to 7.0 properly selected for subcutaneous administration, for example, 20 mM histidine-HCl, 150 mM NaCl. The concentration of anti-IL-6 receptor antibody may be 100 mg/ml or higher, for example, 200 or 300 mg/ml.

There is no limitation on the anti-IL-6 receptor antibodies of the present invention that are stable at high concentrations. The antibodies can be prepared, for example, with the above-described amino acid substitutions or such.

The type of IL-6 receptor is not particularly limited; however, human IL-6 receptor is preferred.

The present invention also provides humanized PM-1 antibodies comprising any one of the amino acid substitutions of (1) to (37) described above and further comprising any of the amino acid substitutions of (a) to (y) described above to improve their binding activity and/or neutralizing activity. In an embodiment, such antibodies include those comprising a heavy chain variable region comprising the amino acid sequence of SEQ ID NO: 22 (PF1_H) and a light chain variable region comprising the amino acid sequence of SEQ ID NO: 23 (PF1_L) (PF1), but are not limited thereto.

Furthermore, the present invention provides anti-IL-6 receptor antibodies of any of the following:

(A) a heavy chain variable region that comprises CDR1 comprising the amino acid sequence of SEQ ID NO: 165 (CDR1 of VH5-M83), CDR2 comprising the amino acid sequence of SEQ ID NO: 166 (CDR2 of VH5-M83), and CDR3 comprising the amino acid sequence of SEQ ID NO: 167 (CDR3 of VH5-M83);

(B) a light chain variable region that comprises CDR1 comprising the amino acid sequence of SEQ ID NO: 101 (CDR1 of VL5), CDR2 comprising the amino acid sequence of SEQ ID NO: 168 (CDR2 of VL5), and CDR3 comprising the amino acid sequence of SEQ ID NO: 79 (CDR3 of VL5);

(C) an antibody that comprises the heavy chain variable region of (A) and the light chain variable region of (B);

(D) a heavy chain variable region that comprises CDR1 comprising the amino acid sequence of SEQ ID NO: 169 (CDR1 of VH3-M73), CDR2 comprising the amino acid sequence of SEQ ID NO: 170 (CDR2 of VH3-M73), and CDR3 comprising the amino acid sequence of SEQ ID NO: 171 (CDR3 of VH3-M73);

(E) a light chain variable region that comprises CDR1 comprising the amino acid sequence of SEQ ID NO: 172 (CDR1 of VL3), CDR2 comprising the amino acid sequence of SEQ ID NO: 173 (CDR2 of VL3), and CDR3 comprising the amino acid sequence of SEQ ID NO: 79 (CDR3 of VL3);

(F) an antibody that comprises the heavy chain variable region of (D) and the light chain variable region of (E);

(G) a heavy chain variable region that comprises CDR1 comprising the amino acid sequence of SEQ ID NO: 169 (CDR1 of VH4-M73), CDR2 comprising the amino acid sequence of SEQ ID NO: 174 (CDR2 of VH4-M73), and CDR3 comprising the amino acid sequence of SEQ ID NO: 171 (CDR3 of VH4-M73);

(H) a light chain variable region that comprises CDR1 comprising the amino acid sequence of SEQ ID NO: 175 (CDR1 of VL1), CDR2 comprising the amino acid sequence of SEQ ID NO: 173 (CDR2 of VL1), and CDR3 comprising the amino acid sequence of SEQ ID NO: 79 (CDR3 of VL1); and (I) an antibody that comprises the heavy chain variable region of (G) and the light chain variable region of (H).

Furthermore, the present invention provides anti-IL-6 receptor antibodies of any of the following:

(a) an antibody that comprises a heavy chain variable region comprising the amino acid sequence of SEQ ID NO: 159 (H96-IgG1 variable region);

(b) an antibody that comprises a heavy chain variable region in which at least one of amino acids of Trp at position 35, Tyr at position 51, Ser at position 63, Lys at position 65, Gly at position 66, Val at position 99, Ile at position 103, Tyr at position 108, Glu at position 111, and Thr at position 113 in the amino acid sequence of SEQ ID NO: 159 (H96-IgG1 variable region) has been substituted with another amino acid;

(c) an antibody that comprises a heavy chain variable region comprising an amino acid sequence in which Lys at position 65, Gly at position 66, Val at position 99, Ile at position 103, Glu at position 111, and Thr at position 113 in the amino acid sequence of SEQ ID NO: 159 (H96-IgG1 variable region) have been substituted with other amino acids;

(d) an antibody that comprises a heavy chain variable region comprising an amino acid sequence in which Trp at position 35, Tyr at position 51, Ser at position 63, Lys at position 65, Gly at position 66, Val at position 99, Ile at position 103, and Tyr at position 108 in the amino acid sequence of SEQ ID NO: 159 (H96-IgG1 variable region) have been substituted with other amino acids;

(e) an antibody that comprises a heavy chain variable region comprising the amino acid sequence of SEQ ID NO: 160 (F2H-IgG1 variable region);

(f) an antibody that comprises a heavy chain variable region comprising the amino acid sequence of SEQ ID NO: 161 (VH5-M83 variable region);

(g) an antibody that comprises a light chain variable region comprising an amino acid sequence in which Gln at position 27 and/or His at position 55 in the amino acid sequence of SEQ ID NO: 23 (PF1L) have been substituted with other amino acids;

(h) an antibody that comprises a light chain variable region comprising the amino acid sequence of SEQ ID NO: 162 (L39 variable region);

(i) an antibody that comprises a light chain variable region comprising the amino acid sequence of SEQ ID NO: 163 (VL5-kappa variable region);

(j) an antibody that comprises a heavy chain variable region comprising the amino acid sequence of SEQ ID NO: 176 (VH3-M73 variable region);

(k) an antibody that comprises a heavy chain variable region comprising the amino acid sequence of SEQ ID NO: 178 (VH4-M73 variable region);

(l) an antibody that comprises a light chain variable region comprising the amino acid sequence of SEQ ID NO: 177 (VL3-kappa variable region);

(m) an antibody that comprises a light chain variable region comprising the amino acid sequence of SEQ ID NO: 179 (VL1-kappa variable region);

(n) an antibody that comprises the heavy chain variable region of (e) and the light chain variable region of (h);

(o) an antibody that comprises the heavy chain variable region of (f) and the light chain variable region of (i) (combination of FV5-M83 variable regions);

(p) an antibody that comprises the heavy chain variable region of (j) and the light chain variable region of (1) (combination of FV4-M73 variable regions); and (q) an antibody that comprises the heavy chain variable region of (k) and the light chain variable region of (m) (combination of FV3-M73 variable regions).

The type of amino acid after substitution is not particularly limited in the amino acid substitution of the heavy chain variable regions of (a) to (d) above; however, substitutions of Val for Trp at position 35, Phe for Tyr at position 51, Thr for Ser at position 63, Gln for Lys at position 65, Asp for Gly at position 66, Leu for Val at position 99, Ala for Ile at position 103, Val for Tyr at position 108, Gln for Glu at position 111, Ile for Thr at position 113 are preferred. Alternatively, the type of amino acid after substitution is not particularly limited in the amino acid substitution of the light chain variable region of (g) above; however, substitutions of Glu for Gln at position 27 and Glu for His at position 55 are preferred. Amino acid substitutions, deletions, insertions, and/or additions other than the amino acid substitution described above may be included.

The antibody constant regions of the present invention are not particularly limited, and any constant regions may be used. For example, constant regions comprising a natural sequence such as IgG1, IgG2, and IgG4 and modified constant regions prepared by introducing amino acid substitutions, deletions, additions, and/or insertions into a constant region comprising a natural sequence can be used. The examples of such modified constant regions include the constant regions described below.

The examples of antibodies using the variable regions of the present invention mentioned above include:

(1) an antibody that comprises a heavy chain comprising the amino acid sequence of SEQ ID NO: 134 (H96-IgG1);

(2) an antibody that comprises a heavy chain comprising the amino acid sequence of SEQ ID NO: 135 (F2H-IgG1);

(3) an antibody that comprises a heavy chain comprising the amino acid sequence of SEQ ID NO: 137 (VH5-IgG1);

(4) an antibody that comprises a heavy chain comprising the amino acid sequence of SEQ ID NO: 139 (VH5-M83);

(5) an antibody that comprises a heavy chain comprising the amino acid sequence of SEQ ID NO: 136 (L39);

(6) an antibody that comprises a heavy chain comprising the amino acid sequence of SEQ ID NO: 138 (VL5-kappa);

(7) an antibody that comprises a heavy chain comprising the amino acid sequence of SEQ ID NO: 180 (VH3-M73);

(8) an antibody that comprises a heavy chain comprising the amino acid sequence of SEQ ID NO: 182 (VH4-M73);

(9) an antibody that comprises a light chain comprising the amino acid sequence of SEQ ID NO: 181 (VL3-kappa);

(10) an antibody that comprises a light chain comprising the amino acid sequence of SEQ ID NO: 183 (VL1-kappa);

(11) an antibody that comprises the heavy chain of (2) and the light chain of (5);

(12) an antibody that comprises the heavy chain of (3) and the light chain of (6);

(13) an antibody that comprises the heavy chain of (4) and the light chain of (6) (FV5-M83);

(14) an antibody that comprises the heavy chain of (7) and the light chain of (9) (FV4-M73);

(15) an antibody that comprises the heavy chain of (8) and the light chain of (10) (FV3-M73); and

(16) an antibody having an activity equivalent to that of any of the antibodies of (1) to (15).

Herein, "having equivalent activity" means that the antigen-binding activity and/or neutralizing activity are equivalent. "Equivalent activity" in the present invention does not necessarily mean completely identical activity, but may be, for example, 50% or more of the activity, preferably 70% or more, and more preferably 90% or more.

Furthermore, the present invention provides CDR and FR of any of the following:
(i) a heavy chain FR1 that comprises the amino acid sequence of SEQ ID NO: 84 (heavy chain FR1 of VH5);
(ii) a heavy chain FR1 that comprises the amino acid sequence of SEQ ID NO: 186 (heavy chain FR1 of VH3 and VH4);
(iii) a heavy chain FR2 that comprises the amino acid sequence of SEQ ID NO: 85 (heavy chain FR2 of VH3, VH4, and VH5);
(iv) a heavy chain FR3 that comprises the amino acid sequence of SEQ ID NO: 184 (heavy chain FR3 of VH3, VH4, and VH5);
(v) a heavy chain FR4 that comprises the amino acid sequence of SEQ ID NO: 133 (heavy chain FR4 of VH3, VH4, and VH5);
(vi) a light chain FR1 that comprises the amino acid sequence of SEQ ID NO: 92 (light chain FR1 of VL1, VL3, and VL5);
(vii) a light chain FR2 that comprises the amino acid sequence of SEQ ID NO: 93 (light chain FR2 of VL1, VL3, and VL5);
(viii) a light chain FR3 that comprises the amino acid sequence of SEQ ID NO: 97 (light chain FR3 of VL1, VL3, and VL5);
(ix) a light chain FR4 that comprises the amino acid sequence of SEQ ID NO: 98 (light chain FR4 of VL1, VL3, and VL5);
(x) a heavy chain CDR1 that comprises the amino acid sequence of SEQ ID NO: 169 (heavy chain CDR1 of VH3 and VH4);
(xi) a heavy chain CDR1 that comprises the amino acid sequence of SEQ ID NO: 165 (heavy chain CDR1 of VH5);
(xii) a heavy chain CDR2 that comprises the amino acid sequence of SEQ ID NO: 170 (heavy chain CDR2 of VH3);
(xiii) a heavy chain CDR2 that comprises the amino acid sequence of SEQ ID NO: 174 (heavy chain CDR2 of VH4);
(xiv) a heavy chain CDR2 that comprises the amino acid sequence of SEQ ID NO: 166 (heavy chain CDR2 of VH5);
(xv) a heavy chain CDR3 that comprises the amino acid sequence of SEQ ID NO: 171 (heavy chain CDR3 of VH3 and VH4);
(xvi) a heavy chain CDR3 that comprises the amino acid sequence of SEQ ID NO: 167 (heavy chain CDR3 of VH5);
(xvii) a light chain CDR1 that comprises the amino acid sequence of SEQ ID NO: 175 (light chain CDR1 of VL1);
(xviii) a light chain CDR1 that comprises the amino acid sequence of SEQ ID NO: 172 (light chain CDR1 of VL3);
(xix) a light chain CDR1 that comprises the amino acid sequence of SEQ ID NO: 101 (light chain CDR1 of VL5);
(xx) a light chain CDR2 that comprises the amino acid sequence of SEQ ID NO: 173 (light chain CDR2 of VL1 and VL3);
(xxi) a light chain CDR2 that comprises the amino acid sequence of SEQ ID NO: 168 (light chain CDR2 of VL5); and
(xxii) a light chain CDR3 that comprises the amino acid sequence of SEQ ID NO: 79 (light chain CDR3 of VL1, VL3, and VL5).

The antibodies of the present invention also include fragments and processed products of antibodies comprising any of the amino acid substitutions described above. Such antibody fragments include, for example, Fab, F(ab')2, Fv, single chain Fv (scFv) in which heavy and light chains are linked together via an appropriate linker, single domain heavy chain and single domain light chain (for example, Nat. Biotechnol. 2005 September; 23(9):1126-36), Unibody (WO2007/059782 A1), and SMIP (WO2007/014278 A2). The origin of antibodies is not particularly limited. The antibodies include human, mouse, rat, and rabbit antibodies. The antibodies of the present invention may be chimeric, humanized, completely humanized antibodies, or such.

Specifically, such antibody fragments are obtained by treating antibodies with an enzyme, for example, papain or pepsin, or by constructing genes to encode such antibody fragments, inserting them into expression vectors, and then expressing them in appropriate host cells (see, for example, Co, M. S. et al., J. Immunol. (1994) 152:2968-2976; Better, M. and Horwitz, A. H. Methods in Enzymology (1989) 178:476-496; Plückthun, A.; Skerra, A., Methods in Enzymology (1989) 178:497-515; Lamoyi, E., Methods in Enzymology (1989) 121:652-663; Rousseaux, J. et al., Methods in Enzymology (1989) 121:663-66; Bird, R. E. et al., TIBTECH (1991) 9:132-137).

scFv is obtained by linking variable regions of antibody heavy and light chains. In such scFv, the heavy chain variable region is linked to the light chain variable region via a linker, preferably a peptide linker (Huston, J. S. et al., Proc. Natl. Acad. Sci. USA (1988) 85:5879-5883). The heavy chain and light chain variable regions in an scFv may be derived from any of the antibodies described above. The peptide linker to link the variable regions includes, for example, arbitrary single chain peptides of 12 to 19 amino acid residues.

<Antibody Constant Regions>

The present invention also provides the antibody constant regions of (i) to (xxi) described below, which have been improved through amino acid substitution. The constant region refers to IgG1, IgG2, or IgG4 type constant region. The amino acid sequences of human IgG1, IgG2, and IgG4 constant regions are known (human IgG1 constant region, SEQ ID NO: 19; human IgG2 constant region, SEQ ID NO: 20; and human IgG4 constant region, SEQ ID NO: 21). The sequence of the human IgG4 constant region has been modified to improve the stability of the hinge region (Mol. Immunol. 1993 January; 30(1):105-8). The present invention also provides antibodies that comprise such an amino acid substitution-containing antibody constant region. The antibody constant regions are preferably human antibody constant regions.

The amino acid substitution-containing antibody constant regions of the present invention may comprise other amino acid substitutions or modifications as long as they comprise the amino acid substitution of any one of (i) to (xxi) described below. Therefore, IgG2 constant regions comprising the amino acid substitutions of the present invention in the IgG2 constant region comprising the amino acid sequence of SEQ ID NO: 20 include IgG2 constant regions that comprise one or more amino acid substitutions and/or modifications in the amino acid sequence of SEQ ID NO: 20 and further comprise the amino acid substitutions of the present invention, as well as IgG2 constant regions that comprise the amino acid substitutions of the present invention and further comprise one or more amino acid substitutions and/or modifications. The same applies to IgG1 constant regions comprising the amino acid sequence of SEQ ID NO: 19 and IgG4 constant regions comprising the amino acid sequence of SEQ ID NO: 21.

Furthermore, the sugar chain at position 297 in the EU numbering system (see sequences of proteins of immunological interest, NIH Publication No. 91-3242) may be of any sugar-chain structure, or there may not be any sugar chain linked at this site (for example, constant regions produced in host cells where glycosylation does not occur, such as *E. coli*).

(i) Improvement of the Stability of IgG2 Constant Region at Acidic Conditions

In an embodiment, the IgG2 constant region of the present invention comprising amino acid substitutions includes IgG2 constant regions in which Met at position 276 (position 397 in the EU numbering system) in the amino acid sequence of SEQ ID NO: 20 has been substituted with another amino acid. The type of amino acid after substitution is not particularly limited; however, substitution to Val is preferred. The antibody stability under acidic conditions can be improved by substituting Met at position 276 (position 397 in the EU numbering system) in the amino acid sequence of SEQ ID NO: 20 with another amino acid.

(ii) Improvement of the Heterogeneity of IgG2 Constant Region

In an embodiment, the IgG2 constant region of the present invention comprising amino acid substitutions includes IgG2 constant regions in which Cys at position 14 (position 131 in the EU numbering system), Arg at position 16 (position 133 in the EU numbering system), and Cys at position 102 (position 219 in the EU numbering system) in the amino acid sequence of SEQ ID NO: 20 have been substituted with other amino acids. The type of amino acid after substitution is not particularly limited; however, substitutions of Ser for Cys at position 14 (position 131 in the EU numbering system), Lys for Arg at position 16 (position 133 in the EU numbering system), and Ser for Cys at position 102 (position 219 in the EU numbering system) (IgG2-SKSC) are preferred.

These substitutions can reduce the heterogeneity originated from the hinge region of IgG2. The IgG2 constant regions of the present invention comprising amino acid substitutions include IgG2 constant regions comprising at least one of the three types of amino acid substitutions described above; however, the IgG2 constant regions preferably comprise substitutions of Cys at position 14 and Cys at position 102 with other amino acids or all three types of the amino acid substitutions described above.

(iii) Impairment of the Binding of IgG2 Constant Region to FcγR

In an embodiment, the present invention also provides IgG2 constant regions comprising an amino acid sequence in which Ala at position 209 (EU330), Pro at position 210 (EU331), and/or Thr at position 218 (EU339) of the amino acid sequence of SEQ ID NO: 20 have been substituted with Ser, Ser, and Ala, respectively. The substitutions for Ala at position 209 (EU330) and for Pro at position 210 (EU331) have already been reported to enable the impairment of the Fcγ receptor binding (Eur. J. Immunol. 1999 August; 29(8): 2613-24). From the perspective of immunogenicity risk, however, these modifications are not preferred because they result in generation of nonhuman derived peptides that can become T-cell epitopes. However, the Fcγ receptor binding of IgG2 can be reduced by substituting Ala for Thr at position 218 (EU339) at the same time, and the 9-12 amino acid peptides which can become T-cell epitopes are derived from human only.

The IgG2 constant regions of the present invention comprising amino acid substitutions comprise at least one of the three types of amino acid substitutions described above; however, the IgG2 constant regions preferably comprise all three types of the amino acid substitutions described above. In a preferred embodiment, the IgG2 constant regions of the present invention comprising amino acid substitutions include IgG2 constant regions comprising an amino acid sequence in which Ala at position 209 (EU330), Pro at position 210 (EU331), and Thr at position 218 (EU339) in the amino acid sequence of SEQ ID NO: 20 have been substituted with Ser, Ser, and Ala, respectively.

(iv) Improvement of the C-Terminal Heterogeneity of IgG2 Constant Region

The present invention provides IgG2 constant regions comprising an amino acid sequence in which Gly at position 325 (position 446 in the EU numbering system) and Lys at position 326 (position 447 in the EU numbering system) have been deleted in the amino acid sequence of SEQ ID NO: 20. The heterogeneity originated from the C terminus of antibody heavy chain can be reduced only when both of the amino acids are deleted.

(v) Improvement of the Retention in Plasma by Modifying IgG2 Constant Region

An embodiment of the IgG2 constant regions with amino acid substitutions of the present invention includes IgG2 constant regions in which His at position 147 (position 268 in the EU numbering system), Arg at position 234 (position 355 in the EU numbering system), and Gln at position 298 (position 419 in the EU numbering system) in the amino acid sequence of SEQ ID NO: 20 have been substituted with other amino acids. These amino acid substitutions enable to improve antibody retention in plasma. The type of amino acid after substitution is not particularly limited; however, substitutions of Gln for His at position 147 (position 268 in the EU numbering system), Gln for Arg at position 234 (position 355 in the EU numbering system), and Glu for Gln at position 298 (position 419 in the EU numbering system) are preferred. The IgG2 constant regions with amino acid substitutions of the present invention include IgG2 constant regions comprising at least one of the three types of the amino acid substitutions described above; however, the IgG2 constant regions preferably comprise all three types of the amino acid substitutions described above.

(vi) Improvement of the Stability of IgG4 Constant Region at Acidic Conditions

The present invention provides IgG4 constant regions comprising an amino acid sequence in which Arg at position 289 (position 409 in the EU numbering system) of the amino acid sequence of SEQ ID NO: 21 has been substituted with another amino acid. The type of amino acid after substitution is not particularly limited; however, substitution to Lys is preferred. The antibody stability under acidic conditions can be improved by substituting Arg at position 289 (position 409 in the EU numbering system) in the amino acid sequence of SEQ ID NO: 21 with another amino acid.

(vii) Improvement of the C-Terminal Heterogeneity of IgG4 Constant Region

The present invention provides IgG4 constant regions comprising an amino acid sequence in which Gly at position 326 (position 446 in the EU numbering system) and Lys at position 327 (position 447 in the EU numbering system) have been deleted in the amino acid sequence of SEQ ID NO: 21. The heterogeneity originated from the C terminus of antibody heavy chain can be reduced only when both of the amino acids are deleted.

(viii) Improvement of the C-Terminal Heterogeneity of IgG1 Constant Region

The present invention provides IgG1 constant regions comprising an amino acid sequence in which Gly at position 329 (position 446 in the EU numbering system) and Lys at position 330 (position 447 in the EU numbering system) have been deleted in the amino acid sequence of SEQ ID NO: 19. The heterogeneity originated from the C terminus of antibody heavy chain can be reduced only when both of the amino acids are deleted.

(ix)

The present invention provides IgG1 constant regions comprising an amino acid sequence in which Asn at position 317 (position 434 in the EU numbering system) in the amino acid sequence of SEQ ID NO: 19 has been substituted with another amino acid.

The type of amino acid after substitution is not particularly limited; however, substitution to Ala is preferred.

(x)

The present invention provides IgG2 constant regions comprising an amino acid sequence in which Ala at position 209 (position 330 in the EU numbering system), Pro at position 210 (position 331 in the EU numbering system), Thr at position 218 (position 339 in the EU numbering system), Met at position 276 (position 397 in the EU numbering system), Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21 (position 138 in the EU numbering system) in the amino acid sequence of SEQ ID NO: 20 have been substituted with other amino acids.

The type of amino acid after substitution is not particularly limited; however, substitutions of Ser for Ala at position 209, Ser for Pro at position 210, Ala for Thr at position 218, Val for Met at position 276, Ser for Cys at position 14, Lys for Arg at position 16, Ser for Cys at position 102, Gly for Glu at position 20, and Gly for Ser at position 21 are preferred.

(xi)

The present invention provides IgG2 constant regions comprising an amino acid sequence in which Ala at position 209 (position 330 in the EU numbering system), Pro at position 210 (position 331 in the EU numbering system), Thr at position 218 (position 339 in the EU numbering system), Met at position 276 (position 397 in the EU numbering system), Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21 (position 138 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 20.

The type of amino acid after substitution is not particularly limited; however, substitutions of Ser for Ala at position 209, Ser for Pro at position 210, Ala for Thr at position 218, Val for Met at position 276, Ser for Cys at position 14, Lys for Arg at position 16, Ser for Cys at position 102, Gly for Glu at position 20, and Gly for Ser at position 21 are preferred.

(xii)

The present invention provides IgG2 constant regions comprising an amino acid sequence in which Met at position 276 (position 397 in the EU numbering system), Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21 (position 138 in the EU numbering system) in the amino acid sequence of SEQ ID NO: 20 have been substituted with other amino acids.

The type of amino acid after substitution is not particularly limited; however, substitutions of Val for Met at position 276, Ser for Cys at position 14, Lys for Arg at position 16, Ser for Cys at position 102, Gly for Glu at position 20, and Gly for Ser at position 21 are preferred.

(xiii)

The present invention provides IgG2 constant regions comprising an amino acid sequence in which Met at position 276 (position 397 in the EU numbering system), Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21 (position 138 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 20.

The type of amino acid after substitution is not particularly limited; however, substitutions of Val for Met at position 276, Ser for Cys at position 14, Lys for Arg at position 16, Ser for Cys at position 102, Gly for Glu at position 20, and Gly for Ser at position 21 are preferred.

(xiv)

The present invention provides IgG2 constant regions comprising an amino acid sequence in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), and Gln at position 298 (position 419 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 20.

The type of amino acid after substitution is not particularly limited; however, substitutions of Ser for Cys at position 14, Lys for Arg at position 16, Ser for Cys at position 102, Gly for Glu at position 20, Gly for Ser at position 21, Gln for His at position 147, Gln for Arg at position 234, and Glu for Gln at position 298 are preferred.

(xv)

The present invention provides IgG2 constant regions comprising an amino acid sequence in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), Gln at position 298 (position 419 in the EU numbering system), and Asn at position 313 (position 434 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 20.

The type of amino acid after substitution is not particularly limited; however, substitutions of Ser for Cys at position 14, Lys for Arg at position 16, Ser for Cys at position 102, Gly for Glu at position 20, Gly for Ser at position 21, Gln for His at position 147, Gln for Arg at position 234, Glu for Gln at position 298, and Ala for Asn at position 313 are preferred.

(xvi)

The present invention provides IgG4 constant regions comprising an amino acid sequence in which Arg at position 289 (position 409 in the EU numbering system), Cys at position 14, Arg at position 16, Glu at position 20, Ser at position 21, Arg at position 97, Ser at position 100, Tyr at position 102, Gly at position 103, Pro at position 104, and Pro at position 105 (positions 131, 133, 137, 138, 214, 217, 219, 220, 221, and 222 in the EU numbering system, respectively), Glu at position 113, Phe at position 114, and Leu at position 115 (positions 233, 234, and 235 in the EU numbering system, respectively) have been substituted with other amino acids, and simultaneously Gly at position 116 (position 236 in the EU numbering system) has been deleted in the amino acid sequence of SEQ ID NO: 21.

The type of amino acid after substitution is not particularly limited; however, substitutions of Ser for Cys at position 14 (position 131 in the EU numbering system), Lys for Arg at position 16 (position 133 in the EU numbering system), Gly for Glu at position 20 (position 137 in the EU numbering system), Gly for Ser at position 21 (position 138 in the EU numbering system), Thr for Arg at position 97 (position 214 in the EU numbering system), Arg for Ser at position 100 (position 217 in the EU numbering system), Ser for Tyr at position 102 (position 219 in the EU numbering system), Cys for Gly at position 103 (position 220 in the EU numbering system), Val for Pro at position 104 (position 221 in the EU numbering system), Glu for Pro at position 105 (position 222 in the EU numbering system), Pro for Glu at position 113 (position 233 in the EU numbering system), Val for Phe at position 114 (position 234 in the EU numbering system), Ala for Leu at position 115 (position 235 in the EU numbering system), and Lys for Arg at position 289 (position 409 in the EU numbering system) are preferred.

(xvii)

The present invention provides IgG4 constant regions comprising an amino acid sequence in which Arg at position 289 (position 409 in the EU numbering system), Cys at position 14, Arg at position 16, Glu at position 20, Ser at position 21, Arg at position 97, Ser at position 100, Tyr at position 102, Gly at position 103, Pro at position 104, and Pro at position 105 (positions 131, 133, 137, 138, 214, 217, 219, 220, 221, and 222 in the EU numbering system, respectively), Glu at position 113, Phe at position 114, and Leu at position 115 (positions 233, 234, and 235 in the EU numbering system, respectively) have been substituted with other amino acids, and simultaneously Gly at position 116 (position 236 in the EU numbering system), Gly at position 326 (position 446 in the EU numbering system), and Lys at position 327 (position 447 in the EU numbering system) have been deleted in the amino acid sequence of SEQ ID NO: 21.

The type of amino acid after substitution is not particularly limited; however, substitutions of Ser for Cys at position 14 (position 131 in the EU numbering system), Lys for Arg at position 16 (position 133 in the EU numbering system), Gly for Glu at position 20 (position 137 in the EU numbering system), Gly for Ser at position 21 (position 138 in the EU numbering system), Thr for Arg at position 97 (position 214 in the EU numbering system), Arg for Ser at position 100 (position 217 in the EU numbering system), Ser for Tyr at position 102 (position 219 in the EU numbering system), Cys for Gly at position 103 (position 220 in the EU numbering system), Val for Pro at position 104 (position 221 in the EU numbering system), Glu for Pro at position 105 (position 222 in the EU numbering system), Pro for Glu at position 113 (position 233 in the EU numbering system), Val for Phe at position 114 (position 234 in the EU numbering system), Ala for Leu at position 115 (position 235 in the EU numbering system), and Lys for Arg at position 289 (position 409 in the EU numbering system) are preferred.

(xviii)

The present invention provides IgG1 constant regions comprising an amino acid sequence in which Asn at position 317 (position 434 in the EU numbering system) has been substituted with another amino acid, and simultaneously Gly at position 329 (position 446 in the EU numbering system) and Lys at position 330 (position 447 in the EU numbering system) have been deleted in the amino acid sequence of SEQ ID NO: 19.

The type of amino acid after substitution of Asn at position 317 (position 434 in the EU numbering system) is not particularly limited; however, substitution to Ala is preferred.

(xix)

Below is a preferred embodiment of IgG2 of the present invention, which has reduced heterogeneity in the hinge region and/or reduced Fcγ receptor-binding activity.

Antibodies comprising an IgG2 constant region comprising an amino acid sequence in which Ala at position 209, Pro at position 210, Thr at position 218, Cys at position 14, Arg at position 16, Cys at position 102, Glu at position 20, and Ser at position 21 in the amino acid sequence of SEQ ID NO: 20 have been substituted with other amino acids.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 191 (M86).

In another preferred embodiment, IgG2 constant regions of the present invention include IgG2 constant regions resulting from the deletion of Gly at position 325 and Lys at position 326 in the above-described IgG2 constant regions to reduce C-terminal heterogeneity. Such antibodies include, for example, IgG2 that comprises a constant region comprising the amino acid sequence of SEQ ID NO: 192 (M86ΔGK).

(xx)

Below is another preferred embodiment of the IgG2 constant regions of the present invention, which have reduced heterogeneity in the hinge region.

IgG2 constant regions comprising an amino acid sequence in which Cys at position 14, Arg at position 16, Cys at position 102, Glu at position 20, and Ser at position 21 in the amino acid sequence of SEQ ID NO: 20 have been substituted with other amino acids.

The type of amino acid after substitution is not particularly limited; however, substitutions of Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 193 (M40).

In another preferred embodiment, the IgG2 constant regions of the present invention include IgG2 constant regions further comprising the deletion of Gly at position 325 and Lys at position 326 in the above-described IgG2 constant regions. Such antibodies include, for example, IgG2 constant regions comprising the amino acid sequence of SEQ ID NO: 194 (M40ΔGK).

(xxi) M14ΔGK, M17ΔGK, M11ΔGK, M31ΔGK, M58, M73, M86ΔGK, and M40ΔGK

The present invention also provides an antibody constant region comprising the amino acid sequence of SEQ ID NO: 24 (M14ΔGK). The present invention also provides an antibody constant region comprising the amino acid sequence of SEQ ID NO: 116 (M17ΔGK). The present invention also provides an antibody constant region comprising the amino acid sequence of SEQ ID NO: 25 (M11ΔGK). The present invention further provides an antibody constant region comprising the amino acid sequence of SEQ ID NO: 118 (M31ΔGK). The present invention further provides an antibody constant region comprising the amino acid sequence of SEQ ID NO: 151 (M58). The present invention further provides an antibody constant region comprising the amino acid sequence of SEQ ID NO: 153 (M73). The present invention further provides an antibody constant region comprising the amino acid sequence of SEQ ID NO: 164 (M83). The present invention further provides an antibody constant region comprising the amino acid sequence of SEQ ID NO: 192 (M86ΔGK). The present invention further provides an antibody constant region comprising the amino acid sequence of SEQ ID NO: 194 (M40ΔGK). These antibody constant regions have been optimized to have reduced Fcγ receptor binding activity, reduced immunogenicity risk, improved stability under acidic conditions, reduced heterogeneity, improved retention in plasma, and/or higher stability in preparations in comparison with the IgG1 constant region.

The present invention provides antibodies comprising the antibody constant region of any one of (i) to (xxi) described above. There is no limitation on the type of antigen and origin of antibody, as long as the antibodies comprise an antibody constant region described above. The preferred antibodies include, for example, antibodies that bind to IL-6 receptor. Alternatively, the preferred antibodies include, for example, humanized antibodies. Such antibodies include, for example, antibodies comprising the variable region of humanized PM-1 antibody. Such a variable region of humanized PM-1 antibody may comprise any of the above-described amino acid substitutions, or other amino acid substitutions, deletions, additions, and/or insertions. Specifically, the substitutions include, for example, modifications that improve the affinity of (a) to (y) described above; modifications that lower the isoelectric point of (i) to (viii) described above, modifications that improve the stability of (α) to (ξ) described below; and modifications that reduce immunogenicity, but are not limited thereto.

In one embodiment, such antibodies include antibodies that comprise a heavy chain variable region comprising the amino acid sequence of SEQ ID NO: 113 (PF_1+M14ΔGK) and a light chain variable region comprising the amino acid sequence of SEQ ID NO: 23 (PF1_L) (the light chain constant region may be kappa or lambda, or a modified form thereof) (PF1), but are not limited thereto.

Alternatively, the antibody constant regions described above and/or antibody molecules comprising an antibody constant region described above can be linked as a form of Fc fusion molecule to antibody-like binding molecule (scaffold molecules), bioactive peptides, binding peptides, or such.

The antibodies of the present invention can also be obtained by, for example, the following methods in addition to those described in the Examples. In one embodiment to obtain antibodies of the present invention, one or more amino acid residues are first substituted with amino acids of interest in at least one region selected from the group consisting of CDR, FR, and constant regions of an anti-IL-6 receptor antibody known to those skilled in the art. Methods for obtaining anti-IL-6 receptor antibodies known to those skilled in the art are not limited. Methods for substituting one or more amino acid residues with amino acids of interest in at least one region selected from the group consisting of the CDR, FR, and constant regions include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152:271-275; Zoller, M. J., and Smith, M. Oligonucleotide-directed mutagenesis of DNA fragments cloned into M13 vectors. Methods Enzymol. (1983) 100:468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12:9441-9456; Kramer W., and Fritz H. J. Oligonucleotide-directed construction of mutations via gapped duplex DNA Methods. Enzymol. (1987) 154:350-367; Kunkel, T. A. Rapid and efficient site-specific mutagenesis without phenotypic selection. Proc. Natl. Acad. Sci. USA (1985) 82:488-492). These methods can be used to substitute target amino acids in antibodies with amino acids of interest. Methods for substituting amino acids include library technologies such as framework shuffling (Mol. Immunol. 2007 April; 44(11): 3049-60) and CDR repair (US2006/0122377). Using these methods, amino acids can be substituted into appropriate frameworks and CDRs.

In another embodiment to obtain antibodies, an antibody that binds to IL-6 receptor is first prepared by methods known to those skilled in the art. When the prepared antibody is derived from a nonhuman animal, it can be humanized. Then, the prepared antibody is tested to assess whether it has neutralizing activity by using methods known to those skilled in the art. The binding activity and neutralizing activity of antibodies can be determined, for example, by the methods described in the Examples; however, such methods are not limited thereto. Next, one or more amino acid residues in at least one selected from the group consisting of CDR, FR, and constant regions of antibody are substituted with amino acids of interest.

More specifically, the present invention relates to methods for producing antibodies with improved neutralizing activity, binding activity, or stability, or reduced immunogenicity, which comprise the steps of:

(a) expressing a DNA encoding a heavy chain in which one or more amino acid residues in at least one region selected from the group consisting of CDR, FR, and constant regions are substituted with amino acids of interest, and a DNA encoding a light chain in which one or more amino acid residues in at least one region selected from the group consisting of CDR and FR regions are substituted with amino acids of interest; and (b) collecting the expression products of step (a).

The first step of the production methods of the present invention is expressing a DNA encoding a mutant anti-IL-6 receptor antibody heavy chain in which one or more amino acid residues in at least one region selected from the group consisting of CDR, FR, and constant regions are substituted with amino acids of interest, and a DNA encoding an anti-IL-6 receptor antibody light chain in which one or more amino acid residues in at least one region selected from the group consisting of CDR and FR regions are substituted with amino acids of interest. A DNA encoding a heavy chain in which one or more amino acid residues in at least one region selected from the group consisting of CDR, FR, and constant regions are substituted with amino acids of interest can be prepared, for example, by obtaining a DNA encoding the CDR, FR, or constant region of a wild type heavy chain, and introducing an appropriate substitution so that a codon encoding a particular amino acid in at least one selected from the group consisting of the CDR, FR, and constant regions encodes an amino acid of interest. Furthermore, a DNA encoding a light chain in which one or more amino acid residues in at least one selected from the group consisting of CDR and FR regions are substituted with amino acids of interest can be prepared, for example, by obtaining a DNA encoding the CDR and/or FR regions of a wild type light chain and introducing an appropriate substitution so that a codon encoding a particular amino acid in the CDR and/or FR regions encodes an amino acid of interest.

Alternatively, a DNA encoding a heavy chain in which one or more amino acid residues in at least one selected from the group consisting of CDR, FR, and constant regions are substituted with amino acids of interest can also be prepared by designing and then chemically synthesizing a DNA encoding a protein in which one or more amino acid residues in at least one selected from the group consisting of CDR, FR, and constant regions of the wild type heavy chain are substituted with amino acids of interest. Furthermore, a DNA encoding a light chain in which one or more amino acid residues in the CDR and/or FR regions are substituted with amino acids of interest can also be prepared by designing and then chemically synthesizing a DNA encoding a protein in which one or more amino acid residues in the CDR and/or FR regions of a wild type light chain are substituted with amino acids of interest.

The type of amino acid substitution includes the substitutions described herein, but is not limited thereto.

Alternatively, a DNA encoding a heavy chain in which one or more amino acid residues in at least one region selected from the group consisting of CDR, FR, and constant regions are substituted with amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc domain, but are not limited thereto. A DNA encoding a light chain can also be prepared as a combination of partial DNAs.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, a light chain expression vector is constructed by inserting a DNA encoding a light chain variable region into an expression vector along with a DNA encoding a light chain constant region. Alternatively, these heavy and light chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as CHO (Chinese hamster ovary) cells as well as microorganisms such as *E. coli*, yeast, and *Bacillus subtilis*, and plants and animals (Nature Biotechnology (2007) 25:563-565; Nature Biotechnology (1998) 16:773-777; Biochemical and Biophysical Research Communications (1999) 255:444-450; Nature Biotechnology (2005) 23:1159-1169; Journal of Virology (2001) 75:2803-2809; Biochemical and Biophysical Research Communications (2003) 308:94-100). The transformation can be preferably achieved by using electroporation, the lipofectin method (R. W. Malone et al., Proc. Natl. Acad. Sci. USA (1989) 86:6077; P. L. Felgner et al., Proc. Natl. Acad. Sci. USA (1987) 84:7413), calcium phosphate method (F. L. Graham & A. J. van der Eb, Virology (1973) 52:456-467), DEAE-Dextran method, and the like.

In the next step of antibody production, the expression products obtained in step (a) are collected. The expression products can be collected, for example, by culturing the transformants and then separating the products from the transformed cells or culture media. Separation and purification of antibodies can be achieved by an appropriate combination of methods such as centrifugation, ammonium sulfate fractionation, salting out, ultrafiltration, columns of 1q, FcRn, Protein A, and Protein G, affinity chromatography, ion exchange chromatography, and gel filtration chromatography.

Those skilled in the art can appropriately prepare the constant regions of the present invention according to the methods for preparing antibodies.

The present invention further relates to methods for enhancing the activity of an anti-IL-6 receptor antibody to bind or neutralize an IL-6 receptor, which comprise at least one step selected from the group consisting of:

(A) substituting Ser at position 1 in the amino acid sequence of SEQ ID NO: 1 (HCDR1) with another amino acid;

(B) substituting Trp at position 5 in the amino acid sequence of SEQ ID NO: 1 (HCDR1) with another amino acid;

(C) substituting Tyr at position 1 in the amino acid sequence of SEQ ID NO: 2 (HCDR2) with another amino acid;

(D) substituting Thr at position 8 in the amino acid sequence of SEQ ID NO: 2 (HCDR2) with another amino acid;

(E) substituting Thr at position 9 in the amino acid sequence of SEQ ID NO: 2 (HCDR2) with another amino acid;

(F) substituting Ser at position 1 in the amino acid sequence of SEQ ID NO: 3 (HCDR3) with another amino acid;

(G) substituting Leu at position 2 in the amino acid sequence of SEQ ID NO: 3 (HCDR3) with another amino acid;

(H) substituting Thr at position 5 in the amino acid sequence of SEQ ID NO: 3 (HCDR3) with another amino acid;

(I) substituting Ala at position 7 in the amino acid sequence of SEQ ID NO: 3 (HCDR3) with another amino acid;

(J) substituting Met at position 8 in the amino acid sequence of SEQ ID NO: 3 (HCDR3) with another amino acid;

(K) substituting Ser at position 1 and Thr at position 5 in the amino acid sequence of SEQ ID NO: 3 (HCDR3) with other amino acids;

(L) substituting Leu at position 2, Ala at position 7, and Met at position 8 in the amino acid sequence of SEQ ID NO: 3 (HCDR3) with other amino acids;
(M) substituting Arg at position 1 in the amino acid sequence of SEQ ID NO: 4 (LCDR1) with another amino acid;
(N) substituting Gln at position 4 in the amino acid sequence of SEQ ID NO: 4 (LCDR1) with another amino acid;
(O) substituting Tyr at position 9 in the amino acid sequence of SEQ ID NO: 4 (LCDR1) with another amino acid;
(P) substituting Asn at position 11 in the amino acid sequence of SEQ ID NO: 4 (LCDR1) with another amino acid;
(Q) substituting Thr at position 2 in the amino acid sequence of SEQ ID NO: 5 (LCDR2) with another amino acid;
(R) substituting Gln at position 1 in the amino acid sequence of SEQ ID NO: 6 (LCDR3) with another amino acid;
(S) substituting Gly at position 3 in the amino acid sequence of SEQ ID NO: 6 (LCDR3) with another amino acid;
(T) substituting Tyr at position 9 in the amino acid sequence of SEQ ID NO: 4 (LCDR1) and Gly at position 3 in the amino acid sequence of SEQ ID NO: 6 (LCDR3) with other amino acids;
(U) substituting Thr at position 5 in the amino acid sequence of SEQ ID NO: 6 (LCDR3) with another amino acid;
(V) substituting Gln at position 1 and Thr at position 5 in the amino acid sequence of SEQ ID NO: 6 (LCDR3) with other amino acids; and
(W) substituting Thr at position 9 in the amino acid sequence of SEQ ID NO: 2 (HCDR2), and Ser at position 1 and Thr at position 5 in the amino acid sequence of SEQ ID NO: 3 (HCDR3) with other amino acids; or
(X) a step comprising (V) and (W).

In (A) described above, the type of amino acid after substitution is not particularly limited as long as the affinity is improved; however, substitution to Trp, Thr, Asp, Asn, Arg, Val, Phe, Ala, Gln, Tyr, Leu, His, Glu, or Cys is preferred.

In (B) described above, the type of amino acid after substitution is not particularly limited as long as the affinity is improved; however, substitution to Ile or Val is preferred.

In (C) described above, the type of amino acid after substitution is not particularly limited as long as the affinity is improved; however, substitution to Phe is preferred.

In (D) described above, the type of amino acid after substitution is not particularly limited as long as the affinity is improved; however, substitution to Arg is preferred.

In (E) described above, the type of amino acid after substitution is not particularly limited as long as the affinity is improved; however, substitution to Ser or Asn is preferred.

In (F) described above, the type of amino acid after substitution is not particularly limited as long as the affinity is improved; however, substitution to Ile, Val, Thr, or Leu is preferred.

In (G) described above, the type of amino acid after substitution is not particularly limited as long as the affinity is improved; however, substitution to Thr is preferred.

In (H) described above, the type of amino acid after substitution is not particularly limited as long as the affinity is improved; however, substitution to Ala, Ile, or Ser is preferred. Other preferred substitutions include substitution of Ser for Thr at position 5.

In (I) described above, the type of amino acid after substitution is not particularly limited as long as the affinity is improved; however, substitution to Ser or Val is preferred.

In (J) described above, the type of amino acid after substitution is not particularly limited as long as the affinity is improved; however, substitution to Leu is preferred.

In (K) described above, the type of amino acid after substitution is not particularly limited as long as the affinity is improved; however, substitutions of Leu for Ser at position 1 and Ala for Thr at position 5 are preferred. Other preferred substitutions include those of Val for Ser at position 1 and Ala for Thr at position 5; Ile for Ser at position 1 and Ala for Thr at position 5; Thr for Ser at position 1 and Ala for Thr at position 5; Val for Ser at position 1 and Ile for Thr at position 5; Ile for Ser at position 1 and Ile for Thr at position 5; Thr for Ser at position 1 and Ile for Thr at position 5; and Leu for Ser at position 1 and Ile for Thr at position 5.

In (L) described above, the type of amino acid after substitution is not particularly limited as long as the affinity is improved; however, substitution of Thr for Leu at position 2, Val for Ala at position 7, and Leu for Met at position 8 are preferred.

In (M) described above, the type of amino acid after substitution is not particularly limited as long as the affinity is improved; however, substitution to Phe is preferred.

In (N) described above, the type of amino acid after substitution is not particularly limited as long as the affinity is improved; however, substitution to Arg or Thr is preferred.

In (O) described above, the type of amino acid after substitution is not particularly limited as long as the affinity is improved; however, substitution to Phe is preferred.

In (P) described above, the type of amino acid after substitution is not particularly limited as long as the affinity is improved; however, substitution to Ser is preferred.

In (Q) described above, the type of amino acid after substitution is not particularly limited as long as the affinity is improved; however, substitution to Gly is preferred.

In (R) described above, the type of amino acid after substitution is not particularly limited as long as the affinity is improved; however, substitution to Gly, Asn, or Ser is preferred.

In (S) described above, the type of amino acid after substitution is not particularly limited as long as the affinity is improved; however, substitution to Ser is preferred.

In (T) described above, the type of amino acid after substitution is not particularly limited as long as the affinity is improved; however, substitutions of Phe for Tyr in the amino acid sequence of SEQ ID NO: 4 (LCDR1) and Ser for Gly in the amino acid sequence of SEQ ID NO: 6 (LCDR3) are preferred.

In (U) described above, the type of amino acid after substitution is not particularly limited as long as the affinity is improved; however, substitution to Arg or Ser is preferred.

In (V) described above, the type of amino acid after substitution is not particularly limited as long as the affinity is improved; however, substitutions of Gly for Gln at position 1 and Ser for Thr at position 5 are preferred. Other preferred substitutions include those of Gly for Gln at position 1 and Arg for Thr at position 5.

In (W) described above, substitution of Asn for Thr at position 9 in the amino acid sequence of SEQ ID NO: 2 (HCDR2) is preferred. The preferred combinations of amino acids after substitution for Ser at position 1 and Thr at position 5 in the amino acid sequence of SEQ ID NO: 3 (HCDR3) include Leu and Ala, Val and Ala, Ile and Ala, Thr and Ala, Val and Ile, Ile and Ile, Thr and Ile, and Leu and Ile.

In the steps of (A) to (X) above, the method for amino acid substitution is not particularly limited. The substitution can be achieved, for example, by site-directed mutagenesis described above or a method described in the Examples. When an amino acid is substituted in a heavy chain variable region, the original amino acid sequence of the heavy chain variable region before substitution is preferably an amino acid sequence of the heavy chain variable region of a humanized PM-1 antibody. Alternatively, when an amino acid is substituted in a light chain variable region, the original amino acid sequence of the light chain variable region before substitution is preferably an amino acid sequence of the light chain variable region of a humanized PM-1 antibody. Furthermore, it is preferable to introduce the amino acid substitutions of steps (A) to (X) described above into the humanized PM-1 antibody.

The methods of the present invention for enhancing the binding or neutralizing activity of an anti-IL-6 receptor antibody comprise at least any one of the steps of (A) to (X) described above. Specifically, the methods of the present invention may comprise two or more of the steps of (A) to (X) described above. Furthermore, the methods of the present invention may comprise other steps (for example, amino acid substitutions, deletions, additions and/or insertions other than those of (A) to (X) described above) as long as they comprise any one of the steps of (A) to (X) described above. Furthermore, for example, FR may comprise amino acid substitutions, deletions, additions and/or insertions, and the constant region may comprise amino acid substitutions, deletions, additions and/or insertions. It is preferable to introduce the amino acid substitutions described above into the humanized PM-1 antibody.

<Methods for Reducing the Immunogenicity Risk of an Anti-IL-6 Receptor Antibody>

The present invention also relates to methods for reducing the immunogenicity of an anti-IL-6 receptor antibody, which comprise the step of substituting Gly for Thr at position 2 in the amino acid sequence of SEQ ID NO: 5 (LCDR2). The methods of the present invention for reducing the immunogenicity of an anti-IL-6 receptor antibody may comprise other steps of amino acid substitution, as long as they comprise the step of substituting Gly for Thr at position 2 in the amino acid sequence of SEQ ID NO: 5 (LCDR2). The method for amino acid substitution is not particularly limited. The substitution can be achieved, for example, by site-directed mutagenesis described above or a method described in the Examples.

It is preferable to introduce the amino acid substitutions described above into the humanized PM-1 antibody or a variant thereof comprising substitutions, deletions, and/or insertions.

<Methods for Lowering the Isoelectric Point of an Anti-IL-6 Receptor Antibody>

The present invention also relates to methods for lowering the isoelectric point of an anti-IL-6 receptor antibody, which comprise at least one step selected from the group consisting of:

(i) substituting Gln at position 16 in the amino acid sequence of SEQ ID NO: 7 (HFR1) with another amino acid;
(ii) substituting Arg at position 8 in the amino acid sequence of SEQ ID NO: 8 (HFR2) with another amino acid;
(iii) substituting Arg at position 16 in the amino acid sequence of SEQ ID NO: 9 (HFR3) with another amino acid;
(iv) substituting Gln at position 3 in the amino acid sequence of SEQ ID NO: 10 (HFR4) with another amino acid;
(v) substituting Arg at position 18 in the amino acid sequence of SEQ ID NO: 11 (LFR1) with another amino acid;
(vi) substituting Lys at position 11 in the amino acid sequence of SEQ ID NO: 12 (LFR2) with another amino acid;
(vii) substituting Gln at position 23 in the amino acid sequence of SEQ ID NO: 13 (LFR3) with another amino acid;
(viii) substituting Lys at position 10 in the amino acid sequence of SEQ ID NO: 14 (LFR4) with another amino acid;
(ix) substituting Ser at position 1 in the amino acid sequence of SEQ ID NO: 1 (HCDR1) with another amino acid;
(x) substituting Arg at position 1 in the amino acid sequence of SEQ ID NO: 4 (LCDR1) with another amino acid;
(xi) substituting Arg at position 4 in the amino acid sequence of SEQ ID NO: 5 (LCDR2) with another amino acid;
(xii) substituting Arg at position 13 in the amino acid sequence of SEQ ID NO: 7 (HFR1) with another amino acid;
(xiii) substituting Lys at position 15 and/or Ser at position 16 in the amino acid sequence of SEQ ID NO: 2 (HFR1) or 100 with other amino acids;
(xiv) substituting Gln at position 4 in the amino acid sequence of SEQ ID NO: 4 (LCDR1) or 101 with another amino acid; and
(xv) substituting His at position 6 in the amino acid sequence of SEQ ID NO: 5 (LCDR2) or 103 with another amino acid.

In (i) described above, the type of amino acid after substitution is not particularly limited as long as the isoelectric point is lowered; however, substitution to Glu is preferred.

In (ii) described above, the type of amino acid after substitution is not particularly limited as long as the isoelectric point is lowered; however, substitution to Glu is preferred.

In (iii) described above, the type of amino acid after substitution is not particularly limited as long as the isoelectric point is lowered; however, substitution to Lys is preferred.

In (iv) described above, the type of amino acid after substitution is not particularly limited as long as the isoelectric point is lowered; however, substitution to Glu is preferred.

In (v) described above, the type of amino acid after substitution is not particularly limited as long as the isoelectric point is lowered; however, substitution to Ser is preferred.

In (vi) described above, the type of amino acid after substitution is not particularly limited as long as the isoelectric point is lowered; however, substitution to Glu is preferred.

In (vii) described above, the type of amino acid after substitution is not particularly limited as long as the isoelectric point is lowered; however, substitution to Glu is preferred.

In (viii) described above, the type of amino acid after substitution is not particularly limited as long as the isoelectric point is lowered; however, substitution to Glu is preferred.

In (ix) described above, the type of amino acid after substitution is not particularly limited as long as the isoelectric point is lowered; however, substitution to Asp is preferred.

In (x) described above, the type of amino acid after substitution is not particularly limited as long as the isoelectric point is lowered; however, substitution to Gln is preferred.

In (xi) described above, the type of amino acid after substitution is not particularly limited as long as the isoelectric point is lowered; however, substitution to Glu is preferred.

In (xii) described above, the type of amino acid after substitution is not particularly limited as long as the isoelectric point is lowered; however, substitution to Lys is preferred.

In (xiii) described above, the type of amino acid after substitution is not particularly limited as long as the isoelectric point is lowered; however, substitutions to Gln for Lys at position 15 and Asp for Ser at position 16 are preferred.

In (xiv) described above, the type of amino acid after substitution is not particularly limited as long as the isoelectric point is lowered; however, substitution to Glu is preferred.

In (xv) described above, the type of amino acid after substitution is not particularly limited as long as the isoelectric point is lowered; however, substitution to Glu is preferred.

In the steps of (i) to (xv) described above, the method for amino acid substitution is not particularly limited. The substitution can be achieved, for example, by site-directed mutagenesis described above or a method described in the Examples. When an amino acid is substituted in a heavy chain variable region, the original amino acid sequence of the heavy chain variable region before substitution is preferably an amino acid sequence of the heavy chain variable region of a humanized PM-1 antibody. Alternatively, when an amino acid is substituted in a light chain variable region, the original amino acid sequence of the light chain variable region before substitution is preferably an amino acid sequence of the light chain variable region of a humanized PM-1 antibody. Furthermore, it is preferable to introduce the amino acid substitutions of the steps of (i) to (xv) described above into the humanized PM-1 antibody.

The methods of the present invention for lowering the isoelectric point of an anti-IL-6 receptor antibody comprise at least any one of the steps of (i) to (xv) described above. Specifically, the methods of the present invention may comprise two or more of the steps of (i) to (xv) described above. Furthermore, the methods of the present invention may comprise other steps (for example, amino acid substitutions, deletions, additions and/or insertions other than those of (i) to (xv) described above) as long as they comprise any one of the steps of (i) to (xv) described above. Furthermore, for example, the constant region may comprise amino acid substitutions, deletions, additions and/or insertions.

<Methods for Improving the Stability of an Anti-IL-6 Receptor Antibody>

The present invention also relates to methods for increasing the stability of an anti-IL-6 receptor antibody, which comprise at least one step selected from the group consisting of:

(α) substituting Met at position 4 in the amino acid sequence of SEQ ID NO: 9 (HFR3) with another amino acid;
(β) substituting Leu at position 5 in the amino acid sequence of SEQ ID NO: 9 (HFR3) with another amino acid;
(γ) substituting Thr at position 9 in the amino acid sequence of SEQ ID NO: 2 (HCDR2) with another amino acid;
(δ) substituting Thr at position 5 in the amino acid sequence of SEQ ID NO: 6 (LCDR3) with another amino acid;
(ε) substituting Ser at position 16 in the amino acid sequence of SEQ ID NO: 2 (HCDR2) with another amino acid; and
(ξ) substituting Ser at position 5 in the amino acid sequence of SEQ ID NO: 10 (FR4) with another amino acid.

In (α) described above, the type of amino acid after substitution is not particularly limited as long as the stability is improved; however, substitution to Ile is preferred.

In (β) described above, the type of amino acid after substitution is not particularly limited as long as the stability is improved; however, substitution to Ser is preferred.

In (γ) described above, the type of amino acid after substitution is not particularly limited as long as the stability is improved; however, substitution to Asn is preferred.

In (δ) described above, the type of amino acid after substitution is not particularly limited as long as the stability is improved; however, substitution to Ser is preferred.

In (ε) described above, the type of amino acid after substitution is not particularly limited as long as the stability is improved; however, substitution to Gly is preferred.

In (ξ) described above, the type of amino acid after substitution is not particularly limited as long as the stability is improved; however, substitution to Ile is preferred.

In the steps of (α) to (ξ) described above, the method for amino acid substitution is not particularly limited. The substitution can be achieved, for example, by site-directed mutagenesis described above or a method described in the Examples. When an amino acid is substituted in a heavy chain variable region, the original amino acid sequence of the heavy chain variable region before substitution is preferably an amino acid sequence of the heavy chain variable region of a humanized PM-1 antibody. Alternatively, when an amino acid is substituted in a light chain variable region, the original amino acid sequence of the light chain variable region before substitution is preferably an amino acid sequence of the light chain variable region of a humanized PM-1 antibody. Furthermore, it is preferable to introduce the amino acid substitutions of (α) to (ξ) described above into the humanized PM-1 antibody.

The methods of the present invention for improving the stability of an anti-IL-6 receptor antibody comprise at least any one of the steps of (α) to (ξ) described above. Specifically, the methods of the present invention may comprise two or more of the steps of (α) to (ξ) described above. Furthermore, the methods of the present invention may comprise other steps (for example, amino acid substitutions, deletions, additions and/or insertions other than those of (α) to (ξ) described above) as long as they comprise any one of the steps of (α) to (ξ) described above. Furthermore, for example, the constant region may comprise amino acid substitutions, deletions, additions and/or insertions.

<Methods for Reducing the Immunogenicity of an Anti-IL-6 Receptor Antibody>

The present invention also relates to methods for reducing the immunogenicity of an anti-IL-6 receptor antibody, in particular, a humanized PM-1 antibody, which comprise the step of substituting Lys for Arg at position 13, Glu for Gln at position 16, Ala for Thr at position 23, and/or Ser for Thr at position 30 in the amino acid sequence of SEQ ID NO: 7 (HFR1). The methods of the present invention for reducing the immunogenicity of an anti-IL-6 receptor antibody may comprise other steps of amino acid substitution, as long as they comprise the step of substituting Ser for Thr at position 30 in the amino acid sequence of SEQ ID NO: 7 (HFR1).

The present invention further relates to methods for reducing the immunogenicity of an anti-IL-6 receptor antibody, in particular, a humanized PM-1 antibody, which comprise the step of substituting Val for Ala at position 27 in the amino acid sequence of SEQ ID NO: 90 (HFR3). The methods of the present invention for reducing the immunogenicity of an anti-IL-6 receptor antibody may comprise other steps of amino acid substitution, as long as they comprise the step of substituting Val for Ala at position 27 in the amino acid sequence of SEQ ID NO: 90 (HFR3).

The method for amino acid substitution is not particularly limited. The substitution can be achieved, for example, by site-directed mutagenesis described above or a method described in the Examples.

The present invention further relates to methods for reducing antibody immunogenicity, which comprise converting the FR3 of an anti-IL-6 receptor antibody, in particular, a humanized PM-1 antibody, H53/L28, or PF1 antibody, into an FR3 comprising the amino acid sequence of SEQ ID NO: 128 or 129.

<Methods for Improving Antibody Stability Under Acidic Conditions>

The present invention also relates to methods for improving antibody stability under acidic conditions, which comprise the step of substituting Met at position 276 (position 397 in the EU numbering system) in the amino acid sequence of SEQ ID NO: 20 (IgG2) with another amino acid. The methods of the present invention for improving antibody stability under acidic conditions may comprise other steps of amino acid substitution, as long as they comprise the step of substituting Met at position 276 (position 397 in the EU numbering system) in the amino acid sequence of SEQ ID NO: 20 (IgG2) with another amino acid. The type of amino acid after substitution is not particularly limited; however, substitution to Val is preferred. The method for amino acid substitution is not particularly limited. The substitution can be achieved, for example, by site-directed mutagenesis described above or a method described in the Examples.

The kind of target antibody is not particularly limited; however, the antibody is preferably an anti-human IL-6 receptor antibody, more preferably a humanized PM-1 antibody or a variant thereof comprising substitutions, deletions, and/or insertions.

<Methods for Reducing the Heterogeneity Originated from the Hinge Region of IgG2 Constant Region>

The present invention also relates to methods for reducing antibody heterogeneity, which comprise the step of substituting Cys at position 14 (position 131 in the EU numbering system), Arg at position 16 (position 133 in the EU numbering system), and/or Cys at position 102 (position 219 in the EU numbering system) in the amino acid sequence of SEQ ID NO: 20 (IgG2) with other amino acids. The type of amino acid after substitution is not particularly limited; however, substitutions of Ser for Cys at position 14, Lys for Arg at position 16, and Ser for Cys at position 102 are preferred. The methods of the present invention for reducing antibody heterogeneity may comprise other steps of amino acid substitution, as long as they comprise the step of substituting Cys at position 14 (position 131 in the EU numbering system), Arg at position 16 (position 133 in the EU numbering system), and/or Cys at position 102 (position 219 in the EU numbering system) in the amino acid sequence of SEQ ID NO: 20 (IgG2). The method for amino acid substitution is not particularly limited. The substitutions can be achieved, for example, by site-directed mutagenesis described above or a method described in the Examples. In the amino acid substitution, all of the three amino acids described above may be substituted or one or two (for example, positions 14 and 102) of them may be substituted.

The kind of target antibody is not particularly limited; however, the antibody is preferably an anti-human IL-6 receptor antibody, more preferably a humanized PM-1 antibody or a variant thereof comprising substitutions, deletions, and/or insertions.

<Methods for Reducing the Heterogeneity Originated from Deletion of C-Terminal Amino Acids in an IgG2 Constant Region>

The present invention also relates to methods for reducing antibody heterogeneity, which comprise the step of deleting Gly at position 325 (position 446 in the EU numbering system) and Lys at position 326 (position 447 in the EU numbering system) in an IgG2 constant region comprising the amino acid sequence of SEQ ID NO: 20. The methods of the present invention for reducing antibody heterogeneity may comprise other steps of amino acid substitution, as long as they comprise the step of deleting Gly at position 325 (position 446 in the EU numbering system) and Lys at position 326 (position 447 in the EU numbering system) in an IgG2 constant region comprising the amino acid sequence of SEQ ID NO: 20. The method for amino acid substitution is not particularly limited. The substitution can be achieved, for example, by site-directed mutagenesis described above or a method described in the Examples.

The kind of target antibody is not particularly limited; however, the antibody is preferably an anti-human IL-6 receptor antibody, more preferably a humanized PM-1 antibody or a variant thereof comprising substitutions, deletions, and/or insertions.

<Methods for Reducing the FcγR Binding while Maintaining the Human Sequence in the IgG2 Constant Region>

The present invention also relates to methods for reducing the FcγR binding of an antibody, which comprise the step of substituting Ser for Ala at position 209 (EU330), Ser for Pro at position 210 (EU331), and Ala for Thr at position 218 (EU339) in an IgG2 constant region comprising the amino acid sequence of SEQ ID NO: 20. The methods of the present invention for reducing the FcγR binding of an antibody may comprise other steps of amino acid substitution, as long as they comprise the step of substituting Ser for Ala at position 209 (EU330), Ser for Pro at position 210 (EU331), and Ala for Thr at position 218 (EU339) in an IgG2 constant region comprising the amino acid sequence of SEQ ID NO: 20. The method for amino acid substitution is not particularly limited. The substitution can be achieved, for example, by site-directed mutagenesis described above or a method described in the Examples.

<Methods for Improving the Retention in Plasma by Substituting Amino Acids of IgG2 Constant Region>

The present invention also relates to methods for improving the retention in plasma of an antibody, which comprise the step of substituting His at position 147 (EU268), Arg at position 234 (EU355), and/or Gln at position 298 (EU419) in an IgG2 constant region comprising the amino acid sequence of SEQ ID NO: 20. The methods of the present invention for improving the retention in plasma of an antibody may comprise other steps of amino acid substitution, as long as they comprise the above-described step. The type of amino acid after substitution is not particularly limited; however, substitutions of Gln for His at position 147 (EU268), Gln for Arg at position 234 (EU355), and Glu for Gln at position 298 (EU419) are preferred.

The present invention also relates to methods for improving the retention in plasma of an antibody, which comprise the step of substituting Asn at position 313 (EU434) in an IgG2 constant region comprising the amino acid sequence of SEQ ID NO: 20 or 151 (M58). The type of amino acid after substitution is not particularly limited; however, substitution to Ala is preferred. The methods of the present invention for improving the retention in plasma of an antibody may comprise other steps of amino acid substitution, as long as they comprise the above-described step.

The kind of target antibody is not particularly limited; however, the antibody is preferably an anti-human IL-6 receptor antibody, more preferably a humanized PM-1 antibody or a variant thereof comprising substitutions, deletions, and/or insertions.

The present invention also relates to methods for reducing antibody heterogeneity originated from the hinge region of IgG2, methods for improving antibody stability under acidic conditions, methods for reducing antibody heterogeneity originated from C-terminus, and/or methods for reducing the FcγR binding of an antibody, all of which comprise in an IgG2 constant region comprising the amino acid sequence of SEQ ID NO: 20 (M14ΔGK), the steps of:

(a) substituting Ser for Ala at position 209 (position 330 in the EU numbering system) in the amino acid sequence of SEQ ID NO: 20;
(b) substituting Ser for Pro at position 210 (position 331 in the EU numbering system) in the amino acid sequence of SEQ ID NO: 20;
(c) substituting Ala for Thr at position 218 (position 339 in the EU numbering system) in the amino acid sequence of SEQ ID NO: 20;
(d) substituting Val for Met at position 276 (position 397 in the EU numbering system) in the amino acid sequence of SEQ ID NO: 20;
(e) substituting Ser for Cys at position 14 (position 131 in the EU numbering system) in the amino acid sequence of SEQ ID NO: 20;
(f) substituting Lys for Arg at position 16 (position 133 in the EU numbering system) in the amino acid sequence of SEQ ID NO: 20;
(g) substituting Ser for Cys at position 102 (position 219 in the EU numbering system) in the amino acid sequence of SEQ ID NO: 20;
(h) substituting Gly for Glu at position 20 (position 137 in the EU numbering system) in the amino acid sequence of SEQ ID NO: 20;
(i) substituting Gly for Ser at position 21 (position 138 in the EU numbering system) in the amino acid sequence of SEQ ID NO: 20; and
(j) deleting Gly at position 325 and Lys at position 326 (positions 446 and 447 in the EU numbering system, respectively) in the amino acid sequence of SEQ ID NO: 20.

The methods of the present invention may comprise other steps such as amino acid substitution and deletion, as long as they comprise the steps described above. The methods for amino acid substitution and deletion are not particularly limited. The substitution and deletion can be achieved, for example, by site-directed mutagenesis described above or a method described in the Examples.

The kind of target antibody is not particularly limited; however, it is preferably an anti-human IL-6 receptor antibody, more preferably a humanized PM-1 antibody or a variant thereof comprising substitutions, deletions, and/or insertions.

The present invention also relates to methods for reducing the heterogeneity originated from the hinge region of IgG2, methods for improving antibody stability under acidic conditions, and/or methods for reducing antibody heterogeneity originated from C-terminus, all of which comprise in an IgG2 constant region comprising the amino acid sequence of SEQ ID NO: 20 (M31ΔGK), the steps of:

(a) substituting Val for Met at position 276 (position 397 in the EU numbering system) in the amino acid sequence of SEQ ID NO: 20;
(b) substituting Ser for Cys at position 14 (position 131 in the EU numbering system) in the amino acid sequence of SEQ ID NO: 20;
(c) substituting Lys for Arg at position 16 (position 133 in the EU numbering system) in the amino acid sequence of SEQ ID NO: 20;
(d) substituting Ser for Cys at position 102 (position 219 in the EU numbering system) in the amino acid sequence of SEQ ID NO: 20;
(e) substituting Gly for Glu at position 20 (position 137 in the EU numbering system) in the amino acid sequence of SEQ ID NO: 20;
(f) substituting Gly for Ser at position 21 (position 138 in the EU numbering system) in the amino acid sequence of SEQ ID NO: 20; and
(g) deleting Gly at position 325 and Lys at position 326 (positions 446 and 447 in the EU numbering system, respectively) in the amino acid sequence of SEQ ID NO: 20.

The present invention also relates to methods for reducing antibody heterogeneity originated from the hinge region of IgG2, methods for improving antibody retention in plasma, and/or methods for reducing antibody heterogeneity originated from C-terminus, all of which comprise in an IgG2 constant region comprising the amino acid sequence of SEQ ID NO: 20 (M58), the steps of:

(a) substituting Ser for Cys at position 14 (position 131 in the EU numbering system) in the amino acid sequence of SEQ ID NO: 20;
(b) substituting Lys for Arg at position 16 (position 133 in the EU numbering system) in the amino acid sequence of SEQ ID NO: 20;
(c) substituting Ser for Cys at position 102 (position 219 in the EU numbering system) in the amino acid sequence of SEQ ID NO: 20;
(d) substituting Gly for Glu at position 20 (position 137 in the EU numbering system) in the amino acid sequence of SEQ ID NO: 20;
(e) substituting Gly for Ser at position 21 (position 138 in the EU numbering system) in the amino acid sequence of SEQ ID NO: 20;
(f) substituting Gln for His at position 147 (position 268 in the EU numbering system) in the amino acid sequence of SEQ ID NO: 20;
(g) substituting Gln for Arg at position 234 (position 355 in the EU numbering system) in the amino acid sequence of SEQ ID NO: 20;
(h) substituting Glu for Gln at position 298 (position 419 in the EU numbering system) in the amino acid sequence of SEQ ID NO: 20; and
(i) deleting Gly at position 325 and Lys at position 326 (positions 446 and 447 in the EU numbering system, respectively) in the amino acid sequence of SEQ ID NO: 20.

The present invention also relates to methods for reducing antibody heterogeneity originated from the hinge region of IgG2, methods for improving antibody retention in plasma, and/or methods for reducing antibody heterogeneity originated from C-terminus, all of which comprise in an IgG2 constant region comprising the amino acid sequence of SEQ ID NO: 20 (M73), the steps of:

(a) substituting Ser for Cys at position 14 (position 131 in the EU numbering system) in the amino acid sequence of SEQ ID NO: 20;
(b) substituting Lys for Arg at position 16 (position 133 in the EU numbering system) in the amino acid sequence of SEQ ID NO: 20;

(c) substituting Ser for Cys at position 102 (position 219 in the EU numbering system) in the amino acid sequence of SEQ ID NO: 20;
(d) substituting Gly for Glu at position 20 (position 137 in the EU numbering system) in the amino acid sequence of SEQ ID NO: 20;
(e) substituting Gly for Ser at position 21 (position 138 in the EU numbering system) in the amino acid sequence of SEQ ID NO: 20;
(f) substituting Gln for His at position 147 (position 268 in the EU numbering system) in the amino acid sequence of SEQ ID NO: 20;
(g) substituting Gln for Arg at position 234 (position 355 in the EU numbering system) in the amino acid sequence of SEQ ID NO: 20;
(h) substituting Glu for Gln at position 298 (position 419 in the EU numbering system) in the amino acid sequence of SEQ ID NO: 20;
(i) substituting Ala for Asn at position 313 (position 434 in the EU numbering system) in the amino acid sequence of SEQ ID NO: 20; and
(j) deleting Gly at position 325 and Lys at position 326 (positions 446 and 447 in the EU numbering system, respectively) in the amino acid sequence of SEQ ID NO: 20.

The present invention also relates to methods for reducing the heterogeneity originated from the hinge region of IgG2, methods for reducing antibody heterogeneity originated from C-terminus, and/or methods for reducing the FcγR binding of an antibody, all of which comprise, in an IgG2 constant region comprising the amino acid sequence of SEQ ID NO: 20 (M86ΔGK), the steps of:
(a) substituting Ala at position 209 (position 330 in the EU numbering system) in the amino acid sequence of SEQ ID NO: 20 with another amino acid;
(b) substituting Pro at position 210 (position 331 in the EU numbering system) in the amino acid sequence of SEQ ID NO: 20 with another amino acid;
(c) substituting Thr at position 218 (position 339 in the EU numbering system) in the amino acid sequence of SEQ ID NO: 20 with another amino acid;
(d) substituting Cys at position 14 (position 131 in the EU numbering system) in the amino acid sequence of SEQ ID NO: 20 with another amino acid;
(e) substituting Arg at position 16 (position 133 in the EU numbering system) in the amino acid sequence of SEQ ID NO: 20 with another amino acid;
(f) substituting Cys at position 102 (position 219 in the EU numbering system) in the amino acid sequence of SEQ ID NO: 20 with another amino acid;
(g) substituting Glu at position 20 (position 137 in the EU numbering system) in the amino acid sequence of SEQ ID NO: 20 with another amino acid;
(h) substituting Ser at position 21 (position 138 in the EU numbering system) in the amino acid sequence of SEQ ID NO: 20 with another amino acid; and
(i) deleting Gly at position 325 and Lys at position 326 (positions 446 and 447 in the EU numbering system, respectively) in the amino acid sequence of SEQ ID NO: 20.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The present invention further relates to methods for reducing the heterogeneity originated from the hinge region of IgG2 and/or methods for reducing antibody heterogeneity originated from C-terminus, which comprise in an IgG2 constant region comprising the amino acid sequence of SEQ ID NO: 20 (M40ΔGK), the steps of:
(a) substituting Cys at position 14 (position 131 in the EU numbering system) in the amino acid sequence of SEQ ID NO: 20 with another amino acid;
(b) substituting Arg at position 16 (position 133 in the EU numbering system) in the amino acid sequence of SEQ ID NO: 20 with another amino acid;
(c) substituting Cys at position 102 (position 219 in the EU numbering system) in the amino acid sequence of SEQ ID NO: 20 with another amino acid;
(d) substituting Glu at position 20 (position 137 in the EU numbering system) in the amino acid sequence of SEQ ID NO: 20 with another amino acid;
(e) substituting Ser at position 21 (position 138 in the EU numbering system) in the amino acid sequence of SEQ ID NO: 20 with another amino acid; and
(f) deleting Gly at position 325 and Lys at position 326 (positions 446 and 447 in the EU numbering system, respectively) in the amino acid sequence of SEQ ID NO: 20.

The type of amino acid after substitution is not particularly limited; however, substitutions of Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The methods of the present invention may comprise other steps such as amino acid substitution and deletion, as long as they comprise the steps described above. The methods for amino acid substitution and deletion are not particularly limited. The substitution and deletion can be achieved, for example, by site-directed mutagenesis described above or a method described in the Examples.

The kind of target antibody is not particularly limited; however, it is preferably an anti-human IL-6 receptor antibody, more preferably a humanized PM-1 antibody or a variant thereof comprising substitutions, deletions, and/or insertions.

<Methods for Improving the Stability of an IgG4 Constant Region Under Acidic Conditions>

The present invention also relates to methods for improving antibody stability under acidic conditions, which comprise the step of substituting Arg at position 289 (position 409 in the EU numbering system) of an IgG4 constant region comprising the amino acid sequence of SEQ ID NO: 21 (Mol. Immunol. 1993 January; 30(1):105-8) with another amino acid. The methods of the present invention for improving antibody stability under acidic conditions may comprise other steps of amino acid substitution, as long as they comprise the step of substituting Arg at position 289 (position 409 in the EU numbering system) in the amino acid sequence of SEQ ID NO: 21 (human IgG4 constant region) with another amino acid. The type of amino acid after substitution is not particularly limited; however, substitution to Lys is preferred. The method for amino acid substitution is not particularly limited. The substitution can be achieved, for example, by site-directed mutagenesis described above or a method described in the Examples.

The kind of target antibody is not particularly limited; however, the antibody is preferably an anti-human IL-6 receptor antibody, more preferably a humanized PM-1 antibody or a variant thereof comprising substitutions, deletions, and/or insertions.

<Methods for Reducing the Heterogeneity Originated from Deletion of C-Terminal Amino Acids in an IgG4 Constant Region>

The present invention also relates to methods for reducing the heterogeneity of an antibody, which comprise the step of deleting Gly at position 326 (position 446 in the EU numbering system) and Lys at position 327 (position 447 in the EU numbering system) in an IgG4 constant region comprising the amino acid sequence of SEQ ID NO: 21 (Mol. Immunol. 1993 January; 30(1):105-8). The methods of the present invention for reducing the heterogeneity may comprise other steps of amino acid substitution, as long as they comprise the step of deleting Lys at position 327 (position 447 in the EU numbering system) and/or Gly at position 326 (position 446 in the EU numbering system) in an IgG4 constant region comprising the amino acid sequence of SEQ ID NO: 21 (Mol. Immunol. 1993 January; 30(1):105-8). The method for amino acid substitution is not particularly limited. The substitution can be achieved, for example, by site-directed mutagenesis described above or a method described in the Examples.

The kind of target antibody is not particularly limited; however, the antibody is preferably an anti-human IL-6 receptor antibody, more preferably a humanized PM-1 antibody or a variant thereof comprising substitutions, deletions, and/or insertions.

The present invention also relates to methods for improving the stability under acidic conditions, methods for reducing the heterogeneity originated from C-terminus, and/or methods for reducing the FcγR binding of an antibody, all of which comprise in an IgG4 constant region comprising the amino acid sequence of SEQ ID NO: 21 (Mol. Immunol. 1993 January; 30(1):105-8) (M11ΔGK), the steps of:

(a) substituting Ser for Cys at position 14 (position 131 in the EU numbering system) in the amino acid sequence of SEQ ID NO: 21;
(b) substituting Lys for Arg at position 16 (position 133 in the EU numbering system) in the amino acid sequence of SEQ ID NO: 21;
(c) substituting Gly for Glu at position 20 (position 137 in the EU numbering system) in the amino acid sequence of SEQ ID NO: 21;
(d) substituting Gly for Ser at position 21 (position 138 in the EU numbering system) in the amino acid sequence of SEQ ID NO: 21;
(e) substituting Thr for Arg at position 97 (position 214 in the EU numbering system) in the amino acid sequence of SEQ ID NO: 21;
(f) substituting Arg for Ser at position 100 (position 217 in the EU numbering system) in the amino acid sequence of SEQ ID NO: 21;
(g) substituting Ser for Tyr at position 102 (position 219 in the EU numbering system) in the amino acid sequence of SEQ ID NO: 21;
(h) substituting Cys for Gly at position 103 (position 220 in the EU numbering system) in the amino acid sequence of SEQ ID NO: 21;
(i) substituting Val for Pro at position 104 (position 221 in the EU numbering system) in the amino acid sequence of SEQ ID NO: 21;
(j) substituting Glu for Pro at position 105 (position 222 in the EU numbering system) in the amino acid sequence of SEQ ID NO: 21;
(k) substituting Pro for Glu at position 113 (position 233 in the EU numbering system) in the amino acid sequence of SEQ ID NO: 21;
(l) substituting Val for Phe at position 114 (position 234 in the EU numbering system) in the amino acid sequence of SEQ ID NO: 21;
(m) substituting Ala for Leu at position 115 (position 235 in the EU numbering system) in the amino acid sequence of SEQ ID NO: 21;
(n) deleting Gly at position 116 (position 236 in the EU numbering system) in the amino acid sequence of SEQ ID NO: 21;
(o) substituting Lys for Arg at position 289 (position 409 in the EU numbering system) in the amino acid sequence of SEQ ID NO: 21; and
(p) deleting Gly at position 236 and Lys at position 237 (positions 446 and 447 in the EU numbering system, respectively) in the amino acid sequence of SEQ ID NO: 21.

The methods of the present invention may comprise other steps, such as amino acid substitution and deletion, as long as they comprise the steps described above. The method for amino acid substitution and deletion are not particularly limited. The substitution and deletion can be achieved, for example, by site-directed mutagenesis described above or a method described in the Examples.

The kind of target antibody is not particularly limited; however, the antibody is preferably an anti-human IL-6 receptor antibody, more preferably a humanized PM-1 antibody or a variant thereof comprising substitutions, deletions, and/or insertions.

<Methods for Reducing the Heterogeneity Originated from Deletion of C-Terminal Amino Acids in an IgG1 Constant Region>

The present invention also relates to methods for reducing antibody heterogeneity, which comprise the step of deleting Gly at position 329 (position 446 in the EU numbering system) and Lys at position 330 (position 447 in the EU numbering system) in an IgG1 constant region comprising the amino acid sequence of SEQ ID NO: 19. The methods of the present invention for reducing antibody heterogeneity may comprise other steps of amino acid substitutions, as long as they comprise the step of deleting Lys at position 330 (position 447 in the EU numbering system) and Gly at position 329 (position 446 in the EU numbering system) in an IgG1 constant region comprising the amino acid sequence of SEQ ID NO: 19. The method for amino acid substitution is not particularly limited. The substitution can be achieved, for example, by site-directed mutagenesis described above or a method described in the Examples.

<Methods for Improving the Retention in Plasma by Substituting Amino Acids of IgG1 Constant Region>

The present invention relates to methods for improving the antibody retention in plasma, which comprise the step of substituting Asn at position 317 (EU434) in an IgG1 constant region comprising the amino acid sequence of SEQ ID NO: 19 with another amino acid. The type of amino acid after substitution is not particularly limited; however, substitution to Ala is preferred. The methods of the present invention for improving the retention in plasma may comprise other steps of amino acid substitution, as long as they comprise the above-described step.

The present invention also relates to methods for improving the retention in plasma and/or methods for reducing the heterogeneity originated from C-terminus, both of which comprise, in an IgG1 constant region comprising the amino acid sequence of SEQ ID NO: 19 (M83), the steps of:
(a) substituting Ala for Asn at position 317 (EU 434) in the amino acid sequence of SEQ ID NO: 19; and
(b) deleting Lys at position 330 (position 447 in the EU numbering system) and Gly at position 329 (position 446 in the EU numbering system) in the amino acid sequence of SEQ ID NO: 19.

The kind of target antibody is not particularly limited; however, the antibody is preferably an anti-human IL-6 receptor antibody, more preferably a humanized PM-1 antibody or a variant thereof comprising substitutions, deletions, and/or insertions.

The constant regions of the present invention described above can be combined with any antibody variable regions, and preferably with variable regions derived from antibodies against human IL-6 receptor. Variable regions of antibodies against human IL-6 receptor include, for example, variable regions of a humanized PM-1 antibody. The variable regions of a humanized PM-1 antibody may not comprise any amino acid substitutions or may comprise substitutions such as those described above.

The present invention provides pharmaceutical compositions comprising an antibody of the present invention. The pharmaceutical compositions of the present invention are useful in treating diseases associated with IL-6, such as rheumatoid arthritis.

The pharmaceutical compositions of the present invention can be formulated, in addition to the antibodies, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dose of the pharmaceutical composition containing an antibody or a polynucleotide encoding an antibody can be selected, for example, from the range of 0.0001 to 1,000 mg per kg of body weight. Alternatively, the dose may be, for example, in the range of 0.001 to 100,000 mg/person. However, the dose is not limited to these values. The dose and method of administration vary depending on the patient's body weight, age, and symptoms, and can be appropriately selected by those skilled in the art.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Herein below, the present invention is specifically described with reference to the Examples, but it is not to be construed as being limited thereto.

[Example 1] Improvement of Antigen-Binding Activity Through CDR Modification Using Affinity Maturation Technology Preparation of SR344

A CHO cell line constitutively expressing a sequence of N-terminal $1^{st}$ to $344^{th}$ amino acids of soluble human IL-6R (hereinafter "SR344") reported in J. Biochem. (1990) 108: 673-676 (Yamasaki et al., Science (1988) 241:825-828 (GenBank #X12830)) was prepared.

SR344 was purified from the culture supernatant of SR344-expresssing CHO cells using three types of column chromatography: Blue Sepharose 6 FF column chromatography, affinity chromatography with an SR344-specific antibody-immobilized column, and gel filtration column chromatography.

The culture supernatant was directly loaded onto a Blue Sepharose 6 FF column (GE Healthcare Bio-Sciences) equilibrated with 20 mM Tris-HCl buffer (pH 8.0), and the non-adsorbed fraction was thoroughly washed off using the same buffer. Then, the column was washed with the same buffer containing 300 mM KCl. The adsorbed protein was then eluted using the same buffer in the presence of 300 mM KCl with a linear concentration gradient of 0 to 0.5 M KSCN. Fractions eluted with the KSCN concentration gradient were analyzed by Western blotting using an SR344-specific antibody, and fractions containing SR344 were collected.

The SR344-specific antibody-immobilized column was pre-equilibrated with Tris-buffered saline (TB S). The SR344 fraction obtained in the first step was concentrated by ultrafiltration using Amicon Ultra-15 (Millipore; molecular weight cut-off of 10 kDa), and diluted two fold with TBS before it was loaded onto the column. After the column was washed with TBS, the adsorbed protein was eluted with 100 mM glycine-HCl buffer (pH 2.5). The eluted fractions were neutralized by adding 1 M Tris (pH 8.1). The obtained fractions were analyzed by SDS-PAGE to collect SR344-containing fractions.

The fraction obtained in the second step was concentrated using Amicon Ultra-15 (molecular weight cut-off of 10 kDa) and loaded onto a Superdex 200 column (GE Healthcare Bio-Sciences) equilibrated with PBS. The fraction eluted as the major peak was used as the final purified sample of SR344.

Establishment of a Human Gp130-Expressing BaF3 Cell Line

A BaF3 cell line expressing human gp130 was established by the procedure described below, to obtain a cell line that proliferates in an IL-6-dependent manner.

A full-length human gp130 cDNA (Hibi et al., Cell (1990) 63:1149-1157 (GenBank #NM_002184)) was amplified by PCR and cloned into the expression vector pCOS2Zeo to construct pCOS2Zeo/gp130. pCOS2Zeo is an expression vector constructed by removing the DHFR gene expression region from pCHOI (Hirata et al., FEBS Letter (1994) 356:244-248) and inserting the expression region of the Zeocin resistance gene. The full-length human IL-6R cDNA was amplified by PCR and cloned into pcDNA3.1(+) (Invitrogen) to construct hIL-6R/pcDNA3.1(+).

10 µg of pCOS2Zeo/gp130 was mixed with BaF3 cells ($0.8 \times 10^7$ cells) suspended in PBS, and then pulsed at 0.33 kV and 950 µFD using Gene Pulser (Bio-Rad). The BaF3 cells having the gene introduced by electroporation were cultured for one whole day and night in RPMI 1640 medium (Invitrogen) supplemented with 0.2 ng/ml mouse interleukin-3 (Peprotech) and 10% FBS (HyClone), and selected by adding RPMI 1640 medium supplemented with 100 ng/ml human interleukin-6 (R&D systems), 100 ng/ml human interleukin-6 soluble receptor (R&D systems), and 10% FBS to establish a human gp130-expressing BaF3 cell line (hereinafter "BaF3/gp130"). This BaF/gp130 proliferates in the presence of human interleukin-6 (R&D systems) and SR344, and thus can be used to assess the growth inhibition activity (or IL-6 receptor neutralizing activity) of an anti-IL-6 receptor antibody.

Construction of a Library of Modified CDRs

First, a humanized PM-1 antibody (Cancer Res. 1993 Feb. 15; 53(4):851-6) was converted into scFv. The heavy chain variable region and light chain variable region regions were amplified by PCR to prepare a humanized PM-1 HL scFv having the linker sequence GGGGSGGGGSGGGGS (SEQ ID NO: 106) between heavy chain variable region and light chain variable region.

Two types of libraries were constructed by PCR using the prepared humanized PM-1 HL scFv-encoding DNA as a template. One was a target library where one of the amino acids in a CDR is designed as X, and the other was a library where only the hot spot sequences in a CDR are substituted with random sequences. The target library where one of the amino acids in each CDR is designed as X was constructed as follows. The library portion was constructed by PCR using a primer containing NNS for the amino acids to be incorporated into the library, while the remaining was prepared by standard PCR. The two were linked together by assembly PCR. In this construction, only one CDR was diversified as a library (see J. Mol. Biol. (1996) 256:77-88). Likewise, the library where only the hot spot sequences were substituted with random sequences was constructed by PCR using a primer containing NNS for all hot spot amino acids. In this construction, two libraries were constructed: one was a library where only the hot spot in heavy chain variable region was diversified, and the other was a library where only the hot spot in light chain variable region was diversified (see Nature Biotechnology 1999 June; 17:568-572).

A ribosome display library was constructed using the above-described libraries according to J. Immunological Methods (1999) 231:119-135. To perform in vitro translation based on the cell-free *E. coli* system, an SDA sequence (ribosome binding site) and T7 promoter were attached to the 5' end and a partial gene3 sequence was ligated as a ribosome display linker to the 3' end using SfiI.

Selection of High Affinity scFv by Ribosome Display

Ribosome display-based panning was carried out (Nature Biotechnology 2000 December; 18:1287-1292). The prepared SR344 was biotinylated using NHS-PEO4-Biotin (Pierce) and then used as an antigen. Off-rate selection was performed to obtain high affinity scFv with high efficiency (JBC (2004) 279(18):18870-18877). The concentrations of biotinylated antigen and competitor antigen were 1 nM and 1 µM, respectively. The time of competition in the fourth round was 10 O/N.

scFv: Insertion into Phagemid, Antigen-Binding Activity and Sequence Analysis

PCR was performed to reconstruct HL scFv using the template DNA pool obtained in the fourth round and specific primers. After digestion with SfiI, the fragment was inserted into the phagemid vector pELBG lad predigested with SfiI. XL1-Blue (Stratagene) was transformed with the resulting construct. Using the yielded colonies, antigen-binding activity was assessed by phage ELISA and the HL scFv sequence was analyzed. The phage ELISA was carried out using plates coated with SR344 at 1 µg/ml (J. Mol. Biol. (1992) 227: 381-388). Clones exhibiting SR344 binding activity were analyzed for their sequences using specific primers.

Conversion of scFv into IgG, and Expression and Purification of IgG

IgG expression was conducted using animal cell expression vectors. Clones enriched with a particular mutation were subjected to PCR to amplify their light chain variable regions and heavy chain variable regions. After XhoI/NheI digestion and EcoRI digestion, the amplified DNAs were inserted into an animal cell expression vector. The nucleotide sequence of each DNA fragment was determined using a DNA sequencer (ABI PRISM 3730xL DNA Sequencer or ABI PRISM 3700 DNA Sequencer (Applied Biosystems)) using the BigDye Terminator Cycle Sequencing Kit (Applied Biosystems) according to the method described in the attached instruction manual.

Expression of IgG-Converted Antibodies

Antibody expression was performed by the method described below. Human embryonic kidney cancer-derived HEK293H cells (Invitrogen) were suspended in DMEM (Invitrogen) supplemented with 10% FBS (Invitrogen). The cells (10-ml/plate; cell density of 5 to $6 \times 10^5$ cells/ml) were plated on dishes for adherent cells (10 cm in diameter; CORNING) and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid DNA mixture (13.8 µg in total) was combined with 20.7 µl of 1 µg/ml Polyethylenimine (Polysciences Inc.) and 690 µl of CHO-S-SFMII medium. The resulting mixture was incubated at room temperature for 10 minutes, and then added to the cells in each dish. The cells were incubated in a $CO_2$ incubator (at 37° C. under 5% $CO_2$) for four to five hours. Then, 6.9 ml of CHO-S-SFM-II medium (Invitrogen) was added to the dishes, and the cells were incubated in a $CO_2$ incubator for three days. The culture supernatants were collected and centrifuged (approx. 2,000 g, five minutes, room temperature) to remove the cells, and sterilized through 0.22-µm filter MILLEX®-GV (Millipore). The samples were stored at 4° C. until use.

Purification of IgG-Converted Antibodies

50 µl of rProtein A Sepharose™ Fast Flow (Amersham Biosciences) suspended in TBS was added to the obtained culture supernatants, and the combined solutions were mixed by inversion at 4° C. for four hours or more. The solutions were transferred into 0.22-µm filter cups of Ultrafree®-MC (Millipore). After washing three times with 500 µl of TBS, the rProtein A Sepharose™ resin was suspended in 100 µl of 50 mM sodium acetate (pH 3.3) aqueous solution, and the mixture was incubated for two minutes to elute the antibody. Immediately, the eluate was neutralized by adding 6.7 µl of 1.5 M Tris-HCl (pH 7.8). Elution was carried out twice, yielding 200 µl of purified antibody. The absorbance at 280 nm was determined using ND-1000 Spectrophotometer (NanoDrop) or spectrophotometer DU-600 (Beckman) using 2 or 50 µl of the antibody solution, respectively. The antibody concentration was calculated from the obtained value according to the following formula:

[Antibody Concentration (mg/ml)]=(Absorbance× Dilution Fold)/14.6×10

Assessment of the IgG-Converted Clones for Human IL-6 Receptor-Neutralizing Activity The IL-6 receptor neutralizing activity was assessed using BaF3/gp130 which proliferates in an IL-6/IL-6 receptor-dependent manner. After three washes with RPMI1640 supplemented with 10% FBS, BaF3/gp130 cells were suspended at $5 \times 10^4$ cells/ml in RPMI1640 supplemented with 60 ng/ml human interleukin-6 (TORAY), 60 ng/ml recombinant soluble human IL-6 receptor (SR344), and 10% FBS. The cell suspensions were dispensed (50 µl/well) into 96-well plates (Corning). Then, the purified antibodies were diluted with RPMI1640 containing 10% FBS, and added to each well (50 µl/well). The cells were cultured at 37° C. under 5% $CO_2$ for three days. WST-8 Reagent (Cell Counting Kit-8; Dojindo Laboratories) was diluted two-fold with PBS. Immediately after 20 µl of the reagent was added to each well, the absorbance at 450 nm (reference wavelength: 620 nm) was measured using SUNRISE CLASSIC (TECAN). After culturing for two hours, the absorbance at 450 nm (reference wavelength: 620 nm) was measured again. The IL-6 receptor neutralizing activity was assessed using the change of absorbance during two hours as an indicator.

As a result, a number of antibodies whose activities were higher than that of the humanized PM-1 antibody (wild type (WT)) were obtained. Mutations in the antibodies whose activities were higher than that of WT are shown in FIG. 4. For example, as shown in FIG. 1, the neutralizing activity of RD_6 was about 50 times higher than WT in terms of 100% inhibitory concentration.

Biacore-Based Affinity Analysis of the IgG-Converted Clones

The clones whose activities were higher than that of the wild type were analyzed for antigen-antibody reaction kinetics using Biacore T100 (Biacore). The antigen-antibody interaction was measured by immobilizing 1,800 to 2,600 RU (resonance units) of rec-Protein A (Zymed) (hereinafter "Protein A") onto a sensor chip, binding various antibodies onto the chip, and then flowing the antigen over the chip as an analyte. Various concentrations of recombinant human IL-6R sR (R&D systems) (hereinafter "rhIL-6sR") were used as the antigen. All measurements were carried out at 25° C. The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (Biacore).

Figure 2:
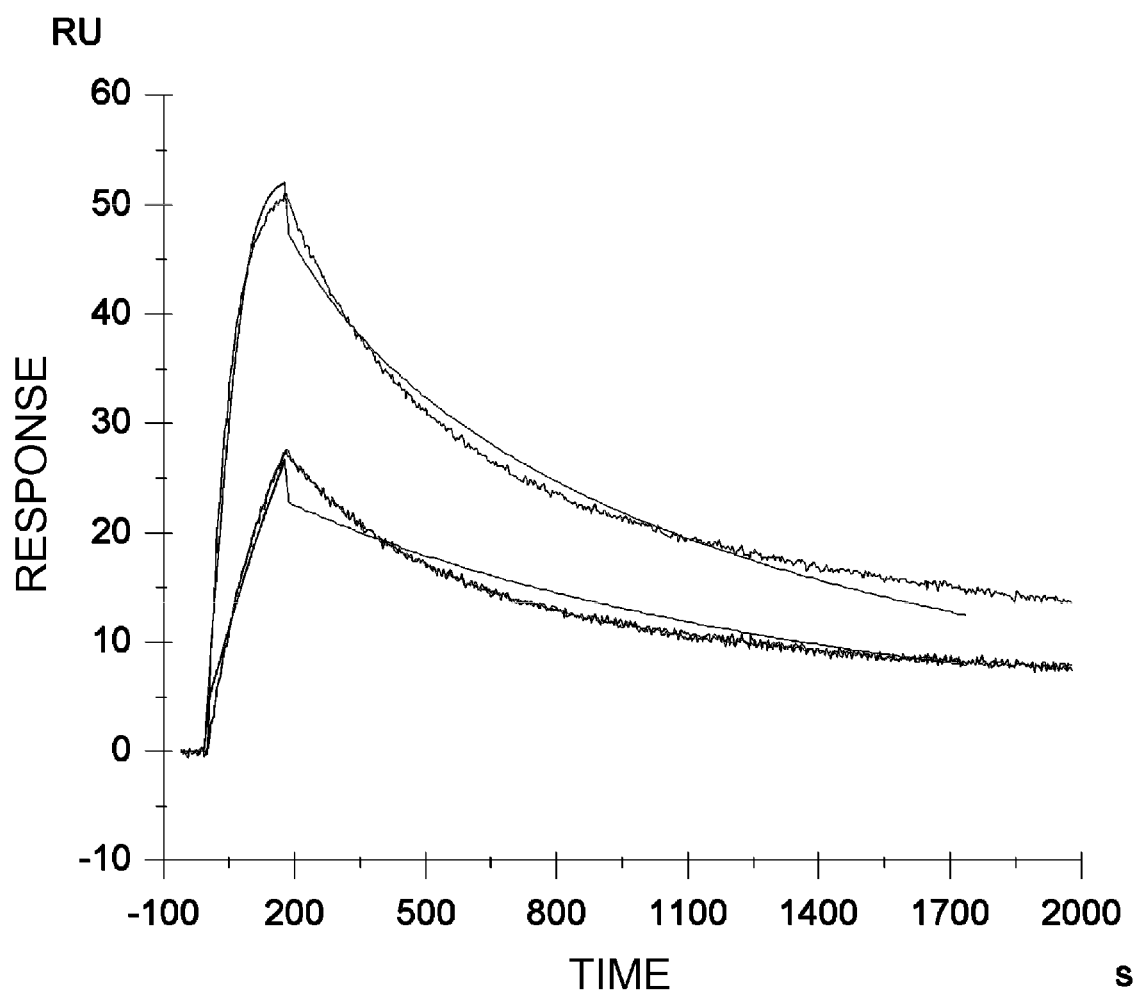
FIG. 2 is a graph showing a sensorgram for the interaction between rhIL-s6R (R&D systems) and WT.
Figure 3:
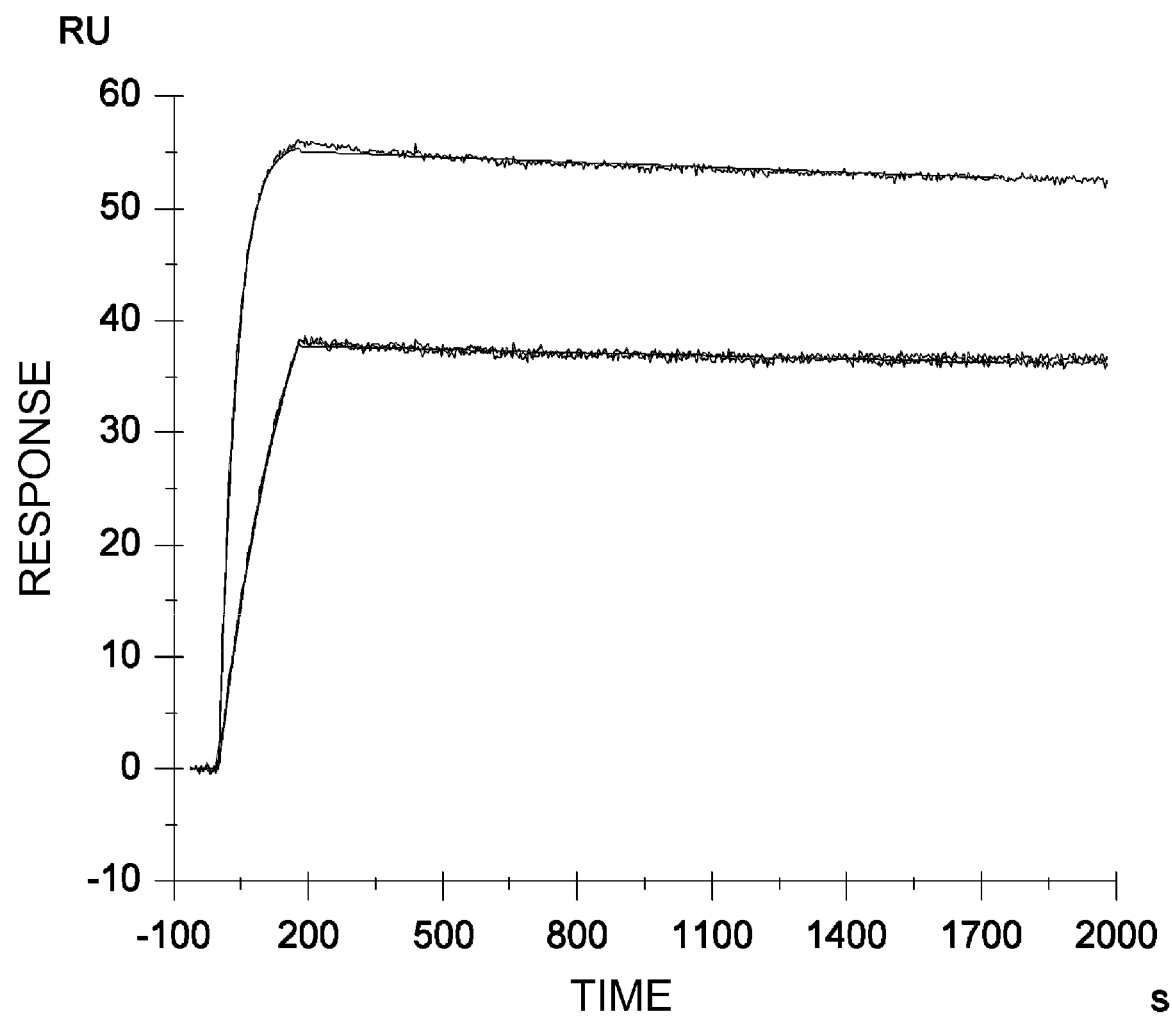
FIG. 3 is a graph showing a sensorgram for the interaction between rhIL-s6R (R&D systems) and RD_6.

As a result, a number of antibodies exhibiting higher affinity than the humanized PM-1 antibody (wild type (WT)) were obtained. As an example, sensorgrams of the wild type (WT) and RD_6 are shown in FIGS. 2 and 3, respectively. The result of kinetic parameter analysis revealed that RD_6 had about 50 times higher affinity than WT (Table 1). In addition to RD_6, antibodies exhibiting affinity dozens of times higher than WT were also obtained. Mutations that result in higher affinity than WT are shown in FIG. 4.

TABLE 1

| SAMPLE | $k_a$ (1/Ms) | $k_d$ (1/s) | $K_D$ (M) |
|---|---|---|---|
| WT | 2.8E+6 | 1.8E−3 | 6.5E−10 |
| RD_6 | 2.3E+6 | 2.8E−5 | 1.2E−11 |

[Example 2] Improvement of Antigen-Binding Activity Through Various Combinations of CDR Modifications Mutations associated with strong activity or high affinity were combined to create antibodies with stronger activity and higher affinity.

Production, Expression, and Purification of Modified Antibodies

Amino acids at selected sites were modified to produce modified antibodies. Specifically, mutations were introduced into the prepared H(WT) variable region (H(WT), SEQ ID NO: 107) and L(WT) variable region (L(WT), SEQ ID NO: 108) using the QuikChange Site-Directed Mutagenesis Kit (Stratagene) by the method described in the attached instruction manual. After it was confirmed that the antibody heavy chain gene fragment inserted into a plasmid was the humanized antibody variable region gene sequence of interest, the plasmid was digested with XhoI and NotI. A plasmid containing the antibody light chain gene fragment as an insert was digested with EcoRI. Then, the reaction mixtures were subjected to electrophoresis in 1% agarose gel. A DNA fragment of the expected size (about 400 bp) was purified using the QIAquick Gel Extraction Kit (QIAGEN) by the method described in the attached instruction manual. The DNA was eluted with 30 µl of sterile water. Then, the antibody heavy chain gene fragment was inserted into an animal cell expression vector to construct the heavy chain expression vector of interest. An expression vector for the light chain was also constructed in the same way. Ligation was carried out using the Rapid DNA Ligation Kit (Roche Diagnostics). The *E. coli* strain DH5a (Toyobo) was transformed with the plasmids. The nucleotide sequence of each DNA fragment was determined with a DNA sequencer (ABI PRISM 3730xL DNA Sequencer or ABI PRISM 3700 DNA Sequencer (Applied Biosystems)) using the BigDye Terminator Cycle Sequencing Kit (Applied Biosystems) according to the method described in the attached instruction manual. The antibodies were expressed using the constructed expression vectors and purified by the method described in Example 1.

Assessment for the Activity of Neutralizing Human IL-6 Receptor

Figure 6:
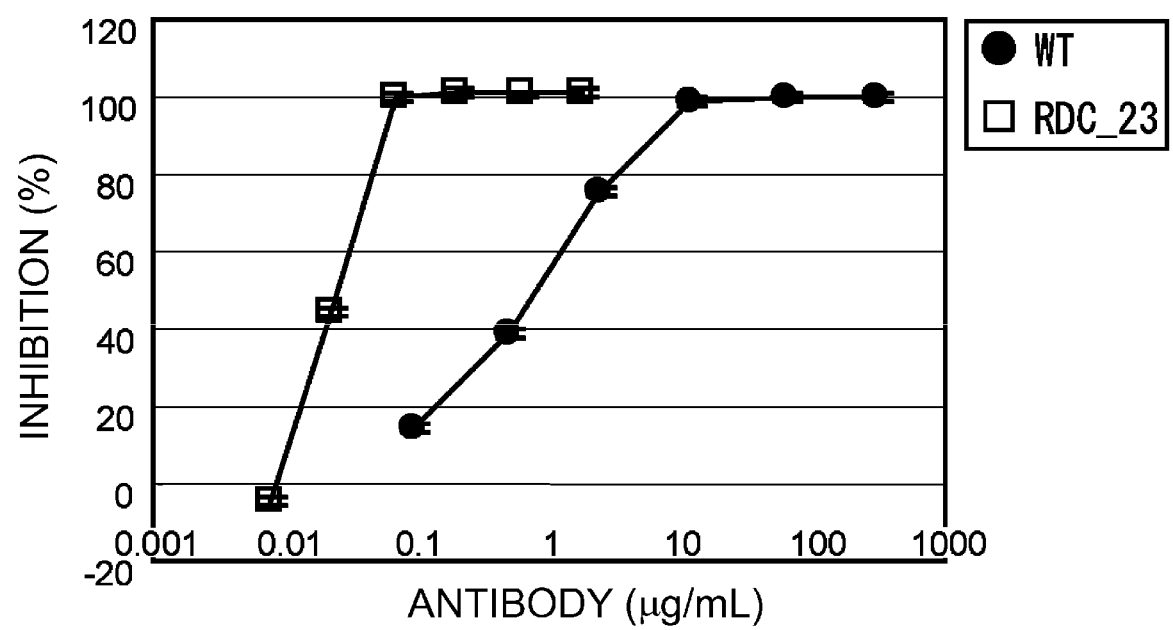
FIG. 6 is a graph showing the BaF/gp130-neutralizing activities of WT and RDC23.

The purified antibodies were assessed for their neutralizing activity by the method described in Example 1. The neutralizing activity was assessed using 600 ng/ml human interleukin-6 (TORAY). A number of novel antibodies with stronger activity than WT were obtained. The CDR sequences of the antibodies are shown in FIG. 5. Of them, the antibody with the strongest activity (referred to as RDC_23) has RDC_5H as a heavy chain and RDC_11L as a light chain. The neutralizing activity of RDC_23 is shown in FIG. 6. The activity of RDC_23 was demonstrated to be about 100 times higher than WT in terms of 100% inhibitory concentration. Improved neutralizing activity was observed not only in RDC_23, which is an antibody having RDC_5H as a heavy chain and RDC_11L as a light chain, but also in antibodies RDC_2, RDC_3, RDC_4, RDC_5, RDC_6, RDC_7, RDC_8, RDC_27, RDC_28, RDC_29, RDC_30, and RDC_32, which all have L(WT) as a light chain, and RDC_2H, RDC_3H, RDC_4H, RDC_5H, RDC_6H, RDC_7H, RDC_8H, RDC_27H, RDC_28H, RDC_29H, RDC_30H, and RDC_32H as a heavy chain, respectively, as well as in an antibody referred to as RDC_11, which has H(WT) and RDC_11L as heavy and light chains, respectively. It was thus shown that antibodies having stronger neutralizing activity could be obtained by combining mutations discovered by affinity maturation. Furthermore, since antibodies containing such a combination of mutations had improved neutralizing activity, they were also expected to have improved affinity.

Biacore-Based Affinity Analysis Using Protein A

Figure 7:
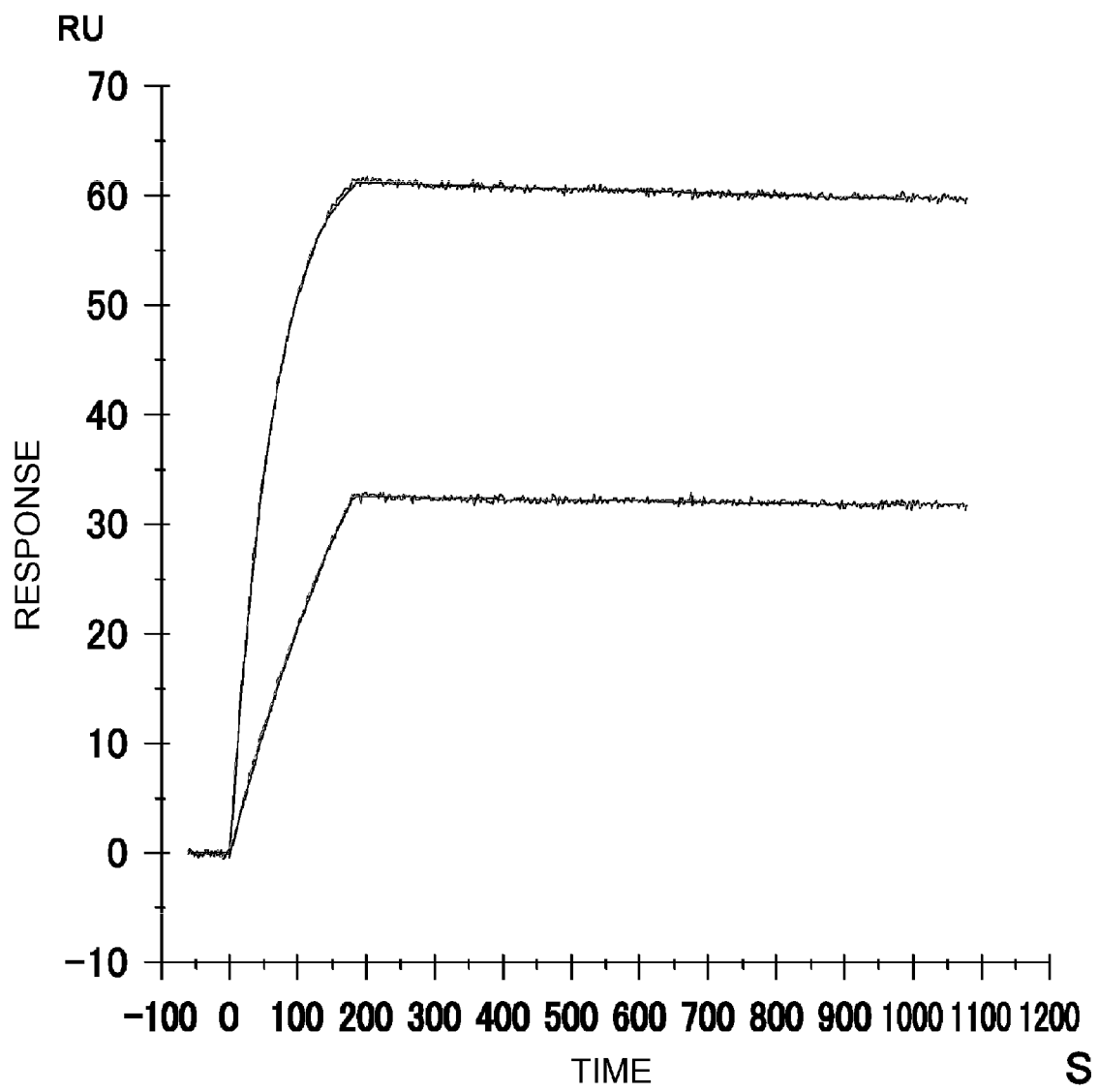
FIG. 7 is a graph showing a sensorgram for the interaction between rhIL-s6R (R&D systems) and RDC23.
Figure 8:
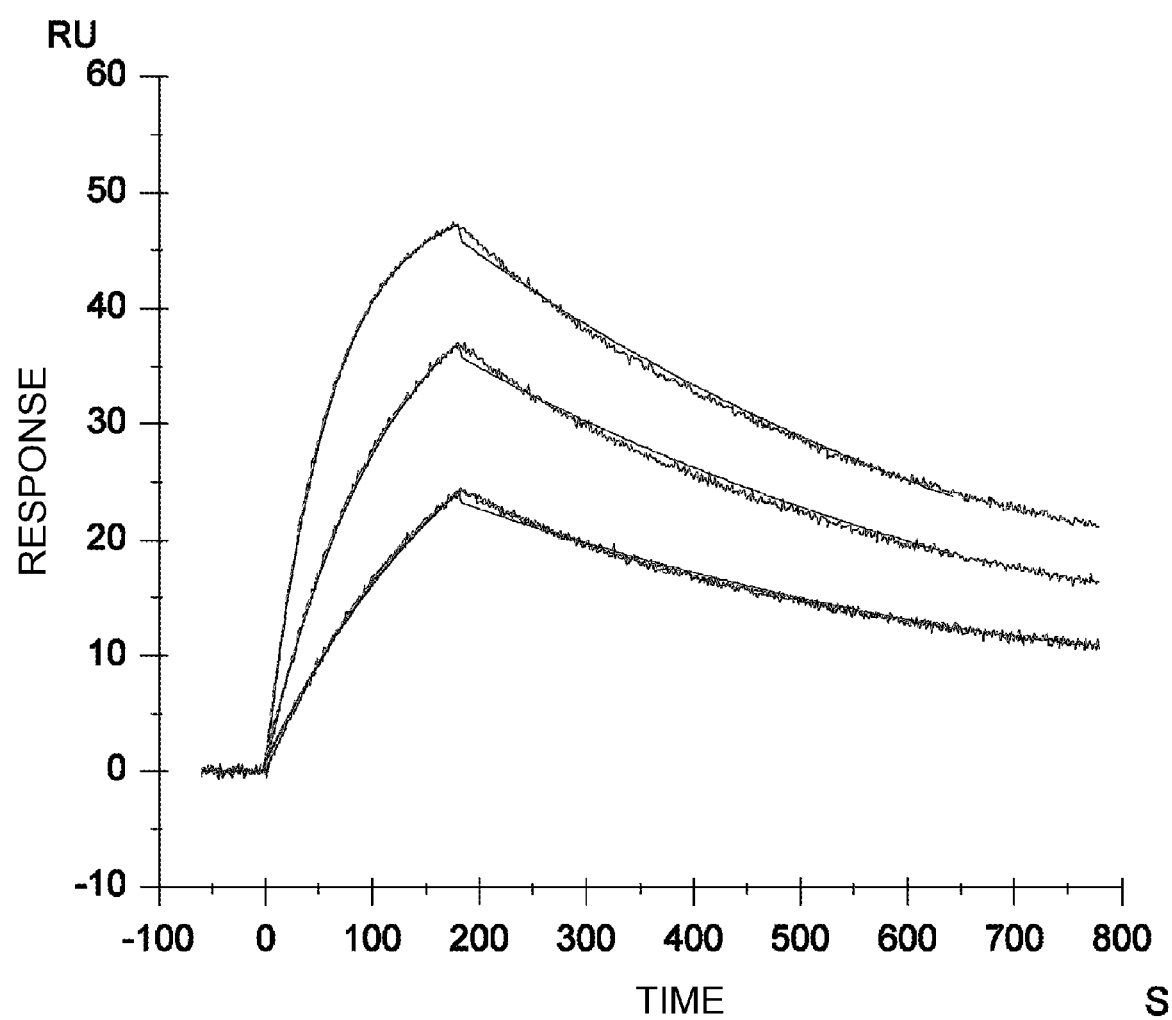
FIG. 8 is a graph showing a sensorgram for the interaction between rhsIL-6R and WT.
Figure 9:
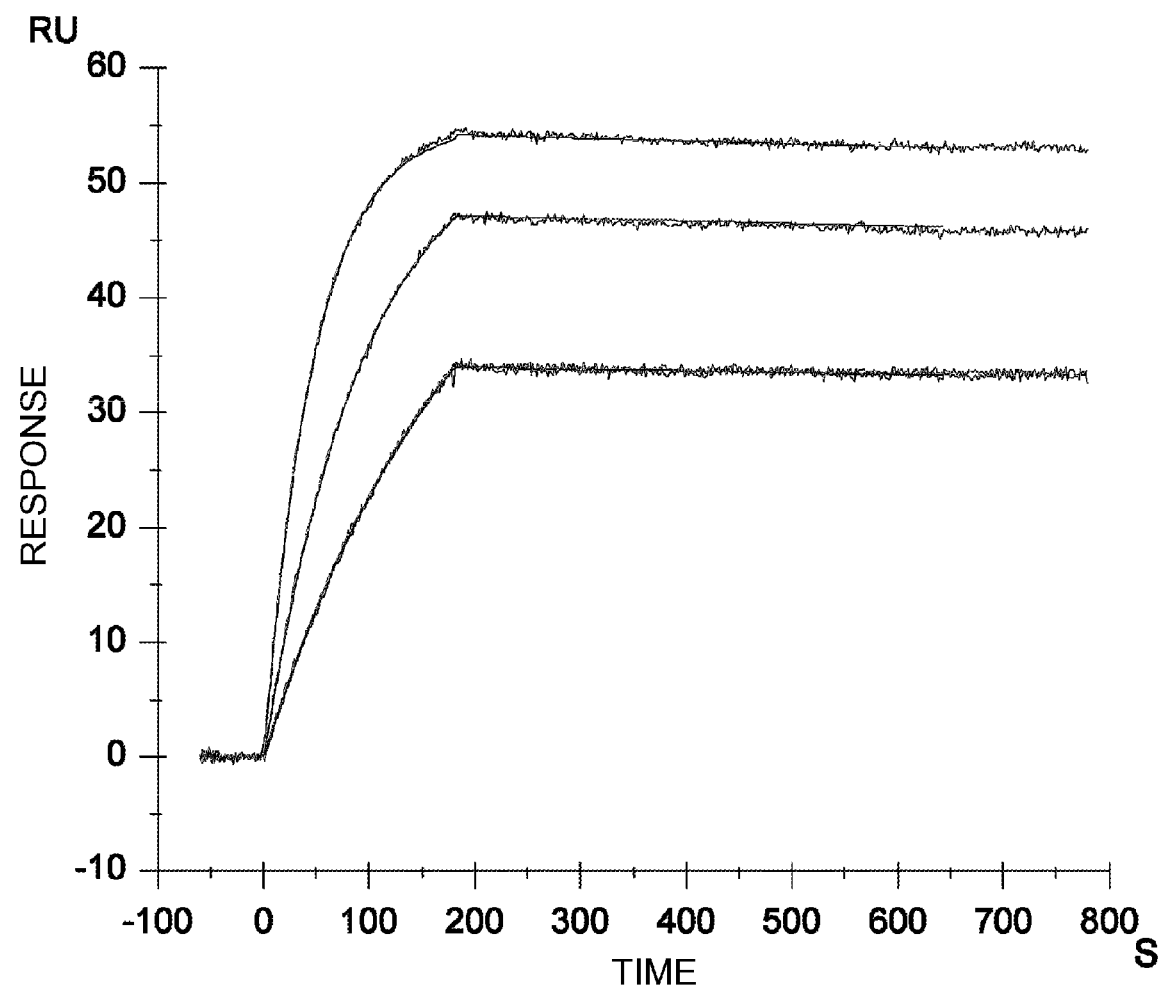
FIG. 9 is a graph showing a sensorgram for the interaction between rhsIL-6R and RDC23.
Figure 10:
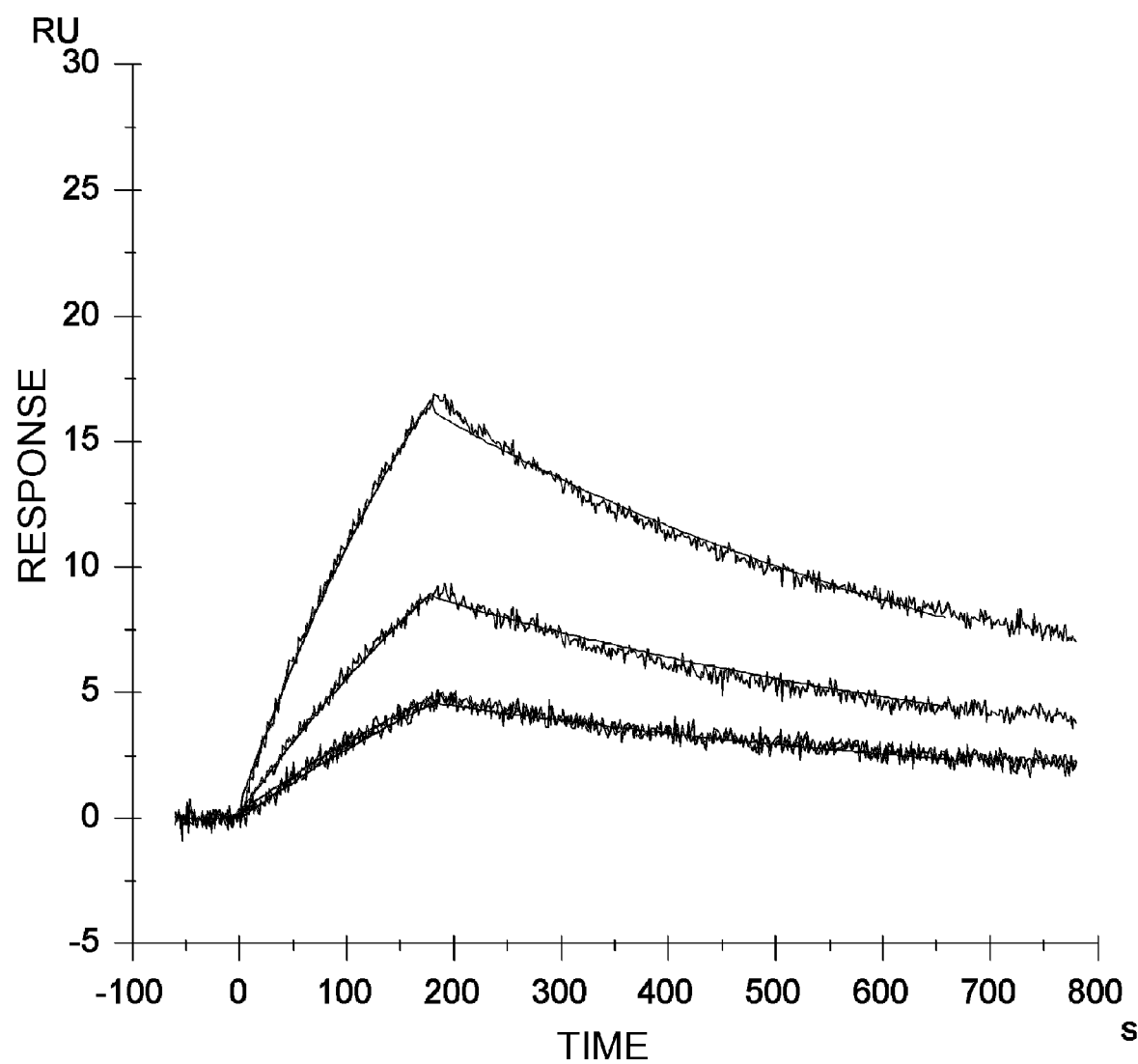
FIG. 10 is a graph showing a sensorgram for the interaction between SR344 and WT.
Figure 11:
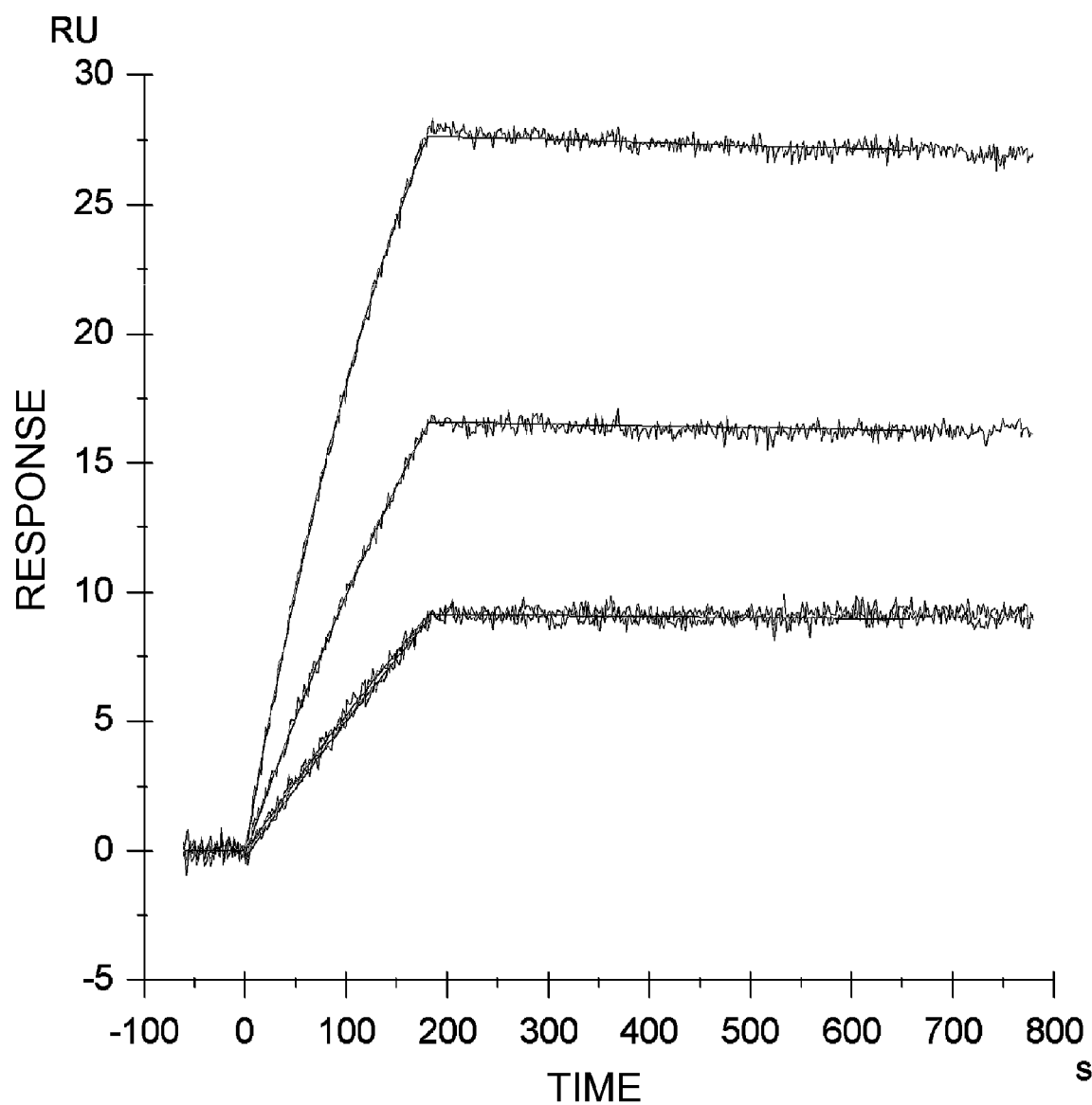
FIG. 11 is a graph showing a sensorgram for the interaction between SR344 and RDC23.

Thus, of the antibodies with improved neutralizing activity, RDC_2, RDC_3, RDC_4, RDC_5, RDC_6, RDC_7, RDC_8, RDC_11, and RDC_23 were analyzed for antigen-antibody reaction kinetics using Biacore T100 (Biacore). The antigen-antibody interaction was measured by immobilizing 4,400 to 5,000 RU of rec-Protein A (Zymed) immobilized onto a sensor chip by the amine coupling method, binding various antibodies onto the chip, and then flowing the antigen over the chip as an analyte. For the antigen, various concentrations of rhIL-6sR were used. All measurements were carried out at 25° C. The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (Biacore). The result showed that RDC_2, RDC_3, RDC_4, RDC_5, RDC_6, RDC_7, RDC_8, RDC_11, and RDC_23, all of which contained a combination of mutations, had a smaller $K_D$ value than RD_28 which contains a single mutation (Table 2). The sensorgram for RDC_23 which has a higher affinity than others is shown in FIG. 7.

TABLE 2

| SAMPLE | ka (1/Ms) | kd (1/s) | KD (M) |
|---|---|---|---|
| RD_28 | 9.4E+05 | 1.1E−04 | 1.2E−10 |
| RDC_2 | 1.1E+06 | 2.5E−05 | 2.2E−11 |
| RDC_3 | 1.0E+06 | 3.7E−05 | 3.7E−11 |
| RDC_4 | 1.1E+06 | 2.9E−05 | 2.7E−11 |
| RDC_5 | 1.2E+06 | 2.8E−05 | 2.2E−11 |
| RDC_6 | 1.2E+06 | 3.5E−05 | 2.9E−11 |
| RDC_7 | 1.1E+06 | 4.2E−05 | 3.8E−11 |
| RDC_8 | 1.4E+06 | 3.6E−05 | 2.5E−11 |
| RDC_11 | 1.1E+06 | 7.0E−05 | 6.5E−11 |
| RDC_23 | 1.2E+06 | 3.1E−05 | 2.5E−11 |

This finding suggests that these antibodies have higher affinities than the parental antibodies that do not have the combinations of mutations. As in the case of the neutralizing activity, this indicates that antibodies having greater affinity can be obtained by combining mutations discovered by affinity maturation. The amino acid sequences of variants having higher activity or affinity than WT are shown below (mutations relative to WT are underlined).

```
(HCDR2)
                                          SEQ ID NO: 45
YISYSGITNYNPSLKS (HCDR3)
                                          SEQ ID NO: 57
LLARATAMDY

SEQ ID NO: 58
VLARATAMDY

SEQ ID NO: 59
ILARATAMDY

SEQ ID NO: 60
TLARATAMDY

SEQ ID NO: 61
VLARITAMDY

SEQ ID NO: 62
ILARITAMDY

SEQ ID NO: 63
TLARITAMDY

SEQ ID NO: 64
LLARITAMDY (LCDR3)
                                          SEQ ID NO: 79
GQGNRLPYT
```

Specifically, an anti-IL-6 receptor antibody with markedly improved affinity and neutralizing activity as compared to WT can be produced by designing the antibody to have Asn at amino acid position 9 in HCDR2, Leu, Val, Ile, or Thr at amino acid position 1 in HCDR3, Ala or Ile at amino acid position 5 in HCDR3, Gly at amino acid position 1 in LCDR3, and Arg at amino acid position 5 in LCDR3.

Biacore-based affinity analysis using Protein A/G

WT and RDC_23 were analyzed for antigen-antibody reaction kinetics using Biacore T100 (Biacore). The antigen-antibody interaction was measured by immobilizing purified Recomb Protein A/G (Pierce) (hereinafter "Protein A/G") onto a sensor chip, binding various antibodies onto the chip, and then flowing the antigen as an analyte over the chip. Various concentrations of rhIL-6sR (R&D systems) and recombinant soluble IL-6 receptor (SR344 prepared in Example 1) were used as the antigen. The sugar chain structure of rhIL-6sR produced by baculovirus-infected insect cells is of high-mannose type. On the other hand, the sugar chain structure of SR344 produced by CHO cells is assumed to be of the complex sugar chain type with sialic acid at its end. Since the sugar chain structure of soluble IL-6 receptor in an actual human body is assumed to be of the complex sugar chain type with sialic acid at its end, SR344 is expected to have a structure closer to that of soluble IL-6 receptor in the human body. Thus, a comparison test between rhIL-6sR and SR344 was carried out in this experiment.

The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (Biacore).

A sensor chip was prepared by immobilizing about 3,000 RU of Protein A/G onto CM5 (Biacore) with the amine coupling method. The kinetics of the interaction between the two types of soluble IL-6 receptors (rhIL-6sR and SR344) and the antibodies (WT and RDC_23) bound to Protein A/G was analyzed using the prepared sensor chip. The running buffer used was HBS-EP+, and the flow rate was 20 µl/min. Each antibody was prepared so that about 100 RU of the antibody was bound to Protein A/G. For the analyte, rhIL-6sR was prepared at 0, 0.156, 0.313, and 0.625 µg/ml using HBS-EP+, while SR344 was adjusted to 0, 0.0654, 0.131, and 0.261 µg/ml. In the first step of the measurement, the antibodies of interest, WT and RDC_23, were bound to Protein A/G, and an analyte solution was added thereto. After three minutes of interaction, the solution was switched with HBS-EP+(Biacore), and the dissociation phase was monitored for ten minutes. After measurement of the dissociation phase, the sensor chip was regenerated by washing with 10 µl of 10 mM glycine-HCl (pH 1.5). The association, dissociation, and regeneration constituted one analytic cycle. All experiments were carried out at 37° C.

WT and RDC_23 were measured according to the above cycle. The resulting sensorgrams for the two types of soluble IL-6 receptors, rhIL-6sR and SR344, are shown in FIGS. 8, 9, 10, and 11. The obtained sensorgrams were kinetically analyzed using Biacore T100 Evaluation Software, which is a data analysis software specific for Biacore (Table 3). The result showed that when comparing rhIL-6sR and SR344, the affinities of both WT and RDC_23 for SR344 were two- to three-fold weaker For both rhIL-6sR and SR344, RDC_23 had affinities that are about 40 to 60 times improved as compared to WT. Thus, it was demonstrated that because of the combination of respective CDR modifications obtained by affinity maturation, RDC_23 also had a markedly higher affinity than WT for SR344 whose structure is presumably close to that of soluble IL-6 receptor in the human body. All measurements described hereinafter in the Examples were carried out at 37° C. to kinetically analyze the antigen-antibody reaction using SR344 and protein A/G.

TABLE 3

| SAMPLE | ANALYTE | $k_a$ (1/Ms) | $k_d$ (1/s) | $K_D$ (M) |
|---|---|---|---|---|
| WT | rhIL-6sR | 1.3E+6 | 1.5E−3 | 1.2E−9 |
|  | SR344 | 4.9E+5 | 2.0E−3 | 4.0E−9 |
| RDC_23 | rhIL-6sR | 1.6E+6 | 4.5E−5 | 2.8E−11 |
|  | SR344 | 6.4E+5 | 4.3E−5 | 6.7E−11 |

[Example 3] Generation of H53/L28 with Improved Plasma Retention and Reduced Immunogenicity Risk Through Modifications of CDR and Framework The antibody obtained by humanizing a mouse PM-1 antibody (hereinafter referred to as "wild type" or "WT"; the WT heavy and light chains are referred to as "H(WT)" and "L(WT)", respectively) as described in Cancer Res. 1993 Feb. 15; 53(4):851-6, was modified to improve the retention in plasma, reduce the immunogenicity risk, and increase the stability. The modifications are described below. For the purpose of improving the retention in plasma, the heavy and light chain variable region sequences of WT were modified to lower the isoelectric point.

Creation of a Three-Dimensional Structure Model for the Humanized PM-1 Antibody

First, to identify amino acid residues exposed on the surface of the variable regions of the humanized PM-1 antibody (H(WT)/L(WT)), a model for the Fv domain of the antibody obtained by humanizing a mouse PM-1 antibody was created by homology modeling using the MOE software (Chemical Computing Group Inc.).

Selection of Modification Sites to Reduce the Isoelectric Point of the Humanized PM-1 Antibody A detailed analysis of the model created suggested that of the surface exposed amino acids in the FR sequence, H16, H43, H81, H105, L18, L45, L79, and L107 (Kabat's numbering; Kabat E A et al., 1991, Sequences of Proteins of Immunological Interest, NIH), and of those in the CDR sequence, H31, H64, H65, L24, L27, L53, and L55, were potential candidates for the sites of modification to reduce the isoelectric point without decreasing the activity or stability.

Removal of Remaining Mouse Sequences from the Humanized PM-1 Antibody

The humanized PM-1 antibody is an antibody whose sequence was obtained by humanizing the mouse PM-1 antibody (Cancer Res. 1993 Feb. 15; 53(4):851-6). The heavy chain of the humanized PM-1 antibody was obtained by grafting CDR onto the NEW framework which is a human antibody variable region. However, mouse sequences remain at H27, H28, H29, H30, and H71 in the heavy chain to maintain the activity. From the perspective of immunogenicity risk, the best result is expected when the number of mouse sequences is minimized. Thus, the present inventors searched for sequences for converting H27, H28, H29, and H30 into human sequences.

Selection of Modification Sites to Improve the Stability of the Humanized PM-1 Antibody The present inventors speculated that it might be possible to improve the stability of the humanized PM-1 antibody (H(WT)/L(WT)) by substituting glycine for serine at H65 (stabilization of the turn structure; stabilization through conversion into an HCDR2 consensus sequence), isoleucine for methionine at H69 (stabilization of the hydrophobic core structure), serine for leucine at H70 (stabilization through replacement of the surface exposed residue with a hydrophilic residue), asparagine for threonine at H58 (stabilization through conversion into an HCDR2 consensus sequence), serine for threonine at L93 (stabilization through replacement of the surface exposed residue with a hydrophilic residue), and isoleucine for serine at H107 (stabilization of the sheet) in its variable regions, and considered these modifications as candidates for increasing stability.

Removal of in Silico Predicted T-Cell Epitopes from the Humanized PM-1 Antibody

First, the variable regions of the humanized PM-1 antibody (H(WT)/L(WT)) were analyzed using TEPITOPE (Methods 2004 December; 34(4):468-75). The result showed that the light chain CDR2 contained many T-cell epitopes that bind to HLA. Thus, TEPITOPE analysis was carried out to find modifications that would reduce the immunogenicity risk of the light chain CDR2 without decreasing the stability, binding activity, or neutralizing activity. The result demonstrated that HLA-binding T-cell epitopes can be removed without decreasing the stability, binding activity, or neutralizing activity by substituting glycine for threonine at L51 in the light chain CDR2.

Selection of Respective Framework Sequences

Homology search can be performed for the individual frames by using a database constructed with the data of human antibody amino acid sequences available from the public databases: Kabat Database (ftp.ebi.ac.uk/pub/databases/kabat/) and IMGT Database (imgt.cines.fr/). From the perspectives of reducing the isoelectric point, removing remaining mouse sequences, and improving the stability, human frameworks were selected by searching the database for human framework sequences containing the modifications described above. The result showed that the modified antibody H53/L28 met the requirements described above without decreasing the binding activity or neutralizing activity when its respective frameworks were constituted of the sequences indicated below. SOURCE indicates origins of the human sequences. Underlined amino acid residues in each sequence represent modified amino acids relative to WT.

TABLE 4

| H53 | SOURCE | SEQUENCE |
|---|---|---|
| FR1 | Germline: IMGT_hVH_4_b | QVQLQESGPGLVKPSETLSLTCAVSGYSIS |
| FR2 | Blood 1996 88: 4620-4629 | WVRQPPGEGLEWIG |
| FR3 | Germline: IMGT_hVH_4_b (EXCEPT BOLD-INDICATED H71 & H89) | RVTISRDTSKNQFSLKLSSVTAADTAAYYCAR |
| FR4 | J IMMUNOL 142: 4027-4033 (1989) | WGEGTLVTVSS |
| L28 | SOURCE | SEQUENCE |
| FR1 | Immunology. 1988 Aug 64(4):573-9 | DIQMTQSPSSLSASVGDSVTITC |
| FR2 | Germline: IMGT_hVk_1D_8 | WYQQKPGKAPELLIY |
| FR3 | Germline: IMGT_hVk_6D_41 | GVPSRFSGSGSGTDFTFTISSLEAEDAATYYC |
| FR4 | J. Exp. Med. 1997 185: 1435-1446 | FGQGTKVEIE |

Furthermore, the above-described FR3 of H53 contains a nonhuman sequence; thus, it is preferable to further reduce the immunogenicity risk. A possible modification for reducing the immunogenicity risk is a sequence substitution resulting in an exchange of Ala at H89 to Val (SEQ ID NO: 127). Moreover, since Arg at H71 in FR3 of H53 is important for the binding activity (Cancer Res. 1993 Feb. 15; 53(4):851-6), anti-human IL-6 receptor antibodies containing heavy and light chains whose frameworks consist of a fully human sequence may be produced by using an FR3 sequence of the human VH1 subclass (SEQ ID NO: 128) or the human VH3 subclass (SEQ ID NO: 129) where Arg at H71 is conserved.

Selection of Respective CDR Sequences

The respective CDR sequences of H53/L28 were selected as shown below, from the perspectives of reducing the isoelectric point, improving the stability, and removing T-cell epitopes, and most importantly, not decreasing the binding activity or neutralizing activity.

TABLE 5

| H53 | SEQUENCE |
|---|---|
| CDR1 | DDHAWS |
| CDR2 | YISYSGITNYNPSLKG |
| CDR3 | SLARTTAMDY |
| L28 | SEQUENCE |
| CDR1 | QASQDISSYLN |
| CDR2 | YGSELHS |
| CDR3 | QQGNSLPYT |

Construction of Expression Vector for Modified Antibody, Expression and Purification of the Antibody An expression vector for modified antibody was constructed, and the antibody was expressed and purified by the method described in Example 1. The humanized mouse PM-1 antibody was successively modified to have the framework and CDR sequences selected for mutagenesis vectors for H(WT) and L(WT) of the antibody. Using the finally obtained H53/L28-encoding animal cell expression vector (antibody amino acid sequences: H53, SEQ ID NO: 104; and L28, SEQ ID NO: 105) having the selected framework and CDR sequences, H53/L28 was expressed and purified, and then used in the assessment described below.

Assessment of Modified Antibody H53/L28 for the Isoelectric Point by Isoelectric Focusing WT and the modified antibody H53/L28 were analyzed by isoelectric focusing to assess the change in the isoelectric point of the whole antibody caused by the amino acid modifications in the variable regions. The procedure of isoelectric focusing is described below. Using Phastsystem Cassette (Amersham Biosciences), Phast-Gel Dry IEF gel (Amersham Biosciences) was rehydrated for about 30 minutes in the rehydration solution indicated below.

| | | | | | |
|---|---|---|---|---|---|
| Milli-Q water | | | | | 1.5 ml |
| Pharmalyte 5-8 for IEF (Amersham Biosciences) | | | | | 50 µl |
| Pharmalyte 8-10.5 for IEF (Amersham Biosciences) | | | | | 50 µl |

Electrophoresis was carried out in PhastSystem (Amersham Biosciences) using the rehydrated gel according to the program indicated below. The samples were loaded onto the gel in Step 2. Calibration Kit for DI (Amersham Biosciences) was used as the pI markers.

| | | | | | |
|---|---|---|---|---|---|
| Step 1: | 2000 V | 2.5 mA | 3.5 W | 15° C. | 75 Vh |
| Step 2: | 200 V | 2.5 mA | 3.5 W | 15° C. | 15 Vh |
| Step 3: | 2000 V | 2.5 mA | 3.5 W | 15° C. | 410 Vh |

After electrophoresis, the gel was fixed with 20% TCA, and then silver-stained using the Silver Staining Kit, protein (Amersham Biosciences), according to the protocol attached to the kit. After staining, the isoelectric point of the sample (the whole antibody) was calculated from the known isoelectric points of pI markers. The result showed that the isoelectric point of WT was about 9.3, and the isoelectric point of the modified antibody H53/L28 was about 6.5 to 6.7. The amino acid substitution in WT yielded H53/L28 whose isoelectric point is about 2.7 lowered. The theoretical isoelectric point of the variable regions of H53/L28 (heavy chain variable region and light chain variable region sequences) was calculated by GENETYX (GENETYX CORPORATION). The determined theoretical isoelectric point was 4.52. Meanwhile, the theoretical isoelectric point of WT was 9.20. Thus, the amino acid substitution in WT yielded H53/L28 having a variable region whose theoretical isoelectric point is about 4.7 lowered.

Assessment of H53/L28 for the Human IL-6 Receptor-Neutralizing Activity

Figure 12:
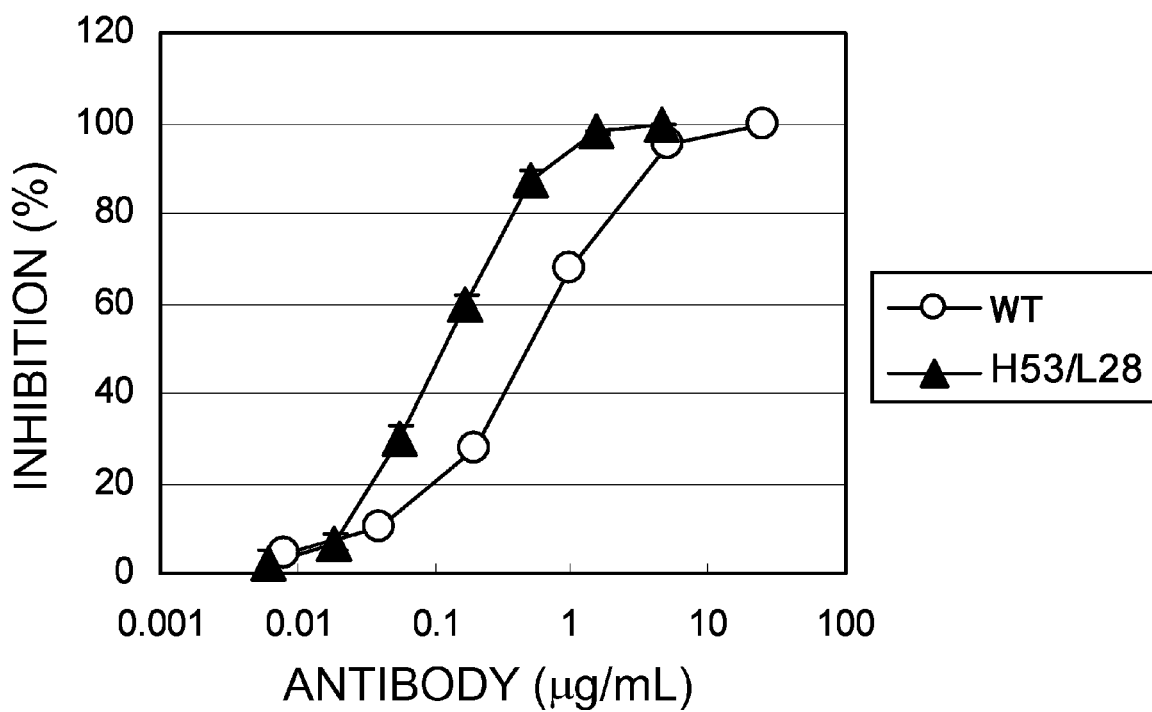
FIG. 12 is a graph showing the BaF/gp130-neutralizing activities of WT and H53L28.

WT and H53/L28 were assessed by the method described in Example 1. The result is shown in FIG. 12. The activity of modified antibody H53/L28 to neutralize BaF/gp130 improved several fold in comparison to WT. Specifically, the comparison of H53/L28 with WT revealed that the isoelectric point could be reduced while improving the neutralizing activity.

Biacore-Based Analysis of H53/L28 for the Affinity for Human IL-6 Receptor

The affinities of WT and H53/L28 for human IL-6 receptor were assessed by kinetic analysis using Biacore T100 (Biacore). The antigen-antibody interaction was measured by immobilizing purified Recomb Protein A/G (Pierce) (hereinafter "Protein A/G") onto a sensor chip, binding various antibodies onto the chip, and then flowing the antigen over the chip as an analyte. Various concentrations of recombinant soluble IL-6 receptor (SR344) were used as the antigen. The measurement conditions were the same as described in Example 2.

Figure 13:
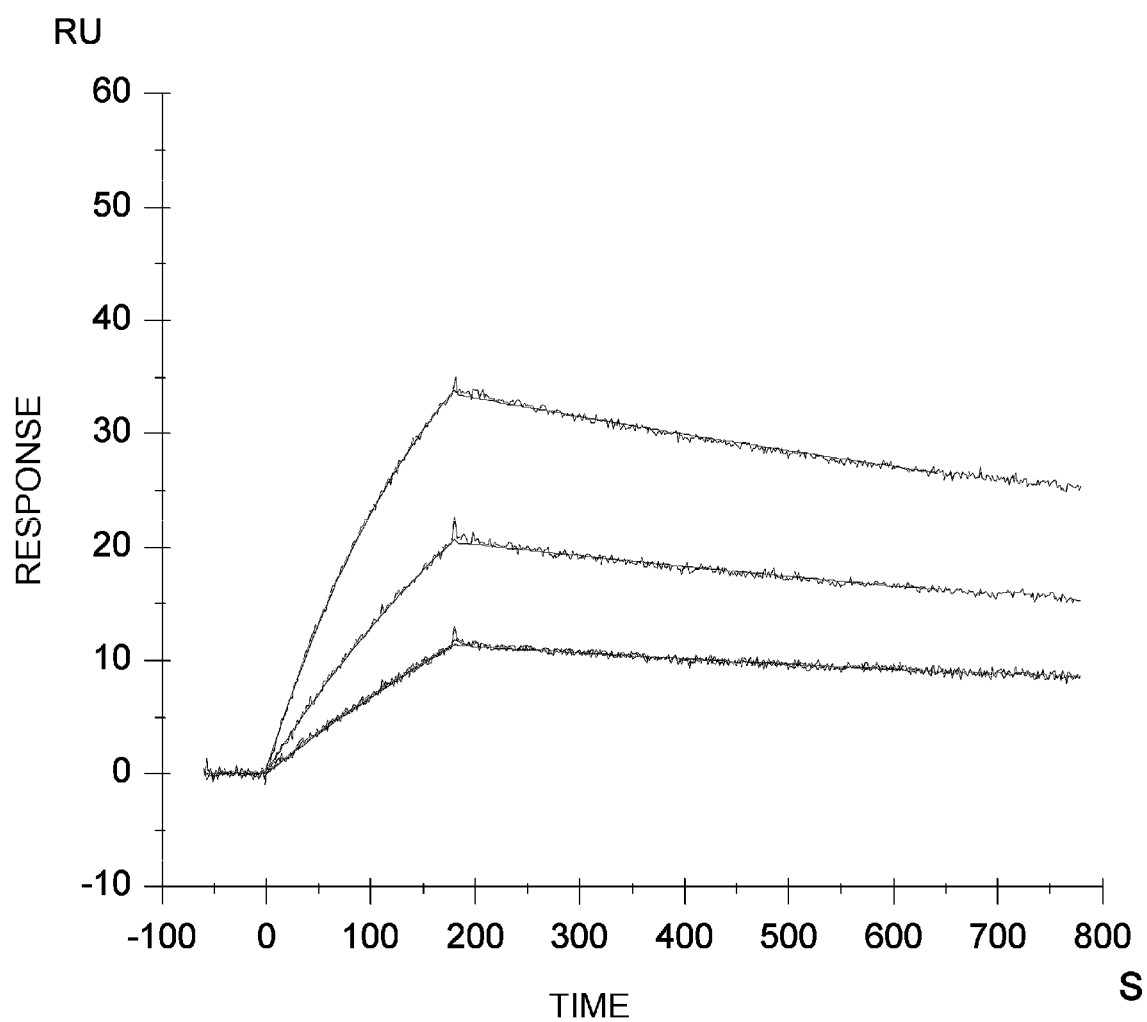
FIG. 13 is a graph showing a sensorgram for the interaction between SR344 and H53/L28.

The sensorgrams obtained for WT and H53/L28 are shown in FIG. 13. Kinetic analysis was carried out using Biacore-specific data analysis software Biacore T100 Evaluation Software. The result is shown in Table 6. The result showed that $K_D$ in H53/L28 was reduced about six-fold compared to WT, and this means the affinity was improved about six-fold. Specifically, the comparison of H53/L28 with WT revealed that the affinity could be improved six-fold while reducing the isoelectric point at the same time. A detailed analysis suggested that the amino acid mutation that contributed to the affinity improvement was the substitution of glycine for threonine at L51. In other words, it is thought that the affinity can be improved by substituting glycine for threonine at L51.

TABLE 6

| SAMPLE | $k_a$ (1/Ms) | $k_d$ (1/s) | $K_D$ (M) |
|---|---|---|---|
| WT | 4.9E+5 | 2.0E−3 | 4.0E−9 |
| H53/L28 | 7.6E+5 | 5.2E−4 | 6.8E−10 |

Prediction of T-Cell Epitopes in H53/L28 Using TEPITOPE

H53/L28 was analyzed by TEPITOPE (Methods. 2004 December; 34(4):468-75). The result showed that the number of potential HLA-binding peptides was significantly reduced in H53/L28 as compared to WT. This suggests reduction of the immunogenicity risk in human.

[Example 4] Assessment of the Plasma Retention of H53/L28

Assessment of the Modified Antibody H53/L28 for its Plasma Pharmacokinetics in Normal Mice To assess the retention in plasma of the modified antibody H53/L28 with reduced isoelectric point, the plasma pharmacokinetics was compared between WT and the modified antibody H53/L28 using normal mice.

A single dose of WT or H53/L28 was intravenously or subcutaneously administered at 1 mg/kg to mice (C57BL/6J; Charles River Japan, Inc.). The blood was collected before administration and 15 minutes, 2 hours, 8 hours, 1 day, 2 days, 5 days, 7 days, 14 days, 21 days, and 28 days after administration. Note that the blood was collected at 15 minutes after administration only from the intravenous administration groups. The collected blood was immediately centrifuged at 4° C. and 15,000 rpm for 15 minutes to obtain plasma. The separated blood plasma was stored until use in a freezer at −20° C. or below.

Figure 14:
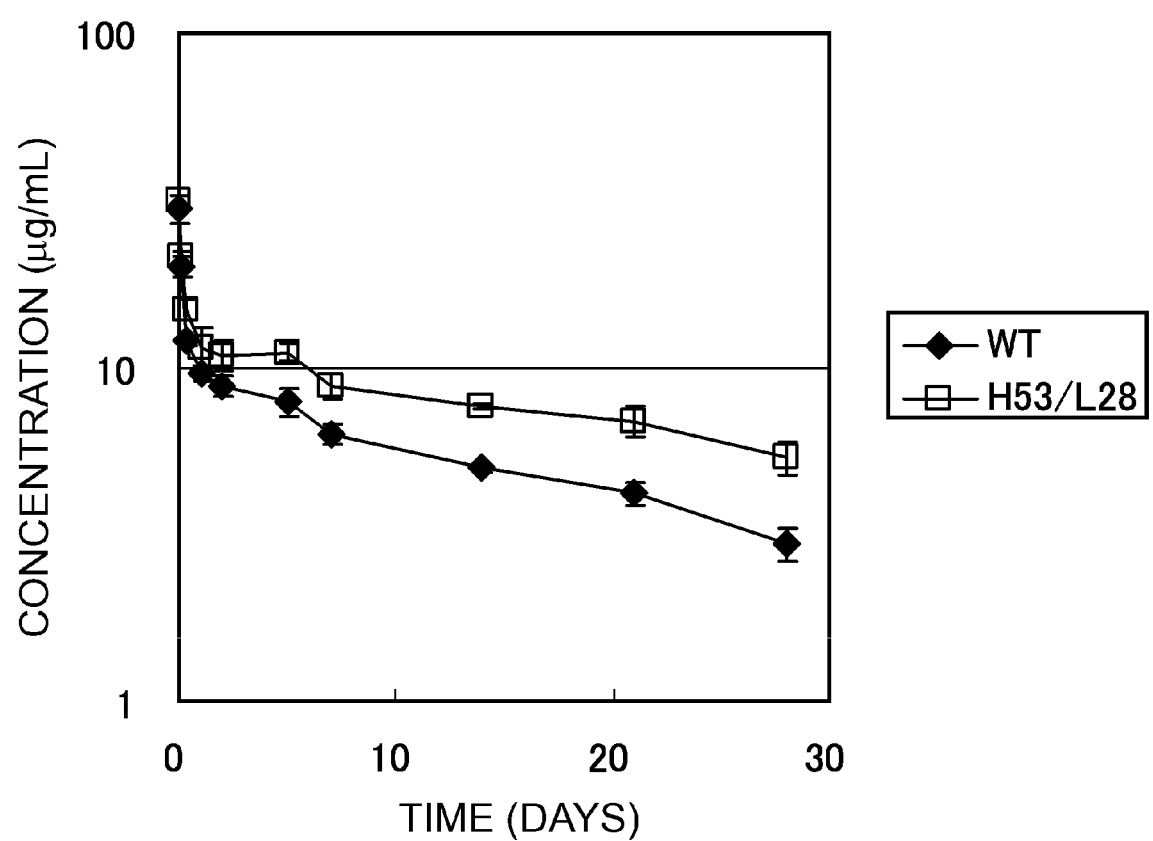
FIG. 14 is a graph showing transitions in the plasma concentrations of WT and H53/L28 after intravenous administration to mice.
Figure 15:
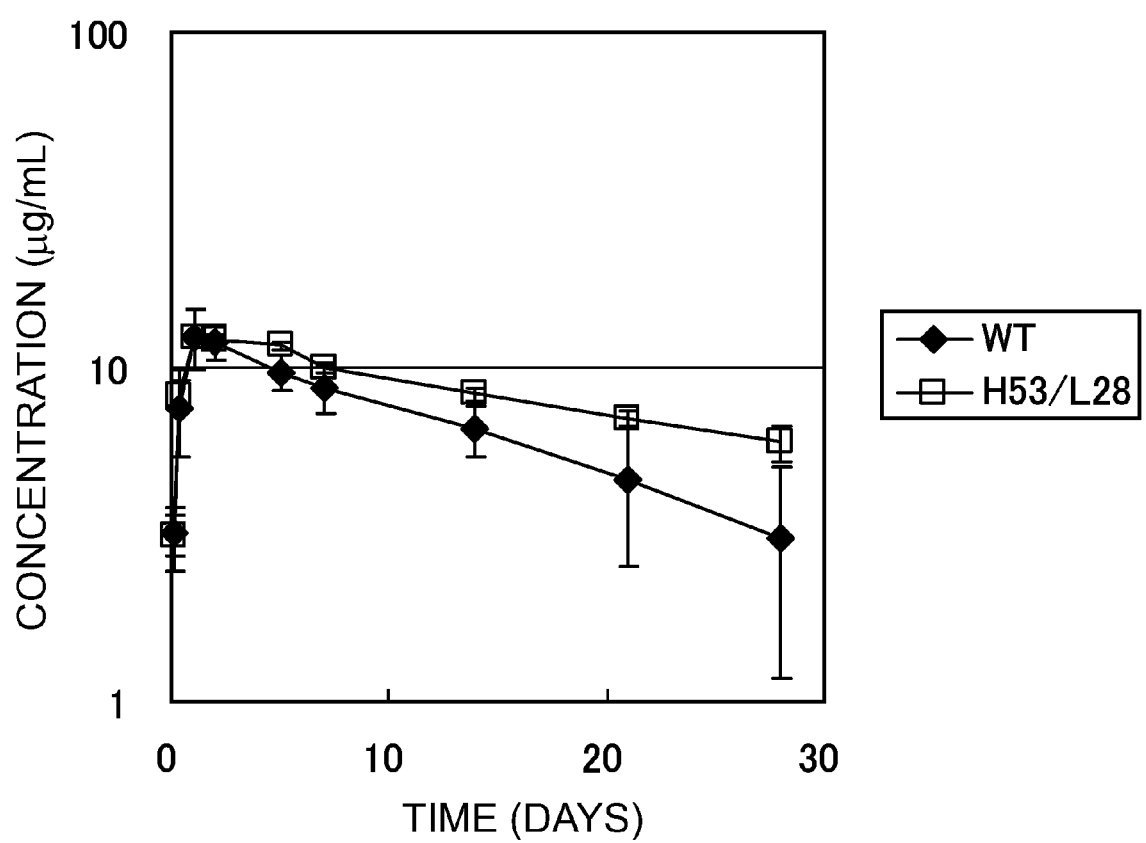
FIG. 15 is a graph showing transitions in the plasma concentrations of WT and H53/L28 after subcutaneous administration to mice.

The concentration in the mouse plasma was determined by ELISA. First, Recombinant Human IL-6 sR (R&D Systems) was biotinylated using EZ-Link™ Sulfo-NFS-Biotinylation Kit (PIERCE). The biotinylated human-sIL-6R was dispensed into Reacti-Bind Streptavidin High Binding Capacity (HBC) Coated Plates (PIERCE), and then incubated at room temperature for one hour or more. Thus, human-sIL-6R-immobilized plates were prepared as described above. Mouse plasma samples and standard samples (plasma concentrations: 3.2, 1.6, 0.8, 0.4, 0.2, 0.1, and 0.05 µg/ml) were prepared and dispensed into the human-sIL-6R-immobilized plates. The samples were incubated at room temperature for one hour, and then anti-human IgG-AP (Sigma) was added for reaction. After color development using the BluePhos Microwell Phosphatase Substrates System (Kirkegaard & Perry Laboratories) as a substrate, the absorbance at 650 nm was measured with a microplate reader. The plasma concentrations in the mice were determined based on the absorbance of the calibration curve using the analytical software SoftMax Pro (Molecular Devices). The time courses for the plasma concentrations of WT and H53/L28 after intravenous administration and subcutaneous administration are shown in FIGS. 14 and 15, respectively.

The obtained plasma concentration-time data were evaluated by a model-independent analysis using the pharmacokinetic analysis software WinNonlin (Pharsight) to estimate pharmacokinetic parameters (AUC, clearance (CL), and half-life (T1/2)). T1/2 was estimated from the plasma concentrations at the last three points or those in the terminal phase automatically selected by WinNonlin. BA was calculated from the ratio of AUC after subcutaneous administration versus AUC after intravenous administration. The determined pharmacokinetic parameters are shown in Table 7.

TABLE 7

|  | iv | | sc | | |
| --- | --- | --- | --- | --- | --- |
|  | CL mL/h/kg | T½ day | CL/F mL/h/kg | T½ day | BA % |
| WT | 0.177 | 18.5 | 0.180 | 14.7 | 113 |
| H53/L28 | 0.102 | 23.5 | 0.086 | 29.7 | 121 |

The half-life (T1/2) of H53/L28 in plasma after intravenous administration was prolonged to about 1.3 times that of WT, while the clearance was reduced about 1.7 times. T1/2 of H53/L28 after subcutaneous administration was prolonged to about twice that of WT, while the clearance was reduced about 2.1 times. Thus, the retention of H53/L28 in plasma could be significantly improved by lowering the isoelectric point of WT.

H53/L28 is a humanized anti-IL-6 receptor antibody with improved binding activity and neutralizing activity, reduced immunogenicity risk, and significantly improved retention in plasma as compared to the humanized PM-1 antibody (WT). Therefore, the modifications used to create H53/L28 may be very useful in the development of pharmaceuticals.

[Example 5] Preparation of the PF1 Antibody

Construction of Expression and Mutagenesis Vectors for the Humanized PM-1 Antibody A total of four CDR mutations discovered in Example 2 which improved the affinity of RDC_23 (two each in the heavy and light chains) were introduced into H53/L28 created in Example 4. The heavy and light chains obtained by introducing the mutations of RDC_23 into H53/L28 were named PF1_H and PF1_L, respectively. The modified antibody was prepared, expressed, and purified by the method described in Example 1. The amino acid sequences of PF1_H and PF1_L are shown in SEQ ID NOs: 22 and 23, respectively.

Assessment for the Human IL-6 Receptor-Neutralizing Activity

Figure 16:
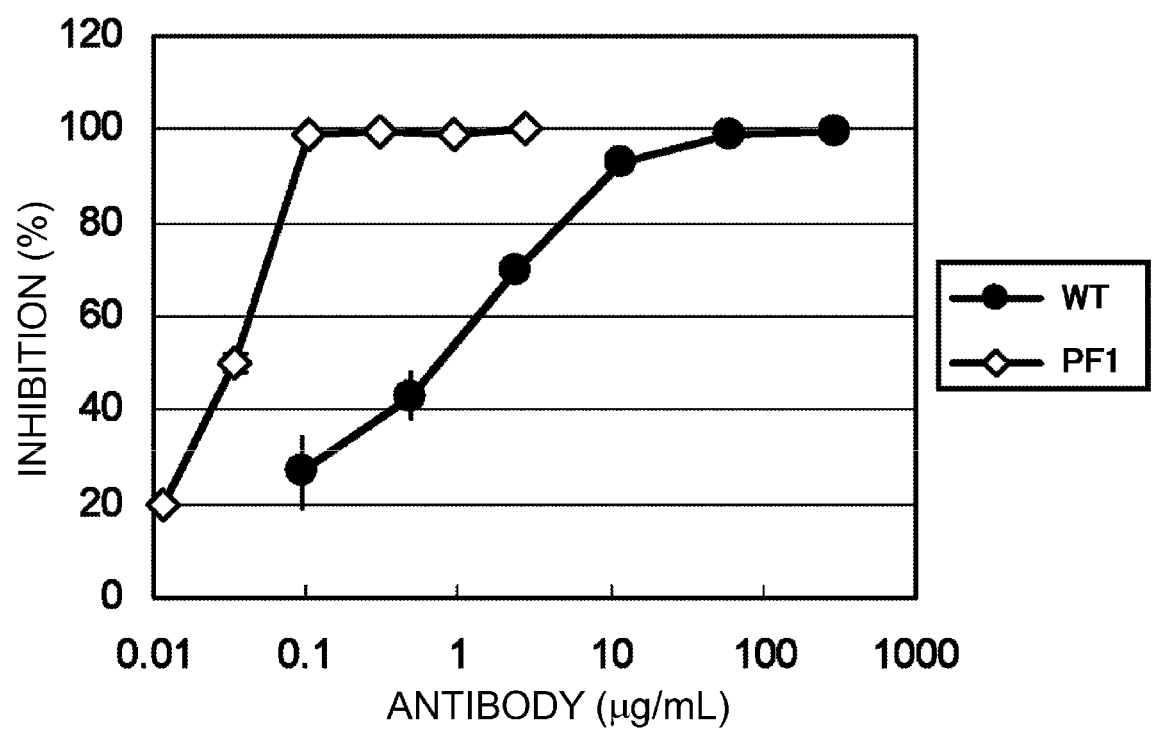
FIG. 16 is a graph showing the BaF/gp130-neutralizing activities of WT and PF1.

The neutralizing activity of the purified PF1 antibody was assessed by the method described in Example 1. The neutralizing activity assessment was carried out using 600 ng/ml human interleukin-6 (TORAY). The neutralizing activities of WT and PF1 are shown in FIG. 16. PF1 was demonstrated to have an activity about 100 to 1,000 times higher than WT in terms of 100% inhibitory concentration.

Biacore-Based Analysis of the PF1 Antibody for the Affinity for Human IL-6 Receptor This measurement was carried out under the same conditions described in Example 2. The running buffer used was HBS-EP+, and the flow rate was 20 µl/min. Each antibody was prepared so that about 100 RU of the antibody was bound to Protein A/G. SR344 was prepared at 0, 0.065, 0.131, and 0.261 µg/ml using HBS-EP+ and used as an analyte. In the first step of the measurement, the antibody in solution was bound to Protein A/G, and the analyte solution was allowed to interact therewith. After three minutes of interaction, the solution was switched to HBS-EP+, and the dissociation phase was monitored for 10 or 15 minutes. After measurement of the dissociation phase, the sensor chip was regenerated by washing with 10 µl of 10 mM glycine-HCl (pH 1.5). The association, dissociation, and regeneration constitute one analysis cycle. Each antibody was measured according to this cycle.

Figure 17:
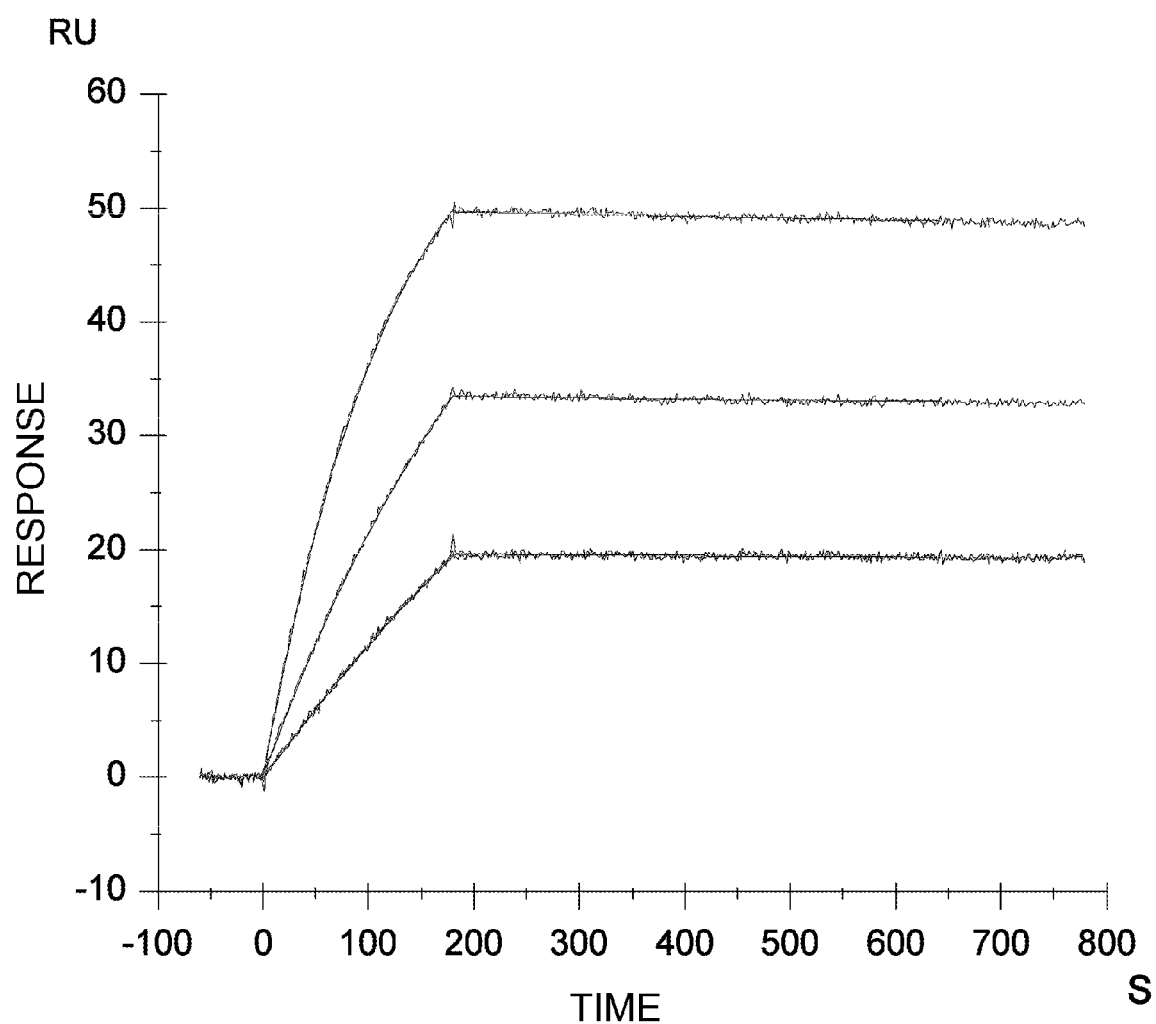
FIG. 17 is a graph showing a sensorgram for the interaction between SR344 and PF1.

The obtained sensorgram for PF1 is shown in FIG. 17. The sensorgram was kinetically analyzed using the Biacore-specific data analysis software, Biacore T100 Evaluation Software. The result is shown along with those for WT and H53/L28 in Table 8. The result showed that the affinity of PF1 was about 150 times improved as compared to WT. RDC_23 has a high affinity as a result of combination through affinity maturation, and H53/L28 has a prolonged retention in plasma and improved affinity. Through combination of both, PF1 obtained a higher affinity than RDC_23 or H53/L28 by an additive effect.

TABLE 8

| SAMPLE | $k_a$ (1/Ms) | $k_d$ (1/s) | $K_D$ (M) |
| --- | --- | --- | --- |
| WT | 4.9E+05 | 2.0E−03 | 4.0E−09 |
| RDC_23 | 6.4E+05 | 4.3E−05 | 6.7E−11 |
| H53/L28 | 7.6E+05 | 5.2E−04 | 6.8E−10 |
| PF1 | 1.3E+06 | 3.5E−05 | 2.7E−11 |

Assessment of the PF1 Antibody for Thermal Stability by DSC

To assess the thermal stability of the PF1 antibody, the midpoint of thermal denaturation (Tm value) was determined by DSC. The purified antibodies of WT and PF1 were dialyzed against a solution of 20 mM sodium acetate, 150 mM NaCl, pH 6.0 (EasySEP, TOMY). DSC measurement was carried out at a heating rate of 1° C./min from 40° C. to 100° C. at a protein concentration of about 0.1 mg/ml. The result showed that the Tm of the WT Fab domain was about 94° C. and that of the PF1 Fab domain was 91° C. The Tm of the Fab domain of an IgG1 type antibody molecule is generally within the range of about 60° C. to 85° C. (Biochem. Biophys. Res. Commun. 2007 Apr. 13; 355(3): 751-7; Mol Immunol. 2007 April; 44(11):3049-60). Thus, the observed thermal stability of the PF1 antibody was extremely high as compared to those of typical IgG1 molecules.

Assessment of the PF1 Antibody for Stability at High Concentrations

The PF1 antibody was assessed for stability in high concentration formulations. Purified WT and PF1 antibodies were dialyzed against a solution of 20 mM histidine chloride, 150 mM NaCl, pH 6.5 (EasySEP, TOMY), and then concentrated by ultrafilters. The antibodies were tested for stability at high concentrations. The conditions were as follows.

Figure 18:
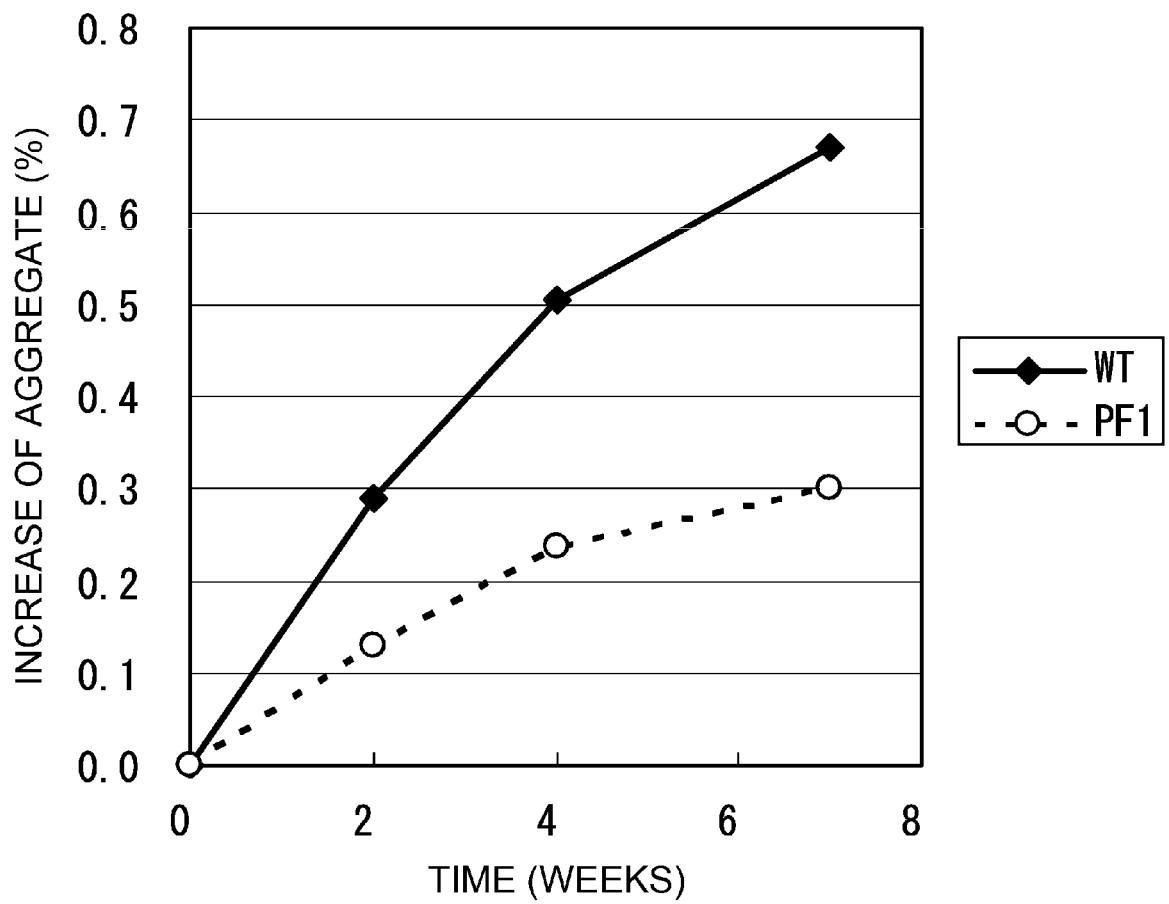
FIG. 18 is a graph showing the result of testing the stability of WT and PF1 at high concentrations.

Antibodies: WT and PF1
Buffer: 20 mM histidine chloride, 150 mM NaCl, pH 6.0
Concentration: 145 mg/ml
Storage temperature and time period: 25° C. for two weeks, 25° C. for four weeks, or 25° C. for seven weeks
Aggregation assessment method:
System: Waters Alliance
Column: G3000SWxl (TOSOH)
Mobile phase: 50 mM sodium phosphate, 300 mM KCl, pH 7.0
Flow rate, wavelength: 0.5 ml/min, 220 nm
100 times diluted samples were analyzed The contents of aggregate in the initial formulations (immediately after preparation) and formulations stored under various conditions were evaluated by the gel filtration chromatography described above. Differences (amounts increased) in the content of aggregate relative to the initial formulations are shown in FIG. 18. As a result, the following findings were obtained: (1) both WT and PF1 were very stable; (2) the amount of aggregate increased during seven weeks at 25° C. was about 0.7% for WT and about 0.3% for PF1, which means that the amount of aggregate increased per month at 25° C. was about 0.4% and about 0.17%, respectively; and (3) PF1 was markedly stable at high concentrations. WO 2003/039485 has disclosed data on the stability of Daclizumab, which is available as a high concentration IgG formulation on the market, at 25° C. in a 100 mg/ml preparation. The amount of aggregate increased per month at 25° C. is about 0.3% in the formulation of 100 mg/ml Daclizumab. Even when compared to Daclizumab, PF1 exhibits an excellent stability at high concentrations. The increase of the number of aggregates is very problematic in developing high-concentration liquid formulations as pharmaceuticals. The increase of PF1 antibody aggregate was demonstrated to be very small even when the concentration of the PF1 antibody was high.

PF1 is a molecule resulting from modification of WT. The purposes of the modification include improvement of the antigen-binding activity, improvement of the retention in plasma by lowering its isoelectric point, reduction of the immunogenicity risk by removing T-cell epitopes and remaining mouse sequences, and improvement of the stability. Indeed, the stability of PF1 in 100 mg/ml or higher concentration preparations was demonstrated to be very high even when compared to WT. Stable and highly convenient high-concentration formulations for subcutaneous administration can be provided by using such molecules.

[Example 6] PK/PD Test of the PF1 Antibody Using Human IL-6 Receptor Transgenic Mice Test for Pharmacokinetics (In Vivo Kinetics) Using Human IL-6 Receptor Transgenic Mice WT and PF1 prepared in Example 5 were assessed for their pharmacokinetics (in vivo kinetics) in human IL-6 receptor transgenic mice (hIL-6R tg mice; Proc. Natl. Acad. Sci. USA. 1995 May 23; 92(11):4862-6) and their human soluble IL-6 receptor-neutralizing activity in vivo. WT and PF1 were intravenously administered once at 10 mg/kg into hIL-6R tg mice. Blood was collected before administration and 15 minutes, two, four, and eight hours, one day, two, four, and seven days after administration. The blood collected was immediately centrifuged at 4° C. and 15,000 rpm for 15 minutes to obtain blood plasma. The separated plasma was stored in a freezer at −20° C. or below until use.

Figure 19:
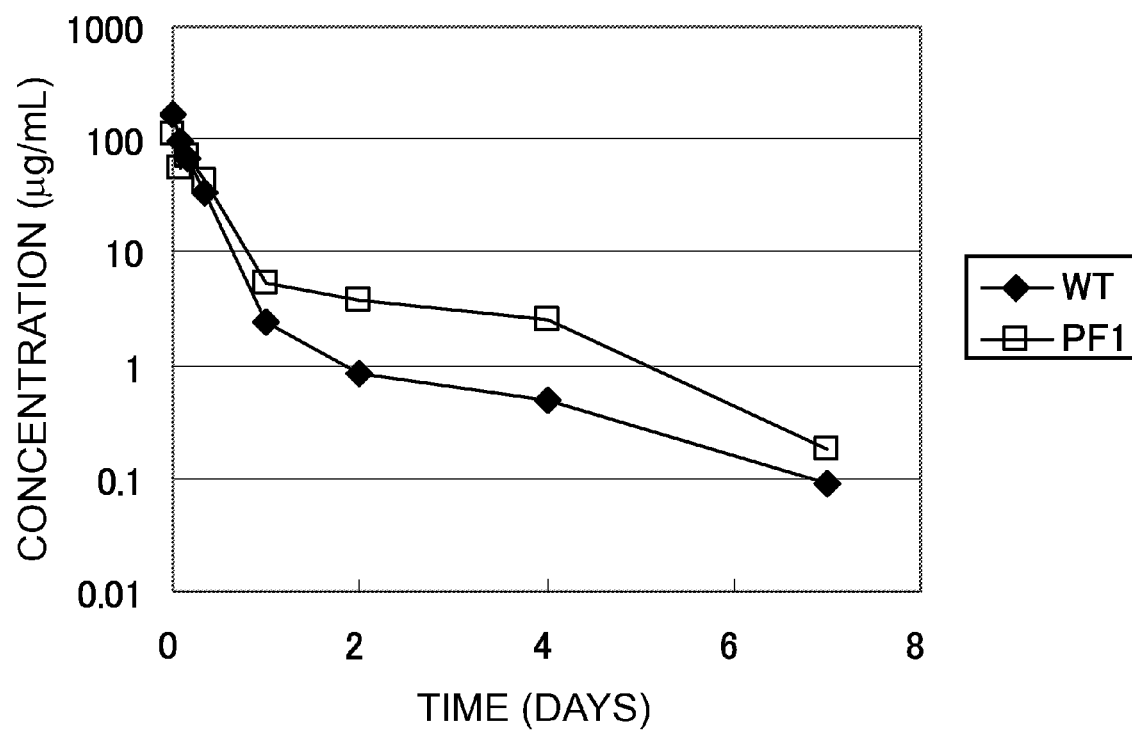
FIG. 19 is a graph showing transitions in the plasma concentrations of WT and PF1 after intravenous administration to human IL-6 receptor transgenic mice.

The concentrations in the mouse plasma were determined by ELISA. Standard samples were prepared at 6.4, 3.2, 1.6, 0.8, 0.4, 0.2, and 0.1 µg/ml as concentrations in plasma. Mouse plasma samples and standard samples were dispensed into immunoplates (Nunc-Immuno Plate, MaxiSorp (Nalge Nunc International)) immobilized with Anti-human IgG (γ-chain specific) F(ab')2 (Sigma). The samples were incubated at room temperature for one hour, and then Goat Anti-Human IgG-BIOT (Southern Biotechnology Associates) and Streptavidin-alkaline phosphatase conjugate (Roche Diagnostics) were subsequently added for reaction. After color development using the BluePhos Microwell Phosphatase Substrates System (Kirkegaard & Perry Laboratories) as a substrate, the absorbance at 650 nm was measured with a microplate reader. The concentrations in the mouse plasma were determined based on the absorbance of the calibration curve using the analytical software SoftMax Pro (Molecular Devices). The time courses for the plasma concentrations of WT and PF1 are shown in FIG. 19. The plasma PF1 concentration four days after administration was about five times higher than WT. This suggests that the retention of PF1 in the plasma of human IL-6 receptor transgenic mice is improved as compared to WT.

The human IL-6 receptor transgenic mice have been demonstrated to produce plasma circulating human soluble IL-6 receptor. Thus, the human soluble IL-6 receptor-neutralizing efficacy in plasma can be assessed by administering anti-human IL-6 receptor antibodies to human IL-6 receptor transgenic mice.

The concentration of free human soluble IL-6 receptor in mouse plasma was determined to assess the degree of neutralization of human soluble IL-6 receptor by administration of WT or PF1.

6 µl of the mouse plasma was diluted two-fold with a dilution buffer containing BSA. The diluted plasma was loaded onto an appropriate amount of rProtein A Sepharose Fast Flow resin (GE Healthcare) dried in 0.22-µm filter cup (Millipore), and all IgG type antibodies (mouse IgG, anti-human IL-6 receptor antibody, and anti-human IL-6 receptor antibody-human soluble IL-6 receptor complex) in the plasma were adsorbed by Protein A. Then, the solution in the cup was spinned down using a high-speed centrifuge to collect the solution that passed through. Since the solution that passed through does not contain Protein A-bound anti-human IL-6 receptor antibody-human soluble IL-6 receptor complex, the concentration of free soluble IL-6 receptor can be determined by measuring the concentration of human soluble IL-6 receptor in the passed solution. The concentration of soluble IL-6 receptor was determined using Quantikine Human IL-6 sR (R&D Systems). The concentration of free soluble IL-6 receptor in mice was measured 4, 8, 24, 48, 96, and 168 hours after administration of WT or PF1 according to the attached instruction manual.

Figure 20:
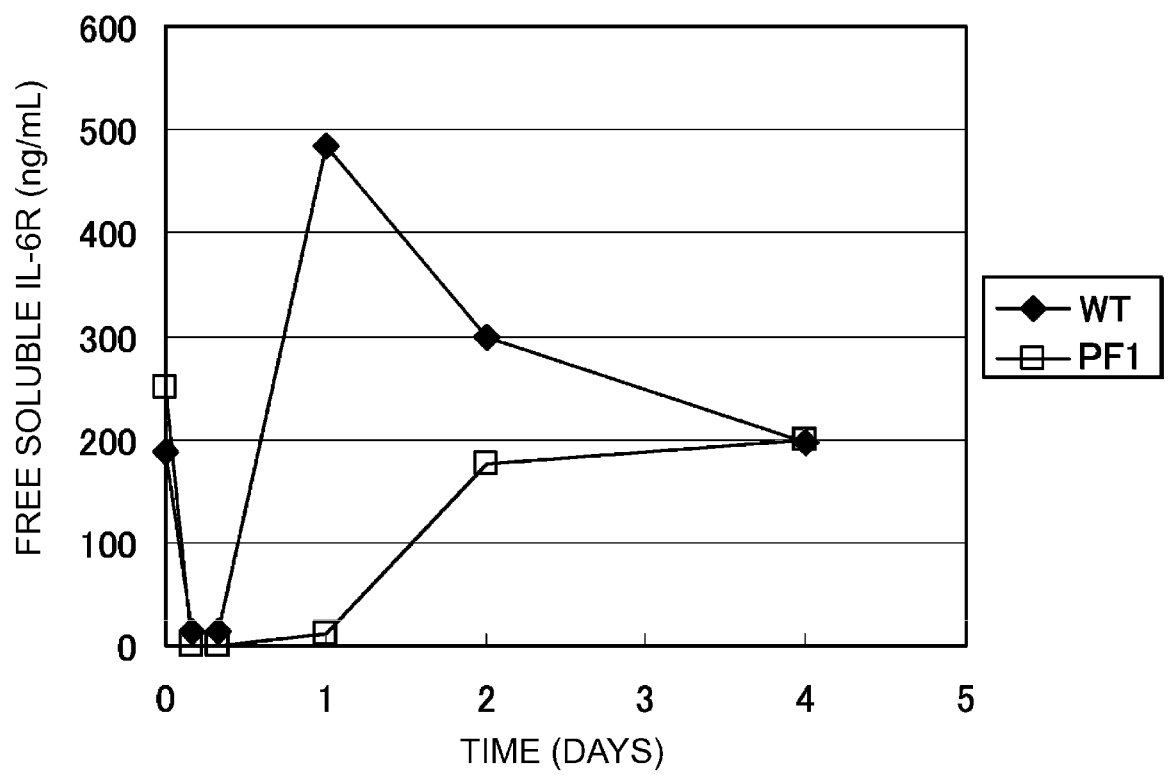
FIG. 20 is a graph showing transitions in the plasma concentrations of free human soluble IL-6 receptor after intravenous administration of WT or PF1 to human IL-6 receptor transgenic mice.

The result is shown in FIG. 20. In both cases of WT and PF1, the concentration of free soluble IL-6 receptor was 10 ng/ml or less, four hours and up to eight hours after intravenous administration of a single dose of WT or PF1 at 10 mg/kg, indicating that the human soluble IL-6 receptor was neutralized. However, while the concentration of free soluble IL-6 receptor was about 500 ng/ml 24 hours after WT administration, it was 10 ng/ml or less after PF1 administration. This indicates that PF1 neutralizes human soluble IL-6 receptor in a more sustainable way than WT.

PF1 was created by combining RDC_23 discovered through affinity maturation and H53/L28 exhibiting improved properties such as prolonged retention in plasma, and thus predicted to be able to exhibit prolonged retention in plasma and high neutralizing activity in vivo. Indeed, as compared to WT, PF1 was demonstrated to be more sustainable in plasma and to exhibit a prolonged neutralizing effect in human IL-6 receptor transgenic mice producing human soluble IL-6 receptor.

PF1 is more superior than WT (humanized PM-1 antibody) in terms of immunogenicity risk and stability in high concentration preparations, as well as retention in plasma and IL-6 receptor-neutralizing effect in human IL-6 receptor transgenic mice. Thus, the modifications made to create PF1 may be very useful in the development of pharmaceuticals.

[Example 7] Improvement of the Stability of IgG2 and IgG4 Under Acidic Condition Construction of Expression Vectors for IgG2- or IgG4-Converted Humanized IL-6 Receptor Antibodies and Expression of the Antibodies To reduce the Fcγ receptor-binding activity, the constant region of humanized PM-1 antibody (Cancer Res. 1993 Feb. 15; 53(4):851-6), which is of the IgG1 isotype, was substituted with IgG2 or IgG4 (Mol. Immunol. 1993 January; 30(1):105-8) to generate molecules WT-IgG2 (SEQ ID NO:

109) and WT-IgG4 (SEQ ID NO: 110). An animal cell expression vector was used to express the IgGs. An expression vector, in which the constant region of humanized PM-1 antibody (IgG1) used in Example 1 was digested with NheI NotI and then substituted with the IgG2 or IgG4 constant region by ligation, was constructed. The nucleotide sequence of each DNA fragment was determined with a DNA sequencer (ABI PRISM 3730xL DNA Sequencer or ABI PRISM 3700 DNA Sequencer (Applied Biosystems)) using the BigDye Terminator Cycle Sequencing Kit (Applied Biosystems) according to the attached instruction manual. Using the WT light chain, WT-IgG1, WT-IgG2, and WT-IgG4 were expressed by the method described in Example 1.

(1) Humanized PM-1 antibody (WT-IgG1) heavy chain, SEQ ID NO: 15 (amino acid sequence)
(2) WT-IgG2 heavy chain, SEQ ID NO: 109 (amino acid sequence)
(3) WT-IgG4 heavy chain, SEQ ID NO: 110 (amino acid sequence)

Purification of WT-IgG1, WT-IgG2, and WT-IgG4 Through Elution from Protein a Using Hydrochloric Acid 50 µl of rProtein A Sepharose™ Fast Flow (Amersham Biosciences) suspended in TBS was added to the obtained culture supernatants, and the combined solutions were mixed by inversion at 4° C. for four hours or more. The solutions were transferred into 0.22-µm filter cups of Ultrafree®-MC (Millipore). After washing three times with 500 µl of TBS, the rProtein A Sepharose™ resins were suspended in 100 µl of 10 mM HCl/150 mM NaCl (pH 2.0) and the mixtures were incubated for two minutes to elute the antibodies (hydrochloric acid elution). Immediately, the eluates were neutralized by adding 6.7 µl of 1.5 M Tris-HCl (pH 7.8). The elution was carried out twice, yielding 200 µl of purified antibodies.

Gel Filtration Chromatography Analysis of WT-IgG1, WT-IgG2, and WT-IgG4 Purified by Hydrochloric Acid Elution The contents of aggregate in the purified samples obtained by hydrochloric acid elution were assessed by gel filtration chromatography analysis.

Figure 21:
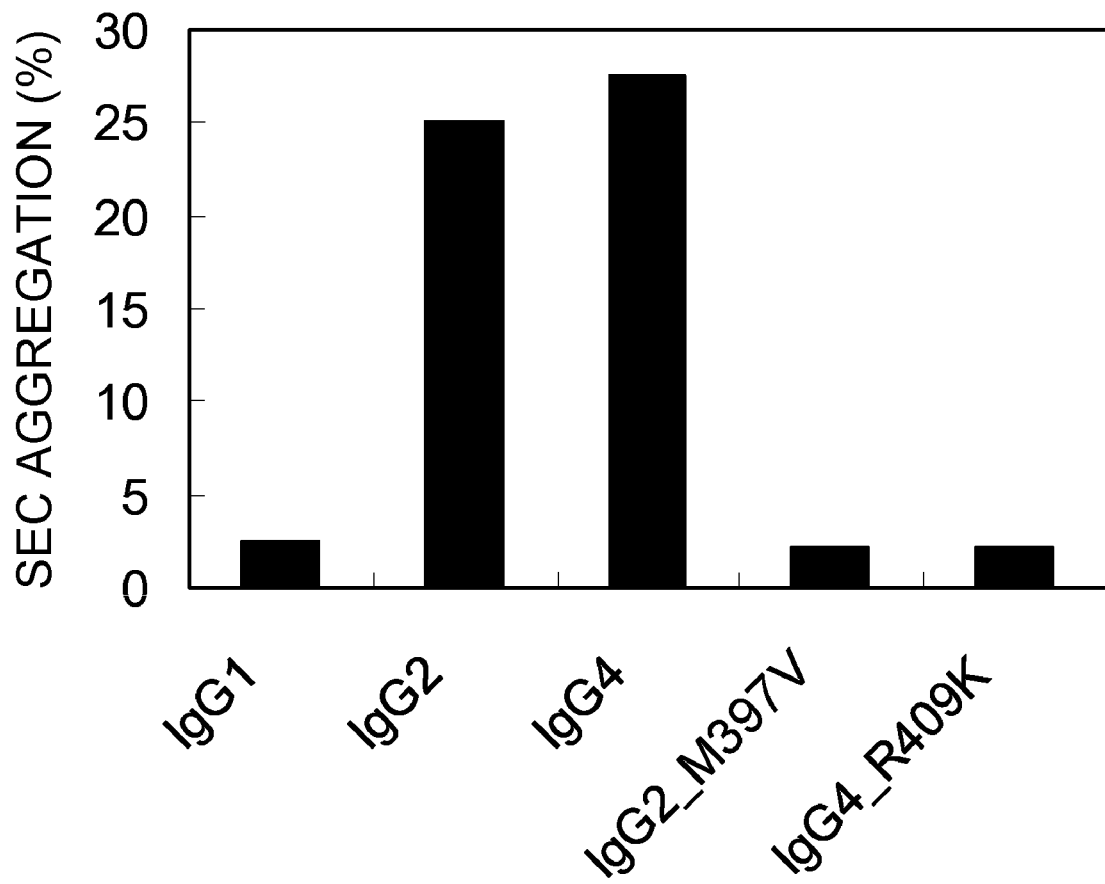
FIG. 21 is a graph showing the result of using gel filtration chromatography to analyze the content of aggregates in WT-IgG1, WT-IgG2, WT-IgG4, IgG2-M397V, and IgG4-R409K purified by hydrochloric acid elution.

Aggregation Assessment Method:
  System: Waters Alliance
  Column: G3000SWx1 (TOSOH)
  Mobile phase: 50 mM sodium phosphate, 300 mM KCl, pH 7.0
  Flow rate, wavelength: 0.5 ml/min, 220 nm The result is shown in FIG. 21. While the content of aggregate in WT-IgG1 after purification was about 2%, those of WT-IgG2 and WT-IgG4 after purification were about 25%. This suggests that IgG1 is stable to acid during hydrochloric acid elution, and by contrast, IgG2 and IgG4 are unstable and underwent denaturation/aggregation. Thus, the stability of IgG2 and IgG4 under acidic condition was demonstrated to be lower than that of IgG1. Protein A has been frequently used to purify IgG molecules, and the IgG molecules are eluted from Protein A under acidic condition. In addition, virus inactivation, which is required when developing IgG molecules as pharmaceuticals, is generally carried out under acidic condition. It is thus desirable that the stability of IgG molecules under acidic condition is higher. However, the stability of IgG2 and IgG4 molecules under acidic condition was found to be lower than that of IgG1, and suggests for the first time that there is a problem of denaturation/aggregation under acidic condition in developing IgG2 and IgG4 molecules as pharmaceuticals. It is desirable that this problem of denaturation/aggregation be overcome when developing them as pharmaceuticals. To date, however, no report has been published on a method for solving this problem through amino acid substitution.

Preparation and Assessment of WT-IgG2 and WT-IgG4 Having a Modified CH3 Domain

The stability of IgG2 and IgG4 molecules under acidic condition was demonstrated to be lower than that of IgG1. Thus, modified forms of IgG2 and IgG4 molecules were tested to improve the stability under acidic condition. According to models for the constant regions of IgG2 and IgG4 molecules, one of the potential destabilizing factors under acidic condition was thought to be the instability at the CH3-CH3 domain interface. As a result of various examinations, methionine at position 397 in the EU numbering system in IgG2, or arginine at position 409 in the EU numbering system in IgG4 was thought to destabilize the CH3/CH3 interface. Then, modified IgG2 and IgG4 antibodies were prepared. A modified IgG2 antibody comprises the substitution of valine for methionine at position 397 in the EU numbering system (IgG2-M397V, SEQ ID NO: 111 (amino acid sequence)) and a modified IgG4 antibody comprises the substitution of lysine for arginine at position 409 in the EU numbering system (IgG4-R409K, SEQ ID NO: 112 (amino acid sequence)).

The methods used for constructing expression vectors for the antibodies of interest, and expressing and purifying the antibodies, were the same as those used for the hydrochloric acid elution described above. Gel filtration chromatography analysis was carried out to estimate the contents of aggregate in the purified samples obtained by hydrochloric acid elution from Protein A.

Aggregation Assessment Method:
  System: Waters Alliance
  Column: G3000SWx1 (TOSOH)
  Mobile phase: 50 mM sodium phosphate, 300 mM KCl, pH 7.0
  Flow rate, wavelength: 0.5 ml/min, 220 nm The result is shown in FIG. 21. While the content of aggregate in WT-IgG1 after purification was about 2%, those in WT-IgG2 and WT-IgG4 after purification were about 25%. By contrast, the contents of aggregate in variants with modified CH3 domain, IgG2-M397V and IgG4-R409K, were comparable (approx. 2%) to that in IgG1. This finding demonstrates that the stability of an IgG2 or IgG4 antibody under acidic condition can be improved by substituting valine for methionine of IgG2 at position 397 in the EU numbering system or lysine for arginine of IgG4 at position 409 in the EU numbering system, respectively. Furthermore, the midpoint temperatures of thermal denaturation of WT-IgG2, WT-IgG4, IgG2-M397V, and IgG4-R409K were determined by the same method as described in Example 5. The result showed that the Tm value for the modified CH3 domain was higher in IgG2-M397V and IgG4-R409K as compared to WT-IgG2 and WT-IgG4, respectively. This suggests that IgG2-M397V and IgG4-R409K are also superior in terms of thermal stability as compared to WT-IgG2 and WT-IgG4, respectively.

IgG2 and IgG4 are exposed to acidic condition in virus inactivation process and in the purification process using Protein A. Thus, denaturation/aggregation in the above processes was problematic. However, it was discovered that the problem could be solved by using IgG2-M397V and IgG4-R409K for the sequences of IgG2 and IgG4 constant regions. Thus, these modifications were revealed to be very useful in developing IgG2 and IgG4 antibody pharmaceuticals. Furthermore, the usefulness of IgG2-M397V and IgG4-R409K was also demonstrated by the finding that they are superior in thermal stability.

[Example 8] Improvement of Heterogeneity Derived from Disulfide Bonds in IgG2

Purification of WT-IgG1, WT-IgG2, and WT-IgG4 Through Acetic Acid Elution from Protein A 50 µl of rProtein A Sepharose™ Fast Flow (Amersham Biosciences) suspended in TBS was added to the culture supernatants obtained in Example 7, and the combined solutions were mixed by inversion at 4° C. for four hours or more. The solutions were transferred into 0.22-µm filter cups of Ultrafree®-MC (Millipore). After washing three times with 500 µl of TBS, the rProtein A Sepharose™ resins were suspended in 100 µl of aqueous solution of 50 mM sodium acetate (pH 3.3) and the mixtures were incubated for two minutes to elute the antibodies. Immediately, the eluates were neutralized by adding 6.7 µl of 1.5 M Tris-HCl (pH 7.8). The elution was carried out twice, yielding 200 µl of purified antibodies.

Analysis of WT-IgG1, WT-IgG2, and WT-IgG4 by Cation Exchange Chromatography (IEC)

Purified WT-IgG1, WT-IgG2, and WT-IgG4 were analyzed for homogeneity by cation exchange chromatography.
Assessment Method Using IEC:
System: Waters Alliance
Column: ProPac WCX-10 (Dionex)
Mobile phase A: 25 mM MES-NaOH, pH 6.1
  B: 25 mM MES-NaOH, 250 mM Na-Acetate, pH 6.1
Flow rate, wavelength: 0.5 ml/min, 280 nm
Gradient B: 50%-75% (75 minutes) in the analysis of WT-IgG1
  B: 30%-55% (75 minutes) in the analysis of WT-IgG2 and WT-IgG4

Figure 22:
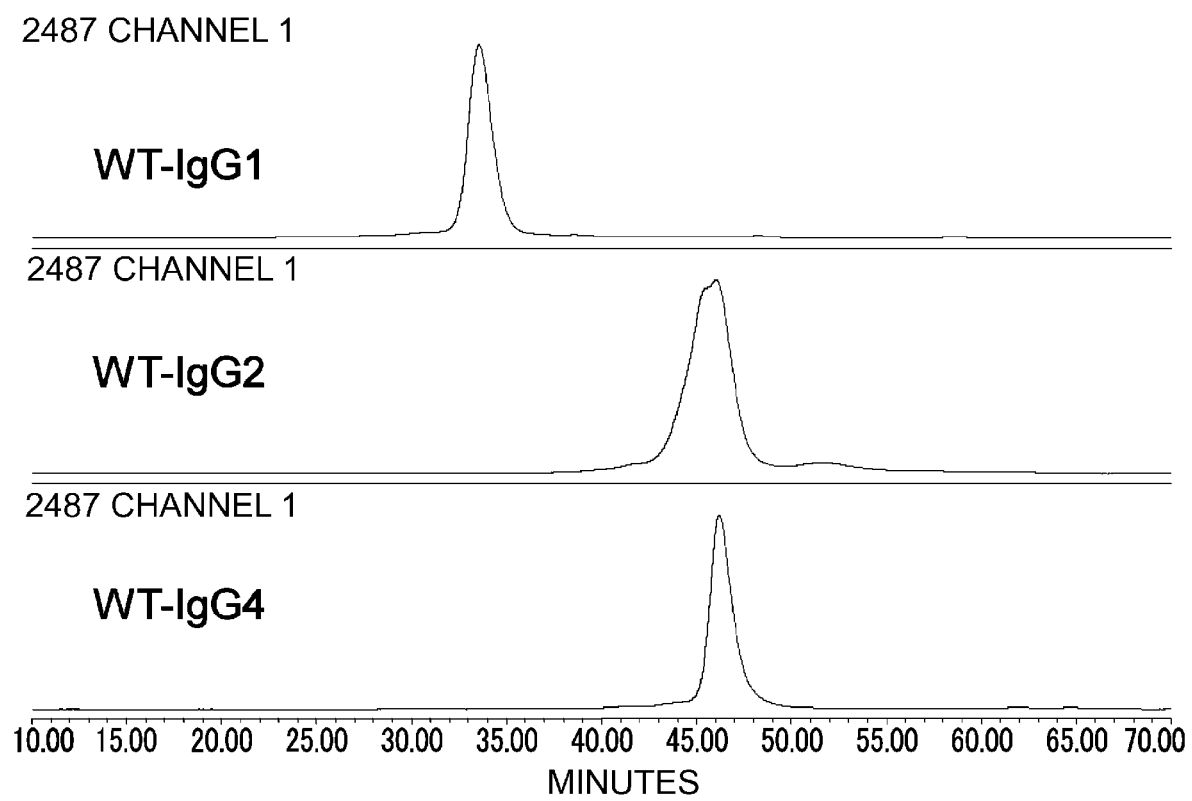
FIG. 22 is a diagram showing the result of cation exchange chromatography (IEC) analysis of WT-IgG1, WT-IgG2, and WT-IgG4.

The result is shown in FIG. 22. WT-IgG2 showed more than one peak in the ion exchange analysis while WT-IgG1 and WT-IgG4 exhibited a single peak. This suggests that the IgG2 molecule is more heterogeneous as compared to IgG1 and IgG4. Indeed, IgG2 isotypes have been reported to have heterogeneity derived from disulfide bonds in the hinge region (Chu G C et al., Pharm. Res. 2007 Mar. 24; 24(6): 1145-56). Thus, the hetero-peaks of IgG2 shown in FIG. 22 are also assumed to be desired substance/related substances derived from the disulfide bonds. It is difficult to produce antibody pharmaceuticals on a large scale while maintaining the difference in the heterogeneity of a desired substance/related substances between productions, and thus, antibody molecules to be developed as pharmaceuticals are desirably substances that are as homogeneous (less heterogeneous) as possible. For wild type IgG2, there is a problem of homogeneity which is important in developing antibody pharmaceuticals. Indeed, US20060194280 (A1) has shown that natural IgG2 gives various hetero-peaks as a result of the disulfide bonds in ion exchange chromatography analysis, and that the biological activity varies among these peaks. US20060194280 (A1) reports refolding in the purification process as a method for combining the hetero-peaks into a single one, but use of such a process in the production is costly and complicated. Thus, a preferred method for combining the hetero-peaks into a single one is based on amino acid substitution. Although the heterogeneity originated from disulfide bonds in the hinge region should be overcome to develop IgG2 as pharmaceuticals, no report has been published to date on a method for solving this problem through amino acid substitution.

Preparation and Assessment of Modified WT-IgG2 CH1 Domain and Hinge Region

Figure 23:
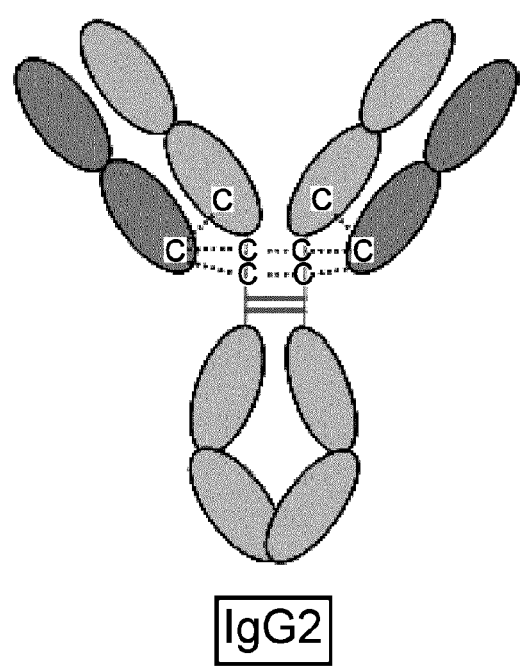
FIG. 23 is a diagram showing predicted disulfide bonding in the hinge region of WT-IgG2.

As shown in FIG. 23, there are various potential disulfide bond patterns for an IgG2 molecule. Possible causes of the heterogeneity derived from the hinge region of IgG2 were differential pattern of disulfide bonding and free cysteines. IgG2 has two cysteines (at positions 219 and 220 in the EU numbering system) in the upper hinge region, and cysteines adjacent to the two upper-hinge cysteines include cysteine at position 131 in the EU numbering system in the heavy chain CH1 domain and light chain C-terminal cysteine, and two corresponding cysteines in the heavy chain upper hinge of the dimerization partner. Specifically, there are eight cysteines in total in the vicinity of the upper hinge region of IgG2 when the antibody is in the associated form of H2L2. This may be the reason for the various heterogeneous patterns due to wrong disulfide bonding and free cysteines.

Figure 24:
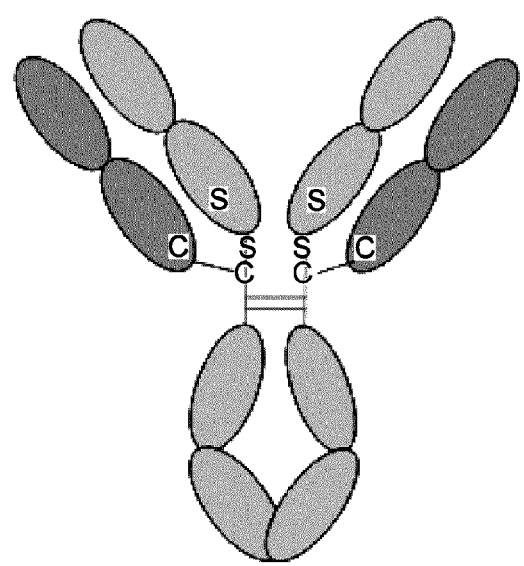
FIG. 24 is a diagram showing predicted disulfide bonding in the hinge region of WT-IgG2-SKSC.

The hinge region sequence and CH1 domain of IgG2 were modified to reduce the heterogeneity originated from the IgG2 hinge region. Examinations were conducted to avoid the heterogeneity of IgG2 due to differential pattern of disulfide bonding and free cysteines. The result of examining various modified antibodies suggested that the heterogeneity could be avoided without decreasing the thermal stability by substituting serine and lysine for cysteine and arginine at positions 131 and 133 in the EU numbering system, respectively, in the heavy chain CH1 domain, and substituting serine for cysteine at position 219, EU numbering, in the upper hinge of heavy chain of the wild type IgG2 constant region sequence (hereinafter "IgG2-SKSC") (IgG2-SKSC, SEQ ID NO: 120). These substitutions would enable IgG2-SKSC to form a homogenous covalent bond between heavy and light chains, which is a disulfide bond between the C-terminal cysteine of the light chain and cysteine at position 220 in the EU numbering system (FIG. 24).

The methods described in Example 1 were used to construct an expression vector for IgG2-SKSC and to express and purify IgG2-SKSC. The purified IgG2-SKSC and wild type IgG2 (WT-IgG2) were analyzed for homogeneity by cation exchange chromatography.
Assessment Method Using IEC:
System: Waters Alliance
Column: ProPac WCX-10 (Dionex)
Mobile phase A: 25 mM MES-NaOH, pH 5.6
  B: 25 mM MES-NaOH, 250 mM Na-Acetate, pH 5.6
Flow rate, wavelength: 0.5 ml/min, 280 nm
Gradient B: 50%-100% (75 minutes)

Figure 25:
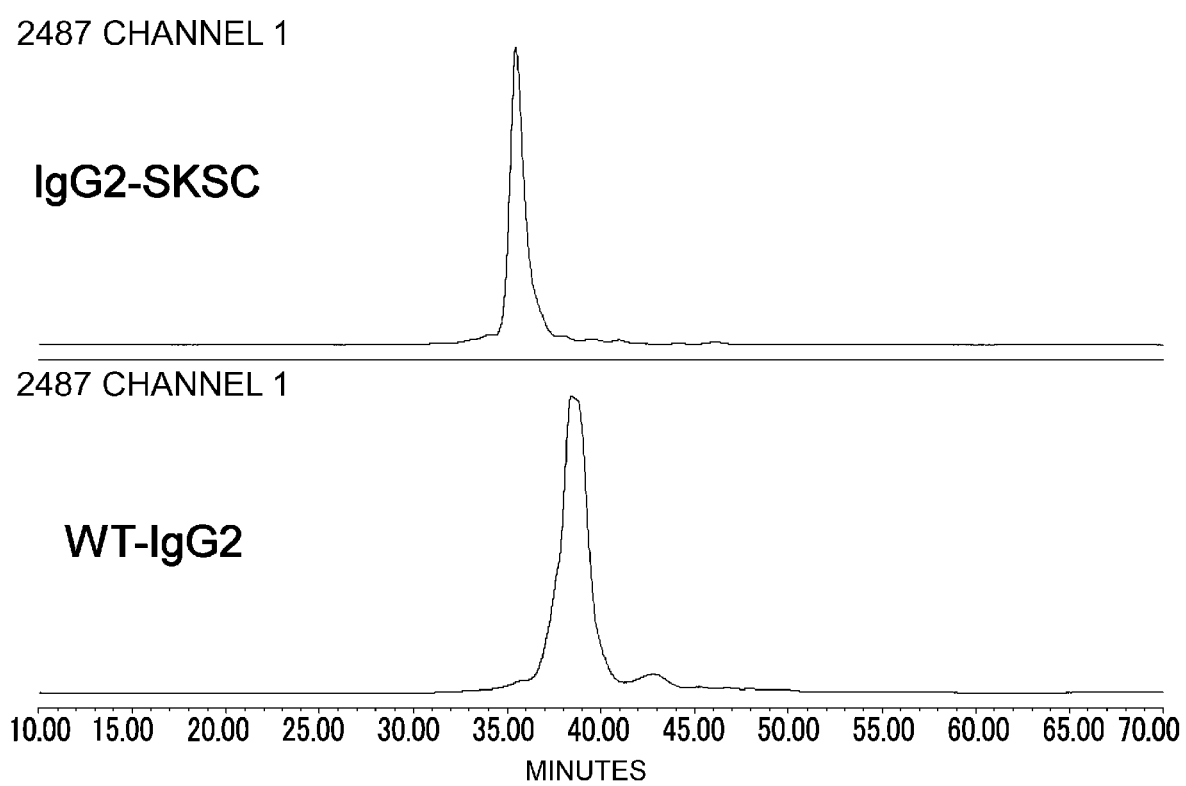
FIG. 25 is a diagram showing the result of cation exchange chromatography (IEC) analysis of WT-IgG2 and IgG2-SKSC.

The result is shown in FIG. 25. As expected above, IgG2-SKSC was shown to be eluted at a single peak while WT-IgG2 gave multiple peaks. This suggests that the heterogeneity derived from disulfide bonds in the hinge region of IgG2 can be avoided by using modifications such as those used to generate IgG2-SKSC, which allow formation of a single disulfide bond between the C-terminal cysteine of the light chain and cysteine at position 220 in the EU numbering system. The midpoint temperatures of thermal denaturation of WT-IgG1, WT-IgG2, and IgG2-SKSC were determined by the same methods as described in Example 5. The result showed that WT-IgG2 gave a peak for Fab domain which has a lower Tm value than WT-IgG1, while IgG2-SKSC did not give such a peak. This suggests that IgG2-SKSC is also superior in thermal stability as compared to WT-IgG2.

Although wild type IgG2 was thought to have a homogeneity problem which is important in developing antibody pharmaceuticals, it was found that this problem could be solved by using IgG2-SKSC for the constant region sequence of IgG2. Thus, IgG2-SKSC is very useful in developing IgG2 antibody pharmaceuticals. Furthermore, the usefulness of IgG2-SKSC was also demonstrated by the finding that it is superior in thermal stability.

[Example 9] Improvement of C-Terminal Heterogeneity in IgG Molecules

Construction of an Expression Vector for Heavy Chain C-Terminal ΔGK Antibody from WT-IgG1

There is a report on the heterogeneity of antibody C-terminal sequence, which results from the deletion of C-terminal amino acid lysine residue and the amidation of the C-terminal amino group due to deletion of the two C-terminal amino acids glycine and lysine (Johnson K A et al., Anal. Biochem. 2007 Jan. 1; 360(1):75-83). The absence of such heterogeneity is preferred when developing antibody pharmaceuticals. Actually, in humanized PM-1 antibody TOCILIZUMAB, the major component is the sequence that lacks the C-terminal amino acid lysine, which is encoded by the nucleotide sequence but deleted in post-translational modification, and the minor component having the lysine also coexists as heterogeneity. Thus, the C-terminal amino acid sequence was modified to reduce the C-terminal heterogeneity. Specifically, the present inventors modified the nucleotide sequence of wild type IgG1 to delete the C-terminal lysine and glycine from the heavy chain constant region of the IgG1, and assessed whether the amidation of the C-terminal amino group could be suppressed by deleting the two C-terminal amino acids glycine and lysine.

Mutations were introduced into the C-terminal sequence of the heavy chain using pB-CH vector encoding the humanized PM-1 antibody (WT) obtained in Example 1. The nucleotide sequence encoding Lys at position 447 and/or Gly at position 446 in the EU numbering system was converted into a stop codon by introducing a mutation using the QuikChange Site-Directed Mutagenesis Kit (Stratagene) according to the method described in the attached instruction manual. Thus, expression vectors for antibody engineered to lack the C-terminal amino acid lysine (position 447 in the EU numbering system) and antibody engineered to lack the two C-terminal amino acids glycine and lysine (positions 446 and 447 in the EU numbering system, respectively) were constructed. Heavy chain C-terminal ΔK and ΔGK antibodies were obtained by expressing the engineered heavy chains and the light chain of the humanized PM-1 antibody. The antibodies were expressed and purified by the method described in Example 1.

Purified heavy chain C-terminal ΔGK antibody was analyzed by cation exchange chromatography according to the following procedure. The effect of the C-terminal deletion on heterogeneity was assessed by cation exchange chromatography analysis using the purified heavy chain C-terminal ΔGK antibody according to the method described below. The conditions of cation exchange chromatography analysis are described below. Chromatograms for humanized PM-1 antibody, heavy chain C-terminal ΔK antibody, and heavy chain C-terminal ΔGK antibody were compared.

Figure 26:
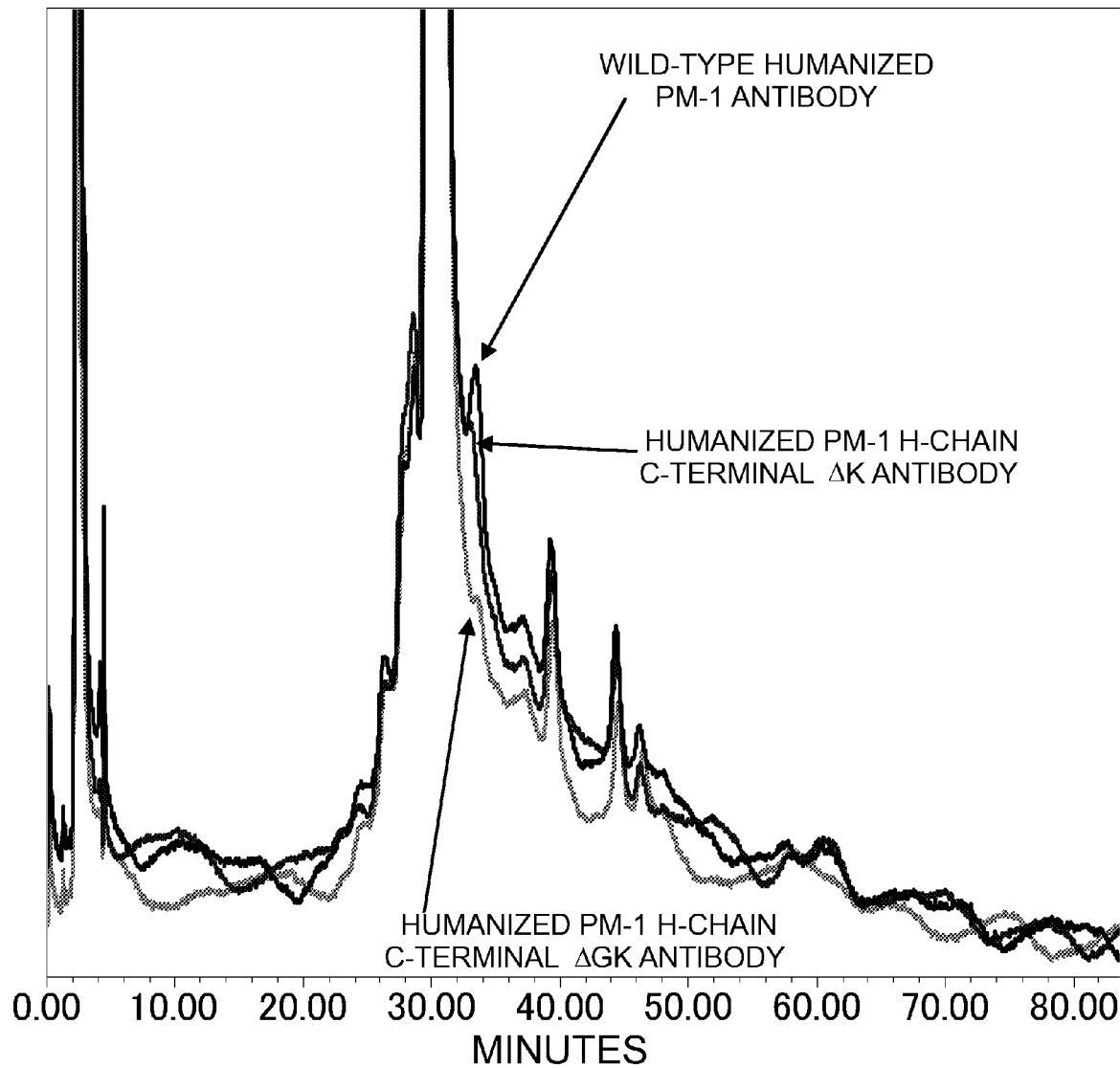
FIG. 26 is a diagram showing the result of cation exchange chromatography (IEC) analysis of humanized PM-1 antibody, heavy chain C-terminal ΔK antibody, and heavy chain C-terminal ΔGK antibody.

Column: ProPac WCX-10, 4×250 mm (Dionex)
Mobile phase A: 25 mmol/l MES/NaOH, pH 6.1
  B: 25 mmol/l MES/NaOH, 250 mmol/l NaCl, pH 6.1
Flow rate: 0.5 ml/min
Gradient: 25% B (5 minutes)→(105 minutes)→67% B→(1 minute)→100% B (5 minutes)
Detection: 280 nm The analysis result for the non-modified humanized PM-1 antibody, heavy chain C-terminal ΔK antibody, and heavy chain C-terminal ΔGK antibody is shown in FIG. 26. According to Chu G C et al., Pharm Res. 2007 Mar. 24; 24(6):1145-56, a basic peak with more prolonged retention time than that of the main peak contains a heavy chain C terminus with Lys at position 449 and a heavy chain C terminus with amidated Pro at position 447. The intensity of the basic peak was significantly reduced in the heavy chain C-terminal ΔGK antibody, while no such significant reduction was observed in the heavy chain C-terminal ΔK antibody. This suggests that the C-terminal heterogeneity of the heavy chain can be reduced only when the two C-terminal amino acids are deleted from the heavy chain.

The temperature of thermal denaturation of the heavy chain C-terminal ΔGK antibody was determined by DSC to assess the effect of the deletion of the two residues at the heavy chain C terminus on thermal stability. For the DSC measurement, the antibody was dialyzed against 20 mM acetic acid buffer (pH 6.0) containing 150 mM NaCl to change the buffer. After thorough deaeration, the humanized PM-1 antibody and heavy chain C-terminal ΔGK antibody solutions, and the reference solution (outer dialysate) were enclosed in calorimetric cells, and thoroughly thermally equilibrated at 40° C. Then, the samples were scanned at from 40° C. to 100° C. with a rate of about 1 K/min. The resulting denaturation peaks were assigned (Rodolfo et al., Immunology Letters, 1999, p 47-52). The result showed that the C-terminal deletion had no effect on the thermal denaturation temperature of CH3 domain.

Thus, the heterogeneity originated from the C-terminal amino acid can be reduced without affecting the thermal stability of antibody by deleting the C-terminal lysine and glycine from the heavy chain constant region at the nucleotide sequence level. Since all of the constant regions of human antibodies IgG1, IgG2, and IgG4 contain Gly and Lys at positions 446 and 447 in the EU numbering system in their C-terminal sequences, the method for reducing the C-terminal amino acid heterogeneity discovered in this example and others is also expected to be applicable to IgG2 and IgG4 constant regions and variants thereof.

[Example 10] Construction of M14ΔGK with a Novel Optimized Constant Region Sequence When an antibody pharmaceutical is aimed at neutralizing an antigen, effector functions such as ADCC of Fc domain are unnecessary and therefore the binding to Fcγ receptor is unnecessary. The binding to Fcγ receptor is assumed to be unfavorable from the perspectives of immunogenicity and adverse effect (Strand V et al., Nat. Rev. Drug Discov. 2007 January; 6(1):75-92; Gessner J E et al., Ann. Hematol. 1998 June; 76(6):231-48). The humanized anti-IL-6 receptor IgG1 antibody TOCILIZUMAB does not need to bind to Fcγ receptor, because it only needs to specifically bind to IL-6 receptor and neutralize its biological activity in order to be used as a therapeutic agent for diseases associated with IL-6, such as rheumatoid arthritis.

Construction and Assessment of M14ΔGK, a Fcγ Receptor-Nonbinding, Optimized Constant Region A possible method for impairing the Fcγ receptor binding is to convert the IgG antibody from IgG1 isotype to IgG2 or IgG4 isotype (Ann. Hematol. 1998 June; 76(6):231-48). As a method for completely eliminating the binding to Fcγ receptor, a method of introducing an artificial modification into Fc domain has been reported. For example, since the effector functions of anti-CD3 antibody and anti-CD4 antibody cause adverse effects, amino acid mutations that are not present in the wild type sequence have been introduced into the Fcγ receptor-binding region of Fc domain (Cole M S et al., J. Immunol. 1997 Oct. 1; 159(7):3613-21; Reddy M P et al., J. Immunol. 2000 Feb. 15; 164(4):1925-33), and the resulting Fcγ receptor-nonbinding anti-CD3 and anti-CD4 antibodies are under clinical trials (Strand V et al., Nat. Rev. Drug Discov. 2007 January; 6(1):75-92; Chau L A et al., Transplantation 2001 Apr. 15; 71(7):941-50). According to another report (Kim S J et al., Mol Cells. 2005 Aug. 31; 20(1):17-29 Review), Fcγ receptor-nonbinding antibodies can be prepared by converting the FcγR-binding domain of IgG1 (at positions 233, 234, 235, 236, 327, 330, and 331 in the EU numbering system) into the sequence of IgG2 (at positions 233, 234, 235, and 236 in the EU numbering system) or IgG4 (at positions 327, 330, and 331 in the EU numbering system). However, if all of the above mutations are introduced into IgG1, novel peptide sequences of nine amino acids, which potentially serve as non-natural T-cell epitope peptides, will be generated, and this increases the immunogenicity risk. The immunogenicity risk should be minimized in developing antibody pharmaceuticals.

To overcome the above problem, modifications in the IgG2 constant region were considered. In the FcγR-binding domain of IgG2 constant region, residues at positions 327, 330, and 331 in the EU numbering system are different from the nonbinding sequence of IgG4 while those at positions 233, 234, 235, and 236 in the EU numbering system are amino acids of nonbinding type. Thus, it is necessary to modify the amino acids at positions 327, 330, and 331 in the EU numbering system to the sequence of IgG4 (G24a described in Eur. J. Immunol. 1999 August; 29(8):2613-24). However, since the amino acid at position 339 in the EU numbering system in IgG4 is alanine while the corresponding residue in IgG2 is threonine, a simple modification of the amino acids at positions 327, 330, and 331 in the EU numbering system to the sequence of IgG4 unfavorably generates a novel peptide sequence of 9 amino acids, potentially serving as a non-natural T-cell epitope peptide, and thus increases the immunogenicity risk. Then, the present inventors found that the generation of novel peptide sequence could be prevented by introducing the substitution of alanine for threonine at position 339 in the EU numbering system in IgG2, in addition to the modification described above.

In addition to the mutations described above, other mutations were introduced, and they were the substitution of valine for methionine at position 397 in the EU numbering system in IgG2, which was discovered in Example 7 to improve the stability of IgG2 under acidic condition; and the substitution of serine for cysteine at position 131 in the EU numbering system, the substitution of lysine for arginine at position 133 in the EU numbering system, and the substitution of serine for cysteine at position 219 in the EU numbering system, which were discovered in Example 8 to improve the heterogeneity originated from disulfide bonds in the hinge region. Furthermore, since the mutations at positions 131 and 133 generate a novel peptide sequence of 9 amino acids, potentially serving as a non-natural T-cell epitope peptide, and thus generate the immunogenicity risk, the peptide sequence around positions 131 to 139 was converted into a natural human sequence by introducing the substitution of glycine for glutamic acid at position 137 in the EU numbering system and the substitution of glycine for serine at position 138 in the EU numbering system. Furthermore, glycine and lysine at positions 446 and 447 in the EU numbering system were deleted from the C terminus of heavy chain to reduce the C-terminal heterogeneity. The constant region sequence having all of the mutations introduced was named M14ΔGK (M14ΔGK, SEQ ID NO: 24). Although there is a mutation of cysteine at position 219 to serine in M14ΔGK as a novel 9-amino acid peptide sequence which potentially serves as a T-cell epitope peptide, the immunogenicity risk was considered very low since the amino acid property of serine is similar to that of cysteine. The immunogenicity prediction by TEPITOPE also suggested that there was no difference in immunogenicity.

An expression vector for the antibody heavy chain sequence whose variable region was WT and constant region was M14ΔGK (M14ΔGK, SEQ ID NO: 24; WT-M14ΔGK, SEQ ID NO: 113) was constructed by the method described in Example 1. An antibody having WT-M14ΔGK as heavy chain and WT as light chain was expressed and purified by the method described in Example 1.

Furthermore, WT-M17ΔGK (M17ΔGK, SEQ ID NO: 116; WT-M17ΔGK, SEQ ID NO: 115) was constructed with the same method by introducing mutations into the IgG1 constant region at positions 233, 234, 235, 236, 327, 330, 331, and 339 in the EU numbering system (G1Δab described in Eur. J. Immunol. 1999 August; 29(8):2613-24) to impair the Fcγ receptor binding and by deleting the amino acids at positions 446 and 447 in the EU numbering system to reduce the C-terminal heterogeneity (Example 9). An expression vector for WT-M11ΔGK (M11ΔGK, SEQ ID NO: 25; WT-M11ΔGK, SEQ ID NO: 114) was constructed. In WT-M11ΔGK, mutations were introduced into the IgG4 constant region at positions 233, 234, 235, and 236 in the EU numbering system (G4Δb described in Eur. J. Immunol. 1999 August; 29(8):2613-24; this modification newly generates nonhuman sequence and thus increases the immunogenicity risk) to reduce the Fcγ receptor binding. In addition to the above modification, to reduce the immunogenicity risk, mutations were introduced at positions 131, 133, 137, 138, 214, 217, 219, 220, 221, and 222 in the EU numbering system so that the pattern of disulfide bonding in the hinge region was the same as that of M14ΔGK; a mutation was introduced at position 409 in the EU numbering system (Example 7) to improve the stability under acidic condition; and the amino acids at positions 446 and 447 in the EU numbering system were deleted (Example 9) to reduce the C-terminal heterogeneity. WT-M17ΔGK or WT-M11ΔGK was used as the heavy chain, and WT was used as the light chain. These antibodies were expressed and purified by the method described in Example 1.

Figure 27:
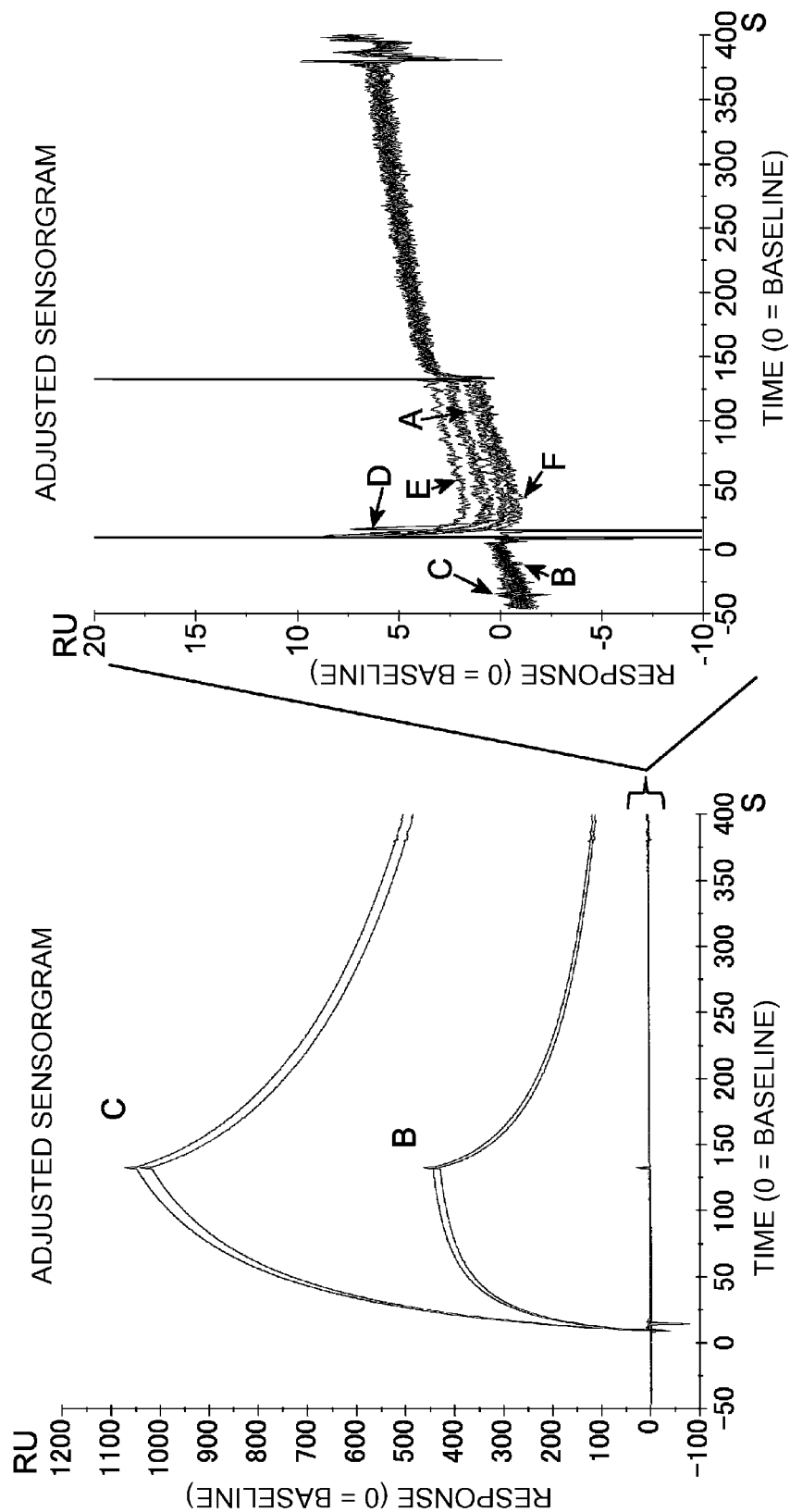
FIG. 27 shows comparison of the amounts WT-IgG1, WT-IgG2, WT-IgG4, WT-M14ΔGK, WT-M17ΔGK, and WT-M11ΔGK bound to FcγRI.

Assessment of WT-M14ΔGK, WT-M17ΔGK, and WT-M11ΔGK for Fcγ Receptor-Binding Activity The FcγRI binding was assessed by the procedure described below. Using Biacore T100, human-derived Fcγ receptor I (hereinafter "FcγRI") immobilized onto a sensor chip was allowed to interact with IgG1, IgG2, IgG4, M11ΔGK, M14ΔGK, or M14GK 7 as an analyte. The amounts of bound antibody were compared. The measurement was conducted using Recombinant Human FcRIA/CD64 (R&D systems) as human-derived FcγRI, and IgG1, IgG2, IgG4, M11ΔGK, M14ΔGK, and M17ΔGK as samples. FcγRI was immobilized onto the sensor chip CM5 (Biacore) by the amine coupling method. The final amount of immobilized hFcγ RI was about 13,000 RU. The running buffer used was HBS-EP+, and the flow rate was 20 μl/min. The sample concentration was adjusted to 100 μg/ml using HBS-EP+. The analysis included two steps: two minutes of association phase where 10 μl of an antibody solution was injected and the subsequent four minutes of dissociation phase where the injection was switched with HBS-EP+. After the dissociation phase, the sensor chip was regenerated by injecting 20 μl of 5 mM sodium hydroxide. The association, dissociation, and regeneration constitute one analysis cycle. Various antibody solutions were injected to obtain sensorgrams. As analytes, IgG4, IgG2, IgG1, M11, M14, and M17 were injected in this order. This series of injection was repeated twice. The result of comparison of data on the determined amounts of bound antibody is shown in FIG. 27. The comparison shows that the amount of bound antibody is reduced in the order of: IgG1>IgG4>>IgG2=M11ΔGK=M14ΔGK=M17ΔGK. Thus, it was revealed that the FcγRI binding of wild type IgG2, M11ΔGK, M14ΔGK, and M17ΔGK was weaker than that of wild type IgG1 and IgG4.

The FcγRIIa binding was assessed by the procedure described below. Using Biacore T100, human-derived Fcγ receptor IIa (hereinafter "FcγRIIa") immobilized onto a sensor chip was allowed to interact with IgG1, IgG2, IgG4, M11ΔGK, M14ΔGK, or M17ΔGK as an analyte. The amounts of bound antibody were compared. The measurement was conducted using Recombinant Human FcRIIA/CD32a (R&D systems) as human-derived FcγRIIa, and IgG1, IgG2, IgG4, M11ΔGK, M14ΔGK, and M17ΔGK as samples. FcγRIIa was immobilized onto the sensor chip CM5 (Biacore) by the amine coupling method. The final amount of immobilized FcγRIIa was about 3,300 RU. The running buffer used was HBS-EP+, and the flow rate was 20 μl/min. Then, the running buffer was injected until the baseline was stabilized. The measurement was carried out after the baseline was stabilized. The immobilized FcγRIIa was allowed to interact with an antibody of each IgG isotype (IgG1, IgG2, or IgG4) or antibody introduced with mutations (M11ΔGK, M14ΔGK, or M17ΔGK) as an analyte. The amount of bound antibody was observed. The running buffer used was HBS-EP+, and the flow rate was 20 μl/min. The measurement temperature was 25° C. The concentration of each IgG or modified form thereof was adjusted to 100 μg/ml. 20 μl of an analyte was injected and allowed to interact with the immobilized FcγRIIa.

Figure 28:
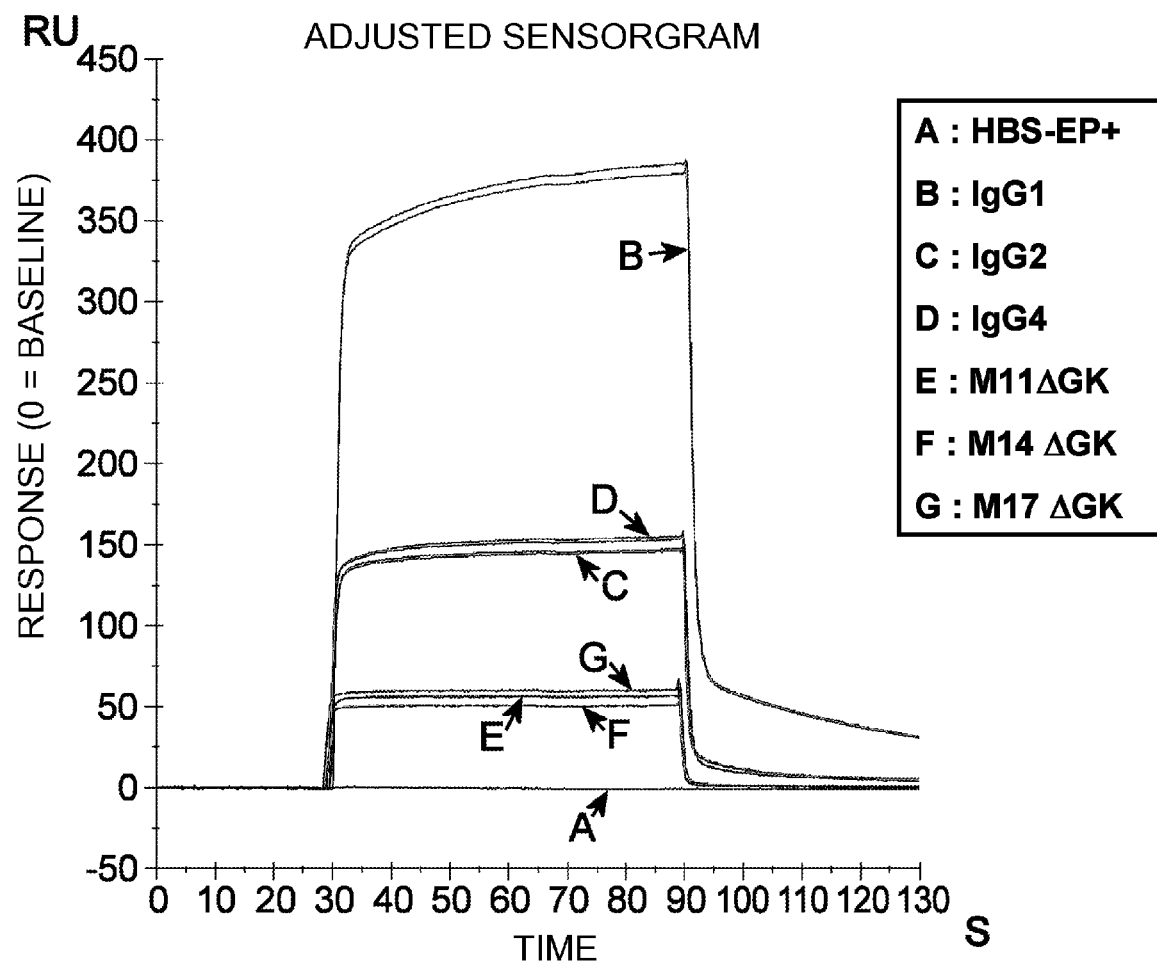
FIG. 28 is a graph showing comparison of the amounts WT-IgG1, WT-IgG2, WT-IgG4, WT-M14ΔGK, WT-M17ΔGK, and WT-M11ΔGK bound to FcγRIIa.

After interaction, the analyte was dissociated from FcγRIIa and the sensor chip was regenerated by injecting 200 μl of the running buffer. As analytes, IgG4, IgG2, IgG1, M11ΔGK, M14ΔGK, and M17ΔGK were injected in this order. This series of injection was repeated twice. The result of comparison of data on the amounts of bound antibody determined is shown in FIG. 28. The comparison shows that the amount of bound antibody is reduced in the order of: IgG1>IgG2=IgG4>M11ΔGK=M14ΔGK=M17ΔGK. Thus, it was revealed that the FcγRIIa binding of M11ΔGK, M14ΔGK, and M17ΔGK was weaker than that of wild type IgG1, IgG2, and IgG4.

Figure 29:
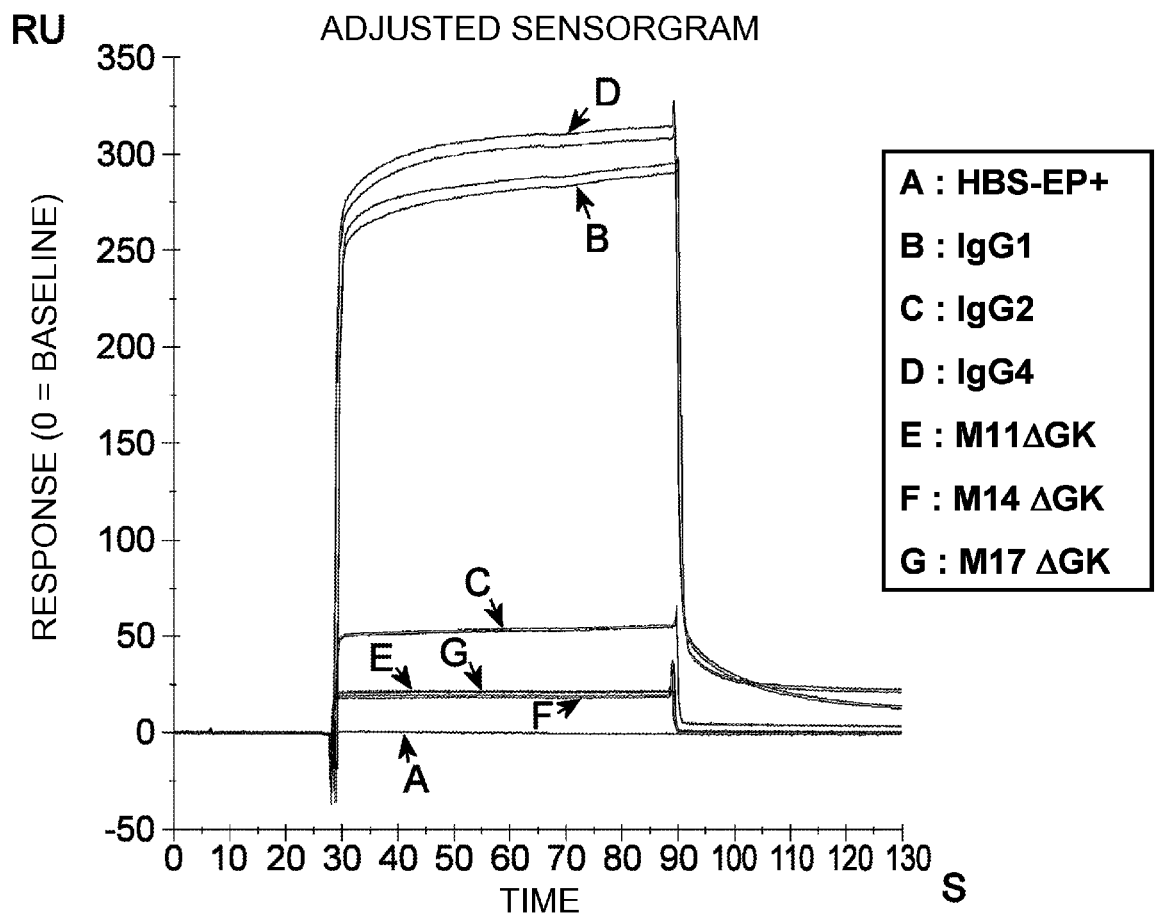
FIG. 29 is a graph showing comparison of the amounts WT-IgG1, WT-IgG2, WT-IgG4, WT-M14ΔGK, WT-M17ΔGK, and WT-M11ΔGK bound to FcγRIIb.

The FcγRIIb binding was assessed by the procedure described below. Using Biacore T100, human-derived Fcγ receptor IIb (hereinafter "FcγRIIb") immobilized onto a sensor chip was allowed to interact with IgG1, IgG2, IgG4, M11ΔGK, M14ΔGK, or M17ΔGK as an analyte. The amounts of bound antibody were compared. The measurement was conducted using Recombinant Human FcRIIB/C (R&D systems) as human-derived FcγRIIb, and IgG1, IgG2, IgG4, M11ΔGK, M14ΔGK, and M17ΔGK as samples. FcγRIIb was immobilized onto the sensor chip CM5 (Biacore) by the amine coupling method. The final amount of immobilized FcγRIIb was about 4,300 RU. Then, the running buffer was injected until the baseline was stabilized. The measurement was carried out after the baseline was stabilized. The immobilized FcγRIIb was allowed to interact with an antibody of each IgG isotype (IgG1, IgG2, or IgG4) or antibody introduced with mutations (M11ΔGK, M14ΔGK, or M17ΔGK) as an analyte. The amount of bound antibody was observed. The running buffer used was HBS-EP+(10 mM HEPES, 0.15 M NaCl, 3 mM EDTA, 0.05% v/v Surfactant P20), and the flow rate was 20 μl/min. The measurement temperature was 25° C. The concentration of each IgG or modified form thereof was adjusted to 200 μg/ml. 20 μl of an analyte was injected and allowed to interact with the immobilized FcγRIIb. After interaction, the analyte was dissociated from FcγRIIb and the sensor chip was regenerated by injecting 200 μl of the running buffer. As analytes, IgG4, IgG2, IgG1, M11ΔGK, M14ΔGK, and M17ΔGK were injected in this order. This series of injection was repeated twice. The result of comparison of data on the amounts of bound antibody determined is shown in FIG. 29. The comparison shows that the amount of bound antibody is reduced in the order of: IgG4>IgG1>IgG2>M11ΔGK=M14ΔGK=M17ΔGK. Thus, it was revealed that the FcγRIIb binding of M11ΔGK, M14ΔGK, and M17ΔGK was weaker than that of wild type IgG1, IgG2, and IgG4.

Figure 30:
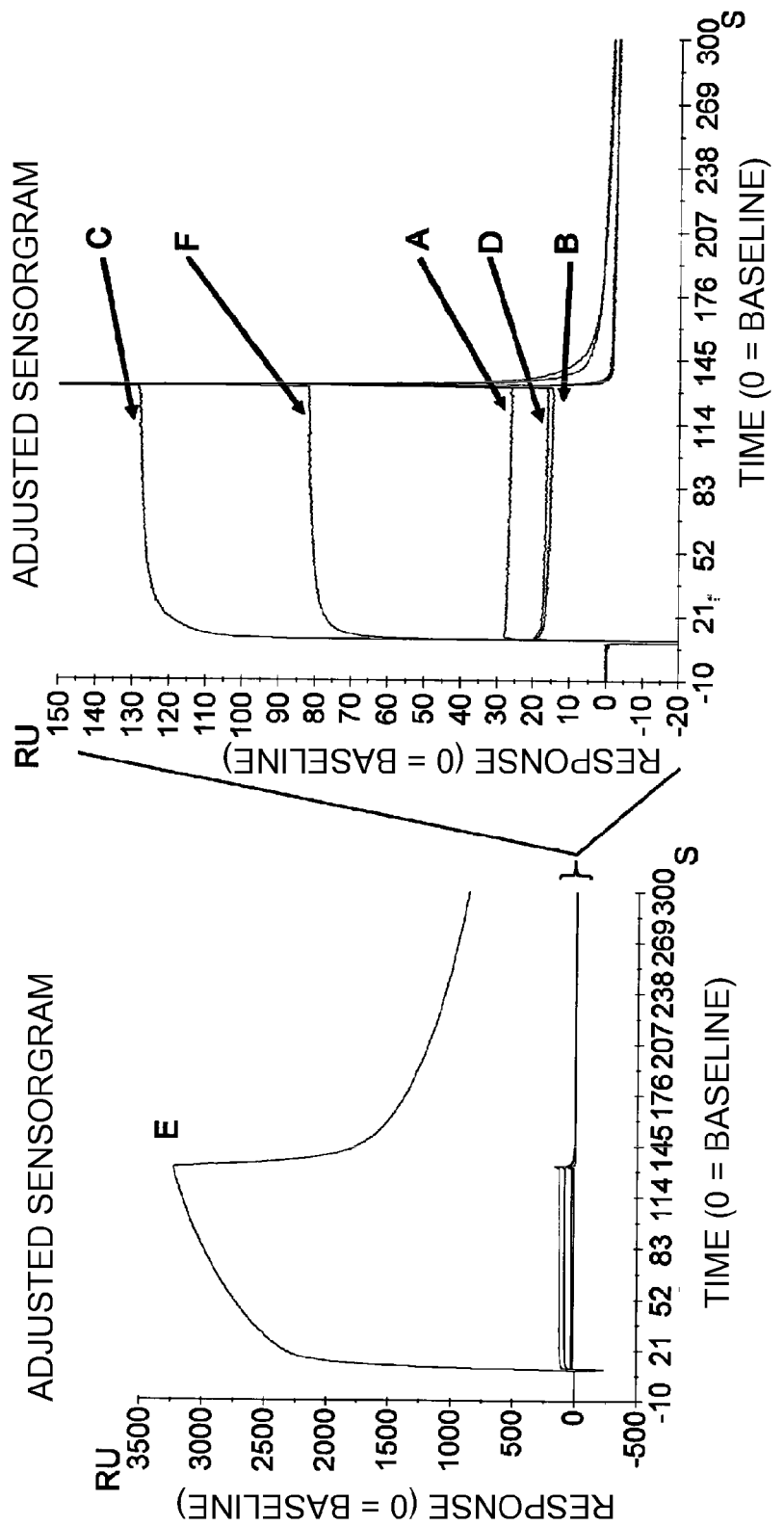
FIG. 30 is a graph showing comparison of the amounts WT-IgG1, WT-IgG2, WT-IgG4, WT-M14ΔGK, WT-M17ΔGK, and WT-M11ΔGK bound to FcγRIIIa (Val).

The FcγRIIIa binding was assessed by the procedure described below. Using Biacore T100, human-derived Fcγ receptor IIIa (hereinafter "FcγRIIIa") immobilized onto a sensor chip was allowed to interact with IgG1, IgG2, IgG4, M11ΔGK, M14ΔGK, or M17ΔGK as an analyte. The amounts of bound antibody were compared. The measurement was conducted using hFcγ RIIIaV-His6 (recombinant hFcγ RIIIaV-His6 prepared in the applicants' company) as human-derived FcγRIIIa, and IgG1, IgG2, IgG4, M11ΔGK, M14ΔGK, and M17ΔGK as samples. FcγRIIIa was immobilized onto the sensor chip CM5 (Biacore) by the amine coupling method. The final amount of immobilized hFcγ RIIIaV-His6 was about 8200 RU. The running buffer used was HBS-EP+, and the flow rate was 5 μl/min. The sample concentration was adjusted to 250 μg/ml using HBS-EP+. The analysis included two steps: two minutes of association phase where 10 μl of an antibody solution was injected and the subsequent four minutes of dissociation phase where the injection was switched with HBS-EP+. After the dissociation phase, the sensor chip was regenerated by injecting 20 μl of 5 mM hydrochloric acid. The association, dissociation, and regeneration constitute one analysis cycle. Various antibody solutions were injected to obtain sensorgrams. As analytes, IgG4, IgG2, IgG1, M11ΔGK, M14ΔGK, and M17ΔGK were injected in this order. The result of comparison of data on the determined amounts of bound antibody is shown in FIG. 30. The comparison shows that the amount of bound antibody is reduced in the order of: IgG1>>IgG4>IgG2>M17ΔGK>M11ΔGK=M14ΔGK. Thus, it was revealed that the FcγRIIIa binding of M11ΔGK, M14ΔGK, and M17ΔGK was weaker than that of wild type IgG1, IgG2, and IgG4. Furthermore, the FcγRIIIa binding of M11ΔGK and M14ΔGK was found to be weaker than that of M17ΔGK containing the mutation G1Δab reported in Eur. J. Immunol. 1999 August; 29(8):2613-24.

The finding described above demonstrates that the Fcγ receptor binding of WT-M14ΔGK, WT-M17ΔGK, and WT-M11ΔGK is markedly reduced as compared to wild type IgG1. The immunogenicity risk due to Fcγ receptor-mediated internalization into APC and adverse effects caused by the effector function such as ADCC can be avoided by using WT-M14ΔGK, WT-M17ΔGK, or WT-M11ΔGK as a constant region. Thus, WT-M14ΔGK, WT-M17ΔGK, and WT-M11ΔGK are useful as constant region sequence of antibody pharmaceuticals aimed at neutralizing antigens.

Assessment of WT-M14ΔGK, WT-M17ΔGK, and WT-M11ΔGK for Stability at High Concentrations WT-M14ΔGK, WT-M17ΔGK, and WT-M11ΔGK were assessed for stability at high concentrations. The purified antibodies of WT-IgG1, WT-M14ΔGK, WT-M17ΔGK, and WT-M11ΔGK were dialyzed against a solution of 20 mM histidine chloride, 150 mM NaCl, pH 6.5 (EasySEP, TOMY), and then concentrated by ultrafilters. The antibodies were tested for stability at high concentrations. The conditions were as follows.

Figure 31:
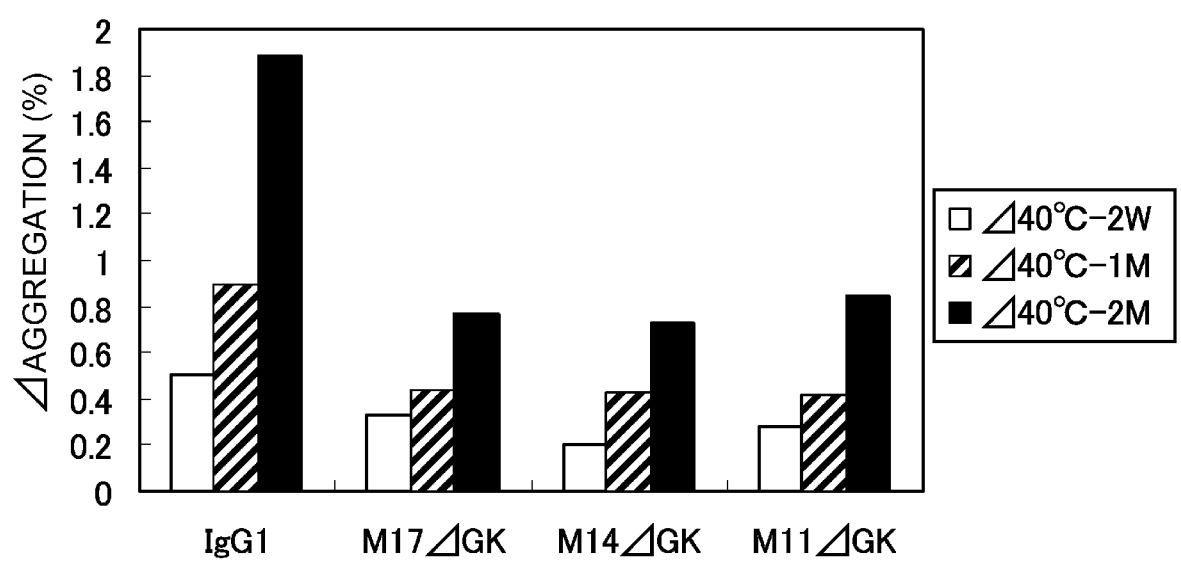
FIG. 31 is a graph showing the increase of aggregation in a stability test for WT-IgG1, WT-M14ΔGK, WT-M17ΔGK, and WT-M11ΔGK at high concentrations.
Figure 32:
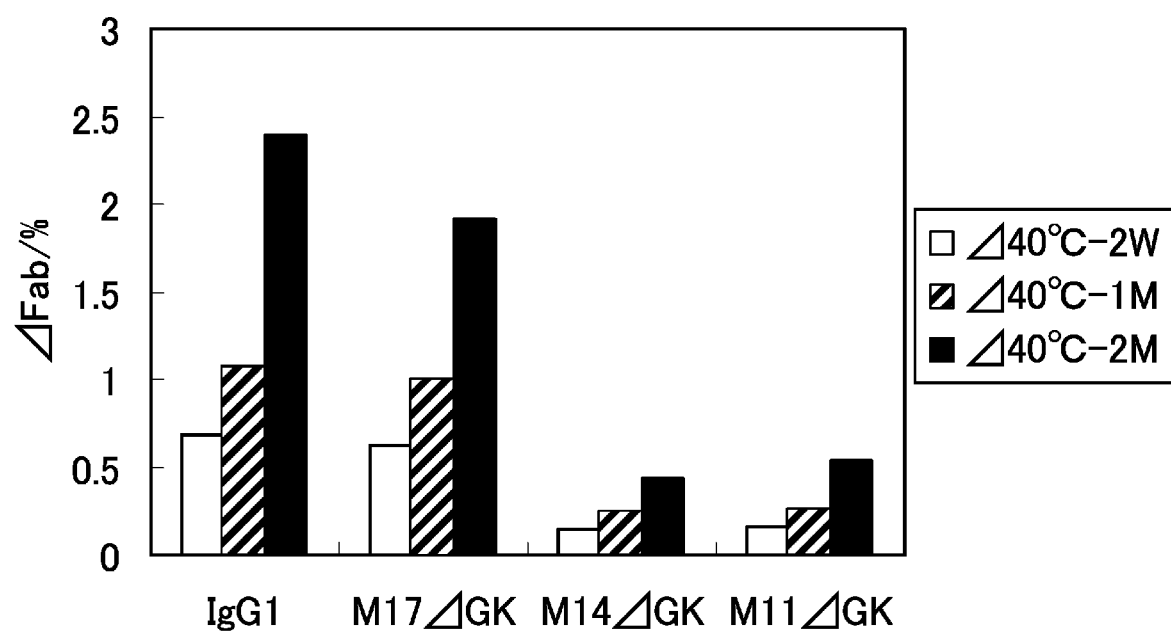
FIG. 32 is a graph showing the increase of Fab fragments in a stability test for WT-IgG1, WT-M14ΔGK, WT-M17ΔGK, and WT-M11ΔGK at high concentrations.

Antibodies: WT-IgG1, WT-M14ΔGK, WT-M17ΔGK, and WT-M11ΔGK
Buffer: 20 mM histidine chloride, 150 mM NaCl, pH 6.5
Concentration: 61 mg/ml
Storage temperature and time period: 40° C. for two weeks, 40° C. for one month, 40° C. for two months
Aggregation Assessment Method:
System: Waters Alliance
Column: G3000SWx1 (TOSOH)
Mobile phase: 50 mM sodium phosphate, 300 mM KCl, pH 7.0
Flow rate, wavelength: 0.5 ml/min, 220 nm
100 times diluted samples were analyzed The contents of aggregate in the initial formulations (immediately after preparation) and formulations stored under various conditions were estimated by gel filtration chromatography described above. Differences (amounts increased) in the content of aggregate relative to the initial formulations are shown in FIG. 31. The result showed that the amounts of aggregate in WT-M14ΔGK, WT-M17ΔGK, and WT-M11ΔGK increased only slightly as compared to WT-IgG1 and were about half of the content in WT. Furthermore, as shown in FIG. 32, the amount of increased Fab fragment was comparable between WT-IgG1 and WT-M17ΔGK, while the amounts increased in WT-M14ΔGK and WT-M11ΔGK were about one quarter of the amount in WT. Degeneration pathways of IgG type antibody formulations include formation of aggregate and generation of Fab degradate as described in WO 2003/039485. Based on the two criteria, aggregation and Fab fragment generation, WT-M14ΔGK and WT-M11ΔGK were demonstrated to have a superior stability in formulations as compared to WT-IgG1. Thus, even for antibodies that have an IgG1 constant region with poor stability and could not be prepared as antibody pharmaceuticals in high-concentration liquid formulations, the use of WT-M14ΔGK, WT-M17ΔGK, or WT-M11ΔGK as a constant region was expected to allow production of more stable high-concentration liquid formulations.

In particular, M14ΔGK was expected to be very useful as a novel constant region sequence that would (1) overcome the instability of the original IgG2 molecule under acidic condition; (2) improve the heterogeneity originated from disulfide bonds in the hinge region; (3) not bind to Fcγ receptor; (4) have a minimized number of novel peptide sequences of 9 amino acids which potentially serve as T-cell epitope peptides; and (5) have a better stability than IgG1 in high-concentration formulations.

[Example 11] Preparation of PF1-M14ΔGK Antibody

The variable region of PF1 (whose constant region is IgG1) constructed in Example 5 was excised using XhoI and NheI. The constant region of M14ΔGK (whose variable region is WT) constructed in Example 7 was excised using NheI and NotI. The two antibody heavy chain gene fragments were inserted into an animal cell expression vector to construct an expression vector for the heavy chain of interest, PF1-M14ΔGK (PF1_H-M14ΔGK, SEQ ID NO: 117). The light chain used was PF1_L. The antibody PF1-M14ΔGK was expressed and purified by the method described in Example 1.

The antibody PF1-M14ΔGK was superior in various aspects as compared to WT (humanized PM-1 antibody) and thus expected to be very useful as anti-IL-6 receptor antibody pharmaceuticals.

[Example 12] Preparation and Assessment of M314GK

M14ΔGK prepared in Example 10 was modified by substituting the IgG2 sequence for the amino acids at positions 330, 331, and 339 in the EU numbering system to construct M314GK (M314GK, SEQ ID NO: 118). An expression vector for a sequence of antibody heavy chain whose variable region is WT and constant region sequence is M314GK (WT-M314GK, SEQ ID NO: 119) was constructed by the method described in Example 1. Using WT-M314GK heavy chain and WT light chain, WT-M31 was expressed and purified by the method described in Example 1.

Figure 33:
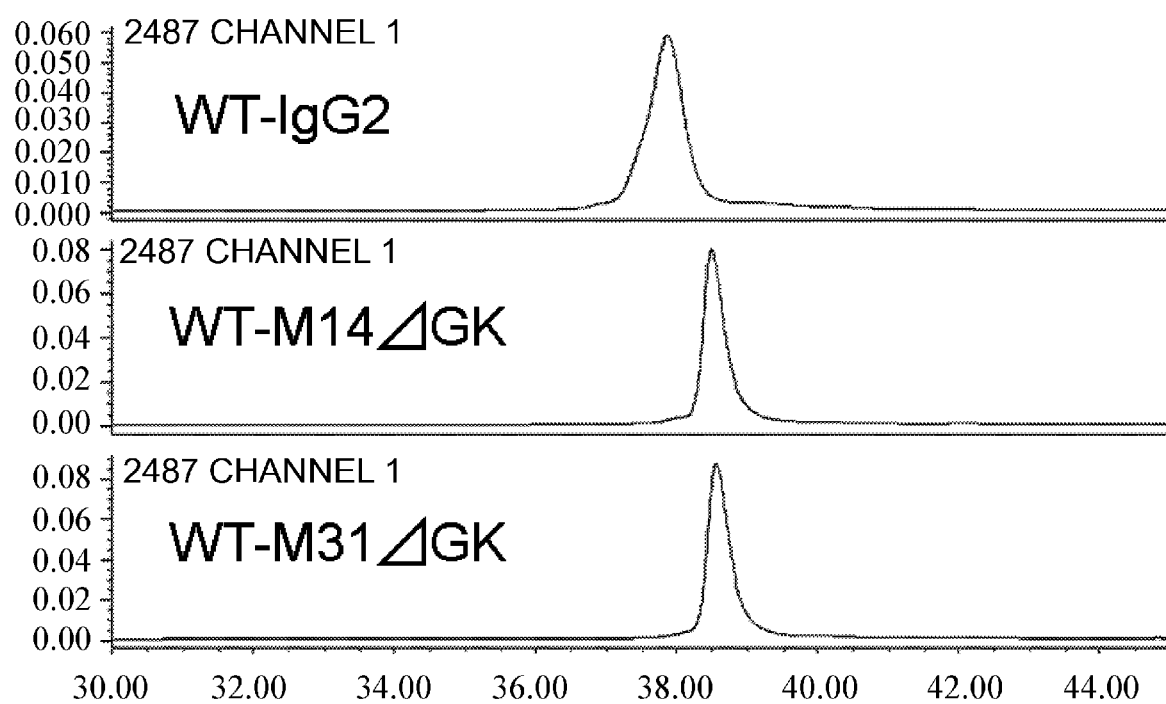
FIG. 33 is a diagram showing the result of cation exchange chromatography (IEC) analysis of WT-IgG2, WT-M14ΔGK, and WT-M31ΔGK.

In addition to WT-M31, WT-IgG2 and WT-M14ΔGK were expressed and purified at the same time, and analyzed by cation exchange chromatography by the procedure described below. The conditions used in the cation exchange chromatography analysis were as follows. Chromatograms for WT-IgG2, WT-M14ΔGK, and WT-M314GK were compared.
Column: ProPac WCX-10, 4×250 mm (Dionex)
Mobile phase A: 25 mmol/l MES/NaOH, pH 6.1
B: 25 mmol/l MES/NaOH, 250 mmol/l NaCl, pH 6.1
Flow rate: 0.5 ml/min
Gradient: 0% B (5 minutes)→(65 minutes)→100% B→(1 minute)
Detection: 280 nm The analysis result for WT-IgG2, WT-M14ΔGK, and WT-M314GK is shown in FIG. 33. Like WT-M14ΔGK, WT-M314GK was demonstrated to be eluted as a single peak, while WT-IgG2 gave multiple peaks. This indicates that the heterogeneity derived from disulfide bonds in the hinge region of IgG2 can also be avoided in WT-M314GK.

[Example 13] Preparation of a Fully Humanized Antibody F2H/L39-IgG1

Complete Humanization of the Framework Sequence of the PF1 Antibody

Arginine at position 71 (Kabat's numbering; Kabat E A et al., 1991. Sequences of Proteins of Immunological Interest. NIH) is the only mouse sequence that remains in PF1_H prepared in Example 5. This is unpreferable from the perspective of immunogenicity. In general, the residue at position 71 in the heavy chain is an important sequence for the conformation of HCDR2. In fact, it has been reported that during generation of the humanized PM1 antibody, the residue at position 71 is essential for the binding activity of mouse PM1 antibody. The binding activity was demonstrated to be significantly reduced by substituting valine at position 71 (Cancer Research (1993) 53:851-856). Meanwhile, PF1_H is classified into the VH4 family of human germ-line genes, and valine at position 71 is highly conserved in the VH4 family. The neutralizing activity was also demonstrated to be significantly reduced by substituting valine for arginine at position 71.

Thus, to completely remove the mouse sequence while maintaining the arginine at position 71, the present inventors searched among sequences of human germ-line genes and reported human antibodies for sequences that have arginine at position 71 and share conserved residues important for the maintenance of antibody tertiary structure. As a result, the inventors discovered a candidate sequence which contains important conserved residues although its homology to PF1_H is low as shown in Table 9.

TABLE 9

| KABAT NUMBERING | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 | source |
|---|---|---|---|---|---|---|---|---|---|---|---|---|---|---|---|---|---|---|---|---|---|---|---|---|---|---|---|---|---|---|---|---|---|
| PF1_H | R | V | T | I | S | R | D | T | S | K | N | Q | F | S | L | K | L | S | S | V | T | A | A | D | T | A | A | Y | Y | C | A | R | Germline: IMGT_nVH_4_b (EXCEPT H71 & H89) |
| CANDIDATE SEQUENCE | R | V | T | I | S | R | D | N | S | K | N | T | L | Y | L | Q | M | N | S | L | R | A | E | D | T | A | V | Y | Y | C | A | R | Mol. Immunol. 44(4): 412-422 (2007) |

H96-IgG1 (amino acid sequence of SEQ ID NO: 134) was designed by substituting the above-described candidate sequence for the region of positions 66 to 94 in PF1_H-IgG1, Kabat's numbering. The antibody variable region was prepared by PCR (assembly PCR) using a combination of synthetic oligo-DNAs. The constant region was amplified from an expression vector for IgG1 by PCR. The antibody variable region and constant region were linked together by assembly PCR, and then inserted into an animal cell expression vector. H96/PF1L-IgG1 was expressed and purified by the method described in Example 1.

Assessment of H96/PF1L-IgG1, an Antibody with Fully Humanized Framework

The Tm of purified H96/PF1L-IgG1 was determined by the method described in Example 5. The affinity measurement was carried out under essentially the same conditions used in Example 5. Note that the concentration of SR344 was adjusted to 0, 0.36, and 1.4 µg/ml, and the dissociation phase was monitored for 15 minutes. The result showed that the Tm and affinity of H96/PF1L-IgG1 were almost the same as those of PF1-IgG1 (Table 10).

TABLE 10

|  | Tm (°C.) | $k_a$(1/Ms) | $k_d$(1/s) | KD(M) |
| --- | --- | --- | --- | --- |
| PF1 ANTIBODY | 91.3 | 1.4E+06 | 4.2E−05 | 3.1E−11 |
| H96/PF1L-IgG1 | 89.8 | 1.2E+06 | 4.8E−05 | 3.9E−11 |

As described above, the present inventors generated an antibody with a completely humanized PF1 antibody framework, using H96 for the PF1 antibody heavy chain to completely remove the remaining mouse sequence from the PF1 antibody while maintaining its Tm and affinity. Since the framework sequence of H96/PF1L-IgG1 has no mouse-derived sequence, H96/PF1L-IgG1 is expected to be superior, especially from the perspective of immunogenicity.

Construction of F2H/L39-IgG1 with Lowered Isoelectric Point and Attenuated Immunogenicity Risk As demonstrated in Example 4, the retention in plasma can be prolonged by lowering isoelectric point through modification of amino acids in the antibody variable region. Thus, the amino acid substitutions shown below were further introduced into H96-IgG1 constructed above. To lower isoelectric point, glutamine was substituted for lysine at position 64, and aspartic acid was substituted for glycine at position 65. Furthermore, to reduce the immunogenicity risk, glutamine was substituted for glutamic acid at position 105 and isoleucine was substituted for threonine at position 107. In addition, to achieve affinity enhancement such as that in Example 2, modification was introduced where leucine was substituted for valine at position 95 and alanine was substituted for isoleucine at position 99. To prepare F2H-IgG1 (amino acid sequence of SEQ ID NO: 135), these amino acid substitutions were introduced into H96-IgG1 by the method described in Example 1.

Furthermore, the following amino acid substitutions were introduced into PF1L. To lower isoelectric point, glutamic acid was substituted for glutamine at position 27 and glutamic acid was substituted for leucine at position 55. To prepare L39 (amino acid sequence of SEQ ID NO: 136), these amino acid substitutions were introduced into PF1L by the method described in Example 1. Using F2H-IgG1 as heavy chain and L39 as light chain, F2H/L39-IgG1 was expressed and purified by the method described in Example 1.

Biacore-Based Analysis of F2H/L39-IgG1 for the Affinity for Human IL-6 Receptor

Humanized PM1 antibody (wild type (WT)), PF1 antibody (constructed in Example 5), and F2H/L39-IgG1 were analyzed for affinity. This measurement was carried out under essentially the same conditions used in Example 4. Note that the concentration of SR344 was adjusted to 0, 0.36, and 1.4 µg/ml, and the dissociation phase was monitored for 15 minutes (Table 11).

TABLE 11

| SAMPLE | $k_a$(1/Ms) | $k_d$(1/s) | KD(M) |
| --- | --- | --- | --- |
| PF1-IgG1 | 1.5E+06 | 4.4E−05 | 3.0E−11 |
| F2H/L39-IgG1 | 7.7E+05 | 4.0E−05 | 5.2E−11 |

The result showed that F2H/L39-IgG1 had very strong affinity (maintaining a KD in the order of $10^{-11}$) but its $k_a$ was decreased to about half of that of PF1-IgG1.

Assessment of F2H/L39-IgG1 for its Human IL-6 Receptor-Neutralizing Activity

Figure 34:
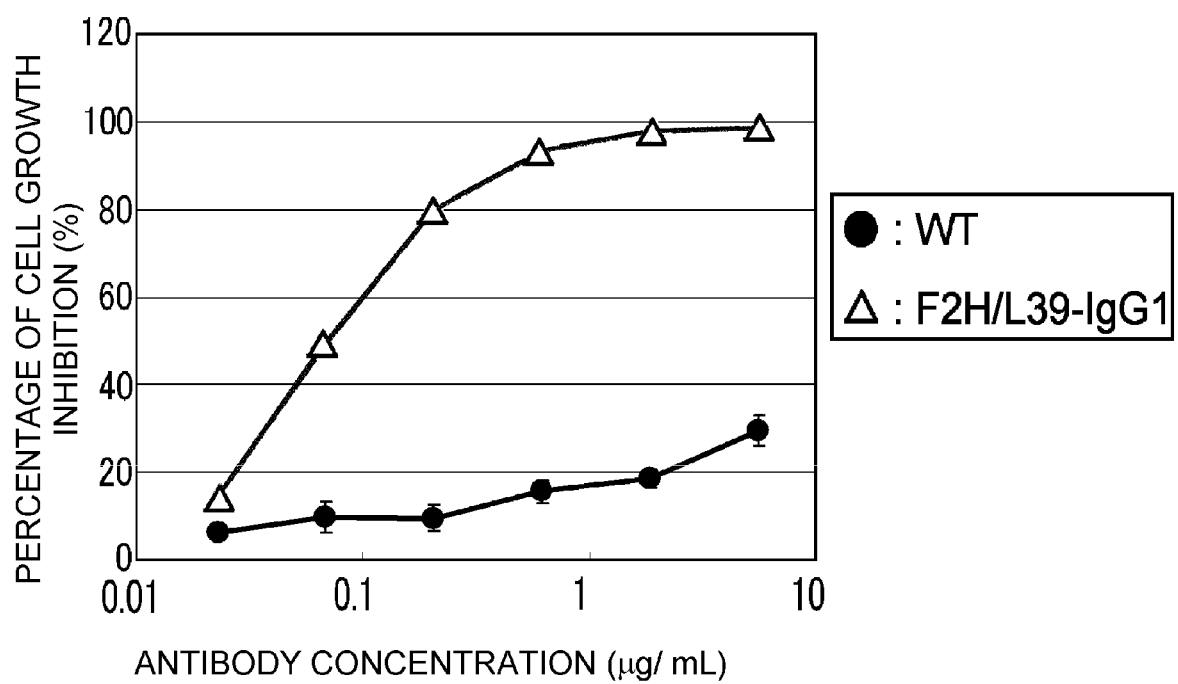
FIG. 34 is a graph showing the BaF/gp130-neutralizing activities of WT and F2H/L39-IgG1.

The neutralizing activities of humanized PM1 antibody (wild type (WT)) and F2H/L39-IgG1 were assessed by the method described in Example 1. The assessment of neutralizing activity was carried out using 600 ng/ml human interleukin-6 (TORAY). As shown in FIG. 34, F2H/L39-IgG1 was demonstrated to have a very strong activity, 100 or more times higher than WT in terms of 100% inhibitory concentration.

Assessment of F2H/L39-IgG1 for its Isoelectric Point by Isoelectric Focusing

The isoelectric point of F2H/L39-IgG1 was determined by the method described in Example 3. The isoelectric point of F2H/L39-IgG1 was 5.5, suggesting that its retention in plasma was prolonged due to a lower isoelectric point relative to the PF1 antibody prepared in Example 5.

The theoretical isoelectric point of the variable regions of F2H/L39 (heavy chain variable region and light chain variable region sequences) was calculated to be 4.3 by using GENETYX (GENETYX CORPORATION). Meanwhile, the theoretical isoelectric point of WT was 9.20. Thus, WT has been converted through amino acid substitution into F2H/L39 which has a variable region with a theoretical isoelectric point decreased by about 4.9.

PK/PD Test of F2H/L39-IgG1 Using Cynomolgus Monkeys

Figure 35:
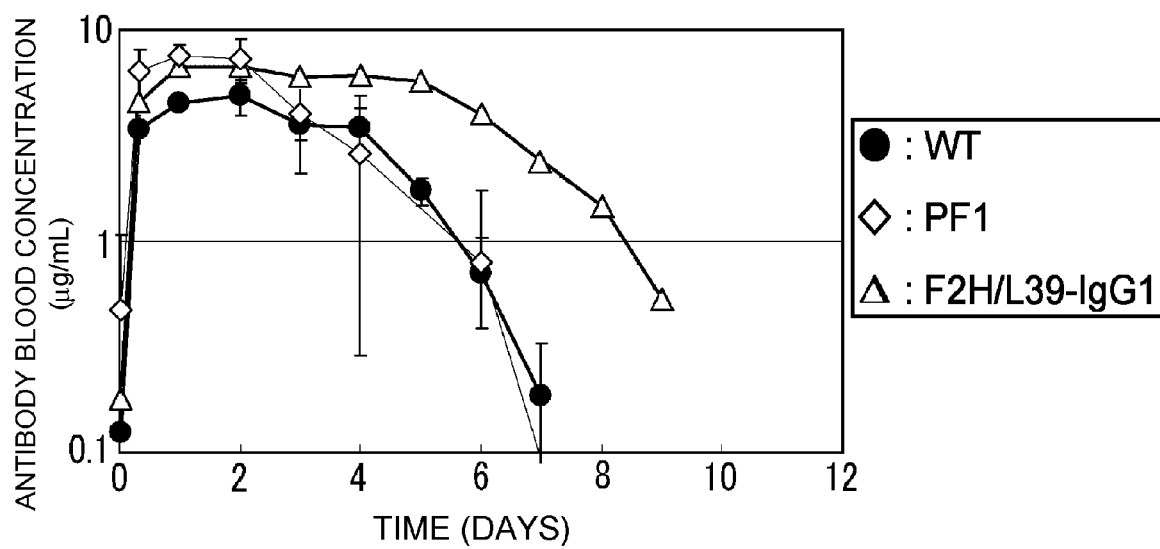
FIG. 35 is a graph showing the plasma concentration time courses of antibodies after subcutaneous administration of WT, PF1, or F2H/L39-IgG1 at 1.0 mg/kg to cynomolgus monkeys.
Figure 36:
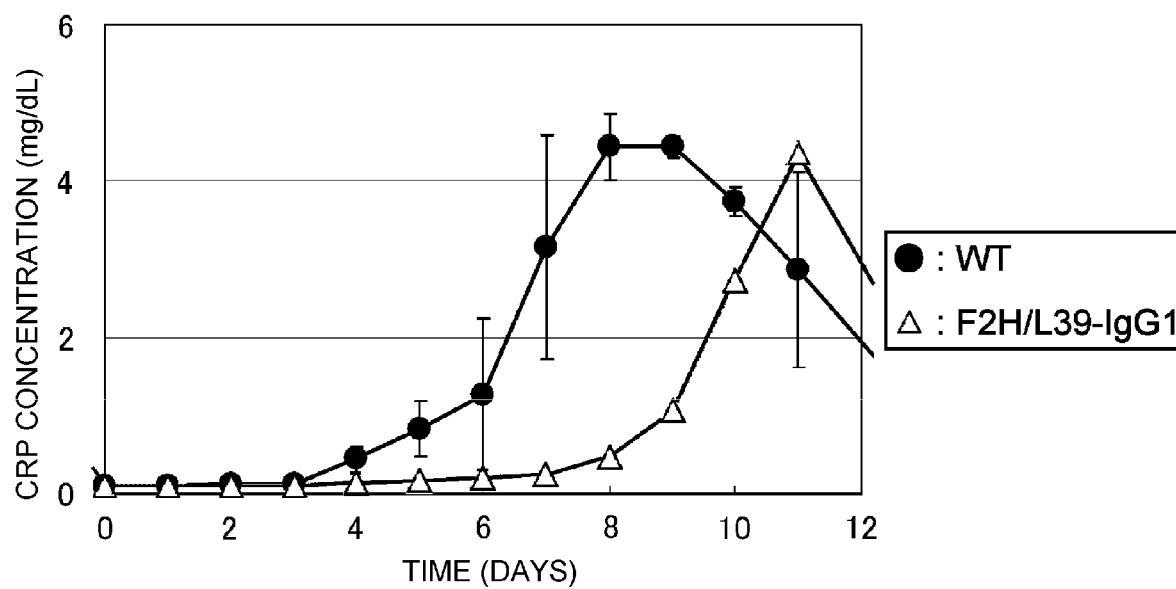
FIG. 36 is a graph showing the time courses of CRP concentration in the groups of cynomolgus monkeys administered with WT or F2H/L39-IgG1.
Figure 37:
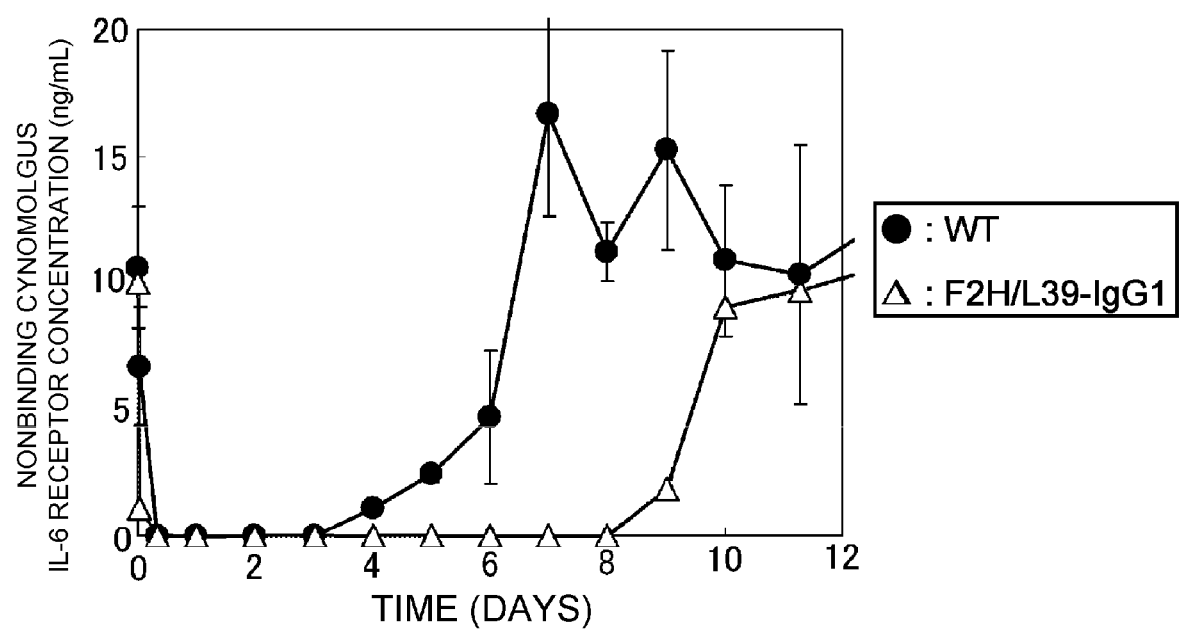
FIG. 37 is a graph showing the time courses of free cynomolgus monkey IL-6 receptor concentration in the groups of cynomolgus monkeys administered with WT or F2H/L39-IgG1.

The humanized PM1 antibody (wild type (WT)), PF1 antibody, and F2H/L39-IgG1 were assessed for their pharmacokinetics (PK) and pharmacodynamics (PD) in cynomolgus monkeys. WT, PF1, and F2H/L39-IgG1 were subcutaneously administered once at 1.0 mg/kg, and blood was collected before administration and over the time course. The concentration of each antibody in plasma was determined in the same way as described in Example 6. The plasma concentration time courses of WT, PF1, and F2H/L39-IgG1 are shown in FIG. 35. The efficacy of each antibody to neutralize membrane-bound cynomolgus monkey IL-6 receptor was assessed. Cynomolgus monkey IL-6 was administered subcutaneously in the lower back at 5 µg/kg every day from Day 3 to Day 10 after antibody administration, and the CRP concentration in each animal was determined 24 hours later. The time courses of CRP concentration after administration of WT or F2H/L39 are shown in FIG. 36. To assess the efficacy of each antibody to neutralize soluble cynomolgus monkey IL-6 receptor, the concentration of free soluble cynomolgus monkey IL-6 receptor in the plasma of cynomolgus monkeys was determined. The time courses of free soluble cynomolgus monkey IL-6 receptor concentration after administration of WT or F2H/L39 are shown in FIG. 37.

These results showed that the plasma concentration time courses of WT and PF1 were comparable to each other; however, the plasma concentration of F2H/L39-IgG1, which has a reduced isoelectric point, was maintained higher than that of these two antibodies. Meanwhile, when compared to WT, F2H/L39-IgG1 which has a high affinity for IL-6 receptor was found to maintain lower concentrations of CRP and free soluble cynomolgus monkey IL-6 receptor.

[Example 14] Assessment of the Plasma Retention of WT-M14

Method for Estimating the Retention in Human Plasma

The prolonged retention (slow elimination) of IgG molecule in plasma is known to be due to the function of FcRn which is known as a salvage receptor of IgG molecule (Nat. Rev. Immunol. 2007 September; 7(9):715-25). When incorporated into endosomes via pinocytosis, under the acidic conditions within endosome (approx. pH 6.0), IgG molecules bind to FcRn expressed in endosomes. While IgG molecules that do not bind to FcRn are transferred and degraded in lysosomes, those bound to FcRn are translocated to the cell surface and then released from FcRn back into plasma again under the neutral conditions in plasma (approx. pH 7.4).

Known IgG-type antibodies include the IgG1, IgG2, IgG3, and IgG4 isotypes. The plasma half-lives of these isotypes in human are reported to be about 36 days for IgG1 and IgG2; about 29 days for IgG3; and 16 days for IgG4 (Nat. Biotechnol. 2007 December; 25(12):1369-72). Thus, the retention of IgG1 and IgG2 in plasma is believed to be the longest. In general, the isotypes of antibodies used as pharmaceutical agents are IgG1, IgG2, and IgG4. Methods reported for further prolonging the retention of these IgG antibodies in plasma include methods for improving the above-described binding activity to human FcRn, and this is achieved by modifying the sequence of IgG constant region (J. Biol. Chem. 2007 Jan. 19; 282(3):1709-17; J. Immunol. 2006 Jan. 1; 176(1):346-56).

There are species-specific differences between mouse FcRn and human FcRn (Proc. Natl. Acad. Sci. USA. 2006 Dec. 5; 103(49):18709-14). Therefore, to predict the plasma retention of IgG antibodies that have a modified constant region sequence in human, it is desirable to assess the binding to human FcRn and retention in plasma in human FcRn transgenic mice (Int. Immunol. 2006 December; 18(12):1759-69).

Assessment of the Binding to Human FcRn

FcRn is a complex of FcRn and β2-microglobulin. Oligo-DNA primers were prepared based on the human FcRn gene sequence disclosed (J. Exp. Med. (1994) 180(6):2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into an animal cell expression vector (the amino acid sequence of human FcRn as set forth in SEQ ID NO: 140). Likewise, oligo-DNA primers were prepared based on the human β2-microglobulin gene sequence disclosed (Proc. Natl. Acad. Sci. USA. (2002) 99(26):16899-16903). A DNA fragment encoding the whole gene was prepared by PCR using human cDNA (Hu-Placenta Marathon-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into an animal cell expression vector (the amino acid sequence of human β2-microglobulin as set forth in SEQ ID NO: 141).

Soluble human FcRn was expressed by the following procedure. The plasmids constructed for human FcRn and β2-microglobulin were introduced into cells of the human embryonic kidney cancer-derived cell line HEK293H (Invitrogen) using 10% FBS (Invitrogen) by lipofection. The resulting culture supernatant was collected, and FcRn was purified using IgG Sepharose 6 Fast Flow (Amersham Biosciences) by the method described in J. Immunol. 2002 Nov. 1; 169(9):5171-80, followed by further purification using HiTrap Q HP (GE Healthcare).

The binding to human FcRn was assessed using Biacore 3000. An antibody was bound to Protein L or rabbit anti-human IgG Kappa chain antibody immobilized onto a sensor chip, human FcRn was added as an analyte for interaction with the antibody, and the affinity (KD) was calculated from the amount of bound human FcRn. Specifically, Protein L or rabbit anti-human IgG Kappa chain antibody was immobilized onto sensor chip CM5 (Biacore) by the amine coupling method using 50 mM Na-phosphate buffer (pH 6.0) containing 150 mM NaCl as the running buffer. Then, an antibody was diluted with a running buffer containing 0.02% Tween20, and injected to be bound to the chip. Human FcRn was then injected and the binding activity of the human FcRn to antibody was assessed.

The affinity was computed using BIAevaluation Software. The obtained sensorgram was used to calculate the amount of hFcRn bound to the antibody immediately before the end of human FcRn injection. The affinity of the antibody for human FcRn was calculated by fitting with the steady state affinity method.

Assessment for the Plasma Retention in Human FcRn Transgenic Mice

The pharmacokinetics in human FcRn transgenic mice (B6.mFcRn−/−.hFcRn Tg line 276+/+ mice; Jackson Laboratories) was assessed by the following procedure. An antibody was intravenously administered once at a dose of 1 mg/kg to mice, and blood was collected at appropriate time points. The collected blood was immediately centrifuged at 15,000 rpm and 4° C. for 15 minutes to obtain blood plasma. The separated plasma was stored in a freezer at −20° C. or below until use. The plasma concentration was determined by ELISA.

Predictive Assessment of the Plasma Retention of WT-M14 in Human

The activities of WT-IgG1 and WT-M14 to bind to human FcRn were assessed by Biacore. As shown in Table 12, the result indicated that the binding activity of WT-M14 was slightly greater than that of WT-IgG1.

TABLE 12

| | KD(μM) |
|---|---|
| WT-IgG1 | 2.07 |
| WT-M14 | 1.85 |

Figure 38:
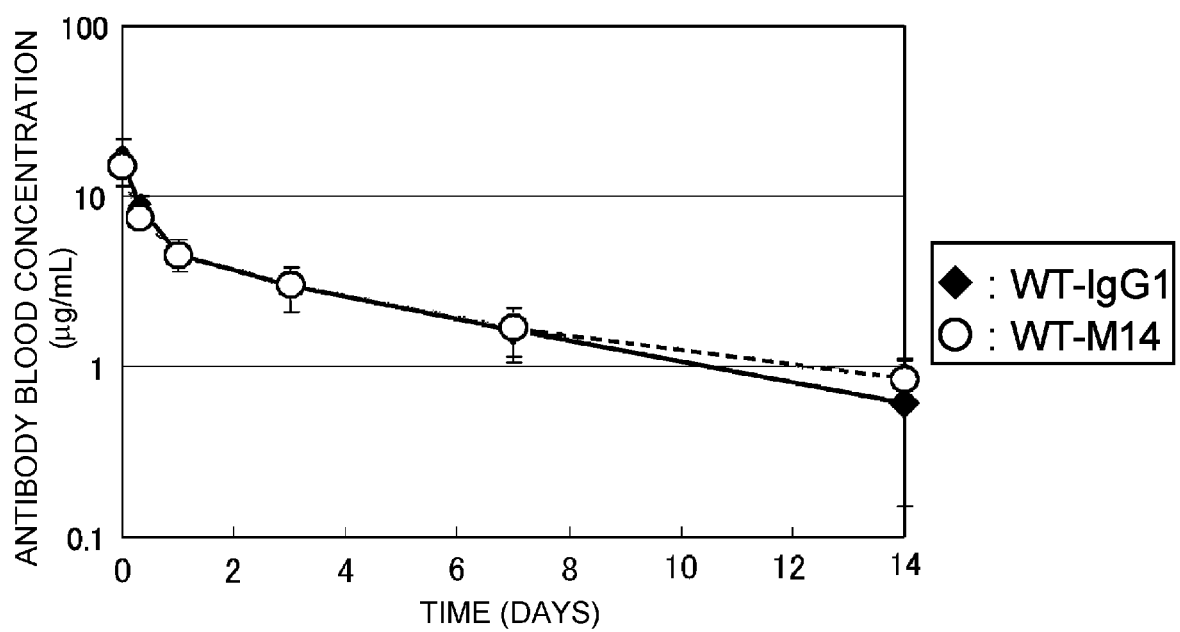
FIG. 38 is a graph showing the time courses of plasma concentrations of WT-IgG1 and WT-M14 after intravenous administration to human FcRn transgenic mice.

As shown in FIG. 38, however, the retention in plasma was comparable between WT-IgG1 and WT-M14 when assessed using human FcRn transgenic mice. This finding suggests that the plasma retention of the M14 constant region in human is comparable to that of the IgG1 constant region.

[Example 15] Preparation of WT-M44, WT-M58, and WT-M73 which have Improved Retention in Plasma Preparation of the WT-M58 Molecule As described in Example 14, the plasma retention of WT-M14 in human FcRn transgenic mice was comparable to that of WT-IgG1. Known methods to improve plasma retention include those to lower the isoelectric point of an antibody and those to enhance the binding activity to FcRn. Here, the modifications described below were introduced to improve the plasma retention of WT-M14. Specifically, the following substitutions were introduced into WT-M314GK, which was prepared from WT-M14 as described in Example 4: substitution of methionine for valine at position 397; substitution of glutamine for histidine at position 268; substitution of glutamine for arginine at position 355; and substitution of glutamic acid for glutamine at position 419 in the EU numbering system. These four substitutions were introduced into WT-M314GK to generate WT-M58 (amino acid sequence of SEQ ID NO: 142). Expression vectors were prepared by the same method described in Example 1. WT-M58 and L(WT) were used as heavy chain and light chain, respectively. WT-M58 was expressed and purified by the method described in Example 1.

Construction of the WT-M73 Molecule

On the other hand, WT-M44 (amino acid sequence of SEQ ID NO: 143) was generated by introducing into IgG1 a substitution of alanine for the amino acid at position 434, EU numbering. WT-M83 (amino acid sequence of SEQ ID NO: 185) was also generated by deletions of glycine at position 446, EU numbering and lysine at position 447, EU numbering to reduce heavy chain C-terminal heterogeneity. Furthermore, WT-M73 (amino acid sequence of SEQ ID NO: 144) was generated by introducing into WT-M58 a substitution of alanine at position 434, EU numbering.

Expression vectors for the above antibodies were constructed by the method described in Example 1. WT-M44, WT-M58, or WT-M73 was used as heavy chain, while L (WT) was used as light chain. WT-M44, WT-M58, and WT-M73 were expressed and purified by the method described in Example 1.

Predictive Assessment of the Plasma Retention of WT-M44, WT-M58, and WT-M73 in Human The binding activities of WT-IgG1, WT-M44, WT-M58, and WT-M73 to human FcRn were assessed by Biacore. As shown in Table 13, the result indicates that the binding activities of WT-M44, WT-M58, and WT-M73 are greater than WT-IgG1, and about 2.7, 1.4, and 3.8 times of that of WT-IgG1, respectively.

TABLE 13

| | KD(µM) |
|---|---|
| WT-IgG1 | 1.62 |
| WT-M44 | 0.59 |
| WT-M58 | 1.17 |
| WT-M73 | 0.42 |

Figure 39:
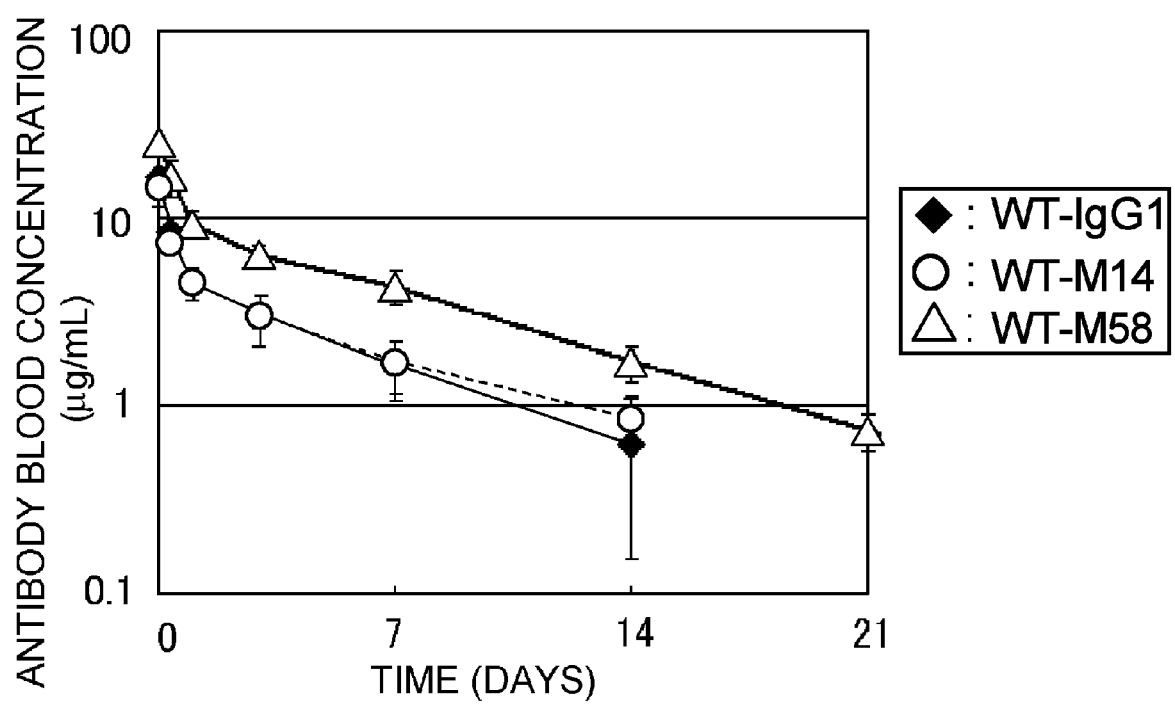
FIG. 39 is a graph showing the time courses of plasma concentrations of WT-IgG1, WT-M14, and WT-M58 after intravenous administration to human FcRn transgenic mice.
Figure 40:
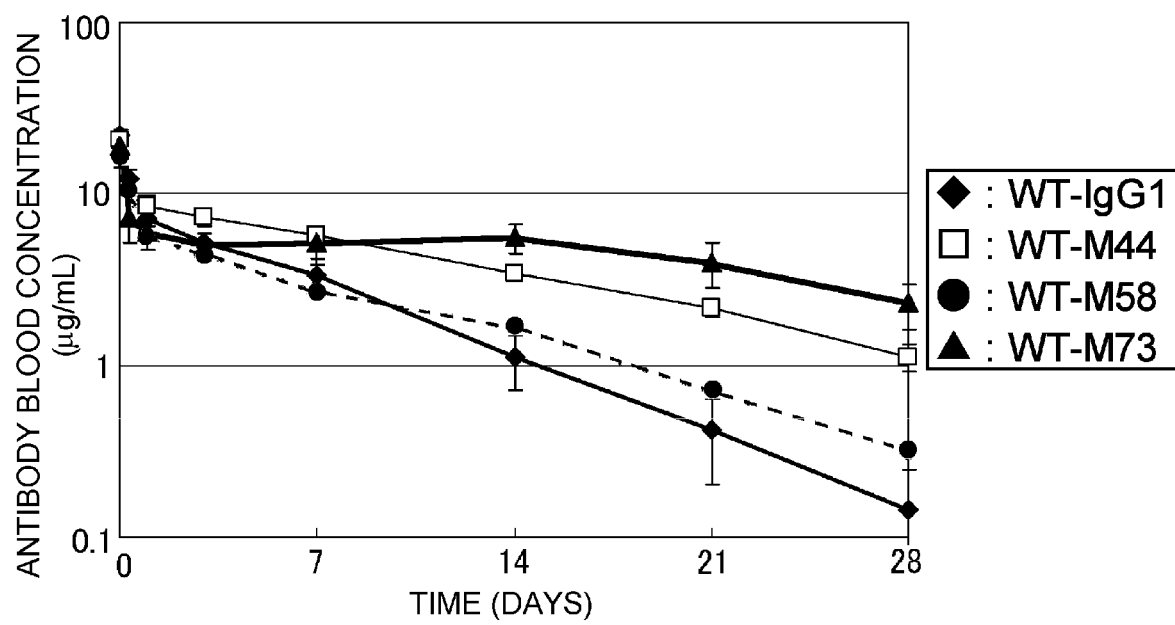
FIG. 40 is a graph showing the time courses of plasma concentrations of WT-IgG1, WT-M44, WT-M58, and WT-M73 after intravenous administration to human FcRn transgenic mice.

As a result of assessing WT-IgG1, WT-M14, and WT-M58 for their plasma retention in human FcRn transgenic mice, as shown in FIG. 39, WT-M58 was confirmed to have increased retention in plasma relative to WT-IgG1 and WT-M14. Furthermore, WT-IgG1, WT-M44, WT-M58, and WT-M73 were assessed for their plasma retention in human FcRn transgenic mice. As shown in FIG. 40, all of WT-M44, WT-M58, and WT-M73 were confirmed to have improved retention in plasma relative to WT-IgG1. The plasma retention-improving effect correlated with the binding activity to human FcRn. In particular, the plasma level of WT-M73 at Day 28 was improved to about 16 times of that of WT-IgG1. This finding suggests that the plasma retention of antibodies with the M73 constant region in human is also significantly increased when compared to antibodies with the IgG1 constant region.

[Example 16] Effect of the Novel Constant Regions M14 and M58 in Reducing Heterogeneity in Various Antibodies As described in Example 8, it was demonstrated that the heterogeneity originated from the hinge region of IgG2 could be reduced by converting the IgG2 constant region to M14 in the humanized anti-IL-6 receptor PM1 antibody (WT). IgG2 type antibodies other than the humanized PM1 antibody were also tested to assess whether the heterogeneity can be reduced by converting their constant regions into M14 or M58.

Antibodies other than the humanized PM1 antibody were: the anti IL-6 receptor antibody F2H/L39 (the amino acid sequences of F2H/L39_VH and F2H/L39 light chain variable region as set forth in SEQ ID NOs: 145 and 146, respectively); anti-IL-31 receptor antibody H0L0 (the amino acid sequences of H0L0 VH and H0L0_VL as set forth in SEQ ID NOs: 147 and 148, respectively); and anti-RANKL antibody DNS (the amino acid sequences of DNS_VH and DNS_VL as set forth in SEQ ID NOs: 149 and 150, respectively). For each of these antibodies, antibodies with IgG1 constant region (SEQ ID NO: 19), IgG2 constant region (SEQ ID NO: 20), or M14 (SEQ ID NO: 24) or M58 (SEQ ID NO: 151) were generated.

The generated antibodies were assessed for heterogeneity by cation exchange chromatography using an adequate gradient and an appropriate flow rate on a ProPac WCX-10 (Dionex) column (mobile phase A: 20 mM sodium acetate (pH 5.0), mobile phase B: 20 mM sodium acetate/1M NaCl (pH 5.0)). The assessment result obtained by cation exchange chromatography (IEC) is shown in FIG. 41.

Figure 41:
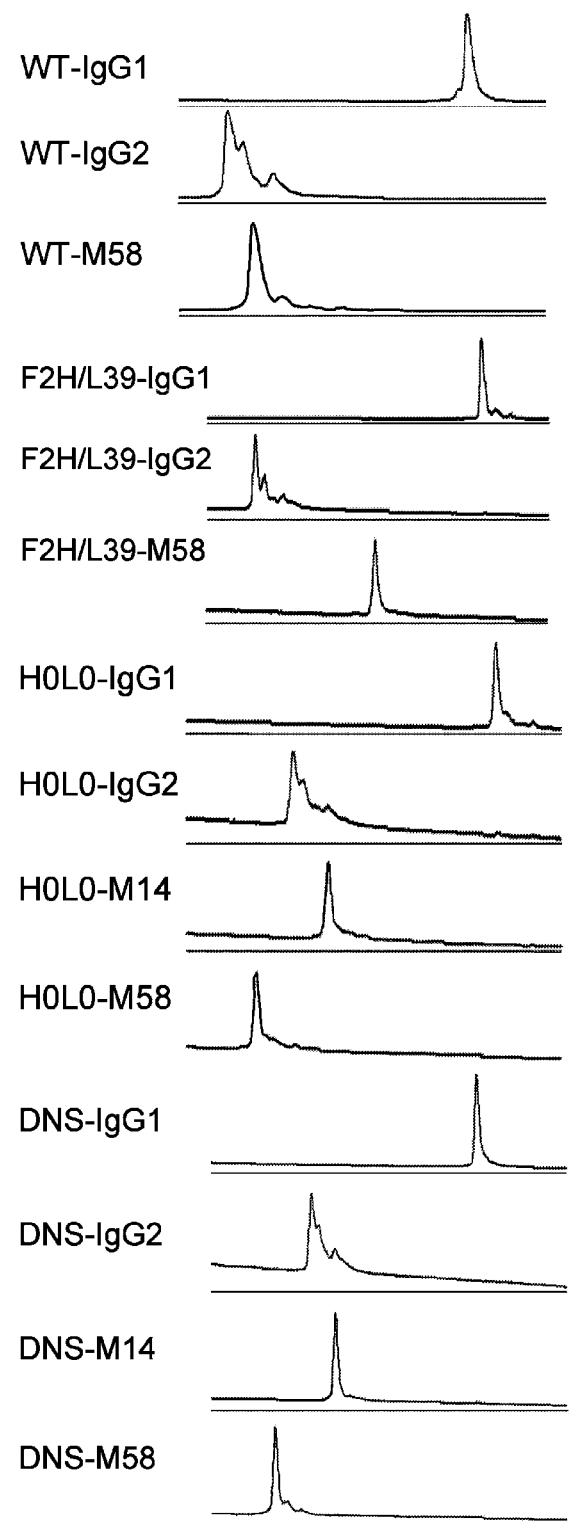
FIG. 41 is a diagram showing a cation exchange chromatography-based assessment of the effect on heterogeneity by the constant region of anti IL-6 receptor antibodies WT and F2H/L39, anti-IL-31 receptor antibody H0L0, and anti-RANKL antibody DNS.

As shown in FIG. 41, conversion of the constant region from an IgG1 type into an IgG2 type was demonstrated to increase heterogeneity not only in the humanized anti-IL-6 receptor PM1 antibody (WT), but also in the anti-IL-6 receptor antibody F2H/L39, anti-IL-31 receptor antibody H0L0, and anti-RANKL antibody DNS. In contrast, heterogeneity could be decreased in all of these antibodies by converting their constant region into M14 or M58. Thus, it was demonstrated that, regardless of the type of antigen or antibody variable region sequence, the heterogeneity originated from natural IgG2 could be reduced by substituting serines for cysteines at position 131, EU numbering, in the heavy-chain CH1 domain and at position 219, EU numbering, in the upper hinge of heavy chain.

[Example 17] Effect of the Novel Constant Region M58 to Improve the Plasma Retention in Various Antibodies As described in Example 15, it was demonstrated that conversion of the constant region from IgG1 into M58 in the humanized anti-IL-6 receptor PM1 antibody (WT) improved the binding activity to human FcRn and plasma retention in human FcRn transgenic mice. So, IgG1 type antibodies other than the humanized PM1 antibody were also tested to assess whether their retention in plasma can be improved by converting their constant region into M58.

Antibodies other than the humanized PM1 antibody (WT) were the anti-IL-31 receptor antibody H0L0 (the amino acid sequences of H0L0 VH and H0L0 VL as set forth in SEQ ID NOs: 147 and 148, respectively) and anti-RANKL antibody DNS (the amino acid sequences of DNS_VH and DNS_VL as set forth in SEQ ID NOs: 149 and 150, respectively). For each of these antibodies, antibodies with IgG1 constant region (SEQ ID NO: 19) or M58 (SEQ ID NO: 151) were generated, and assessed for their binding activity to human FcRn by the method described in Example 14. The result is shown in Table 14.

TABLE 14

| | KD (μM) | | |
|---|---|---|---|
| | WT | H0L0 | DNS |
| IgG1 | 1.42 | 1.07 | 1.36 |
| M58 | 1.03 | 0.91 | 1.03 |

As shown in Table 14, it was demonstrated that as a result of conversion of the constant region from the IgG1 type to M58, as with anti-IL-6 receptor antibody WT, the binding activities of both the anti-IL-31 receptor antibody H0L0 and anti-RANKL antibody DNS to human FcRn were improved. This suggests the possibility that regardless of the type of antigen or sequence of antibody variable region, the plasma retention in human is improved by converting the constant region from the IgG1 type to M58.

[Example 18] Effect of Cysteine in the CH1 Domain on Heterogeneity and Stability As described in Example 8, cysteines in the hinge region and CH1 domain of IgG2 were substituted to decrease the heterogeneity of natural IgG2. Assessment of various modified antibodies revealed that heterogeneity could be reduced without decreasing stability by using SKSC (SEQ ID NO: 154). SKSC (SEQ ID NO: 154) is a modified constant region obtained by substituting serine for cysteine at position 131 and lysine for arginine at position 133, EU numbering, in the heavy-chain CH1 domain, and serine for cysteine at position 219, EU numbering, in the heavy-chain upper hinge of the wild type IgG2 constant region sequence.

Meanwhile, another possible method for decreasing heterogeneity is a single substitution of serine for cysteine at position 219, or serine for cysteine at position 220, EU numbering, in the heavy-chain upper hinge. The modified IgG2 constant region SC (SEQ ID NO: 155) was prepared by substituting serine for cysteine at position 219 and CS (SEQ ID NO: 156) was prepared by substituting serine for cysteine at position 220, EU numbering, in IgG2. WT-SC (SEQ ID NO: 157) and WT-CS (SEQ ID NO: 158) were prepared to have SC and CS, respectively, and compared with WT-IgG1, WT-IgG2, WT-SKSC, and WT-M58 in terms of heterogeneity and thermal stability. Furthermore, F2H/L39-IgG1, F2H/L39-IgG2, F2H/L39-SC, F2H/L39-CS, F2H/L39-SKSC, and F2H/L39-M14, which have the constant region of IgG1 (SEQ ID NO: 19), IgG2 (SEQ ID NO: 20), SC (SEQ ID NO: 155), CS (SEQ ID NO: 156), SKSC (SEQ ID NO: 154), or M14 (SEQ ID NO: 24), respectively, were prepared from F2H/L39 (the amino acid sequences of F2H/L39 VH and F2H/L39_VL as set forth in SEQ ID NOs: 145 and 146, respectively), which is an anti IL-6 receptor antibody different from WT. The antibodies were compared with regard to heterogeneity and stability.

WT-IgG1, WT-IgG2, WT-SC, WT-CS, WT-SKSC, WT-M58, F2H/L39-IgG1, F2H/L39-IgG2, F2H/L39-SC, F2H/L39-CS, F2H/L39-SKSC, and F2H/L39-M14 were assessed for heterogeneity by cation exchange chromatography using an adequate gradient and an appropriate flow rate on a ProPac WCX-10 (Dionex) column (mobile phase A: 20 mM sodium acetate (pH 5.0), mobile phase B: 20 mM sodium acetate/1M NaCl (pH 5.0)). The assessment result obtained by cation exchange chromatography is shown in FIG. 42.

Figure 42:
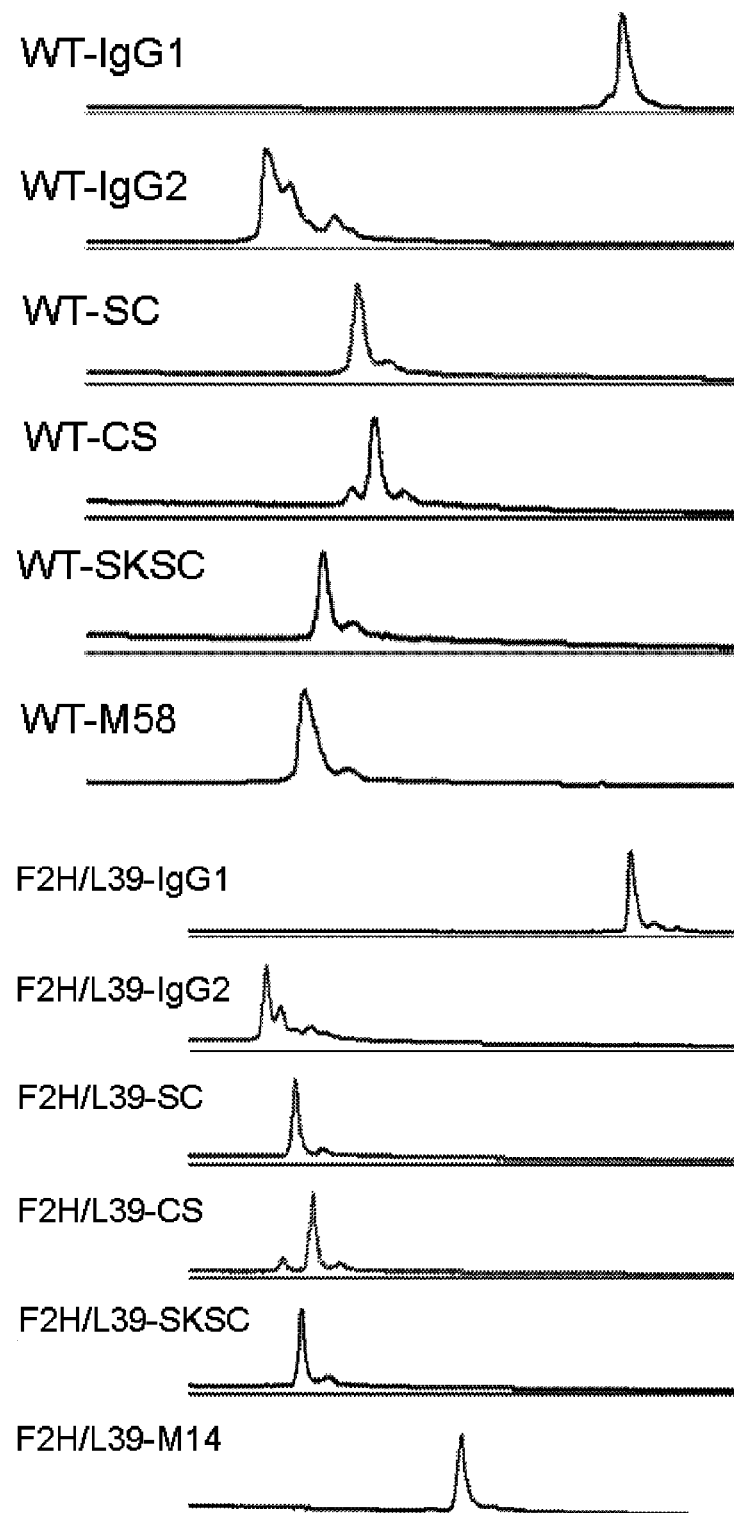
FIG. 42 is a diagram showing a cation exchange chromatography-based assessment of the effect on heterogeneity by the CH1 domain cysteine of anti IL-6 receptor antibodies WT and F2H/L39.

As shown in FIG. 42, conversion of the constant region from an IgG1 type to an IgG2 type was demonstrated to increase heterogeneity in both WT and F2H/L39. In contrast, heterogeneity was significantly decreased by converting the constant region into SKSC and M14 or M58. Meanwhile, conversion of the constant region into SC significantly decreased heterogeneity, as in the case of SKSC. However, conversion into CS did not sufficiently improve heterogeneity.

Figure 43:
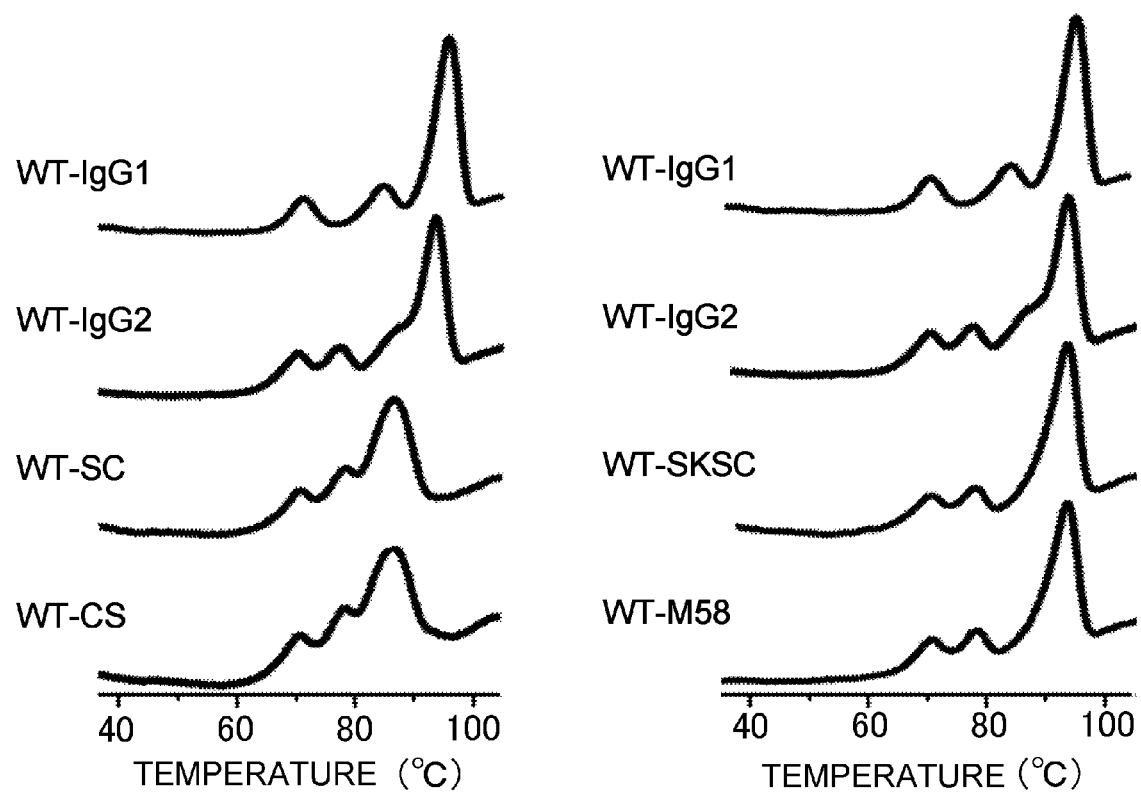
FIG. 43 is a diagram showing a DSC-based assessment of the effect on denaturation peak by the CH1 domain cysteine of anti IL-6 receptor antibody WT.

In addition to low heterogeneity, high stability is generally desired when preparing stable formulations in development of antibody pharmaceuticals. Thus, to assess stability, the midpoint temperature of thermal denaturation (Tm value) was determined by DSC (VP-DSC; Microcal). The midpoint temperature of thermal denaturation (Tm value) serves as an indicator of stability. In order to prepare stable formulations as pharmaceutical agents, a higher midpoint temperature of thermal denaturation (Tm value) is preferred (J. Pharm. Sci. 2008 April; 97(4):1414-26). WT-IgG1, WT-IgG2, WT-SC, WT-CS, WT-SKSC, and WT-M58 were dialyzed (EasySEP; TOMY) against a solution of 20 mM sodium acetate, 150 mM NaCl, pH 6.0. DSC measurement was carried out at a heating rate of 1° C./min in a range of 40° C. to 100° C., and at a protein concentration of about 0.1 mg/ml. The denaturation curves obtained by DSC are shown in FIG. 43. The Tm values of the Fab domains are listed in Table 15 below.

TABLE 15

| | Tm/° C. |
|---|---|
| WT-IgG1 | 94.8 |
| WT-IgG2 | 93.9 |
| WT-SC | 86.7 |
| WT-CS | 86.4 |
| WT-SKSC | 93.7 |
| WT-M58 | 93.7 |

The Tm values of WT-IgG1 and WT-IgG2 were almost the same (about 94° C.; Tm of IgG2 was about 1° C. lower). Meanwhile, the Tm values of WT-SC and WT-CS were about 86° C., and thus significantly lower than those of WT-IgG1 and WT-IgG2. On the other hand, the Tm values of WT-M58 and WT-SKSC were about 94° C., and comparable to those of WT-IgG1 and WT-IgG2. This suggests that WT-SC and WT-CS are markedly unstable as compared to IgG2, and thus, WT-SKSC and WT-M58, both of which also comprise substitution of serine for cysteine in the CH1 domain, are preferred in the development of antibody pharmaceuticals. The reason for the significant decrease of Tm in WT-SC and WT-CS relative to IgG2 is thought to be differences in the disulfide-bonding pattern between WT-SC or WT-CS and IgG2.

Furthermore, comparison of DSC denaturation curves showed that WT-IgG1, WT-SKSC, and WT-M58 each gave a sharp and single denaturation peak for the Fab domain. In contrast, WT-SC and WT-CS each gave a broader denaturation peak for the Fab domain. WT-IgG2 also gave a shoulder peak on the lower temperature side of the Fab domain denaturation peak. In general, it is considered that a single component gives a sharp DSC denaturation peak, and when two or more components with different Tm values (namely, heterogeneity) are present, the denaturation peak becomes broader. Specifically, the above-described result suggests the possibility that each of WT-IgG2, WT-SC, and WT-CS contains two or more components, and thus the natural-IgG2 heterogeneity has not been sufficiently reduced in WT-SC and WT-CS. This finding suggests that not only cysteines in the hinge region but also those in the CH1 domain are involved in the wild type-IgG2 heterogeneity, and it is necessary to modify not only cysteines in the hinge region but also those in the CH1 domain to decrease the DSC heterogeneity. Furthermore, as described above, stability comparable to that of wild type IgG2 can be achieved only when cysteines in both the hinge region and CH1 domain are substituted.

The above finding suggests that from the perspective of heterogeneity and stability, SC and CS, which are constant regions introduced with serine substitution for only the hinge region cysteine, are insufficient as constant regions to decrease heterogeneity originated from the hinge region of IgG2. It was thus discovered that the heterogeneity could be significantly decreased while maintaining an IgG2-equivalent stability, only when the cysteine at position 131, EU numbering, in the CH1 domain was substituted with serine in addition to cysteine at hinge region. Such constant regions include M14, M31, M58, and M73 described above. In particular, M58 and M73 are stable and less heterogeneous, and exhibit improved retention in plasma, and therefore are expected to be very useful as constant regions for antibody pharmaceuticals.

[Example 19] Generation of Fully Humanized Anti-IL-6 Receptor Antibodies with Improved PK/PD To generate a fully humanized anti-IL-6 receptor antibody with improved PK/PD, the molecules described below were created by modifying TOCILIZUMAB (heavy chain, WT-IgG1 (SEQ ID NO: 15); light chain, WT (SEQ ID NO: 105).

To improve the ka of F2H-IgG1, substitutions of valine for tryptophan at position 35, phenylalanine for tyrosine at position 50, and threonine for serine at position 62, which are the affinity enhancing substitution obtained in Example 2, were carried out. Furthermore, to lower isoelectric point without increasing immunogenicity risk, substitutions of valine for tyrosine at position 102, glutamic acid for glutamine at position 105, and threonine for isoleucine at position 107 were carried out, and conversion of the constant region from an IgG1 type to an M83 type was carried out and generated VH5-M83 (amino acid sequence of SEQ ID NO: 139). In addition, to improve the ka of L39, VL5-kappa (amino acid sequence of SEQ ID NO: 181) was prepared and it comprises a substitution of glutamine for glutamic acid at position 27. Furthermore, TOCILIZUMAB variants were prepared by combining two or more of the mutations in variable and constant regions described in the above examples and newly discovered mutations. The following fully humanized IL-6 receptor antibodies were discovered using various screening tests: Fv3-M73 (heavy chain, VH4-M73, SEQ ID NO: 182; light chain, VL1-kappa, SEQ ID NO: 183), Fv4-M73 (heavy chain, VH3-M73, SEQ ID NO: 180; light chain, VL3-kappa, SEQ ID NO: 181), and Fv5-M83 (heavy chain, VH5-M83, SEQ ID NO: 139; light chain, VL5-kappa, SEQ ID NO: 138).

Figure 44:
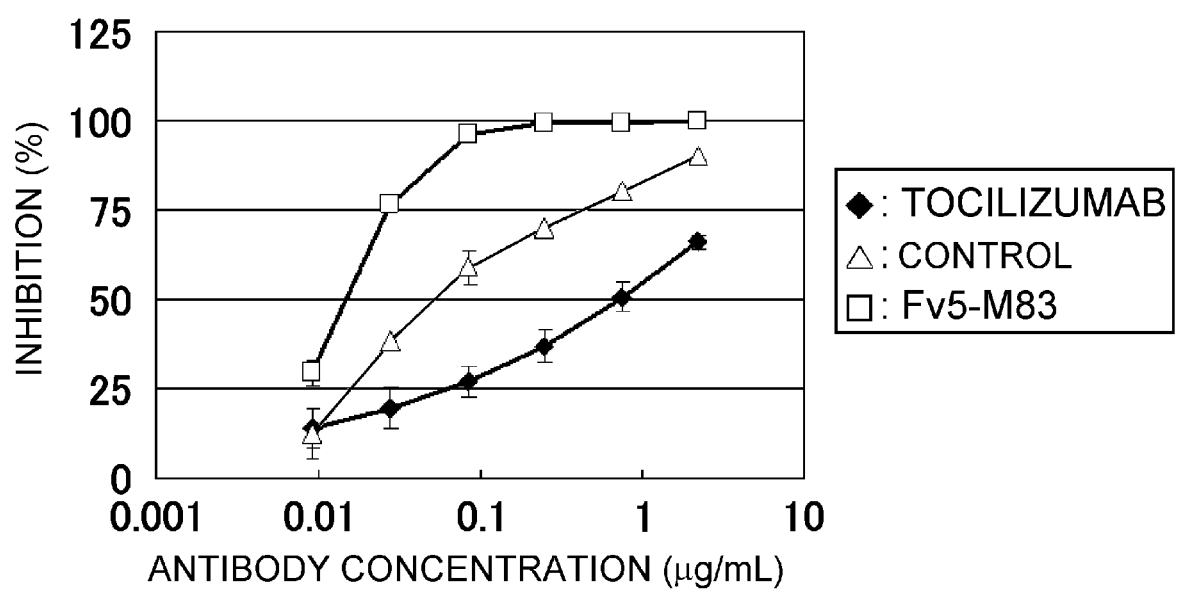
FIG. 44 is a graph showing the activities of TOCILIZUMAB, the control, and Fv5-M83 to neutralize BaF/g130.
Figure 45:
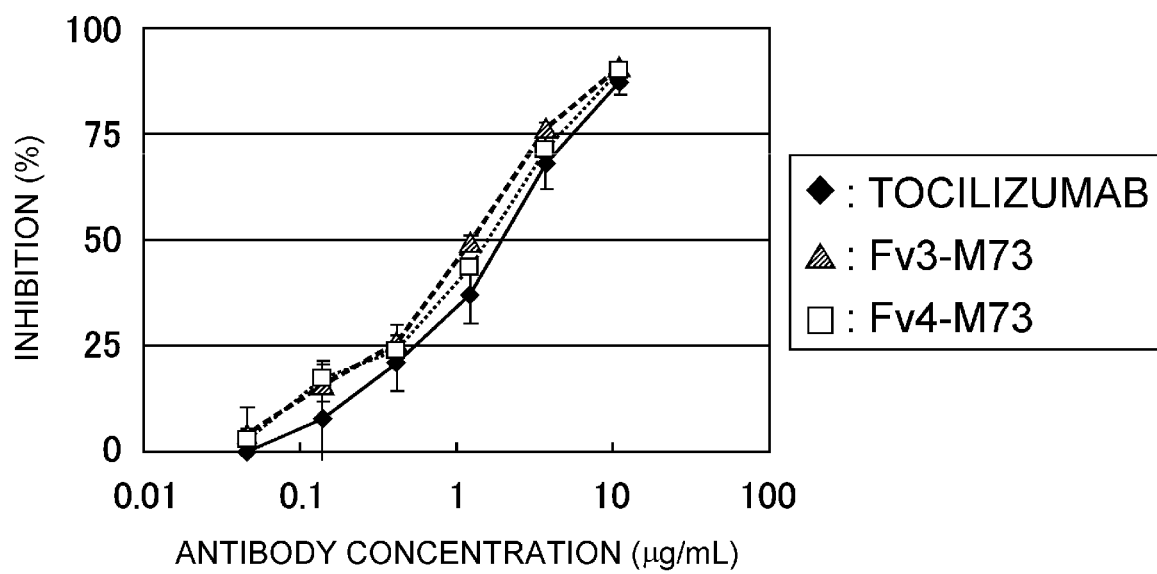
FIG. 45 is a graph showing the activities of TOCILIZUMAB, Fv3-M73, and Fv4-M73 to neutralize BaF/gp130.

The affinities of prepared Fv3-M73, Fv4-M73, and Fv5-M83 against IL-6 receptor were compared to that of TOCILIZUMAB. The affinities of these anti-IL-6 receptor antibodies determined are shown in Table 16. Furthermore, their BaF/gp130-neutralizing activities were compared to those of TOCILIZUMAB and the control (the known high affinity anti-IL-6 receptor antibody described in Reference Example, and VQ8F11-21 hIgG1 described in US 2007/0280945). The results obtained by determining the biological activities of these antibodies using BaF/gp130 are shown in FIG. 44 (TOCILIZUMAB, the control, and Fv5-M83 with a final IL-6 concentration of 300 ng/ml) and FIG. 45 (TOCILIZUMAB, Fv3-M73, and Fv4-M73 with a final IL-6 concentration of 30 ng/ml). As shown in Table 16, Fv3-M73 and Fv4-M73 have about two to three times higher affinity than TOCILIZUMAB, while Fv5-M83 exhibits about 100 times higher affinity than TOCILIZUMAB (since it was difficult to measure the affinity of Fv5-M83, instead the affinity was determined using Fv5-IgG1, which has an IgG1-type constant region; the constant region is generally thought to have no effect on affinity). As shown in FIG. 45, Fv3-M73 and Fv4-M73 exhibit slightly stronger activities than TOCILIZUMAB. As shown in FIG. 44, Fv5-M83 has a very strong activity, which is more than 100 times greater than that of TOCILIZUMAB in terms of 50% inhibitory concentration. Fv5-M83 also exhibits about ten times higher neutralizing activity in terms of 50% inhibitory concentration than the control (the known high-affinity anti-IL-6 receptor antibody).

TABLE 16

| | $k_a$(1/Ms) | $k_d$(1/s) | KD (M) |
|---|---|---|---|
| TOCILIZUMAB | 4.0E+05 | 1.1E−03 | 2.7E−09 |
| Fv3-M73 | 8.5E+05 | 8.7E−04 | 1.0E−09 |
| Fv4-M73 | 7.5E+05 | 1.0E−03 | 1.4E−09 |
| Fv5-M83 | 1.1E+06 | 2.8E−05 | 2.5E−11 |

The isoelectric points of TOCILIZUMAB, the control, Fv3-M73, Fv4-M73, and Fv5-M83 were determined by isoelectric focusing using a method known to those skilled in the art. The result showed that the isoelectric point was about 9.3 for TOCILIZUMAB; about 8.4 to 8.5 for the control; about 5.7 to 5.8 for Fv3-M73; about 5.6 to 5.7 for Fv4-M73; and 5.4 to 5.5 for Fv5-M83. Thus, each antibody had a significantly lowered isoelectric point when compared to TOCILIZUMAB and the control. Furthermore, the theoretical isoelectric point of the variable regions VH/VL was calculated by GENETYX (GENETYX CORPORATION). The result showed that the theoretical isoelectric point was 9.20 for TOCILIZUMAB; 7.79 for the control; 5.49 for Fv3-M73; 5.01 for Fv4-M73; and 4.27 for Fv5-M83. Thus, each antibody had a significantly lowered isoelectric point when compared to TOCILIZUMAB and the control. Accordingly, the plasma retention of Fv3-M73, Fv4-M73, and Fv5-M83 was thought to be improved when compared to TOCILIZUMAB and the control.

T-cell epitopes in the variable region sequence of TOCILIZUMAB, Fv3-M73, Fv4-M73, or Fv5-M83 were analyzed using TEPITOPE (Methods. 2004 December; 34(4):468-75). As a result, TOCILIZUMAB was predicted to have T-cell epitopes, of which many could bind to HLA.

In contrast, the number of sequences that were predicted to bind to T-cell epitopes was significantly reduced in Fv3-M73, Fv4-M73, and Fv5-M83. In addition, the framework of Fv3-M73, Fv4-M73, or Fv5-M83 has no mouse sequence and is thus fully humanized. These suggest the possibility that immunogenicity risk is significantly reduced in Fv3-M73, Fv4-M73, and Fv5-M83 when compared to TOCILIZUMAB.

Figure 46:
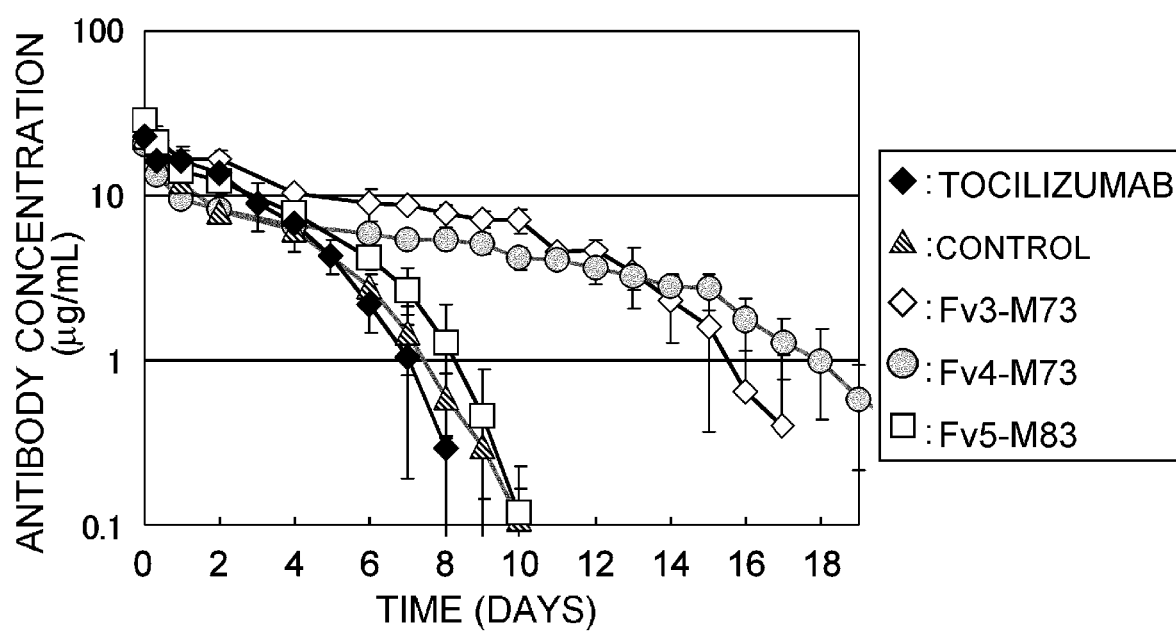
FIG. 46 is a graph showing the plasma concentration time courses of TOCILIZUMAB, the control, Fv3-M73, Fv4-M73, and Fv5-M83 in cynomolgus monkeys after intravenous administration.

[Example 20] PK/PD Test of Fully Humanized Anti-IL-6 Receptor Antibodies in Monkeys Each of TOCILIZUMAB, the control, Fv3-M73, Fv4-M73, and Fv5-M83 was intravenously administered once at a dose of 1 mg/kg to cynomolgus monkeys to assess the time courses of their plasma concentrations (see Reference Example for method). The plasma concentration time courses of TOCILIZUMAB, Fv3-M73, Fv4-M73, and Fv5-M83 after intravenous administration are shown in FIG. 46. The result showed that each of Fv3-M73, Fv4-M73, and Fv5-M83 exhibited significantly improved plasma retention in cynomolgus monkeys when compared to TOCILIZUMAB and the control. Of them, Fv3-M73 and Fv4-M73 exhibited substantially improved plasma retention when compared to TOCILIZUMAB.

Figure 47:
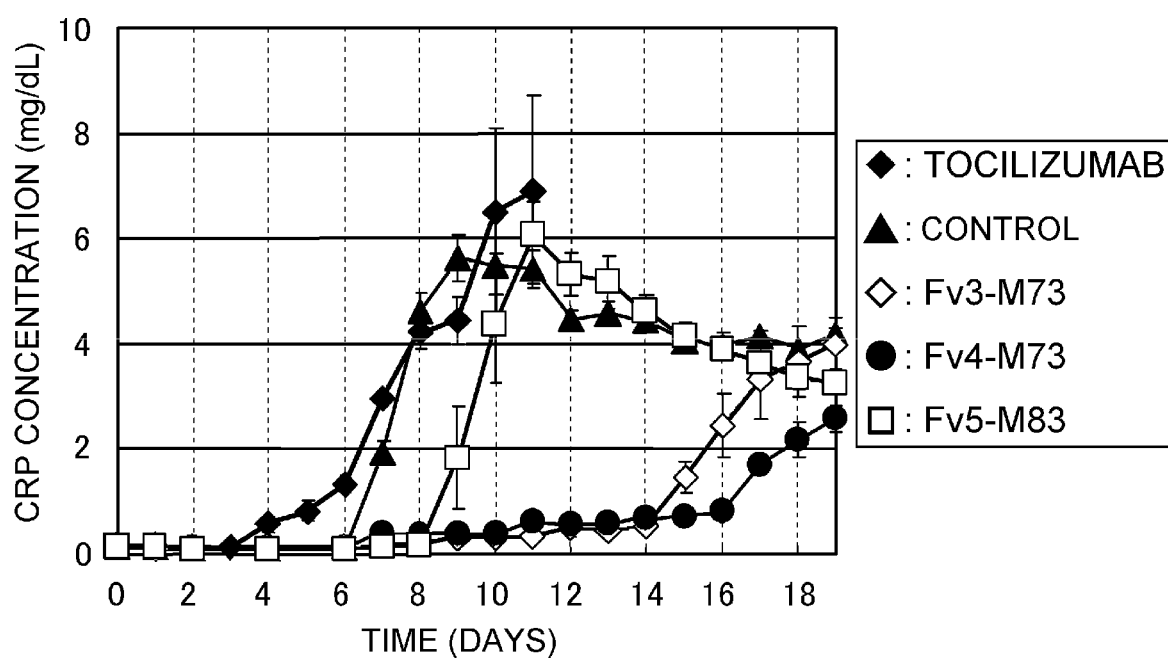
FIG. 47 is a graph showing the time courses of CRP concentration in cynomolgus monkeys after intravenous administration of TOCILIZUMAB, the control, Fv3-M73, Fv4-M73, or Fv5-M83.
Figure 48:
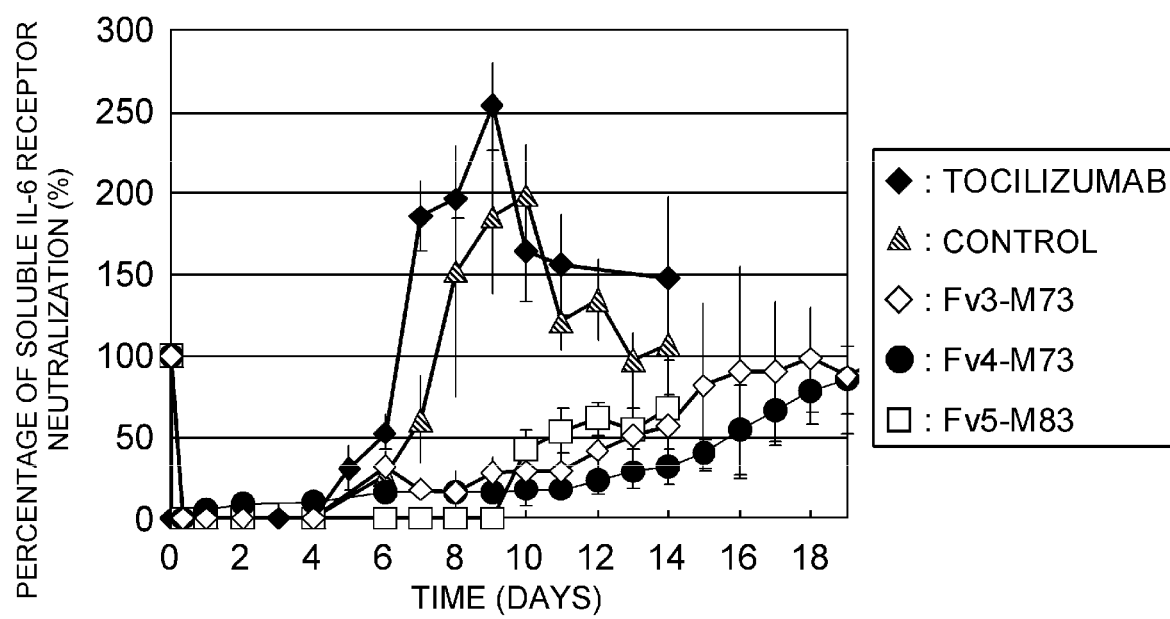
FIG. 48 is a graph showing the time courses of percentage of soluble IL-6 receptor neutralization in cynomolgus monkeys after intravenous administration of TOCILIZUMAB, the control, Fv3-M73, Fv4-M73, or Fv5-M83.

The efficacy of each antibody to neutralize membrane-bound cynomolgus monkey IL-6 receptor was assessed. Cynomolgus monkey IL-6 was administered subcutaneously in the lower back at 5 µg/kg every day from Day 6 to Day 18 after antibody administration (Day 3 to Day 10 for TOCILIZUMAB), and the CRP concentration in each animal was determined 24 hours later (see Reference Example for method). The time course of CRP concentration after administration of each antibody is shown in FIG. 47. To assess the efficacy of each antibody to neutralize soluble cynomolgus monkey IL-6 receptor, the plasma concentration of free soluble cynomolgus monkey IL-6 receptor in the cynomolgus monkeys was determined and percentage of soluble IL-6 receptor neutralization were calculated (see Reference Example for method). The time course of percentage of soluble IL-6 receptor neutralization after administration of each antibody is shown in FIG. 48.

Each of Fv3-M73, Fv4-M73, and Fv5-M83 neutralized membrane-bound cynomolgus monkey IL-6 receptor in a more sustainable way, and suppressed the increase of CRP over a longer period when compared to TOCILIZUMAB and the control (the known high-affinity anti-IL-6 receptor antibody). Furthermore, each of Fv3-M73, Fv4-M73, and Fv5-M83 neutralized soluble cynomolgus monkey IL-6 receptor in a more sustainable way, and suppressed the increase of free soluble cynomolgus monkey IL-6 receptor over a longer period when compared to TOCILIZUMAB and the control. These findings demonstrate that all of Fv3-M73, Fv4-M73, and Fv5-M83 are superior in sustaining the neutralization of membrane-bound and soluble IL-6 receptors than TOCILIZUMAB and the control. Of them, Fv3-M73 and Fv4-M73 are remarkably superior in sustaining the neutralization. Meanwhile, Fv5-M83 suppressed CRP and free soluble cynomolgus monkey IL-6 receptor more strongly than Fv3-M73 and Fv4-M73. Thus, Fv5-M83 is considered to be stronger than Fv3-M73, Fv4-M73, and the control (the known high-affinity anti-IL-6 receptor antibody) in neutralizing membrane-bound and soluble IL-6 receptors. It was considered that results in in vivo of cynomolgus monkeys reflect the stronger affinity of Fv5-M83 for IL-6 receptor and stronger biological activity of Fv5-M83 in the BaF/gp130 assay system relative to the control.

These findings suggest that Fv3-M73 and Fv4-M73 are highly superior in sustaining their activities as an anti-IL-6 receptor-neutralizing antibody when compared to TOCILIZUMAB and the control, and thus enable to significantly reduce the dosage and frequency of administration. Furthermore, Fv5-M83 was demonstrated to be remarkably superior in terms of the strength of activity as an anti-IL-6 receptor-neutralizing antibody as well as sustaining their activity. Thus, Fv3-M73, Fv4-M73, and Fv5-M83 are expected to be useful as pharmaceutical IL-6 antagonists.

Reference Example

Preparation of Soluble Recombinant Cynomolgus Monkey IL-6 Receptor (cIL-6R)

Oligo-DNA primers were prepared based on the disclosed gene sequence for Rhesus monkey IL-6 receptor (Birney et al., Ensembl 2006, Nucleic Acids Res. 2006 Jan. 1; 34 (Database issue):D556-61). A DNA fragment encoding the whole cynomolgus monkey IL-6 receptor gene was prepared by PCR using the primers, and as a template, cDNA prepared from the pancreas of cynomolgus monkey. The resulting DNA fragment was inserted into an animal cell expression vector, and a stable expression CHO line (cyno.sIL-6R-producing CHO cell line) was prepared using the vector. The culture medium of cyno.sIL-6R-producing CHO cells was purified using a HisTrap column (GE Healthcare Bioscience) and then concentrated with Amicon Ultra-15 Ultracel-10k (Millipore). A final purified sample of soluble cynomolgus monkey IL-6 receptor (hereinafter "cIL-6R") was obtained through further purification on a Superdex200 pg16/60 gel filtration column (GE Healthcare Bioscience).

Preparation of Recombinant Cynomolgus Monkey IL-6 (cIL-6)

Cynomolgus monkey IL-6 was prepared by the procedure described below. The nucleotide sequence encoding 212 amino acids deposited under SWISSPROT Accession No. P79341 was prepared and cloned into an animal cell expression vector. The resulting vector was introduced into CHO cells to prepare a stable expression cell line (cyno.IL-6-producing CHO cell line). The culture medium of cyno.IL-6-producing CHO cells was purified using a SP-Sepharose/ FF column (GE Healthcare Bioscience) and then concentrated with Amicon Ultra-15 Ultracel-5k (Millipore). A final purified sample of cynomolgus monkey IL-6 (hereinafter "cIL-6") was obtained through further purification on a Superdex75 pg26/60 gel filtration column (GE Healthcare Bioscience), followed by concentration with Amicon Ultra-15 Ultracel-5k (Millipore).

Preparation of a Known High-Affinity Anti-IL-6 Receptor Antibody

An animal cell expression vector was constructed to express VQ8F11-21 hIgG1, a known high-affinity anti-IL-6 receptor antibody. VQ8F11-21 hIgG1 is described in US 2007/0280945 A1 (US 2007/0280945 A1; the amino acid sequences of heavy chain and light chain as set forth in SEQ ID NOs: 19 and 27, respectively). The antibody variable region was constructed by PCR using a combination of synthetic oligo DNAs (assembly PCR). IgG1 was used as the constant region. The antibody variable and constant regions were combined together by assembly PCR, and then inserted into an animal cell expression vector to construct expression vectors for the heavy chain and light chain of interest. The nucleotide sequences of the resulting expression vectors were determined by a method known to those skilled in the art. The high-affinity anti-IL-6 receptor antibody (hereinafter abbreviated as "control") was expressed and purified using the constructed expression vectors by the method described in Example 1.

Biacore-Based Analysis of Binding to IL-6 Receptor

Antigen-antibody reaction kinetics was analyzed using Biacore T100 (GE Healthcare). The SR344-antibody interaction was measured by immobilizing appropriate amounts of anti-IgG (γ-chain specific) F(ab')$_2$ onto a sensor chip by amine coupling method, binding antibodies of interest onto the chip at pH 7.4, and then flowing IL-6 receptor SR344 adjusted to be various concentrations at pH 7.4 over the chip as an analyte. All measurements were carried out at 37° C. The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (GE Healthcare).

PK/PD Test to Determine the Plasma Concentrations of Antibodies, CRP, and Free Soluble IL-6 Receptor in Monkeys The plasma concentrations in cynomolgus monkeys were determined by ELISA using a method known to those skilled in the art. The concentration of CRP was determined with an automated analyzer (TBA-120FR; Toshiba Medical Systems Co.) using Cias R CRP (KANTO CHEMICAL CO., INC.).

The plasma concentration of free soluble cynomolgus monkey IL-6 receptor in cynomolgus monkeys was determined by the procedure described below. All IgG antibodies (cynomolgus monkey IgG, anti-human IL-6 receptor antibody, and anti-human IL-6 receptor antibody-soluble cynomolgus monkey IL-6 receptor complex) in the plasma were adsorbed onto Protein A by loading 30 µl of cynomolgus monkey plasma onto an appropriate amount of rProtein A Sepharose Fast Flow resin (GE Healthcare) dried in a 0.22-µm filter cup (Millipore). Then, the solution in cup was spinned down using a high-speed centrifuge to collect the solution that passed through. The solution that passed through does not contain Protein A-bound anti-human IL-6 receptor antibody-soluble cynomolgus monkey IL-6 receptor complex. Therefore, the concentration of free soluble IL-6 receptor can be determined by measuring the concentration of soluble cynomolgus monkey IL-6 receptor in the solution that passed through Protein A. The concentration of soluble cynomolgus monkey IL-6 receptor was determined using a method known to those skilled in the art for measuring the concentrations of soluble human IL-6 receptor. Soluble cynomolgus monkey IL-6 receptor (cIL-6R) prepared as described above was used as a standard.

Then the percentage of soluble IL-6 receptor neutralization was calculated by following formula.

[(Free soluble IL-6 receptor concentration after antibody administration)/(soluble IL-6 receptor concentration before antibody administration)]×100

Example 21

(1) Preparation of Point Mutant Genes of Humanized Antibody H0L0

Various point mutant genes were constructed using as a starting material the gene encoding a glypican 3 antibody comprising the CDR of humanized antibody GC33 disclosed in WO2006/046751. Oligo DNAs were designed and synthesized based on forward and reverse sequences containing a mutation site. A number of point mutant genes were prepared using QuikChange Site-Directed Mutagenesis Kit (Stratagene) available on the market. The genes comprising point mutations were prepared by PCR under the conditions below. A reaction mixture consisting of 10 ng of template plasmid, 10 pmol each of forward and reverse synthetic oligo DNAs, 10× Buffer appended to the kit, dNTP mix, and Pfu turbo DNA polymerase was treated by heating at 95° C. for 30 seconds, followed by PCR of 18 cycles consisting of: 95° C. for 30 seconds, 55° C. for one minute, and 68° C. for four minutes. DpnI included in the kit was added to the reaction mixture, followed by one hour of restriction enzyme digestion at 37° C. As a result of transforming DH5α competent cells (TOYOBO) with the reaction mixture, transformants were obtained. Plasmid DNAs were isolated from the transformants and then sequenced. The point mutant genes, which were confirmed to have introduced point mutations based on the determined nucleotide sequences of the plasmid DNAs, were cloned into expression vectors that enabled the expression of insert genes in animal cells. The modified genes were obtained by modifications described below.

Humanized antibody H0L0 and its point mutants were transiently expressed using polyethyleneimine (Polysciences Inc.). HEK293 cells were detached using Trypsin EDTA (Invitrogen) and plated at 6×10$^6$ cells/10 ml in 10-cm$^2$ culture dishes. On the next day, 4.6 µg and 9.2 µg of the heavy chain and light chain expression plasmid DNAs, respectively, were combined with 690 µl of SFMII medium and 20.8 µg of polyethyleneimine. After mixing the combined materials, the mixture was incubated at room temperature for ten minutes. The whole mixture was added dropwise to each of the culture dishes where HEK293 cells had been plated as described above, and the culture supernatant was collected after about 72 hours. The expressed humanized antibody H0L0 and its point mutants were purified from the culture supernatants using rProteinA Sepharose™ Fast Flow (GE Healthcare) according to the appended protocol.

(1-1) Modification of Tm Value of Humanized Antibody H0L0

Thermal denaturation midpoint temperature (Tm) is defined as the top of denaturation peak in thermograms (Cp vs T) obtained as a result of heating a test sample solution at a constant programmed heating rate. To determine the Tm value of humanized antibody H0L0, a sample solution for DSC assay was prepared by the following procedure. First, a solution containing 50 to 100 µg of an antibody was placed into a dialysis membrane and dialyzed for one whole day and night against 20 mol/l sodium acetate buffer (pH 6.0) containing 150 mmol/l sodium chloride as the outer dialysate. Then, a sample solution was prepared by adjusting the antibody concentration to 50 to 100 µg/ml using the outer dialysate, and used as a test sample solution for DSC assay.

Figure 49:
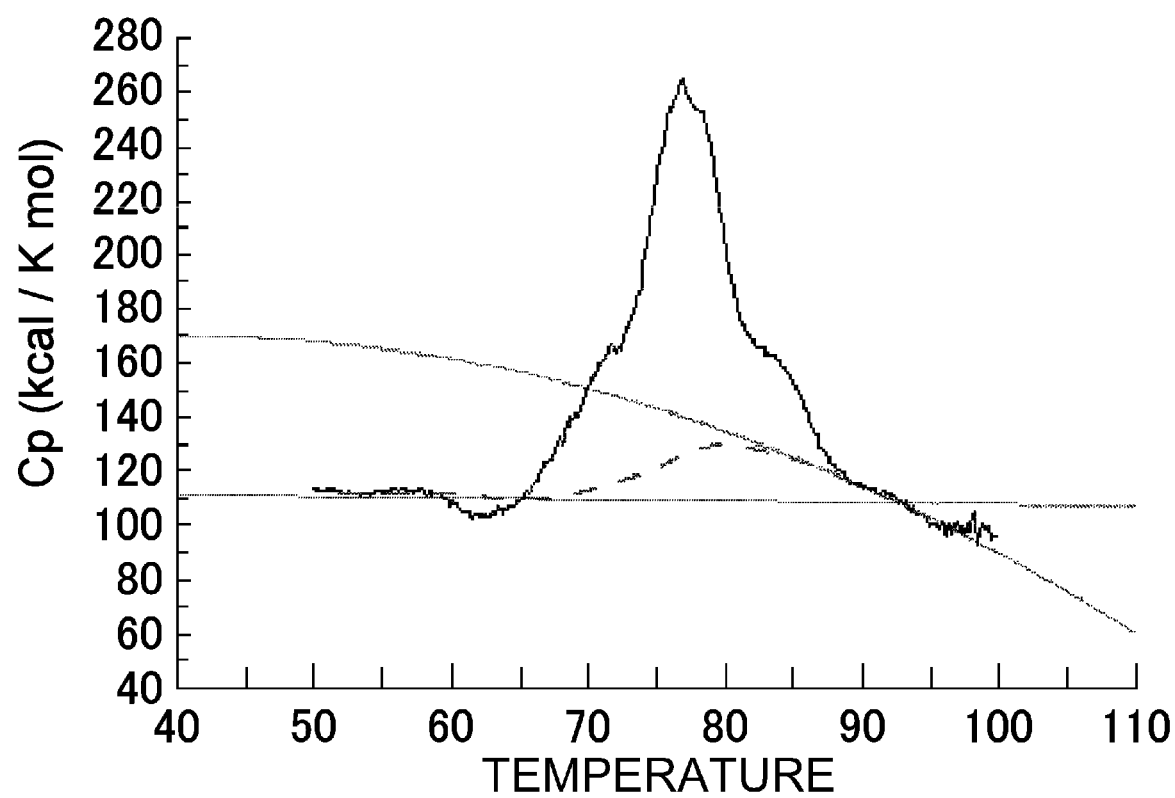
FIG. 49 is a chart obtained by DSC measurement of the Hspu2.2Lspu2.2 (Hu2.2Lu2.2) antibody.

An appropriate DSC device, for example, DSC-II (calorimetry Sciences Corporation) is preferably used in this experiment. After thorough deaeration, the sample solution prepared by the method described above and the reference solution (outer dialysate) were enclosed in calorimetric cells, and thoroughly thermally equilibrated at 40° C. Then, the solutions were scanned from 40° C. to 100° C. with a scanning rate of about 1 K/min. The assay result was displayed as the top of denaturation peak which is a function of temperature. The peaks for the Fab domain were assigned to determine the thermal denaturation midpoint temperature for humanized antibody H0L0, based on a non-patent document (Rodolfo et al., Immunology Letters (1999) 47-52). As a specific example, a DSC chart obtained for the Hspu2.2Lspu2.2 (Hu2.2Lu2.2) antibody is shown in FIG. 49.

According to calculation by the method described above, the Tm value of humanized antibody H0L0 comprising the heavy chain of SEQ ID NO: 195 and the light chain of SEQ ID NO: 201 was 76.6° C. As examples of known antibodies, the Tm values of Synagis and Herceptin were calculated to be 85.4° C. and 81.8° C., respectively. This suggests that the Tm value of humanized antibody H0L0 is lower than those of known antibodies.

In order to increase the Tm value of humanized antibody H0L0, a modified antibody was prepared. H15 (SEQ ID NO: 196) was prepared by modifying FR2 of the H0L0 antibody heavy chain (SEQ ID NO: 195) with modifications V37I, A40P, M48I, and L51I which converted the subclass from VH1b to VH4. The Tm value was improved to 79.1° C. L4 (SEQ ID NO: 202) was prepared by modifying FR2 of the H0L0 antibody light chain (SEQ ID NO: 201) with modifications L42Q, S48A, and Q50R which converted the subclass from VK2 to VK3, and by substituting V2 of FR1 with a germ-line sequence, I (V2I modification). The Tm value was improved to 77.2° C. Antibody H15L4 was prepared by combining these two modified antibodies, and as a result, the Tm value was improved to 80.5° C.

(1-2) Modification of Isoelectric Point Value of Humanized Antibody H0L0

The blood half-life of an antibody is prolonged as the isoelectric point value of the antibody decreases. Conversely, an increase in the antibody isoelectric point value improves the transfer of the antibody into tissues. It is still remains unknown whether the tumor-suppressing effect of antibodies that are effective in cancer therapy is potentiated by an increase or a decrease in the antibody isoelectric point value. Thus, modified antibodies were prepared from humanized antibody H0L0, one of which had a decreased isoelectric point and the other had an increased isoelectric point. The tumor-suppressing effect was compared between the two antibodies to test which modification results in a stronger tumor-suppressing effect.

The isoelectric point value of each antibody was calculated based on the isoelectric focusing analysis according to the following procedure. Phast-Gel Dry IEF gel (Amercham Bioscience) was swollen for about 60 minutes in Phastsystem Cassette (Amercham Bioscience) using a swelling solution with either of the following compositions.

(a) Composition of high isoelectric point swelling solution:
  1.5 ml of 10% glycerol
  100 µl Pharmalyte 8-10.5 for IEF (Amercham Bioscience)
(b) Composition of low isoelectric point swelling solution:
  1.5 ml of purified water
  20 µl of Pharmalyte 8-10.5 for IEF (Amercham Bioscience)
  80 µl of Pharmalyte 5-8 for IEF (Amercham Bioscience)

About 0.5 µg of antibody was loaded onto the swollen gel, and isoelectric focusing was carried out using programmed PhastSystem (Amercham Bioscience). The samples were added to the gel at Step 2 in the program indicated below. pI Calibration Kit was used as pI markers (Amercham Bioscience).

Figure 50:
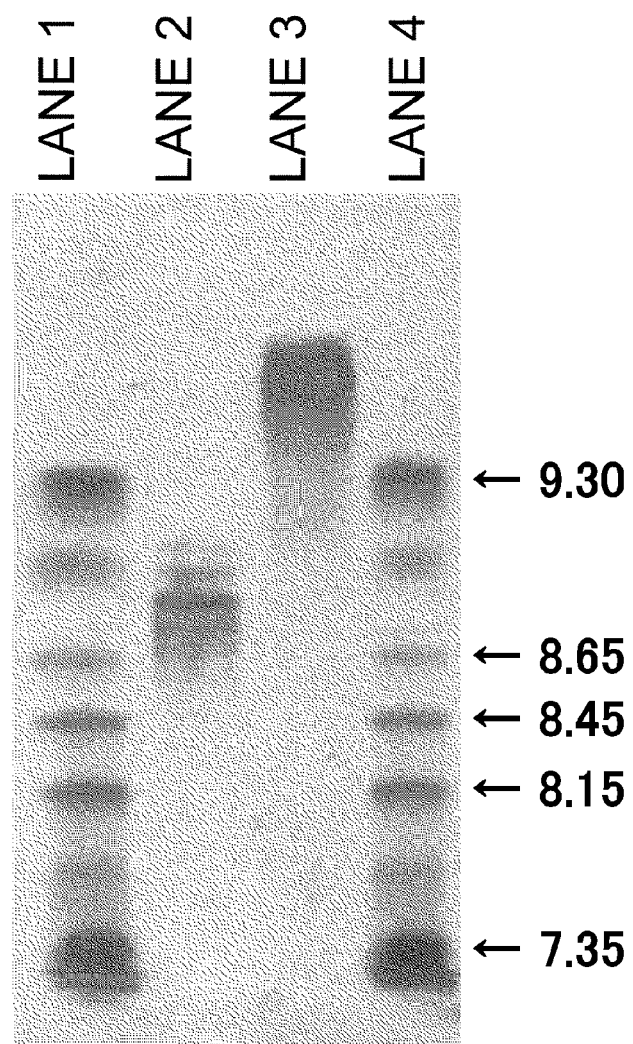
FIG. 50 is an electrophoretic image of the H0L0 and Hspu2.2Lspu2.2 (Hu2.2Lu2.2) antibodies by high-pI isoelectric focusing.
Figure 51:
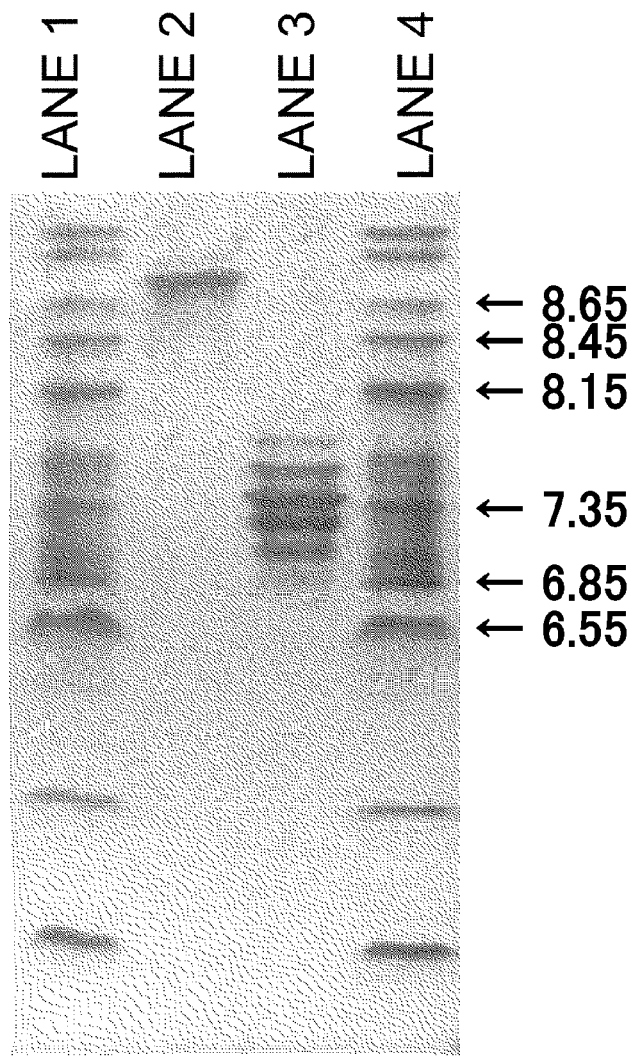
FIG. 51 is an electrophoretic image of the H0L0 and Hspd1.8Lspd1.6 (Hd1.8Ld1.6) antibodies by low-pI isoelectric focusing.

Step 1: 2,000 V, 2.5 mA, 3.5 W, 15° C., 75 Vh
  Step 2: 200 V, 2.5 mA, 3.5 W, 15° C., 15 Vh
  Step 3: 2,000 V, 2.5 mA, 3.5 W, 15° C., 410 Vh After electrophoresis, the gel was fixed with 20% TCA, and then sliver-stained using Silver Staining Kit, protein (Amercham Bioscience) according to the appended protocol. After staining, the isoelectric point of each antibody as a test sample was calculated based on the known isoelectric points of the pI markers. Electrophoretic patterns of high pI and low pI isoelectric focusing are shown in FIGS. 50 and 51, respectively.

(a) Modifications Resulting in an Increase of Isoelectric Point

Hspu2.2 (Hu2.2) (SEQ ID NO: 200) was prepared by further modifying H15 by Q43K, D52N, and Q107R. Lspu2.2 (Lu2.2) (SEQ ID NO: 206) was prepared by further modifying L4 by E17Q, Q27R, and Q105R, as well as S25A (substitution of S25 in CDR2 by A which is highly frequent in the germ line). The Tm value and isoelectric point value of the Hspu2.2Lspu2.2 antibody (Hu2.2Lu2.2) consisting of Hspu2.2 (Hu2.2) and Lspu2.2 (Lu2.2) were determined to be 76.8° C. and 9.6, respectively. The isoelectric point value of the H0L0 antibody is 8.9. Thus, the isoelectric point value has been increased by 0.7 in the Hspu2.2Lspu2.2 antibody (Hu2.2Lu2.2).

(b) Modifications Resulting in a Decrease of Isoelectric Point

Hspd1.8 (Hd1.8) (SEQ ID NO: 199) was prepared by further modifying H15 by K19T, Q43E, K63S, K65Q, and G66D. Lspd1.6 (Ld1.6) (SEQ ID NO: 205) was prepared by further modifying L4 by Q27E, substitution of TISSLQ for KISRVE at positions 79 to 84 in FR3 of L4, and the same modification S25A as in Lspu2.2 (Lu2.2). The Tm value and isoelectric point value of the Hspd1.8Lspd1.6 antibody (Hd1.8Ld1.6) consisting of Hspd1.8 (Hd1.8) and Lspd1.6 (Ld1.6) were determined to be 72.6° C. and 7.4, respectively. The isoelectric point value of the H0L0 antibody is 8.9. Thus, the isoelectric point value has been decreased by 1.5 in the Hspd1.8Lspd1.6 antibody (Hd1.8Ld1.6).

(2) Assessment of Antibody H0L0 Point Mutants for Binding Activity by Competitive ELISA The H0L0 antibody and its point mutants were purified as described in (1) and assessed by competitive ELISA. The concentration of soluble GPC3 core polypeptide (SEQ ID NO: 207) was adjusted to 1 µg/ml. 100 µl of the polypeptide solution was added to each well of a 96-well plate. The plate was incubated overnight at 4° C. to immobilize the soluble GPC3 core polypeptide onto the plate. The plate immobilized with the soluble GPC3 core polypeptide was washed three times with washing buffer using SkanWasher 400 (Molecular Devices). After 200 µl of blocking buffer was added, the plate was blocked at 4° C. overnight or longer. Then, the plate immobilized with the soluble GPC3 core polypeptide was washed three times with washing buffer using SkanWasher 400. Next, various concentrations of the H0L0 antibody or its point mutants were mixed with a final concentration of 0.3 µg/ml biotinylated H0L0 antibody, and each mixture was added to the plate at 100 µl/well. The H0L0 antibody was biotinylated using Biotin Labeling Kit (Roche) according to the appended protocol. The plate was incubated at room temperature for one hour, and then washed five times with washing buffer using SkanWasher 400 (Molecular Devices). Goat anti-streptavidin alkaline phosphatase (Zymed) was 20,000-times diluted with substrate buffer and added to the plate at 100 µl/well. The plate was incubated at room temperature for one hour, and then washed five times with washing buffer using SkanWasher 400. The concentration of phosphatase substrate (Sigma) was adjusted to 1 mg/ml using the substrate buffer, and the solution was added to the plate at 100 µl/well. The plate was incubated for one hour. The absorbance of reaction mixture at 405 nm in each well was determined using Benchmark Plus (Bio-Rad). The wavelength of reference absorbance used was 655 nm.

Figure 52:
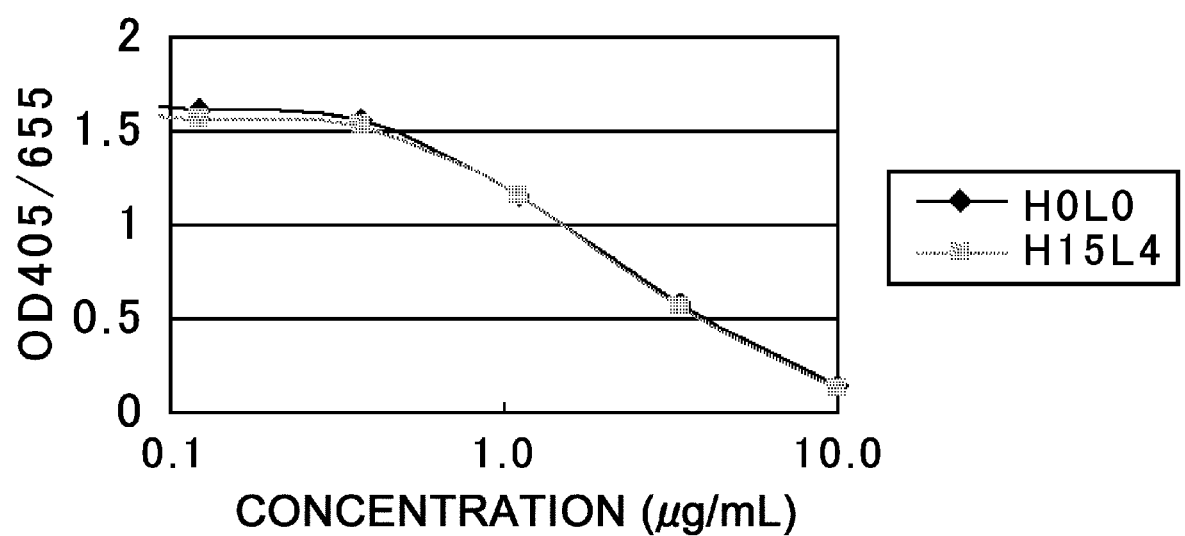
FIG. 52 is a graph showing the glypican 3 (antigen)-binding activities of the H15L4 and H0L0 antibodies determined by competitive ELISA.
Figure 53:
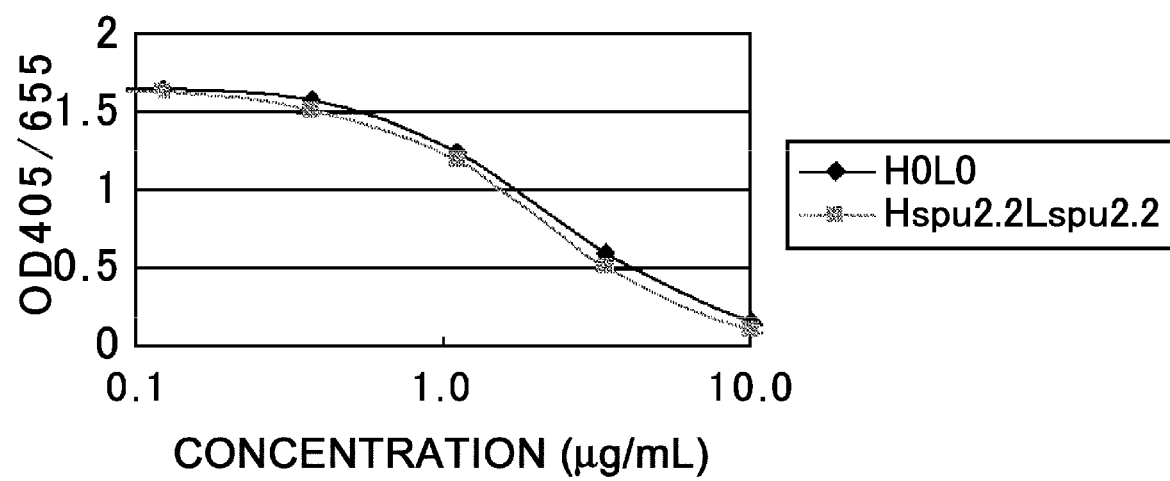
FIG. 53 is a graph showing the glypican 3 (antigen)-binding activities of the Hspu2.2Lspu2.2 (Hu2.2Lu2.2) and H0L0 antibodies determined by competitive ELISA.
Figure 54:
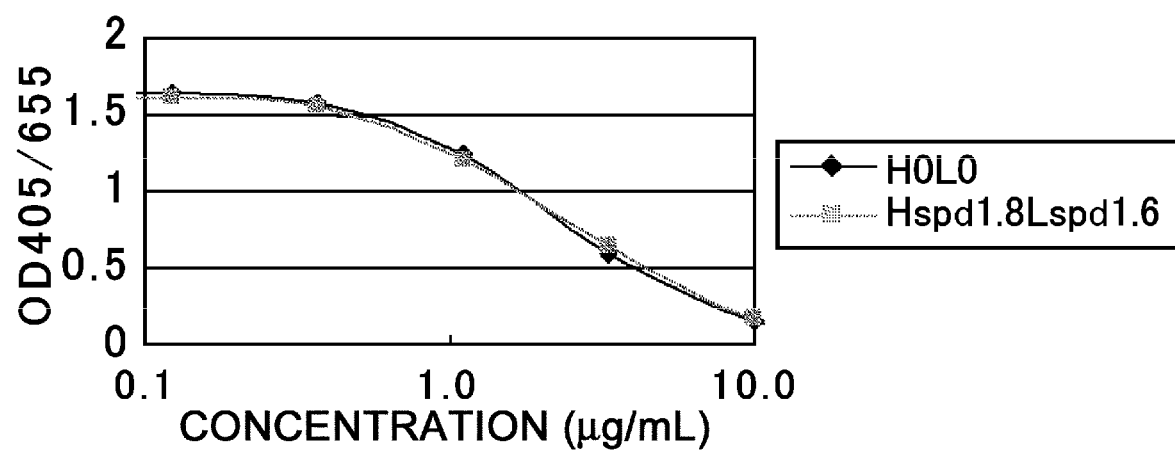
FIG. 54 is a graph showing the glypican 3 (antigen)-binding activities of the Hspd1.8Lspd1.6 (Hd1.8Ld1.6) and H0L0 antibodies determined by competitive ELISA.

As shown in FIG. 52, the antigen-binding activity of antibody H15L4 was comparable to that of the H0L0 antibody which was subjected to modification. Furthermore, as shown in FIG. 53, the antigen-binding activity of the Hspu2.2Lspu2.2 antibody (Hu2.2Lu2.2) was comparable to that of the H0L0 antibody which was subjected to modification. In addition, as shown in FIG. 54, the antigen-binding activity of the Hspd1.8Lspd1.6 antibody (Hd1.8Ld1.6) was comparable to that of the H0L0 antibody which was subjected to modification.

[Reference Experimental Example 22] Disruption of Fucose Transporter Gene in CHO Cells (1) Construction of Targeting Vectors (1-1) Construction of KO1 Vector A BamHI site and a TGCGC sequence were added to the 5' end of the start codon of hygromycin resistance gene (Hygr) by PCR using pcDNA3.1/Hygro (Invitrogen) and the Hyg5-BH and Hyg3-NT primers to make the same as the sequence adjacent to the 5' end of the start codon of fucose transporter gene. A NotI site was added to the 3' end of the region containing up to the SV40 polyA addition signal. The resulting Hygr was excised.

```
Forward primer
Hyg5-BH:
                                    (SEQ ID NO: 208)
5'-GGATCCTGCGCATGAAAAAGCCTGAACTCACC-3'

Reverse primer
Hyg3-NT:
                                    (SEQ ID NO: 209)
5'-GCGGCCGCCTATTCCTTTGCCCTCGGACG-3'
```

The fucose transporter targeting vector ver.1 (herein referred to as "KO1 vector") was constructed by inserting into pMC1DT-A vector (Yagi T, Proc. Natl. Acad. Sci. USA (1990) 87:9918-22) the 5' (SmaI at position 2780 to BamHI at position 4232 in the nucleotide sequence of SEQ ID NO: 210) and 3' (from position 4284 to SacI at position 10934) segments of fucose transporter, and an Hygr fragment. The characteristic of the KO1 vector is that Hygr is expressed from the fucose transporter promoter when homologous recombination occurs because no promoter is attached to the Hygr fragment. However, Hygr is not always expressed sufficiently to acquire resistance to hygromycin B when only a single copy of the vector is introduced into a cell by homologous recombination. The KO1 vector was introduced into cells after NotI digestion. The fucose transporter was expected to lose 41 base pairs of exon 1 including the start codon from introduction of the KO1 vector, which would result in the loss of its function.

(1-2) Construction of pBSK-Pgk-1-Hygr

The mouse pgk-1 gene promoter was excised from a pKJ2 vector (Popo H, Biochemical Genetics (1990) 28:299-308) with EcoRI and PstI, and cloned into pBluescript (Stratagene) at the site between EcoRI and PstI to prepare pBSK-pgk-1. An EcoT22I site and a Kozak sequence were added to the 5' end of Hygr by PCR using pcDNA3.1/Hygro and the Hyg5-AV and Hyg3-BH primers. A BamHI site was added to the 3' end of the region containing up to the SV40 polyA addition signal. The resulting Hygr was excised.

```
Forward primer
Hyg5-AV:
                                    (SEQ ID NO: 211)
5'-ATGCATGCCACCATGAAAAAGCCTGAACTCACC-3'

Reverse primer
Hyg3-BH:
                                    (SEQ ID NO: 212)
5'-GGATCCCAGGCTTTACACTTTATGCTTC-3'
```

The Hygr (EcoT22I-BamHI) fragment was inserted into pBSK-pgk-1 at PstI-BamHI site to prepare pB SK-pgk-1-Hygr.

(1-3) Construction of KO2 Vector

The fucose transporter targeting vector ver.2 (herein referred to as "KO2 vector") was constructed by inserting into a pMC1DT-A vector the 5' (SmaI at position 2780 to BamHI at position 4232 in the nucleotide sequence of SEQ ID NO: 210) and 3' (from position 4284 to SacI at position 10934) segments of fucose transporter, and a pgk-1-Hygr fragment. Unlike the KO1 vector, the KO2 vector carries Hygr linked to the promoter of pgk-1 gene. Therefore, once a single copy of the vector is introduced into cells via homologous recombination, the cells acquire hygromycin B resistance. The KO2 vector was introduced into cells after NotI digestion. The fucose transporter was expected to lose 46 base pairs of exon 1 including the start codon by introduction of the KO2 vector, which would result in the loss of its function.

(1-4) Construction of pB SK-Pgk-1-Puror

A pPUR vector (BD Biosciences) was digested with PstI and BamHI. The excised fragment (Puror) was inserted into pB SK-pgk-1 at the PstI-BamHI site to prepare pBSK-pgk-1-Puror.

(1-5) Construction of KO3 Vector

The fucose transporter targeting vector ver.3 (herein referred to as "KO3 vector") was constructed by inserting into a pMC1DT-A vector the 5' (SmaI at position 2780 to BamHI at position 4232 in the nucleotide sequence of SEQ ID NO: 210) and 3' (from position 4284 to SacI at position 10934) segments of fucose transporter, and a pgk-1-Puror fragment. A sequence for annealing with the screening primer indicated below was attached to the 3' end of pgk-1-Puror in advance. The KO3 vector was introduced into cells after NotI digestion. The fucose transporter was expected to lose 46 base pairs of exon 1 including the start codon from introduction of the KO3 vector, which would result in the loss of its function.

```
Reverse primer
RSGR-A:
                                    (SEQ ID NO: 213)
5'-GCTGTCTGGAGTACTGTGCATCTGC-3'
```

The fucose transporter gene was knocked out using the three types of targeting vectors described above.

(2) Introduction of Vectors into CHO Cells

CHO-S-SFMII HT-(Invitrogen) was supplemented with 1/100 volume of HT Supplement (100×) (Invitrogen) and penicillin-streptomycin (Invitrogen), and used as a culture medium (hereinafter referred to as "SFMII(+)"). A CHO cell line DXB11 was passaged using the medium. SFMII(+) was also used to culture the cells after gene transfer. $8 \times 10^6$ CHO cells were suspended in 0.8 ml of Dulbecco's phosphate buffered saline (hereinafter abbreviated as "PBS"; Invitrogen). The cell suspension was combined with 30 μg of a targeting vector, and transferred into Gene Pulser Cuvette (4 mm) (Bio-Rad). After ten minutes of incubation on ice, the vector was introduced into the cells by electroporation under the conditions of 1.5 kV and 25 µFD using Gene-Pulser II (Bio-Rad). After vector transfer, the cells were suspended in 200 ml of SFMII(+) medium and plated in twenty 96-well round-bottomed plates (Iwaki) at 100 µl/well. The plates were incubated in a $CO_2$ incubator at 37° C. for 24 hours, and then a drug was added thereto.

(3) First Knockout

The KO1 or KO2 vector was introduced into CHO cells. Selection was carried out 24 hours after gene transfer using hygromycin B (Invitrogen). Hygromycin B was dissolved at a concentration of 0.3 mg/ml in SFMII(+), and a 100-µl aliquot was added to each well.

(4) PCR Screening for Homologous Recombinants (4-1) Preparation of PCR Samples

Homologous recombinants were screened by PCR. CHO cells used in the screening were cultured in 96-well flat-bottomed plates. After removing the culture supernatants, 50 µl of cell lysis buffer was added to each well and the plates were incubated at 55° C. for two hours. Then, proteinase K was inactivated by heating at 95° C. for 15 minutes. The resulting samples were used as PCR templates. The composition of cell lysis buffer per well was: 5 µl of 10× LA buffer II (appended to Takara LATaq), 2.5 µl of 10% NP-40 (Roche), 4 µl of proteinase K (20 mg/ml; Takara), and 38.5 µl of distilled water (Nacalai Tesque).

(4-2) PCR Conditions

The PCR mixtures consisted of 1 µl of a PCR sample described above, 5 µl of 10× LA buffer II, 5 µl of $MgCl_2$ (25 mM), 5 µl of dNTP (2.5 mM), 2 µl of primers each (10 µM each), 0.5 µl of LA Taq (5 IU/µl), and 29.5 µl of distilled water (50 µl in total). TP-F4 and THygro-R1 were used as PCR primers in the screening for cells introduced with the KO1 vector, and TP-F4 and THygro-F1 were used in the screening for cells introduced with the KO2 vector.

The PCR conditions used to assess cells introduced with the KO1 vector were: pre-heating at 95° C. for one minute, and 40 amplification cycles of 95° C. for 30 seconds, 60° C. for 30 seconds, and 72° C. for two minutes, followed by heating at 72° C. for seven minutes. The PCR conditions used to assess cells introduced with KO2 vector were: pre-heating at 95° C. for one minute, and 40 amplification cycles of 95° C. for 30 seconds and 70° C. for three minutes, followed by heating at 70° C. for seven minutes.

The primers are shown below. In cell samples where homologous recombination is mediated by the KO1 vector, the size of the amplified DNA is about 1.6 kb. In cell samples where homologous recombination is mediated by the KO2 vector, the size of the amplified DNA is about 2.0 kb. The TP-F4 primer has been designed to be placed outside the vector and within the 5' genomic region of fucose transporter. The THygro-F1 and THygro-R1 primers have been designed to be placed within Hygr of the vector.

```
Forward primers (KO1 and KO2)
TP-F4:
                                    (SEQ ID NO: 214)
5'-GGAATGCAGCTTCCTCAAGGGACTCGC-3'

Reverse primer (KO1)
THygro-R1:
                                    (SEQ ID NO: 215)
5'-TGCATCAGGTCGGAGACGCTGTCGAAC-3'

Reverse primer (KO2)
THygro-F1:
                                    (SEQ ID NO: 216)
5'-GCACTCGTCCGAGGGCAAAGGAATAGC-3'
```

(5) PCR Screening Results 918 cells introduced with KO1 vector were analyzed, and only one was assessed to be a homologous recombinant cell (the frequency of homologous recombination was about 0.1%). 537 cells introduced with the KO2 vector were analyzed, and 17 cells were assessed to be homologous recombinant cells (the frequency of homologous recombination was about 3.2%).

(6) Southern Blot Analysis

Furthermore, Southern blotting was also used to confirm the recombinant cells. 10 µg of genomic DNA was prepared from cultured cells according to a conventional method and analyzed by Southern blotting. A 387-bp probe was prepared from the region of positions 2113 to 2500 in the nucleotide sequence of SEQ ID NO: 210 by PCR using the pair of primers shown below, and used in Southern blotting to confirm the recombinant cells. The genomic DNAs were digested with BglII.

```
Forward primer
Bgl-F:
                                    (SEQ ID NO: 217)
5'-TGTGCTGGGAATTGAACCCAGGAC-3'

Reverse primer
Bgl-R:
                                    (SEQ ID NO: 218)
5'-CTACTTGTCTGTGCTTTCTTCC-3'
```

BglII digestion yielded an approximately 3.0-kb band of chromosomal fucose transporter, and approximately 4.6-kb and 5.0-kb bands from chromosomes that have undergone homologous recombination mediated by the KO1 and KO2 vectors, respectively. One and seven cells that had undergone homologous recombination mediated by the KO1 and KO2 vectors, respectively, were used in the experiments. The only cell line obtained using the KO1 vector was named 5C1. In fact, subsequent analyses revealed that the cell line included different cell populations. Thus, the cell line was recloned by limiting dilution and then used in subsequent experiments. One of the cell lines obtained using the KO2 vector was named 6E2.

(7) Second Knockout

A cell line completely deficient in the fucose transporter gene was established using three types of vectors from a cell line in which the KO1 and KO2 vectors successfully mediated homologous recombination. The combinations of vector and cell line were as follows. Method 1, KO2 vector and cell line 5C1 (KO1); Method 2, KO2 vector and cell line 6E2 (KO2); and Method 3, KO3 vector and cell line 6E2 (KO2). The vectors were introduced into cells of the respective cell lines. Selection was carried out 24 hours after vector transfer using hygromycin B and puromycin (Nacalai Tesques). The final concentration of hygromycin B was 1 mg/ml in Method 1 and 7 mg/ml in Method 2. In Method 3, hygromycin B and puromycin were added at final concentrations of 0.15 mg/ml and 8 µg/ml, respectively.

(8) PCR Screening for Homologous Recombinants

Samples were prepared by the same method described above. For the screening in Method 1, both of the PCR methods described above were used to detect cells that had undergone homologous recombination mediated with the KO1 and KO2 vectors. TPS-F1 and SHygro-R1 were placed in the regions of positions 3924 to 3950 and 4248 to 4274 in the nucleotide sequence of SEQ ID NO: 210. These PCR primers were designed for Method 2, and used to amplify a 350-bp region of the fucose transporter gene that is deficient in the KO2 vector. Accordingly, when the 350-bp region was not amplified in the PCR screening of Method 2, the cells were considered to be completely deficient in the fucose transporter gene. The PCR conditions used were: pre-heating at 95° C. for one minute, and 35 amplification cycles of 95° C. for 30 seconds and 70° C. for one minute, followed by heating at 70° C. for seven minutes.

```
Forward primer
TPS-F1:
                                   (SEQ ID NO: 219)
5'-CTCGACTCGTCCCTATTAGGCAACAGC-3'

Reverse primer
SHygro-R1:
                                   (SEQ ID NO: 220)
5'-TCAGAGGCAGTGGAGCCTCCAGTCAGC-3'
```

The forward and reverse primers used in Method 3 were TP-F4 and RSGR-A, respectively. The PCR conditions used were: pre-heating at 95° C. for one minute, and 35 amplification cycles of 95° C. for 30 seconds, 60° C. for 30 seconds, and 72° C. for two minutes, followed by heating at 72° C. for seven minutes. An approximately 1.6-kb DNA is amplified when the sample is cells that have undergone homologous recombination mediated by the KO3 vector. The PCR was carried out to detect cells that had undergone homologous recombination mediated by the KO3 vector, as well as to confirm that the homologous recombination mediated by the KO2 vector remained.

(9) PCR Screening Results 616 cells were analyzed by Method 1, and 18 were assessed to be homologous recombinants (the frequency of homologous recombination was about 2.9%). 524 cells were analyzed by Method 2, and two were assessed to be homologous recombinants (the frequency of homologous recombination was about 0.4%). Furthermore, 382 cells were analyzed by Method 3, and seven were asssed to be homologous recombinants (the frequency of homologous recombination was about 1.8%).

(10) Southern Blot Analysis

As a result of analysis according to the method described above, one of the analyzed cell lines was found to be completely deficient in the fucose transporter gene. In the first knockout, the results of PCR and Southern blot analyses were consistent with each other. However, the PCR result was not consistent with Southern blotting in the second knockout.

(11) Analysis of Fucose Expression

Furthermore, 26 cell lines that had been assessed to be homologous recombinants by PCR were analyzed for fucose expression. $1 \times 10^6$ cells were stained using 100 µl of PBS containing 5 µg/ml Lens culinaris Agglutinin, FITC Conjugate (Vector Laboratories), 2.5% FBS, and 0.02% sodium azide (hereinafter referred to as "FACS lysis solution") on ice for one hour. Then, the cells were washed three times with FACS lysis solution, and assayed using FACSCalibur (Becton Dickinson). The result of Southern blot analysis showed that the expression level of fucose was reduced only in the FTP-KO cell line which had been assessed to be completely deficient in the fucose transporter gene.

[Reference Experimental Example 23]
Establishment of Antibody-Producing Cells Derived from the FTP-KO Line and Purification of Antibody Produced by the Cells Hygromycin B was prepared at a final concentration of 1 mg/ml in SFMII(+) medium. The fucose transporter-deficient cell line (FT-KO cell; clone name, 3F2) obtained as described in Example 21 was cultured in this medium. $8 \times 10^6$ cells of 3F2 were suspended in 0.8 ml of Dulbecco's phosphate buffered saline. The cell suspension was combined with 25 µg of the expression vector for humanized glypican 3 antibody, and transferred into a Gene Pulser Cuvette. After ten minutes of incubation on ice, the vector was introduced into the cells by electroporation under the conditions of 1.5 kV and 25 µFD using Gene Pulser II. After vector transfer, the cells were suspended in 40 ml of SFMII (+) medium, and plated onto a 96-well flat-bottomed plate (Iwaki) in an amount of 100 µl/well. The plate was incubated at 37° C. in a $CO_2$ incubator for 24 hours, and then Geneticin (Invitrogen) was added thereto at a final concentration of 0.5 mg/ml. The levels of antibody produced by the drug-resistant cells were determined to establish humanized glypican 3 antibody-producing cell lines.

Supernatants were collected from cultures of the antibody-producing cells, and loaded onto a Hitrap rProtein A (Pharmacia) column using a P-1 pump (Pharmacia). After the column was washed with binding buffer (20 mM sodium phosphate (pH 7.0)), bound antibody was eluted with elution buffer (0.1 M glycine-HCl (pH 2.7)). Immediately, the eluates were neutralized with neutralization buffer (1M Tris-HCl (pH 9.0)). The eluted antibody fractions were selected by DC Protein Assay (Bio-Rad), and the pooled fractions were concentrated up to about 2 ml using Centriprep YM 10 (Millipore). Next, the concentrated solutions were subjected to gel filtration using Superdex 200 26/60 (Pharmacia) equilibrated with 20 mM acetic acid buffer (pH 6.0) containing 150 mM NaCl. Peak monomer fractions of the eluates were collected, and concentrated using Centriprep YM 10. After filtration with MILLEX-GW 0.22-µm Filter Unit (Millipore), the concentrated solutions were stored at 4° C. The concentrations of purified antibodies were determined by calculation using the molar extinction coefficient and absorbance at a wavelength of 280 nm.

[Reference Experimental Example 24] Analysis of Sugar Chains Linked to Humanized Anti-Glypican 3 Antibody Produced by FT-KO Cells (1) Preparation of 2-Aminobenzamide-Labeled Sugar Chains (2-AB-Labeled Sugar Chains)

The antibodies produced by the FT-KO cells of the present invention and antibodies produced by CHO cells as a control sample were treated with N-glycosidase F (Roche Diagnostics) to release the sugar chains from the protein (Weitzhandler M. et al., Journal of Pharmaceutical Sciences (1994) 83(12):1670-1675). After deproteination using ethanol (Schenk B. et al., The Journal of Clinical Investigation (2001) 108(11):1687-1695), the free sugar chains were concentrated to dryness, and fluorescently labeled with 2-aminopyridine (Bigge J. C. et al., Analytical Biochemistry (1995) 230(2):229-238). The reagent was removed from the 2-AB-labeled sugar chains by solid phase extraction using a cellulose cartridge. After concentration by centrifugation, purified 2-AB-labeled sugar chains were obtained for use in the analyses. Next, the purified 2-AB-labeled sugar chains were treated with β-galactosidase (Seikagaku Co.) to obtain agalactosyl 2-AB-labeled sugar chains.

(2) Analysis of Agalactosyl 2-AB-Labeled Sugar Chains by Normal Phase HPLC

Agalactosyl 2-AB-labeled sugar chains were prepared by the above method, using as the starting materials sugar chains freed from antibodies produced by the FT-KO cells of the present invention or antibodies produced by CHO cells (control). The sugar chains were analyzed by normal phase HPLC using an amide column TSKgel Amide-80 (Tosoh Co.), and the chromatograms were compared to each other. In the antibodies produced by CHO cells, the main component of sugar chain was G(0), and G(0)-Fuc which had no fucose was estimated to account for about 4% of total sugar chains based on the calculation of the peak area ratio. On the other hand, in the antibodies produced by the FT-KO cells, G(0)-Fuc was the main component, and based on the calculation of the peak area ratio, 90% or more of total sugar chains had no fucose in the antibodies produced by any of the antibody-producing cell lines.

TABLE 17

RELATIVE RATIO OF AGALACTOSYL 2-AB-LABELED SUGAR CHAIN ESTIMATED BY NORMAL PHASE HPLC

| SUGAR CHAIN | CHO | FT-KO-a | FT-KO-b | FT-KO-c |
|---|---|---|---|---|
| G(0)-Fuc | 4.0% | 92.4% | 92.5% | 93.2% |
| G(0) | 96.0% | 7.6% | 7.5% | 6.8% |

[Example 25] Establishment of Cell Lines Stably Expressing Humanized Antibody H0L0 or its Point Mutants The genes encoding antibodies were cloned into expression vectors. The antibodies were: Hspu2.2Lspu2.2 (Hu2.2Lu2.2) and Hspd1.8Lspd1.6 (Hd1.8Ld1.6), which were prepared as modified antibodies from the H0L0 antibody by the method described in Example 21; and the H0L0 antibody, which was used for such modifications. The respective genes encoding the heavy chain and light chain of each antibody were cloned into different expression vectors to express the genes. Two types of expression vectors were selected to carry a desired combination of genes encoding the heavy chain and light chain as described above, and after digestion with PvuI, they were introduced by electroporation into cells of FTP-KO line produced as described in Reference Experimental Example 22.

The transformed cell lines stably producing the H0L0 antibody or its modified antibodies were produced by electroporation using Gene Pulser II (Bio-Rad). 10 µg each of the expression plasmid DNAs for the heavy and light chains, which provided a desired combination of heavy and light chains, were mixed with 0.75 ml of suspension of CHO cells ($1 \times 10^7$ cells/ml) in PBS. The mixture was incubated on ice for ten minutes, transferred into a Gene Pulser II Cuvette, and then electrically pulsed at 1.5 kV and 25 µFD. The pulsed mixture was incubated at room temperature for ten minutes, and then suspended in CHO-S-SFMII/1% HT/1% PS medium. The same medium as used to prepare 5×, 10×, and 50× dilutions, and the suspensions were aliquoted (100 µl) into each well of 96-well culture plates. The plates were incubated under 5% $CO_2$ in a $CO_2$ incubator for 24 hours. Then, Geneticin (GIBCO) and Zeocin (Invitrogen) were added at final concentrations of 500 and 600 µg/ml to each well, respectively. The plates were further incubated for two weeks. Colonies of transformed cells resistant to both Geneticin and Zeocin were selected by culturing in the same medium supplemented with 500 µg/ml Geneticin (GIBCO) and 600 µg/ml Zeocin (Invitrogen). The antibody concentrations in culture supernatants of transformed cells thus selected were assessed using BiacoreQ (Biacore). Accordingly, transformant lines highly expressing a desired antibody were established. The antibody concentrations in culture supernatants were determined according to the protocol appended to BiacoreQ (Biacore).

[Example 26] Drug Efficacy Test of Humanized Antibody H0L0 and its Point Mutants by In Vivo Model (1) Maintenance of Cell Lines that are Subjected to Transplantation in an In Vivo Model The Hep G2 cell line (ATCC) was used and maintained by culturing in Minimum Essential Eagle Medium (Sigma) supplemented with 10% FBS, 1 mmol/l MEM Sodium Pyruvate (Invitrogen), and 1 mmol/l MEM Non-Essential Amino Acids (Invitrogen) (hereinafter referred to as "passaging medium").

(2) Preparation of Hep G2-Grafted Mouse Model

A Hep G2 cell suspension was prepared at $5 \times 10^7$ cells/ml using a solution containing 1:1 ratio of the passaging medium and Matrigel Matrix (BD Bioscience). 100 µl of the cell suspension ($5 \times 10^6$ cells/head) was transplanted subcutaneously at an abdominal site into SCID mice (male, five weeks old) (CLEA Japan Inc.). On the day before cell transplantation, 100 µl of an anti-asialo GM1 antibody (Wako Pure Chemical Industries; the content of one vial was dissolved in 5 ml of the solution) was administered into the peritoneal cavities of the mice. The tumor volume was calculated based on the formula:

$$(\text{Tumor volume}) = (\text{major axis}) \times (\text{minor axis}) \times (\text{minor axis})/2.$$

When the mean tumor volume reached 130 to 330 mm³, the mouse was assessed to be acceptable for the model.

(3) Preparation of Samples Containing Each Test Antibody for Administration

On the day of administration, samples for administration were prepared using physiological saline so that each contained one of antibodies H0L0, Hu2.2Lu2.2, and Hd1.8Ld1.6 at 0.5 mg/ml (group administrated with an antibody at 5 mg/kg) or 0.1 mg/ml (group administrated with an antibody at 1 mg/kg).

(4) Administration of Antibody-Containing Samples for Administration 27 days after transplantation of Hep G2 cells to the mouse model prepared as described above in (2), the samples prepared as described above in (3) were administered at a dose of 10 ml/kg into the caudal vein once a week for three weeks. As a negative control, physiological saline was administered in the same way at a dose of 10 ml/kg into the caudal vein once a week for three weeks. Each group included five mice, and was administered with a sample containing any one of the respective test antibodies. Almost simultaneously with administration, venous blood was collected from three mice in each of the respective groups as test samples to determine the concentration of each antibody in mouse blood. Specifically, blood was collected from the dorsal metatarsal vein at two time points: half an hour after the first administration and immediately before the second administration. 20 µl of collected blood was heparinated, and plasma was obtained by centrifugation.

(5) Assessment of Test Antibodies for Antitumor Effect

The antitumor effect of each test antibody in a model mouse transplanted with human liver cancer was assessed by measuring the tumor volume one week after the final administration of the samples. The result shown in FIG. 55 demonstrates the trendency that the effect is enhanced with the Hspd1.8Lspd1.6 antibody (Hd1.8Ld1.6), and the effect is impaired with the Hspu2.2Lspu2.2 antibody (Hu2.2Lu2.2).

(6) Concentration of Each Test Antibody in Blood

The concentrations of test antibodies in mouse plasma were determined according to the ELISA method described in Example 21. Samples with a plasma concentration of 12.8, 6.4, 3.2, 1.6, 0.8, 0.4, or 0.2 µg/ml were prepared as calibration standards. The standard samples and test samples of mouse plasma appropriately diluted at a desired concentration were aliquoted into immunoplates (Nunc-Immuno Plate, MaxiSoup (Nalge Nunc International)) immobilized with soluble glypican-3 core (Chugai Pharmaceutical Co. Ltd.). The plates were incubated at room temperature for one hour. Then, goat anti-human IgG-BIOT (Southern Biotechnology Associates) and streptavidin-alkaline phosphatase conjugate (Roche Diagnostics) were sequentially aliquoted, and color development was achieved using as the substrate BluePhos Microwell Phosphatase Substrates System (Kirkegaard & Perry Laboratories). The degree of color development of the reaction mixture in each well was calculated by measuring the absorbance of the reaction mixture at 650 nm on a microplate reader. The antibody concentrations in mouse plasma were calculated using analysis software SoftMax Pro (Molecular Devices) based on the calibration curves prepared from absorbance of the standard samples.

Figure 56:
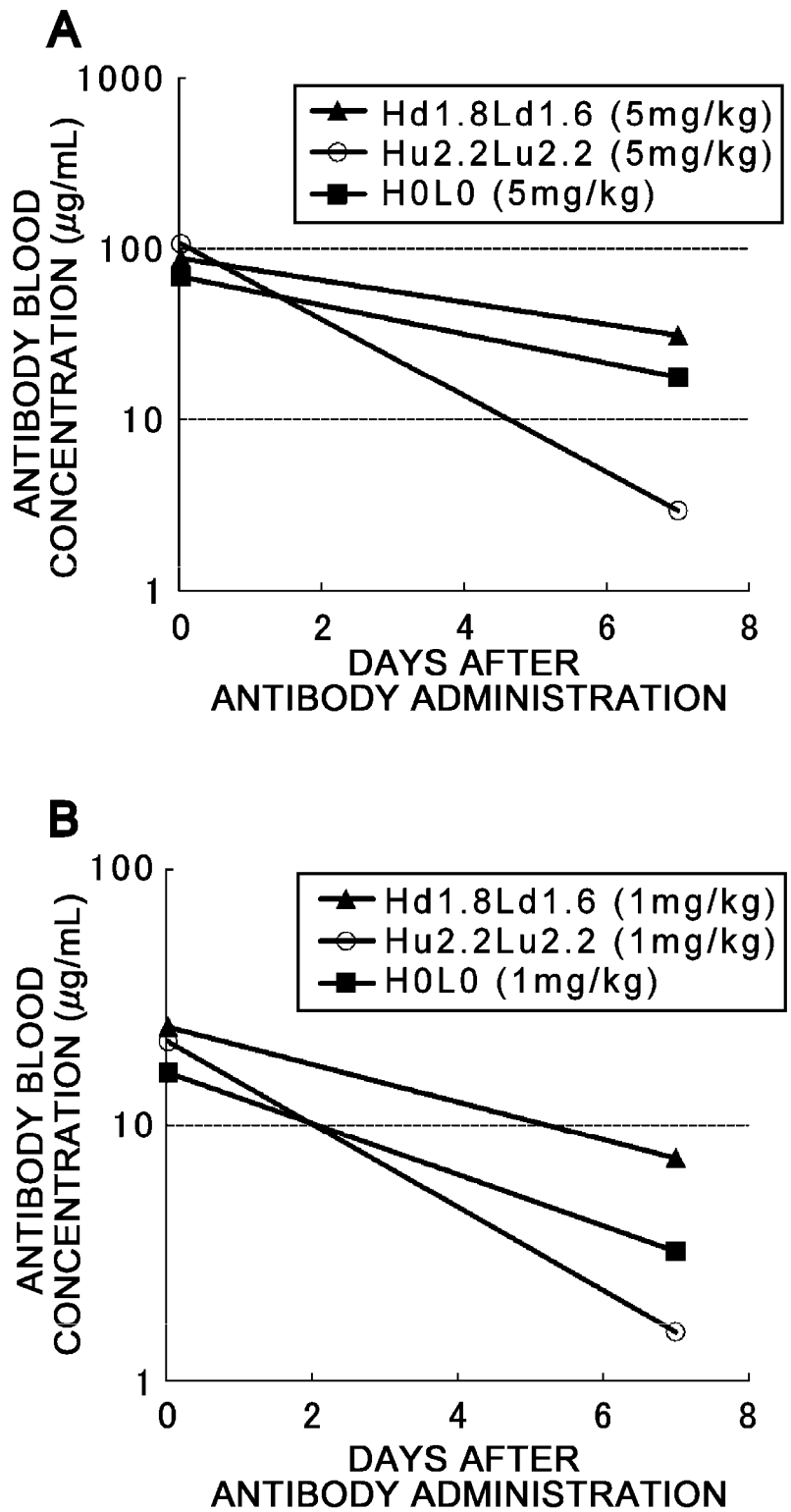
FIG. 56A shows the plasma concentration of the H0L0 antibody, Hspu2.2Lspu2.2 (Hu2.2Lu2.2) antibody, and the Hspd1.8Lspd1.6 (Hd1.8Ld1.6) antibody administered to a human liver cancer-transplant mouse model when each test antibody was administered to the mouse model at a dose of 5 mg/kg, wherein the black triangle shows the plasma concentration of the Hspd1.8Lspd1.6 (Hd1.8Ld1.6) antibody, the white circle shows the plasma concentration of the Hspu2.2Lspu2.2 (Hu2.2Lu2.2) antibody, and the black square shows the plasma concentration of the H0L0 antibody.
FIG. 56B shows the plasma concentration of the H0L0 antibody, Hspu2.2Lspu2.2 (Hu2.2Lu2.2) antibody, and the Hspd1.8Lspd1.6 (Hd1.8Ld1.6) antibody in a human liver cancer-transplant mouse model when each test antibody was administered to the model at a dose of 1 mg/kg, wherein the black triangle shows the plasma concentration of the Hspd1.8Lspd1.6 (Hd1.8Ld1.6) antibody, the white circle shows the plasma concentration of the Hspu2.2Lspu2.2 (Hu2.2Lu2.2) antibody, and the black square shows the plasma concentration of the H0L0 antibody.

The concentrations in mouse plasma 30 minutes and seven days after administration are shown in FIG. 56. It was demonstrated that with any antibody dosage, the lower the isoelectric point of a test antibody, the higher the antibody concentration in plasma seven days after administration.

[Example 27] ADCC of Each Test Antibody when Human Peripheral Blood Mononuclear Cells are Used as Effector Cells ADCC of each test antibody was assayed using human peripheral blood mononuclear cells (hereinafter referred to as "human PBMC") as effector cells by the procedure described below.

(1) Preparation of Human PBMC Solutions

Using syringes pre-filled with 200 µl of 1,000 units/ml heparin solution (Novo-Heparin 5000 units for Injection; Novo Nordisk), 50 ml of peripheral blood was collected from healthy volunteers (male adult) affiliated with Chugai Pharmaceutical Co. Ltd. The peripheral blood was diluted two-fold with PBS(-), and divided into four equal parts, each of which was transferred into a pre-centrifuged leukocyte separation tube Leucosep (Greiner Bio-One) containing 15 ml of Ficoll-Paque PLUS. The separation tubes containing an aliquot of the peripheral blood were centrifuged at 2,150 rpm and room temperature for ten minutes. Then, the resulting mononuclear cell fractions were collected. The cells in each fraction was washed once with Dulbecco's Modified Eagle's Medium (Sigma) containing 10% FBS (hereinafter referred to as "10% FBS/D-MEM"), and then suspended at a density of $5 \times 10^6$ cells/ml in 10% FBS/D-MEM. The cell suspensions were used as human PBMC solutions in the subsequent experiments.

(2) Preparation of Target Cells

Hep G2 cells were detached from dishes, and then plated at $1 \times 10^4$ cells/well on 96-well round-bottomed plates. The plates were incubated under 5% carbon dioxide gas in a $CO_2$ incubator at 37° C. overnight. On the next day, 5.55 MBq of Cr-51 was added to each well of the plates. Then, the plates were incubated under 5% carbon dioxide gas in a $CO_2$ incubator at 37° C. for three hours. The Hep G2 cells in the plates were used as target cells in the subsequent ADCC assay.

(3) Chrome Release Assay (ADCC)

ADCC is assessed based on specific chrome release rate determined by chrome release assay. The target cells prepared as described in (2) were washed with medium. 100 µl of the H0L0, Hu2.2Lu2.2, or Hd1.8Ld1.6 antibodies was added to the cells at various concentrations (0, 0.004, 0.04, 0.4, 4, and 40 µg/ml). After the plates were incubated at room temperature for 15 minutes, the antibody solutions were removed. Then, 100 µl of culture medium was added to each well. The plates were incubated under 5% carbon dioxide gas in a $CO_2$ incubator at 37° C. for one hour. 100 µl of human PBMC solution prepared as described in (1) was added to each well ($5 \times 10^5$ cells/well). The plates were incubated under 5% carbon dioxide gas in a $CO_2$ incubator at 37° C. for four hours, and then centrifuged. 100 µl of culture supernatant in each well of the plates was measured for radioactivity using a gamma counter. The specific chrome release rate was determined by the following formula:

$$[\text{Specific chrome release rate (\%)}] = (A-C) \times 100/(B-C).$$

In this formula, "A" represents mean radioactivity (cpm) of 100 µl of culture supernatant in each well. "B" represents mean radioactivity (cpm) of 100 µl of culture supernatant in a well containing target cells, 100 µl of 2% NP-40 aqueous solution (Nonidet P-40; Nacalai Tesques), and 50 µl of 10% FBS/D-MEM. Furthermore, "C" represents mean radioactivity (cpm) of 100 µl of culture supernatant in a well containing target cells and 150 µl of 10% FBS/D-MEM. The test was conducted in triplicate. The mean and standard deviation of the specific chrome release rate (%) which reflects the ADCC of each test antibody were calculated based on the assay described above.

(4) Assessment of ADCC of Each Test Antibody

Figure 57:
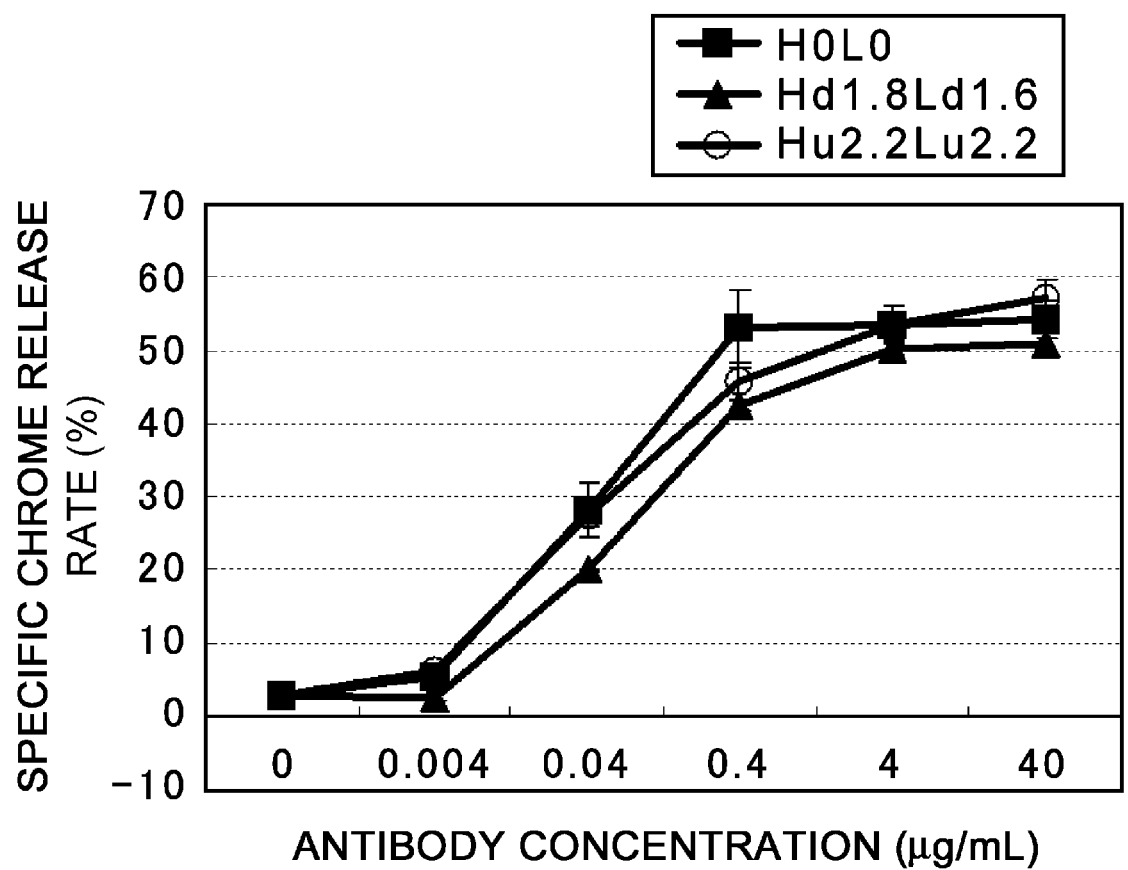
FIG. 57 shows ADCC of each test antibody against cells of the human hepatocarcinoma line Hep G2.

The test antibody-mediated ADCC of human PBMC was assessed. The result showed that all the antibodies tested exhibited ADCC. The result is shown in FIG. 57. A significance test was performed on the specific chrome release rates determined for various concentrations of each test antibody. The result showed that the specific chrome release rate was not significantly different among the respective test antibodies at any antibody concentration. SAS preclinical package (SAS Institute Inc.) was used for statistical analysis. These results showed that there was no difference in ADCC among the respective test antibodies with a modified isoelectric point.

[Example 28] Preparation of Anti-Human IL-6 Receptor Antibody, Anti-Human GPC3 Antibody, and Anti-Human IL-31 Receptor Antibody 1. Preparation of Anti-Human IL-6 Receptor Antibody Two types of anti-human IL-6 receptor antibodies were prepared: 6R_a_H1L1 consisting of 6R_a_H1 (SEQ ID NO: 221) as the heavy chain and 6R_a_L1 (SEQ ID NO: 224) as the light chain, and 6R_b_H1L1 consisting of 6R_b_H1 (SEQ ID NO: 227) as the heavy chain and 6R_b_L1 (SEQ ID NO: 229) as the light chain. Animal cell expression vectors encoding each amino acid sequence were prepared, and the antibodies were expressed and purified by the methods described in Reference Examples 1 and 2.

2. Preparation of Anti-Human Gpc3 Antibody

An anti-human GPC3 antibody, GPC3_H1L1, which consists of GPC3_H1 (SEQ ID NO: 233) as the heavy chain and GPC3 L1 (SEQ ID NO: 236) as the light chain was prepared. Animal cell expression vectors encoding each amino acid sequence were prepared, and the antibody was expressed and purified by the methods described in Reference Examples 1 and 2.

3. Anti-Human IL-31 Receptor Antibody

An anti-human IL-31 receptor antibody 31R_H1L1 consisting of 31R_H1 (SEQ ID NO: 239) as the heavy chain and 31R_L1 (SEQ ID NO: 242) as the light chain was prepared. Animal cell expression vectors encoding each amino acid sequence were prepared, and the antibody was expressed and purified by the methods described in Reference Examples 1 and 2.

[Example 29] Reduction of the Isoelectric Point of Anti-Human IL-6 Receptor Antibody, Anti-Human GPC3 Antibody, or Anti-Human IL-31 Receptor Antibody Via Amino Acid Substitution 1. Search for CDR Sequences that Reduce the Isoelectric Point without Reduction of Antigen-Binding Activity WO/2007/114319 describes examples of controlling the isoelectric point by substitution of amino acids in CDR, where amino acid substitutions were introduced into heavy chain CDR3. Heavy chain CDR3 is closely associated with antibody-antigen-binding activity; thus, it is anticipated that for some kinds of antibodies, the isoelectric point could not be reduced by substituting amino acids at same positions without reducing antigen-binding activity. Therefore, the present inventors searched for candidate CDR sequences that allow reduction of isoelectric point without reducing antigen-binding activity regardless of antibody specificity. Such candidate CDR sequences that allow reduction of isoelectric point without reducing antigen-binding activity were found to include H31, H52, H61, H62, H64, and H65 in the heavy chain variable region, and L24, L27, L27a, L53, L54, L55, and L56 in the light chain variable region (Kabat numbering). Then, some of the candidate CDR sequences were introduced into the anti-human IL-6 receptor antibody, anti-human GPC3 antibody, and anti-human IL-31 receptor antibody mentioned below by amino acid substitution, and the resulting antibodies were tested to assess whether their isoelectric points can be reduced without reducing the antigen-binding activity.

2. Preparation of Anti-Human IL-6 Receptor Antibodies with a Reduced Isoelectric Point, Binding Activity Assessment, and Isoelectric Point Determination To construct 6R_a_H2 (SEQ ID NO: 222) and 6R_a_L2 (SEQ ID NO: 225), amino acid substitutions for reducing the isoelectric point and other amino acid substitutions were introduced into each of 6R_a_H1 (SEQ ID NO: 221) and 6R_a_L1 (SEQ ID NO: 224) constituting the anti-human IL-6 receptor antibody 6R_a_H1L1. After vector construction, 6R_a_H2L2 was expressed and purified by the methods described in Reference Examples 1 and 2. Furthermore, to construct 6R_a_H3 (SEQ ID NO: 223) and 6R_a_L3 (SEQ ID NO: 226), amino acid substitutions for isoelectric point reduction and other amino acid substitutions were introduced into 6R_a_H2L2. Vectors were constructed by the method described in Reference Example 1, and then 6R_a_H3L3 was expressed and purified.

The dissociation constants (KD) of 6R_a_H1L1, 6R_a_H2L2, and 6R_a_H3L3 from their antigen, human IL-6 receptor, were determined by the Biacore T100-based method described in Reference Example 3. The dissociation constants (KD) of 6R_a_H1L1, 6R_a_H2L2, and 6R_a_H3L3 for IL-6 receptor were comparable to each other as shown in Table 18 below, and the introduced amino acid substitutions did not significantly reduce the antigen-binding activity.

TABLE 18

| | DISSOCIATION CONSTANT (KD) |
|---|---|
| 6R_a_H1L1 | 6.70E−11 |
| 6R_a_H2L2 | 3.00E−11 |
| 6R_a_H3L3 | 5.20E−11 |

The isoelectric point was determined by isoelectric focusing known to those skilled in the art. The isoelectric point of 6R_a_H1L1 was about 9.2, while the isoelectric points of 6R_a_H2L2 and 6R_a_H3L3 comprising amino acid substitutions for isoelectric point reduction were about 6.1 and 5.4, respectively. The isoelectric points were reduced by about 3.1 and 3.8 relative to 6R_a_H1L1, respectively. Furthermore, the theoretical isoelectric point of the variable region VH/VL was calculated using GENETYX (GENETYX CORPORATION). The theoretical isoelectric point of 6R_a_H1L1 was 9.37, while those of 6R_a_H2L2 and 6R_a_H3L3 were 4.63 and about 4.27, respectively. The theoretical isoelectric point was reduced by 4.74 and 5.10 in 6R_a_H2L2 and 6R_a_H3L3 relative to 6R_a_H1L1, respectively. These results are summarized in Table 19.

TABLE 19

| | ANTI-HUMAN IL-6 RECEPTOR ANTIBODY | | |
|---|---|---|---|
| | 6R_a_H1L1 | 6R_a_H2L2 | 6R_a_H3L3 |
| ACTUAL pI | 9.24 | 6.06 | 5.44 |
| THEORETICAL pI | 9.37 | 4.63 | 4.27 |

The amino acid substitutions introduced into the CDR sequence of 6R_a_H1L1 are summarized in Table 20 below. It was revealed that these CDR amino acid substitutions could reduce the isoelectric point of the 6R_a_H1L1 molecule, which is an anti-human IL-6 receptor antibody, without significantly reducing its antigen-binding activity.

TABLE 20

| CLASSIFICATION | MODIFIED POSITION (KABAT NO) | H1 SEQUENCE | AMINO ACID AFTER MODIFICATION |
|---|---|---|---|
| CDR1 | 31 | S | D |
| CDR2 | 64 | K | Q |
| CDR2 | 65 | S | D |

| CLASSIFICATION | MODIFIED POSITION (KABAT NO) | L1 SEQUENCE | AMINO ACID AFTER MODIFICATION |
|---|---|---|---|
| CDR1 | 24 | R | Q |
| CDR2 | 53 | R | E |
| CDR2 | 55 | R | E |

Next, to construct 6R_b_H2 (SEQ ID NO: 228) and 6R_b_L2 (SEQ ID NO: 230), amino acid substitutions for isoelectric point reduction and other amino acid substitutions were introduced into 6R_b_H1 (SEQ ID NO: 227) and 6R_b_L1 (SEQ ID NO: 229) constituting 6R_b_H1L1, which is another anti-human IL-6 receptor antibody. After vector construction, 6R_b_H2L2 was expressed and purified by the methods described in Reference Examples 1 and 2. Furthermore, to construct 6R_b_L3 (SEQ ID NO: 231) and 6R_b_L4 (SEQ ID NO: 232), amino acid substitutions for isoelectric point reduction and other amino acid substitutions were introduced into 6R_b_H2L2. Vectors were constructed by the method described in Reference Example 1, and then 6R_b_H2L3 and 6R_b_H2L4 were expressed and purified.

Figure 58:
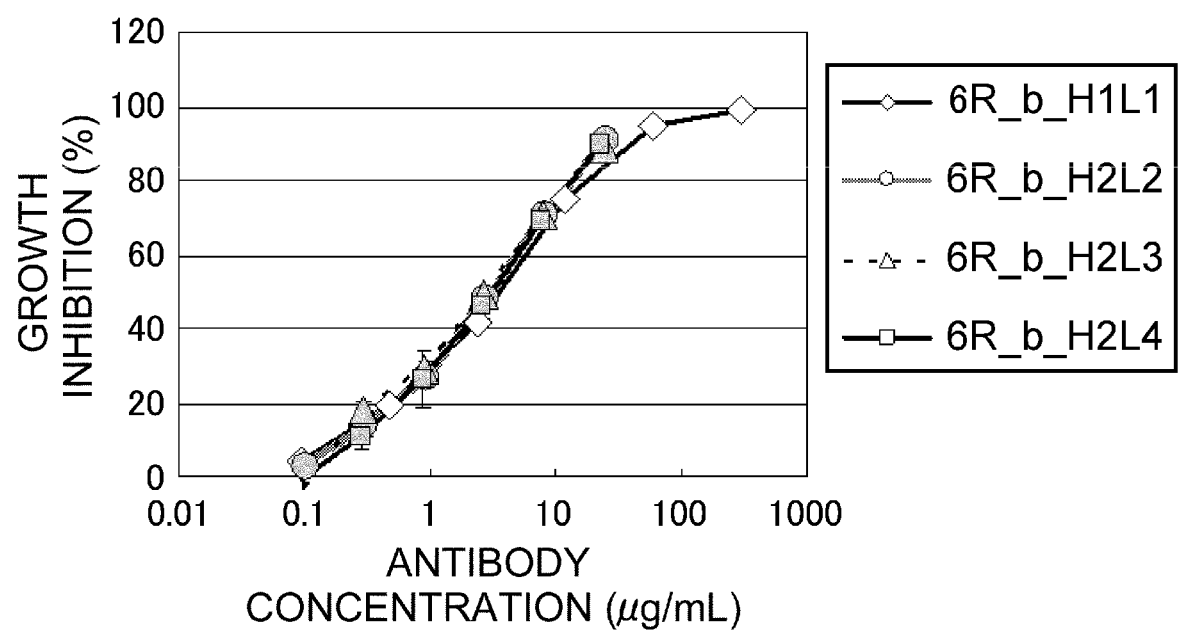
FIG. 58 is a graph showing the IL-6 receptor-neutralizing activities of 6R_b_H1L1, 6R_b_H2L2, 6R_b_H2L3, and 6R_b_H2L4 in BaF/6R.

6R_b_H1L1, 6R_b_H2L2, 6R_b_H2L3, and 6R_b_H2L4 were assayed using the method described in Reference Example 4 for their activity to neutralize the antigen, human IL-6 receptor. As shown in FIG. 58, the neutralizing activities of 6R_b_H1L1, 6R_b_H2L2, 6R_b_H2L3, and 6R_b_H2L4 were comparable to each other. The amino acid substitutions did not significantly reduce the antigen-binding activity.

The isoelectric point was determined by isoelectric focusing known to those skilled in the art. The isoelectric point of 6R_b_H1L1 was about 9.3, while the isoelectric point of 6R_b_H2L2 comprising amino acid substitutions for isoelectric point reduction was about 5.9. The isoelectric point of 6R_b_H2L2 was reduced by about 3.4 relative to 6R_b_H1L1. Furthermore, the theoretical isoelectric point of the variable region VH/VL was calculated using GENETYX (GENETYX CORPORATION). The theoretical isoelectric point of 6R_b_H1L1 was 9.20, while those of 6R_b_H2L2, 6R_b_H2L3, and 6R_b_H2L4 were 4.52, about 4.46, and about 4.37, respectively. The theoretical isoelectric point was reduced by 4.68, 4.74, and 4.83 in 6R_b_H2L2, 6R_b_H2L3, and 6R_b_H2L4 relative to 6R_b_H1L1, respectively. These results are summarized in Table 21.

3. Preparation of Anti-Human GPC3 Antibodies with a Reduced Isoelectric Point, Binding Activity Assessment, and Isoelectric Point Determination To construct GPC3_H2 (SEQ ID NO: 234) and GPC3 L2 (SEQ ID NO: 237), amino acid substitutions for isoelectric point reduction and other amino acid substitutions were introduced into GPC3_H1 (SEQ ID NO: 233) and GPC3 L1 (SEQ ID NO: 236) constituting the anti-human GPC3 antibody GPC3_H1L1. After vector construction, GPC3_H2L2 was expressed and purified by the methods described in Reference Examples 1 and 2. Furthermore, to construct GPC3_H3 (SEQ ID NO: 235) and GPC3 L3 (SEQ ID NO: 238), amino acid substitutions for isoelectric point reduction and other amino acid substitutions were introduced into GPC3_H2L2. Vectors were constructed by the method described in Reference Example 1, and then GPC3_H3L3 was expressed and purified.

Figure 59:
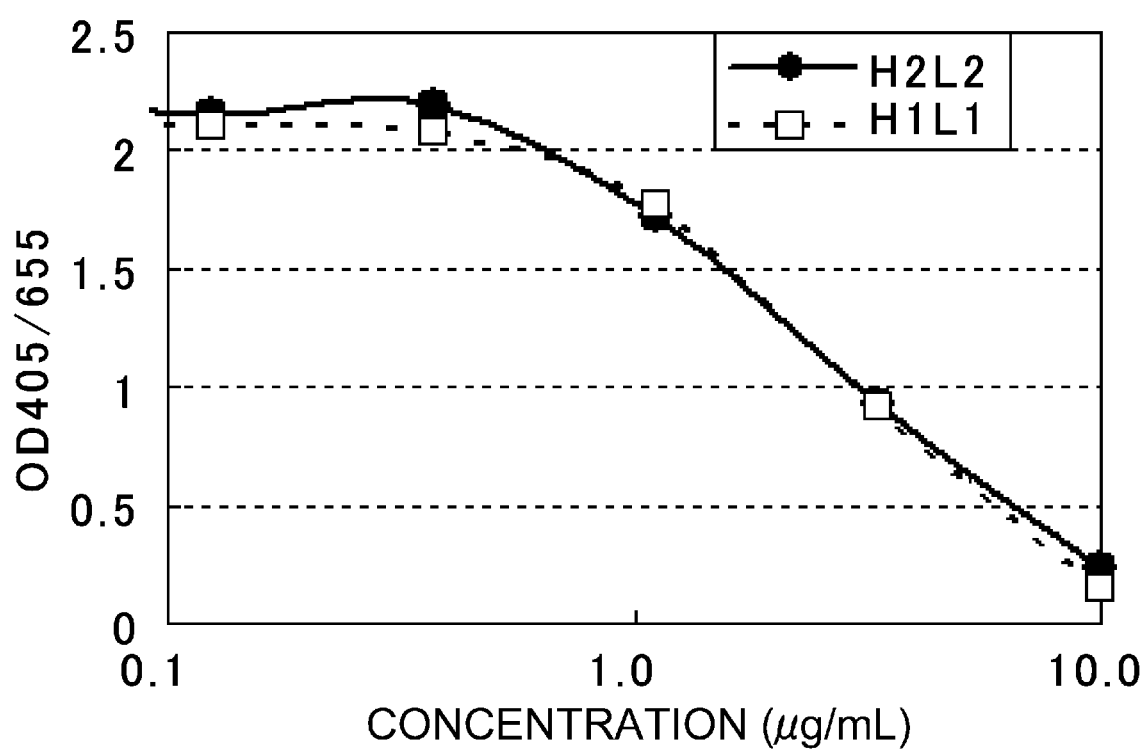
FIG. 59 is a graph showing the glypican 3 (antigen)-binding activities of the GPC_H1L1 and GPC_H2L2 antibodies determined by competitive ELISA.
Figure 60:
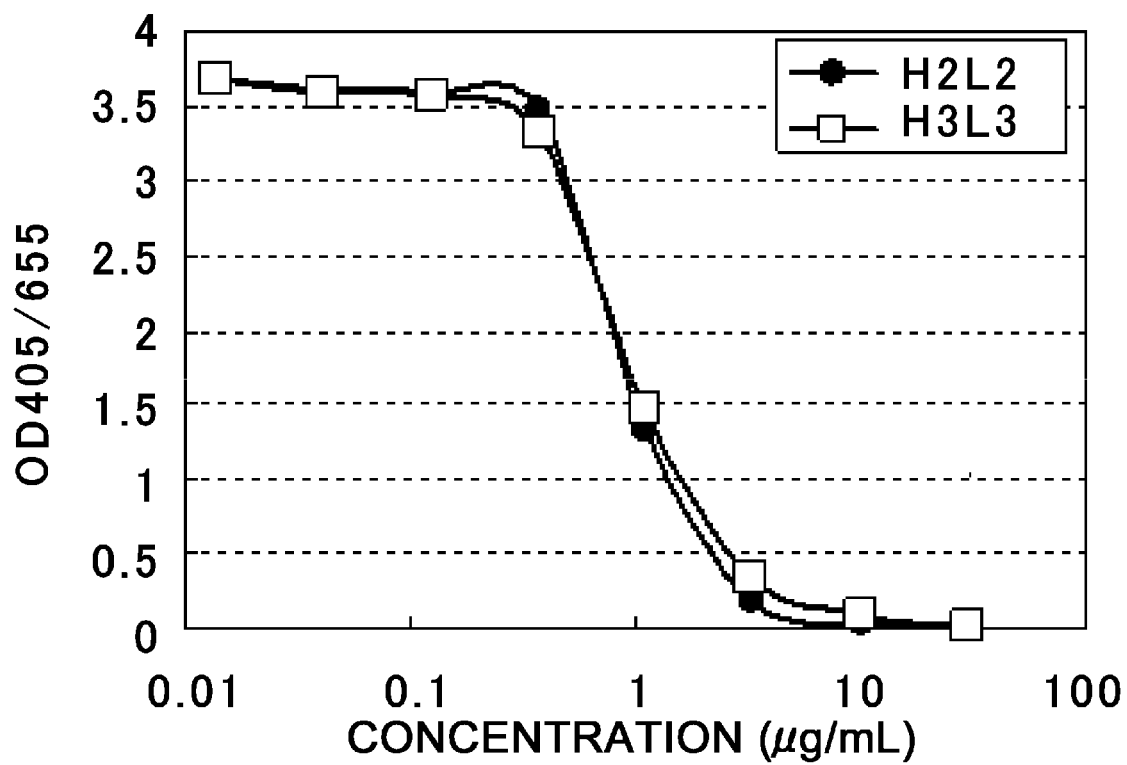
FIG. 60 is a graph showing the glypican 3 (antigen)-binding activities of the GPC_H2L2 and GPC_H3L3 antibodies determined by competitive ELISA.
Figure 61:
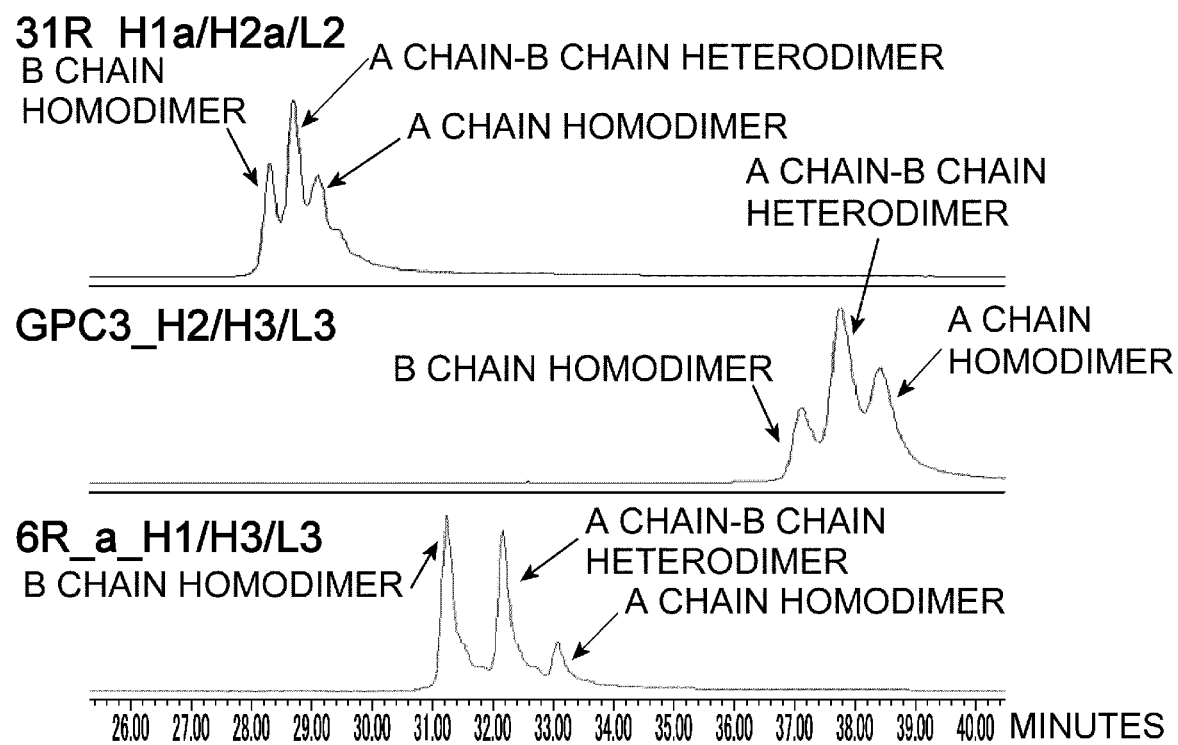
FIG. 61 is a diagram showing peak separation for A chain-B chain heterodimer, A chain homodimer, and B chain homodimer in cation exchange chromatography of 6R_a_H1H3L3, GPC3_H2H3L3, and 31R_H1aH2aL2.

GPC3_H1L1, GPC3_H2L2, and GPC3_H3L3 were assessed by the competitive ELISA method described in Reference Example 5 for their binding activity to the antigen, human GPC3. The result is shown in FIGS. 59 and 60. The glypican 3 binding activity was comparable between GPC3-H1L1 and GPC3-H2L2 and between GPC3-H2L2 and GPC3-H3L3. The amino acid substitutions did not significantly reduce the antigen-binding activity.

The isoelectric point was determined by isoelectric focusing known to those skilled in the art. The isoelectric point of GPC3_H1L1 was about 9.6, while the isoelectric point of GPC3_H2L2 comprising amino acid substitutions for isoelectric point reduction was about 8.9. The isoelectric point of GPC3_H2L2 was reduced by 0.7 relative to GPC3_H1L1. Furthermore, the isoelectric point of GPC3_H2L2 was about 8.7, while the isoelectric point of GPC3_H3L3 comprising

TABLE 21

| | ANTI-HUMAN IL-6 RECEPTOR ANTIBODY | | | |
| --- | --- | --- | --- | --- |
| | 6R_b_H1L1 | 6R_b_H2L2 | 6R_b_H2L3 | 6R_b_H2L4 |
| ACTUAL pI | 9.20 | 5.94 | N.T. | N.T. |
| THEORETICAL pI | 9.20 | 4.52 | 4.46 | 4.37 |

N.T.: Not tested

The amino acid substitutions introduced into the CDR sequence of 6R_b_H1L1 are summarized in Table 22 below. It was revealed that these CDR amino acid substitutions could reduce the isoelectric point of the 6R_b_H1L1 molecule, which is an anti-human IL-6 receptor antibody, without significantly reducing its antigen-binding activity.

TABLE 22

| CLASSIFICATION | MODIFIED POSITION (KABAT NO) | H1 SEQUENCE | AMINO ACID AFTER MODIFICATION |
| --- | --- | --- | --- |
| CDR1 | 31 | S | D |

| CLASSIFICATION | MODIFIED POSITION (KABAT NO) | L1 SEQUENCE | AMINO ACID AFTER MODIFICATION |
| --- | --- | --- | --- |
| CDR1 | 24 | R | Q |
| CDR2 | 53 | R | E |
| CDR2 | 54 | L | E |
| CDR2 | 55 | R | E | amino acid substitutions for isoelectric point reduction was about 6.5. The isoelectric point of GPC3_H3L3 was reduced by 2.2 relative to GPC3_H2L2. In addition, the theoretical isoelectric point of GPC3_H1L1 was 9.65, while that of GPC3_H2L2 was 8.47. Thus, the theoretical isoelectric point of GPC3_H2L2 was reduced by 1.18 relative to GPC3_H1L1. Likewise, the theoretical isoelectric point of GPC3_H2L2 was 8.47, while that of GPC3_H3L3 was 4.93. The theoretical isoelectric point of GPC3_H3L3 was reduced by 3.54 relative to GPC3_H2L2. These results are summarized in Table 23.

TABLE 23

| | ANTI-HUMAN GPC3 ANTIBODY | |
| --- | --- | --- |
| | H1L1 | H2L2 |
| ACTUAL pI | 9.6 | 8.9 |
| THEORETICAL pI | 9.65 | 8.47 |

TABLE 23-continued

| | ANTI-HUMAN GPC3 ANTIBODY | |
|---|---|---|
| | H2L2 | H3L3 |
| ACTUAL pI | 8.7 | 6.5 |
| THEORETICAL pI | 8.47 | 4.93 |

The amino acid substitutions introduced into the CDR sequence of GPC3_H1L1 are summarized in Table 24 below. It was revealed that these CDR amino acid substitutions could reduce the isoelectric point of the GPC3_H1L1 molecule, which is an anti-human GPC3 antibody, without significantly reducing its antigen-binding activity.

TABLE 24

| CLASSIFICATION | MODIFIED POSITION (KABAT NO) | H1 SEQUENCE | AMINO ACID AFTER MODIFICATION |
|---|---|---|---|
| CDR2 | 61 | Q | E |
| CDR2 | 62 | K | S |
| CDR2 | 64 | K | Q |
| CDR2 | 65 | G | D |

| CLASSIFICATION | MODIFIED POSITION (KABAT NO) | L1 SEQUENCE | AMINO ACID AFTER MODIFICATION |
|---|---|---|---|
| CDR1 | 24 | R | Q |
| CDR1 | 27 | R | Q |
| CDR1 | 27 | R | E |

4. Preparation of Anti-Human IL-31 Receptor Antibodies with a Reduced Isoelectric Point, Binding Activity Assessment, and Isoelectric Point Determination To construct 31R_H2 (SEQ ID NO: 240) and 31R_L2 (SEQ ID NO: 243), amino acid substitutions for isoelectric point reduction and other amino acid substitutions were introduced into 31R_H1 (SEQ ID NO: 239) and 31R_L1 (SEQ ID NO: 242) constituting 31R_H1L1. After vector construction, 31R_H2L2 was expressed and purified by the methods described in Reference Examples 1 and 2. Furthermore, to construct 31R_H3 (SEQ ID NO: 241), amino acid substitutions for isoelectric point reduction and other amino acid substitutions were introduced into 31R_H2L2. Vectors were constructed by the method described in Reference Example 1, and then 31R_H3L2 was expressed and purified.

31R_H2L2 and 31R_H3L2 were assessed for their IL-31-binding affinity by the Biacore-based method described in Reference Example 6. The result is summarized in Table 25. As shown in Table 25, the NR10-binding activities of 31R_H2L2 and 31R_H3L2 were comparable to that of 31R_H1L1. Thus, the amino acid substitutions did not significantly reduce the antigen-binding activity.

TABLE 25

| | ka (1/Ms) | kd (1/s) | KD (M) |
|---|---|---|---|
| 31R_H1L1 | 3.7E+05 | 1.2E-03 | 3.3E-09 |
| 31R_H2L2 | 4.2E+05 | 1.6E-03 | 3.9E-09 |
| 31R_H3L2 | 4.4E+05 | 1.6E-03 | 3.6E-09 |

The isoelectric point was determined by isoelectric focusing known to those skilled in the art. The isoelectric point of 31R_H1L1 was about 7.76, while the isoelectric points of 31R_H2L2 and 31R_H3L2 comprising amino acid substitutions for isoelectric point reduction were about 5.49 and about 5.43, respectively. The isoelectric point was reduced by about 2.27 and about 2.33 relative to 31R_H1L1, respectively. Furthermore, the theoretical isoelectric point of 31R_H1L1 was about 7.76, while the theoretical isoelectric points of 31R_H2L2 and 31R_H3L2 were 4.63 and about 4.54, respectively. The theoretical isoelectric points were reduced by about 3.13 and about 3.22 relative to 31R_H1L1. These results are summarized in Table 26.

TABLE 26

| | ANTI-HUMAN IL-31 RECEPTOR ANTIBODY | | |
|---|---|---|---|
| | H1L1 | H2L2 | H3L2 |
| ACTUAL pI | 7.76 | 5.49 | 5.43 |
| THEORETICAL pI | 7.76 | 4.63 | 4.54 |

The amino acid substitutions introduced into the CDR sequence of 31R_H1L1 are summarized in Table 27 below. It was revealed that these CDR amino acid substitutions could reduce the isoelectric point of the 31R_H1L1 molecule, which is an anti-human IL-31 receptor antibody, without significantly reducing the antigen-binding activity.

TABLE 27

| CLASSIFICATION | MODIFIED POSITION (KABAT NO) | H1 SEQUENCE | AMINO ACID AFTER MODIFICATION |
|---|---|---|---|
| CDR2 | 61 | Q | D |
| CDR2 | 62 | K | Q |
| CDR2 | 64 | K | Q |
| CDR2 | 65 | G | D |

| CLASSIFICATION | MODIFIED POSITION (KABAT NO) | L1 SEQUENCE | AMINO ACID AFTER MODIFICATION |
|---|---|---|---|
| CDR1 | 24 | R | Q |
| CDR2 | 54 | L | E |

5. CDR Sequences that Allow Reduction of the Isoelectric Point of Anti-Human IL-6 Receptor Antibodies, Anti-Human GPC3 Antibody, or Anti-Human IL-31 Receptor Antibody without Reducing their Antigen-Binding Activity The heavy chain and light chain CDR sequences of the two types of anti-human IL-6 receptor antibodies (6R_a and 6R_b), anti-human GPC3 antibody (GPC3), and anti-human IL-31 receptor antibody (31R) prepared as described in the above assessment sections are shown in Tables 28 and 29, respectively. Amino acid substitutions that reduced the isoelectric point without reducing the antigen-binding activity are marked.

TABLE 28

| CDR | | HCDR1 | | | | | | HCDR2 | | | | | | | | | | | | | | | | | HCDR3 | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Number | | 31 | 32 | 32a | 33 | 34 | 35 | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 100 | 100a | 100b | 100c | 100d | 101 | 102 |
| 6R_a_H1 | | S | D | H | A | W | S | Y | I | S | - | Y | S | G | I | T | T | Y | N | P | S | L | K | S | V | L | A | R | I | T | A | - | - | M | D | Y |
| 6R_a_H2 | | D | D | H | A | W | S | Y | I | S | - | Y | S | G | I | T | T | Y | N | P | S | L | K | G | V | L | A | R | I | T | A | - | - | M | D | Y |
| 6R_a_H3 | | D | D | H | A | W | S | Y | I | S | - | Y | S | G | I | T | N | Y | N | P | S | L | Q | D | L | L | A | R | A | T | A | - | - | M | D | Y |
| 6R_b_H1 | | S | D | H | A | W | S | Y | I | S | - | Y | S | G | I | T | T | Y | N | P | S | L | K | G | S | L | A | R | T | T | A | - | - | M | D | Y |
| 6R_b_H2 | | D | D | H | A | W | S | Y | I | S | - | Y | S | G | I | T | T | Y | N | P | S | L | K | G | S | L | A | R | T | T | A | - | - | M | D | Y |
| 6R_b_H3 | | D | D | H | A | W | S | Y | I | S | - | Y | S | G | I | T | N | Y | N | P | S | L | K | G | F | Y | S | Y | Y | - | - | - | - | - | - | - |
| GPC3_H1 | | D | Y | - | E | M | H | A | I | N | P | K | T | G | D | T | A | Y | S | Q | K | F | K | G | S | Y | S | Y | S | - | - | - | - | - | - | - |
| GPC3_H2 | | D | Y | - | E | M | H | A | I | N | P | K | T | G | D | T | A | Y | S | Q | K | F | K | G | F | Y | S | Y | S | - | - | - | - | - | - | - |
| GPC3_H3 | | D | Y | - | E | M | H | A | I | D | P | K | T | G | D | T | A | Y | S | E | S | F | Q | D | F | Y | Y | Y | Y | - | - | - | - | - | - | - |
| 31R_H1 | | G | Y | - | I | M | N | L | I | N | P | Y | N | G | G | T | S | Y | N | Q | K | F | K | G | D | D | Y | D | D | G | P | Y | T | M | D | Y |
| 31R_H2 | | G | Y | - | I | M | N | L | I | N | P | Y | N | G | G | T | S | Y | N | Q | Q | F | Q | D | D | D | Y | D | T | G | P | Y | T | M | T | Y |
| 31R_H3 | | G | Y | - | I | M | N | L | I | N | P | Y | N | G | G | T | S | Y | N | D | Q | F | Q | D | D | D | Y | D | T | G | P | Y | T | M | D | Y |
| POSITION EFFECTIVE IN MULTIPLE ANTIBODIES | | ○ | | | | | | | | | | | | | | | | | | | ○ | | ○ | ○ | | | | | | | | | | | | |

TABLE 29

| CDR | | | | | | LCDR1 | | | | | | | | | | | LCDR2 | | | | | | | LCDR3 | | | | | | | | | |
|---|---|---|---|---|---|---|---|---|---|---|---|---|---|---|---|---|---|---|---|---|---|---|---|---|---|---|---|---|---|---|---|---|
| Number | 24 | 25 | 26 | 27 | 27a | 27b | 27c | 27d | 27e | 28 | 29 | 30 | 31 | 32 | 33 | 34 | 50 | 51 | 52 | 53 | 54 | 55 | 56 | 89 | 90 | 91 | 92 | 93 | 94 | 95 | 96 | 97 |
| 6R_a_L1 | R | A | S | Q | D | - | - | - | - | - | I | S | S | Y | L | N | Y | T | S | R | L | H | S | G | Q | G | N | R | L | P | Y | T |
| 6R_a_L2 | Q | A | S | Q | D | - | - | - | - | - | H | S | S | Y | L | N | Y | G | S | E | L | H | S | G | Q | G | N | R | L | P | Y | T |
| 6R_a_L3 | Q | A | S | E | D | - | - | - | - | - | H | S | S | Y | L | N | Y | G | S | E | L | E | S | G | Q | G | N | R | L | P | Y | T |
| 6R_b_L1 | R | A | S | Q | D | - | - | - | - | - | I | S | S | Y | L | N | Y | T | S | R | L | H | S | Q | Q | G | N | T | L | P | Y | T |
| 6R_b_L2 | Q | A | S | Q | D | - | - | - | - | - | H | S | S | Y | L | N | Y | G | S | E | L | H | S | Q | Q | G | N | S | L | P | Y | T |
| 6R_b_L3 | Q | A | S | Q | D | - | - | - | - | - | H | S | S | Y | L | N | Y | G | S | E | L | H | S | Q | Q | G | N | S | L | P | Y | T |
| 6R_b_L4 | Q | A | S | Q | D | - | - | - | - | - | H | S | S | Y | L | N | Y | G | S | E | L | E | S | Q | Q | G | N | S | L | P | Y | T |
| GPC3_L1 | R | A | S | R | S | L | V | H | S | N | R | N | T | Y | L | H | K | V | S | N | R | F | S | S | Q | N | T | H | V | P | P | T |
| GPC3_L2 | R | S | S | Q | S | L | V | H | S | N | R | N | T | Y | L | H | K | V | S | N | R | F | S | S | Q | N | T | H | V | P | P | T |
| GPC3_L3 | Q | A | S | E | S | L | V | H | S | N | R | N | T | Y | L | H | K | V | S | N | R | F | S | S | Q | N | T | H | V | P | P | T |
| 31R_L1 | R | T | S | E | N | - | - | - | - | - | I | Y | S | F | L | A | N | A | K | T | L | A | K | Q | H | H | Y | E | S | L | L | T |
| 31R_L2 | Q | T | S | E | D | - | - | - | - | - | H | Y | S | F | L | A | N | A | Q | T | E | A | Q | Q | H | H | Y | E | S | P | L | T |
| POSITION EFFECTIVE IN MULTIPLE ANTIBODIES | o | | | o | | | | | | | | | | | | | | | | o | o | | | | | | | | | | | |

The above result demonstrates that positions H31, H61, H62, H64, and H65 in the heavy chain variable region and positions L24, L27, L53, L54, and L55 in the light chain variable region (Kabat numbering) are common CDR position, regardless of antibody specificity, where amino acid substitutions for reducing isoelectric point of antibody can be introduced without significantly reducing antigen-binding activity.

WO/2007/114319 describes that IgG pharmacokinetics can be improved by reducing the antibody isoelectric point. In WO/2007/114319, amino acids were substituted mainly in the antibody framework of antibody variable region to avoid reduction of antigen-binding activity. The changes in the measured and theoretical isoelectric points of anti-Factor IXa antibody were about 0.9 and 1.0, respectively. The changes in the measured and theoretical isoelectric points of anti-Factor X antibody were about 0.5 and 0.1, respectively. The isoelectric point changes were small.

In the present invention, CDR sequences that do not result in reduction of antibody-antigen binding activity were discovered, and amino acid substitutions can be introduced not only into the variable region framework but also into the antibody CDR to reduce isoelectric point. As a result, the measured and theoretical isoelectric points were reduced by about 3.8 and about 5.1, respectively, in the anti-human IL-6 receptor antibody described above; the measured and theoretical isoelectric points were reduced by about 3.1 and about 4.7, respectively, in the anti-human GPC3 antibody; and the measured and theoretical isoelectric points were reduced by about 3.2 and about 2.3, respectively, in the anti-human IL-31 receptor antibody. The present invention revealed that amino acid substitutions in the CDR could result in significant reduction of the isoelectric point as compared to amino acid substitutions in the framework alone.

[Example 30] Assessment of Pharmacokinetics of Anti-Human IL-6 Receptor Antibodies, Anti-Human GPC3 Antibodies, and Anti-Human IL-31 Receptor Antibodies with a Reduced Isoelectric Point 1. Assessment of Anti-Human IL-6 Receptor Antibodies for their Pharmacokinetics in Cynomolgus Monkeys and Mice 6R_a_H1L1, an anti-human IL-6 receptor antibody, and 6R_a_H2L2 and 6R_a_H3L3, anti-human IL-6 receptor antibodies with a decreased isoelectric point, were assessed for their pharmacokinetics in cynomolgus monkeys. 6R_a_H1L1 or 6R_a_H2L2 was intravenously administered once at 1.0 mg/kg. Blood was collected over time before and after administration. Furthermore, 6R_a_H2L2 or 6R_a_H3L3 was subcutaneously administered once at 1.0 mg/kg. Blood was collected over time before and after administration.

The plasma concentrations were measured by ELISA. Appropriate concentrations of standard samples and test plasma samples were aliquoted into wells of immunoplates (Nunc-Immuno Plate, MaxiSorp (Nalge Nunc International)) coated with anti-human IgG (γ-chain specific) F(ab')2 (Sigma). The samples were incubated at room temperature for one hour, and then Goat Anti-Human IgG-BIOT (Southern Biotechnology Associates) and streptavidin-alkaline phosphatase conjugate (Roche Diagnostics) were subsequently reacted. After color development using the BluePhos Microwell Phosphatase Substrates System (Kirkegaard & Perry Laboratories) as a substrate, the absorbance at 650 nm was measured with a microplate reader. The plasma concentrations were determined based on the absorbance of the calibration curve using the analytical software SoftMax Pro (Molecular Devices). The obtained plasma concentration-time data were evaluated by model-free analysis using the pharmacokinetic analysis software WinNonlin (Pharsight) to estimate clearance (CL). The result is shown in Table 30. When administered intravenously, 6R_a_H2L2, which has a reduced isoelectric point, exhibited slower clearance than 6R_a_H1L1. This suggests that the pharmacokinetics is improved by reducing the isoelectric point. Furthermore, when administered subcutaneously, 6R_a_H3L3, which has a reduced isoelectric point, exhibited slower clearance than 6R_a_H2L2. This suggests that the pharmacokinetics is improved by reducing the isoelectric point.

TABLE 30

|  | CL (mL/h/kg) |
|---|---|
| 6R_a_H1L1 iv | 1.82 |
| 6R_a_H2L2 iv | 0.91 |
| 6R_a_H2L2 sc | 1.43 |
| 6R_a_H3L3 sc | 0.93 |

Next, 6R_b_H1L1, which is another anti-human IL-6 receptor antibody, and 6R_b_H2L2, an anti-human IL-6 receptor antibody with a reduced isoelectric point, were assessed for their pharmacokinetics in mice (C57BL/6J; Charles River Japan, Inc.). 6R_b_H1L1 or 6R_b_H2L2 was intravenously administered once at 1.0 mg/kg. Blood was collected over time before and after administration. Furthermore, 6R_b_H1L1 or 6R_b_H2L2 was subcutaneously administered once at 1.0 mg/kg. Blood was collected over time before and after administration.

The plasma concentrations were measured by ELISA. First, Recombinant Human IL-6 sR (R&D Systems) was biotinylated using EZ-Link™ Sulfo-NFS-Biotinylation Kit (Pierce). The biotinylated human-sIL-6R was aliquoted into wells of Reacti-Bind Streptavidin High Binding Capacity (HBC) Coated Plates (Pierce), and incubated at room temperature for one hour or more to prepare human-sIL-6R-immobilized plates. Appropriate concentrations of standard samples and mouse test plasma samples were prepared and aliquoted into wells of the human-sIL-6R-immobilized plates. The samples were incubated at room temperature for one hour, and then reacted with Anti-human IgG-AP (Sigma). After color development using the BluePhos Microwell Phosphatase Substrates System (Kirkegaard & Perry Laboratories) as a substrate, the absorbance at 650 nm was measured with a microplate reader. The plasma concentrations were determined based on the absorbance of the calibration curve using the analytical software SoftMax Pro (Molecular Devices). The obtained plasma concentration-time data were evaluated by model-free analysis using the pharmacokinetic analysis software WinNonlin (Pharsight) to estimate the clearance (CL). The result is shown in Table 31. In every case of the intravenous administration and subcutaneous administration, 6R_a_H2L2, which has a reduced isoelectric point, exhibited slower clearance than 6R_a_H1L1. This suggests that the pharmacokinetics can be improved by reducing the isoelectric point.

TABLE 31

|  | CL (mL/h/kg) |
|---|---|
| 6R_b_H1L1 iv | 0.18 |
| 6R_b_H2L2 iv | 0.10 |

TABLE 31-continued

| | CL (mL/h/kg) |
|---|---|
| 6R_b_H1L1 sc | 0.18 |
| 6R_b_H2L2 sc | 0.09 |

2. Assessment of Anti-Human GPC3 Antibodies for their Pharmacokinetics in Mice

GPC3_H1L1, an anti-human GPC3 antibody, and GPC3_H2L2 and GPC3_H3L3, anti-human GPC3 antibodies with a reduced isoelectric point, were assessed for their pharmacokinetics in C.B-17/Icr scid mice. GPC3_H1L1, GPC3_H2L2, or GPC3_H3L3 was intravenously administered once at 5.0 mg/kg. Blood was collected over time before and after administration.

The plasma concentrations were measured by ELISA. Appropriate concentrations of standard samples, and test samples of mouse plasma appropriately diluted to desired concentrations were aliquoted into wells of immunoplates (Nunc-Immuno Plate, MaxiSoup (Nalge Nunc International)) immobilized with the antigen GPC3 (Chugai Pharmaceutical Co. Ltd.). The plates were incubated at room temperature for one hour, and then Goat Anti-Human IgG-BIOT (Southern Biotechnology Associates) and streptavidin-alkaline phosphatase conjugate (Roche Diagnostics) were aliquoted in succession. After color development using the BluePhos Microwell Phosphatase Substrates System (Kirkegaard & Perry Laboratories) as a substrate, the absorbance at 650 nm was measured with a microplate reader. The plasma concentrations were determined based on the absorbance of the calibration curve using the analytical software SoftMax Pro (Molecular Devices). The obtained plasma concentration-time data were evaluated by model-free analysis using the pharmacokinetic analysis software WinNonlin (Pharsight) to estimate clearance (CL). The result is shown in Table 32. GPC3_H2L2, which has a reduced isoelectric point, exhibited slower clearance than GPC3_H1L1. Furthermore, GPC3_H3L3, which has a further reduced isoelectric point, exhibited slower clearance than GPC3_H2L2. This suggests that the pharmacokinetics can be improved by reducing isoelectric point.

TABLE 32

| | CL(mL/h/kg) |
|---|---|
| GPC3_H1L1 | 2.34 |
| GPC3_H2L2 | 0.38 |
| GPC3_H3L3 | 0.22 |

3. Assessment of Anti-Human IL-31 Receptor Antibodies for their Pharmacokinetics in Mice 31R_H1L1, an anti-human IL-31 receptor antibody, and 31R_H2L2, an anti-human IL-31 receptor antibody with a reduced isoelectric point, were assessed for their pharmacokinetics in mice (C57BL/6J; Charles River Japan, Inc.). 31R_H1L1 or 31R_H2L2 was intravenously administered once at 1.0 mg/kg. Blood was collected over time before and after administration.

The plasma concentrations were measured by ELISA. Appropriate concentrations of standard samples and test plasma samples were aliquoted into wells of immunoplates (Nunc-Immuno Plate, MaxiSorp (Nalge Nunc International)) immobilized with anti-human IgG (Fc-specific) antibody (Sigma). The samples were incubated at room temperature for one hour. Goat Anti-Human IgG-ALP (Sigma) was reacted at room temperature for one hour. After color development using the BluePhos Microwell Phosphatase Substrates System (Kirkegaard & Perry Laboratories) as a substrate, the absorbance at 650 nm was measured with a microplate reader. The plasma concentrations were determined based on the absorbance of the calibration curve using the analytical software SoftMax Pro (Molecular Devices).

The obtained plasma concentration-time data were evaluated by model-free analysis using the pharmacokinetic analysis software WinNonlin (Pharsight) to estimate clearance (CL). The result is shown in Table 33. 31R_H2L2, which has a reduced isoelectric point, exhibited slower clearance than 31R_H1L1. This suggests that the clearance rate is decreased by reducing the isoelectric point.

TABLE 33

| | CL(mL/h/kg) |
|---|---|
| 31 R_H1L1 | 0.15 |
| 31 R_H2L2 | 0.13 |

3. Conclusions

The present invention revealed that the pharmacokinetics of various antibodies against different antigens can be improved by reducing their isoelectric points without reducing the antibody-antigen binding activity through substitution of amino acids in the CDR sequence. It was shown that among amino acid substitutions in the CDR sequence, those at positions H31, H61, H62, H64, and H65 in the heavy chain variable region, and those at positions L24, L27, L53, L54, and L55 in the light chain variable region (Kabat numbering) are amino acid substitutions that can be introduced to reduce antibody isoelectric point without significantly reducing the antigen-binding activity, and can thus improve antibody pharmacokinetics regardless of the antibody specificity. These mutation positions in the CDR sequence are considered useful as positions for amino acid substitution to improve antibody pharmacokinetics regardless of the antibody specificity, since amino acid substitutions at these positions can reduce antibody isoelectric point without significantly reducing the antibody-antigen binding activity.

[Example 31] Separation of Homodimer and Heterodimer Peaks of Anti-Human IL-6 Receptor Antibody, Anti-Human GPC3 Antibody, or Anti-Human IL-31 Receptor Antibody with a Decreased Isoelectric Point by Conventional Chromatography 1. Expression of Heterodimer of Anti-Factor IX Antibody/Anti-Factor X Antibody The patent document WO/2007/114325 has reported methods for purifying IgG-type bispecific antibodies having a common L chain. To express IgG-type bispecific antibodies having a common L chain, it is necessary to express two types of heavy chains (A chain and B chain) and a common light chain. In this case, not only A chain-B chain heterodimer, which is the bispecific antibody of interest, but also A chain homodimer and B chain homodimer are expressed; thus, the bispecific antibody of interest, A chain-B chain heterodimer, has to be purified from the mixture of three kinds of antibodies. This patent document also describes that conventional methods were not able to purify A chain-B chain heterodimer by separating the A chain-B chain heterodimer peak from the peaks of A chain and B chain homodimers by conventional chromatography, but the A chain-B chain heterodimer can be purified by separating the peaks of A chain-B chain heterodimer, and A chain and B chain homodimers by conventional cation exchange chromatography when the difference between the isoelectric points of A chain and B chain homodimers was increased by substituting amino acids in the variable regions of the two kinds of heavy chains, namely A chain and B chain. In this patent, amino acids were substituted in the framework alone, because amino acid substitutions in the variable region CDR were considered to affect the antibody-antigen binding activity. However, as described above, amino acid substitutions in the framework do not cause significant changes in isoelectric point. Thus, to achieve efficient purification of A chain-B chain heterodimer, it is preferred to further increase the difference between the isoelectric points of A chain and B chain homodimers. In this context, it was tested whether the peaks of A chain-B chain heterodimer, A chain homodimer, and B chain homodimer could be separated by introducing the CDR amino acid substitutions in Example 28 that reduce antibody isoelectric point without significantly reducing antibody-antigen binding activity.

2. Expression of Heterodimer of Anti-Human IL-6 Receptor Antibody/Anti-Human IL-6 Receptor Antibody with a Reduced Isoelectric Point 6R_a_H1H3L3 (mixture of A chain-B chain heterodimer (6R_a_H1/H3/L3), A chain homodimer (6R_a_H1/L3), and B chain homodimer (6R_a_H3/L3)) was expressed and purified by the method described in Reference Example 2 using 6R_a_L3 (SEQ ID NO: 226) as a common light chain, 6R_a_H1 (SEQ ID NO: 221) as an A chain, and 6R_a_H3 (SEQ ID NO: 223) as a B chain whose isoelectric point had been reduced without reducing the antigen-binding activity to increase the difference in isoelectric point when compared to the A chain.

3. Expression of Heterodimer Anti-Human GPC3 Antibody/Anti-Human GPC3 Antibody with a Reduced Isoelectric Point GPC3_H2H3L3 (mixture of A chain-B chain heterodimer (GPC3_H2/H3/L3), A chain homodimer (GPC3_H2/L3), and B chain homodimer (GPC3_H3/L3)) was expressed and purified by the method described in Reference Example 2 using GPC3 L3 (SEQ ID NO: 238) as a common light chain, GPC3_H2 (SEQ ID NO: 234) as an A chain, and GPC3_H3 (SEQ ID NO: 235) as a B chain whose isoelectric point had been reduced without reduction of the antigen-binding activity to increase the difference in isoelectric point when compared to the A chain.

4. Expression of Heterodimer of Anti-Human IL-31 Receptor Antibody/Anti-Human IL-31 Receptor Antibody with a Reduced Isoelectric Point 31R_H1aH2aL2 (mixture of A chain-B chain heterodimer (31R_H1a/H2a/L2), A chain homodimer (31R_H1a/L2), and B chain homodimer (31R_H2a/L2)) was expressed and purified by the method described in Reference Example 2 using 31R_L2 (SEQ ID NO: 243) as a common light chain, and as a A chain 31R_H1a (SEQ ID NO: 244) which was obtained by modifying the constant region of 31R_H1, and 31R_H2a (SEQ ID NO: 245) as a B chain which was obtained by modifying the constant region of 31R_H2 whose isoelectric point had been reduced without reduction of the antigen-binding activity to increase the difference in isoelectric point when compared to the A chain.

5. Assessment of Expressed Antibody by Cation Exchange Chromatography

The differences in the theoretical VH/VL isoelectric point between antibody A chain and B chain homodimers prepared as described above are summarized in Table 34. By introducing into not only the heavy-chain framework but also the heavy-chain CDR sequence, amino acid substitutions that reduce the isoelectric point without loss of binding activity, the difference in the theoretical isoelectric point can be increased up to 1.56 between A chain and B chain homodimers. The patent document WO/2007/114325 has reported that the difference in the theoretical VH/VL isoelectric point between A chain and B chain homodimers can be increased up to 1.13 by reducing the isoelectric point of the A chain homodimer by amino acid substitution in its framework alone and simultaneously increasing the isoelectric point of the B chain homodimer by amino acid substitution in its framework alone. The result of assessment described herein shows that the difference in the theoretical isoelectric point can be increased up to 1.56 by introducing amino acid substitutions into not only the framework but also the CDR sequence even when amino acid substitutions are only introduced into one chain (i.e., only the isoelectric point of one chain is reduced). Specifically, the present invention demonstrated that in order to separate A chain and B chain homodimers, the difference in the isoelectric point between the two kinds of homodimers could be further increased by introducing amino acid substitutions into not only the framework but also the CDR sequence without loss of binding activity. In general, the separation by conventional ion exchange chromatography depends on the difference in the isoelectric point between the two components to be separated. Thus, the substitutions described above enable easy separation of the two components.

TABLE 34

| MOLECULE NAME | | THEORETICAL pI OF VH/VL | THEORETICAL pI DIFFERENCE |
|---|---|---|---|
| A CHAIN HOMODIMER | 6a_H1_L3 | 4.86 | 0.59 |
| B CHAIN HOMODIMER | 6a_H3_L3 | 4.27 | |
| A CHAIN HOMODIMER | GPC3_H2_L3 | 6.49 | 1.56 |
| B CHAIN HOMODIMER | GPC3_H3_L3 | 4.93 | |
| A CHAIN HOMODIMER | 31R_H1_L2 | 5.06 | 0.43 |
| B CHAIN HOMODIMER | 31R_H2_L2 | 4.63 | |

6R_a_H1H3L3, GPC3_H2H3L3, and 31R_H1aH2aL2 were tested to assess whether they can be separated individually as peaks of A chain-B chain heterodimer, A chain homodimer, and B chain homodimer by cation exchange chromatography. ProPac WCX-10 (Dionex) was used as a column of conventional cation exchange chromatography. The chromatography was carried out with an appropriate flow rate and gradient using 25 mM IVIES (pH 5.0) as mobile phase A and 25 mM MES containing 1 M NaCl (pH 5.0) as mobile phase B. The result of assessment by cation exchange chromatography is shown in FIG. 61. All of 6R_a_H1H3L3, GPC3_H2H3L3, and 31R_H1aH2aL2 were demonstrated to be separated into peaks of A chain-B chain heterodimer, A chain homodimer, and B chain homodimer.

Regardless of the antibody specificity, amino acid substitutions at positions of H31, H61, H62, H64, and H65 (Kabat numbering) in the heavy chain variable region can reduce antibody isoelectric point without significantly reducing antibody-antigen binding activity. It was thus revealed that the amino acid substitutions enabled separation of the heterodimer and homodimers by cation exchange chromatography. Mutations at these positions in the CDR sequence can reduce antibody isoelectric point without significantly reducing the antibody-antigen binding activity regardless of the antibody specificity. Thus, the positions are useful as positions for amino acid substitution to increase the difference in isoelectric point between the bispecific antibody heterodimer and homodimers.

[Reference Example 1] Construction of Genes for Antibody-Expression Vectors

Each mutant was constructed using the QuikChange Site-Directed Mutagenesis Kit (Stratagene) or by assemble PCR. When the QuikChange Site-Directed Mutagenesis Kit (Stratagene) was used, mutants were constructed by the method described in the appended protocol. Alternatively, assemble PCR was carried out using either of the methods described below. In the first method, oligo DNAs were synthesized based on forward and reverse sequences including modification sites. Two fragments, namely 5' and 3' fragments, including modification sites were constructed by PCR using PrimeSTAR (Takara), and combinations of forward oligo DNA including modification site and reverse oligo DNA that bound to the vector carrying the gene to be modified, and reverse oligo DNA including modification site and forward oligo DNA that bound to the vector carrying the gene to be modified. Each mutant was constructed by linking the two fragments by assemble PCR. In the second method, an appropriate number of oligo DNAs were prepared so as to cover the entire variable region. The complete variable region was constructed by linking the oligo DNAs by assemble PCR. Mutants constructed by the methods described above were inserted into expression vectors capable of expressing insert genes in animal cells. The nucleotide sequences of the obtained expression vectors were determined by a method known to those skilled in the art.

[Reference Example 2] Expression and Purification of Antibodies

Antibodies were expressed by the method described below. Cells of human fetal renal carcinoma line HEK293H (Invitrogen) were suspended at a density of $5 \times 10^5$ to $6 \times 10^5$ cells/ml in DMEM (Invitrogen) supplemented with 10% FBS (Invitrogen), and plated into adhesion cell dishes (10-cm diameter; Corning) at 10 ml/dish. The cells were cultured in a $CO_2$ incubator (37° C., 5% $CO_2$) for one whole day and night. Then, the medium was removed by aspiration, and 6.9 ml of CHO-S-SFM-II medium (Invitrogen) was added to the dish. The prepared plasmids were introduced into cells by lipofection. The supernatants obtained after culturing were collected, and then the cells were removed by centrifugation (at room temperature and about 2,000 g for five minutes). The culture supernatants were sterilized by filtration with 0.22-μm filter MILLEX (R)-GV (Millipore). Antibodies were purified from the resulting culture supernatants using rProtein A Sepharose™ Fast Flow (Amersham Biosciences) by a method known to those skilled in the art. The concentrations of the purified antibodies were determined from the absorbance at 280 nm measured with a spectrophotometer. The antibody concentrations were calculated from the determined values using extinction coefficient determined by the PACE method (Protein Science (1995) 4:2411-2423).

[Reference Example 3] Biacore-Based Method for Assessing the Affinity of Anti-Human IL-6 Receptor Antibody for IL-6 Receptor 1. Preparation of Soluble Human IL-6 Receptor Recombinant human IL-6 receptor, which is the antigen, was prepared by the method described below. A CHO cell line constitutively expressing the sequence of N-terminal amino acids 1 to 344 of soluble human IL-6 receptor (Yamasaki et al., Science (1988) 241:825-828 (GenBank # X12830)) reported in J. Biochem. (1990) 108:673-676 was prepared. The soluble human IL-6 receptor was purified from the culture supernatant of soluble human IL-6 receptor-expressing CHO cells using three types of column chromatography: Blue Sepharose 6 FF column chromatography, affinity chromatography on a column immobilized with a soluble human IL-6 receptor specific antibody, and gel filtration column chromatography. The fraction eluted as the major peak was used as the final purified sample.

2. Biacore-Based Assessment of Affinity for Soluble Human IL-6 Receptor

The antigen-antibody reaction kinetics between anti-human IL-6 receptor antibody and soluble human IL-6 receptor was analyzed using Biacore T100 (GE Healthcare Biosciences). The antigen-antibody interaction was measured by immobilizing rec-Protein A (Zymed) (hereinafter "Protein A") onto a sensor chip, capturing an antibody with the immobilized Protein A, and then reacting the antibody with the antigen as an analyte using a method known to those skilled in the art. The running buffer used was HBS-EP+, and the flow rate was 20 μl/min. Each antibody was prepared so that about 100 RU of the antibody was bound to Protein A/G. Soluble human IL-6 receptor was prepared at 0, 0.065, 0.131, and 0.261 μg/ml using HBS-EP+ and used as an analyte. In the first step of the measurement, the antibody in solution was bound to Protein A/G, and the analyte solution was allowed to interact with the antibody. After three minutes of interaction, the solution was switched to HBS-EP+, and the dissociation phase was monitored for 10 or 15 minutes. After measurement of the dissociation phase, the sensor chip was regenerated by washing with 10 μl of 10 mM glycine-HCl (pH 1.5). The association, dissociation, and regeneration constitute one analysis cycle. Each antibody was measured according to this cycle. The obtained sensorgrams were kinetically analyzed using the Biacore-specific data analysis software, Biacore T100 Evaluation Software (GE Healthcare Biosciences).

[Reference Example 4] Method for Assessing the IL-6 Receptor-Neutralizing Activity of Anti-Human IL-6 Receptor Antibody Using BaF/6R Cells To obtain a cell line that proliferates in an IL-6-dependent manner, a BaF3 cell line expressing human gp130 and human IL-6R was established by the procedure described below. The full-length human IL-6R cDNA was amplified by PCR and cloned into pcDNA3.1(+) (Invitrogen) to construct hIL-6R/pcDNA3.1(+). pCOS2Zeo/gp130 was introduced into BaF3 cells by electroporation. A BaF3 cell line expressing human gp130 (hereinafter "BaF/gp130") was established by selection in the presence of human interleukin-6 (R&D systems) and 100 ng/ml human interleukin-6 soluble receptor (R&D systems). Next, the full-length human IL-6R cDNA was amplified by PCR and cloned into pcDNA3.1(+) (Invitrogen) to construct hIL-6R/pcDNA3.1 (+). By electroporation, pcDNA3.1(+)/hIL-6R was introduced into the BaF/gp130 cell prepared described above. A BaF3 cell line expressing human IL-6R (hereinafter "BaF/6R") was established by selection in the presence of human interleukin-6 (R&D systems). Since BaF/6R proliferates in the presence of human interleukin-6 (R&D systems), it can be used to assess the growth inhibition activity of an anti-human IL-6 receptor antibody (namely, the human IL-6 receptor-neutralizing activity).

The anti-human IL-6 receptor antibody was assessed for its human IL-6 receptor-neutralizing activity using BaF/6R. After washing three times with RPMI1640 supplemented with 10% FBS, BaF/6R was suspended at $2.5 \times 10^4$ to $5.0 \times 10^4$ cells/ml in RPMI1640 containing 10% FBS and 20 ng/ml human interleukin-6 (Toray) (at a final concentration of 10 ng/ml), and aliquoted (50 μl) into each well of 96 well-plates (Corning). Then, the anti-human IL-6 receptor antibody was diluted with RPMI1640 containing 10% FBS and added to each well (50 μl/well). The cells were cultured at 37° C. under 5% $CO_2$ for three days. WST-8 Reagent (Cell Counting Kit-8; Dojindo Laboratories) was diluted two-fold with PBS. Immediately after 20 μl of the reagent was added to each well, the absorbance at 450 nm (reference wavelength: 620 nm) was measured using SUNRISE CLASSIC (TECAN). After culturing for two hours, the absorbance at 450 nm (reference wavelength: 620 nm) was measured again. The human IL-6 receptor-neutralizing activity was assessed using the change of absorbance during two to four hours as an indicator.

[Reference Example 5] Assessment of Modified Anti-Human GPC3 Antibodies for their Binding Activity by Competitive ELISA The binding activities of prepared antibodies were determined by competitive ELISA. The soluble GPC3 core polypeptide (SEQ ID NO: 207) prepared at 1 μg/ml was added to 96-well plates (100 μl/well). The plates were incubated at 4° C. overnight to immobilize the soluble GPC3 core polypeptide onto the plates. After washing the plates immobilized with the soluble GPC3 core polypeptide three times with washing buffer using SkanWasher 400 (Molecular Devices), 200 μl of blocking buffer was added thereto. The plates were incubated at 4° C. for 30 minutes or more for blocking. The plates immobilized with the soluble GPC3 core polypeptide and blocked were washed three times with washing buffer using SkanWasher 400. Then, 100 μl of various concentrations of antibody GPC3-H2L2 or a different antibody were combined with 100 μl of biotinylated antibody GPC3-H2L2 at a final concentration of 0.3 μg/ml, and the resulting mixtures were added to the wells (200 μl/well). The GPC3-H2L2 antibody was biotinylated using a Biotin Labeling kit (Roche) according to the appended protocol. The plates were incubated at room temperature for one hour, and then washed five times with washing buffer using SkanWasher 400 (Molecular Devices). 100 μl of goat anti streptavidin alkaline phosphatase (Zymed) 20,000-times diluted with substrate buffer was added to each well. The plates were incubated at room temperature for one hour, and then washed five times with washing buffer using SkanWasher 400. Phosphatase Substrate (Sigma) was prepared at 1 mg/ml using substrate buffer, and added to each well (100 μl). The plates were incubated for one hour. The absorbance of the reaction mixture in each well was measured at 405 nm with reference absorbance at 655 nm using Benchmark Plus (Bio-Rad).

[Reference Example 6] Biacore-Based Method for Assessing the Affinity of Anti-Human IL-31 Receptor Antibody for IL-31 Receptor 1. Preparation of Soluble Human IL-31 Receptor The extracellular domain of human IL-31 receptor was amplified by PCR using human IL-31 receptor cDNA as a template. After attaching a FLAG tag sequence to the C-terminal end, the PCR product was inserted into a mammalian cell expression vector. 10 μg of the linearized vector was introduced into Chinese hamster ovary cell line DG44 by electroporation (Bio-Rad Gene Pulser II; 25 μF, 1.5 kV). A cell line showing high level expression was obtained. The cell line was cultured on a large scale. Soluble NR10 was purified from the culture supernatant using anti-FLAG antibody column (Sigma) and gel filtration. The amino acid sequence of soluble human IL-31 receptor is shown in SEQ ID NO: 246.

2. Biacore-Based Assessment of the Affinity for Soluble Human IL-31 Receptor

The antigen-antibody reaction kinetics between anti-human IL-31 receptor antibody and soluble human IL-31 receptor was analyzed using Biacore T100 (GE Healthcare Biosciences). The antigen-antibody interaction was measured by immobilizing rec-Protein A (Zymed) (hereinafter "Protein A") onto a sensor chip, capturing an antibody with the immobilized Protein A, and then reacting the antibody with the antigen as an analyte using a method known to those skilled in the art. Each antibody was prepared so that an appropriate amount of the antibody was bound to Protein A/G. Soluble human IL-31 receptor was prepared at 0, 38.5, 77.0, and 154 nM using HBS-EP+ and used as an analyte. In the first step of the measurement, the antibody in solution was bound to Protein A/G, and the analyte solution was allowed to interact with the antibody. After three minutes of interaction, the solution was switched to HBS-EP+, and the dissociation phase was monitored for five minutes. After measurement of the dissociation phase, the sensor chip was regenerated by washing with 10 μl of 10 mM glycine-HCl (pH 1.5). The association, dissociation, and regeneration constitute one analysis cycle. Each antibody was measured according to this cycle. The obtained sensorgrams were kinetically analyzed using the Biacore-specific data analysis software, Biacore T100 Evaluation Software (GE Healthcare Biosciences).

INDUSTRIAL APPLICABILITY

The present invention provides methods for modifying the isoelectric points of antibodies, methods for purifying multispecific antibodies, and methods for improving antibody pharmacokinetics in plasma, all of which are based on modification of the charge of at least one exposable amino acid residue on the surface of the complementarity determining region (CDR) while retaining antigen-binding activity; pharmaceutical compositions comprising as an active ingredient an antibody with a modified isoelectric point; and methods for producing the compositions. Multispecific antibodies can be efficiently purified to high purity by modifying antibody isoelectric point. Furthermore, antibody pharmacokinetics in plasma can be improved by modifying antibody isoelectric point. Such antibodies can produce a prolonged therapeutic effect even when the administration frequency is reduced. It should be noted that antibodies obtained by the methods of the present invention retain antigen-binding activity.

The invention claimed is:

1. A method for producing a modified antigen-binding molecule comprising a heavy chain variable region and a light chain variable region that bind to an antigen, the method comprising:

preparing the modified antigen-binding molecule by substituting at least two exposable amino acid residues on the surface of a complementary determining region (CDR) or CDRs in a heavy chain variable region of a starting antigen-binding molecule that binds to the antigen, to make the charge of the modified antigen-binding molecule more positive than the charge of the starting antigen-binding molecule, while retaining 80% or more of the starting antigen-binding molecule's antigen-binding activity as measured by a surface plasmon resonance (SPR) technique in which the respective antigen-binding molecule is immobilized, the antigen serves as analyte, and the following conditions are used: 0.01 M HEPES pH 7.4, 0.15 M NaCl, 3 mM ethylene diamine tetraacetic acid (EDTA), 0.05% polysorbate 20, at 37° C., wherein the starting antigen-binding molecule comprises an FcRn-binding domain, wherein the starting antigen-binding molecule is a chimeric IgG antibody, humanized IgG antibody, or human IgG antibody, wherein a plasma pharmacokinetics parameter of the modified antigen-binding molecule is altered compared to that of the starting antigen-binding molecule, and wherein each of the at least two exposable amino acid residues is independently substituted in accordance with any of the following:

(i) substitution of a non-charged amino acid for a negatively charged amino acid in the starting antigen-binding molecule; or (ii) substitution of a positively charged amino acid for a negatively charged amino acid in the starting antigen-binding molecule; or (iii) substitution of a positively charged amino acid for a non-charged amino acid in the starting antigen-binding molecule.

2. The method of claim 1, wherein the modified antigen-binding molecule comprises an FcRn-binding domain and is a chimeric IgG antibody, humanized IgG antibody, or human IgG antibody.

3. The method of claim 1, wherein the modified antigen-binding molecule is a multispecific IgG antibody that binds to at least two types of antigens.

4. The method of claim 1, wherein the at least two exposable amino acid residues in the starting antigen-binding molecule are substituted with positively charged amino acid residues in the modified antigen-binding molecule.

5. The method of claim 1, wherein the method further comprises:

assaying the plasma pharmacokinetics parameter of the modified antigen-binding molecule and determining that the parameter is altered compared to that of the starting antigen-binding molecule, wherein the parameter is: mean retention time in plasma, half-life in plasma (t1/2), area under the concentration curve (AUC), or clearance (CL) from plasma.

6. A method for producing an antigen-binding molecule with altered plasma pharmacokinetics, the method comprising:

(a) identifying the nucleotide sequence of a first set of one or more nucleic acids that together encode a first antigen-binding molecule comprising a heavy chain variable region, a light chain variable region, and an FcRn-binding domain, wherein the first antigen-binding molecule binds to an antigen and is a chimeric IgG antibody, humanized IgG antibody, or human IgG antibody;

(b) providing a host cell containing a second set of one or more nucleic acids that together encode a second antigen-binding molecule that binds to the antigen, the second antigen-binding molecule differing from the first antigen-binding molecule by amino acid substitutions at at least two exposable positions on the surface of a CDR or CDRs in a heavy chain variable region of the first antigen-binding molecule, wherein the isoelectric point of the second antigen-binding molecule is higher than the isoelectric point of the first antigen-binding molecule, as measured by isoelectric focusing, wherein the second antigen-binding molecule has 80% or more of the first antigen-binding molecule's antigen-binding activity as measured by a SPR technique in which the respective antigen-binding molecule is immobilized, the antigen serves as analyte, and the following conditions are used: 0.01 M HEPES pH 7.4, 0.15 M NaCl, 3 mM EDTA, 0.05% polysorbate 20, at 37° C., wherein a plasma pharmacokinetics parameter of the second antigen-binding molecule is altered compared to that of the first antigen-binding molecule, and wherein the amino acid substitution at each of the at least two exposable positions is independently selected from the following:

(i) substitution of a non-charged amino acid for a negatively charged amino acid in the first antigen-binding molecule; or (ii) substitution of a positively charged amino acid for a negatively charged amino acid in the first antigen-binding molecule; or (iii) substitution of a positively charged amino acid for a non-charged amino acid in the first antigen-binding molecule;

(c) culturing the host cell to express the second set of one or more nucleic acids; and (d) collecting the second antigen-binding molecule from the host cell.

7. The method of claim 6, wherein the second antigen-binding molecule comprises an FcRn-binding domain and is a chimeric IgG antibody, humanized IgG antibody, or human IgG antibody.

8. The method of claim 6, wherein the second antigen-binding molecule is a multispecific IgG antibody that binds to at least two types of antigens.

9. The method of claim 6, wherein the at least two exposable positions in the second antigen-binding molecule are occupied by positively charged amino acid residues.

10. The method of claim 6, wherein the method further comprises:

assaying the plasma pharmacokinetics parameter of the second antigen-binding molecule and determining that the parameter is altered compared to that of the first antigen-binding molecule, wherein the parameter is: mean retention time in plasma, half-life in plasma (t1/2), area under the concentration curve (AUC), or clearance (CL) from plasma.

11. A method for producing a modified antigen-binding molecule with altered plasma pharmacokinetics, the method comprising:

(a) introducing into a host cell a modified set of one or more nucleic acids that together encode a modified antigen-binding molecule comprising a heavy chain variable region and a light chain variable region that bind to an antigen, the modified set of one or more nucleic acids having been previously generated by mutating a starting set of one or more nucleic acids that together encode a starting antigen-binding molecule comprising a starting heavy chain variable region and a starting light chain variable region that bind to the antigen, to substitute amino acids at two or more exposable positions on the surface of a CDR or CDRs in the starting heavy chain variable region, wherein the isoelectric point of the modified antigen-binding molecule is higher than the isoelectric point of the starting antigen-binding molecule, as measured by isoelectric focusing,
wherein the modified antigen-binding molecule has 80% or more of the starting antigen-binding molecule's antigen-binding activity as measured by a SPR technique in which the respective antigen-binding molecule is immobilized, the antigen serves as analyte, and the following conditions are used: 0.01 M HEPES pH 7.4, 0.15 M NaCl, 3 mM EDTA, 0.05% polysorbate 20, at 37° C.,
wherein a plasma pharmacokinetics parameter of the modified antigen-binding molecule is altered compared to that of the starting antigen-binding molecule,
wherein the starting antigen-binding molecule comprises an FcRn-binding domain,
wherein the starting antigen-binding molecule is a chimeric IgG antibody, humanized IgG antibody, or human IgG antibody, and
wherein the amino acid substitution at each of the two or more exposable positions is independently selected from the following:
(i) substitution of a non-charged amino acid for a negatively charged amino acid in the starting antigen-binding molecule; or
(ii) substitution of a positively charged amino acid for a negatively charged amino acid in the starting antigen-binding molecule; or
(iii) substitution of a positively charged amino acid for a non-charged amino acid in the starting antigen-binding molecule;
(b) culturing the host cell to express the modified set of one or more nucleic acids; and
(c) collecting the modified antigen-binding molecule from the host cell.

12. The method of claim 11, wherein the modified antigen-binding molecule comprises an FcRn-binding domain and is a chimeric IgG antibody, humanized IgG antibody, or human IgG antibody.

13. The method of claim 11, wherein the modified antigen-binding molecule is a multispecific IgG antibody that binds to at least two types of antigens.

14. The method of claim 11, wherein the two or more exposable positions in the second antigen-binding molecule are occupied by positively charged amino acid residues.

15. The method of claim 11, wherein the method further comprises:
assaying the plasma pharmacokinetics parameter of the modified antigen-binding molecule and determining that the parameter is altered compared to that of the starting antigen-binding molecule, wherein the parameter is: mean retention time in plasma, half-life in plasma (t1/2), area under the concentration curve (AUC), or clearance (CL) from plasma.

16. A method for producing an antigen-binding molecule with altered plasma pharmacokinetics, the method comprising:

(a) identifying the nucleotide sequence of a first set of one or more nucleic acids that together encode a first antigen-binding molecule that binds to an antigen and that comprises a heavy chain variable region, a light chain variable region, and an FcRn-binding domain, wherein the first antigen-binding molecule is a chimeric IgG antibody, humanized IgG antibody, or human IgG antibody;

(b) providing a host cell containing a second set of one or more nucleic acids that together encode a second antigen-binding molecule comprising a second heavy chain variable region and a second light chain variable region, the second antigen-binding molecule differing from the first antigen-binding molecule by amino acid substitutions at two or more exposable positions on the surface of a CDR or CDRs in the heavy chain variable region of the first antigen-binding molecule, wherein the second antigen-binding molecule binds to the antigen and has 80% or more of the first antigen-binding molecule's antigen-binding activity as measured by a SPR technique in which the respective antigen-binding molecule is immobilized, the antigen serves as analyte, and the following conditions are used: 0.01 M HEPES pH 7.4, 0.15 M NaCl, 3 mM EDTA, 0.05% polysorbate 20, at 37° C., wherein amino acid substitution at each of the two or more exposable positions makes the charge at that position more negative, wherein the isoelectric point of the second antigen-binding molecule is lower than the isoelectric point of the first antigen-binding molecule, as measured by isoelectric focusing, and wherein the amino acid substitution at each of the two or more exposable positions is independently selected from the following:

(i) substitution of a non-charged amino acid for a positively charged amino acid in the first antigen-binding molecule; or (ii) substitution of a negatively charged amino acid for a positively charged amino acid in the first antigen-binding molecule; or (iii) substitution of a negatively charged amino acid for a non-charged amino acid in the first antigen-binding molecule;

(c) culturing the host cell to express the second set of one or more nucleic acids;

(d) collecting the second antigen-binding molecule from the host cell; and (e) assaying a plasma pharmacokinetics parameter of the second antigen-binding molecule and determining that the parameter is altered compared to that of the first antigen-binding molecule, wherein the parameter is: mean retention time in plasma, half-life in plasma (t1/2), area under the concentration curve (AUC), or clearance (CL) from plasma.

17. The method of claim 16, wherein the second antigen-binding molecule comprises an FcRn-binding domain and is a chimeric IgG antibody, humanized IgG antibody, or human IgG antibody.

18. The method of claim 16, wherein the second antigen-binding molecule is a multispecific IgG antibody that binds to at least two types of antigens.

19. The method of claim 16, wherein the two or more exposable positions in the second antigen-binding molecule are occupied by negatively charged amino acid residues.

20. A method for producing a modified antigen-binding molecule comprising a heavy chain variable region and a light chain variable region that bind to an antigen, the method comprising:

preparing the modified antigen-binding molecule by substituting at least two exposable amino acid residues on the surface of a complementary determining region (CDR) or CDRs in a heavy chain variable region of a starting antigen-binding molecule that binds to the antigen, to make the charge of the modified antigen-binding molecule more negative than the charge of the starting antigen-binding molecule, while retaining 80% or more of the starting antigen-binding molecule's antigen-binding activity as measured by a SPR technique in which the respective antigen-binding molecule is immobilized, the antigen serves as analyte, and the following conditions are used: 0.01 M HEPES pH 7.4, 0.15 M NaCl, 3 mM EDTA, 0.05% polysorbate 20, at 37° C.; and assaying a plasma pharmacokinetics parameter of the modified antigen-binding molecule and determining that the parameter is altered compared to that of the starting antigen-binding molecule, wherein the parameter is: mean retention time in plasma, half-life in plasma (t1/2), area under the concentration curve (AUC), or clearance (CL) from plasma, wherein the starting antigen-binding molecule comprises an FcRn-binding domain, wherein the starting antigen-binding molecule is a chimeric IgG antibody, humanized IgG antibody, or human IgG antibody, and wherein each of the at least two exposable amino acid residues is independently substituted in accordance with any of the following:
  (i) substitution of a non-charged amino acid for a positively charged amino acid in the starting antigen-binding molecule; or
  (ii) substitution of a negatively charged amino acid for a positively charged amino acid in the starting antigen-binding molecule; or
  (iii) substitution of a negatively charged amino acid for a non-charged amino acid in the starting antigen-binding molecule.

21. The method of claim 20, wherein the modified antigen-binding molecule comprises an FcRn-binding domain and is a chimeric IgG antibody, humanized IgG antibody, or human IgG antibody.

22. The method of claim 20, wherein the modified antigen-binding molecule is a multispecific IgG antibody that binds to at least two types of antigens.

23. The method of claim 20, wherein the at least two exposable amino acid residues in the starting antigen-binding molecule are substituted with negatively charged amino acid residues in the modified antigen-binding molecule.

24. A method for producing a modified antigen-binding molecule with altered plasma pharmacokinetics, the method comprising:
  (a) introducing into a host cell a modified set of one or more nucleic acids that together encode a modified antigen-binding molecule comprising a heavy chain variable region and a light chain variable region that bind to an antigen, the modified set of one or more nucleic acids having been previously generated by mutating a starting set of one or more nucleic acids that together encode a starting antigen-binding molecule comprising a starting heavy chain variable region and a starting light chain variable region that bind to the antigen, to substitute amino acids at two or more exposable positions on the surface of a CDR or CDRs in the starting heavy chain variable region,
    wherein the isoelectric point of the modified antigen-binding molecule is lower than the isoelectric point of the starting antigen-binding molecule, as measured by isoelectric focusing,
    wherein the modified antigen-binding molecule has 80% or more of the starting antigen-binding molecule's antigen-binding activity as measured by a SPR technique in which the respective antigen-binding molecule is immobilized, the antigen serves as analyte, and the following conditions are used: 0.01 M HEPES pH 7.4, 0.15 M NaCl, 3 mM EDTA, 0.05% polysorbate 20, at 37° C.,
    wherein the starting antigen-binding molecule comprises an FcRn-binding domain,
    wherein the starting antigen-binding molecule is a chimeric IgG antibody, humanized IgG antibody, or human IgG antibody, and
    wherein the amino acid substitution at each of the two or more exposable positions is independently selected from one of the following:
      (i) substitution of a non-charged amino acid for a positively charged amino acid in the starting antigen-binding molecule; or
      (ii) substitution of a negatively charged amino acid for a positively charged amino acid in the starting antigen-binding molecule; or
      (iii) substitution of a negatively charged amino acid for a non-charged amino acid in the starting antigen-binding molecule;
  (b) culturing the host cell to express the modified set of one or more nucleic acids;
  (c) collecting the modified antigen-binding molecule from the host cell; and
  (e) assaying a plasma pharmacokinetics parameter of the modified antigen-binding molecule and determining that the parameter is altered compared to that of the starting antigen-binding molecule, wherein the parameter is: mean retention time in plasma, half-life in plasma (t1/2), area under the concentration curve (AUC), or clearance (CL) from plasma.

25. The method of claim 24, wherein the modified antigen-binding molecule comprises an FcRn-binding domain and is a chimeric IgG antibody, humanized IgG antibody, or human IgG antibody.

26. The method of claim 24 wherein the modified antigen-binding molecule is a multispecific IgG antibody that binds to at least two types of antigens.

27. The method of claim 24 wherein the two or more exposable positions in the second antigen-binding molecule are occupied by negatively charged amino acid residues.

28. A method for producing a modified antigen-binding molecule comprising a heavy chain variable region and a light chain variable region that bind to an antigen, the method comprising:
  (a) identifying a starting antigen-binding domain comprising a starting heavy chain variable region and a starting light chain variable region that bind the antigen;
  (b) preparing a library comprising a plurality of variants of the starting antigen-binding domain,
    wherein each of the variants comprises a heavy chain variable region and a light chain variable region,
    wherein each variant differs from the starting antigen-binding domain by substitution of at least two exposable amino acid residues on the surface of a CDR or CDRs in one or both of the variant's heavy and light chain variable regions, and
    wherein each such substitution makes the charge of the variant be more negative than the charge of the starting antigen-binding domain;
  (c) screening the library to select a variant that binds to the antigen with 80% or more of the starting antigen-binding domain's antigen-binding activity as measured by a SPR technique in which a molecule comprising the starting antigen-binding domain or the variant's antigen-binding domain is immobilized, the antigen serves as analyte, and the following conditions are used: 0.01 M HEPES pH 7.4, 0.15 M NaCl, 3 mM EDTA, 0.05% polysorbate 20, at 37° C.;

(d) producing an IgG molecule comprising the selected variant's heavy and light chain variable regions; and (e) confirming that a plasma pharmacokinetics parameter of the IgG molecule of (d) is altered compared to that of a control IgG molecule in which the antigen-binding domain comprises the starting heavy chain variable region and the starting light chain variable region, wherein the parameter is: mean retention time in plasma, half-life in plasma (t1/2), area under the concentration curve (AUC), or clearance (CL) from plasma, and wherein each of the at least two exposable amino acid residues is independently substituted in accordance with any of the following:

(i) substitution of a non-charged amino acid for a positively charged amino acid in the starting antigen-binding molecule; or (ii) substitution of a negatively charged amino acid for a positively charged amino acid in the starting antigen-binding molecule; or (iii) substitution of a negatively charged amino acid for a non-charged amino acid in the starting antigen-binding molecule.

* * * * *